(12) United States Patent
Kiss et al.

(10) Patent No.: US 9,353,082 B2
(45) Date of Patent: May 31, 2016

(54) PHARMACEUTICAL COMPOUNDS

(75) Inventors: Laszlo Erno Kiss, São Mamede do Coronado (PT); David Alexander Learmonth, São Mamede do Coronado (PT); Carla Patrícia da Costa Pereira Rosa, São Mamede do Coronado (PT); Rita Gusmãmo de Noronha, São Mamede do Coronado (PT); Pedro Nuno Leal Palma, São Mamede do Coronado (PT); Patrício Manuel Vieira Araújo Soares da Silva, São Mamede do Coronado (PT); Alexander Beliaev, São Mamede do Coronado (PT)

(73) Assignee: BIAL—PORTELA & CA, S.A., Sao Mamede Do Coronado (PT)

( * ) Notice: Subject to any disclaimer, the term of this patent is extended or adjusted under 35 U.S.C. 154(b) by 446 days.

(21) Appl. No.: 13/141,205

(22) PCT Filed: Dec. 23, 2009

(86) PCT No.: PCT/PT2009/000080
§ 371 (c)(1),
(2), (4) Date: Sep. 1, 2011

(87) PCT Pub. No.: WO2010/074588
PCT Pub. Date: Jul. 1, 2010

(65) Prior Publication Data
US 2012/0065191 A1  Mar. 15, 2012

Related U.S. Application Data

(60) Provisional application No. 61/242,472, filed on Sep. 15, 2009, provisional application No. 61/221,166, filed on Jun. 29, 2009, provisional application No. 61/174,712, filed on May 1, 2009, provisional application No. 61/159,281, filed on Mar. 11, 2009, provisional application No. 61/140,640, filed on Dec. 24, 2008.

(51) Int. Cl.
| | | |
|---|---|---|
| C07D 413/10 | (2006.01) |
| C07D 401/12 | (2006.01) |
| C07D 231/12 | (2006.01) |
| C07D 233/56 | (2006.01) |
| C07D 233/60 | (2006.01) |
| C07D 249/10 | (2006.01) |
| C07D 249/18 | (2006.01) |
| C07D 401/04 | (2006.01) |
| C07D 401/10 | (2006.01) |
| C07D 401/14 | (2006.01) |
| C07D 405/10 | (2006.01) |
| C07D 405/12 | (2006.01) |
| C07D 409/04 | (2006.01) |
| C07D 413/06 | (2006.01) |
| C07D 413/14 | (2006.01) |
| C07D 417/14 | (2006.01) |

(52) U.S. Cl.
CPC ............ *C07D 401/12* (2013.01); *C07D 231/12* (2013.01); *C07D 233/56* (2013.01); *C07D 233/60* (2013.01); *C07D 249/10* (2013.01); *C07D 249/18* (2013.01); *C07D 401/04* (2013.01); *C07D 401/10* (2013.01); *C07D 401/14* (2013.01); *C07D 405/10* (2013.01); *C07D 405/12* (2013.01); *C07D 409/04* (2013.01); *C07D 413/06* (2013.01); *C07D 413/10* (2013.01); *C07D 413/14* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 3,868,458 A | 2/1975 | Baker et al. | |
| 3,932,444 A * | 1/1976 | Ellis | 548/312.7 |
| 3,940,484 A * | 2/1976 | Baker et al. | 514/235.8 |
| 4,707,487 A | 11/1987 | Arrang et al. | |
| 5,290,790 A | 3/1994 | Arrang et al. | |
| 6,797,824 B2 | 9/2004 | Thurkauf et al. | |
| 2005/0014765 A1 | 1/2005 | Mailliet et al. | |
| 2011/0166138 A1 | 7/2011 | Makriyannis et al. | |

FOREIGN PATENT DOCUMENTS

| | | |
|---|---|---|
| JP | 63-10767 A | 1/1988 |
| WO | 2007014290 A2 | 2/2007 |
| WO | 2009073620 A2 | 6/2009 |

OTHER PUBLICATIONS

Zhang. Neuropharmacology, 2007, 52, 1095-1105.*
Asano et al., "Discovery, synthesis and biological evaluation of isoquinolones as novel and highly selective JNK inhibitors (2)," Bioorganic & Medicinal Chemistry 16(8), 4699-714, 2008.
Hagiwara et al., "Preparation of 2-(2-pyridyl)imidazole compounds as agricultural fungicides," Chem. Abstr. 779478, 1998 (compounds of JP 1031676), 2 pages.
Hirano et al., "Phosgene-free preparation of carbonyldiazole compounds from silylazoles," Chem. Abstr. 791907, 2001 (compounds of JP 2001 302640), 3 pages.
Kihara et al., "Preparation of 2-(carbamoylthio)imidazole derivatives for improvement of cerebral function," Chem. Abstr. 98527, 1990 (compounds of JP 1203368).

(Continued)

*Primary Examiner* — Noble Jarrell
(74) *Attorney, Agent, or Firm* — Banner & Witcoff, Ltd.

(57) ABSTRACT

The invention relates to compounds and compositions for inhibiting the enzyme fatty acid amide hydrolase (FAAH), the use of the compounds in therapy and, in particular, for treating or preventing conditions whose development or symptoms are linked to substrates of the FAAH enzyme, and methods of treatment or prevention using the compounds and compositions.

64 Claims, No Drawings

(56) References Cited

OTHER PUBLICATIONS

Kitamura et al., "Preparation of isoquinoline derivatives as c-Jun N-terminal kinase (JNK) inhibitors," Chem. Abstr. 141054, 2005 (compounds in WO 2005/014576), 3 pages.

Lahm et al., "Preparation of insecticidal anthranilamides," Chem. Abstr. No. 713292, 2001 (compounds in WO 2001/70671), 9 pages.

Yano et al., "Preparation of tribromoimidazoles as insecticides for cockroaches," Chem. Abstr. No. 123311, 1992 (compounds in JP3246206), 3 pages.

Deng, "Recent advances in the discovery and evaluation of fatty acid amide hydrolase inhibitors," Expert Op. Drug Disc. [Early Online] 2010, 1-33.

Pacher et al., "The Endocannabinoid System as an Emerging Target of Pharmacotherapy," Pharmacol. Rev. 58, 389-462, 2006.

Schlosburg et al., "Targeting Fatty Acid Amide Hydrolase (FAAH) to Treat Pain and Inflammation," The AAPS Journal, published online Jan. 29, 2009, pp. 1-6.

Gomper et al., "Umsetzungen von Imidazolen mit lsocyanaten," Chemische Berichte, 1959, vol. 92, pp. 550-563, including the compound on the right side of the reaction formula on p. 551.

Dinsmore et al., Bioorganic and Medicinal Chemistry Letters (2001);11(4): 537-40.

Castro et al., "Synthesis, Biological Evaluation and Modeling Studies of Dual Binding Ache Inhibitors," Medicinal Chemistry Research, 2002, 11(4), 219-237.

Ma et al., "A Kind of Novel Nonmetallocene Catalysts for Ethylene Polymerization," Journal of Polymer Science, Polymer Chemistry, 2008, 46(1), 33-37.

Registry Extract: RN:526190-56-7, RN:432017-91-9, RN:432016-58-5, RN:432002-54-5, 2014.

Rivett and Wilshire, "Reactions of NN.Diphenylcarbannoyl Chloride," Australian Journal of Chemistry, 1966, 19(1), 165-168.

\* cited by examiner

PHARMACEUTICAL COMPOUNDS

The present invention relates to compounds and their uses, and in particular to compounds and their therapeutic use in the treatment or prevention of conditions having an association with substrates, such as the neurotransmitter anandamide, which are broken down by the fatty acid amide hydrolase (FAAH) enzyme.

FAAH enzyme breaks down fatty acid amides such as anandamide (N-arachidonoylethanolamine), N-oleoylethanolamine, N-palmitoylethanolamine and oleamide. Anandamide, also known as N-arachidonoylethanolamine or AEA, is an endogenous cannabinoid neurotransmitter found in animal and human organs, especially in the brain. It has also been found that anandamide binds to the vanilloid receptor. Anandamide is degraded by the fatty acid amide hydrolase (FAAH) enzyme to ethanolamine and arachidonic acid. Accordingly, inhibitors of FAAH lead to elevated anandamide levels.

Anandamide is a neurotransmitter in the endocannabinoid system and stimulates the cannabinoid receptors. Cannabinoid receptors, such as CB1 and CB2, are G protein-coupled receptors. CB1 is found mainly in the central nervous system whereas CB2 is found mainly in peripheral tissue. The endocannabinoid system has been implicated in a growing number of physiological functions, both in the central and peripheral nervous systems and in peripheral organs. Modulation of the activity of the endocannabinoid system has been shown to have a potentially therapeutic effect on a wide range of disparate diseases and pathological conditions. Therefore, the endocannabinoid system, and the FAAH enzyme in particular, has become a therapeutic target for developing potential treatments for many diseases. The endocannabinoid system has been implicated in appetite regulation, obesity, metabolic disorders, cachexia, anorexia, pain, inflammation, neurotoxicity, neurotrauma, stroke, multiple sclerosis, spinal cord injury, Parkinson's disease, levodopa-induced dyskinesia, Huntington's disease, Gilles de la Tourette's syndrome, tardive dyskinesia, dystonia, amyotrophic lateral sclerosis, Alzheimer's disease, epilepsy, schizophrenia, anxiety, depression, insomnia, nausea, emesis, alcohol disorders, drug addictions such as opiates, nicotine, cocaine, alcohol and psychostimulants, hypertension, circulatory shock, myocardial reperfusion injury, atherosclerosis, asthma, glaucoma, retinopathy, cancer, inflammatory bowel disease, acute and chronic liver disease such as hepatitis and liver cirrhosis, arthritis and osteoporosis. The endocannabinoid system and the conditions with which it is associated is discussed in detail in Pacher et al. (2006) *Pharmacol. Rev.* 58:389-462.

In order to modulate the level of endogenous FAAH substrates, such as anandamide, which in turn modulate the endocannabinoid system, inhibitors of the FAAH enzyme have been developed. This allows conditions and diseases associated with the endocannabinoid system to be at least partially treated or prevented.

Since the substrates of FAAH bind to other receptors, e.g. the vanilloid receptor, and/or are involved in other signalling pathways, inhibitors of FAAH may also allow conditions or diseases associated with other pathways or systems, e.g. the vanilloid system, to be at least partially treated or prevented.

FR 2915198 and FR 2915199 disclose compounds which are inhibitors of FAAH.

U.S. Pat. No. 7,208,504 and FR2915197 also disclose a range of compounds which are not dissimilar to those disclosed in FR 2915198 and FR 2915199. These compounds are disclosed as being suitable for inhibiting hormone sensitive lipase (HSL) and monoacyl glycerol lipase (MAGL), respectively. However, these compounds are not disclosed as being suitable for inhibiting FAAH.

WO 2009/117444 discloses compounds which are inhibitors of both FAAH and MAGL.

In accordance with a first aspect of the invention, there is provided a compound having Formula I or Formula II:

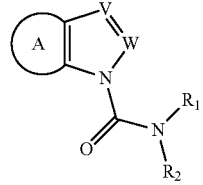

Formula I

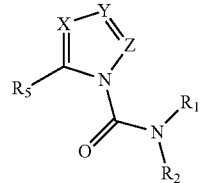

Formula II wherein:
R1 and R2 can each be independently selected from H, $C_{1-20}$ alkyl, $C_{1-6}$ alkoxy, aryl, heteroaryl, partially or fully saturated heterocyclyl, $C_{3-10}$ cycloalkyl, aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, R1a, halogen, OH, OR1a, OCOR1a, SH, SR1a, SCOR1a, $NH_2$, NHR1a, $NHSO_2NH_2$, $NHSO_2R1a$, NR1aCOR1b, NHCOR1a, NR1aR1b, COR1a, CSR1a, CN, COOH, COOR1a, $CONH_2$, CONHOH, CONHR1a, CONHOR1a, $SO_2R1a$, $SO_3H$, $SO_2NH_2$, CONR1aR1b, $SO_2NR1aR1b$, wherein R1a and R1b are independently selected from $C_{1-6}$ alkyl, substituted $C_{1-6}$ alkyl, aryl, heteroaryl, $C_{3-8}$ cycloalkyl and heterocyclyl, or R1a and R1b, together with the heteroatom to which they are joined, can form heterocyclyl,
wherein, when R1 or R2 is $C_{1-20}$ alkyl, alkoxy, aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, $C_{1-6}$ alkyl, $C_{3-8}$ cycloalkyl or is a group containing one or more of these moieties, each of these moieties may optionally be substituted with one or more groups selected from R1c, halogen, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{1-6}$ alkylamino, $C_{1-6}$ dialkylamino, $C_{1-10}$ alkyl, OH, OR1c, OCOR1c, SH, SR1c, SCOR1c, $NH_2$, $NO_2$, NHR1c, $NHSO_2NH_2$, $NHSO_2R1c$, NR1cCOR1d, $NHC(NH)NH_2$, NHCOR1c, NR1cR1d, COR1c, CSR1c, CN, COOH, COOR1c, $CONH_2$, CONHOH, CONHR1c, CONHOR1c, $C(NOH)NH_2$, CONR1cR1d, $SO_2R1c$, $SO_3H$, $SO_2NH_2$, $SO_2NR1cR1d$, wherein R1c and R1d are independently selected from $C_{1-6}$ alkyl, substituted $C_{1-6}$ alkyl, aryl, heteroaryl, $C_{3-8}$ cycloalkyl and heterocyclyl, or R1c and R1d, together with the heteroatom to which they are joined, can form heterocyclyl,
wherein, when the substituent of R1 or R2 is $C_{1-10}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{1-6}$ alkylamino, $C_{1-6}$ dialkylamino, $C_{1-6}$ alkyl, $C_{3-8}$ cycloalkyl or is a group containing one or more of these moieties, each of these moieties may optionally be substituted with one or more groups selected from R1e, halogen, $C_{1-10}$ alkyl, OH, OR1e, OCOR1e, SH, SR1e, SCOR1e, $NH_2$, $NO_2$, NHR1e, $NHSO_2NH_2$, $NHSO_2R1e$, NR1eCOR1f, $NHC(NH)NH_2$, NHCOR1e, NR1eR1f, COR1e, CSR1e, CN, COOH, COOR1e, $CONH_2$, CONHOH, CONHR1e, CONHOR1e, $C(NOH)NH_2$, CONR1eR1f, $SO_2R1e$, $SO_3H$, $SO_2NH_2$, $SO_2NR1eR1f$, wherein R1e and R1f are independently selected from $C_{1-6}$ alkyl, substituted $C_{1-6}$ alkyl, aryl, heteroaryl, $C_{3-8}$ cycloalkyl and heterocyclyl, or R1e and R1f, together with the heteroatom to which they are joined, can form heterocyclyl, with the exception that R1 and R2 are not both H or both unsubstituted methyl, or R1 and R2, together with the N to which they are attached, can form a heteroaryl or heterocyclyl group, each of which may optionally be substituted with one or more oxygen atoms or one or more groups selected from aryl, heteroaryl, partially or fully saturated heterocyclyl, $C_{3-8}$ cycloalkyl, $C_{1-6}$ alkyl, aryl $C_{1-6}$ alkyl, heteroaryl $C_{1-6}$ alkyl, heterocyclyl $C_{1-6}$ alkyl, $C_{3-8}$ cycloalkyl $C_{1-6}$ alkyl, $C_{1-6}$ alkoxy, aryloxy, heteroaryloxy, heterocyclyloxy, R2a, halogen, OH, OR2a, OCOR2a, SH, SR2a, SCOR2a, $NH_2$, $NO_2$, NHR2a, $NHSO_2NH_2$, $NHSO_2R2a$, NR2aCOR2b, $NHC(NH)NH_2$, NHCOR2a, NR2aR2b, COR2a, CSR2a, CN, COOH, COOR2a, $CONH_2$, CONHOH, CONHR2a, CONHOR2a, $C(NOH)NH_2$, CONR2aR2b, $SO_2R2a$, $SO_3H$, $SO_2NH_2$, $SO_2NR2aR2b$, wherein R2a and R2b are independently selected from $C_{1-6}$ alkyl, substituted $C_{1-6}$ alkyl, aryl, heteroaryl, $C_{3-8}$ cycloalkyl and heterocyclyl, or R2a and R2b, together with the heteroatom to which they are joined, can form heterocyclyl, wherein, when the substituent of the heteroaryl or heterocyclyl formed by R1 and R2 together is aryl, heteroaryl, heterocyclyl, $C_{3-8}$ cycloalkyl, $C_{1-6}$ alkyl, aryl $C_{1-6}$ alkyl, heteroaryl $C_{1-6}$ alkyl, heterocyclyl $C_{1-6}$ alkyl, $C_{3-8}$ cycloalkyl $C_{1-6}$ alkyl, $C_{1-6}$ alkoxy, aryloxy, heteroaryloxy, heterocyclyloxy, or a group containing one or more of these moieties, each of these moieties may optionally be substituted with one or more groups selected from halogen, hydroxyl, $C_{1-6}$ alkyl, aryl, heteroaryl, heterocyclyl, $C_{3-8}$ cycloalkyl, $C_{1-4}$ alkoxy, aryloxy, heteroaryloxy, heterocyclyloxy, $C_{3-8}$ cycloalkyloxy, aryl $C_{1-4}$ alkoxy, heteroaryl $C_{1-6}$ alkoxy, heterocyclyl $C_{1-4}$ alkoxy, $C_{3-8}$ cycloalkyl $C_{1-4}$ alkoxy, R2c, OR2c, OCOR2c, SH, SR2c, SCOR2c, $NH_2$, $NO_2$, NHR2c, $NHSO_2NH_2$, $NHSO_2R2c$, NR2cCOR2d, $NHC(NH)NH_2$, NHCOR2c, NR2cR2d, COR2c, CSR2c, CN, COOH, COOR2c, $CONH_2$, CONHOH, CONHR2c, CONHOR2c, $C(NOH)NH_2$, CONR2cR2d, $SO_2R2c$, $SO_3H$, $SO_2NH_2$, $SO_2NR2cR2d$, wherein R2c and R2d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, wherein, when the substituent of the substituent of the heteroaryl or heterocyclyl formed by R1 and R2 together is $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, $C_{3-8}$ cycloalkyloxy, aryl $C_{1-4}$ alkoxy, heteroaryl $C_{1-4}$ alkoxy, heterocyclyl $C_{1-4}$ alkoxy, $C_{3-8}$ cycloalkyl $C_{1-4}$ alkoxy, or is a group containing one or more of these moieties, each of these moieties may optionally be substituted with one or more groups selected from $C_{1-4}$ alkoxy, R2e, halogen, OH, OR2e, OCOR2e, SH, SR2e, SCOR2e, $NH_2$, $NO_2$, NHR2e, $NHSO_2NH_2$, $NHSO_2R2e$, NR2eCOR2f, $NHC(NH)NH_2$, NR2eR2f, NHCOR2e, COR2e, CSR2e, CN, COOH, COOR2e, $CONH_2$, CONHOH, CONHR2e, CONHOR2e, $C(NOH)NH_2$, CONR2eR2f, $SO_2R2e$, $SO_3H$, $SO_2NH_2$, $SO_2NR2eR2f$, wherein R2e and R2f are independently selected from $C_{1-6}$ alkyl, substituted $C_{1-6}$ alkyl, aryl, heteroaryl, $C_{3-8}$ cycloalkyl and heterocyclyl, or R2e and R2f, together with the heteroatom to which they are joined, can form heterocyclyl;

Ring A is selected from aryl, heteroaryl and heterocyclyl moieties, each of which may optionally be substituted with one or more groups selected from halogen, $C_{1-6}$ alkyl, aryl, heteroaryl, heterocyclyl, $C_{1-6}$ alkoxy, aryloxy, heteroaryloxy, heterocyclyloxy, Ra, $C_{1-10}$ alkyl, OH, ORa, OCORa, SH, SRa, SCORa, $NH_2$, $NO_2$, NHRa, $NHSO_2NH_2$, $NHSO_2Ra$, NRaCORb, NHCORa, $NHC(NH)NH_2$, NRaRb, CORa, CSRa, CN, COOH, COORa, $CONH_2$, CONHRa, CONHOH, CONHORa, $C(NOH)NH_2$, CONRaRb, $SO_2Ra$, $SO_3H$, $SO_2NH_2$, $SO_2NRaRb$, wherein Ra and Rb are independently selected from $C_{1-6}$ alkyl, substituted $C_{1-6}$ alkyl, aryl, heteroaryl, $C_{3-8}$ cycloalkyl and heterocyclyl, or Ra and Rb, together with the heteroatom to which they are joined, can form heterocyclyl, wherein, when Ring A is substituted with $C_{1-6}$ alkyl, aryl, heteroaryl, heterocyclyl, $C_{1-6}$ alkoxy, aryloxy, heteroaryloxy, heterocyclyloxy, $C_{1-10}$ alkyl, $C_{3-8}$ cycloalkyl or is substituted with a group containing one or more of these moieties, each of these moieties may optionally be substituted with one or more groups selected from halogen, Rc, $C_{1-10}$ alkyl, aryl $C_{1-6}$ alkyl, heteroaryl $C_{1-6}$ alkyl, heterocyclyl $C_{1-6}$ alkyl, OH, ORc, OCORc, SH, SRc, SCORc, $NH_2$, $NO_2$, NHRc, $NHSO_2NH_2$, $NHSO_2Rc$, NRcCORd, NHCORc, $NHC(NH)NH_2$, NRcRd, CORc, CSRc, CN, COOH, COORc, $CONH_2$, CONHOH, CONHRc, CONHORc, $C(NOH)NH_2$, CONRcRd, $SO_2Rc$, $SO_3H$, $SO_2NH_2$, $SO_2NRcRd$, wherein Rc and Rd are independently selected from $C_{1-6}$ alkyl, substituted $C_{1-6}$ alkyl, aryl, heteroaryl, $C_{3-8}$ cycloalkyl and heterocyclyl, or Rc and Rd, together with the heteroatom to which they are joined, can form heterocyclyl;

V can be N, CH or C—R3, wherein R3 is halogen, $C_{1-10}$ alkyl, aryl, heteroaryl, heterocyclyl, $C_{3-8}$ cycloalkyl, $C_{1-6}$ alkoxy, aryloxy, heteroaryloxy, heterocyclyloxy, R3a, OH, OR3a, SH, SR3a, OCOR3a, SCOR3a, $NH_2$, $NO_2$, NHR3a, $NHSO_2NH_2$, $NHSO_2R3a$, NR3aCOR3b, NHCOR3a, $NHC(NH)NH_2$, NR3aR3b, COR3a, CSR3a, CN, COOH, COOR3a, $CONH_2$, CONHOH, CONHR3a, CONHOR3a, $C(NOH)NH_2$, CONR3aR3b, $SO_2R3a$, $SO_3H$, $SO_2NH_2$, $SO_2NR3aR3b$, wherein R3a and R3b are independently selected from $C_{1-6}$ alkyl, substituted $C_{1-6}$ alkyl, aryl, heteroaryl, $C_{3-8}$ cycloalkyl and heterocyclyl, or R3a and R3b, together with the heteroatom to which they are joined, can form heterocyclyl, wherein, when R3 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R3c, $C_{1-10}$ alkyl, OH, OR3c, OCOR3c, SH, SR3c, SCOR3c, $NH_2$, $NO_2$, NHR3c, $NHSO_2NH_2$, $NHSO_2R3c$, NR3cCOR3d, NHCOR3c, $NHC(NH)NH_2$, NR3cR3d, COR3c, CSR3c, CN, COOH, COOR3c, $CONH_2$, CONHOH, CONHR3c, CONHOR3c, $C(NOH)NH_2$, CONR3cR3d, $SO_2R3c$, $SO_3H$, $SO_2NH_2$, $SO_2NR3cR3d$, wherein R3c and R3d are independently selected from $C_{1-6}$ alkyl, substituted $C_{1-6}$ alkyl, aryl, heteroaryl, $C_{3-8}$ cycloalkyl and heterocyclyl, or R3c and R3d, together with the heteroatom to which they are joined, can form heterocyclyl, wherein, when the substituent of R3 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, R3e, $C_{1-10}$ alkyl, OH, OR3e, OCOR3e, SH, SR3e, SCOR3e, $NH_2$, $NO_2$, NHR3e, $NHSO_2NH_2$, $NHSO_2R3e$, NR3eCOR3f, NHCOR3e, NHC(NH)$NH_2$, NR3eR3f, COR3e, CSR3e, CN, COOH, COOR3e, $CONH_2$, CONHOH, CONHR3e, CONHOR3e, C(NOH)$NH_2$, CONR3eR3f, $SO_2R3e$, $SO_3H$, $SO_2NH_2$, $SO_2NR3eR3f$, wherein R3e and R3f are independently selected from $C_{1-6}$ alkyl, substituted $C_{1-6}$ alkyl, aryl, heteroaryl, $C_{3-8}$ cycloalkyl and heterocyclyl, or R3e and R3f, together with the heteroatom to which they are joined, can form heterocyclyl;

W can be N, CH or C—R4, wherein R4 is halogen, $C_{1-10}$ alkyl, aryl, heteroaryl, heterocyclyl, $C_{1-6}$ alkoxy, aryloxy, heteroaryloxy, heterocyclyloxy, $C_{3-8}$ cycloalkyl, R4a, OH, OR4a, SH, SR4a, OCOR4a, SCOR4a, $NH_2$, $NO_2$, NHR4a, $NHSO_2NH_2$, $NHSO_2R4a$, NR4aCOR4b, NHCOR4a, NHC(NH)$NH_2$, NR4aR4b, COR4a, CSR4a, CN, COOH, COOR4a, $CONH_2$, CONHOH, CONHR4a, CONHOR4a, C(NOH)$NH_2$, CONR4aR4b, $SO_2R4a$, $SO_3H$, $SO_2NH_2$, $SO_2NR4aR4b$, wherein R4a and R4b are independently selected from $C_{1-6}$ alkyl, substituted $C_{1-6}$ alkyl, aryl, heteroaryl, $C_{3-8}$ cycloalkyl and heterocyclyl, or R4a and R4b, together with the heteroatom to which they are joined, can form heterocyclyl, wherein, when R4 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R4c, $C_{1-10}$ alkyl, OH, OR4c, OCOR4c, SH, SR4c, SCOR4c, $NH_2$, $NO_2$, NHR4c, $NHSO_2NH_2$, $NHSO_2R4c$, NR4cCOR4d, NHCOR4c, NHC(NH)$NH_2$, NR4cR4d, COR4c, CSR4c, CN, COOH, COOR4c, $CONH_2$, CONHOH, CONHR4c, CONHOR4c, C(NOH)$NH_2$, CONR4cR4d, $SO_2R4c$, $SO_3H$, $SO_2NH_2$, $SO_2NR4cR4d$, wherein R4c and R4d are independently selected from $C_{1-6}$ alkyl, substituted $C_{1-6}$ alkyl, aryl, heteroaryl, $C_{3-8}$ cycloalkyl and heterocyclyl, or R4c and R4d, together with the heteroatom to which they are joined, can form heterocyclyl, wherein, when the substituent of R4 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, R4e, $C_{1-10}$ alkyl, OH, OR4e, OCOR4e, SH, SR4e, SCOR4e, $NH_2$, $NO_2$, NHR4e, $NHSO_2NH_2$, $NHSO_2R4e$, NR4eCOR4f, NHCOR4e, NHC(NH)$NH_2$, NR4eR4f, COR4e, CSR4e, CN, COOH, COOR4e, $CONH_2$, CONHOH, CONHR4e, CONHOR4e, C(NOH)$NH_2$, CONR4eR4f, $SO_2R4e$, $SO_3H$, $SO_2NH_2$, $SO_2NR4eR4f$, wherein R4e and R4f are independently selected from $C_{1-6}$ alkyl, substituted $C_{1-6}$ alkyl, aryl, heteroaryl, $C_{3-8}$ cycloalkyl and heterocyclyl, or R4e and R4f, together with the heteroatom to which they are joined, can form heterocyclyl;

R5 together with the ring carbon to which it is attached, can form a carbonyl group, with the double bond in the ring of Formula II to which it is attached being rearranged and/or saturated accordingly, or R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, $NO_2$, NHR5a, $NHSO_2NH_2$, $NHSO_2R5a$, NR5aCOR5b, NHCOR5a, NHC(NH)$NH_2$, NR5aR5b, COR5a, CSR5a, CN, COOH, COOR5a, $CONH_2$, CONHOH, CONHR5a, CONHOR5a, C(NOH)$NH_2$, CONR5aR5b, $SO_2R5a$, $SO_3H$, $SO_2NH_2$, $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl, wherein, when R5 is $C_{1-6}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R5c, $C_{1-6}$ alkyl, OH, OR5c, OCOR5c, SH, SR5c, SCOR5c, $NH_2$, $NO_2$, NHR5c, $NHSO_2NH_2$, $NHSO_2R5c$, NR5cCOR5d, NHCOR5c, NHC(NH)$NH_2$, NR5cR5d, COR5c, CSR5c, CN, COOH, COOR5c, $CONH_2$, CONHOH, CONHR5c, CONHOR5c, C(NOH)$NH_2$, CONR5cR5d, $SO_2R5c$, $SO_3H$, $SO_2NH_2$, $SO_2NR5cR5d$, wherein R5c and R5d are independently selected from $C_{1-6}$ alkyl, substituted $C_{1-6}$ alkyl, aryl, heteroaryl, $C_{3-8}$ cycloalkyl and heterocyclyl, or R5c and R5d, together with the heteroatom to which they are joined, can form heterocyclyl, wherein, when the substituent of R5 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with one or more groups selected from halogen, R5e, $C_{1-6}$ alkyl, OH, OR5e, OCOR5e, SH, SR5e, SCOR5e, $NH_2$, $NO_2$, NHR5e, $NHSO_2NH_2$, $NHSO_2R5e$, NR5eCOR5f, NHCOR5e, NHC(NH)$NH_2$, NR5eR5f, COR5e, CSR5e, CN, COOH, COOR5e, $CONH_2$, CONHOH, CONHR5e, CONHOR5e, C(NOH)$NH_2$, CONR5eR5f, $SO_2R5e$, $SO_3H$, $SO_2NH_2$, $SO_2NR5eR5f$, wherein R5e and R5f are independently selected from $C_{1-6}$ alkyl, substituted $C_{1-6}$ alkyl, aryl, heteroaryl, $C_{3-8}$ cycloalkyl and heterocyclyl, or R5e and R5f, together with the heteroatom to which they are joined, can form heterocyclyl;

X can be O (with the ring double bond attached to X in Formula II replaced by a single bond accordingly), N, CH or C—R6, wherein R6 is selected from $C_{1-6}$ alkyl, aryl, heteroaryl, heterocyclyl, $C_{1-6}$ alkoxy, aryloxy, heteroaryloxy, heterocyclyloxy, R6a, halogen, OH, OR6a, SH, SR6a, OCOR6a, SCOR6a, $NH_2$, $NO_2$, NHR6a, $NHSO_2NH_2$, $NHSO_2R6a$, NR6aCOR6b, NHCOR6a, NHC(NH)$NH_2$, NR6aR6b, COR6a, CSR6a, CN, COOH, COOR6a, $CONH_2$, CONHOH, CONHR6a, CONHOR6a, C(NOH)$NH_2$, CONR6aR6b, $SO_2R6a$, $SO_3H$, $SO_2NH_2$, $SO_2NR6aR6b$, wherein R6a and R6b are independently selected from $C_{1-6}$ alkyl, substituted $C_{1-6}$ alkyl, aryl, heteroaryl, $C_{3-8}$ cycloalkyl and heterocyclyl, or R6a and R6b, together with the heteroatom to which they are joined, can form heterocyclyl, wherein, when R6 is heteroaryl or heterocyclyl, each of these moieties may optionally be substituted with one or more oxygen atoms, and when R6 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with one or more groups selected from halogen, R6c, $C_{1-6}$ alkyl, $C_{1-6}$ alkynyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, OR6c, OCOR6c, SH, SR6c, SCOR6c, $NH_2$, $NO_2$, NHR6c, NHC(NH)$NH_2$, $NHSO_2NH_2$, $NHSO_2R6c$, NR6cCOR6d, NHCOR6c, NR6cR6d, COR6c, CSR6c, CN, COOH, COOR6c, CONH$_2$, CONHR6c, CONHOR6c, CONHOH, C(NOH)NH$_2$, CONR6cR6d, SO$_2$R6c, SO$_3$H, SO$_2$NH$_2$, SO$_2$NR6cR6d, wherein R6c and R6d are independently selected from C$_{1-6}$ alkyl, substituted C$_{1-6}$ alkyl, aryl, heteroaryl, C$_{3-8}$ cycloalkyl and heterocyclyl, or R6c and R6d, together with the heteroatom to which they are joined, can form heterocyclyl, wherein, when the substituent of R6 is heteroaryl or heterocyclyl, each of these moieties may optionally be substituted with one or more oxygen atoms, or when the substituent of R6 is C$_{1-6}$ alkyl, C$_{1-6}$ alkynyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{3-8}$ cycloalkyl, or is a group containing one or more of these moieties, each of these moieties may optionally be substituted with one or more groups selected from halogen, R6e, C$_{1-4}$ alkyl, C$_{1-4}$ alkoxy, OH, OR6e, OCOR6e, SH, SR6e, SCOR6e, NH$_2$, NO$_2$, NHR6e, NHC(NH)NH$_2$, NHSO$_2$NH$_2$, NHSO$_2$R6e, NR6eCOR6f, NHCOR6e, NR6eR6f, COR6e, CSR6e, CN, COOH, COOR6e, CONH$_2$, CONHOH, CONHR6e, CONHOR6e, C(NOH)NH$_2$, CONR6eR6f, SO$_2$R6e, SO$_3$H, SO$_2$NH$_2$, SO$_2$NR6eR6f, wherein R6e and R6f are independently selected from C$_{1-6}$ alkyl, substituted C$_{1-6}$ alkyl, aryl, heteroaryl, C$_{3-8}$ cycloalkyl and heterocyclyl, or R6e and R6f, together with the heteroatom to which they are joined, can form heterocyclyl;

Y can be N, CH or C—R7, wherein R7 is selected from C$_{1-6}$ alkyl, aryl, heteroaryl, heterocyclyl, C$_{1-6}$ alkoxy, aryloxy, heteroaryloxy, heterocyclyloxy, R7a, halogen, OH, OR7a, SH, SR7a, OCOR7a, SCOR7a, NH$_2$, NO$_2$, NHR7a, NHSO$_2$NH$_2$, NHSO$_2$R7a, NR7aCOR7b, NHCOR7a, NHC(NH)NH$_2$, NR7aR7b, COR7a, CSR7a, CN, COOH, COOR7a, CONH$_2$, CONHOH, CONHR7a, CONHOR7a, C(NOH)NH$_2$, CONR7aR7b, SO$_2$R7a, SO$_3$H, SO$_2$NH$_2$, SO$_2$NR7aR7b, wherein R7a and R7b are independently selected from C$_{1-6}$ alkyl, substituted C$_{1-6}$ alkyl, aryl, heteroaryl, C$_{3-8}$ cycloalkyl and heterocyclyl, or R7a and R7b, together with the heteroatom to which they are joined, can form heterocyclyl, wherein, when R7 is heteroaryl or heterocyclyl, each of these moieties may optionally be substituted with one or more oxygen atoms, and when R7 is C$_{1-6}$ alkyl, aryl, heteroaryl, heterocyclyl, C$_{1-6}$ alkoxy, aryloxy, heteroaryloxy, heterocyclyloxy, C$_{3-8}$ cycloalkyl or is a group containing one or more of these moieties, each of these moieties may optionally be substituted with one or more groups selected from halogen, R7c, C$_{1-6}$ alkyl, C$_{1-6}$ alkynyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, OH, O7c, OCOR7c, SH, SR7c, SCOR7c, NH$_2$, NO$_2$, NHR7c, NHC(NH)NH$_2$, NHSO$_2$NH$_2$, NHSO$_2$R7c, NR7cCOR7d, NHCOR7c, NR7cR7d, COR7c, CSR7c, CN, COOH, COOR7c, CONH$_2$, CONHR7c, CONHOR7c, CONHOH, C(NOH)NH$_2$, CONR7cR7d, SO$_2$R7c, SO$_3$H, SO$_2$NH$_2$, SO$_2$NR7cR7d, wherein R7c and R7d are independently selected from C$_{1-6}$ alkyl, substituted C$_{1-6}$ alkyl, aryl, heteroaryl, C$_{3-8}$ cycloalkyl and heterocyclyl, or R7c and R7d, together with the heteroatom to which they are joined, can form heterocyclyl, wherein, when the substituent of R7 is heteroaryl or heterocyclyl, each of these moieties may optionally be substituted with one or more oxygen atoms, or when the substituent of R7 is C$_{1-6}$ alkyl, C$_{1-6}$ alkynyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{3-8}$ cycloalkyl, or is a group containing one or more of these moieties, each of these moieties may optionally be substituted with one or more groups selected from halogen, aryl, heteroaryl, heterocyclyl, aryl C$_{1-6}$ alkyl, heteroaryl C$_{1-6}$ alkyl, heterocyclyl C$_{1-6}$ alkyl, C$_{1-4}$ alkoxy, R7e, C$_{1-6}$ alkyl, OH, OR7e, OCOR7e, SH, SR7e, SCOR7e, NH$_2$, NO$_2$, NHR7e, NHSO$_2$NH$_2$, NHSO$_2$R7e, NHC(NH)NH$_2$, NR7eCOR7f, NHCOR7e, NR7eR7f, COR7e, CSR7e, CN, COOH, COOR7e, CONH$_2$, CONHOH, CONHR7e, CONHOR7e, C(NOH)NH$_2$, CONR7eR7f, SO$_2$R7e, SO$_3$H, SO$_2$NH$_2$, SO$_2$NR7eR7f, wherein R7e and R7f are independently selected from C$_{1-6}$ alkyl, substituted C$_{1-6}$ alkyl, aryl, heteroaryl, C$_{3-8}$ cycloalkyl and heterocyclyl, or R7e and R7f, together with the heteroatom to which they are joined, can form heterocyclyl;

Z can be N, CH or C—R8, wherein R8 is selected from C$_{1-10}$ alkyl, aryl, heteroaryl, heterocyclyl, C$_{1-6}$ alkoxy, aryloxy, heteroaryloxy, heterocyclyloxy, R8a, halogen, OH, OR8a, SH, SR8a, OCOR8a, SCOR8a, NH$_2$, NO$_2$, NHR8a, NHSO$_2$NH$_2$, NHSO$_2$R8a, NR8aCOR8b, NHCOR8a, NHC(NH)NH$_2$, NR8aR8b, COR8a, CSR8a, CN, COOH, COOR8a, CONH$_2$, CONHOH, CONHR8a, CONHOR8a, C(NOH)NH$_2$, CONR8aR8b, SO$_2$R8a, SO$_3$H, SO$_2$NH$_2$, SO$_2$NR8aR8b, wherein R8a and R8b are independently selected from C$_{1-6}$ alkyl, substituted C$_{1-6}$ alkyl, aryl, heteroaryl, C$_{3-8}$ cycloalkyl and heterocyclyl, or R8a and R8b, together with the heteroatom to which they are joined, can form heterocyclyl, wherein, when R8 is C$_{1-6}$ alkyl, C$_{1-10}$ alkyl, aryl, heteroaryl, heterocyclyl, C$_{1-6}$ alkoxy, aryloxy, heteroaryloxy, heterocyclyloxy, C$_{3-8}$ cycloalkyl, or is a group containing one or more of these moieties, each of these moieties may optionally be substituted with one or more groups selected from halogen, R8c, C$_{1-6}$ alkyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, OH, OR8c, OCOR8c, SH, SR8c, SCOR8c, NH$_2$, NO$_2$, NHR8c, NHSO$_2$NH$_2$, NHSO$_2$R8c, NR8cCOR8d, NHCOR8c, NHC(NH)NH$_2$, NR8cR8d, COR8c, CSR8c, CN, COOH, COOR8c, CONH$_2$, CONHOH, CONHR8c, CONHOR8c, C(NOH)NH$_2$, CONR8cR8d, SO$_2$R8c, SO$_3$H, SO$_2$NH$_2$, SO$_2$NR8cR8d, wherein R8c and R8d are independently selected from C$_{1-6}$ alkyl, substituted C$_{1-6}$ alkyl, aryl, heteroaryl, C$_{3-8}$ cycloalkyl and heterocyclyl, or R8c and R8d, together with the heteroatom to which they are joined, can form heterocyclyl, wherein, when the substituent of R8 is C$_{1-6}$ alkyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{3-8}$ cycloalkyl, or is a group containing one or more of these moieties, each of these moieties may optionally be substituted with one or more groups selected from halogen, R8e, C$_{1-6}$ alkyl, OH, OR8e, OCOR8e, SH, SR8e, SCOR8e, NH$_2$, NO$_2$, NHR8e, NHSO$_2$NH$_2$, NHSO$_2$R8e, NR8eCOR8f, NHCOR8e, NHC(NH)NH$_2$, NR8eR8f, COR8e, CSR8e, CN, COOH, COOR8e, CONH$_2$, CONHOH, CONHR8e, CONHOR8e, C(NOH)NH$_2$, CONR8eR8f, SO$_2$R8e, SO$_3$H, SO$_2$NH$_2$, SO$_2$NR8eR8f, wherein R8e and R8f are independently selected from C$_{1-6}$ alkyl, substituted C$_{1-6}$ alkyl, aryl, heteroaryl, C$_{3-8}$ cycloalkyl and heterocyclyl, or R8e and R8f, together with the heteroatom to which they are joined, can form heterocyclyl;

wherein, at most, two of the atoms or groups denoted X, Y and Z can be N;

wherein, when W is N, the CONR1R2 group may be joined to W instead, with the double bonds in Formula I rearranged accordingly;
or a pharmaceutically acceptable salt or ester thereof;
provided that when R1 and R2 together form piperidinyl in compounds having Formula I, the piperidinyl is not substituted with methyl, dimethyl, ethyl, isopropyl, tert-butyl, methoxycarbonyl, trifluoromethyl, chloro, bromo or benzyl,
provided that R1 and R2 together in compounds having Formula I do not form 6,7-dimethoxy-3,4-dihydro-1H-isoquinolin-2-yl, 6-methoxy-3,4-dihydro-1H-isoquinolin-2-yl, 7-methoxy-3,4-dihydro-1H-isoquinolin-2-yl, 7-amino-3,4-dihydro-1H-isoquinolin-2-yl, 7-nitro-3,4-dihydro-1H-isoquinolin-2-yl, 3,4-dihydro-1H-isoquinolin-2-yl, 3,4-dihydro-1H-isoquinolin-1-yl, 3,4-dihydro-2H-quinolin-1-yl, pyrrolidin-1-yl, 3,6-dihydro-2H-pyridin-1-yl, 8-aza-spiro[4.5]dec-8-yl, 1,3-dihydroisoindol-2-yl, octahydroisoindol-2-yl, 1,2,6-triaza-spiro[2.5]oct-1-en-6-yl or azepan-1-yl,
provided that when R1 or R2 is unsubstituted methyl, the other of R1 or R2 is not 4-chlorobutyl, 4-azidobutyl, or 4-isothiocyanatobutyl,
provided that Ring A in compounds having Formula I does not form a pyridine, pyrimidine, substituted pyridine or substituted pyrimidine, when R1 and R2, together with the N to which they are attached, form piperidinyl, piperazinyl, substituted piperidinyl or substituted piperazinyl, and
provided that the compound is not (4-phenyl-1H-imidazol-1-yl)(4-(quinolin-2-ylmethyl)piperazin-1-yl)methanone.

The compounds of the invention have been found to modulate the activity of the enzyme fatty acid amide hydrolase (FAAH). In particular, the compounds possess inhibitory properties for this enzyme and show inhibition of FAAH in vitro at a concentration of 10 µM or less. Further, many of these compounds show strong inhibition of FAAH in vitro at a concentration of 100 nM or less and also show in vivo inhibition in central nervous system tissue and peripheral tissue. The compounds of the invention have also been found to be relatively specific for FAAH so that they show relatively low inhibition of other serine hydrolases, e.g. monoacylglycerol hydrolase. They are also relatively metabolically stable and show relatively high affinity for FAAH. This means that they may be expected to provide relatively long acting inhibition of FAAH.

Further, some compounds of the invention have been found to be selective such that they inhibit FAAH to a greater extent in central nervous system tissue compared to peripheral tissue. Other compounds have been found to be selective such that they inhibit FAAH to a greater extent in peripheral tissue compared to central nervous system tissue.

Certain compounds of the invention have been found to be particularly suitable for administration to the lungs of a subject. It has been found that the compounds can effectively inhibit FAAH in the lung whilst not passing into the bloodstream of the subject. In this way, they have a localised inhibitory effect on FAAH rather than a systemic effect.

The term '$C_{x-y}$ alkyl' as used herein refers to a linear or branched saturated hydrocarbon group containing from x to y carbon atoms. For example, $C_{1-6}$ alkyl refers to a linear or branched saturated hydrocarbon group containing from 1 to 6 carbon atoms. Examples of $C_{1-6}$ alkyl groups include methyl, ethyl, n-propyl, isopropyl, n-butyl, isobutyl, sec-butyl, tert butyl, n-pentyl, isopentyl, neopentyl and hexyl. Preferably, the hydrocarbon group is linear. The group $C_{1-10}$ alkyl is preferably $C_{1-6}$ alkyl. The term '$C_{x-y}$ alkyl' is also used to mean a linear or branched saturated hydrocarbon group containing from x to y carbon atoms and in which a terminal methyl group is further substituted, i.e. so as to render a $C_{x-y}$ alkylene group.

The term '$C_{x-y}$ alkynyl' as used herein refers to a linear or branched hydrocarbon group containing from x to y carbon atoms and at least one carbon-carbon triple bond. For example, $C_{1-6}$ alkynyl refers to a linear or branched hydrocarbon group containing from 1 to 6 carbon atoms. Examples of $C_{1-6}$ alkynyl groups include, ethynyl, methylbutynyl (e.g. 3-methyl-1-butynyl), 1,3-butadiynyl and 1,3,5-hexatriynyl.

The term 'aryl' as used herein refers to a $C_{6-12}$ monocyclic or bicyclic hydrocarbon ring wherein at least one ring is aromatic. Examples of such groups include phenyl, naphthalenyl and tetrahydronaphthalenyl.

The term 'heteroaryl' as used herein refers to a 5-6 membered monocyclic aromatic or a fused 8-10 membered bicyclic aromatic ring which monocyclic or bicyclic ring contains 1 to 4 heteroatoms selected from oxygen, nitrogen and sulphur. Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazinyl, tetrazinyl and the like. Examples of such bicyclic aromatic rings include quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridyl, furopyridyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and imidazopyridyl.

The term 'heteroaryl substituted with one or more oxygen atoms' refers to a heteroaryl ring which has one or more oxygen atoms bonded to the ring. It does not mean that the heteroaryl ring contains one or more oxygen atoms as ring atoms, although in some embodiments, this may be the case. Preferably, the one or more oxygen atoms is bonded to a nitrogen heteroatom in the heteroaryl ring. A heteroaryl substituted with an oxygen atom may contain an N-oxide. An example of a heteroaryl substituted with one or more oxygen atoms is 1-oxidopyridyl in which the pyridyl nitrogen is oxidised.

The term 'heterocyclyl' refers to a 3-8 (preferably 4-8 and, more preferably, 4-7) membered monocyclic ring or a fused 8-12 membered bicyclic ring which may be saturated or partially unsaturated, which monocyclic or bicyclic ring contains 1 to 4 heteroatoms selected from oxygen, nitrogen, silicon or sulphur. Examples of such monocyclic rings include oxaziridinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl and azepanyl. Examples of such bicyclic rings include indolinyl, isoindolinyl, benzopyranyl, quinuclidinyl, 2,3,4,5-tetrahydro-1H-3-benzazepine, 4-(benzo[d][1,3]dioxol-5-ylmethyl)piperazin-1-yl, and, tetrahydroisoquinolinyl.

The term 'heterocyclyl substituted with one or more oxygen atoms' refers to a heterocyclyl ring which has one or more oxygen atoms bonded to the ring. It does not mean that the heterocyclyl ring contains one or more oxygen atoms as ring atoms, although in some embodiments, this may be the case. Preferably, the one or more oxygen atoms is bonded to a heteroatom, such as nitrogen or sulphur, in the heterocyclyl ring. An example of a heterocyclyl substituted with one or more oxygen atoms is 1,1-dioxido-1,3-thiazolidinyl.

The terms 'bicyclic ring' and 'fused' in the context of a bicyclic ring refers to two rings which are joined together across a bond between two atoms (e.g. naphthalene), across a sequence of atoms to form a bridge (e.g. quinuclidine) or together at a single atom to form a spiro compound (e.g. 1,4-dioxa-8-aza-spiro[4.5]decane and N,3,3-dimethyl-1,5-dioxaspirol[5.5]undecan-9-yl).

The term '$C_{x-y}$ cycloalkyl' as used herein refers to a saturated hydrocarbon ring of x to y carbon atoms which can be mono, bi or tricyclic. For example, $C_{3-10}$ cycloalkyl refers to a saturated mono, bi or tricyclic hydrocarbon ring of 3 to 10 carbon atoms. Examples of $C_{3-10}$ cycloalkyl groups include cyclopropyl, cyclobutyl, cyclopentyl, cyclohexyl, cycloheptyl, cyclooctyl and adamantyl.

The term 'aryl $C_{x-y}$ alkyl' as used herein refers to an aryl group as defined above attached to a $C_{x-y}$ alkyl as defined above. For example, aryl $C_{1-6}$ alkyl refers to an aryl group attached to a linear or branched saturated hydrocarbon group containing from 1 to 6 carbon atoms. Examples of aryl $C_{1-6}$ alkyl groups include benzyl, phenylethyl, phenylpropyl, phenylbutyl, phenylpentyl and phenylhexyl.

The terms 'heteroaryl $C_{x-y}$ alkyl', 'heterocyclyl $C_{x-y}$ alkyl' and '$C_{x-y}$ cycloalkyl $C_{x-y}$ alkyl' as used herein refers to a heteroaryl, heterocyclyl or $C_{x-y}$ cycloalkyl group as defined above attached to a $C_{x-y}$ alkyl as defined above.

The term '$C_{x-y}$ alkoxy' as used herein refers to an —O—$C_{x-y}$ alkyl group wherein $C_{x-y}$ alkyl is as defined above. Examples of such groups include methoxy, ethoxy, propoxy, butoxy, pentoxy and hexoxy.

The term 'aryloxy' as used herein refers to an —O-aryl group. Examples of such groups include phenoxy. The terms 'heteroaryloxy' and 'heterocyclyloxy' as used herein refer to an —O-heteroaryl and —O-heterocyclyl group respectively.

The term 'halogen' as used herein refers to a fluorine, chlorine, bromine or iodine atom, unless otherwise specified.

The term '$C_{x-y}$ alkylamino' as used herein refers to a secondary amine group (—NH(R)) of which the R group is selected from a linear or branched saturated hydrocarbon group containing from x to y carbon atoms. Examples of $C_{x-y}$ alkylamino groups include methylamino, ethylamino and propylamino.

The term '$C_{x-y}$ dialkylamino' as used herein refers to a tertiary amine group (—NR(R*)) of which the R and R* groups are each independently selected from a linear or branched saturated hydrocarbon group containing from x to y carbon atoms. Examples of $C_{x-y}$ dialkylamino groups include dimethylamino, methylethylamino and diethylamino.

The term 'substituted $C_{1-6}$ alkyl' used herein with reference to the identity of the various groups identified as R (for example, in the phrase 'wherein R8e and R8f are independently selected from $C_{1-6}$ alkyl, substituted $C_{1-6}$ alkyl, aryl, heteroaryl, $C_{3-8}$ cycloalkyl and heterocyclyl') means that the particular R group (e.g. R1a, R2c, R4d, R5e, etc.) can be substituted with one or more groups selected from R', halogen, OH, OR', SH, SR', OCOR', SCOR', $NH_2$, $NO_2$, NHR', $NHSO_2NH_2$, $NHSO_2R'$, NR'COR'', NHC(NH)$NH_2$, NHCOR', NR'R'', COR', CSR', CN, COOH, COOR', $CONH_2$, CONHOH, CONHR', CONR'R'', CONHOR', C(NOH)$NH_2$, $SO_2R'$, $SO_3H$, $SO_2NH_2$, $SO_2NR'R''$, wherein R' and R'' are independently selected from $C_{1-6}$ alkyl, aryl, heteroaryl, $C_{3-8}$ cycloalkyl and heterocyclyl, or R' and R'', together with the heteroatom to which they are joined, can form heterocyclyl.

'Pharmaceutically acceptable salts' of compounds of the present invention include salts with inorganic bases, salts with organic bases, salts with inorganic acids, salts with organic acids and salts with basic or acidic amino acids. Salts with acids may, in particular, be employed in some instances. Exemplary salts include hydrochloride salt, acetate salt, trifluoroacetate salt, methanesulfonate salt, 2-hydroxypropane-1,2,3-tricarboxylate salt, (2R,3R)-2,3-dihydroxysuccinate salt, phosphate salt and oxalate salt. The compound of the present invention may be in either solvate (e.g. hydrate) or non-solvate (e.g. non-hydrate) form. When in a solvate form, additional solvents may be alcohols such as propan-2-ol.

'Pharmaceutically acceptable esters' of compounds of the invention are derivatives in which one or more carboxyl (i.e. —C(O)OH) groups of the said compounds are modified by reaction with an alcoholic moiety U—OH so as to yield —C(O)OU groups, wherein U may be $C_{1-18}$ alkyl (e.g. $C_{1-6}$ alkyl), aryl, heteroaryl, $C_{3-8}$ cycloalkyl or combinations thereof.

General methods for the preparation of salts and esters are well known to the person skilled in the art. Pharmaceutical acceptability of salts and esters will depend on a variety of factors, including formulation processing characteristics and in vivo behaviour, and the skilled person would readily be able to assess such factors having regard to the present disclosure.

Where compounds of the invention exist in different enantiomeric and/or diastereoisomeric forms (including geometric isomerism about a double bond), these compounds may be prepared as isomeric mixtures or racemates, although the invention relates to all such enantiomers or isomers, whether present in an optically pure form or as mixtures with other isomers. Individual enantiomers or isomers may be obtained by methods known in the art, such as optical resolution of products or intermediates (for example chiral chromatographic separation (e.g. chiral HPLC)), or an enantiomeric synthesis approach. Similarly, where compounds of the invention may exist as alternative tautomeric forms (e.g. keto/enol, amide/imidic acid), the invention relates to the individual tautomers in isolation, and to mixtures of the tautomers in all proportions.

In compounds of Formula II, zero, one or two of the atoms or groups denoted X, Y and Z can be N.

In a particular embodiment, the compound of the invention has a formula selected from Formula I or Formula II:

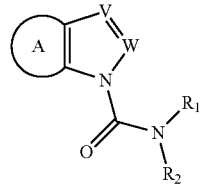

Formula I

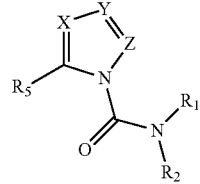

Formula II wherein:
R1 and R2 can each be independently selected from H, $C_{1-20}$ alkyl, alkoxy, aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which, with the exception of H, may optionally be substituted with one or more groups selected from halogen, $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, amino, $C_{1-6}$ alkylamino and $C_{1-6}$ dialkylamino, with the exception that R1 and R2 are not both H, or R1 and R2, together with the N to which they are attached, can form a heteroaryl or heterocyclyl group, each of which may optionally be substituted with one or more groups selected from hydroxy, aryl, heteroaryl, heterocyclyl, $C_{3-8}$ cycloalkyl, $C_{1-6}$ alkyl, aryl $C_{1-6}$ alkyl, heteroaryl $C_{1-6}$ alkyl, heterocyclyl $C_{1-6}$ alkyl, $C_{3-8}$ cycloalkyl $C_{1-6}$ alkyl, $C_{1-6}$ alkoxy, aryloxy, heteroaryloxy, and heterocyclyloxy, each of which may optionally be substituted with a group selected from halogen, hydroxyl, $C_{1-4}$ alkyl, aryl, heteroaryl, $C_{1-4}$ alkoxy, aryloxy, heteroaryloxy, aryl $C_{1-4}$ alkoxy and heteroaryl $C_{1-4}$ alkoxy, each of which, with the exception of halogen and hydroxyl, may optionally be substituted with $C_{1-4}$ alkoxy;

Ring A is selected from aryl, heteroaryl and heterocyclyl moiety, each of which may optionally be substituted with one or more groups selected from halogen, hydroxyl, aryl, heteroaryl, heterocyclyl, $C_{1-6}$ alkoxy, aryloxy, heteroaryloxy and heterocyclyloxy, each of which, with the exception of halogen and hydroxyl, may optionally be substituted with halogen, cyano, amide and carboxylic acid;

V can be N, CH or C—R3, wherein R3 is halogen, aryl, heteroaryl, heterocyclyl or $C_{3-8}$ cycloalkyl, each of which, with the exception of halogen, may optionally be substituted with halogen;

W can be N, CH or C—R4, wherein R4 is $C_{1-10}$ alkyl, aryl, heteroaryl, heterocyclyl or $C_{3-8}$ cycloalkyl, each of which may optionally be substituted with halogen;

R5 is selected from H, $C_{1-6}$ alkyl, aryl, heteroaryl, heterocyclyl and $C_{3-8}$ cycloalkyl, each of which, with the exception of H, may optionally be substituted with halogen;

X can be N, CH or C—R6, wherein R6 is selected from $C_{1-6}$ alkyl, aryl, heteroaryl and heterocyclyl, each of which, with the exception of H, may optionally be substituted with one or more groups selected from halogen, hydroxyl, amine, amide, cyano, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy and heterocyclyl $C_{1-6}$ alkoxy;

Y can be N, CH or C—R7, wherein R7 is selected from $C_{1-6}$ alkyl, aryl, heteroaryl and heterocyclyl, each of which, with the exception of H, may optionally be substituted with one or more groups selected from halogen, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy and heterocyclyl $C_{1-6}$ alkoxy, each of which may optionally be substituted with $C_{1-4}$ alkyl, cyano, amine, amide, halogen, aryl, heteroaryl, heterocyclyl, aryl $C_{1-6}$ alkyl, heteroaryl $C_{1-6}$ alkyl and heterocyclyl $C_{1-6}$ alkyl;

Z can be N, CH or C—R8, wherein R8 is selected from $C_{1-10}$ alkyl, aryl, heteroaryl, heterocyclyl or $C_{3-8}$ cycloalkyl, each of which may optionally be substituted with halogen;

or a pharmaceutically acceptable salt or ester thereof; provided that when R1 and R2 together form piperidinyl in compounds having Formula I, the piperidinyl is not substituted with methyl, dimethyl, ethyl, isopropyl, tert-butyl, trifluoromethyl, chloro, bromo or benzyl.

In accordance with another embodiment of the invention, there is provided a compound having Formula I or Formula II:

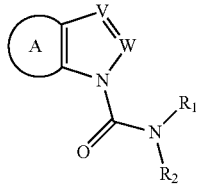

Formula I

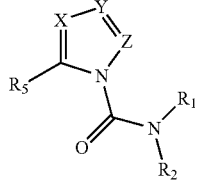

Formula II wherein:

R1 and R2 can each be independently selected from H, $C_{1-20}$ alkyl, alkoxy, aryl, heteroaryl, partially or fully saturated heterocyclyl, $C_{3-10}$ cycloalkyl, aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, R1a, halogen, OH, OR1a, SH, SR1a, OCOR1a, SCOR1a, $NH_2$, NHR1a, NR1aR1b, COR1a, CSR1a, CN, COOH, COOR1a, $CONH_2$, $SO_2$R1a, $SO_3H$, $SO_2NH_2$, CONR1aR1b, $SO_2$NR1aR1b, wherein R1a and R1b are independently selected from $C_{1-6}$ alkyl, substituted $C_{1-6}$ alkyl, $C_{3-8}$ cycloalkyl and heterocyclyl, and R1a and R1b, together with the adjacent heteroatom, can form heterocyclyl, wherein, when R1 or R2 is $C_{1-20}$ alkyl, alkoxy, aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, $C_{1-6}$ alkyl, $C_{3-8}$ cycloalkyl or is a group containing one or more of these moieties, each of these moieties may optionally be substituted with R1c, halogen, $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{1-6}$ alkylamino, $C_{1-6}$ dialkylamino, $C_{1-10}$ alkyl, OH, OR1c, OCOR1c, SH, SR1c, SCOR1c, $NH_2$, NHR1c, NR1cR1d, COR1c, CSR1c, CN, COOH, COOR1c, $CONH_2$, $SO_2$R1c, $SO_3H$, $SO_2NH_2$, CONR1cR1d, $SO_2$NR1cR1d, wherein R1c and R1d are independently selected from $C_{1-6}$ alkyl, substituted $C_{1-6}$ alkyl, $C_{3-8}$ cycloalkyl and heterocyclyl, and R1c and R1d, together with the adjacent heteroatom, can form heterocyclyl, wherein, when the substituent of R1 or R2 is $C_{1-10}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{1-6}$ alkylamino, $C_{1-6}$ dialkylamino, $C_{1-6}$ alkyl, $C_{3-8}$ cycloalkyl or is a group containing one or more of these moieties, each of these moieties may optionally be substituted with R1e, $C_{1-10}$ alkyl, OH, OR1e, OCOR1e, SH, SR1e, SCOR1e, $NH_2$, NHR1e, NR1eR1f, COR1e, CSR1e, CN, COOH, COOR1e, $CONH_2$, $SO_2$R1e, $SO_3H$, $SO_2NH_2$, CONR1eR1f, $SO_2$NR1eR1f, wherein R1e and R1f are independently selected from $C_{1-6}$ alkyl, substituted $C_{1-6}$ alkyl, $C_{3-8}$ cycloalkyl and heterocyclyl, and R1e and R1f, together with the adjacent heteroatom, can form heterocyclyl, with the exception that R1 and R2 are not both H, or R1 and R2, together with the N to which they are attached, can form a heteroaryl or heterocyclyl group, each of which may optionally be substituted with one or more groups selected from hydroxy, aryl, heteroaryl, partially or fully heterocyclyl, $C_{3-8}$ cycloalkyl, $C_{1-6}$ alkyl, aryl $C_{1-6}$ alkyl, heteroaryl $C_{1-6}$ alkyl, heterocyclyl $C_{1-6}$ alkyl, $C_{3-8}$ cycloalkyl $C_{1-6}$ alkyl, $C_{1-6}$ alkoxy, aryloxy, heteroaryloxy, heterocyclyloxy, R2a, halogen, OH, OR2a, SH, SR2a, OCOR2a, SCOR2a, $NH_2$, NHR2a, NR2aR2b, COR2a, CSR2a, CN, COOH, COOR2a, $CONH_2$, $SO_2R2a$, $SO_3H$, $SO_2NH_2$, CONR2aR2b, $SO_2NR2aR2b$, wherein R2a and R2b are independently selected from $C_{1-6}$ alkyl, substituted $C_{1-6}$ alkyl, $C_{3-8}$ cycloalkyl and heterocyclyl, and R2a and R2b, together with the adjacent heteroatom, can form heterocyclyl, wherein, when the substituent of the heteroaryl or heterocyclyl formed by R1 and R2 together is aryl, heteroaryl, heterocyclyl, $C_{3-8}$ cycloalkyl, $C_{1-6}$ alkyl, aryl $C_{1-6}$ alkyl, heteroaryl $C_{1-6}$ alkyl, heterocyclyl $C_{1-6}$ alkyl, $C_{3-8}$ cycloalkyl $C_{1-6}$ alkyl, $C_{1-6}$ alkoxy, aryloxy, heteroaryloxy, heterocyclyloxy, or a group containing one or more of these moieties, each of these moieties may optionally be substituted with a group selected from halogen, hydroxyl, $C_{1-6}$ alkyl, aryl, heteroaryl, heterocyclyl, $C_{3-8}$ cycloalkyl, $C_{1-4}$ alkoxy, aryloxy, heteroaryloxy, heterocyclyloxy, $C_{3-8}$ cycloalkyloxy, aryl $C_{1-4}$ alkoxy, heteroaryl $C_{1-4}$ alkoxy, heterocyclyl $C_{1-4}$ alkoxy, $C_{3-8}$ cycloalkyl $C_{1-4}$ alkoxy, R2c, OR2c, SH, SR2c, OCOR2c, SCOR2c, $NH_2$, NHR2c, NR2cR2d, COR2c, CSR2c, CN, COOH, COOR2c, $CONH_2$, $SO_2R2c$, $SO_3H$, $SO_2NH_2$, CONR2cR2d, $SO_2NR2cR2d$, wherein R2c and R2d are independently selected from $C_{1-6}$ alkyl, substituted $C_{1-6}$ alkyl, $C_{3-8}$ cycloalkyl and heterocyclyl, and R2c and R2d, together with the adjacent heteroatom, can form heterocyclyl, wherein, when the substituent of the substituent of the heteroaryl or heterocyclyl of R1 and R2 together is $C_{1-4}$ alkyl, aryl, heteroaryl, heterocyclyl, $C_{3-8}$ cycloalkyl, $C_{1-4}$ alkoxy, aryloxy, heteroaryloxy, heterocyclyloxy, $C_{3-8}$ cycloalkyloxy, aryl $C_{1-4}$ alkoxy, heteroaryl $C_{1-4}$ alkoxy, heterocyclyl $C_{1-4}$ alkoxy, $C_{3-8}$ cycloalkyl $C_{1-4}$ alkoxy, or is a group containing one or more of these moieties, each of these moieties may optionally be substituted with $C_{1-4}$ alkoxy, R2e, halogen, OH, OR2e, SH, SR2e, OCOR2e, SCOR2e, $NH_2$, NHR2e, NR2eR2f, COR2e, CSR2e, CN, COOH, COOR2e, $CONH_2$, $SO_2R2e$, $SO_3H$, $SO_2NH_2$, CONR2eR2f, $SO_2NR2eR2f$, wherein R2e and R2f are independently selected from $C_{1-6}$ alkyl, substituted $C_{1-6}$ alkyl, $C_{3-8}$ cycloalkyl and heterocyclyl, and R2e and R2f, together with the adjacent heteroatom, can form heterocyclyl;

Ring A is selected from aryl, heteroaryl and heterocyclyl moiety, each of which may optionally be substituted with one or more groups selected from halogen, $C_{1-6}$ alkyl, hydroxyl, aryl, heteroaryl, heterocyclyl, $C_{1-6}$ alkoxy, aryloxy, heteroaryloxy, heterocyclyloxy, Ra, $C_{1-10}$ alkyl, OH, ORa, OCORa, SH, SRa, SCORa, $NH_2$, NHRa, NRaRb, CORa, CSRa, CN, COOH, COORa, $CONH_2$, $SO_2Ra$, $SO_3H$, $SO_2NH_2$, CONRaRb, $SO_2NRaRb$, wherein Ra and Rb are independently selected from $C_{1-6}$ alkyl, substituted $C_{1-6}$ alkyl, $C_{3-8}$ cycloalkyl and heterocyclyl, and Ra and Rb, together with the adjacent heteroatom, can form heterocyclyl, wherein, when Ring A is substituted with $C_{1-6}$ alkyl, aryl, heteroaryl, heterocyclyl, $C_{1-6}$ alkoxy, aryloxy, heteroaryloxy, heterocyclyloxy, $C_{1-10}$ alkyl, $C_{3-8}$ cycloalkyl or is substituted with a group containing one or more of these moieties, each of these moieties may optionally be substituted with Rc, $C_{1-10}$ alkyl, OH, ORc, OCORc, SH, SRc, SCORc, $NH_2$, NHRc, NRcRd, CORc, CSRc, CN, COOH, COORc, $CONH_2$, $SO_2Rc$, $SO_3H$, $SO_2NH_2$, CONRcRd, $SO_2NRcRd$, wherein Rc and Rd are independently selected from $C_{1-6}$ alkyl, substituted $C_{1-6}$ alkyl, $C_{3-8}$ cycloalkyl and heterocyclyl, and Rc and Rd, together with the adjacent heteroatom, can form heterocyclyl;

V can be N, CH or C—R3, wherein R3 is halogen, $C_{1-10}$ alkyl, aryl, heteroaryl, heterocyclyl, $C_{3-8}$ cycloalkyl, $C_{1-6}$ alkoxy, aryloxy, heteroaryloxy, heterocyclyloxy, R3a, OH, OR3a, SH, SR3a, OCOR3a, SCOR3a, $NH_2$, NHR3a, NR3aR3b, COR3a, CSR3a, CN, COOH, COOR3a, $CONH_2$, $SO_2R3a$, $SO_3H$, $SO_2NH_2$, CONR3aR3b, $SO_2NR3aR3b$, wherein R3a and R3b are independently selected from $C_{1-6}$ alkyl, substituted $C_{1-6}$ alkyl, $C_{3-8}$ cycloalkyl and heterocyclyl, and R3a and R3b, together with the adjacent heteroatom, can form heterocyclyl, wherein, when R3 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with aryl, heteroaryl, heterocyclyl, $C_{1-6}$ alkoxy, aryloxy, heteroaryloxy, heterocyclyloxy, R3c, $C_{1-10}$ alkyl, OH, OR3c, OCOR3c, SH, SR3c, SCOR3c, $NH_2$, NHR3c, NR3cR3d, COR3c, CSR3c, CN, COOH, COOR3c, $CONH_2$, $SO_2R3c$, $SO_3H$, $SO_2NH_2$, CONR3cR3d, $SO_2NR3cR3d$, wherein R3c and R3d are independently selected from $C_{1-6}$ alkyl, substituted $C_{1-6}$ alkyl, $C_{3-8}$ cycloalkyl and heterocyclyl, and R3c and R3d, together with the adjacent heteroatom, can form heterocyclyl, wherein, when the substituent of R3 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with R3e, $C_{1-10}$ alkyl, OH, OR3e, OCOR3e, SH, SR3e, SCOR3e, $NH_2$, NHR3e, NR3eR3f, COR3e, CSR3e, CN, COOH, COOR3e, $CONH_2$, $SO_2R3e$, $SO_3H$, $SO_2NH_2$, CONR3eR3f, $SO_2NR3eR3f$, wherein R3e and R3f are independently selected from $C_{1-6}$ alkyl, substituted $C_{1-6}$ alkyl, $C_{3-8}$ cycloalkyl and heterocyclyl, and R3e and R3f, together with the adjacent heteroatom, can form heterocyclyl;

W can be N, CH or C—R4, wherein R4 is halogen, $C_{1-10}$ alkyl, aryl, heteroaryl, heterocyclyl, $C_{1-6}$ alkoxy, aryloxy, heteroaryloxy, heterocyclyloxy, $C_{3-8}$ cycloalkyl, R4a, OH, OR4a, SH, SR4a, OCOR4a, SCOR4a, $NH_2$, NHR4a, NR4aR4b, COR4a, CSR4a, CN, COOH, COOR4a, $CONH_2$, $SO_2R4a$, $SO_3H$, $SO_2NH_2$, CONR4aR4b, $SO_2NR4aR4b$, wherein R4a and R4b are independently selected from $C_{1-6}$ alkyl, substituted $C_{1-6}$ alkyl, $C_{3-8}$ cycloalkyl and heterocyclyl, and R4a and R4b, together with the adjacent heteroatom, can form heterocyclyl, wherein, when R4 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with aryl, heteroaryl, heterocyclyl, $C_{1-6}$ alkoxy, aryloxy, heteroaryloxy, heterocyclyloxy, R4c, $C_{1-10}$ alkyl, OH, OR4c, OCOR4c, SH, SR4c, SCOR4c, $NH_2$, NHR4c, NR4cR4d, COR4c, CSR4c, CN, COOH, COOR4c, $CONH_2$, $SO_2R4c$, $SO_3H$, $SO_2NH_2$, CONR4cR4d, $SO_2NR4cR4d$, wherein R4c and R4d are independently selected from $C_{1-6}$ alkyl, substituted $C_{1-6}$ alkyl, $C_{3-8}$ cycloalkyl and heterocyclyl, and R4c and R4d, together with the adjacent heteroatom, can form heterocyclyl, wherein, when the substituent of R4 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with R4e, $C_{1-10}$ alkyl, OH, OR4e, OCOR4e, SH, SR4e, SCOR4e, $NH_2$, NHR4e, NR4eR4f, COR4e, CSR4e, CN, COOH, COOR4e, $CONH_2$, $SO_2R4e$, $SO_3H$, $SO_2NH_2$, CONR4eR4f, $SO_2NR4eR4f$, wherein R4e and R4f are independently selected from $C_{1-6}$ alkyl, substituted $C_{1-6}$ alkyl, $C_{3-8}$ cycloalkyl and heterocyclyl, and R4e and R4f, together with the adjacent heteroatom, can form heterocyclyl;

R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, NHR5a, NR5aR5b, COR5a, CSR5a, CN, COOH, COOR5a, $CONH_2$, $SO_2R5a$, $SO_3H$, $SO_2NH_2$, CONR5aR5b, $SO_2NR5aR5b$, wherein R5a and R5b are independently selected from $C_{1-6}$ alkyl, substituted $C_{1-6}$ alkyl, $C_{3-8}$ cycloalkyl and heterocyclyl, and R5a and R5b, together with the adjacent heteroatom, can form heterocyclyl, wherein, when R5 is $C_{1-6}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with aryl, heteroaryl, heterocyclyl, $C_{1-6}$ alkoxy, aryloxy, heteroaryloxy, heterocyclyloxy, R5c, $C_{1-6}$ alkyl, OH, OR5c, OCOR5c, SH, SR5c, SCOR5c, $NH_2$, NHR5c, NR5cR5d, COR5c, CSR5c, CN, COOH, COOR5c, $CONH_2$, $SO_2R5c$, $SO_3H$, $SO_2NH_2$, CONR5cR5d, $SO_2NR5cR5d$, wherein R5c and R5d are independently selected from $C_{1-6}$ alkyl, substituted $C_{1-6}$ alkyl, $C_{3-8}$ cycloalkyl and heterocyclyl, and R5c and R5d, together with the adjacent heteroatom, can form heterocyclyl, wherein, when the substituent of R5 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with R5e, $C_{1-6}$ alkyl, OH, OR5e, OCOR5e, SH, SR5e, SCOR5e, $NH_2$, NHR5e, NR5eR5f, COR5e, CSR5e, CN, COOH, COOR5e, $CONH_2$, $SO_2R5e$, $SO_3H$, $SO_2NH_2$, CONR5eR5f, $SO_2NR5eR5f$, wherein R5e and R5f are independently selected from $C_{1-6}$ alkyl, substituted $C_{1-6}$ alkyl, $C_{3-8}$ cycloalkyl and heterocyclyl, and R5e and R5f, together with the adjacent heteroatom, can form heterocyclyl;

X can be N, CH or C—R6, wherein R6 is selected from $C_{1-6}$ alkyl, aryl, heteroaryl, heterocyclyl, $C_{1-6}$ alkoxy, aryloxy, heteroaryloxy, heterocyclyloxy, R6a, halogen, OH, OR6a, SH, SR6a, OCOR6a, SCOR6a, $NH_2$, NHR6a, NR6aR6b, COR6a, CSR6a, CN, COOH, COOR6a, $CONH_2$, $SO_2R6a$, $SO_3H$, $SO_2NH_2$, CONR6aR6b, $SO_2NR6aR6b$, wherein R6a and R6b are independently selected from $C_{1-6}$ alkyl, substituted $C_{1-6}$ alkyl, $C_{3-8}$ cycloalkyl and heterocyclyl, and R6a and R6b, together with the adjacent heteroatom, can form heterocyclyl, wherein, when R6 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with R6c, $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, OR6c, OCOR6c, SH, SR6c, SCOR6c, $NH_2$, NHR6c, NR6cR6d, COR6c, CSR6c, CN, COOH, COOR6c, $CONH_2$, $SO_2R6c$, $SO_3H$, $SO_2NH_2$, CONR6cR6d, $SO_2NR6cR6d$, wherein R6c and R6d are independently selected from $C_{1-6}$ alkyl, substituted $C_{1-6}$ alkyl, $C_{3-8}$ cycloalkyl and heterocyclyl, and R6c and R6d, together with the adjacent heteroatom, can form heterocyclyl, wherein, when the substituent of R6 is $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{3-8}$ cycloalkyl, or is a group containing one or more of these moieties, each of these moieties may optionally be substituted with R6e, $C_{1-6}$ alkyl, OH, OR6e, OCOR6e, SH, SR6e, SCOR6e, $NH_2$, NHR6e, NR6eR6f, COR6e, CSR6e, CN, COOH, COOR6e, $CONH_2$, $SO_2R6e$, $SO_3H$, $SO_2NH_2$, CONR6eR6f, $SO_2NR6eR6f$, wherein R6e and R6f are independently selected from $C_{1-6}$ alkyl, substituted $C_{1-6}$ alkyl, $C_{3-8}$ cycloalkyl and heterocyclyl, and R6e and R6f, together with the adjacent heteroatom, can form heterocyclyl;

Y can be N, CH or C—R7, wherein R7 is selected from $C_{1-6}$ alkyl, aryl, heteroaryl, heterocyclyl, $C_{1-6}$ alkoxy, aryloxy, heteroaryloxy, heterocyclyloxy, R7a, halogen, OH, OR7a, SH, SR7a, OCOR7a, SCOR7a, $NH_2$, NHR7a, NR7aR7b, COR7a, CSR7a, CN, COOH, COOR7a, $CONH_2$, $SO_2R7a$, $SO_3H$, $SO_2NH_2$, CONR7aR7b, $SO_2NR7aR7b$, wherein R7a and R7b are independently selected from $C_{1-6}$ alkyl, substituted $C_{1-6}$ alkyl, $C_{3-8}$ cycloalkyl and heterocyclyl, and R7a and R7b, together with the adjacent heteroatom, can form heterocyclyl, wherein, when R7 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl or is a group containing one or more of these moieties, each of these moieties may optionally be substituted with R7c, $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, O7c, OCOR7c, SH, SR7c, SCOR7c, $NH_2$, NHR7c, NR7cR7d, COR7c, CSR7c, CN, COOH, COOR7c, $CONH_2$, $SO_2R7c$, $SO_3H$, $SO_2NH_2$, CONR7cR7d, $SO_2NR7cR7d$, wherein R7c and R7d are independently selected from $C_{1-6}$ alkyl, substituted $C_{1-6}$ alkyl, $C_{3-8}$ cycloalkyl and heterocyclyl, and R7c and R7d, together with the adjacent heteroatom, can form heterocyclyl, wherein, when the substituent of R7 is $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{3-8}$ cycloalkyl, or is a group containing one or more of these moieties, each of these moieties may optionally be substituted with R7e, $C_{1-6}$ alkyl, OH, OR7e, OCOR7e, SH, SR7e, SCOR7e, $NH_2$, NHR7e, NR7eR7f, COR7e, CSR7e, CN, COOH, COOR7e, $CONH_2$, $SO_2R7e$, $SO_3H$, $SO_2NH_2$, CONR7eR7f, $SO_2NR7eR7f$, wherein R7e and R7f are independently selected from $C_{1-6}$ alkyl, substituted $C_{1-6}$ alkyl, $C_{3-8}$ cycloalkyl and heterocyclyl, and R7e and R7f, together with the adjacent heteroatom, can form heterocyclyl;

Z can be N, CH or C—R8, wherein R8 is selected from $C_{1-6}$ alkyl, aryl, heteroaryl, heterocyclyl, $C_{1-6}$ alkoxy, aryloxy, heteroaryloxy, heterocyclyloxy, R8a, halogen, OH, OR8a, SH, SR8a, OCOR8a, SCOR8a, $NH_2$, NHR8a, NR8aR8b, COR8a, CSR8a, CN, COOH, COOR8a, $CONH_2$, $SO_2R8a$, $SO_3H$, $SO_2NH_2$, CONR8aR8b, $SO_2NR8aR8b$, wherein R8a and R8b are independently selected from $C_{1-6}$ alkyl, substituted $C_{1-6}$ alkyl, $C_{3-8}$ cycloalkyl and heterocyclyl, and R8a and R8b, together with the adjacent heteroatom, can form heterocyclyl, wherein, when R8 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with R8c, $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, OR8c, OCOR8c, SH, SR8c, SCOR8c, $NH_2$, NHR8c, NR8cR8d, COR8c, CSR8c, CN, COOH, COOR8c, $CONH_2$, SO$_2$R8c, SO$_3$H, SO$_2$NH$_2$, CONR8cR8d, SO$_2$NR8cR8d, wherein R8c and R8d are independently selected from C$_{1-6}$ alkyl, substituted C$_{1-6}$ alkyl, C$_{3-8}$ cycloalkyl and heterocyclyl, and R8c and R8d, together with the adjacent heteroatom, can form heterocyclyl, wherein, when the substituent of R8 is C$_{1-6}$ alkyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{3-8}$ cycloalkyl, or is a group containing one or more of these moieties, each of these moieties may optionally be substituted with R8e, C$_{1-6}$ alkyl, OH, OR8e, OCOR8e, SH, SR8e, SCOR8e, NH$_2$, NHR8e, NR8eR8f, COR8e, CSR8e, CN, COOH, COOR8e, CONH$_2$, SO$_2$R8e, SO$_3$H, SO$_2$NH$_2$, CONR8eR8f, SO$_2$NR8eR8f, wherein R8e and R8f are independently selected from C$_{1-6}$ alkyl, substituted C$_{1-6}$ alkyl, C$_{3-8}$ cycloalkyl and heterocyclyl, and R8e and R8f, together with the adjacent heteroatom, can form heterocyclyl;

or a pharmaceutically acceptable salt or ester thereof;

provided that when R1 and R2 together form piperidinyl in compounds having Formula I, the piperidinyl is not substituted with methyl, dimethyl, ethyl, isopropyl, tert-butyl, trifluoromethyl, chloro, bromo or benzyl, provided that R1 and R2 together in compounds having Formula I do not form 6,7-dimethoxy-3,4-dihydro-1H-isoquinolin-2-yl, 6-methoxy-3,4-dihydro-1H-isoquinolin-2-yl, 7-methoxy-3,4-dihydro-1H-isoquinolin-2-yl, 7-amino-3,4-dihydro-1H-isoquinolin-2-yl, 7-nitro-3,4-dihydro-1H-isoquinolin-2-yl, 3,4-dihydro-1H-isoquinolin-2-yl, 3,4-dihydro-1H-isoquinolin-1-yl, 3,4-dihydro-2H-quinolin-1-yl, pyrrolidin-1-yl, 3,6-dihydro-2H-pyridin-1-yl, 8-aza-spiro[4.5]dec-8-yl, 1,3-dihydroisoindol-2-yl, octahydroisoindol-2-yl, 1,2,6-triaza-spiro[2.5]oct-1-en-6-yl or azepan-1-yl, and provided that Ring A in compounds having Formula I does not form a pyridine, pyrazine, substituted pyridine or substituted pyrazine, when R1 and R2, together with the N to which they are attached, form piperidinyl, piperazinyl, substituted piperidinyl or substituted piperazinyl.

In accordance with a further embodiment of the invention, there is provided a compound having Formula I or Formula II:

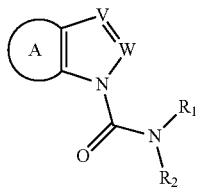

Formula I

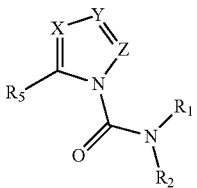

Formula II wherein:

R1 and R2 can each be independently selected from H, C$_{1-20}$ alkyl, C$_{1-6}$ alkoxy, aryl, heteroaryl, partially or fully saturated heterocyclyl, C$_{3-10}$ cycloalkyl, aryl C$_{1-6}$ alkyl, heteroaryl C$_{1-6}$ alkyl, heterocyclyl C$_{1-6}$ alkyl, C$_{3-10}$ cycloalkyl C$_{1-6}$ alkyl, R1a, halogen, OH, OR1a, SH, SR1a, OCOR1a, SCOR1a, NH$_2$, NHR1a, NR1aR1b, COR1a, CSR1a, CN, COOH, COOR1a, CONH$_2$, SO$_2$R1a, SO$_3$H, SO$_2$NH$_2$, CONR1aR1b, SO$_2$NR1aR1b, wherein R1a and R1b are independently selected from C$_{1-6}$ alkyl, substituted C$_{1-6}$ alkyl, aryl, heteroaryl, C$_{3-8}$ cycloalkyl and heterocyclyl, or R1a and R1b, together with the heteroatom to which they are joined, can form heterocyclyl, wherein, when R1 or R2 is C$_{1-20}$ alkyl, alkoxy, aryl, heteroaryl, heterocyclyl, C$_{3-10}$ cycloalkyl, aryl C$_{1-6}$ alkyl, heteroaryl C$_{1-6}$ alkyl, heterocyclyl C$_{1-6}$ alkyl, C$_{3-10}$ cycloalkyl C$_{1-6}$ alkyl, C$_{1-6}$ alkyl, C$_{3-8}$ cycloalkyl or is a group containing one or more of these moieties, each of these moieties may optionally be substituted with one or more groups selected from R1c, halogen, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{1-6}$ alkylamino, C$_{1-6}$ dialkylamino, C$_{1-10}$ alkyl, OH, OR1c, OCOR1c, SH, SR1c, SCOR1c, NH$_2$, NO$_2$, NHR1c, NR1cR1d, COR1c, CSR1c, CN, COOH, COOR1c, CONH$_2$, SO$_2$R1c, SO$_3$H, SO$_2$NH$_2$, CONR1cR1d, SO$_2$NR1cR1d, wherein R1c and R1d are independently selected from C$_{1-6}$ alkyl, substituted C$_{1-6}$ alkyl, aryl, heteroaryl, C$_{3-8}$ cycloalkyl and heterocyclyl, or R1c and R1d, together with the heteroatom to which they are joined, can form heterocyclyl, wherein, when the substituent of R1 or R2 is C$_{1-10}$ alkyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{1-6}$ alkylamino, C$_{1-6}$ dialkylamino, C$_{1-6}$ alkyl, C$_{3-8}$ cycloalkyl or is a group containing one or more of these moieties, each of these moieties may optionally be substituted with one or more groups selected from R1e, halogen, C$_{1-10}$ alkyl, OH, OR1e, OCOR1e, SH, SR1e, SCOR1e, NH$_2$, NO$_2$, NHR1e, NR1eR1f, COR1e, CSR1e, CN, COOH, COOR1e, CONH$_2$, SO$_2$R1e, SO$_3$H, SO$_2$NH$_2$, CONR1eR1f, SO$_2$NR1eR1f, wherein R1e and R1f are independently selected from C$_{1-6}$ alkyl, substituted C$_{1-6}$ alkyl, aryl, heteroaryl, C$_{3-8}$ cycloalkyl and heterocyclyl, or R1e and R1f, together with the heteroatom to which they are joined, can form heterocyclyl, with the exception that R1 and R2 are not both H, or R1 and R2, together with the N to which they are attached, can form a heteroaryl or heterocyclyl group, each of which may optionally be substituted with one or more oxygen atoms or one or more groups selected from hydroxy, aryl, heteroaryl, partially or fully saturated heterocyclyl, C$_{3-8}$ cycloalkyl, C$_{1-6}$ alkyl, aryl C$_{1-6}$ alkyl, heteroaryl C$_{1-6}$ alkyl, heterocyclyl C$_{1-6}$ alkyl, C$_{3-8}$ cycloalkyl C$_{1-6}$ alkyl, C$_{1-6}$ alkoxy, aryloxy, heteroaryloxy, heterocyclyloxy, R2a, halogen, OH, OR2a, SH, SR2a, OCOR2a, SCOR2a, NH$_2$, NO$_2$, NHR2a, NR2aR2b, COR2a, CSR2a, CN, COOH, COOR2a, CONH$_2$, SO$_2$R2a, SO$_3$H, SO$_2$NH$_2$, CONR2aR2b, SO$_2$NR2aR2b, wherein R2a and R2b are independently selected from C$_{1-6}$ alkyl, substituted C$_{1-6}$ alkyl, aryl, heteroaryl, C$_{3-8}$ cycloalkyl and heterocyclyl, or R2a and R2b, together with the heteroatom to which they are joined, can form heterocyclyl, wherein, when the substituent of the heteroaryl or heterocyclyl formed by R1 and R2 together is aryl, heteroaryl, heterocyclyl, C$_{3-8}$ cycloalkyl, C$_{1-6}$ alkyl, aryl C$_{1-6}$ alkyl, heteroaryl C$_{1-6}$ alkyl, heterocyclyl C$_{1-6}$ alkyl, C$_{3-8}$ cycloalkyl C$_{1-6}$ alkyl, C$_{1-6}$ alkoxy, aryloxy, heteroaryloxy, heterocyclyloxy, or a group containing one or more of these moieties, each of these moieties may optionally be substituted with one or more groups selected from halogen, hydroxyl, C$_{1-6}$ alkyl, aryl, heteroaryl, heterocyclyl, C$_{3-8}$ cycloalkyl, C$_{1-4}$ alkoxy, aryloxy, heteroaryloxy, heterocyclyloxy, C$_{3-8}$ cycloalkyloxy, aryl C$_{1-4}$ alkoxy, heteroaryl $C_{1-6}$ alkoxy, heterocyclyl $C_{1-4}$ alkoxy, $C_{3-8}$ cycloalkyl $C_{1-4}$ alkoxy, R2c, OR2c, SH, SR2c, OCOR2c, SCOR2c, $NH_2$, $NO_2$, NHR2c, NR2cR2d, COR2c, CSR2c, CN, COOH, COOR2c, $CONH_2$, $SO_2R2c$, $SO_3H$, $SO_2NH_2$, CONR2cR2d, $SO_2NR2cR2d$, wherein R2c and R2d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, wherein, when the substituent of the substituent of the heteroaryl or heterocyclyl formed by R1 and R2 together is $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, $C_{3-8}$ cycloalkyloxy, aryl $C_{1-4}$ alkoxy, heteroaryl $C_{1-4}$ alkoxy, heterocyclyl $C_{1-4}$ alkoxy, $C_{3-8}$ cycloalkyl $C_{1-4}$ alkoxy, or is a group containing one or more of these moieties, each of these moieties may optionally be substituted with one or more groups selected from $C_{1-4}$ alkoxy, R2e, halogen, OH, OR2e, SH, SR2e, OCOR2e, SCOR2e, $NH_2$, $NO_2$, NHR2e, NR2eR2f, NHCOR2e, COR2e, CSR2e, CN, COOH, COOR2e, $CONH_2$, $SO_2R2e$, $SO_3H$, $SO_2NH_2$, CONR2eR2f, $SO_2NR2eR2f$, wherein R2e and R2f are independently selected from $C_{1-6}$ alkyl, substituted $C_{1-6}$ alkyl, aryl, heteroaryl, $C_{3-8}$ cycloalkyl and heterocyclyl, or R2e and R2f, together with the heteroatom to which they are joined, can form heterocyclyl;

Ring A is selected from aryl, heteroaryl and heterocyclyl moieties, each of which may optionally be substituted with one or more groups selected from halogen, $C_{1-6}$ alkyl, hydroxyl, aryl, heteroaryl, heterocyclyl, $C_{1-6}$ alkoxy, aryloxy, heteroaryloxy, heterocyclyloxy, Ra, $C_{1-10}$ alkyl, OH, ORa, OCORa, SH, SRa, SCORa, $NH_2$, $NO_2$, NHRa, NRaRb, CORa, CSRa, CN, COOH, COORa, $CONH_2$, CONHOH, CONHORa, $SO_2Ra$, $SO_3H$, $SO_2NH_2$, CONRaRb, $SO_2NRaRb$, wherein Ra and Rb are independently selected from $C_{1-6}$ alkyl, substituted $C_{1-6}$ alkyl, aryl, heteroaryl, $C_{3-8}$ cycloalkyl and heterocyclyl, or Ra and Rb, together with the heteroatom to which they are joined, can form heterocyclyl, wherein, when Ring A is substituted with $C_{1-6}$ alkyl, aryl, heteroaryl, heterocyclyl, $C_{1-6}$ alkoxy, aryloxy, heteroaryloxy, heterocyclyloxy, $C_{1-10}$ alkyl, $C_{3-8}$ cycloalkyl or is substituted with a group containing one or more of these moieties, each of these moieties may optionally be substituted with one or more groups selected from halogen, Rc, $C_{1-10}$ alkyl, aryl $C_{1-6}$ alkyl, OH, ORc, OCORc, SH, SRc, SCORc, $NH_2$, $NO_2$, NHRc, NRcRd, CORc, CSRc, CN, COOH, COORc, $CONH_2$, $SO_2Rc$, $SO_3H$, $SO_2NH_2$, CONRcRd, $SO_2NRcRd$, wherein Rc and Rd are independently selected from $C_{1-6}$ alkyl, substituted $C_{1-6}$ alkyl, aryl, heteroaryl, $C_{3-8}$ cycloalkyl and heterocyclyl, or Rc and Rd, together with the heteroatom to which they are joined, can form heterocyclyl;

V can be N, CH or C—R3, wherein R3 is halogen, $C_{1-10}$ alkyl, aryl, heteroaryl, heterocyclyl, $C_{3-8}$ cycloalkyl, $C_{1-6}$ alkoxy, aryloxy, heteroaryloxy, heterocyclyloxy, R3a, OH, OR3a, SH, SR3a, OCOR3a, SCOR3a, $NH_2$, $NO_2$, NHR3a, NR3aR3b, COR3a, CSR3a, CN, COOH, COOR3a, $CONH_2$, $SO_2R3a$, $SO_3H$, $SO_2NH_2$, CONR3aR3b, $SO_2NR3aR3b$, wherein R3a and R3b are independently selected from $C_{1-6}$ alkyl, substituted $C_{1-6}$ alkyl, aryl, heteroaryl, $C_{3-8}$ cycloalkyl and heterocyclyl, or R3a and R3b, together with the heteroatom to which they are joined, can form heterocyclyl, wherein, when R3 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R3c, $C_{1-10}$ alkyl, OH, OR3c, OCOR3c, SH, SR3c, SCOR3c, $NH_2$, $NO_2$, NHR3c, NR3cR3d, COR3c, CSR3c, CN, COOH, COOR3c, $CONH_2$, $SO_2R3c$, $SO_3H$, $SO_2NH_2$, CONR3cR3d, $SO_2NR3cR3d$, wherein R3c and R3d are independently selected from $C_{1-6}$ alkyl, substituted $C_{1-6}$ alkyl, aryl, heteroaryl, $C_{3-8}$ cycloalkyl and heterocyclyl, or R3c and R3d, together with the heteroatom to which they are joined, can form heterocyclyl, wherein, when the substituent of R3 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, R3e, $C_{1-10}$ alkyl, OH, OR3e, OCOR3e, SH, SR3e, SCOR3e, $NH_2$, $NO_2$, NHR3e, NR3eR3f, COR3e, CSR3e, CN, COOH, COOR3e, $CONH_2$, $SO_2R3e$, $SO_3H$, $SO_2NH_2$, CONR3eR3f, $SO_2NR3eR3f$, wherein R3e and R3f are independently selected from $C_{1-6}$ alkyl, substituted $C_{1-6}$ alkyl, aryl, heteroaryl, $C_{3-8}$ cycloalkyl and heterocyclyl, or R3e and R3f, together with the heteroatom to which they are joined, can form heterocyclyl;

W can be N, CH or C—R4, wherein R4 is halogen, $C_{1-10}$ alkyl, aryl, heteroaryl, heterocyclyl, $C_{1-6}$ alkoxy, aryloxy, heteroaryloxy, heterocyclyloxy, $C_{3-8}$ cycloalkyl, R4a, OH, OR4a, SH, SR4a, OCOR4a, SCOR4a, $NH_2$, $NO_2$, NHR4a, NR4aR4b, COR4a, CSR4a, CN, COOH, COOR4a, $CONH_2$, $SO_2R4a$, $SO_3H$, $SO_2NH_2$, CONR4aR4b, $SO_2NR4aR4b$, wherein R4a and R4b are independently selected from $C_{1-6}$ alkyl, substituted $C_{1-6}$ alkyl, aryl, heteroaryl, $C_{3-8}$ cycloalkyl and heterocyclyl, or R4a and R4b, together with the heteroatom to which they are joined, can form heterocyclyl, wherein, when R4 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R4c, $C_{1-10}$ alkyl, OH, OR4c, OCOR4c, SH, SR4c, SCOR4c, $NH_2$, $NO_2$, NHR4c, NR4cR4d, COR4c, CSR4c, CN, COOH, COOR4c, $CONH_2$, $SO_2R4c$, $SO_3H$, $SO_2NH_2$, CONR4cR4d, $SO_2NR4cR4d$, wherein R4c and R4d are independently selected from $C_{1-6}$ alkyl, substituted $C_{1-6}$ alkyl, aryl, heteroaryl, $C_{3-8}$ cycloalkyl and heterocyclyl, or R4c and R4d, together with the heteroatom to which they are joined, can form heterocyclyl, wherein, when the substituent of R4 is $C_{1-10}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, R4e, $C_{1-10}$ alkyl, OH, OR4e, OCOR4e, SH, SR4e, SCOR4e, $NH_2$, $NO_2$, NHR4e, NR4eR4f, COR4e, CSR4e, CN, COOH, COOR4e, $CONH_2$, $SO_2R4e$, $SO_3H$, $SO_2NH_2$, CONR4eR4f, $SO_2NR4eR4f$, wherein R4e and R4f are independently selected from $C_{1-6}$ alkyl, substituted $C_{1-6}$ alkyl, aryl, heteroaryl, $C_{3-8}$ cycloalkyl and heterocyclyl, or R4e and R4f, together with the heteroatom to which they are joined, can form heterocyclyl;

R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, $NO_2$, NHR5a, NR5aR5b, COR5a, CSR5a, CN, COOH, COOR5a, $CONH_2$, $SO_2R5a$, $SO_3H$, $SO_2NH_2$, CONR5aR5b, $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl, wherein, when R5 is $C_{1-6}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R5c, $C_{1-6}$ alkyl, OH, OR5c, OCOR5c, SH, SR5c, SCOR5c, $NH_2$, $NO_2$, NHR5c, NR5cR5d, COR5c, CSR5c, CN, COOH, COOR5c, $CONH_2$, $SO_2R5c$, $SO_3H$, $SO_2NH_2$, CONR5cR5d, $SO_2NR5cR5d$, wherein R5c and R5d are independently selected from $C_{1-6}$ alkyl, substituted $C_{1-6}$ alkyl, aryl, heteroaryl, $C_{3-8}$ cycloalkyl and heterocyclyl, or R5c and R5d, together with the heteroatom to which they are joined, can form heterocyclyl, wherein, when the substituent of R5 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with one or more groups selected from halogen, R5e, $C_{1-6}$ alkyl, OH, OR5e, OCOR5e, SH, SR5e, SCOR5e, $NH_2$, $NO_2$, NHR5e, NR5eR5f, COR5e, CSR5e, CN, COOH, COOR5e, $CONH_2$, $SO_2R5e$, $SO_3H$, $SO_2NH_2$, CONR5eR5f, $SO_2NR5eR5f$, wherein R5e and R5f are independently selected from $C_{1-6}$ alkyl, substituted $C_{1-6}$ alkyl, aryl, heteroaryl, $C_{3-8}$ cycloalkyl and heterocyclyl, or R5e and R5f, together with the heteroatom to which they are joined, can form heterocyclyl;

X can be N, CH or C—R6, wherein R6 is selected from $C_{1-6}$ alkyl, aryl, heteroaryl, heterocyclyl, $C_{1-6}$ alkoxy, aryloxy, heteroaryloxy, heterocyclyloxy, R6a, halogen, OH, OR6a, SH, SR6a, OCOR6a, SCOR6a, $NH_2$, $NO_2$, NHR6a, NR6aR6b, COR6a, CSR6a, CN, COOH, COOR6a, $CONH_2$, $SO_2R6a$, $SO_3H$, $SO_2NH_2$, CONR6aR6b, $SO_2NR6aR6b$, wherein R6a and R6b are independently selected from $C_{1-6}$ alkyl, substituted $C_{1-6}$ alkyl, aryl, heteroaryl, $C_{3-8}$ cycloalkyl and heterocyclyl, or R6a and R6b, together with the heteroatom to which they are joined, can form heterocyclyl, wherein, when R6 is heteroaryl or heterocyclyl, each of these moieties may optionally be substituted with one or more oxygen atoms, and when R6 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with one or more groups selected from halogen, R6c, $C_{1-6}$ alkyl, $C_{1-6}$ alkynyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, OR6c, OCOR6c, SH, SR6c, SCOR6c, $NH_2$, $NO_2$, NHR6c, NR6cR6d, COR6c, CSR6c, CN, COOH, COOR6c, $CONH_2$, CONHOH, $C(NOH)NH_2$, $SO_2R6c$, $SO_3H$, $SO_2NH_2$, CONR6cR6d, $SO_2NR6cR6d$, wherein R6c and R6d are independently selected from $C_{1-6}$ alkyl, substituted $C_{1-6}$ alkyl, aryl, heteroaryl, $C_{3-8}$ cycloalkyl and heterocyclyl, or R6c and R6d, together with the heteroatom to which they are joined, can form heterocyclyl, wherein, when the substituent of R6 is heteroaryl or heterocyclyl, each of these moieties may optionally be substituted with one or more oxygen atoms, or when the substituent of R6 is $C_{1-6}$ alkyl, $C_{1-6}$ alkynyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{3-8}$ cycloalkyl, or is a group containing one or more of these moieties, each of these moieties may optionally be substituted with one or more groups selected from halogen, R6e, $C_{1-6}$ alkyl, $C_{1-4}$ alkoxy, OH, OR6e, OCOR6e, SH, SR6e, SCOR6e, $NH_2$, $NO_2$, NHR6e, NR6eR6f, COR6e, CSR6e, CN, COOH, COOR6e, $CONH_2$, $C(NOH)NH_2$, $SO_2R6e$, $SO_3H$, $SO_2NH_2$, CONR6eR6f, $SO_2NR6eR6f$, wherein R6e and R6f are independently selected from $C_{1-6}$ alkyl, substituted $C_{1-6}$ alkyl, aryl, heteroaryl, $C_{3-8}$ cycloalkyl and heterocyclyl, or R6e and R6f, together with the heteroatom to which they are joined, can form heterocyclyl;

Y can be N, CH or C—R7, wherein R7 is selected from $C_{1-6}$ alkyl, aryl, heteroaryl, heterocyclyl, $C_{1-6}$ alkoxy, aryloxy, heteroaryloxy, heterocyclyloxy, R7a, halogen, OH, OR7a, SH, SR7a, OCOR7a, SCOR7a, $NH_2$, $NO_2$, NHR7a, NR7aR7b, COR7a, CSR7a, CN, COOH, COOR7a, $CONH_2$, $SO_2R7a$, $SO_3H$, $SO_2NH_2$, CONR7aR7b, $SO_2NR7aR7b$, wherein R7a and R7b are independently selected from $C_{1-6}$ alkyl, substituted $C_{1-6}$ alkyl, aryl, heteroaryl, $C_{3-8}$ cycloalkyl and heterocyclyl, or R7a and R7b, together with the heteroatom to which they are joined, can form heterocyclyl, wherein, when R7 is heteroaryl or heterocyclyl, each of these moieties may optionally be substituted with one or more oxygen atoms, and when R7 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl or is a group containing one or more of these moieties, each of these moieties may optionally be substituted with one or more groups selected from halogen, R7c, $C_{1-6}$ alkyl, $C_{1-6}$ alkynyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, O7c, OCOR7c, SH, SR7c, SCOR7c, $NH_2$, $NO_2$, NHR7c, NR7cR7d, COR7c, CSR7c, CN, COOH, COOR7c, $CONH_2$, CONHOH, $C(NOH)NH_2$, $SO_2R7c$, $SO_3H$, $SO_2NH_2$, CONR7cR7d, $SO_2NR7cR7d$, wherein R7c and R7d are independently selected from $C_{1-6}$ alkyl, substituted $C_{1-6}$ alkyl, aryl, heteroaryl, $C_{3-8}$ cycloalkyl and heterocyclyl, or R7c and R7d, together with the heteroatom to which they are joined, can form heterocyclyl, wherein, when the substituent of R7 is heteroaryl or heterocyclyl, each of these moieties may optionally be substituted with one or more oxygen atoms, or when the substituent of R7 is $C_{1-6}$ alkyl, $C_{1-6}$ alkynyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{3-8}$ cycloalkyl, or is a group containing one or more of these moieties, each of these moieties may optionally be substituted with one or more groups selected from halogen, aryl, heteroaryl, heterocyclyl, aryl $C_{1-6}$ alkyl, heteroaryl $C_{1-6}$ alkyl, heterocyclyl $C_{1-6}$ alkyl, $C_{1-4}$ alkoxy, R7e, $C_{1-6}$ alkyl, OH, OR7e, OCOR7e, SH, SR7e, SCOR7e, $NH_2$, $NO_2$, NHR7e, NR7eR7f, COR7e, CSR7e, CN, COOH, COOR7e, $CONH_2$, $C(NOH)NH_2$, $SO_2R7e$, $SO_3H$, $SO_2NH_2$, CONR7eR7f, $SO_2NR7eR7f$, wherein R7e and R7f are independently selected from $C_{1-6}$ alkyl, substituted $C_{1-6}$ alkyl, aryl, heteroaryl, $C_{3-8}$ cycloalkyl and heterocyclyl, or R7e and R7f, together with the heteroatom to which they are joined, can form heterocyclyl;

Z can be N, CH or C—R8, wherein R8 is selected from $C_{1-10}$ alkyl, aryl, heteroaryl, heterocyclyl, $C_{1-6}$ alkoxy, aryloxy, heteroaryloxy, heterocyclyloxy, R8a, halogen, OH, OR8a, SH, SR8a, OCOR8a, SCOR8a, $NH_2$, $NO_2$, NHR8a, NR8aR8b, COR8a, CSR8a, CN, COOH, COOR8a, $CONH_2$, $SO_2R8a$, $SO_3H$, $SO_2NH_2$, CONR8aR8b, $SO_2NR8aR8b$, wherein R8a and R8b are independently selected from $C_{1-6}$ alkyl, substituted $C_{1-6}$ alkyl, aryl, heteroaryl, $C_{3-8}$ cycloalkyl and heterocyclyl, or R8a and R8b, together with the heteroatom to which they are joined, can form heterocyclyl, wherein, when R8 is $C_{1-6}$ alkyl, $C_{1-10}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with one or more groups selected from halogen, R8c, $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, OR8c, OCOR8c, SH, SR8c, SCOR8c, $NH_2$, $NO_2$, NHR8c, NR8cR8d, COR8c, CSR8c, CN, COOH, COOR8c, $CONH_2$, $SO_2R8c$, $SO_3H$, $SO_2NH_2$, CONR8cR8d, $SO_2NR8cR8d$, wherein R8c and R8d are independently selected from $C_{1-6}$ alkyl, substituted $C_{1-6}$ alkyl, aryl, heteroaryl, $C_{3-8}$ cycloalkyl and heterocyclyl, or R8c and R8d, together with the heteroatom to which they are joined, can form heterocyclyl, wherein, when the substituent of R8 is $C_{1-6}$ alkyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{3-8}$ cycloalkyl, or is a group containing one or more of these moieties, each of these moieties may optionally be substituted with one or more groups selected from halogen, R8e, $C_{1-6}$ alkyl, OH, OR8e, OCOR8e, SH, SR8e, SCOR8e, $NH_2$, $NO_2$, NHR8e, NR8eR8f, COR8e, CSR8e, CN, COOH, COOR8e, $CONH_2$, $SO_2R8e$, $SO_3H$, $SO_2NH_2$, CONR8eR8f, $SO_2NR8eR8f$, wherein R8e and R8f are independently selected from $C_{1-6}$ alkyl, substituted $C_{1-6}$ alkyl, aryl, heteroaryl, $C_{3-8}$ cycloalkyl and heterocyclyl, or R8e and R8f, together with the heteroatom to which they are joined, can form heterocyclyl;

wherein, at most, two of the atoms or groups denoted X, Y and Z can be N;

wherein, when W is N, the CONR1R2 group may be joined to W instead, with the double bonds in Formula I rearranged accordingly;

or a pharmaceutically acceptable salt or ester thereof;

provided that when R1 and R2 together form piperidinyl in compounds having Formula I, the piperidinyl is not substituted with methyl, dimethyl, ethyl, isopropyl, tert-butyl, methoxycarbonyl, trifluoromethyl, chloro, bromo or benzyl, provided that R1 and R2 together in compounds having Formula I do not form 6,7-dimethoxy-3,4-dihydro-1H-isoquinolin-2-yl, 6-methoxy-3,4-dihydro-1H-isoquinolin-2-yl, 7-methoxy-3,4-dihydro-1H-isoquinolin-2-yl, 7-amino-3,4-dihydro-1H-isoquinolin-2-yl, 7-nitro-3,4-dihydro-1H-isoquinolin-2-yl, 3,4-dihydro-1H-isoquinolin-2-yl, 3,4-dihydro-1H-isoquinolin-1-yl, 3,4-dihydro-2H-quinolin-1-yl, pyrrolidin-1-yl, 3,6-dihydro-2H-pyridin-1-yl, 8-aza-spiro[4.5]dec-8-yl, 1,3-dihydroisoindol-2-yl, octahydroisoindol-2-yl, 1,2,6-triaza-spiro[2.5]oct-1-en-6-yl or azepan-1-yl, and provided that Ring A in compounds having Formula I does not form a pyridine, pyrimidine, substituted pyridine or substituted pyrimidine, when R1 and R2, together with the N to which they are attached, form piperidinyl, piperazinyl, substituted piperidinyl or substituted piperazinyl.

Preferably, the compound of the invention has a formula selected from Formula I, Formula IIa, Formula IIb, Formula IIc and Formula IId.

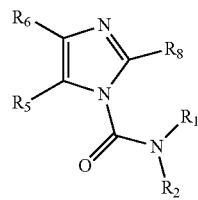

Formula IIa

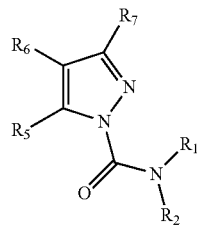

Formula IIb

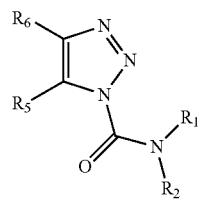

Formula IIc

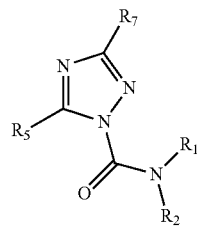

Formula IId

More preferably, the compound has a formula selected from Formula Ia, Formula IIa, Formula IIb, Formula IIb and Formula IId.

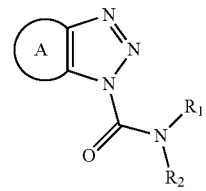

Formula Ia

In one embodiment of the invention, R1 is preferably selected from H and $C_{1-4}$ alkyl. More preferably, R1 is selected from H and $C_{1-3}$ alkyl, even more preferably, R1 is selected from H, methyl and ethyl and most preferably, R1 is selected from H and methyl.

R2 is preferably selected from $C_{1-4}$ alkyl, aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. Preferably, the aryl, heteroaryl, heterocyclyl and $C_{3-10}$ cycloalkyl (including in aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl) have a 6 membered monocyclic ring structure. More preferably, the aryl, heteroaryl, heterocyclyl and $C_{3-10}$ cycloalkyl (including in aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl) are selected from phenyl, cyclohexyl, phenyl $C_{1-6}$ alkyl and cyclohexyl $C_{1-6}$ alkyl, each of which can be substituted or unsubstituted. Preferably, the $C_{1-6}$ alkyl of each of aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl is a linear alkyl.

Alternatively, R2 can be selected from aryl, heteroaryl, heterocyclyl, aryl $C_{1-6}$ alkyl, heteroaryl $C_{1-6}$ alkyl and heterocyclyl $C_{1-6}$ alkyl, each of which may be substituted or unsubstituted and wherein the aryl, heteroaryl and heterocyclyl (including in aryl $C_{1-6}$ alkyl, heteroaryl $C_{1-6}$ alkyl and heterocyclyl $C_{1-6}$ alkyl) have a bicyclic ring structure, preferably, a 10 membered bicyclic ring structure. More preferably, R2 is selected from naphthalenyl and naphthalenyl $C_{1-6}$ alkyl.

Each of the aryl, heteroaryl, heterocyclyl and $C_{3-10}$ cycloalkyl groups of R2 (including in aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl) can be substituted with one or more halogens.

Alternatively, each of the aryl, heteroaryl, heterocyclyl and $C_{3-10}$ cycloalkyl groups (including in aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl) can be substituted with $C_{1-4}$ alkoxy or aryloxy. Preferably, the $C_{1-4}$ alkoxy is methoxy or ethoxy. Preferably, the aryloxy is monocyclic aryloxy and, more preferably, phenoxy.

In a preferred embodiment, R1 is selected from H and $C_{1-4}$ alkyl, and R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. More preferably, R1 is selected from H, methyl and ethyl, and R2 is selected from aryl, heteroaryl, heterocyclyl, and $C_{3-10}$ cycloalkyl each of which may be substituted or unsubstituted. More preferably, R1 is methyl. More preferably, R2 is selected from aryl, heteroaryl, heterocyclyl, and $C_{5-8}$ cycloalkyl each of which are monocyclic and may be substituted or unsubstituted. More preferably still, R2 is selected from saturated heterocyclyl, and $C_{5-8}$ cycloalkyl each of which are monocyclic and may be substituted or unsubstituted. When R2 is a monocyclic $C_{5-8}$ cycloalkyl, it is preferably unsubstituted. Preferably, R2 is a cyclohexyl, such as an unsubstituted cyclohexyl. When R2 is a monocyclic saturated heterocyclyl, the heterocyclyl ring preferably contains a single heteroatom. Preferably, the heteroatom is a nitrogen or oxygen atom. More preferably, the heterocyclyl is six membered, such as a piperidinyl or tetrahydropyranyl group. If the heteroatom is an oxygen atom, the heterocyclyl is preferably unsubstituted. If the heteroatom is a nitrogen atom, the nitrogen heteroatom may be substituted or unsubstituted. If the nitrogen heteroatom is substituted, it is preferably substituted with a group selected from $C_{1-6}$ alkyl, aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. More preferably, the nitrogen heteroatom is substituted with a group selected from $C_{1-4}$ alkyl, aryl $C_{1-4}$ alkyl, heteroaryl $C_{1-4}$ alkyl, heterocyclyl $C_{1-4}$ alkyl and $C_{5-8}$ cycloalkyl $C_{1-4}$ alkyl. More preferably, the nitrogen heteroatom is substituted with a group selected from aryl $C_{1-4}$ alkyl and heteroaryl $C_{1-4}$ alkyl, wherein the aryl and heteroaryl are monocyclic and, preferably, six membered. Preferably, the nitrogen heteroatom is substituted with a group selected from phenyl $C_{1-2}$ alkyl and pyridyl $C_{1-2}$ alkyl. Preferably, the heteroatom in the said heterocyclyl group is at the 4 position relative to the position of attachment of the heterocyclyl group R2 to the urea nitrogen. When R1 and R2 are as defined in this paragraph, the compound preferably has the formula IIa. Preferably, when R1 and R2 are as defined in this paragraph, R6 is a substituted or unsubstituted aryl or heteroaryl and, preferably, a substituted or unsubstituted monocyclic aryl or heteroaryl. The monocyclic aryl or heteroaryl is preferably six membered. In one embodiment, R6 is a substituted or unsubstituted aryl (such as phenyl) and, preferably, unsubstituted. In another embodiment, R6 is a substituted or unsubstituted heteroaryl and, preferably, substituted or unsubstituted pyridyl. In one embodiment, the heteroaryl is substituted with an oxygen atom. For example, the nitrogen heteroatom of pyridyl may be substituted with an oxygen atom so that it is oxidised, i.e. an N-oxide is formed.

It has been found that compounds with the selection of R1 and R2 in the preceding paragraph show relatively high specificity for FAAH. Further, compounds in which R2 is heterocyclyl, such as piperidinyl or tetrahydropyranyl, have been found to be relatively metabolically stable.

In an alternative embodiment, R2 is preferably $C_{2-20}$ alkyl. More preferably, R2 is $C_{3-16}$ alkyl and, more preferably still, R2 is $C_{4-12}$ alkyl. Preferably, the alkyl in a linear alkyl.

In a preferred embodiment, R1 is selected from H and $C_{1-4}$ alkyl, and R2 is $C_{2-20}$ alkyl.

In various embodiments, when R1 is: H or $C_{1-4}$ alkyl; H or $C_{1-3}$ alkyl; H, methyl or ethyl; H or methyl; or methyl, R2 can be selected from $C_{1-6}$ alkoxy, aryl, heteroaryl, partially or fully saturated heterocyclyl, $C_{3-10}$ cycloalkyl, aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, halogen, OH, OR1a, OCOR1a, SH, SR1a, SCOR1a, $NH_2$, NHR1a, $NHSO_2NH_2$, $NHSO_2R1a$, NR1aCOR1b, NHCOR1a, NR1aR1b, COR1a, CSR1a, CN, COOH, COOR1a, $CONH_2$, CONHOH, CONHR1a, CONHOR1a, $SO_2R1a$, $SO_3H$, $SO_2NH_2$, CONR1aR1b, $SO_2NR1aR1b$, wherein R1a and R1b are independently selected from $C_{1-6}$ alkyl, substituted $C_{1-6}$ alkyl, aryl, heteroaryl, $C_{3-8}$ cycloalkyl and heterocyclyl, or R1a and R1b, together with the heteroatom to which they are joined, can form heterocyclyl, wherein R2 can be substituted or unsubstituted.

Alternatively, in other embodiments, when R1 is: H and $C_{1-4}$ alkyl; $L_1$ and $C_{1-3}$ alkyl; H, methyl and ethyl; H and methyl; or methyl, R2 can be selected from aryl, heteroaryl, partially or fully saturated heterocyclyl, $C_{3-10}$ cycloalkyl, aryl $C_{1-6}$ alkyl, heteroaryl $C_{1-6}$ alkyl, heterocyclyl $C_{1-6}$ alkyl, $C_{3-10}$ cycloalkyl $C_{1-6}$ alkyl, wherein R2 can be substituted or unsubstituted.

In a preferred embodiment, R1 and R2, together with the N to which they are attached, form a heterocyclyl group which may be substituted or unsubstituted. Preferably, the heterocyclyl is a 5 or 6 membered monocyclic ring and, more preferably, a 5 membered monocyclic ring. In certain embodiments, the said heterocyclyl contains one or two, preferably 1, additional heteroatoms (i.e. in addition to the N). These additional heteroatoms may be, for example, N, O and/or S. Preferably, the heterocyclyl is oxazolidinyl. Preferably, the oxygen atom in the oxazolidinyl is at the 3 position relative to the urea nitrogen. Preferably, the oxazolidinyl is substituted with one, two or three methyl or ethyl groups. More preferably, the oxazolidinyl is substituted with two methyl or ethyl groups. More preferably still, the oxazolidinyl is substituted with two methyl groups on the same carbon atom. More preferably, the oxazolidinyl is 4,4-dimethyloxazolidin-3-yl. When R1 and R2 are as defined in this paragraph, the compound preferably has the formula Ia or IIa. Preferably, when R1 and R2 are as defined in this paragraph and the compound has the formula IIa, R6 is a substituted or unsubstituted aryl and, more preferably, phenyl. When R1 and R2 are as defined in this paragraph and the compound has the formula Ia, ring A is preferably an unsubstituted or substituted benzo moiety.

Compounds having R1 and R2 as defined in the preceding paragraph have been found to be relatively potent inhibitors of FAAH. They have also been found to have relatively high specificity for FAAH.

In an alternative embodiment, R1 and R2, together with the N to which they are attached, form a heterocyclyl group which may be substituted or unsubstituted. Preferably, the heterocyclyl is a 5 or 6 membered monocyclic ring and, more preferably, a 6 membered monocyclic ring. Preferably, R1 and R2 together form morpholino, piperazinyl oxazolidinyl, pyrrolidinyl or piperidinyl. More preferably, R1 and R2 together form morpholino or piperazinyl.

Preferably, the heterocyclyl of R1 and R2 together is substituted with $C_{1-4}$ alkyl, aryl, heteroaryl, $C_{3-8}$ cycloalkyl aryl $C_{1-6}$ alkyl, heteroaryl $C_{1-6}$ alkyl, aryloxy, heteroaryloxy, aryl $C_{1-6}$ alkoxy and heteroaryl $C_{1-6}$ alkoxy, each of which may optionally be substituted with one or more halogens or $C_{1-4}$ alkyl groups. Preferably, the substituent aryl, heteroaryl or $C_{3-8}$ cycloalkyl is a 5 or 6 membered monocyclic ring. More preferably, the heterocyclyl of R1 and R2 together is substituted with aryl, aryl $C_{1-6}$ alkyl and aryloxy, each of which may optionally be substituted with one or more halogen. More preferably still, the heterocyclyl of R1 and R2 together is substituted with phenyl, phenyl $C_{1-6}$ alkyl or phenoxy, each of which may optionally be substituted with one or more halogen.

Alternatively, the heterocyclyl of R1 and R2 together may be substituted with a heteroaryl or heteroaryl $C_{1-6}$ alkyl. In one embodiment, the heteroaryl has a bicyclic ring structure, for example, benzodioxolylmethyl. Alternatively, the heteroaryl may be monocyclic, for example, pyridyl.

In another alternative, the heterocyclyl of R1 and R2 together may be substituted with a $C_{3-8}$ cycloalkyl. Preferably, the $C_{3-8}$ cycloalkyl is a monocyclic cycloalkyl such as cyclohexyl.

In one embodiment, the heterocyclyl of R1 and R2 together can be 1,4-dioxa-8-azaspiro[4.5]dec-8-yl, dimethyloxazolidinyl, methylpiperazinyl, benzyloxyphenylpiperazinyl, tolyloxypiperidinyl, pyrrolidinyl $C_{1-4}$ alkyl piperidinyl, pyridylpiperidinyl, pyridyloxadiazol-5-ylpiperidinyl or benzyloxypiperidinyl.

In one embodiment, the heterocyclyl of R1 and R2 together is piperidinyl substituted with phenoxy or phenyl $C_{1-4}$ alkoxy and wherein the phenyl may optionally be substituted with halogen.

In one embodiment of the invention, when V is C—R3, R3 is H or halogen.

In another embodiment of the invention, when W is C—R4, R4 is selected from H and aryl. Preferably, R4 is selected from H and phenyl. More preferably, R4 is H.

In the compound according to the invention, ring A is preferably a substituted or unsubstituted monocyclic aryl or heteroaryl moiety and, more preferably, a monocyclic aryl moiety. Preferably, ring A is a substituted or unsubstituted benzo moiety. When the monocyclic aryl of ring A is substituted, the substituent is one or more of halogen, $C_{1-6}$ alkyl or aryl which can optionally be substituted with one or more of halogen, cyano, carboxylic acid or amide. Preferably, the substituent aryl is monocyclic aryl and, more preferably, phenyl. In a preferred embodiment, the compound, having ring A as defined in this paragraph, has formula Ia.

In one embodiment, ring A is substituted with a moiety selected from $C_{1-6}$ alkoxy, $C_{1-6}$ alkoxy $C_{1-6}$ alkyl, and $C_{0-6}$ alkyl-CO—$C_{0-6}$ alkyl, wherein the $C_{1-6}$ alkoxy, $C_{1-6}$ alkoxy $C_{1-6}$ alkyl, or $C_{0-6}$ alkyl-CO—$C_{0-6}$ alkyl is substituted with a moiety selected from aryl, heteroaryl, heterocyclyl, and $C_{3-10}$ cycloalkyl, wherein each of these moieties may optionally be substituted with aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl, and $C_{3-10}$ cycloalkyl $C_{1-6}$ alkyl. Preferably, ring A is substituted with a $C_{0-6}$ alkyl-CO—$C_6$ alkyl, wherein the $C_{0-6}$ alkyl-CO—$C_6$ alkyl is substituted with a moiety selected from aryl, heteroaryl, heterocyclyl, and $C_{3-10}$ cycloalkyl, wherein each of these moieties may optionally be substituted with aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl, and $C_{3-10}$ cycloalkyl $C_{1-6}$ alkyl. Preferably, ring A is substituted with a carbonyl moiety (i.e. $C_0$ alkyl-CO—$C_0$ alkyl). Preferably, the $C_{0-6}$ alkyl-CO—$C_6$ alkyl is substituted with a heterocyclyl, more preferably, a monocyclic heterocyclyl, more preferably still, a heterocyclyl containing one or two nitrogen heteroatoms, even more preferably, a six membered heterocyclyl, and most preferably, piperazine. Preferably, the $C_{1-6}$ alkoxy, $C_{1-6}$ alkoxy $C_{1-6}$ alkyl, or $C_{0-6}$ alkyl-CO—$C_{0-6}$ alkyl is linear. Preferably, compounds as described in this paragraph are of formula Ia.

In another embodiment, ring A is substituted with one or more groups selected from halogen, $C_{1-6}$ alkyl, $C_{1-6}$ alkoxy, OH, ORa, OCORa, SH, SRa, SCORa, $NH_2$, $NO_2$, NHRa, $NHSO_2NH_2$, $NHSO_2Ra$, NRaCORb, NHCORa, NHC(NH)$NH_2$, NRaRb, CORa, CSRa, CN, COOH, COORa, $CONH_2$, CONHRa, CONHOH, CONHORa, C(NOH)$NH_2$, CONRaRb, $SO_2Ra$, $SO_3H$, $SO_2NH_2$, $SO_2NRaRb$, wherein Ra and Rb are $C_{1-6}$ alkyl. Preferably, ring A is substituted with one or more groups selected from halogen, OH, SH, $NH_2$, $NO_2$, NHC(NH)$NH_2$, CN, COOH, $CONH_2$, CONHOH, C(NOH)$NH_2$, $SO_3H$, and $SO_2NH_2$. More preferably, ring A is substituted with one or more groups selected from halogen, OH, $NH_2$, $NO_2$, NHC(NH)$NH_2$, CN, COOH, $CONH_2$, CONHOH, C(NOH)$NH_2$, $SO_3H$, and $SO_2NH_2$. Preferably, compounds as described in this paragraph are of formula Ia.

Preferably, in the compound of the invention, R5 is H or halogen, and, more preferably, R5 is H.

In one embodiment, R5 together with the ring carbon to which it is attached, does not form a carbonyl group. The compound is of Formula II as indicated above.

In another embodiment, X is not O. The compound is of Formula II as indicated above.

In compounds having Formula II, when X is C—R6, R6 is preferably a substituted or unsubstituted aryl. Preferably, the aryl R6 is phenyl or naphthalenyl. More preferably, the aryl R6 is phenyl. Preferably, the aryl R6 is substituted with one or more groups selected from halogen, $C_{1-4}$ alkoxy, hydroxyl, amide, aryl, heterocyclyl, heteroaryl, heterocyclyl, aryloxy, each of which may be substituted or unsubstituted. Preferably, the aryl substituent of R6 is phenyl which may be substituted or unsubstituted. When R6 is defined as in this paragraph, the compound of Formula II is preferably an imidazole (i.e. X is CH or C—R6, Y is N, and Z is CH or C—R8) or a 1,2,3-triazole (i.e. X is CH or C—R6, Y is N, and Z is N). More preferably, the compound has formula IIa.

Alternatively, R6 is preferably H, halogen or aryl and, more preferably, H. When R6 is defined as in this paragraph, the compound of Formula II is preferably a pyrazole (i.e. X is CH or C—R6, Y is CH or C—R7, and Z is N).

In one embodiment of the invention, when Y is C—R7, R7 is selected from aryl or heteroaryl, each of which can be substituted or unsubstituted. Preferably, the aryl and heteroaryl are monocyclic. Preferably, the aryl or heteroaryl is substituted with one or more halogens. In a preferred embodiment of the invention, R7 is substituted or unsubstituted aryl.

When R7 is defined as in this paragraph, the compound of Formula II is preferably a pyrazole (i.e. X is CH or C—R6, Y is CH or C—R7, and Z is N) or a 1,2,4-triazole (i.e. X is N, Y is CH or C—R7, and Z is N).

In one embodiment, when Y is C—R7, R7 is H.

In another embodiment of the invention, when Z is C—R8, R8 is selected from H and aryl. Preferably, R8 is selected from H and phenyl. More preferably, R8 is H.

In one embodiment of the invention, R6 is a group selected from aryl, heteroaryl, heterocyclyl, $C_{3-10}$ cycloalkyl, wherein the R6 group is substituted with a group selected from $C_{1-6}$ alkoxy, $C_{1-6}$ alkoxy $C_{1-6}$ alkyl, and $C_{0-6}$ alkyl-CO—$C_{0-6}$ alkyl, wherein the $C_{1-6}$ alkoxy, $C_{1-6}$ alkoxy $C_{1-6}$ alkyl, or $C_{0-6}$ alkyl-CO—$C_{0-6}$ alkyl group is substituted with a group selected from aryl, heteroaryl, heterocyclyl, and $C_{3-10}$ cycloalkyl. Preferably, R6 is a group selected from aryl, heteroaryl, heterocyclyl, $C_{3-10}$ cycloalkyl, wherein the R6 group is substituted with a group selected from $C_{1-6}$ alkoxy and $C_{1-6}$ alkoxy $C_{1-6}$ alkyl, wherein the $C_{1-6}$ alkoxy or $C_{1-6}$ alkoxy $C_{1-6}$ alkyl group is substituted with a group selected from aryl, heteroaryl, heterocyclyl, and $C_{3-10}$ cycloalkyl. Preferably, R6 is a group selected from aryl, heteroaryl, heterocyclyl, $C_{3-10}$ cycloalkyl, wherein the R6 group is substituted with a group selected from $C_{1-6}$ alkoxy and $C_{1-6}$ alkoxy $C_{1-6}$ alkyl, wherein the $C_{1-6}$ alkoxy or $C_{1-6}$ alkoxy $C_{1-6}$ alkyl group is substituted with a heterocyclyl. More preferably, R6 is an aryl which is substituted with a group selected from $C_{1-6}$ alkoxy and $C_{1-6}$ alkoxy $C_{1-6}$ alkyl, wherein the $C_{1-6}$ alkoxy or $C_{1-6}$ alkoxy $C_{1-6}$ alkyl group is substituted with a heterocyclyl. More preferably still, R6 is an aryl which is substituted with $C_{1-6}$ alkoxy, wherein the $C_{1-6}$ alkoxy is substituted with a heterocyclyl.

Preferably, R6 is an aryl. Preferably, R6 has a monocyclic ring structure such as a monocyclic aryl. In one embodiment, R6 has a six membered ring structure such as phenyl.

Preferably, the $C_{1-6}$ alkoxy, alkoxy $C_{1-6}$ alkyl or $C_{0-6}$ alkyl-CO—$C_{0-6}$ alkyl is linear.

Preferably, the substituent of the $C_{1-6}$ alkoxy or $C_{1-6}$ alkoxy $C_{1-6}$ alkyl is monocyclic. Preferably, the substituent of the $C_{1-6}$ alkoxy or $C_{1-6}$ alkoxy $C_{1-6}$ alkyl is six membered. Preferably, the substituent of the $C_{1-6}$ alkoxy or $C_{1-6}$ alkoxy $C_{1-6}$ alkyl is heterocyclyl. Preferably, the heterocyclyl is fully saturated. Preferably, the heterocyclyl contains one or two heteroatoms such as nitrogen or oxygen. Preferably, the heterocyclyl contains at least one nitrogen heteroatom. In one embodiment, the heterocyclyl is piperidinyl, piperazinyl, or tetrahydropyranyl. In this embodiment, the compound preferably is of formula IIa.

In one embodiment, when W is N, the CONR1R2 group may not be joined to W instead. In this embodiment, the compound is of Formula I as indicated above.

Formula I and Ia

In compounds having formula I and, in particular, compounds having formula Ia, ring A is preferably a substituted or unsubstituted aryl or heteroaryl moiety. More preferably, ring A is a substituted or unsubstituted monocyclic aryl or heteroaryl moiety. More preferably still, ring A is a substituted or unsubstituted six-membered aryl or heteroaryl moiety. Most preferably, ring A is a substituted or unsubstituted monocyclic aryl such as a benzo moiety.

When ring A is substituted, the substituent may be one or more groups selected from halogen, OH, $C_{1-4}$ alkyl, $C_{1-4}$ alkoxy, SH, $NH_2$, $NO_2$, CN, COOH, $CONH_2$, CONHOH, benzoxyaminocarbonyl, $SO_3H$, $SO_2NH_2$, aryl, heteroaryl, heterocyclyl, and $C_{3-8}$ cycloalkyl. When the substituent is $C_{1-4}$ alkyl, aryl, heteroaryl, heterocyclyl, or $C_{3-8}$ cycloalkyl, each of these moieties may optionally be substituted with one or more groups selected from halogen, OH, SH, $NH_2$, $NO_2$, CN, COOH, $CONH_2$, $SO_3H$, $SO_2NH_2$, $C_{1-3}$ alkyl, $C_{1-3}$ alkoxy and benzyl.

Preferably, the substituent of ring A is one or more groups selected from halogen, OH, $C_{1-3}$ alkyl, $C_{1-3}$ alkoxy, $NH_2$, $NO_2$, CN, COOH, $CONH_2$, monocyclic aryl, monocyclic heteroaryl, monocyclic heterocyclyl, and $C_{5-8}$ cycloalkyl. When the substituent is $C_{1-3}$ alkyl, monocyclic aryl, monocyclic heteroaryl, monocyclic heterocyclyl or $C_{5-8}$ cycloalkyl, each of these moieties may optionally be substituted with one or more groups selected from halogen, CN, COOH, $CONH_2$, and $C_{1-3}$ alkoxy.

More preferably, the substituent of ring A is one or more groups selected from halogen, OH, $C_{1-2}$ alkyl, $C_{1-2}$ alkoxy, and phenyl. When the substituent is $C_{1-2}$ alkyl or phenyl, each of these moieties may optionally be substituted with one or more groups selected from halogen, CN, COOH, $CONH_2$, and $C_{1-3}$ alkoxy.

In a preferred embodiment of compounds having formula I and, in particular, compounds having formula Ia, R1 and R2, together with the N to which they are attached, form a heterocyclyl group which may be substituted or unsubstituted. Preferably, the heterocyclyl is a 5 or 6 membered monocyclic ring, more preferably, a 6 membered monocyclic ring. In certain embodiments, the said heterocyclyl contains one or two, preferably 1, additional heteroatoms (i.e. in addition to the N). These additional heteroatoms may be, for example, N, O and/or S. In one embodiment, the heterocyclyl is morpholino. In an alternative embodiment, the heterocyclyl is piperazinyl. In other embodiments, the said heterocyclyl contains no additional heteroatoms (i.e. it contains a single N atom). In one embodiment, the heterocyclyl is piperidinyl. Where the heterocyclyl is substituted, it is preferably substituted with an aryl or an aryl $C_{1-4}$ alkyl, wherein the aryl is preferably monocyclic and more preferably phenyl. The alkyl is preferably linear. More preferably, the heterocyclyl is substituted with an aryl or an aryl $C_{1-2}$ alkyl, wherein the aryl is preferably monocyclic and more preferably phenyl.

In a preferred embodiment of compounds having formula I and, in particular, compounds having formula Ia, R1 is selected from H and $C_{1-4}$ alkyl, and R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. In one embodiment, R1 is selected from H, methyl and ethyl, and R2 is selected from aryl, heteroaryl, heterocyclyl, and $C_{5-8}$ cycloalkyl, each of which are monocyclic and may be substituted or unsubstituted. More preferably, R1 is selected from H and methyl. In one embodiment, R1 is methyl. In an alternative embodiment, R1 is H. More preferably, R2 is selected from saturated heterocyclyl, and $C_{5-8}$ cycloalkyl, each of which are monocyclic and may be substituted or unsubstituted. When R2 is a monocyclic $C_{5-8}$ cycloalkyl, it is preferably unsubstituted. Preferably, R2 is a cyclopentyl or cyclohexyl. More preferably, R2 is a cyclohexyl, such as an unsubstituted cyclohexyl. When R2 is a monocyclic saturated heterocyclyl, the heterocyclyl ring preferably contains a single heteroatom. More preferably, the heterocyclyl is six membered, such as a piperidinyl or tetrahydropyranyl group. The nitrogen heteroatom may be substituted or unsubstituted.

In an alternative embodiment, R1 is selected from H, methyl and ethyl, and R2 is selected from aryl $C_{1-6}$ alkyl, heteroaryl $C_{1-6}$ alkyl, heterocyclyl $C_{1-6}$ alkyl, and $C_{5-8}$ cycloalkyl $C_{1-6}$ alkyl, each of which are monocyclic and may be substituted or unsubstituted. More preferably, R2 is aryl $C_{1-6}$ alkyl in which the aryl is monocyclic and may be substituted or unsubstituted. More preferably still, R2 is aryl $C_{1-6}$ alkyl in which the aryl is monocyclic and may be substituted or unsubstituted and the $C_{1-6}$ alkyl is linear. Even more preferably, R2 is phenyl $C_{1-6}$ alkyl which may be substituted or unsubstituted and the $C_{1-6}$ alkyl is linear. In one embodiment, the phenyl is unsubstituted.

In an alternative embodiment, R1 is selected from H, methyl and ethyl, and R2 is $C_{1-4}$ alkyl substituted with a group selected from aryl $C_{1-4}$ alkoxy, heteroaryl $C_{1-4}$ alkoxy, heterocyclyl $C_{1-4}$ alkoxy, and $C_{5-8}$ cycloalkyl $C_{1-4}$ alkoxy, each of which are monocyclic and may be substituted or unsubstituted. Preferably, R2 is substituted $C_{1-3}$ alkyl. In one embodiment, R2 is substituted $C_{1-2}$ alkyl. Preferably, the substituent of R2 is aryl $C_{1-4}$ alkoxy in which the aryl is monocyclic and may be substituted or unsubstituted. More preferably still, the substituent of R2 is aryl $C_{1-4}$ alkoxy in which the aryl is monocyclic and may be substituted or unsubstituted and the $C_{1-4}$ alkoxy is linear. Even more preferably, the substituent of R2 is phenyl $C_{1-4}$ alkoxy which may be substituted or unsubstituted and the $C_{1-4}$ alkoxy is linear. In one embodiment, the substituent of R2 is aryl $C_{1-3}$ alkoxy in which the aryl is monocyclic (e.g. phenyl) and may be substituted or unsubstituted and the $C_{1-3}$ alkoxy is linear. In some embodiments, the phenyl is unsubstituted.

In yet another embodiment of compounds having formula I and, in particular, compounds having formula Ia, R1 is selected from H and $C_{1-4}$ alkyl, and R2 is selected from heterocyclyl which may be substituted or unsubstituted. Preferably, R1 is H, methyl or ethyl, and R2 is a bicyclic heterocyclyl which may be substituted or unsubstituted. More preferably, R1 is H or methyl, and R2 is a bicyclic heterocyclyl which may be substituted or unsubstituted, wherein one of the rings of the heterocyclyl contains two oxygen atoms. In one embodiment, R2 is 3,3-dimethyl-1,5-dioxaspiro[5,5]undec-9-yl.

In an alternative preferred embodiment of compounds having formula I and, in particular, compounds having formula Ia, R1 is selected from H and $C_{1-4}$ alkyl, and R2 is $C_{2-20}$ alkyl. More preferably, R1 is H, methyl or ethyl and more preferably still, R1 is H or methyl. Preferably, R2 is $C_{3-16}$ alkyl, wherein the alkyl is a linear alkyl. More preferably, R2 is $C_{4-14}$ alkyl, wherein the alkyl is a linear alkyl.

Formula IIa

In a preferred embodiment of compounds having Formula IIa, R1 is selected from H and $C_{1-4}$ alkyl, and R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. More preferably, R1 is selected from H, methyl and ethyl, and R2 is selected from aryl, heteroaryl, heterocyclyl, and $C_{3-10}$ cycloalkyl each of which may be substituted or unsubstituted. More preferably, R1 is methyl. More preferably, R2 is selected from aryl, heteroaryl, heterocyclyl, and $C_{5-8}$ cycloalkyl each of which are monocyclic and may be substituted or unsubstituted. More preferably still, R2 is selected from aryl such as phenyl, saturated heterocyclyl, and $C_{5-8}$ cycloalkyl each of which are monocyclic and may be substituted or unsubstituted. When R2 is a monocyclic $C_{5-8}$ cycloalkyl (i.e. cyclopentyl, cyclohexyl, cycloheptyl or cyclooctyl) or aryl, it is preferably unsubstituted. Preferably, R2 is a cyclohexyl, such as an unsubstituted cyclohexyl. When R2 is a monocyclic saturated heterocyclyl, the heterocyclyl ring preferably contains a single heteroatom, such as nitrogen or oxygen. More preferably, the heterocyclyl is six membered, such as a piperidinyl or tetrahydropyranyl group. In one embodiment, the heteroatom is a nitrogen heteroatom which may be substituted or unsubstituted. Preferably, the heteroatom in the said heterocyclyl group is at the 4-position relative to the position of attachment of the heterocyclyl group R2 to the urea nitrogen. In one embodiment, the nitrogen atom is substituted with monocyclic aryl (preferably phenyl) $C_{1-3}$ alkyl; preferably, the nitrogen atom is substituted with benzyl or phenylethyl; and, more preferably, the nitrogen atom is substituted with benzyl.

In an alternative preferred embodiment of compounds having Formula IIa, R1 and R2, together with the N to which they are attached, form a heterocyclyl group which may be substituted or unsubstituted. Preferably, the heterocyclyl is a 5 or 6 membered monocyclic ring and, more preferably, a 5 membered monocyclic ring. In certain embodiments, the said heterocyclyl contains one or two, preferably 1, additional heteroatoms (i.e. in addition to the N). These additional heteroatoms may be, for example, N, O and/or S. Preferably, the heterocyclyl is oxazolidinyl. Preferably, the oxygen atom in the oxazolidinyl is at the 3 position relative to the urea nitrogen. Preferably, the oxazolidinyl is substituted with one, two or three methyl or ethyl groups. More preferably, the oxazolidinyl is substituted with two methyl or ethyl groups. More preferably still, the oxazolidinyl is substituted with two methyl groups on the same carbon atom. More preferably, the oxazolidinyl is 4,4-dimethyloxazolidin-3-yl.

In yet another preferred embodiment of compounds having formula IIa, R1 and R2, together with the N to which they are attached, form a heterocyclyl group which may be substituted or unsubstituted. Preferably, the heterocyclyl is a 5 or 6 membered monocyclic ring, more preferably, a 6 membered monocyclic ring. In certain embodiments, the said heterocyclyl contains one or two, preferably 1, additional heteroatoms (i.e. in addition to the N). These additional heteroatoms may be, for example, N, O and/or S. In one embodiment, the heterocyclyl is morpholino. In an alternative embodiment, the heterocyclyl is piperazinyl. In other embodiments, the said heterocyclyl contains no additional heteroatoms (i.e. it contains a single N atom). In one embodiment, the heterocyclyl is piperadinyl. Where the heterocyclyl is substituted, it is preferably substituted with aryl, aryl $C_{1-4}$ alkyl, $C_{5-6}$ cycloalkyl, or $C_{5-6}$ cycloalkyl $C_{1-4}$ alkyl, wherein the aryl is preferably monocyclic and more preferably phenyl, and the cycloalkyl is preferably cyclohexyl. The alkyl is preferably linear. In one embodiment, the heterocyclyl is substituted with an aryl or an aryl $C_{1-4}$ alkyl (preferably $C_{1-2}$ alkyl), wherein the aryl is preferably monocyclic and more preferably phenyl. The aryl may optionally be substituted with one or more halogen atoms.

In compounds having formula IIa, R5 is preferably selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, $NO_2$, NHR5a, NR5aR5b, COR5a, CSR5a, CN, COOH, COOR5a, $CONH_2$, $SO_2$R5a, $SO_3H$, $SO_2NH_2$, CONR5aR5b, $SO_2$NR5aR5b, wherein R5a and R5b are independently selected from $C_{1-6}$ alkyl, aryl, heteroaryl, $C_{3-8}$ cycloalkyl and heterocyclyl, and R5a and R5b, together with the heteroatom to which they are joined, can form heterocyclyl. More preferably, R5 is selected from 14, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$. More preferably still, R5 is selected from H, $C_{1-4}$ alkyl, aryl, heteroaryl, heterocyclyl, $C_{5-8}$ cycloalkyl, $C_{1-4}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$, wherein the aryl, heteroaryl, heterocyclyl and $C_{5-8}$ cycloalkyl groups are monocyclic. Even more preferably, R5 is selected from H, $C_{1-3}$ alkyl, aryl, heteroaryl, heterocyclyl, $C_{5-8}$ cycloalkyl, halogen, OH, $NH_2$, COOH and $CONH_2$, wherein the aryl, heteroaryl, heterocyclyl and $C_{5-8}$ cycloalkyl groups are monocyclic. More preferably still, R5 is selected from H, $C_{1-2}$ alkyl and halogen. Even more preferably, R5 is selected from H and halogen such as F, Cl and Br. In one embodiment, R5 is H.

In compounds having formula IIa, R6 is preferably selected from aryl, heteroaryl, heterocyclyl and $C_{3-8}$ cycloalkyl, each of which may be substituted or unsubstituted. More preferably, R6 is selected from aryl and heteroaryl each of which may be substituted or unsubstituted. In one embodiment, the heteroaryl contains one heteroatom, e.g. an oxygen or nitrogen atom. Preferably, the aryl or heteroaryl is monocyclic. More preferably, the aryl or heteroaryl is a six membered monocyclic ring, for example, phenyl or pyridyl. In one embodiment, the heteroaryl contains a nitrogen atom which is substituted with an oxygen atom such as oxidopyridyl. In another embodiment, R6 is unsubstituted monocyclic aryl such as phenyl, or monocyclic aryl such as phenyl substituted with one or more groups selected from halogen, $C_{1-2}$ alkoxy (optionally substituted with one or more halogen atoms), or OH.

In one embodiment, R6 is unsubstituted or substituted 2-oxo-2,3-dihydro-1H-benzo[d]imidazolyl.

When R6 is substituted, the substituent is preferably one or more groups selected from halogen, $C_{1-4}$ alkoxy, aryl, heteroaryl, heterocyclyl, OH, CN, $CONH_2$, $NH_2$, heterocyclyl $C_{1-4}$ alkoxy, aryl $C_{1-4}$ alkoxy, heteroaryl $C_{1-4}$ alkoxy, $NO_2$, $SO_2NH_2$, $SO_3$, $C(NOH)NH_2$, CONHOH, 2H-tetrazol-5-yl, dimethylamino, benzylamino, methylsulfonyl, morpholinosulfonyl and piperidinylsulfonyl. The piperidinylsulfonyl may optionally be substituted with arylmethoxy (preferably benzoxy) or OH. Preferably, the aryl, heteroaryl and heterocyclyl are monocyclic. In one embodiment, the aryl, heteroaryl and heterocyclyl are six-membered monocyclic rings. In a particular embodiment in which R6 is monocyclic aryl, it may optionally be substituted with one or more groups selected from halogen, OH, $C_{1-3}$ alkoxy (preferably $C_{1-2}$ alkoxy), aryl (e.g. a monocyclic aryl such as phenyl), heteroaryl (e.g. monocyclic heteroaryl containing one or two nitrogen atoms, or one oxygen atom), heterocyclyl (e.g. piperazinyl, piperadinyl or morpholino) $C_{1-3}$ alkoxy (preferably $C_{1-2}$ alkoxy), aryl (e.g. monocyclic aryl such as phenyl) $C_{1-3}$ alkoxy (preferably $C_{1-2}$ alkoxy), $CONH_2$, $NH_2$, $NO_2$, $OCHF_2$, $SO_2NH_2$, morpholinosulfonyl and $C(NOH)NH_2$.

In another embodiment in which R6 is monocyclic aryl, it may optionally be substituted with one or more groups selected from halogen, OH, methoxy, phenyl, pyridyl, pyrazinyl, pyranyl, piperazinylmethoxy, piperadinylmethoxy, morpholinomethoxy, benzyloxy, $CONH_2$, $NH_2$, $NO_2$, $OCHF_2$, $SO_2NH_2$, morpholinosulfonyl and $C(NOH)NH_2$.

In one embodiment when R6 is monocyclic aryl such as phenyl, the substituent of R6 is aryl, preferably monocyclic aryl such as phenyl, which may be substituted or unsubstituted. Where it is substituted, preferably it is substituted with $CONH_2$.

When the substituent of R6 is $C_{1-4}$ alkoxy, aryl, heteroaryl, heterocyclyl, heterocyclyl $C_{1-4}$ alkoxy, aryl $C_{1-4}$ alkoxy, heteroaryl $C_{1-4}$ alkoxy or $SO_3$, each of these moieties may optionally be substituted with one or more groups selected from halogen, OH, $C_{1-3}$ alkoxy (which may be substituted with one or more halogen), $CONH_2$, CN, $NCH_3CH_3$, $NHCOCH_3$, methylhydroxybutyl, and methylhydroxybutynyl.

In compounds having formula IIa, R8 is preferably selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R8a, halogen, OH, OR8a, SH, SR8a, OCOR8a, SCOR8a, $NH_2$, $NO_2$, NHR8a, NR8aR8b, COR8a, CSR8a, CN, COOH, COOR8a, $CONH_2$, $SO_2R8a$, $SO_3H$, $SO_2NH_2$, CONR8aR8b, $SO_2NR8aR8b$, wherein R8a and R8b are independently selected from $C_{1-6}$ alkyl, aryl, heteroaryl, $C_{3-8}$ cycloalkyl and heterocyclyl, and R8a and R8b, together with the heteroatom to which they are joined, can form heterocyclyl. More preferably, R8 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$. More preferably still, R8 is selected from H, $C_{1-4}$ alkyl, aryl, heteroaryl, heterocyclyl, $C_{5-8}$ cycloalkyl, $C_{1-4}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$, wherein the aryl, heteroaryl, heterocyclyl and $C_{5-8}$ cycloalkyl groups are monocyclic. Even more preferably, R8 is selected from H, $C_{1-3}$ alkyl, aryl, heteroaryl, heterocyclyl, $C_{5-8}$ cycloalkyl, halogen, OH, $NH_2$, COOH and $CONH_2$, wherein the aryl, heteroaryl, heterocyclyl and $C_{5-8}$ cycloalkyl groups are monocyclic. More preferably still, R8 is selected from H, $C_{1-2}$ alkyl, halogen and monocyclic aryl such as phenyl. Even more preferably, R8 is selected from H, $C_{1-2}$ alkyl, and halogen such as F, Cl and Br. More preferably still, R8 is selected from H and halogen such as F, Cl and Br. In one embodiment, R8 is H.

In one embodiment of compounds having formula IIa, R1 is selected from H and $C_{1-4}$ alkyl, R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may optionally be substituted with one or more groups selected from R2a, halogen, OH, OR2a, OCOR2a, SH, SR2a, SCOR2a, $NH_2$, NHR2a, $NHSO_2NH_2$, $NHSO_2R2a$, NR2aCOR2b, $NHC(NH)NH_2$, NHCOR2a, NR2aR2b, COR2a, CSR2a, CN, COOH, COOR2a, $CONH_2$, CONHOH, CONHR2a, CONHOR2a, $C(NOH)NH_2$, $SO_2R2a$, $SO_3H$, $SO_2NH_2$, CONR2aR2b, $SO_2NR2aR2b$, wherein R2a and R2b are independently selected from $C_{1-6}$ alkyl, substituted $C_{1-6}$ alkyl, aryl, heteroaryl, $C_{3-8}$ cycloalkyl and heterocyclyl, or R2a and R2b, together with the heteroatom to which they are joined, can form heterocyclyl, wherein, when the substituent of R2 is $C_{1-6}$ alkyl, substituted $C_{1-6}$ alkyl, aryl, heteroaryl, $C_{3-8}$ cycloalkyl, heterocyclyl or a group containing one or more of these moieties, each of these moieties may optionally be substituted with one or more groups selected from R2c, halogen, OH, OR2c, OCOR2c, SH, SR2c, SCOR2c, $NH_2$, NHR2c, $NHSO_2NH_2$, $NHSO_2R2c$, NR2cCOR2d, $NHC(NH)NH_2$, NHCOR2c, NR2cR2d, COR2c, CSR2c, CN, COOH, COOR2c, $CONH_2$, CONHOH, CONHR2c, CONHOR2c, $C(NOH)NH_2$, $SO_2R2c$, $SO_3H$, $SO_2NH_2$, CONR2cR2d, $SO_2NR2cR2d$, wherein R2c and R2d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, R5 is selected from H, R5a, halogen, OH, OR5a, OCOR5a, SH, SR5a, SCOR5a, $NH_2$, NHR5a, $NHSO_2NH_2$, $NHSO_2R5a$, NR5aCOR5b, $NHC(NH)NH_2$, NHCOR5a, NR5aR5b, COR5a, CSR5a, CN, COOH, COOR5a, $CONH_2$, CONHOH, CONHR5a, CONHOR5a, $C(NOH)NH_2$, $SO_2R5a$, $SO_3H$, $SO_2NH_2$, CONR5aR5b, $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl, R6 is selected from aryl, heteroaryl, heterocyclyl, $C_{3-10}$ cycloalkyl, each of which may optionally be substituted with one or more groups selected from R6a, halogen, OH, OR6a, OCOR6a, SH, SR6a, SCOR6a, $NH_2$, NHR6a, $NHSO_2NH_2$, $NHSO_2R6a$, NR6aCOR6b, $NHC(NH)NH_2$, NHCOR6a, NR6aR6b, COR6a, CSR6a, CN, COOH, COOR6a, $CONH_2$, CONHOH, CONHR6a, CONHOR6a, $C(NOH)NH_2$, $SO_2R6a$, $SO_3H$, $SO_2NH_2$, $CONR6aR6b$, $SO_2NR6aR6b$, wherein R6a and R6b are independently selected from $C_{1-6}$ alkyl, substituted $C_{1-6}$ alkyl, aryl, heteroaryl, $C_{3-8}$ cycloalkyl and heterocyclyl, or R6a and R6b, together with the heteroatom to which they are joined, can form heterocyclyl, and wherein, when R6 is heteroaryl or heterocyclyl, each of these moieties may optionally be substituted with one or more oxygen atoms, wherein, when the substituent of R6 is $C_{1-6}$ alkyl, substituted $C_{1-6}$ alkyl, aryl, heteroaryl, $C_{3-8}$ cycloalkyl, heterocyclyl or a group containing one or more of these moieties, each of these moieties may optionally be substituted with one or more groups selected from R6c, halogen, OH, OR6c, OCOR6c, SH, SR6c, SCOR6c, $NH_2$, NHR6c, $NHSO_2NH_2$, $NHSO_2R6c$, NR6cCOR6d, $NHC(NH)NH_2$, NHCOR6c, NR6cR6d, COR6c, CSR6c, CN, COOH, COOR6c, $CONH_2$, CONHOH, CONHR6c, CONHOR6c, $C(NOH)NH_2$, $SO_2R6c$, $SO_3H$, $SO_2NH_2$, $CONR6cR6d$, $SO_2NR6cR6d$, wherein R6c and R6d are independently selected from $C_{1-6}$ alkyl, substituted $C_{1-6}$ alkyl, aryl, heteroaryl, $C_{3-8}$ cycloalkyl and heterocyclyl, or R2c and R2d, together with the heteroatom to which they are joined, can form heterocyclyl, and wherein, when the substituent of R6 is heteroaryl or heterocyclyl, each of these moieties may optionally be substituted with one or more oxygen atoms, and R8 is selected from H, R5a, halogen, OH, OR5a, OCOR5a, SH, SR5a, SCOR5a, $NH_2$, NHR5a, $NHSO_2NH_2$, $NHSO_2R5a$, NR5aCOR5b, $NHC(NH)NH_2$, NHCOR5a, NR5aR5b, COR5a, CSR5a, CN, COOH, COOR5a, $CONH_2$, CONHOH, CONHR5a, CONHOR5a, $C(NOH)NH_2$, $SO_2R5a$, $SO_3H$, $SO_2NH_2$, $CONR5aR5b$, $SO_2NR5aR5b$, wherein R5a and R5b are independently selected from $C_{1-6}$ alkyl, substituted $C_{1-6}$ alkyl, aryl, heteroaryl, $C_{3-8}$ cycloalkyl and heterocyclyl, or R5a and R5b, together with the heteroatom to which they are joined, can form heterocyclyl.

In the above embodiment, preferably, R1 is selected from H, methyl and ethyl, and R2 is selected from aryl, heteroaryl, heterocyclyl, and $C_{3-10}$ cycloalkyl each of which may be substituted or unsubstituted. More preferably, R1 is methyl. More preferably, R2 is selected from aryl, heteroaryl, heterocyclyl, and $C_{5-8}$ cycloalkyl each of which are monocyclic and may be substituted or unsubstituted. More preferably still, R2 is selected from heterocyclyl, and $C_{5-8}$ cycloalkyl each of which are monocyclic and may be substituted or unsubstituted. Preferably, the heterocyclyl is fully saturated. When R2 is a monocyclic $C_{5-8}$ cycloalkyl (i.e. cyclopentyl, cyclohexyl, cycloheptyl or cyclooctyl), it is preferably unsubstituted. In one embodiment, R2 is a cyclopentyl or a cyclohexyl, such as an unsubstituted cyclopentyl or unsubstituted cyclohexyl. When R2 is a monocyclic saturated heterocyclyl, the heterocyclyl ring preferably contains a single heteroatom, such as nitrogen or oxygen. Preferably, the heterocyclyl is six membered, such as a piperidinyl or tetrahydropyranyl group. Preferably, the heteroatom in the said heterocyclyl group is at the 4-position relative to the position of attachment of the heterocyclyl group R2 to the urea nitrogen. In one embodiment, the heteroatom is a nitrogen heteroatom which may be substituted or unsubstituted.

In a particular embodiment, the nitrogen atom is substituted with a group selected from CN, $CONH_2$, $C(NOH)NH_2$, $SO_2$—$C_{1-4}$ alkyl, $SO_2$-aryl (optionally substituted with a $C_{1-4}$ alkyl or $C_{1-4}$ haloalkyl, such as trifluoromethyl), CO-heteroaryl (optionally substituted with a heteroaryl or halogen), CO—$C_{1-4}$ alkyl, COO—$C_{1-4}$ alkyl, $C_{1-4}$ alkyl (optionally substituted with OH, CN, COOH), aryl $C_{1-3}$ alkyl, heteroaryl $C_{1-3}$ alkyl such as piperidinyl $C_{1-3}$ alkyl (optionally substituted with COO—$C_{1-3}$ alkyl), heterocyclyl $C_{1-3}$ alkyl, aryl, heteroaryl (optionally substituted with one or more halogens such as chlorine), and heterocyclyl. Preferably, the nitrogen atom is substituted with a group selected from CN, $CONH_2$, $C(NOH)NH_2$, $SO_2$—$C_{1-4}$ alkyl, $SO_2$-monocyclic aryl (optionally substituted with a $C_{1-4}$ haloalkyl, such as trifluoromethyl), CO-monocyclic heteroaryl (optionally substituted with a monocyclic heteroaryl or halogen), CO—$C_{1-4}$ alkyl, COO—$C_{1-4}$ alkyl, $C_{1-4}$ alkyl (optionally substituted with OH, CN, COOH), monocyclic aryl $C_{1-3}$ alkyl, monocyclic heteroaryl $C_{1-3}$ alkyl such as piperidinyl $C_{1-3}$ alkyl (optionally substituted with COO—$C_{1-3}$ alkyl), monocyclic heterocyclyl $C_{1-3}$ alkyl, monocyclic aryl, monocyclic heteroaryl (optionally substituted with one or more halogens such as chlorine), and monocyclic heterocyclyl. More preferably, the nitrogen atom is substituted with a group selected from CN, $C_{1-4}$ alkyl (optionally substituted with OH, CN, COOH), monocyclic aryl $C_{1-3}$ alkyl, and monocyclic heteroaryl $C_{1-3}$ alkyl (preferably piperidinyl $C_{1-3}$ alkyl). More preferably still, the nitrogen atom is substituted with a group selected from $C_{1-4}$ alkyl (optionally substituted with OH, CN, COOH), monocyclic aryl $C_{1-3}$ alkyl, and monocyclic heteroaryl $C_{1-3}$ alkyl (preferably piperidinyl $C_{1-3}$ alkyl).

In one embodiment, the nitrogen atom is substituted with monocyclic aryl (preferably phenyl) $C_{1-3}$ alkyl; preferably, the nitrogen atom is substituted with benzyl or phenylethyl; and, more preferably, the nitrogen atom is substituted with benzyl.

In one embodiment R5 is H, halogen, OH or $C_{1-4}$ alkyl. Preferably, R5 is H.

In another embodiment, R6 is selected from aryl, heteroaryl, and heterocyclyl, each of which may be substituted or unsubstituted. Preferably, R6 is selected from monocyclic aryl (such as phenyl), monocyclic heteroaryl (such as pyridyl), and heterocyclyl, each of which may be substituted or unsubstituted. In one embodiment, R6 is an unsubstituted aryl. When R6 is a substituted aryl, it is preferably substituted with one or more groups selected from halogen, R6a, OH, OR6a, $NH_2$, $NO_2$, $NHC(NH)NH_2$, NHR6a, NR6aR6b, $C(NOH)NH_2$, COR6a, COOH, COOR6a, $CONH_2$, CONHOH, $SO_2R6a$, $SO_2NR6aR6b$, wherein R6a and R6b are independently selected from $C_{1-6}$ alkyl, substituted $C_{1-6}$ alkyl, aryl, heteroaryl, $C_{3-8}$ cycloalkyl and heterocyclyl, wherein R6a and R6b are independently selected from $C_{1-6}$ alkyl, substituted $C_{1-6}$ alkyl, aryl, heteroaryl, $C_{3-8}$ cycloalkyl and heterocyclyl, wherein, when the substituent of R6 is $C_{1-6}$ alkyl, substituted $C_{1-6}$ alkyl, aryl, heteroaryl, $C_{3-8}$ cycloalkyl, heterocyclyl or is a group containing one or more of these moieties, each of these moieties may optionally be substituted with one or more groups selected from OR6c, OH, and $CONH_2$, wherein R6c and R6d are independently selected from $C_{1-6}$ alkyl, substituted $C_{1-6}$ alkyl, aryl, heteroaryl, $C_{3-8}$ cycloalkyl and heterocyclyl, and wherein, when the substituent of R6 is heteroaryl or heterocyclyl, each of these moieties may optionally be substituted with one or more oxygen atoms.

Preferably, when R6 is a substituted aryl, it is substituted with one or more groups selected from halogen, OH, $C_{1-4}$ alkoxy, $CONH_2$, $C(NOH)NH_2$, CONHOH, $SO_2$—$C_{1-4}$ alkyl, heterocyclyl (optionally substituted with an oxygen atom), and aryl (optionally substituted with $CONH_2$). In one embodiment, R6 may be substituted with one or more groups selected from 5-oxo-4,5-dihydro-1,2,4-oxadiazol-3-yl, 3-carbamoylphenyl, 2H-tetrazol-5-yl, $C_{1-4}$ alkoxy, halogen, OH, CONHOH.

When R6 is a heterocyclyl, it is preferably substituted with an oxygen atom. The substituent of R6 may be 2-oxo-2,3-dihydro-1H-benzo[d]imidazol-5-yl or 2-oxo-2,3-dihydrobenzo[d]oxazol-5-yl.

When R6 is a heteroaryl, it is preferably unsubstituted or substituted with an oxygen atom. For example, the heterocyclyl may contain an N-oxide. In one embodiment, R6 is pyridyl or pyridyl oxide.

In another embodiment, R8 is H, halogen, OH or $C_{1-4}$ alkyl. Preferably, R8 is H.

Formula IIb

In a preferred embodiment of compounds having Formula IIb, R1 is selected from H and $C_{1-4}$ alkyl, and R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. More preferably, R1 is selected from H, methyl and ethyl, and R2 is selected from aryl, heteroaryl, heterocyclyl, and $C_{3-10}$ cycloalkyl each of which may be substituted or unsubstituted. More preferably, R1 is methyl. More preferably, R2 is selected from aryl, heteroaryl, heterocyclyl, and $C_{5-8}$ cycloalkyl each of which may be monocyclic and may be substituted or unsubstituted. More preferably still, R2 is monocyclic aryl such as phenyl and may be substituted or unsubstituted. When R2 is substituted, the substituent may be aryl, $C_{1-4}$ alkoxy, aryl $C_{1-4}$ alkoxy or aryloxy. Preferably, the substituent of R2 is aryl, $C_{1-3}$ alkoxy, aryl $C_{1-3}$ alkoxy or aryloxy, wherein the aryl is monocyclic and more preferably, phenyl.

When R2 is a monocyclic $C_{5-8}$ cycloalkyl or aryl, it is preferably unsubstituted. Preferably, R2 is a cyclohexyl, such as an unsubstituted cyclohexyl. When R2 is a monocyclic saturated heterocyclyl, the heterocyclyl ring preferably contains a single heteroatom, such as nitrogen or oxygen. More preferably, the heterocyclyl is six membered, such as a piperidinyl or tetrahydropyranyl group. In one embodiment the heteroatom is a nitrogen heteroatom which may be substituted or unsubstituted. Preferably, the heteroatom in the said heterocyclyl group is at the 4 position relative to the position of attachment of the heterocyclyl group R2 to the urea nitrogen. In one embodiment, the nitrogen atom is substituted with monocyclic aryl (preferably phenyl) $C_{1-3}$ alkyl.

In an alternative preferred embodiment of compounds having Formula IIb, R1 and R2, together with the N to which they are attached, form a heterocyclyl group which may be substituted or unsubstituted. Preferably, the heterocyclyl is a 5 or 6 membered monocyclic ring and, more preferably, a 5 membered monocyclic ring. In certain embodiments, the said heterocyclyl contains one or two, preferably 1, additional heteroatoms (i.e. in addition to the N). These additional heteroatoms may be, for example, N, O and/or S. Preferably, the heterocyclyl is oxazolidinyl. Preferably, the oxygen atom in the oxazolidinyl is at the 3 position relative to the urea nitrogen. Preferably, the oxazolidinyl is substituted with one, two or three methyl or ethyl groups. More preferably, the oxazolidinyl is substituted with two methyl or ethyl groups. More preferably still, the oxazolidinyl is substituted with two methyl groups on the same carbon atom. More preferably, the oxazolidinyl is 4,4-dimethyloxazolidin-3-yl.

In yet another preferred embodiment of compounds having formula IIb, R1 and R2, together with the N to which they are attached, form a heterocyclyl group which may be substituted or unsubstituted. Preferably, the heterocyclyl is a 5 or 6 membered monocyclic ring, more preferably, a 6 membered monocyclic ring. In certain embodiments, the said heterocyclyl contains one or two, preferably 1, additional heteroatoms (i.e. in addition to the N). These additional heteroatoms may be, for example, N, O and/or S. In one embodiment, the heterocyclyl is morpholino. In an alternative embodiment, the heterocyclyl is piperazinyl. In other embodiments, the said heterocyclyl contains no additional heteroatoms (i.e. it contains a single N atom). In one embodiment, the heterocyclyl is piperadinyl. Where the heterocyclyl is substituted, it is preferably substituted with aryl, aryl $C_{1-4}$ alkyl, $C_{5-6}$ cycloalkyl, or $C_{5-6}$ cycloalkyl $C_{1-4}$ alkyl, wherein the aryl is preferably monocyclic and more preferably phenyl, and the cycloalkyl is preferably cyclohexyl. The alkyl is preferably linear. In one embodiment, the heterocyclyl is substituted with an aryl or an aryl $C_{1-4}$ alkyl (preferably $C_{1-2}$ alkyl), wherein the aryl is preferably monocyclic and more preferably phenyl. The aryl may optionally be substituted with one or more halogen.

In compounds having formula IIb, R5 is preferably selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, $NO_2$, NHR5a, NR5aR5b, COR5a, CSR5a, CN, COOH, COOR5a, $CONH_2$, $SO_2R5a$, $SO_3H$, $SO_2NH_2$, CONR5aR5b, $SO_2NR5aR5b$, wherein R5a and R5b are independently selected from $C_{1-6}$ alkyl, aryl, heteroaryl, $C_{3-8}$ cycloalkyl and heterocyclyl, and R5a and R5b, together with the heteroatom to which they are joined, can form heterocyclyl. More preferably, R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$. More preferably still, R5 is selected from H, $C_{1-4}$ alkyl, aryl, heteroaryl, heterocyclyl, $C_{5-8}$ cycloalkyl, $C_{1-4}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$, wherein the aryl, heteroaryl, heterocyclyl and $C_{5-8}$ cycloalkyl groups are monocyclic. Even more preferably, R5 is selected from H, $C_{1-3}$ alkyl, aryl, heteroaryl, heterocyclyl, $C_{5-8}$ cycloalkyl, halogen, OH, $NH_2$, COOH and $CONH_2$, wherein the aryl, heteroaryl, heterocyclyl and $C_{5-8}$ cycloalkyl groups are monocyclic. More preferably still, R5 is selected from H, $C_{1-2}$ alkyl and halogen. Even more preferably, R5 is selected from H and halogen such as F, Cl and Br. In one embodiment, R5 is H.

In compounds having formula IIb, R6 is preferably selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R6a, halogen, OH, OR6a, SH, SR6a, OCOR6a, SCOR6a, $NH_2$, $NO_2$, NHR6a, NR6aR6b, COR6a, CSR6a, CN, COOH, COOR6a, $CONH_2$, $SO_2R6a$, $SO_3H$, $SO_2NH_2$, CONR6aR6b, $SO_2NR6aR6b$, wherein R6a and R6b are independently selected from $C_{1-6}$ alkyl, aryl, heteroaryl, $C_{3-8}$ cycloalkyl and heterocyclyl, and R6a and R6b, together with the heteroatom to which they are joined, can form heterocyclyl. More preferably, R6 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$. More preferably still, R6 is selected from H, $C_{1-4}$ alkyl, aryl, heteroaryl, heterocyclyl, $C_{5-8}$ cycloalkyl, $C_{1-4}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$, wherein the aryl, heteroaryl, heterocyclyl and $C_{5-8}$ cycloalkyl groups are monocyclic. Even more preferably, R6 is selected from H, $C_{1-3}$ alkyl, aryl, heteroaryl, heterocyclyl, $C_{5-8}$ cycloalkyl, halogen, OH, $NH_2$, COOH and $CONH_2$, wherein the aryl, heteroaryl, heterocyclyl and $C_{5-8}$ cycloalkyl groups are monocyclic. More preferably still, R6 is selected from H, $C_{1-2}$ alkyl and halogen. Even more preferably, R6 is selected from H and halogen such as F, Cl and Br. In one embodiment, R6 is H.

In compounds having formula IIb, R7 is preferably selected from aryl, heteroaryl, heterocyclyl and $C_{3-8}$ cycloalkyl each of which may be substituted or unsubstituted. More preferably, R7 is selected from aryl and heteroaryl each of which may be substituted or unsubstituted. In one embodiment, the heteroaryl contains one heteroatom, e.g. an oxygen or nitrogen atom. Preferably, the aryl or heteroaryl is monocyclic. More preferably, the aryl or heteroaryl is a six membered monocyclic ring. In one embodiment, the heteroaryl contains a nitrogen atom which is substituted with an oxygen atom such as oxidopyridyl. In another embodiment, R7 is unsubstituted monocyclic aryl such as phenyl, or monocyclic aryl such as phenyl substituted with one or more groups selected from halogen, $C_{1-2}$ alkoxy (optionally substituted with one or more halogen), or OH. In a particular embodiment, R7 is unsubstituted monocyclic aryl such as phenyl.

When R7 is substituted, the substituent is preferably one or more groups selected from halogen, $C_{1-4}$ alkoxy, aryl, heteroaryl, heterocyclyl, OH, $CONH_2$, $NH_2$, heterocyclyl $C_{1-4}$ alkoxy, aryl $C_{1-4}$ alkoxy, heteroaryl $C_{1-4}$ alkoxy, $NO_2$, $SO_2NH_2$, $SO_3$, $C(NOH)NH_2$ and morpholinosulfonyl. Preferably, the aryl, heteroaryl and heterocyclyl are monocyclic. In one embodiment, the aryl, heteroaryl and heterocyclyl are six membered monocyclic rings. In a particular embodiment in which R7 is monocyclic aryl, it may optionally be substituted with aryl or heteroaryl, each of which are monocyclic.

Formula IIc

In a preferred embodiment of compounds having Formula IIc, R1 is selected from H and $C_{1-4}$ alkyl, and R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. More preferably, R1 is selected from H, methyl and ethyl, and R2 is selected from aryl, heteroaryl, heterocyclyl, and $C_{3-10}$ cycloalkyl each of which may be substituted or unsubstituted. More preferably, R1 is methyl. More preferably, R2 is selected from aryl, heteroaryl, heterocyclyl, and $C_{5-8}$ cycloalkyl each of which are monocyclic and may be substituted or unsubstituted. More preferably still, R2 is selected from aryl such as phenyl, saturated heterocyclyl, and $C_{5-8}$ cycloalkyl each of which are monocyclic and may be substituted or unsubstituted. When R2 is a monocyclic $C_{5-8}$ cycloalkyl or aryl, it is preferably unsubstituted. Preferably, R2 is a cyclohexyl, such as an unsubstituted cyclohexyl. When R2 is a monocyclic saturated heterocyclyl, the heterocyclyl ring preferably contains a single heteroatom such as nitrogen or oxygen. More preferably, the heterocyclyl is six membered, such as a piperidinyl or tetrahydropyranyl group. In one embodiment, the heteroatom is a nitrogen heteroatom which may be substituted or unsubstituted. Preferably, the heteroatom in the said heterocyclyl group is at the 4 position relative to the position of attachment of the heterocyclyl group R2 to the urea nitrogen. In one embodiment, the nitrogen atom is substituted with monocyclic aryl (preferably phenyl) $C_{1-3}$ alkyl.

In an alternative preferred embodiment of compounds having Formula IIc, R1 and R2, together with the N to which they are attached, form a heterocyclyl group which may be substituted or unsubstituted. Preferably, the heterocyclyl is a 5 or 6 membered monocyclic ring and, more preferably, a 5 membered monocyclic ring. In certain embodiments, the said heterocyclyl contains one or two, preferably 1, additional heteroatoms (i.e. in addition to the N). These additional heteroatoms may be, for example, N, O and/or S. Preferably, the heterocyclyl is oxazolidinyl. Preferably, the oxygen atom in the oxazolidinyl is at the 3 position relative to the urea nitrogen. Preferably, the oxazolidinyl is substituted with one, two or three methyl or ethyl groups. More preferably, the oxazolidinyl is substituted with two methyl or ethyl groups. More preferably still, the oxazolidinyl is substituted with two methyl groups on the same carbon atom. More preferably, the oxazolidinyl is 4,4-dimethyloxazolidin-3-yl.

In yet another preferred embodiment of compounds having formula IIe, R1 and R2, together with the N to which they are attached, form a heterocyclyl group which may be substituted or unsubstituted. Preferably, the heterocyclyl is a 5 or 6 membered monocyclic ring, more preferably, a 6 membered monocyclic ring. In certain embodiments, the said heterocyclyl contains one or two, preferably 1, additional heteroatoms (i.e. in addition to the N). These additional heteroatoms may be, for example, N, O and/or S. In one embodiment, the heterocyclyl is morpholino. In an alternative embodiment, the heterocyclyl is piperazinyl. In other embodiments, the said heterocyclyl contains no additional heteroatoms (i.e. it contains a single N atom). In one embodiment, the heterocyclyl is piperadinyl. Where the heterocyclyl is substituted, it is preferably substituted with aryl, aryl $C_{1-4}$ alkyl, $C_{5-6}$ cycloalkyl, or $C_{5-6}$ cycloalkyl $C_{1-4}$ alkyl, wherein the aryl is preferably monocyclic and more preferably phenyl, and the cycloalkyl is preferably cyclohexyl. The alkyl is preferably linear. In one embodiment, the heterocyclyl is substituted with an aryl or an aryl $C_{1-4}$ alkyl (preferably $C_{1-2}$ alkyl), wherein the aryl is preferably monocyclic and more preferably phenyl. The aryl may optionally be substituted with one or more halogen.

In compounds having formula IIc, R5 is preferably selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, $NO_2$, NHR5a, NR5aR5b, COR5a, CSR5a, CN, COOH, COOR5a, $CONH_2$, $SO_2R5a$, $SO_3H$, $SO_2NH_2$, CONR5aR5b, $SO_2NR5aR5b$, wherein R5a and R5b are independently selected from $C_{1-6}$ alkyl, aryl, heteroaryl, $C_{3-8}$ cycloalkyl and heterocyclyl, and R5a and R5b, together with the heteroatom to which they are joined, can form heterocyclyl. More preferably, R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$. More preferably still, R5 is selected from H, $C_{1-4}$ alkyl, aryl, heteroaryl, heterocyclyl, $C_{5-8}$ cycloalkyl, $C_{1-4}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$, wherein the aryl, heteroaryl, heterocyclyl and $C_{5-8}$ cycloalkyl groups are monocyclic. Even more preferably, R5 is selected from H, $C_{1-3}$ alkyl, aryl, heteroaryl, heterocyclyl, $C_{5-8}$ cycloalkyl, halogen, OH, $NH_2$, COOH and $CONH_2$, wherein the aryl, heteroaryl, heterocyclyl and $C_{5-8}$ cycloalkyl groups are monocyclic. More preferably still, R5 is selected from H, $C_{1-2}$ alkyl and halogen. Even more preferably, R5 is selected from H and halogen such as F, Cl and Br. In one embodiment, R5 is H.

In compounds having formula IIc, R6 is preferably selected from aryl, heteroaryl, heterocyclyl and $C_{3-8}$ cycloalkyl each of which may be substituted or unsubstituted. More preferably, R6 is selected from aryl and heteroaryl each of which may be substituted or unsubstituted. In one embodiment, the heteroaryl contains one heteroatom, e.g. an oxygen or nitrogen atom. Preferably, the aryl or heteroaryl is monocyclic. More preferably, the aryl or heteroaryl is a six membered monocyclic ring. In one embodiment, the heteroaryl contains a nitrogen atom which is substituted with an oxygen atom such as oxidopyridyl. In another embodiment, R6 is unsubstituted monocyclic aryl such as phenyl, or monocyclic aryl such as phenyl substituted with one or more groups selected from halogen, $C_{1-2}$ alkoxy (optionally substituted with one or more halogen), or OH. In a preferred embodiment, R6 is unsubstituted aryl and, preferably, a monocyclic aryl such as phenyl.

When R6 is substituted, the substituent is preferably one or more groups selected from halogen, $C_{1-4}$ alkoxy, aryl, heteroaryl, heterocyclyl, OH, $CONH_2$, $NH_2$, heterocyclyl $C_{1-4}$ alkoxy, aryl $C_{1-4}$ alkoxy, heteroaryl $C_{1-4}$ alkoxy, $NO_2$, $SO_2NH_2$, $SO_3$, $C(NOH)NH_2$ and morpholinosulfonyl. Preferably, the aryl, heteroaryl and heterocyclyl are monocyclic. In one embodiment, the aryl, heteroaryl and heterocyclyl are six membered monocyclic rings. In a particular embodiment in which R6 is monocyclic aryl, it may optionally be substituted with one or more groups selected from halogen, OH, $C_{1-3}$ alkoxy, aryl (e.g. a monocyclic aryl such as phenyl), heteroaryl (e.g. monocyclic heteroaryl containing one or two nitrogen atoms, or one oxygen atom), heterocyclyl (e.g. piperazinyl, piperadinyl or morpholino) $C_{1-3}$ alkoxy, aryl (e.g. monocyclic aryl such as phenyl) $C_{1-3}$ alkoxy, $CONH_2$, $NH_2$, $NO_2$, $OCHF_2$, $SO_2NH_2$, morpholinosulfonyl and $C(NOH)NH_2$.

In one embodiment when R6 is monocyclic aryl such as phenyl, the substituent of R6 is aryl, preferably monocyclic aryl such as phenyl, which may be substituted or unsubstituted. Where it is substituted, preferably it is substituted with $CONH_2$.

When the substituent of R6 is $C_{1-4}$ alkoxy, aryl, heteroaryl, heterocyclyl, heterocyclyl $C_{1-4}$ alkoxy, aryl $C_{1-4}$ alkoxy, heteroaryl $C_{1-4}$ alkoxy or $SO_3$, each of these moieties may optionally be substituted with one or more groups selected from halogen, OH, $C_{1-3}$ alkoxy (which may be substituted with one or more halogen), $CONH_2$, CN, $NCH_3CH_3$, $NHCOCH_3$, methylhydroxybutyl, and methylhydroxybutynyl.

Formula IId

In a preferred embodiment of compounds having Formula IId, R1 is selected from H and $C_{1-4}$ alkyl, and R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. More preferably, R1 is selected from H, methyl and ethyl, and R2 is selected from aryl, heteroaryl, heterocyclyl, and $C_{3-10}$ cycloalkyl each of which may be substituted or unsubstituted. More preferably, R1 is methyl. More preferably, R2 is selected from aryl, heteroaryl, heterocyclyl, and $C_{5-8}$ cycloalkyl each of which are monocyclic and may be substituted or unsubstituted. More preferably still, R2 is selected from aryl such as phenyl, saturated heterocyclyl, and $C_{5-8}$ cycloalkyl each of which are monocyclic and may be substituted or unsubstituted. Even more preferably, R2 is aryl, such as phenyl, which is monocyclic and may be substituted or unsubstituted. When R2 is substituted, the substituent is preferably one or more halogen.

In one embodiment, R2 is a cyclohexyl, such as an unsubstituted cyclohexyl. When R2 is a monocyclic saturated heterocyclyl, the heterocyclyl ring preferably contains a single heteroatom such as nitrogen or oxygen. More preferably, the heterocyclyl is six membered, such as a piperidinyl or tetrahydropyranyl group. In one embodiment, the heteroatom is a nitrogen heteroatom which may be substituted or unsubstituted. Preferably, the heteroatom in the said heterocyclyl group is at the 4 position relative to the position of attachment of the heterocyclyl group R2 to the urea nitrogen. In one embodiment, the nitrogen atom is substituted with monocyclic aryl (preferably phenyl) $C_{1-3}$alkyl.

In an alternative preferred embodiment of compounds having Formula IId, R1 and R2, together with the N to which they are attached, form a heterocyclyl group which may be substituted or unsubstituted. Preferably, the heterocyclyl is a 5 or 6 membered monocyclic ring and, more preferably, a 5 membered monocyclic ring. In certain embodiments, the said heterocyclyl contains one or two, preferably 1, additional heteroatoms (i.e. in addition to the N). These additional heteroatoms may be, for example, N, O and/or S. Preferably, the heterocyclyl is oxazolidinyl. Preferably, the oxygen atom in the oxazolidinyl is at the 3 position relative to the urea nitrogen. Preferably, the oxazolidinyl is substituted with one, two or three methyl or ethyl groups. More preferably, the oxazolidinyl is substituted with two methyl or ethyl groups. More preferably still, the oxazolidinyl is substituted with two methyl groups on the same carbon atom. More preferably, the oxazolidinyl is 4,4-dimethyloxazolidin-3-yl.

In yet another preferred embodiment of compounds having formula IId, R1 and R2, together with the N to which they are attached, form a heterocyclyl group which may be substituted or unsubstituted. Preferably, the heterocyclyl is a 5 or 6 membered monocyclic ring, more preferably, a 6 membered monocyclic ring. In certain embodiments, the said heterocyclyl contains one or two, preferably 1, additional heteroatoms (i.e. in addition to the N). These additional heteroatoms may be, for example, N, O and/or S. In one embodiment, the heterocyclyl is morpholino. In an alternative embodiment, the heterocyclyl is piperazinyl. In other embodiments, the said heterocyclyl contains no additional heteroatoms (i.e. it contains a single N atom). In one embodiment, the heterocyclyl is piperadinyl. Where the heterocyclyl is substituted, it is preferably substituted with aryl, aryl $C_{1-4}$ alkyl, $C_{5-6}$ cycloalkyl, or $C_{5-6}$ cycloalkyl $C_{1-4}$ alkyl, wherein the aryl is preferably monocyclic and more preferably phenyl, and the cycloalkyl is preferably cyclohexyl. The alkyl is preferably linear. In one embodiment, the heterocyclyl is substituted with an aryl or an aryl $C_{1-4}$ alkyl (preferably $C_{1-2}$ alkyl), wherein the aryl is preferably monocyclic and more preferably phenyl. The aryl may optionally be substituted with one or more halogens.

In compounds having formula IId, R5 is preferably selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, R5a, halogen, OH, OR5a, SH, SR5a, OCOR5a, SCOR5a, $NH_2$, $NO_2$, NHR5a, NR5aR5b, COR5a, CSR5a, CN, COOH, COOR5a, $CONH_2$, $SO_2R5a$, $SO_3H$, $SO_2NH_2$, CONR5aR5b, $SO_2NR5aR5b$, wherein R5a and R5b are independently selected from $C_{1-6}$ alkyl, aryl, heteroaryl, $C_{3-8}$ cycloalkyl and heterocyclyl, and R5a and R5b, together with the heteroatom to which they are joined, can form heterocyclyl. More preferably, R5 is selected from H, $C_{1-6}$ alkyl, aryl, heteroaryl, heterocyclyl, $C_{3-8}$ cycloalkyl, $C_{1-6}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$. More preferably still, R5 is selected from H, $C_{1-4}$ alkyl, aryl, heteroaryl, heterocyclyl, $C_{5-8}$ cycloalkyl, $C_{1-4}$ alkoxy, aryloxy, heteroaryloxy, heterocyclyloxy, halogen, OH, SH, $NH_2$, $NO_2$, CN, COOH, $CONH_2$, $SO_3H$, $SO_2NH_2$, wherein the aryl, heteroaryl, heterocyclyl and $C_{5-8}$ cycloalkyl groups are monocyclic. Even more preferably, R5 is selected from H, $C_{1-3}$ alkyl, aryl, heteroaryl, heterocyclyl, $C_{5-8}$ cycloalkyl, halogen, OH, $NH_2$, COOH and $CONH_2$, wherein the aryl, heteroaryl, heterocyclyl and $C_{5-8}$ cycloalkyl groups are monocyclic. More preferably still, R5 is selected from H, $C_{1-2}$ alkyl and halogen. Even more preferably, R5 is selected from H and halogen such as F, Cl and Br. In one embodiment, R5 is H.

In compounds having formula IId, R7 is preferably selected from aryl, heteroaryl, heterocyclyl and $C_{3-8}$ cycloalkyl each of which may be substituted or unsubstituted. More preferably, R7 is selected from aryl and heteroaryl each of which may be substituted or unsubstituted. In one embodiment, the heteroaryl contains one heteroatom, e.g. an oxygen or nitrogen atom. Preferably, the aryl or heteroaryl is monocyclic. More preferably, the aryl or heteroaryl is a six membered monocyclic ring. In one embodiment, the heteroaryl contains a nitrogen atom which is substituted with an oxygen atom such as oxidopyridyl. In another embodiment, R7 is unsubstituted monocyclic aryl such as phenyl, or monocyclic aryl such as phenyl substituted with one or more groups selected from halogen, $C_{1-2}$ alkoxy (optionally substituted with one or more halogen), or OH.

When R7 is substituted, the substituent is preferably one or more groups selected from halogen, $C_{1-4}$ alkoxy, aryl, heteroaryl, heterocyclyl, OH, $CONH_2$, $NH_2$, heterocyclyl $C_{1-4}$ alkoxy, aryl $C_{1-4}$ alkoxy, heteroaryl $C_{1-4}$ alkoxy, $NO_2$, $SO_2NH_2$, $SO_3$, $C(NOH)NH_2$ and morpholinosulfonyl. Preferably, the aryl, heteroaryl and heterocyclyl are monocyclic. In one embodiment, the aryl, heteroaryl and heterocyclyl are six membered monocyclic rings. In a particular embodiment in which R7 is monocyclic aryl, it may optionally be substituted with one or more groups selected from halogen, OH, $C_{1-3}$ alkoxy, aryl (e.g. a monocyclic aryl such as phenyl), heteroaryl (e.g. monocyclic heteroaryl containing one or two nitrogen atoms, or one oxygen atom), heterocyclyl (e.g. piperazinyl, piperadinyl or morpholino) $C_{1-3}$ alkoxy, aryl (e.g. monocyclic aryl such as phenyl) $C_{1-3}$ alkoxy, $CONH_2$, $NH_2$, $NO_2$, $OCHF_2$, $SO_2NH_2$, morpholinosulfonyl and $C(NOH)NH_2$. In one embodiment when R7 is monocyclic aryl such as phenyl, the substituent of R7 is aryl (e.g. monocyclic aryl such as phenyl) $C_{1-3}$ alkoxy.

When the substituent of R7 is $C_{1-4}$ alkoxy, aryl, heteroaryl, heterocyclyl, heterocyclyl $C_{1-4}$ alkoxy, aryl $C_{1-4}$ alkoxy, heteroaryl $C_{1-4}$ alkoxy or $SO_3$, each of these moieties may optionally be substituted with one or more groups selected from halogen, OH, $C_{1-3}$ alkoxy (which may be substituted with one or more halogen), $CONH_2$, CN, $NCH_3CH_3$, $NHCOCH_3$, methylhydroxybutyl, and methylhydroxybutynyl.

In an alternative embodiment of the invention, a compound is provided having Formula I or Formula II:

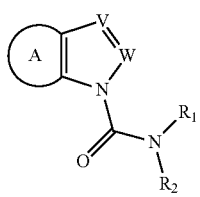

Formula I

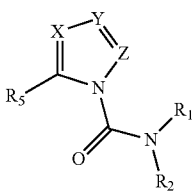

Formula II wherein R1, R2, R5, ring A, V, W, X, Y and Z are as defined above;
or a pharmaceutically acceptable salt or ester thereof;
provided that Ring A in compounds having Formula I does not form a pyridine, pyrimidine, substituted pyridine or substituted pyrimidine, when R1 and R2, together with the N to which they are attached, form piperidinyl, piperazinyl, substituted piperidinyl or substituted piperazinyl, provided that Ring A is not unsubstituted benzo, hydroxybenzo, phenoxybenzo, fluorochlorobenzo, chlorobenzo, bromobenzo, nitrobenzo, aminobenzo, cyanobenzo, methylbenzo, trifluoromethylbenzo, trifluoromethylchlorobenzo, phenylketobenzo, phenylhydroxymethylbenzo, cyclohexylthiobenzo, methoxycarbonylbenzo or methoxybenzo, provided that when R1 or R2 is methyl, the other of R1 or R2 is not 4-chlorobutyl, 4-azidobutyl, or 4-isothiocyanatobutyl, and provided that the compound is not (4-phenyl-1H-imidazol-1-yl)(4-(quinolin-2-ylmethyl)piperazin-1-yl)methanone.

In accordance with a second aspect of the invention, there is provided a pharmaceutical composition comprising a compound according to the first aspect of the invention, together with one or more pharmaceutically acceptable excipients.

Pharmaceutical compositions of this invention comprise any of the compounds of the first aspect of the present invention with any pharmaceutically acceptable carrier, adjuvant or vehicle. Pharmaceutically acceptable carriers, adjuvants and vehicles that may be used in the pharmaceutical compositions of this invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, rectally, nasally, buccally, vaginally or via an implanted reservoir. Oral administration is preferred. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as that described in Ph. Helv, or a similar alcohol.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

The compounds of the present invention may be administered in a dose of around 1 to around 20,000 μg/kg per dose, depending on the condition to be treated or prevented, and the characteristics of the subject being administered with the compound. In many instances, the dose may be around 1 to around 1500 μg/kg per dose. The dosing regimen for a given compound could readily be determined by the skilled person having access to this disclosure.

In one particular embodiment, the pharmaceutical composition of the invention additionally comprises one or more additional active pharmaceutical ingredients. The compound of the invention may be administered with one or more additional active pharmaceutical ingredients. This may be in the form of a single composition comprising the compound of the invention and one or more additional active pharmaceutical ingredients. Alternatively, this may be in two or more separate compositions where the compound of the invention is contained in one composition and the one or more additional active pharmaceutical ingredients are contained in one or more separate compositions.

In a third aspect, the present invention provides a compound according to the first aspect of the invention, or a composition according to the second aspect, for use in therapy.

In a fourth aspect, the invention provides a compound according to the first aspect of the invention, or a composition according to the second aspect, for use in the treatment or prevention of a condition whose development or symptoms are linked to a substrate of the FAAH enzyme, wherein the only provisos of the first aspect which apply are i) that Ring A in compounds having Formula I does not form a pyridine, pyrimidine, substituted pyridine or substituted pyrimidine, when R1 and R2, together with the N to which they are attached, form piperidinyl, piperazinyl, substituted piperidinyl or substituted piperazinyl, ii) when R1 or R2 is methyl, the other of R1 or R2 is not 4-chlorobutyl, 4-azidobutyl, or 4-isothiocyanatobutyl, and iii) the compound is not (4-phenyl-1H-imidazol-1-yl)(4-(quinolin-2-ylmethyl)piperazin-1-yl)methanone.

The invention also provides the use of a compound according to the first aspect of the invention, or a composition according to the second aspect, in the manufacture of a medicament for the treatment or prevention of a condition whose development or symptoms are linked to a substrate of the FAAH enzyme, wherein the only provisos of the first aspect which apply are i) that Ring A in compounds having Formula I does not form a pyridine, pyrimidine, substituted pyridine or substituted pyrimidine, when R1 and R2, together with the N to which they are attached, form piperidinyl, piperazinyl, substituted piperidinyl or substituted piperazinyl, ii) when R1 or R2 is methyl, the other of R1 or R2 is not 4-chlorobutyl, 4-azidobutyl, or 4-isothiocyanatobutyl, and iii) the compound is not (4-phenyl-1H-imidazol-1-yl)(4-(quinolin-2-ylmethyl)piperazin-1-yl)methanone.

A number of conditions whose development or symptoms are linked to a substrate of the FAAH enzyme are known to the skilled person. Some of these are discussed above.

In a fifth aspect, the invention also provides a method of treatment or prevention of a condition whose development or symptoms are linked to a substrate of the FAAH enzyme, the method comprising the administration, to a subject in need of such treatment or prevention, of a therapeutically effective amount of a compound according to the first aspect of the invention, or a composition according to the second aspect, wherein the only provisos of the first aspect which apply are that Ring A in compounds having Formula I does not form a pyridine, pyrimidine, substituted pyridine or substituted pyrimidine, when R1 and R2, together with the N to which they are attached, form piperidinyl, piperazinyl, substituted piperidinyl or substituted piperazinyl, ii) when R1 or R2 is methyl, the other of R1 or R2 is not 4-chlorobutyl, 4-azidobutyl, or 4-isothiocyanatobutyl, and iii) the compound is not (4-phenyl-1H-imidazol-1-yl)(4-(quinolin-2-ylmethyl)piperazin-1-yl)methanone.

A compound according to the fourth aspect, or a method according to the fifth aspect, wherein the condition is a disorder associated with the endocannabinoid system.

In certain embodiments, the condition to be treated may be selected from:
(i) pain, in particular acute or chronic neurogenic pain such as migraine and neuropathic pain (for example diabetic neuropathic pain, post-herpetic neuralgia, trigeminal neauralgia); acute or chronic pain associated with inflammatory diseases such as arthritis, rheumatoid arthritis, osteoarthritis, spondylitis, gout, vasculitis, Crohn's disease, and irritable bowel syndrome; acute or chronic peripheral pain;
(ii) dizziness, vomiting, and nausea, in particular resulting from chemotherapy;
(iii) eating disorders, in particular anorexia and cachexia of various natures;
(iv) neurological and psychiatric pathologies such as tremors, dyskinesias, dystonias, spasticity, obsessive-compulsive behaviour, Tourette's syndrome, all forms of depression and anxiety of any nature and origin, mood disorders, and psychoses;
(v) acute and chronic neurodegenerative diseases such as Parkinson's disease, Alzheimer's disease, senile dementia, Huntington's chorea, lesions related to celebral ischaemia and to cranial and medullary trauma;
(vi) epilepsy;
(vii) sleep disorders, including sleep apnoea;

(viii) cardiovascular diseases such as heart failure, hypertension, cardiac arrhythmias, arteriosclerosis, heart attack, cardiac ischaemia, and renal ischaemia;
(ix) cancers, for example benign skin tumours, brain tumours and papillomas, prostate tumours, and cerebral tumours (glioblastomas, medulloepitheliomas, medulloblastomas, neuroblastomas, tumours of embryonic origin, astrocytomas, astroblastomas, ependymomas, oligodendrogliomas, plexus tumour, neuroepitheliomas, epiphyseal tumour, ependymoblastomas, malignant meningiomas, sarcomatosis, malignant melanomas, and schwannomas);
(x) disorders of the immune system, in particular autoimmune diseases, such as psoriasis, lupus erythematosus, diseases of the connective tissue or collagen diseases, Sjögren's syndrome, ankylosing spondylitis, undifferentiated spondylitis, Behcet's disease, autoimmune haemolytic anaemia, multiple sclerosis, amylotrophic lateral sclerosis, amyloidosis, graft rejection, diseases affecting the plasmacytic line, allergic diseases; immediate or delayed hypersensitivity, allergic rhinitis or conjunctivitis, contact dermatitis;
(xi) parasitic, viral or bacterial infectious diseases such as AIDS, and meningitis;
(xii) inflammatory diseases, in particular joint diseases such as arthritis, rheumatoid arthritis, osteoarthritis, spondylitis, gout, vasculitis, Crohn's disease, irritable bowel syndrome;
(xiii) osteoporosis;
(xiv) eye conditions such as ocular hypertension, and glaucoma;
(xv) pulmonary conditions including diseases of the respiratory tracts, bronchospasm, coughing, asthma, chronic bronchitis, chronic obstruction of the respiratory tract, and emphysema;
(xvi) gastrointestinal diseases such as irritable bowel syndrome, inflammatory intestinal disorders, ulcers, diarrhoea, urinary incontinence and bladder inflammation.

In a sixth aspect, the present invention provides the use of a compound according to the first aspect of the invention in the preparation of a medicament for the treatment or prevention of a condition whose development or symptoms are linked to a substrate of the FAAH enzyme, wherein the only proviso of the first aspect which applies is that Ring A in compounds having Formula I does not form a pyridine, pyrimidine, substituted pyridine or substituted pyrimidine, when R1 and R2, together with the N to which they are attached, form piperidinyl, piperazinyl, substituted piperidinyl or substituted piperazinyl.

Exemplary conditions of relevance to the sixth aspect are mentioned above.

In certain embodiments of the fourth, fifth or sixth aspects, one or both of the other provisos to the first aspect also apply.

The invention will now be described in more detail by way of example only:

1. Synthetic Methodologies

The methods used for synthesis of the compounds of the invention are illustrated by the general schemes below and the preparative examples that follow. All compounds and intermediates were characterised by nuclear magnetic resonance (NMR). The starting materials and reagents used in preparing these compounds are available from commercial suppliers or can be prepared by methods obvious to those skilled in the art. These general schemes are merely illustrative of methods by which the compounds of this invention can be synthesised, and various modifications to these schemes can be made and will be suggested to one skilled in the art having referred to this disclosure.

Room temperature in the following schemes means the temperature ranging from 20° C. to 25° C.

Benzotriazoles

5-Bromo-1H-benzo[d][1,2,3]triazole
(1H-benzo[d][1,2,3]triazole derivative formation)

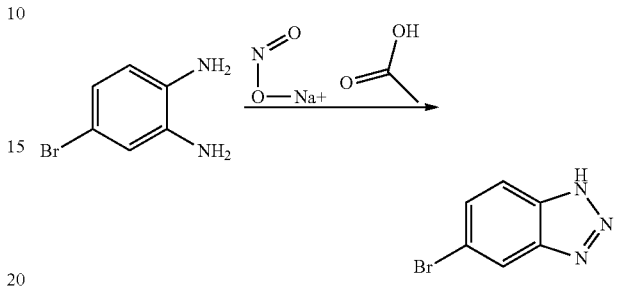

To a solution of 4-bromobenzene-1,2-diamine (10 g, 53.5 mmol) in a mixture of acetic acid (20 ml, 349 mmol) and water (100 ml) at 0-5° C. was added a solution of sodium nitrite (4.06 g, 58.8 mmol) in water (10 ml) dropwise. Stirred in the ice bath for 1 h, more acetic acid (20 ml, 349 mmol) was added, heated to 80-85° C. with stirring during 1 h, the solution was filtered hot to remove insoluble black material, cooled to 0-5° C., aged for 30 min, precipitate collected, washed with water, dried in vacuum at 45° C. Yield 9.48 g (90%).

N-cyclohexyl-N-methyl-1H-benzo[d][1,2,3]triazole-1-carboxamide (disubstituted triazole-1-carboxamide formation)

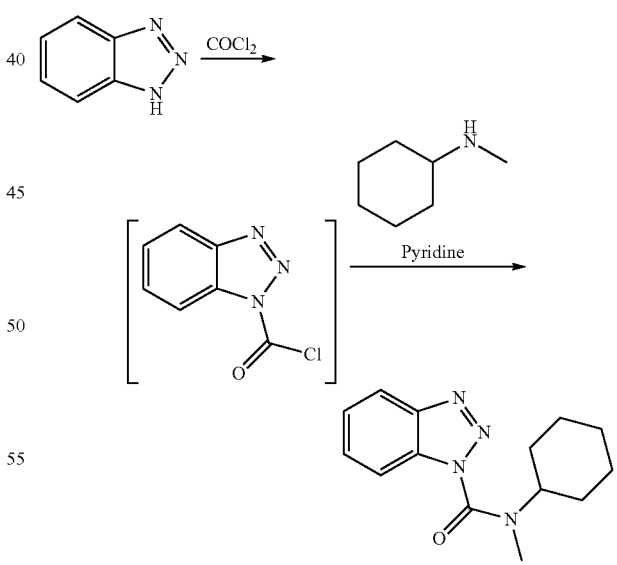

A solution of 1H-benzo[d][1,2,3]triazole (0.5 g, 4.20 mmol) in tetrahydrofuran (25 ml) was added dropwise to a stirred 20% solution of phosgene (5.30 ml, 10.1 mmol) in toluene at 0-5° C. The reaction mixture was allowed to stir at 20-25° C. for 2 h (reaction complete by TLC). Argon was bubbled through the solution for 15 min. Then the solvent was evaporated in vacuum to give 1H-benzo[d][1,2,3]triazole-1- carbonyl chloride (0.763 g, 4.20 mmol) as a clear oil. The product was used without further purification. Pyridine (0.357 ml, 4.41 mmol) was added dropwise to a stirred solution of the oil in Tetrahydrofuran (25 ml) at 0-5° C. This was followed by a dropwise addition of N-methylcyclohexanamine (0.499 g, 4.41 mmol) at 0-5° C. The reaction mixture was allowed to stir overnight at 20-25° C. Water and EtOAc were added and the organic layer was separated, washed with 1M HCl, water and brine. The organic layer was dried (MgSO$_4$) and evaporated in vacuum to give a clear oil. The oil was recrystallised from 2-propanol/DCM, the solid was collected, dried in vacuum at 40-45° C. Yield 230 mg (21%).

(R)—N-(quinuclidin-3-yl)-1H-benzo[d][1,2,3]triazole-1-carboxamide hydrochloride (monosubstituted triazole-1-carboxamide formation)

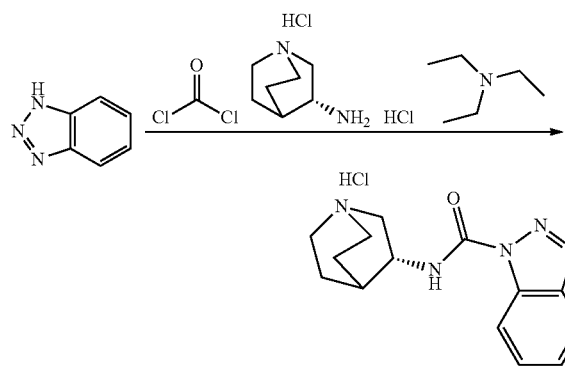

To a solution of 1H-benzo[d][1,2,3]triazole (0.238 g, 2 mmol) in dry DCM (5 ml) was added at 0-5° C. 20% solution of phosgene (1.052 ml, 2.000 mmol) in toluene. The mixture was stirred for 30 min at 20-25° C., cooled to 0-5° C., triethylamine (0.279 ml, 2.000 mmol) was added with stirring. The suspension was diluted with dry DCM (5 ml), solid (R)-quinuclidin-3-amine dihydrochloride (0.398 g, 2.000 mmol) and triethylamine (0.836 ml, 6.00 mmol) added at 0-5° C. The mixture was allowed to warm up to 20-25° C. during 30 min, diluted with 2-propanol, evaporated to dryness. The residue was distributed between water (15 ml) and DCM (15 ml), organic phase dried (MgSO$_4$), concentrated, separated on a column (DCM-MeOH 9:1), fractions collected to give oil. The oil dissolved in ether with minimum of DCM, the solution acidified with 2M HCl in ether to pH 1-2, the precipitate collected, washed with ether, dried in vacuum at 45° C. Yield 0.12 g (19.5%).

N-(4-phenylbutyl)-1H-benzo[d][1,2,3]triazole-1-carboxamide (monosubstituted triazole-1-carboxamide formation)

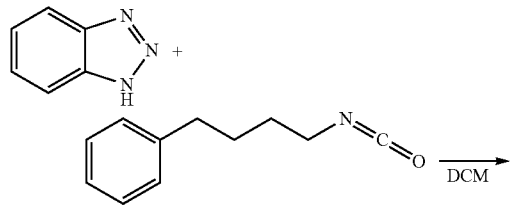

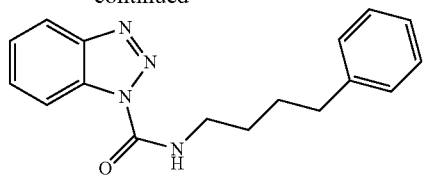

(4-Isocyanatobutyl)benzene (463 mg, 2.64 mmol) was added dropwise to a stirred solution of 1H-benzo[d][1,2,3]triazole (300 mg, 2.52 mmol) in DCM (18 ml) at 0-5° C. The clear reaction mixture was allowed to stir at 20-25° C. overnight. The solvent was removed in vacuum to give a clear oil. The oil solidified on standing into a colourless solid. The product was recrystallised from 2-propanol, the solid was collected, dried in vacuum at 45° C. Yield 477 mg (64%).

Imidazoles 4-(4-Fluorophenyl)-1H-imidazole (imidazole synthesis)

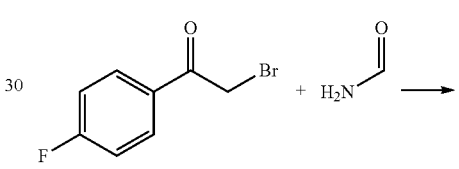

In a 50 ml pear flask 2-bromo-1-(4-fluorophenyl)ethanone (5.93 g, 27.31 mmol), formamide (13.45 ml, 339 mmol) and water (1 ml) were placed. The reaction was heated at 140° C. for 4 hours. Then it was cooled to room temperature and poured into 150 ml of water. The precipitate was filtered off, washed with water. The filtrate's pH was set to 12 by adding 10% NaOH solution. The resultant precipitate was filtered off, washed with water and dried under vacuum. (Yield: 2.02 g, 45%).

(4-Phenyl-1H-imidazol-1-yl)(4-phenylpiperazin-1-0)methanone (acylation)

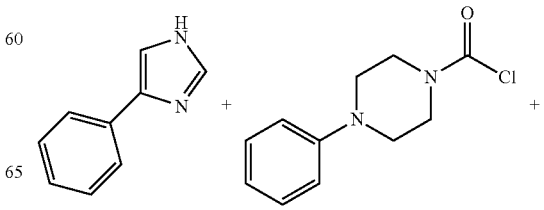

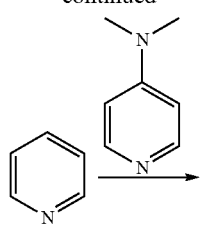

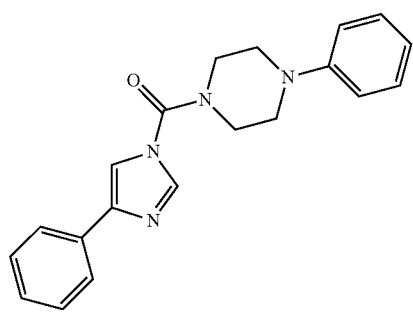

To a stirred solution of 4-phenyl-1H-imidazole (577 mg, 4 mmol) in tetrahydrofuran (20 ml) was added pyridine (0.489 ml, 6.00 mmol) and DMAP (48.9 mg, 0.400 mmol). The pale yellow solution was treated with 4-phenylpiperazine-1-carbonyl chloride (944 mg, 4.20 mmol) and heated to 90° C. for 20 hours. Whereupon, THF was removed by vacuum, the residue was partitioned between DCM:IPA (70:30) mixture and water. The organic phase was dried over MgSO$_4$ and filtered. After evaporation the crude product was recrystallized from hot IPA, filtered and dried under vacuum. (Yield: 777 mg, 58%).

N-(4-Fluorophenyl)-4-(4-hydroxyphenyl)-N-methyl-1H-imidazole-1-carboxamide (deprotection)

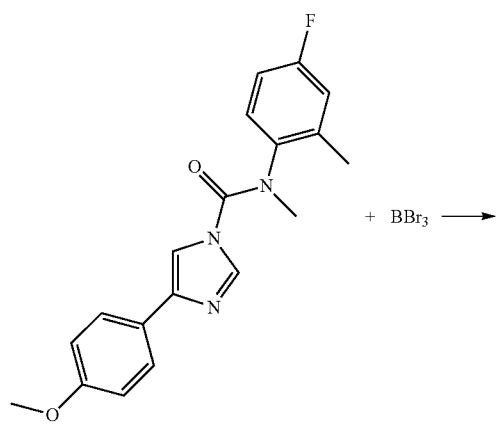

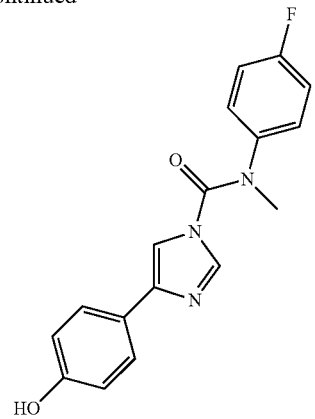

To an methanol-dry ice cooled solution of N-(4-fluorophenyl)-4-(4-methoxyphenyl)-N-methyl-1H-imidazole-1-carboxamide (0.283 g, 0.870 mmol) in dichloromethane (8 ml) was added borontribromide (0.164 ml, 1.740 mmol). The dark reaction mixture was allowed to warm up to room temperature and stirred for 2 hours. TLC showed the reaction to be completed, then was poured into a mixture of ice and water and stirred for 30 min. There was no precipitation. The mixture was extracted with DCM:IPA (70:30), the organic phase was dried over MgSO$_4$ and filtered. DCM was removed by vacuum and the product precipitated from IPA, filtered and dried under vacuum. (Yield: 210 mg, 78%).

1,2,4-Triazoles 3-(4-Chlorophenyl)-1H-1,2,4-triazole (ring synthesis)

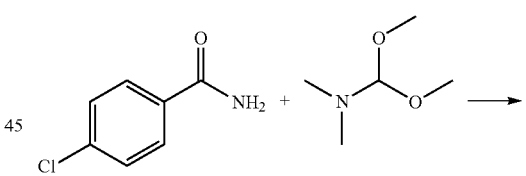

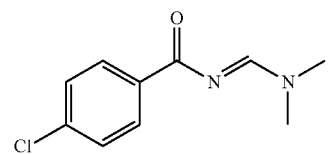

4-Chlorobenzamide (7.371 g, 47.4 mmol) was suspended in 1,1-dimethoxy-N,N-dimethylmethanamine (15.73 ml, 118 mmol). The reaction mixture was heated at 80° C. for 1 hour. Then was cooled to room temperature and the excess of 1,1-dimethoxy-N,N-dimethylmethanamine was removed by vacuum. The resultant solid was triturated with petroleumether, filtered and dried under vacuum. (Yield: 9.44 g, 95%).

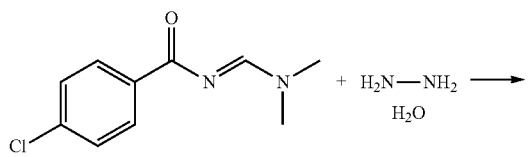

To a stirred solution of (E)-4-chloro-N-((dimethylamino)methylene)benzamide (9.4 g, 44.6 mmol) in acetic Acid (13.5 ml) was added hydrazine hydrate (1.524 ml, 49.1 mmol). The reaction mixture immediately solidified and was heated to 120° C. for 2 hours. Whereupon was cooled to room temperature and azeotroped with toluene. The crystalline residue was stirred with water for a while. The precipitate was filtered off, washed with water and dried under vacuum. (Yield: 7.27 g, 91%).

(3-(4-Methoxyrohenyl)-1H-1,2,4-triazol-1-yl)(moroholino)methanone (acylation)

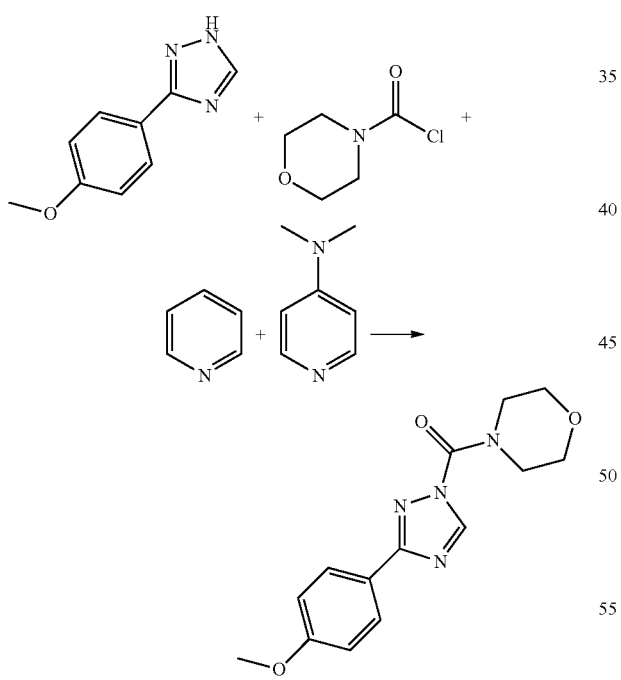

To a stirred solution of 3-(4-methoxyphenyl)-1H-1,2,4-triazole (701 mg, 4 mmol) in tetrahydrofuran (20 ml) was added pyridine (0.489 ml, 6.00 mmol), DMAP (48.9 mg, 0.400 mmol) The solution was treated with morpholine-4-carbonyl chloride (0.490 ml, 4.20 mmol). and heated to 90° C. for 20 hours. TLC showed the reaction to be almost completed. THF was removed by vacuum, the residue was partitioned between DCM and water. The organic phase was dried over MgSO₄, filtered and evaporated. Recrystallization from hot IPA afforded 749 mg white crystals (Yield: 65%).

1,2,3-Triazoles

4-Phenyl-1H-1,2,3-triazole (ring synthesis)

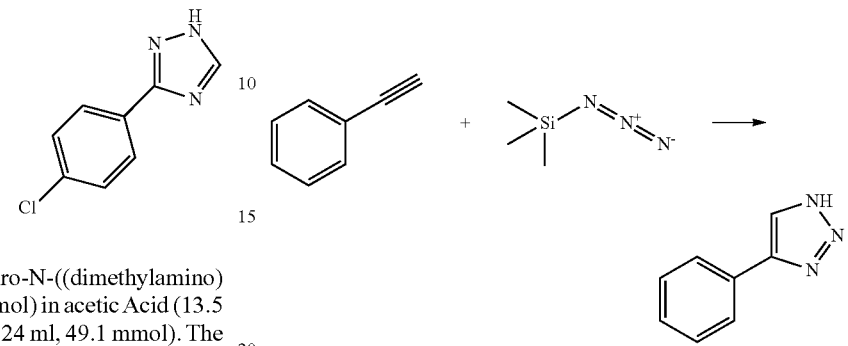

To a stirred solution of phenylacetylene (1.098 ml, 10 mmol) in abs. toluene (10 ml) was added azidotrimethylsilane (2.65 ml, 20.00 mmol) in one portion. The reaction was heated at 100° C. for 3 days, whereupon was cooled to room temperature and toluene was removed by vacuum. The residue was partitioned between DCM and water. The organic phase was dried over MgSO₄ and filtered. After evaporation the crude product was chromatographed in petroleumether: EtOAc=2:1. (Yield: 355 mg, 24%).

Morpholino(4-phenyl-1H-1,23-triazol-1-yl)methanone (acylation)

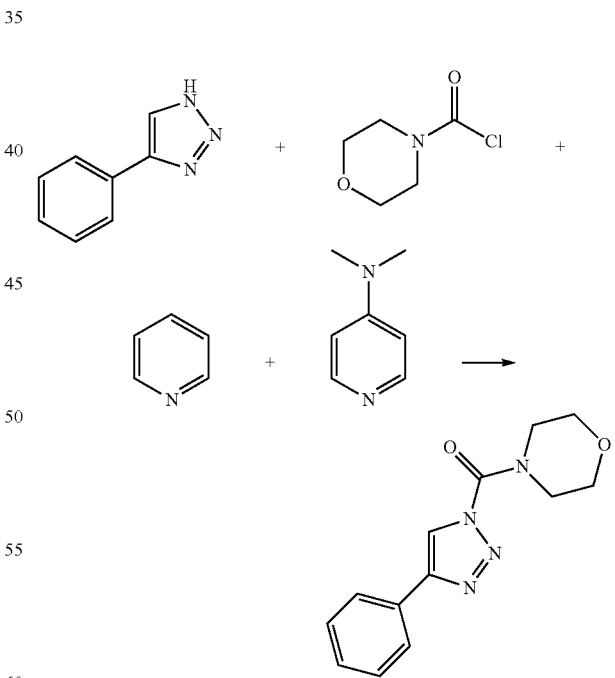

To a stirred solution of 4-phenyl-1H-1,2,3-triazole (0.340 g, 2.342 mmol) in tetrahydrofuran (12 ml) was added pyridine (0.286 ml, 3.51 mmol), DMAP (0.029 g, 0.234 mmol). The solution was treated with morpholine-4-carbonyl chloride (0.287 ml, 2.459 mmol). The reaction was heated to 90° C. for 20 hours. Then THF was removed by vacuum, the residue was partitioned between DCM and water. The organic phase was dried over MgSO₄ and filtered. After evaporation the crude product was recrystallized from IPA, filtered and dried under vacuum. (Yield: 193 mg, 29%).

Pyrazoles

3-phenyl-1H-pyrazole (ring synthesis)

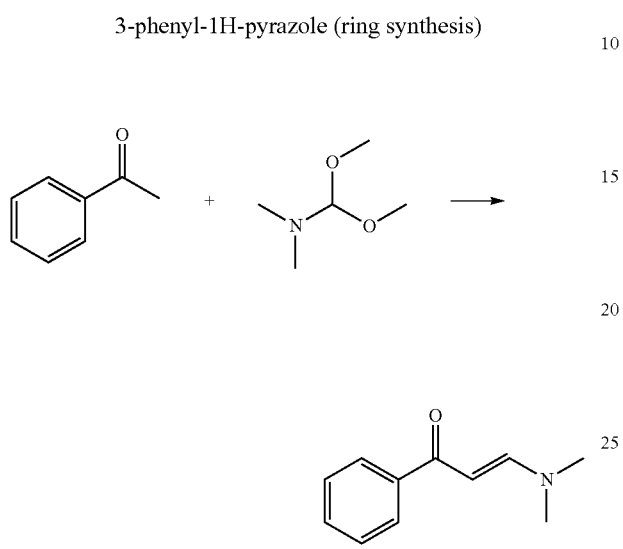

Acetophenone (5.89 ml, 50 mmol) was dissolved in 1,1-dimethoxy-N,N-dimethylmethanamine (13.39 ml, 100 mmol). The reaction mixture was heated at 120° C. for 24 hours. The dark red solution was cooled to room temperature and the excess of 1,1-dimethoxy-N,N-dimethylmethanamine was removed by vacuum. The resultant solid was triturated with petroleumether, filtered and dried under vacuum. (Yield: 6.78 g, 77%).

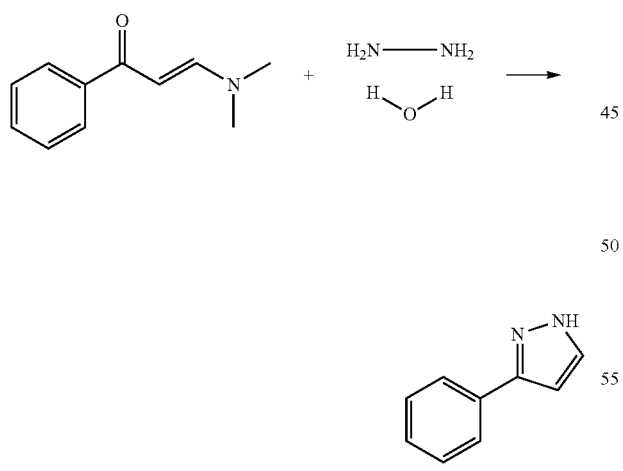

To a stirred solution of (E)-3-(dimethylamino)-1-phenyl-prop-2-en-1-one (2.63 g, 15 mmol) in ethanol (40 ml) was added hydrazine hydrate (1.459 ml, 30.0 mmol). The reaction was heated to 100° C. for 2 hours. Whereupon was cooled to room temperature and ethanol was removed by vacuum. The residue was partitioned between DCM and water. The organic phase was dried over MgSO₄ and filtered. After evaporation the crude product was purified by triturating with a mixture of petroleumether and ethyl acetate. (Yield: 1.59 g, 73%).

Morpholino(3-(pyridin-3-yl)-1H-pyrazol-1-yl)methanone (acylation)

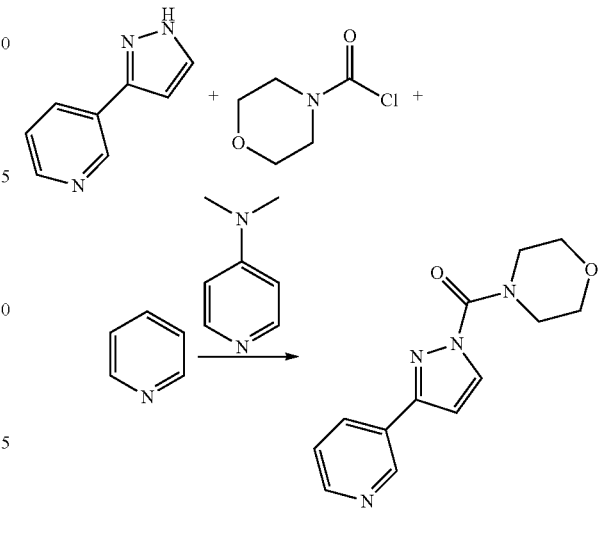

To a stirred solution of 3-(1H-pyrazol-3-yl)pyridine (0.435 g, 3 mmol) in tetrahydrofuran (15 ml) was added pyridine (0.367 ml, 4.50 mmol), DMAP (18.33 mg, 0.150 mmol). The solution was treated with 4-morpholinecarbonyl chloride (0.368 ml, 3.15 mmol). The reaction was heated to 80° C. for 20 hours. THF was removed by vacuum, the residue was partitioned between DCM and water. The organic phase was dried over MgSO₄ and filtered. After evaporation the crude product was chromatographed in petroleumether:EtOAc=2:1. (Yield: 174 mg, 21%).

Benzoimidazoles

N-methyl-N-phenyl-1H-benzo[d]imidazole-1-carboxamide (acylation)

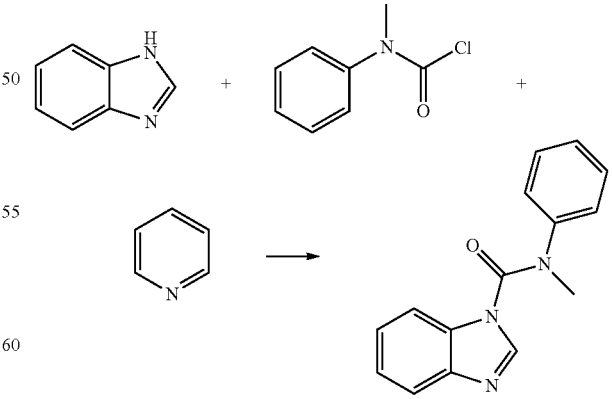

To a stirred solution of 1H-benzo[d]imidazole (354 mg, 3 mmol) in tetrahydrofuran (15 ml) was added pyridine (0.367 ml, 4.50 mmol) followed by addition of methyl(phenyl)carbamic chloride (534 mg, 3.15 mmol). The reaction was heated to 80° C. for 20 hours. THF was removed by vacuum, the residue was partitioned between DCM and water. The organic phase was dried over MgSO$_4$ and filtered. After evaporation the crude product was chromatographed in petroleum ether:EtOAc=2:1.

(Yield: 365 mg, 46%).

In the following section, additional synthetic examples for particular compounds are provided.

Preparation of Compound 362 a) N-cyclohexyl-N-methyl-4-(pyridin-3-yl)-1H-imidazole-1-carboxamide

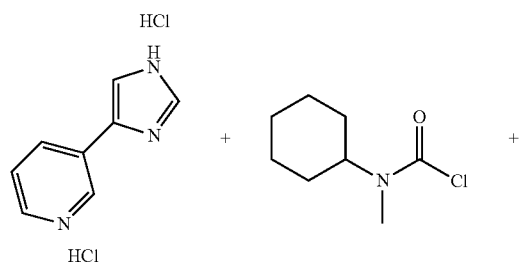

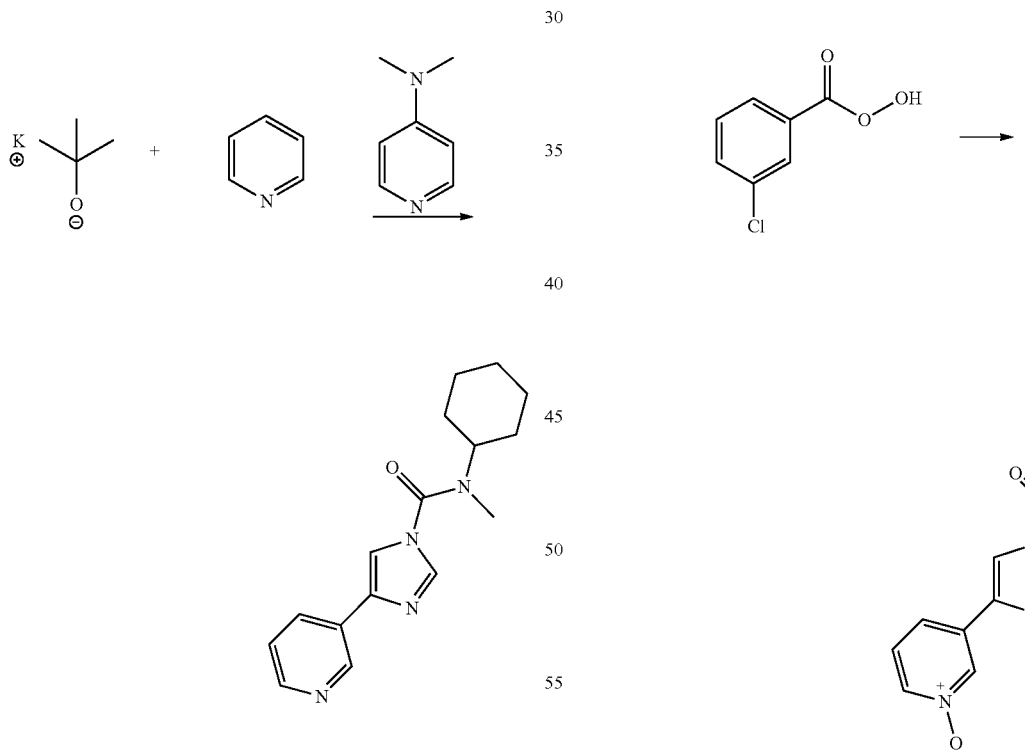

To a stirred suspension of 3-(1H-imidazol-4-yl)pyridine dihydrochloride (1.745 g, 8 mmol) in a mixture of tetrahydrofuran (29 mL) and DMF (2.90 mL) was added potassium 2-methylpropan-2-olate (1.795 g, 16.0 mmol) and the mixture was refluxed for 30 minutes. The resulting brown suspension was cooled to room temperature and treated with pyridine (0.979 mL, 12 mmol) and N,N-dimethylpyridin-4-amine (0.098 g, 0.8 mmol), followed by the addition of cyclohexyl(methyl)carbamic chloride (1.476 g, 8.4 mmol). The reaction was heated to 90° C. overnight, whereupon the mixture was diluted with water and extracted with ethyl acetate. The organic phase was dried (MgSO$_4$) and filtered. After evaporation, the crude product was chromatographed over silica gel using a dichloromethane/methanol (9:1) mixture. Homogenous fractions were pooled and evaporated to leave a white powder, (160 mg, 7%).

b) 3-(1-(cyclohexyl(methyl)carbamoyl)-1H-imidazol-4-yl)pyridine 1-oxide

To a stirred solution of N-cyclohexyl-N-methyl-4-(pyridin-3-yl)-1H-imidazole-1-carboxamide (90 mg, 0.317 mmol) in chloroform (5 mL) was added 3-chlorobenzoperoxoic acid (149 mg, 0.475 mmol) in one portion. The reaction was allowed to stir at room temperature for 20 h. TLC showed the reaction to be complete and the mixture was evaporated to dryness. The residue was triturated with ether and the resulting white crystals were filtered off and dried in air. Recrystallisation from hot isopropanol gave a white powder (46 mg, 46%).

Preparation of Compound 408

N-cyclohexyl-N-methyl-4-(3-(2-morpholinoethoxy)phenyl)-1H-imidazole-1-carboxamide hydrochloride

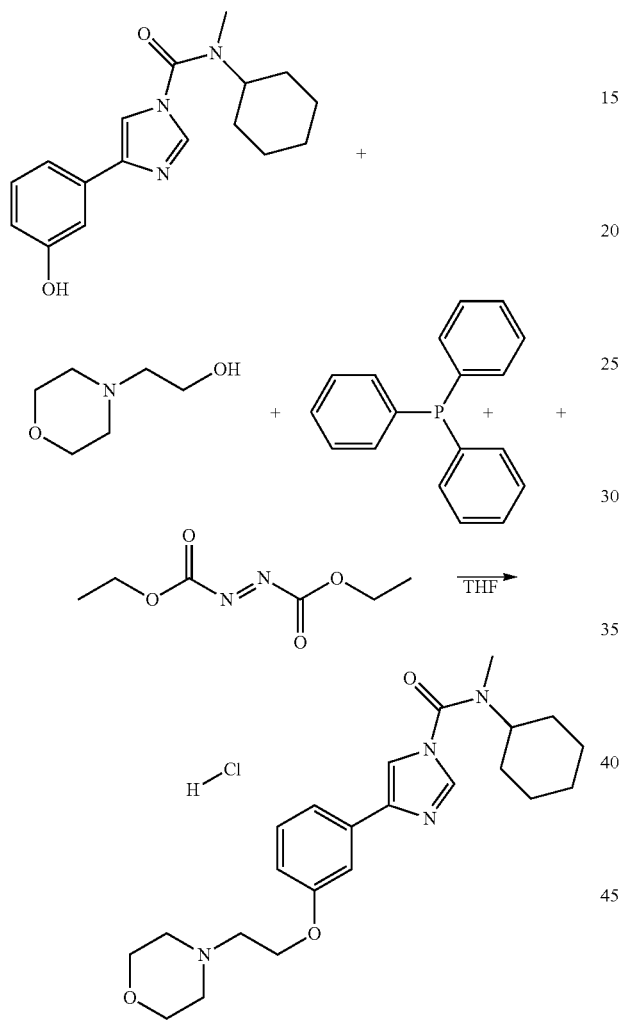

N-cyclohexyl-4-(3-hydroxyphenyl)-N-methyl-1H-imidazole-1-carboxamide (170 mg, 0.568 mmol) was taken up in anhydrous tetrahydrofuran (10 mL) under nitrogen to give a colourless solution. N-beta-Hydroxyethylmorpholine (0.068 mL, 0.568 mmol) was added and the solution was cooled to 0° C. Triphenylphosphine (179 mg, 0.681 mmol) was added followed by DEAD (0.108 mL, 0.68 mmol) dropwise, allowing the yellow colour that formed after addition of each drop to fade before the next drop was added. The resulting pale yellow solution was allowed to warm to room temperature and stirred for 18 h. The reaction mixture was then cooled to 0° C. and another portion of triphenylphosphine (179 mg, 0.681 mmol) and DEAD (0.108 mL, 0.68 mmol) were added. The solution was stirred for another 6 h. The solvent was evaporated and the yellow oil was purified by chromatography (silica gel H; 9/1, 8/2, 6/4, 5/5, 4/6 toluene/acetone).

Fractions with pure product were evaporated and the pale yellow oil was dissolved in ethyl acetate, which then led to precipitation. The suspension was heated to dissolve the solid, and the solution was then cooled to 0° C. Excess 2 N HCl solution in ether was added dropwise. The resulting mixture was stirred at 0° C. for 10 minutes and then allowed to warm to room temperature and stirred for another 15 minutes. The precipitate was filtered, washed with ether and dried. Recrystallisation from ethyl acetate afforded a light cream solid, (39 mg, 14%).

Preparation of Compound 397 a) tert-butyl 4-(2-(4-(1-(cyclohexyl(methyl)carbamoyl)-1H-imidazol-4-yl)phenoxy)ethyl)piperazine-1-carboxylate

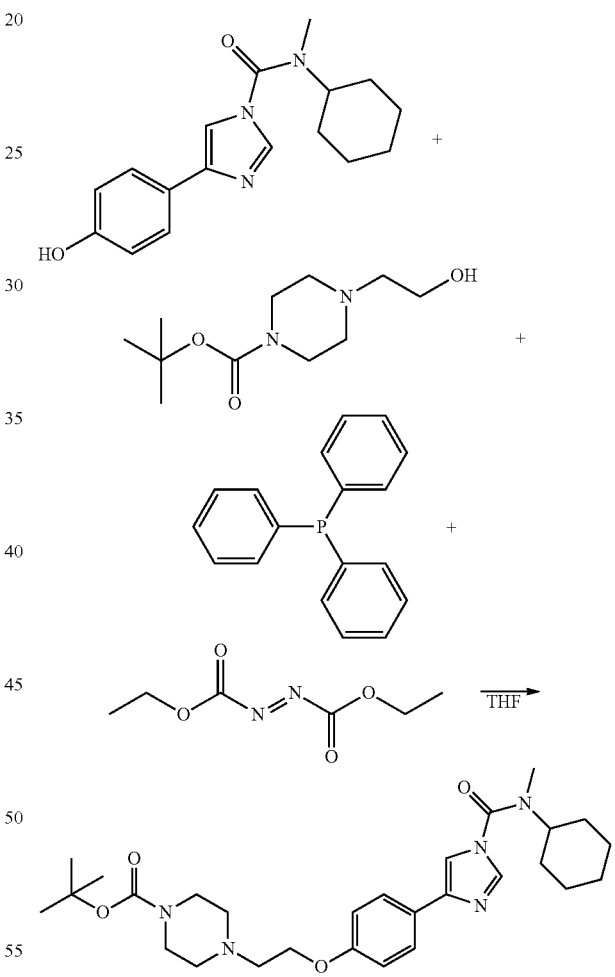

In a 50 mL pear flask was placed N-cyclohexyl-4-(4-hydroxyphenyl)-N-methyl-1H-imidazole-1-carboxamide (200 mg, 0.668 mmol) in tetrahydrofuran (10 mL) under nitrogen to give a pale pink solution. tert-Butyl 4-(2-hydroxyethyl)piperazine-1-carboxylate (184 mg, 0.8 mmol) was added and the solution was cooled to 0° C. Triphenylphosphine (210 mg, 0.801 mmol) was added, followed by DEAD (0.127 mL, 0.8 mmol) dropwise, allowing the yellow colour that formed after addition of each drop to fade before the next drop was added. The resulting pale yellow solution was allowed to warm to room temperature and stirred for 24 h. The solvent was evaporated and the pale yellow oil was purified by chromatography (silica gel H; 10%, 20%, 30%, 40%, 50%, 60% acetone/toluene). Fractions with pure product were evaporated and the beige solid (167 mg) was used in the next step without further purification.

b) N-cyclohexyl-N-methyl-4-(4-(2-(piperazin-1-yl)ethoxy)phenyl)-1H-imidazole-1-carboxamide dihydrochloride

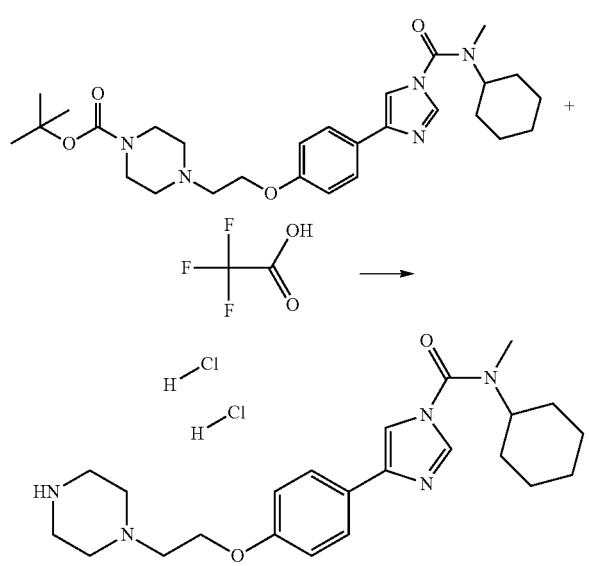

In a 25 mL pear flask was placed tert-butyl 4-(2-(4-(1-(cyclohexyl(methyl)carbamoyl)-1H-imidazol-4-yl)phenoxy)ethyl)piperazine-1-carboxylate (167 mg, 0.326 mmol). Trifluoroacetic acid (3 mL, 38.9 mmol) was added to give a pale yellow solution, which was stirred at room temperature for 1 h. The solvent was evaporated and the residual yellow oil was dissolved in ethyl acetate and cooled to 0° C. Thereupon, excess 2 N HCl solution in ether was added. The mixture was stirred at 0° C. for 10 minutes and then allowed to warm to room temperature and stirred for 15 minutes. The mixture was evaporated and the residue was recrystallized from isopropanol. The crystals were filtered, washed with isopropanol and dried to give the product as a white solid, (115 mg, 69%).

Preparation of Compound 389 a) 1-(4,4-dimethyloxazolidine-3-carbonyl)-1H-benzo[d][1,2,3]triazole-5-carboxylic acid

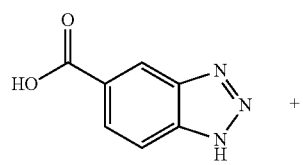

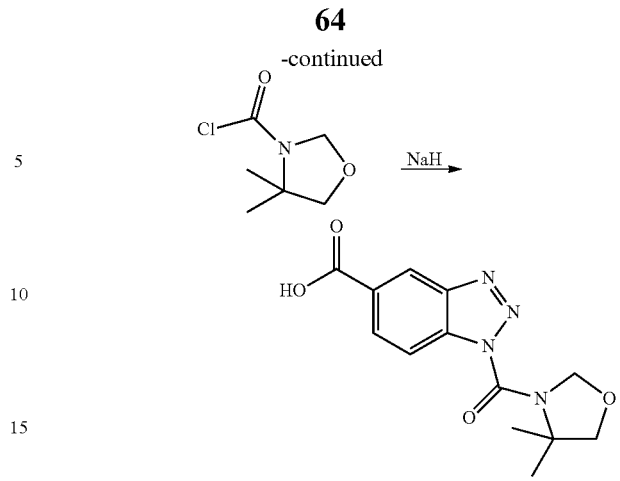

A solution of 1H-benzo[d][1,2,3]triazole-5-carboxylic acid (3 g, 18.39 mmol) in a mixture of tetrahydrofuran (90 mL) and dimethylformamide (50 mL) was added dropwise to a stirred suspension of sodium hydride (1.839 g, 46 mmol) in tetrahydrofuran (30 mL) at 0° C. The suspension was allowed to stir at room temperature for 30 minutes before adding dropwise, at 0° C., a solution of 4,4-dimethyloxazolidine-3-carbonyl chloride (3.16 g, 19.31 mmol) in tetrahydrofuran (10 mL). The reaction mixture was allowed to stir at room temperature for 4 h. Water was added at 0° C. and the solvent was evaporated. A mixture of dichloromethane/isopropanol (7:3) was added and the organic layer was separated. The aqueous layer was re-extracted with dichloromethane and the combined organic layers were dried (MgSO$_4$), filtered and evaporated. The orange residue was recrystallised from isopropanol to give a beige solid (840 mg) that was used in the next step without further purification.

b) 1-(4,4-dimethyloxazolidine-3-carbonyl)-1H-benzo[d][1,2,3]triazole-5-carboxamide

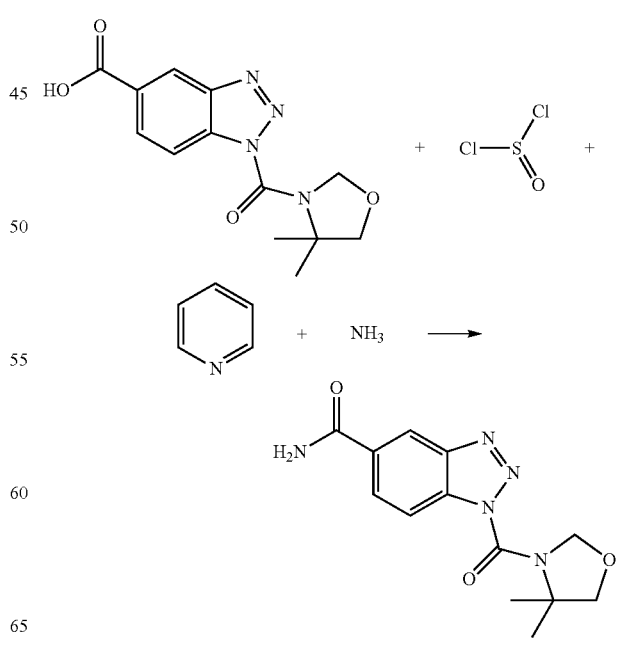

Thionyl chloride (0.633 mL, 8.67 mmol) was added dropwise to a stirred solution of 1-(4,4-dimethyloxazolidine-3-carbonyl)-1H-benzo[d][1,2,3]triazole-6-carboxylic acid (0.763 g, 2.63 mmol) and pyridine (0.702 mL, 8.67 mmol) in dichloromethane (17 mL) at room temperature. The yellow solution was allowed to stir at room temperature for 15 minutes. This solution was then added dropwise to a 1.75 N solution of ammonia (15.02 mL, 26.3 mmol) in ethanol at 0° C., whereupon a white suspension formed. The reaction mixture was allowed to stir at room temperature for a further 30 minutes. Water was added and the ethanol was evaporated. Then the residue was diluted with dichloromethane, and the organic layer was separated and washed with 1 N HCl solution. The organic layer was dried (MgSO$_4$), filtered and evaporated to give a yellow solid. The solid was recrystallised from a dichloromethane/ethanol mixture to give the product as a beige solid (151 mg, 20%).

Preparation of Compound 438

N-cyclohexyl-4-(4-methoxy-3-(2H-tetrazol-5-yl)phenyl)-N-methyl-1H-imidazole-1-carboxamide A mixture of 4-(3-cyano-4-methoxyphenyl)-N-cyclohexyl-N-methyl-1H-imidazole-1-carboxamide (305 mg, 0.901 mmol), dibutylstannanone (28.0 mg, 0.113 mmol) and azidotrimethylsilane (0.239 ml, 1.803 mmol) was heated in toluene (8 mL) at 115° C. for 20 h. The mixture was then cooled to room temperature and evaporated to dryness. The crude product was chromatographed over silica using a mixture of dichlormethane/methanol (95:5). After evaporation of the homogenous fractions, the residual product was triturated with diethyl ether, filtered and dried to give the product as off-white crystals, (196 mg, 54%).

Preparation of Compound 576

4-(3-(2H-tetrazol-5-yl)phenyl)-N-cyclohexyl-N-methyl-1H-imidazole-1-carboxamide

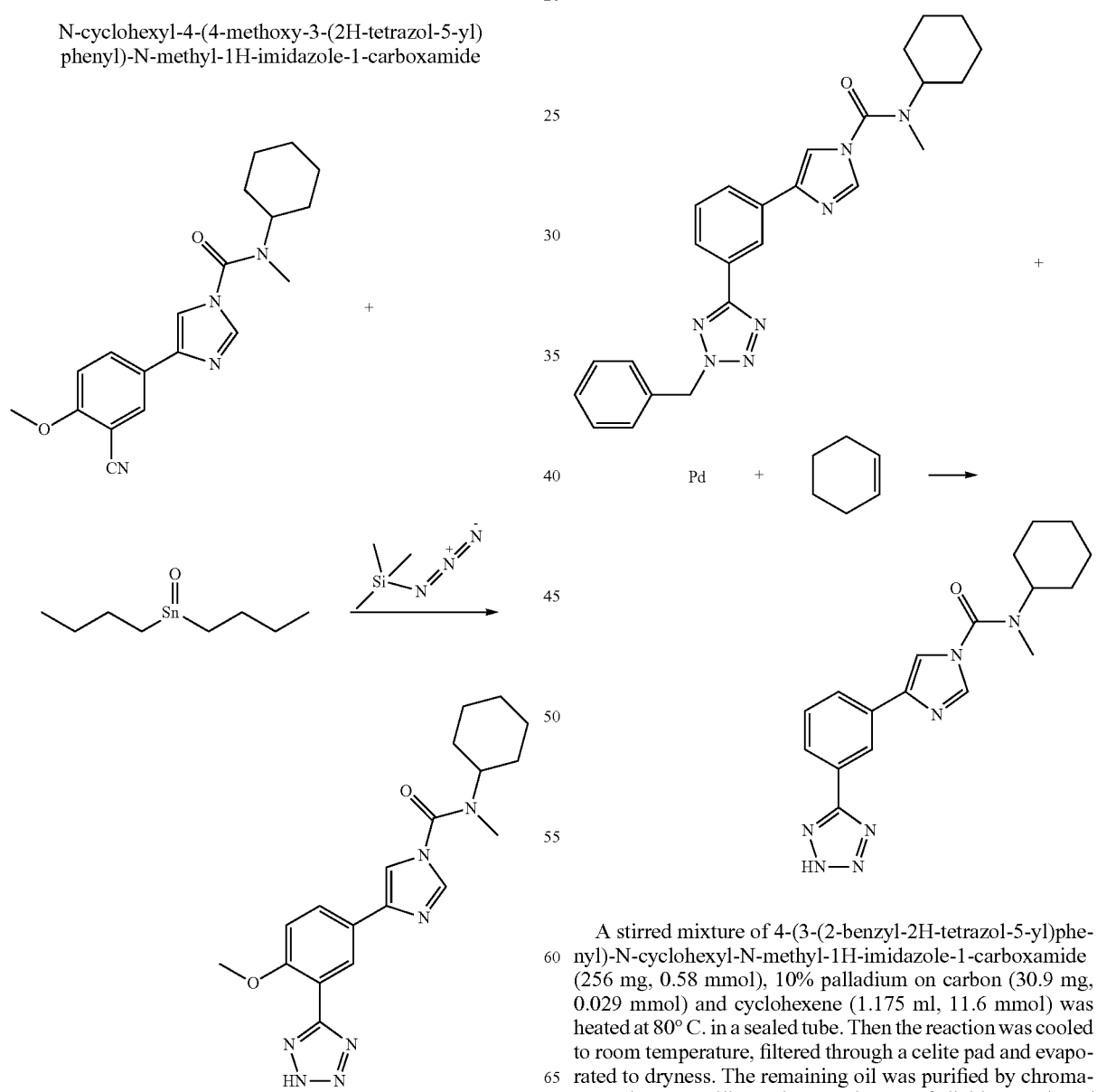

A stirred mixture of 4-(3-(2-benzyl-2H-tetrazol-5-yl)phenyl)-N-cyclohexyl-N-methyl-1H-imidazole-1-carboxamide (256 mg, 0.58 mmol), 10% palladium on carbon (30.9 mg, 0.029 mmol) and cyclohexene (1.175 ml, 11.6 mmol) was heated at 80° C. in a sealed tube. Then the reaction was cooled to room temperature, filtered through a celite pad and evaporated to dryness. The remaining oil was purified by chromatography over silica using a mixture of dichloromethane/methanol (90:10). Homogenous fractions were pooled and evaporated and the residual oil was crystallised from diethyl ether to give the product as an off-white powder, (45 mg, 21%).

Preparation of Compound 423

N-(1-benzylpiperidin-4-yl)-4-(3-(hydroxycarbamoyl) phenyl)-N-methyl-1H-imidazole-1-carboxamide

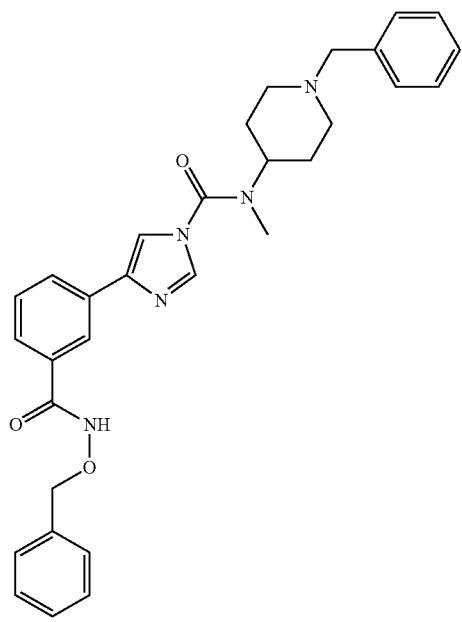

To a stirred suspension of 4-(3-(benzyloxycarbamoyl)phenyl)-N-(1-benzylpiperidin-4-yl)-N-methyl-1,1-imidazole-1-carboxamide (120 mg, 0.229 mmol) in dichloromethane (5 mL) at −78° C. was added tribromoborane (0.022 mL, 0.229 mmol). The reaction was stirred in the cold for 5 minutes and then allowed to warm up to room temperature over 1 h. The mixture was cooled to −20° C. and quenched carefully with methanol. Thereupon, the solvent was evaporated off and the residue was taken up in a mixture of dichloromethane/isopropanol (7:3) and washed with saturated NaHCO$_3$ solution and then dried (MgSO$_4$). After filtration, the dichloromethane was evaporated to a small volume and the resulting precipitate was filtered off, washed with isopropanol and dried to give the product as an off-white powder, (58 mg, 55%).

Preparation of Compound 551 a) (Z)—N-cyclohexyl-4-(4-(N'-hydroxycarbamimidoyl)phenyl)-N-methy 1-1H-imidazole-1-carboxamide

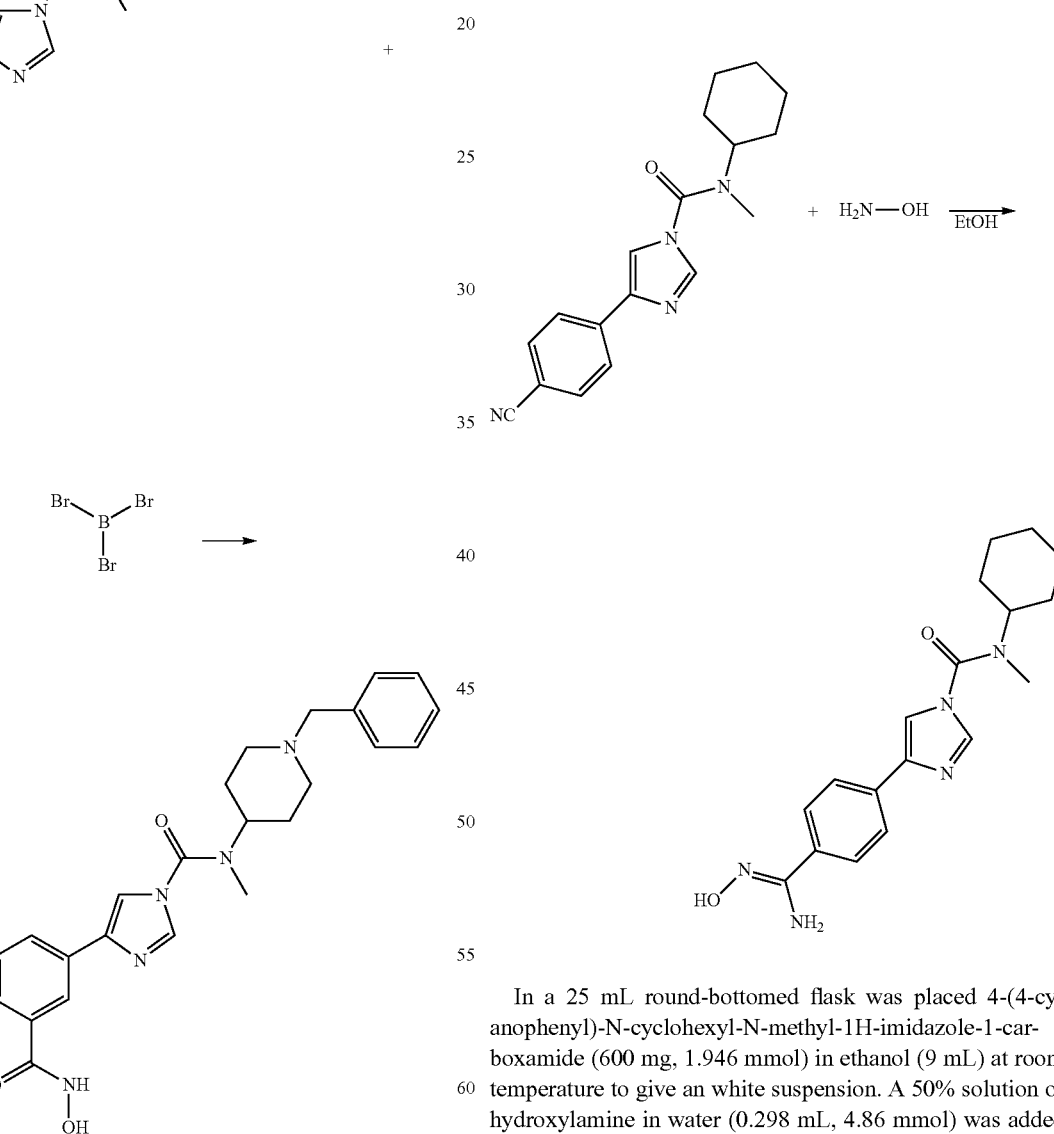

In a 25 mL round-bottomed flask was placed 4-(4-cyanophenyl)-N-cyclohexyl-N-methyl-1H-imidazole-1-carboxamide (600 mg, 1.946 mmol) in ethanol (9 mL) at room temperature to give an white suspension. A 50% solution of hydroxylamine in water (0.298 mL, 4.86 mmol) was added dropwise and the resulting mixture was heated at 90° C. for 90 minutes. The mixture was then cooled to room temperature and some precipitate was formed, that was filtered and washed with ethanol. This solid was recrystallized from a mixture of hot ethyl acetate (~70 mL) and petroleum ether b) (Z)—N-cyclohexyl-4-(4-(N'-(methoxycarbonyloxy)carbamimidoyl)phenyl)-N-methyl-1H-imidazole-1-carboxamide

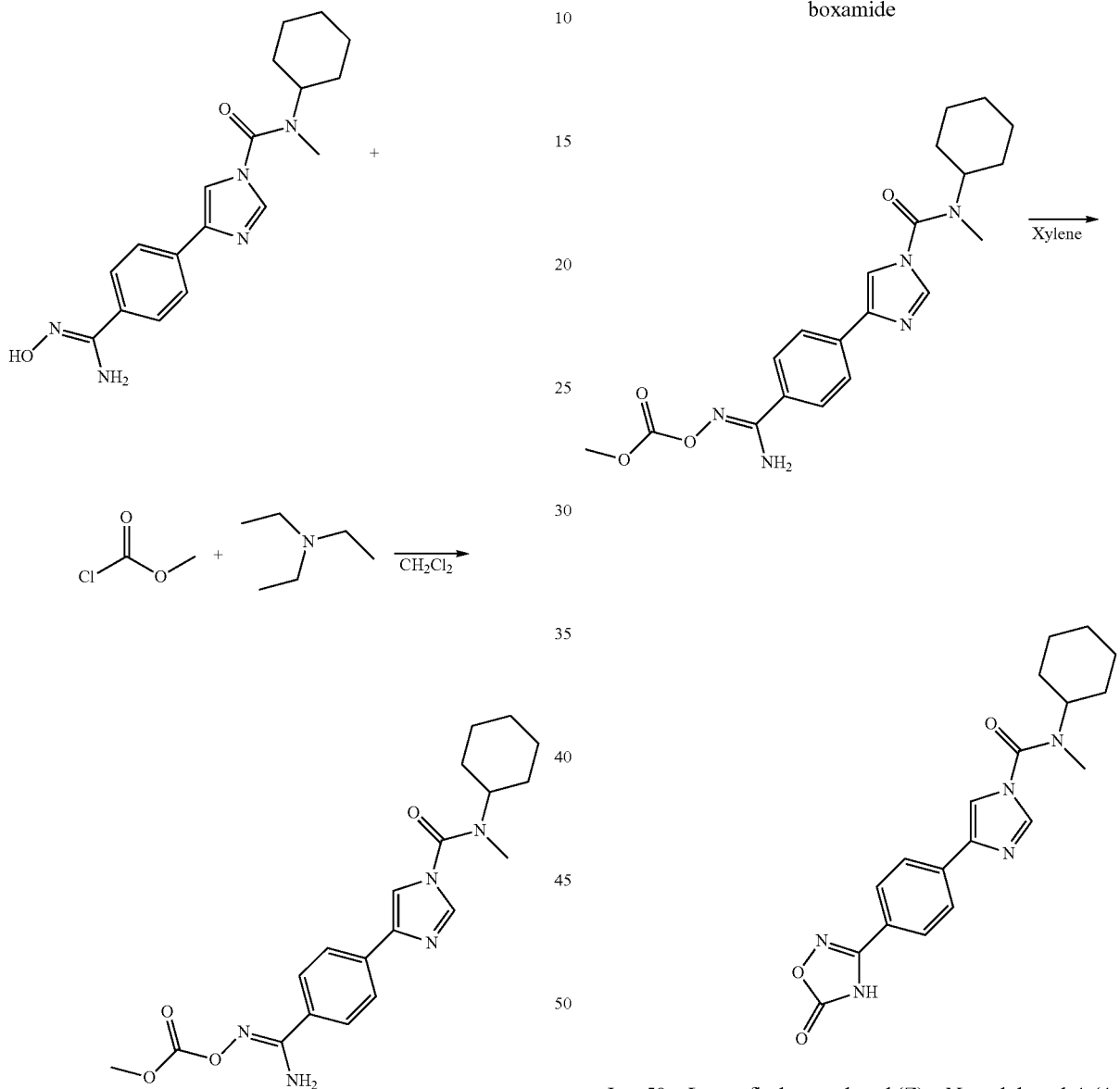

In a 25 mL pear flask was placed (Z)—N-cyclohexyl-4-(4-(N'-hydroxycarbamimidoyl)phenyl)-N-methyl-1H-imidazole-1-carboxamide (228 mg, 0.668 mmol) in anhydrous dichloromethane (3 mL) under nitrogen to give a white suspension. Triethylamine (0.102 mL, 0.735 mmol) was added and the suspension was cooled to 0° C. and stirred for 30 minutes. Thereupon, chloroformic acid, methyl ester (0.065 mL, 0.835 mmol) was added dropwise and the mixture was stirred at 0° C. for 30 minutes and then allowed to warm to room temperature and stirred for another 30 minutes. The precipitate was filtered off and dissolved in a mixture of isopropanol and dichloromethane (3:7). This solution was combined with the filtrate from above, and washed with 1 N HCl, water and brine, then dried (MgSO$_4$), filtered and evaporated to give a white solid, (228 mg, 82%).

c) N-cyclohexyl-N-methyl-4-(4-(5-oxo-4,5-dihydro-1,2,4-oxadiazol-3-yl)phenyl)-1H-imidazole-1-carboxamide

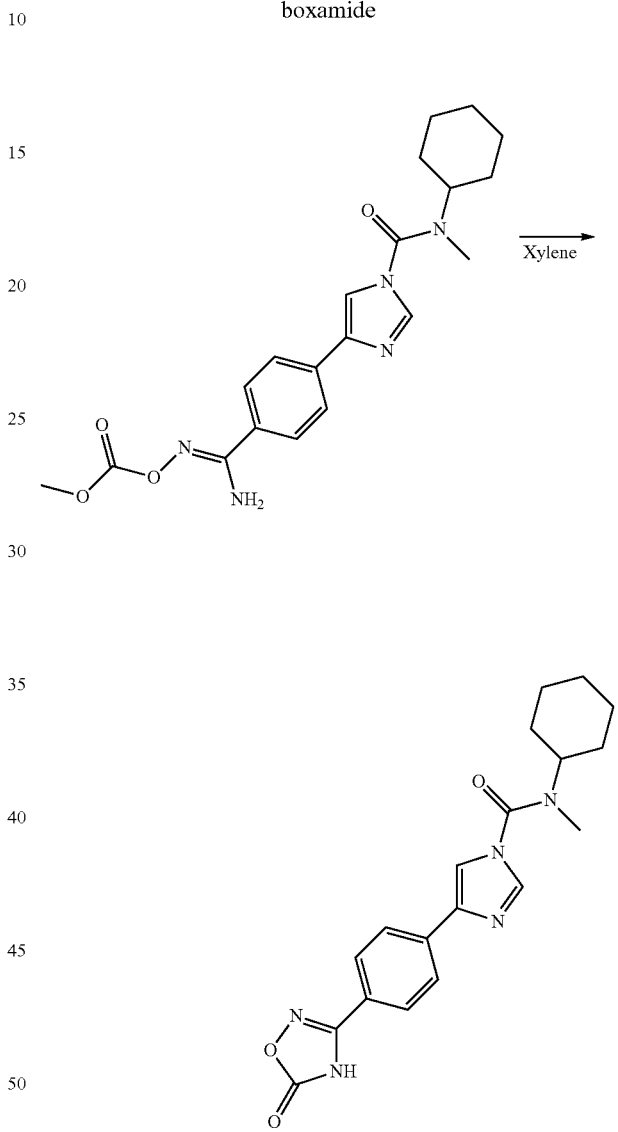

In a 50 mL pear flask was placed (Z)—N-cyclohexyl-4-(4-(N'-(methoxycarbonyloxy)carbamimidoyl)phenyl)-N-methyl-1H-imidazole-1-carboxamide (200 mg, 0.501 mmol) in xylenes (10 mL) under nitrogen to give a white suspension. The mixture was heated at 140° C. for 4 h and then cooled to room temperature. The precipitate that formed was filtered off and the filter cake was washed with xylenes. After drying, this solid was dissolved in a mixture of dichloromethane and isopropanol. After evaporating to a small volume, the solution was cooled to room temperature and the precipitate that formed was filtered off and dried to give the product as a pale pink solid, (134 mg, 69%).

Preparation of Compound 553 a) 4-(3-aminophenyl)-N-cyclohexyl-N-methyl-1H-imidazole-1-carboxamide

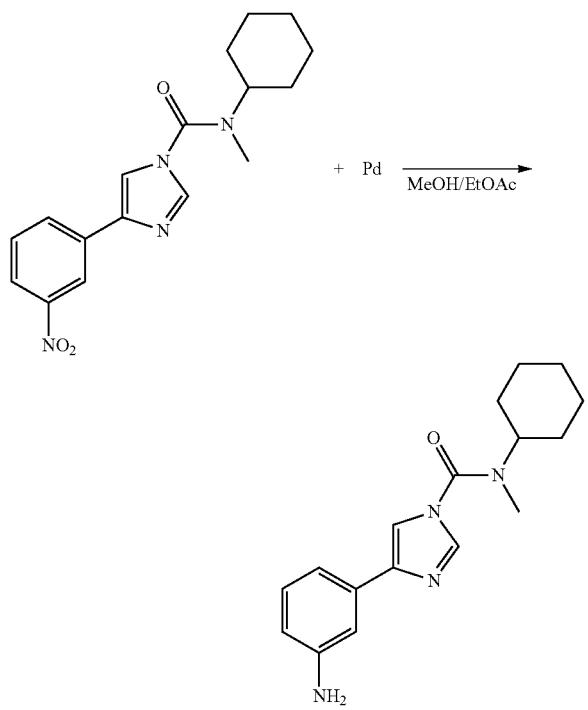

10% Palladium on carbon (0.122 g, 0.115 mmol) was added to a stirred solution of N-cyclohexyl-N-methyl-4-(3-nitrophenyl)-1H-imidazole-1-carboxamide (0.755 g, 2.299 mmol) in a mixture of ethyl acetate (46 mL) and methanol (46 mL) under an atmosphere of argon at room temperature. The mixture was then allowed to stir at room temperature under an atmosphere of hydrogen for 50 minutes. The mixture was filtered through celite and the pad was washed with methanol. The combined filtrate was evaporated to give a clear oil/foam (691 mg, 100%) that was used in the next step without further purification.

b) N-cyclohexyl-4-(3-guanidinophenyl)-N-methyl-1H-imidazole-1-carboxamide hydrochloride

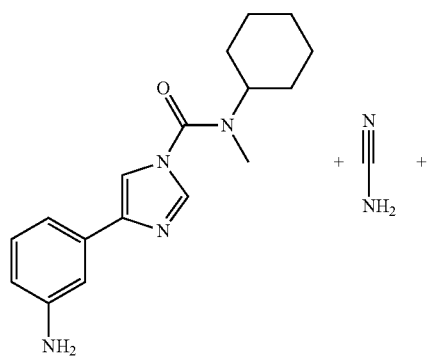

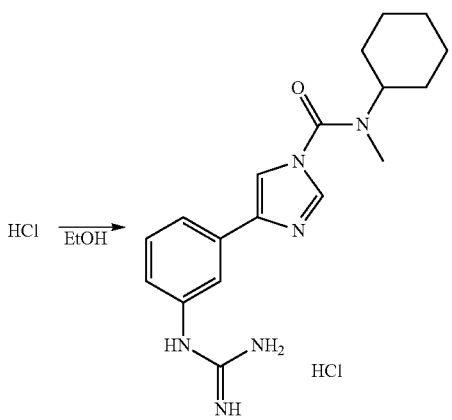

Gaseous anhydrous hydrogen chloride (0.096 mL, 1.156 mmol) was added to a stirred suspension of 4-(3-aminophenyl)-N-cyclohexyl-N-methyl-1H-imidazole-1-carboxamide (0.345 g, 1.156 mmol) and cyanamide (0.135 mL, 1.734 mmol) in ethanol (1.2 mL) at room temperature. The clear solution was allowed to stir at reflux for 1 h and a colourless solid formed. The reaction mixture was allowed to stir at reflux for further 7 h, whereupon the mixture was allowed to cool. The solid was separated by filtration and washed with ethanol to give the product as a colourless solid, (298 mg, 68%).

Preparation of BIA Compound 533 a) N-methyl-N-(piperidin-4-yl)-4-(pyridin-3-yl)-1H-imidazole-1-carboxamide bis(2,2,2-trifluoroacetate)

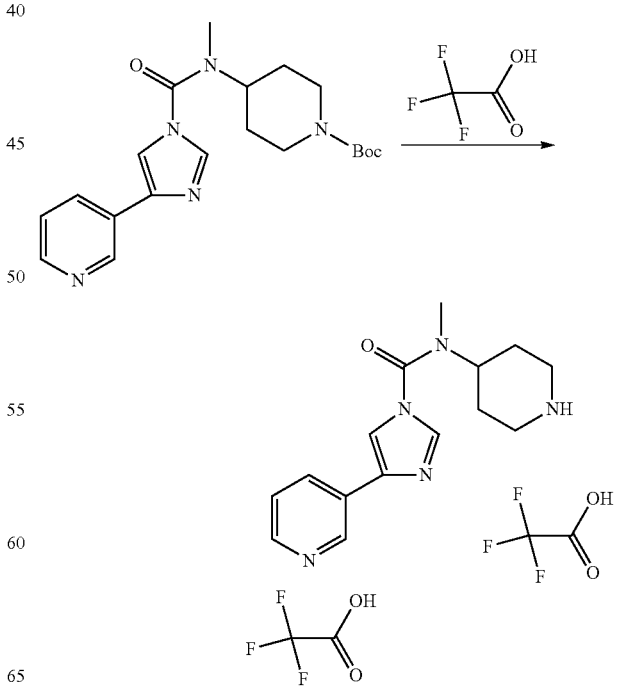

To tert-butyl 4-(N-methyl-4-(pyridin-3-yl)-1H-imidazole-1-carboxamido)piperidine-1-carboxylate (500 mg, 1.297 mmol) was added trifluoroacetic acid (4 mL, 51.9 mmol) to give a turbid solution. The mixture was allowed to stir at room temperature for 1 h, whereupon the solvent was removed by evaporation. The oily residue was triturated with ether, and the resulting white solid was filtered off to give a white solid (653.2 mg, 88% yield).

b) N-methyl-N-(1-(methylsulfonyl)piperidin-4-yl)-4-(pyridin-3-yl)-1H-imidazole-1-carboxamide

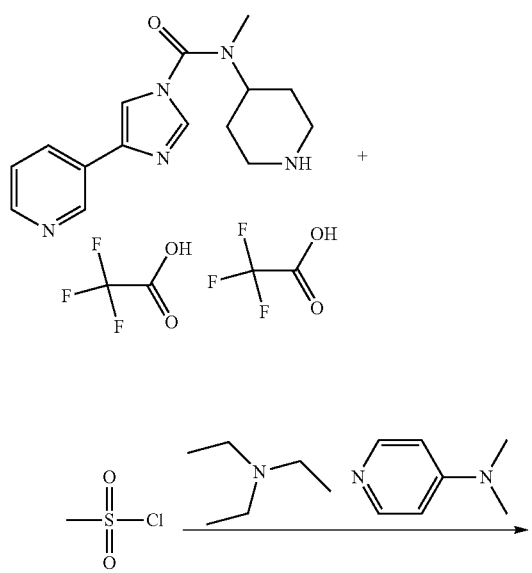

To an ice-water cooled suspension of N-methyl-N-(piperidin-4-yl)-4-(pyridin-3-yl)-1H-imidazole-1-carboxamide bis (2,2,2-trifluoroacetate) (300 mg, 0.584 mmol) in dichloromethane (10 mL) was added DMAP (35.7 mg, 0.292 mmol), followed by the dropwise addition of triethylamine (0.326 mL, 2.337 mmol), followed in turn by addition of methanesulfonyl chloride (0.072 mL, 0.934 mmol). The solution was allowed to stir at room temperature overnight, whereupon it was quenched by the addition of methanol and allowed to stir at room temperature. The white precipitate was collected by filtration, washed with methanol and ether, then dried to give the product as a white solid, (158 mg, 74%).

Preparation of Compound 550

N-(1-benzylpiperidin-4-yl)-4-(3'-carbamoylbiphenyl-3-yl)-N-methyl-1H-imidazole-1-carboxamide

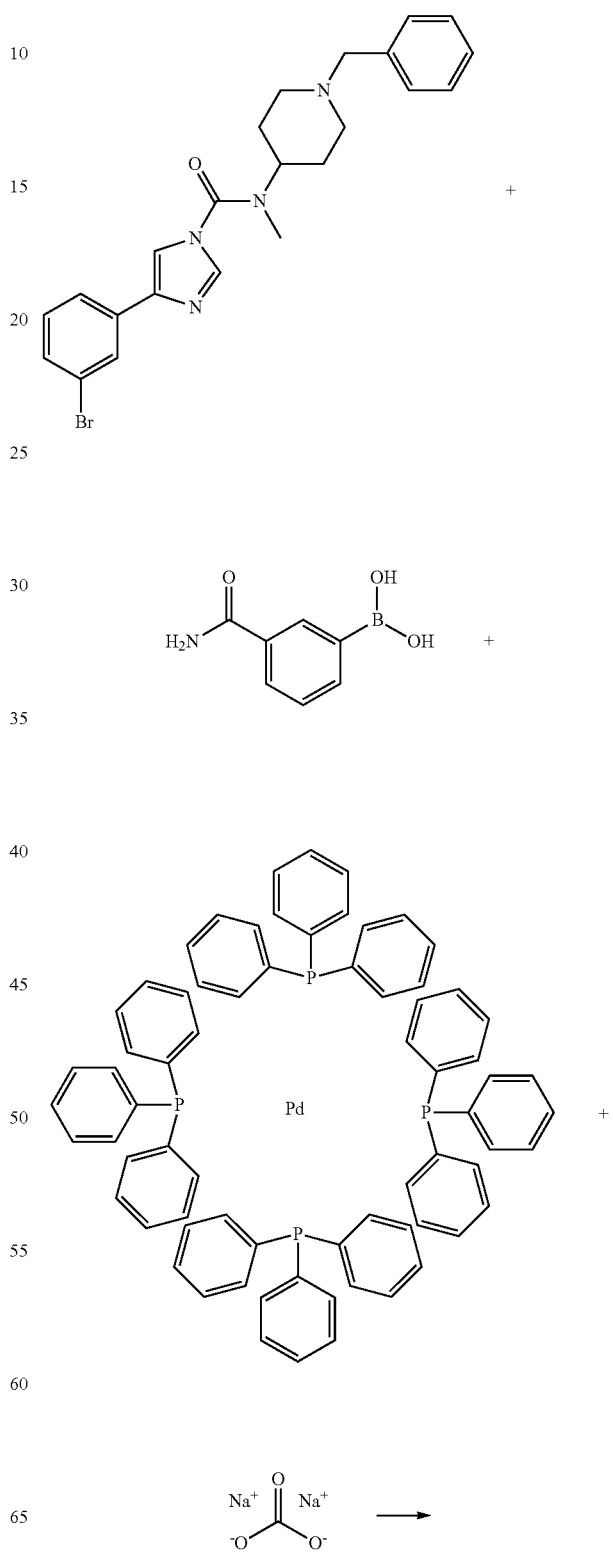

-continued

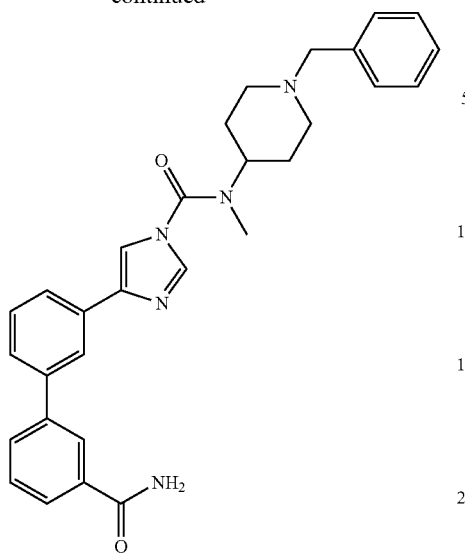

Tetrakis(triphenylphosphine)palladium complex (0.076 g, 0.066 mmol) was added to a stirred dispersion of N-(1-benzylpiperidin-4-yl)-4-(3-bromophenyl)-N-methyl-1H-imidazole-1-carboxamide (0.600 g, 1.323 mmol), 3-carbamoylphenylboronic acid (0.229 g, 1.390 mmol) and a 2 M solution of sodium carbonate (0.794 mL, 1.588 mmol) in a mixture of 1-propanol (5 mL) and water (1 mL) at room temperature. The reaction mixture was allowed to stir at 90° C. for 1 h. Water was added and the organic layer was diluted with a mixture of dichloromethane/isopropanol (7:3). The organic layer was separated, dried (MgSO$_4$), filtered and evaporated to give an orange oil. Column chromatography (silica, dichloromethane/methanol 5%) gave the product as an orange oil. The oil was triturated with a mixture of petroleum ether/ethyl acetate/ether to give the product as a beige solid (123 mg, 17%).

Preparation of Compound 485 a) 4-(3-amino-4-methoxyphenyl)-N-cyclohexyl-N-methyl-1H-imidazole-1-carboxamide

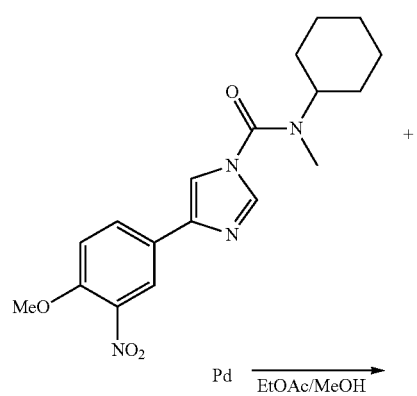

-continued

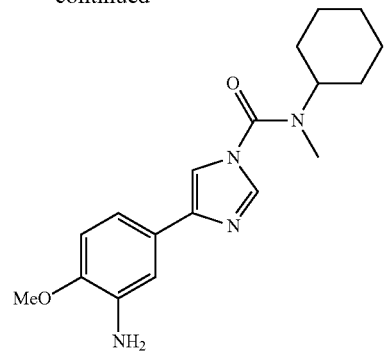

10% Palladium on carbon (0.16 g, 0.15 mmol) was added to a stirred solution of N-cyclohexyl-4-(4-methoxy-3-nitrophenyl)-N-methyl-1H-imidazole-1-carboxamide (1.075 g, 3 mmol) in a mixture of ethyl acetate (50 mL) and methanol (50 mL) at room temperature under an argon atmosphere. Hydrogen was bubbled through the solution for 1 h. The solution was then filtered through celite and the pad was washed with ethyl acetate. The combined filtrate was evaporated to give a brown oily solid that was used in the next step without further purification.

b) N-cyclohexyl-4-(4-methoxy-3-(methylsulfonamido)phenyl)-N-methyl-1H-imidazole-1-carboxamide

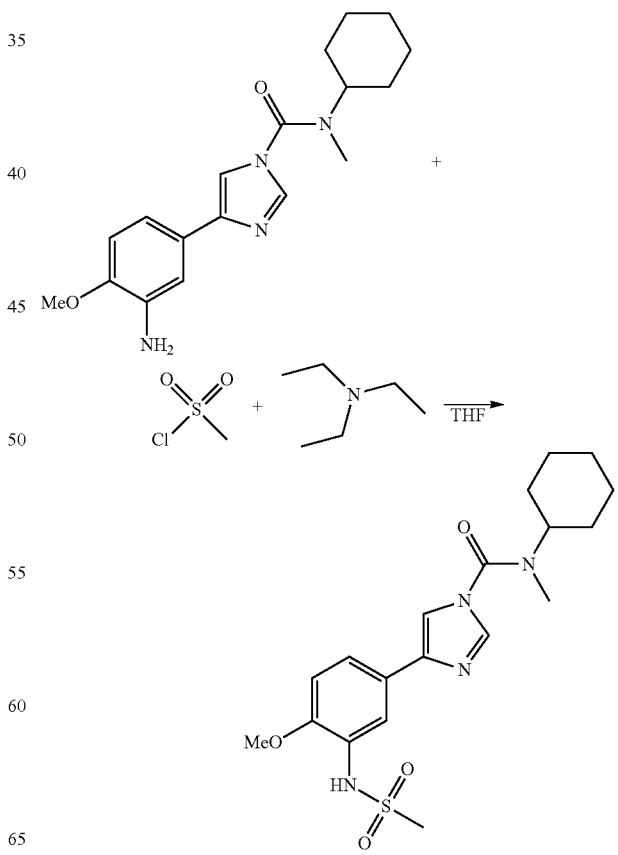

Mesyl chloride (0.247 mL, 3.17 mmol) was added to a stirred solution of 4-(3-amino-4-methoxyphenyl)-N-cyclohexyl-N-methyl-1H-imidazole-1-carboxamide (1.04 g, 3.17 mmol) and triethylamine (0.441 mL, 3.17 mmol) in tetrahydrofuran (6 mL) at room temperature. The brown mixture was allowed to stir at room temperature over the weekend. Water was added and the solvent was evaporated. Then the aqueous layer was acidified and the residue was extracted with ethyl acetate. The aqueous layer was extracted twice with a mixture of dichloromethane/isopropanol (7:3). The organic layer was separated, dried (MgSO₄) filtered and evaporated to give an off-white solid. The solid was recrystallised from an ethanol/dichloromethane mixture to give the product as an off-white solid (434 mg, 34%).

Preparation of Compound 564

N-cyclopentyl-N-methyl-4-(2-oxo-2,3-dihydrobenzo[d]oxazol-5-yl)-1H-imidazole-1-carboxamide

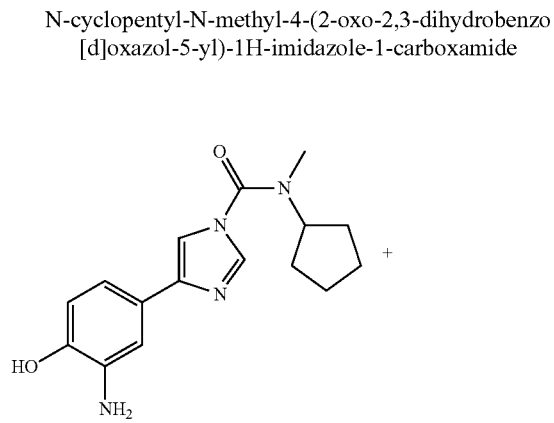

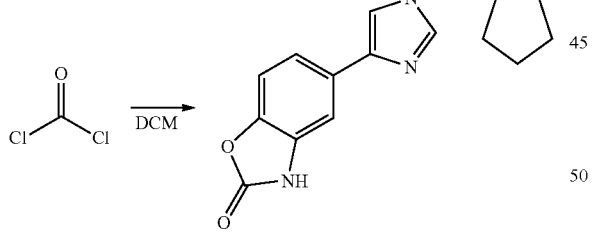

A 20% toluene solution of phosgene (0.590 mL, 1.121 mmol) was added dropwise at room temperature to a stirred solution of 4-(3-amino-4-hydroxyphenyl)-N-cyclopentyl-N-methyl-1H-imidazole-1-carboxamide (0.259 g, 0.862 mmol) in dichloromethane (5 mL) and the off-white suspension was allowed to stir for 5 h. Water was added and the organic layer was diluted with a mixture of dichloromethane/isopropanol (7:3). The organic layer was separated, dried (MgSO₄), filtered and evaporated to give an off-white solid that was triturated with hot methanol. Filtration and drying gave the product as an off-white solid (90 mg, 30%).

Preparation of Compound 580

N-cyclohexyl-N-methyl-4-(4-(sulfamoylamino)phenyl)-1H-imidazole-1-carboxamide

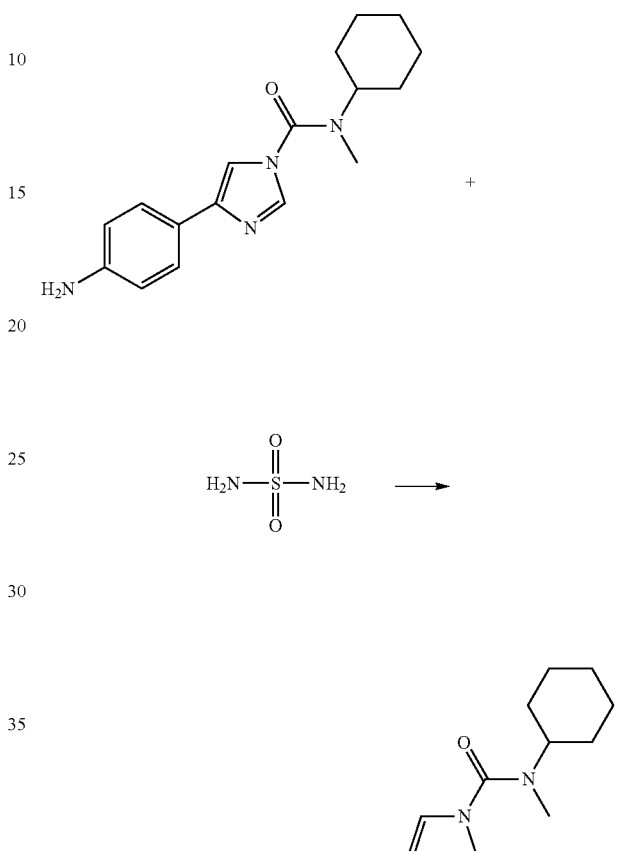

Sulfamide (0.089 g, 0.922 mmol) was added to a stirred suspension of 4-(4-aminophenyl)-N-cyclohexyl-N-methyl-1H-imidazole-1-carboxamide (0.250 g, 0.838 mmol) in dioxane (2 mL) at room temperature. The suspension was heated at reflux for 4 h to give a clear solution, whereupon more sulfamide (0.089 g, 0.922 mmol) was added and the mixture was heated at reflux for a further 2.5 h. The solvent was removed and the brown residue was purified by chromatography (silica, dichloromethane/methanol, 1%, 2%, 5%). Homogenous fractions were pooled and evaporated. The residue was triturated with ethyl acetate and the colourless solid that formed was removed by filtration. The filtrate was evaporated and purified again by preparative TLC (silica, dichloromethane/10% methanol). The product was extracted from the silica with a mixture of ethyl acetate/10% methanol. Evaporation of the solvent gave a clear oil, that was triturated with a mixture of ethyl acetate and methanol to give the product as an off-white solid (19 mg, 6%).

Preparation of Compound 541

N-(1-(2-cyanoethyl)piperidin-4-yl)-4-(3-fluoro-4-methoxyphenyl)-N-methyl-1H-imidazole-1-carboxamide

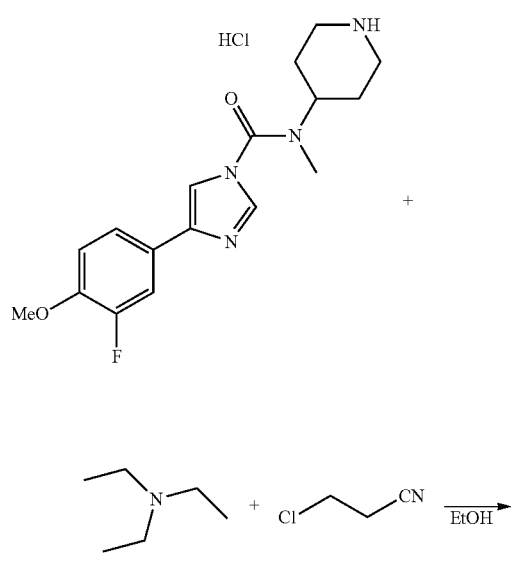

Triethylamine (0.159 mL, 1.139 mmol) was added to a stirred suspension of 4-(3-fluoro-4-methoxyphenyl)-N-methyl-N-(piperidin-4-yl)-1H-imidazole-1-carboxamide hydrochloride (0.200 g, 0.542 mmol) and 3-chloropropanenitrile (0.058 g, 0.651 mmol) at room temperature. The clear solution was allowed to stir at reflux for 2 h, during which time a white suspension formed. The mixture was allowed to cool to room temperature, diluted with a mixture of dichloromethane/isopropanol (7:3) and then washed with water. The organic layer was dried (MgSO$_4$), filtered and evaporated to give a colourless solid that was triturated with ethanol to give the product (142 mg, 64%).

Preparation of Compound 505 a) (1H-benzo[d][1,2,3]triazol-5-yl)(4-cyclohexylpiperazin-1-yl)methanone

In a 100 mL round-bottomed flask was placed 1H-benzo[d][1,2,3]triazole-5-carboxylic acid (510 mg, 3.126 mmol) in anhydrous tetrahydrofuran (10 mL) under nitrogen to give a brown suspension. CDI (558 mg, 3.439 mmol) was added in portions and the mixture was stirred at room temperature for 1.5 h. Then 1-cyclohexylpiperazine (658 mg, 3.908 mmol) was added in portions and the resulting brown solution was stirred at room temperature for another 30 minutes. The solvent was evaporated and the brown oil was partitioned in 30% isopropanol/dichloromethane/water. The phases were separated and organic phase was washed with water and brine, then dried (MgSO$_4$), filtered and evaporated. The resulting beige foam was purified by chromatography (silica gel H; dichloromethane, 2%, 3%, 5% methanol/dichoromethane). Fractions with pure product were evaporated and the pale orange foam was triturated with heptane. The solid was filtered and dried to give a beige solid, (605 mg, 54%).

b) (4-cyclohexylpiperazin-1-yl)(2-(4,4-dimethyloxazolidine-3-carbonyl)-2H-benzo[d][1,2,3]triazol-5-yl)methanone oxalate

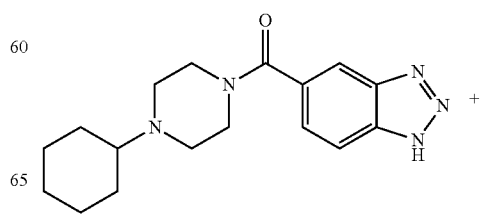

-continued

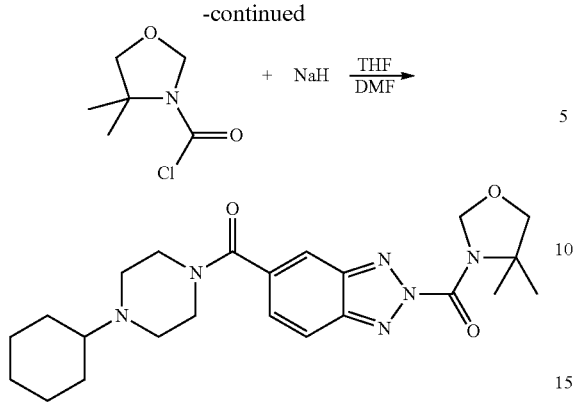

In a 100 mL round-bottomed flask was placed (1H-benzo[d][1,2,3]triazol-5-yl)(4-cyclohexylpiperazin-1-yl)methanone (612 mg, 1.953 mmol) in tetrahydrofuran (15 mL) and N,N-dimethylformamide (3 mL) to give a pale yellow solution. This solution was cooled to 0° C. and a 60% mineral oil dispersion of sodium hydride (70.3 mg, 2.93 mmol) was added. The resulting pale pink solution was allowed to warm to room temperature and stirred for 45 minutes. Then the mixture was cooled again to 0° C. and a solution of 4,4-dimethyloxazolidine-3-carbonyl chloride (351 mg, 2.148 mmol) in tetrahydrofuran (2.5 mL) was added dropwise. The resulting pale yellow solution was allowed to warm to room temperature and stirred for 4 h. The solvent was evaporated and water was added to the residue which was extracted with toluene. The organic phase was washed with water and brine, then dried (MgSO$_4$), filtered and evaporated. The resulting yellow oil was purified by chromatography (silica gel H; dichloromethane, 2% methanol/dichloromethane. Fractions with pure product were pooled and evaporated to give a pale yellow foam, (690 mg, 80%).

In a 50 mL pear flask was placed (4-cyclohexylpiperazin-1-yl)(2-(4,4-dimethyloxazolidine-3-carbonyl)-2H-benzo[d][1,2,3]triazol-5-yl)methanone (300 mg, 0.681 mmol) in methanol (5 mL) at room temperature, to give a yellow solution. Oxalic acid dihydrate (86 mg, 0.681 mmol) was added in one portion, and the solution was stirred at room temperature for 2 h. The solvent was evaporated and the resulting pale yellow foam was crystallized from isopropanol. After filtration and drying, the product was obtained as a white solid, (150 mg, 39%).

Preparation of Compound 595 a) N-(1-cyanopiperidin-4-yl)-4-(4-methoxyphenyl)-N-methyl-1H-imidazole-1-carboxamide

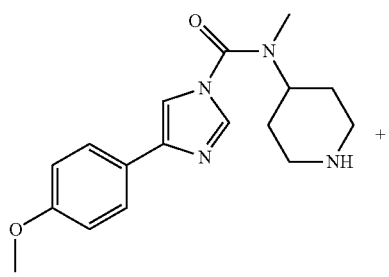

To a solution of 4-(4-methoxyphenyl)-N-methyl-N-(piperidin-4-yl)-1H-imidazole-1-carboxamide hydrochloride (287 mg, 0.818 mmol) in DMF (5 mL) was added potassium tert-butoxide (184 mg, 1.636 mmol) and the mixture was allowed to stir at room temperature for 30 minutes, whereupon it was cooled in an ice/water bath and cyanogen bromide (0.818 mL, 2.454 mmol, 3 N dichloromethane solution) was added dropwise over 10-15 minutes. The reaction mixture was allowed to slowly warm up to room temperature over 1 h, and was then partitioned between water and dichloromethane/isopropanol (7:3). The layers were separated and the organic phase was further washed with water and brine, then dried (Na$_2$SO$_4$), filtered and the solvent was removed under reduced pressure. The residue was dissolved in the minimum volume of chloroform and insoluble material was removed by filtration. The filtrate was concentrated to give an off-white solid, (345 mg, 67%).

b) N-(1-(2H-tetrazol-5-yl)piperidin-4-yl)-4-(4-methoxyphenyl)-N-methyl-1H-imidazole-1-carboxamide

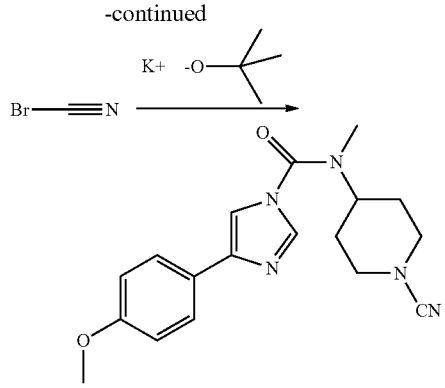

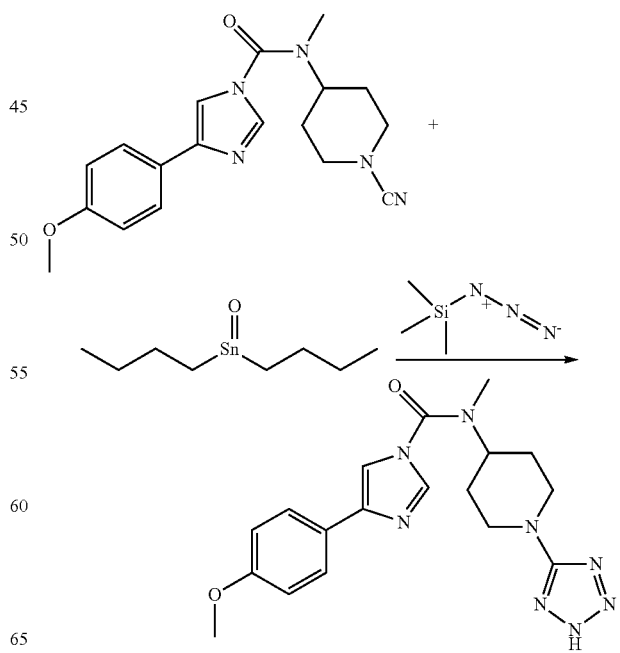

To a suspension of N-(1-cyanopiperidin-4-yl)-4-(4-methoxyphenyl)-N-methyl-1H-imidazole-1-carboxamide (151 mg, 0.445 mmol) in toluene (10 mL) was added dibutylstannanone (13.84 mg, 0.056 mmol) followed by azidotrimethylsilane (0.207 mL, 1.557 mmol). The reaction mixture was heated at reflux for 5 h, whereupon it was filtered still hot and the resulting pink solid was washed sequentially with toluene, dichloromethane and then finally ether. The solid was recrystallised from methanol to give the product as a light pink solid, (100 mg, 56%).

2. Example Compounds

| No. | Structure |
|-----|-----------|
| 1 | 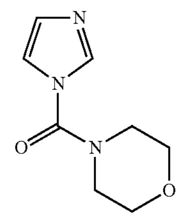 [SMILES: O=C(N1CCOCC1)n1ccnc1] |
| 2 | 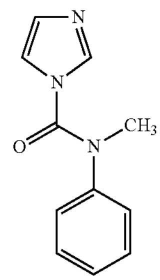 |
| 3 | 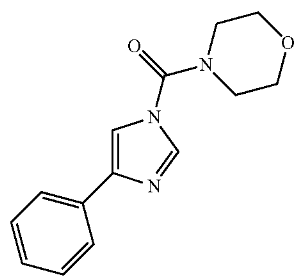 [SMILES: O=C(N1CCOCC1)n1cnc(-c2ccccc2)c1] |
| 4 | 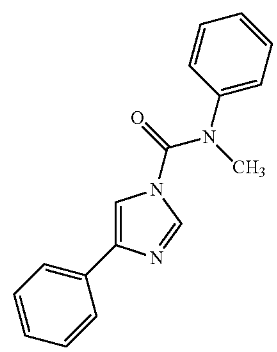 [SMILES: CN(C(=O)n1cnc(-c2ccccc2)c1)c1ccccc1] |
| 5 | 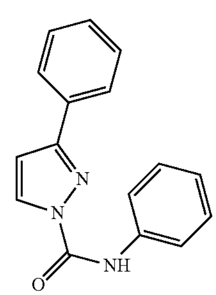 [SMILES: O=C(Nc1ccccc1)n1ccc(-c2ccccc2)n1] |

-continued
| No. | Structure |
|---|---|
| 6 | 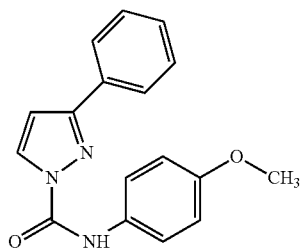 [SMILES: COc1ccc(NC(=O)n2ccc(-c3ccccc3)n2)cc1] |
| 7 | 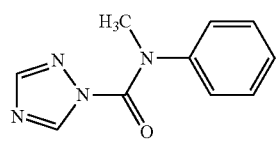 |
| 8 | 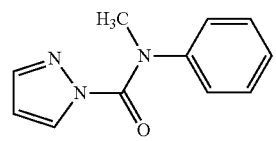 |
| 9 | 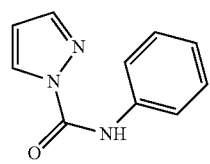 [SMILES: O=C(Nc1ccccc1)n1cccn1] |
| 10 | 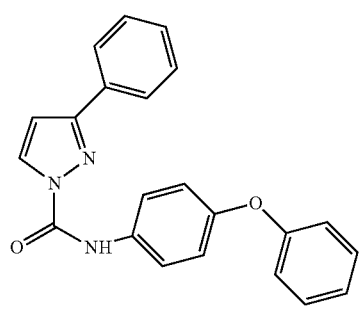 [SMILES: O=C(Nc1ccc(Oc2ccccc2)cc1)n1ccc(-c2ccccc2)n1] |
| 11 | 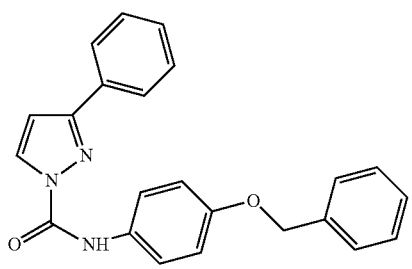 [SMILES: O=C(Nc1ccc(OCc2ccccc2)cc1)n1ccc(-c2ccccc2)n1] |

-continued
| No. | Structure |
|---|---|
| 12 | 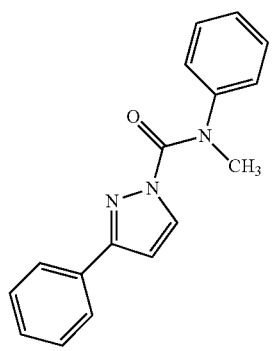 [SMILES: CN(C(=O)n1ccc(-c2ccccc2)n1)c1ccccc1] |
| 13 | 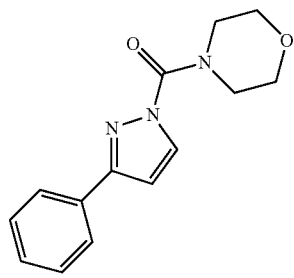 [SMILES: O=C(N1CCOCC1)n1ccc(-c2ccccc2)n1] |
| 14 | 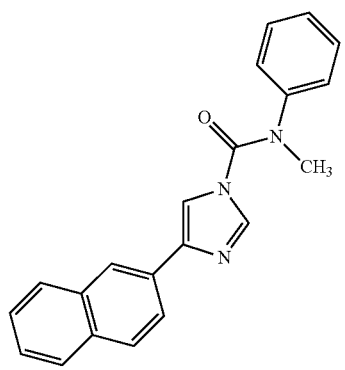 [SMILES: CN(C(=O)n1cnc(-c2ccc3ccccc3c2)c1)c1ccccc1] |
| 15 | 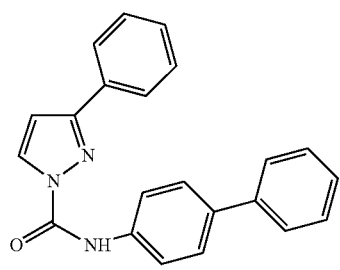 [SMILES: O=C(Nc1ccc(-c2ccccc2)cc1)n1ccc(-c2ccccc2)n1] |

-continued
| No. | Structure |
|---|---|
| 16 | 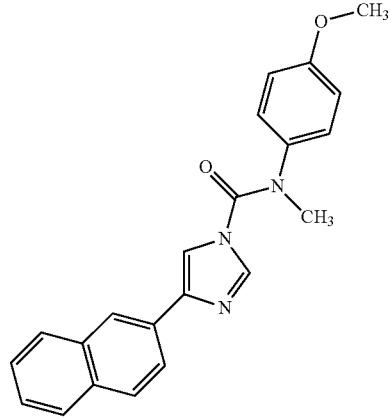 [SMILES: COc1ccc(N(C)C(=O)n2cnc(-c3ccc4ccccc4c3)c2)cc1] |
| 17 | 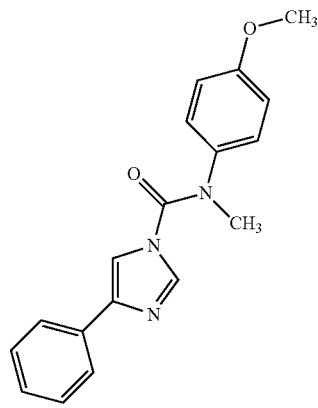 [SMILES: COc1ccc(N(C)C(=O)n2cnc(-c3ccccc3)c2)cc1] |
| 18 | 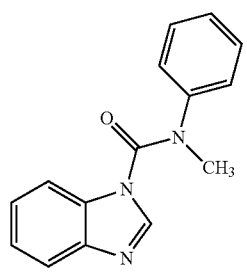 [SMILES: CN(C(=O)n1cnc2ccccc21)c1ccccc1] |
| 19 | 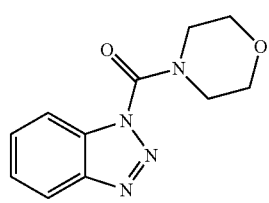 [SMILES: O=C(N1CCOCC1)n1nnc2ccccc21] |

| No. | Structure |
|---|---|
| 20 | 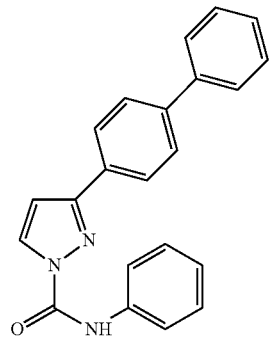 [SMILES: O=C(Nc1ccccc1)n1ccc(-c2ccc(-c3ccccc3)cc2)n1] |
| 21 | 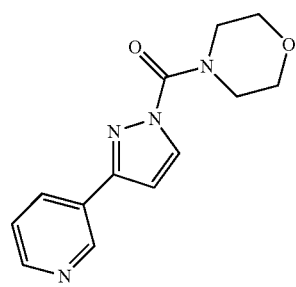 [SMILES: O=C(N1CCOCC1)n1ccc(-c2cccnc2)n1] |
| 22 | 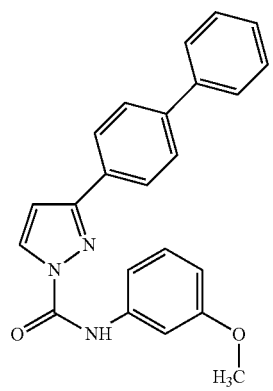 [SMILES: COc1cccc(NC(=O)n2ccc(-c3ccc(-c4ccccc4)cc3)n2)c1] |
| 23 | 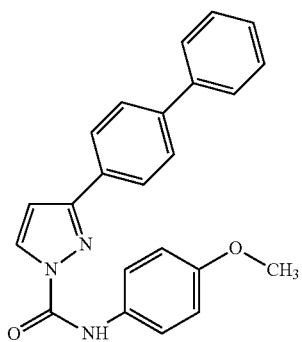 [SMILES: COc1ccc(NC(=O)n2ccc(-c3ccc(-c4ccccc4)cc3)n2)cc1] |

-continued
| No. | Structure |
|---|---|
| 24 | 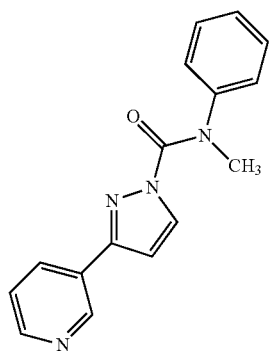 [SMILES: CN(C(=O)n1ccc(-c2cccnc2)n1)c1ccccc1] |
| 25 | 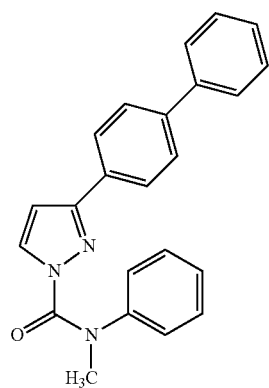 [SMILES: CN(C(=O)n1ccc(-c2ccc(-c3ccccc3)cc2)n1)c1ccccc1] |
| 26 | 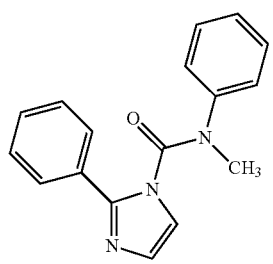 [SMILES: CN(C(=O)n1ccnc1-c1ccccc1)c1ccccc1] |
| 27 | 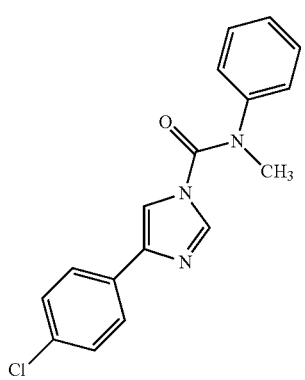 [SMILES: CN(C(=O)n1cnc(-c2ccc(Cl)cc2)c1)c1ccccc1] |

-continued
| No. | Structure |
|---|---|
| 28 | 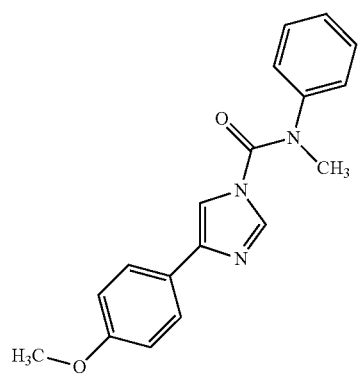 [SMILES: COc1ccc(-c2cn(C(=O)N(C)c3ccccc3)cn2)cc1] |
| 29 | 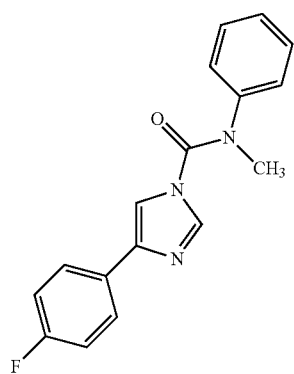 [SMILES: CN(C(=O)n1cnc(-c2ccc(F)cc2)c1)c1ccccc1] |
| 30 | 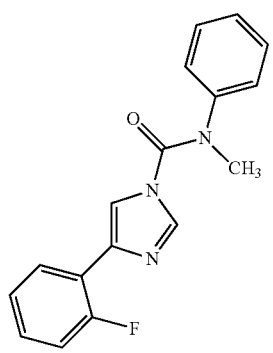 [SMILES: CN(C(=O)n1cnc(-c2ccccc2F)c1)c1ccccc1] |
| 31 | 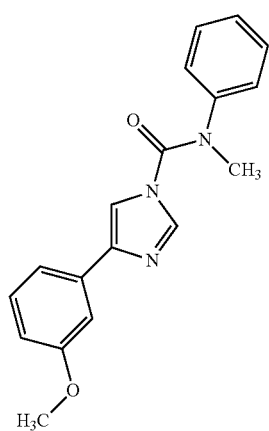 [SMILES: COc1cccc(-c2cn(C(=O)N(C)c3ccccc3)cn2)c1] |

-continued
| No. | Structure |
|---|---|
| 32 | 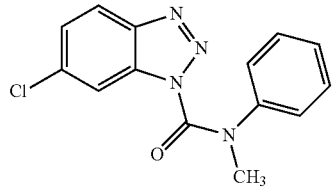 [SMILES: CN(C(=O)n1nnc2ccc(Cl)cc21)c1ccccc1] |
| 33 | 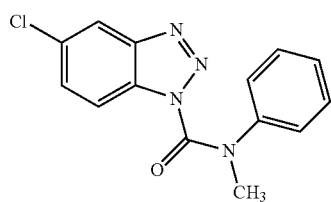 [SMILES: CN(C(=O)n1nnc2cc(Cl)ccc21)c1ccccc1] |
| 34 | 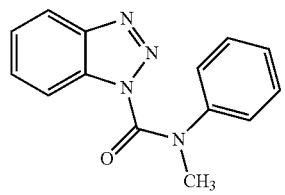 |
| 35 | 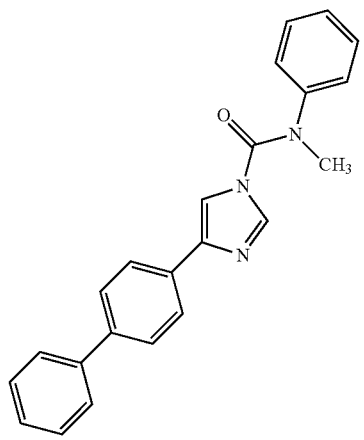 [SMILES: CN(C(=O)n1cnc(-c2ccc(-c3ccccc3)cc2)c1)c1ccccc1] |
| 36 | 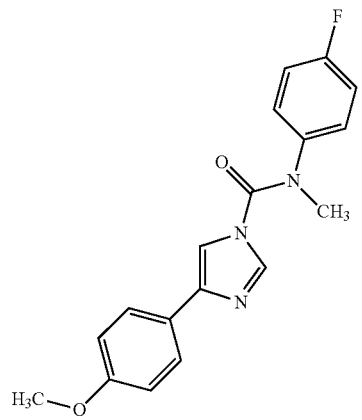 [SMILES: COc1ccc(-c2cn(C(=O)N(C)c3ccc(F)cc3)cn2)cc1] |

-continued
| No. | Structure |
|---|---|
| 37 | 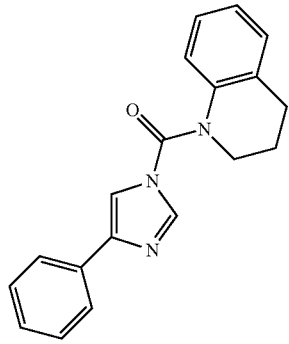 [SMILES: O=C(N1CCCc2ccccc21)n1cnc(-c2ccccc2)c1] |
| 38 | 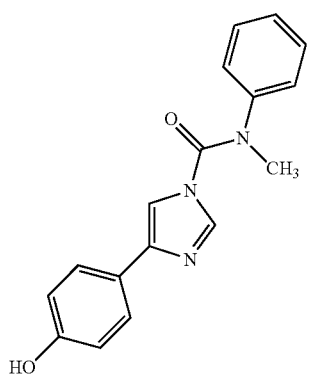 [SMILES: CN(C(=O)n1cnc(-c2ccc(O)cc2)c1)c1ccccc1] |
| 39 | 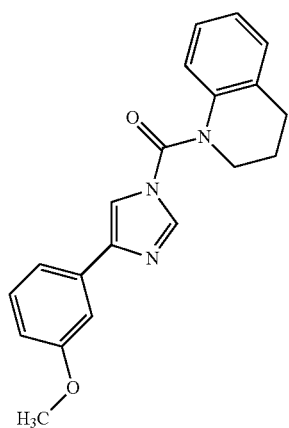 [SMILES: COc1cccc(-c2cn(C(=O)N3CCCc4ccccc43)cn2)c1] |
| 40 | 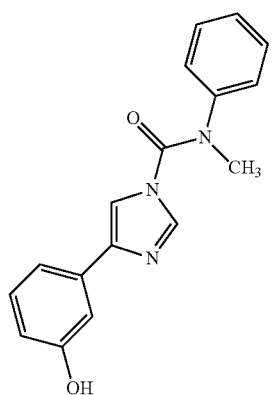 [SMILES: CN(C(=O)n1cnc(-c2cccc(O)c2)c1)c1ccccc1] |

-continued

| No. | Structure |
|---|---|
| 41 | (benzotriazol-1-yl)carbonyl-4-phenylpiperazine |
| 42 | (benzotriazol-1-yl)carbonyl-4-benzylpiperidine |
| 43 | 4-(4-chlorophenyl)-N-(4-fluorophenyl)-N-methyl-1H-imidazole-1-carboxamide |
| 44 | 4-(4-fluorophenyl)-1H-imidazol-1-yl 3,4-dihydroquinolin-1(2H)-yl ketone |

-continued
| No. | Structure |
|---|---|
| 45 | 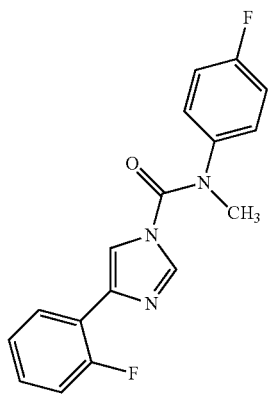 [SMILES: CN(C(=O)n1cnc(-c2ccccc2F)c1)c1ccc(F)cc1] |
| 46 | 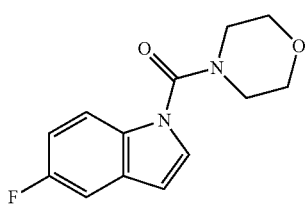 [SMILES: O=C(N1CCOCC1)n1ccc2cc(F)ccc21] |
| 47 | 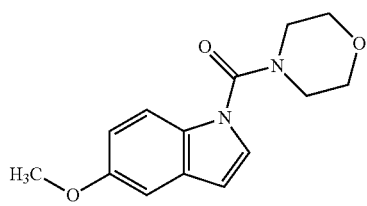 [SMILES: COc1ccc2c(ccn2C(=O)N2CCOCC2)c1] |
| 48 | 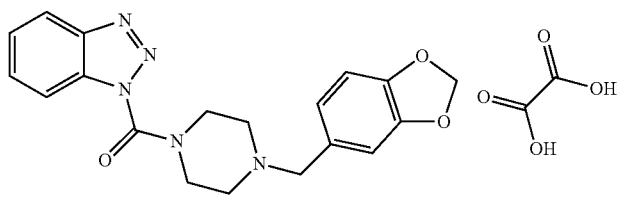 |
| 49 | 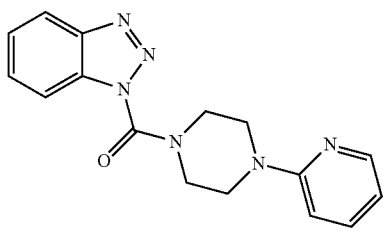 [SMILES: O=C(N1CCN(c2ccccn2)CC1)n1nnc2ccccc21] |
| 50 | 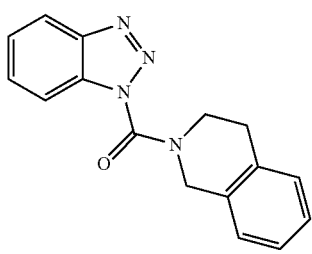 [SMILES: O=C(N1CCc2ccccc2C1)n1nnc2ccccc21] |

-continued
| No. | Structure |
|---|---|
| 51 | 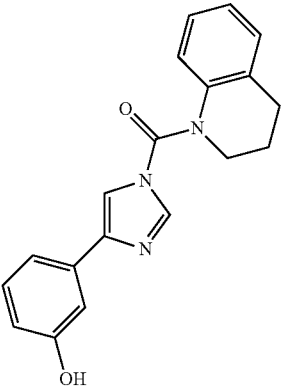 [SMILES: O=C(N1CCCc2ccccc21)n1cnc(-c2cccc(O)c2)c1] |
| 52 | 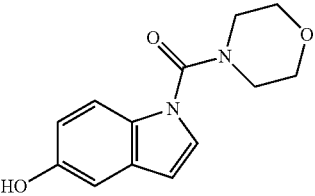 [SMILES: O=C(N1CCOCC1)n1ccc2cc(O)ccc21] |
| 53 | 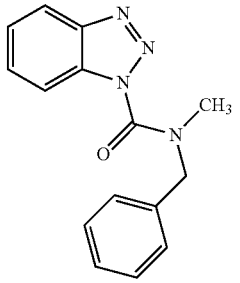 [SMILES: CN(Cc1ccccc1)C(=O)n1nnc2ccccc21] |
| 54 | 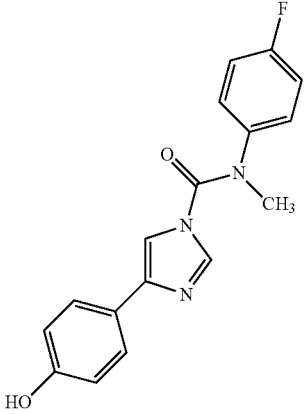 [SMILES: CN(C(=O)n1cnc(-c2ccc(O)cc2)c1)c1ccc(F)cc1] |
| 55 | 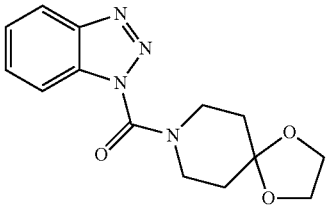 [SMILES: O=C(N1CCC2(CC1)OCCO2)n1nnc2ccccc21] |

| No. | Structure |
|---|---|
| 56 | 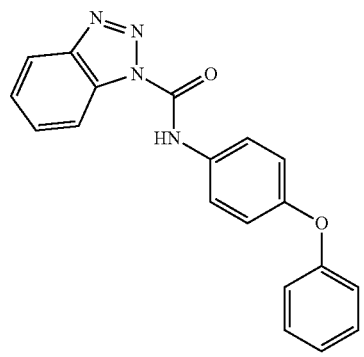 [SMILES: O=C(Nc1ccc(Oc2ccccc2)cc1)n1nnc2ccccc21] |
| 57 | 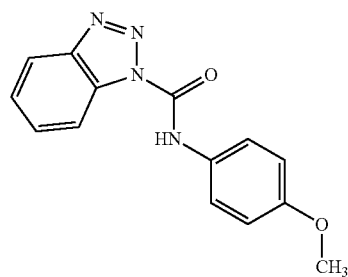 [SMILES: COc1ccc(NC(=O)n2nnc3ccccc32)cc1] |
| 58 | 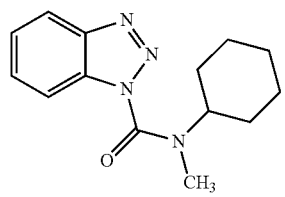 |
| 59 | 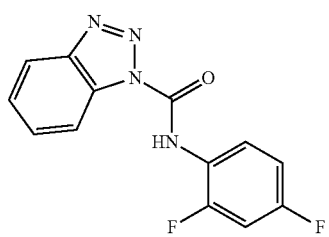 [SMILES: O=C(Nc1ccc(F)cc1F)n1nnc2ccccc21] |
| 60 | 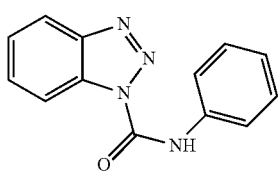 [SMILES: O=C(Nc1ccccc1)n1nnc2ccccc21] |
| 61 | 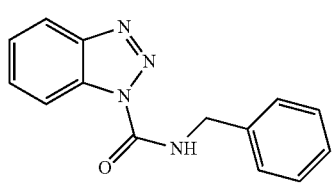 [SMILES: O=C(NCc1ccccc1)n1nnc2ccccc21] |

-continued
| No. | Structure |
|---|---|
| 62 | 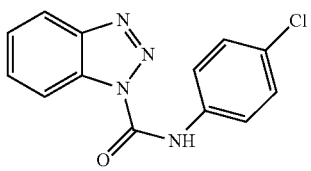 [SMILES: O=C(Nc1ccc(Cl)cc1)n1nnc2ccccc21] |
| 63 | 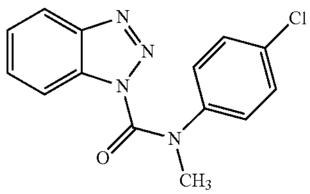 [SMILES: CN(C(=O)n1nnc2ccccc21)c1ccc(Cl)cc1] |
| 64 | 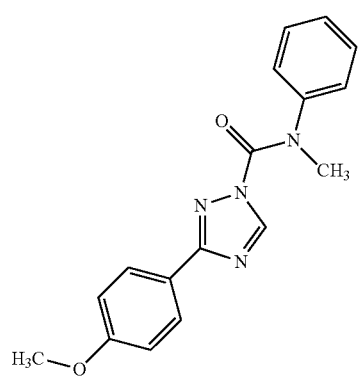 [SMILES: COc1ccc(-c2ncn(C(=O)N(C)c3ccccc3)n2)cc1] |
| 65 | 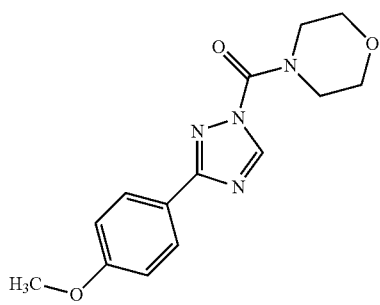 [SMILES: COc1ccc(-c2ncn(C(=O)N3CCOCC3)n2)cc1] |
| 66 | 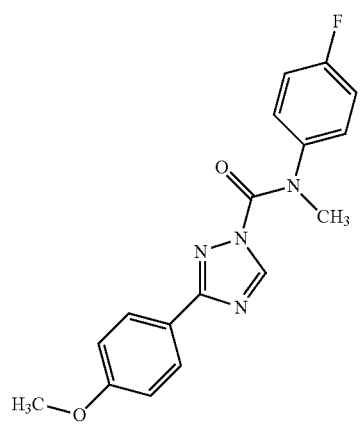 [SMILES: COc1ccc(-c2ncn(C(=O)N(C)c3ccc(F)cc3)n2)cc1] |

-continued
| No. | Structure |
|---|---|
| 67 | 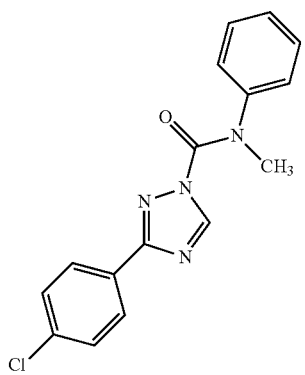 [SMILES: CN(C(=O)n1cnc(-c2ccc(Cl)cc2)n1)c1ccccc1] |
| 68 | 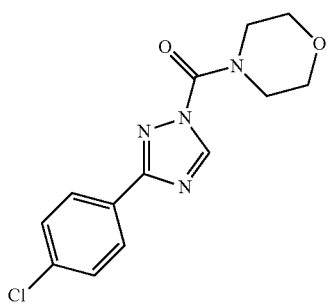 [SMILES: O=C(N1CCOCC1)n1cnc(-c2ccc(Cl)cc2)n1] |
| 69 | 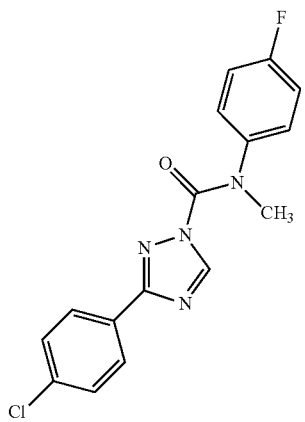 [SMILES: CN(C(=O)n1cnc(-c2ccc(Cl)cc2)n1)c1ccc(F)cc1] |
| 70 | 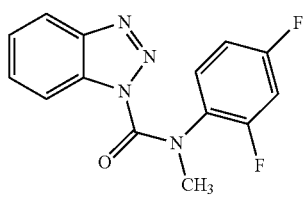 [SMILES: CN(C(=O)n1nnc2ccccc21)c1ccc(F)cc1F] |
| 71 | 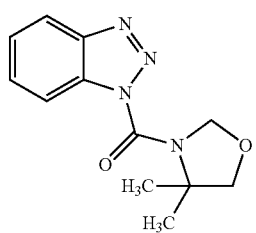 |

-continued

| No. | Structure |
|-----|-----------|
| 72  | 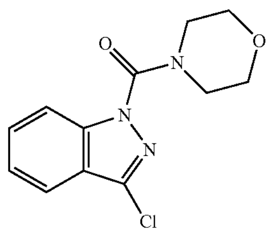 [SMILES: O=C(N1CCOCC1)n1nc(Cl)c2ccccc21] |
| 73  | 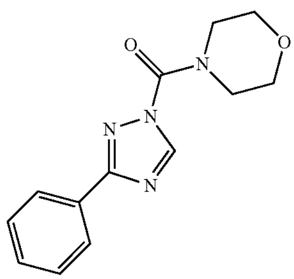 [SMILES: O=C(N1CCOCC1)n1cnc(-c2ccccc2)n1] |
| 74  | 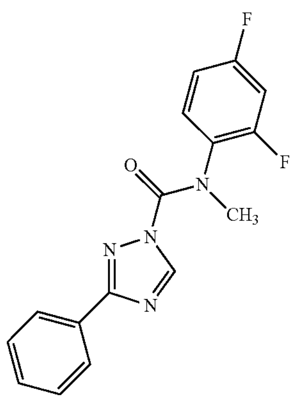 [SMILES: CN(C(=O)n1cnc(-c2ccccc2)n1)c1ccc(F)cc1F] |
| 75  | 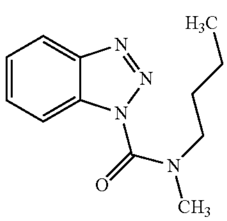 [SMILES: CCCCN(C)C(=O)n1nnc2ccccc21] |
| 76  | 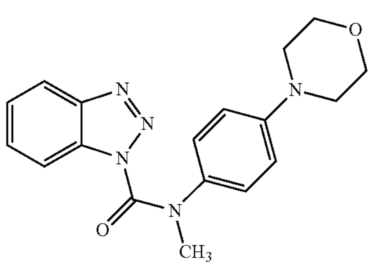 [SMILES: CN(C(=O)n1nnc2ccccc21)c1ccc(N2CCOCC2)cc1] |

| No. | Structure |
|---|---|
| 77 | 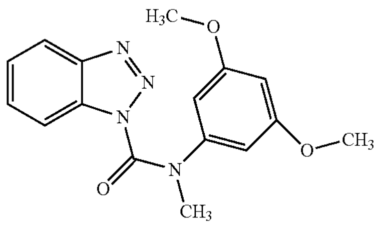 [SMILES: COc1cc(OC)cc(N(C)C(=O)n2nnc3ccccc32)c1] |
| 78 | 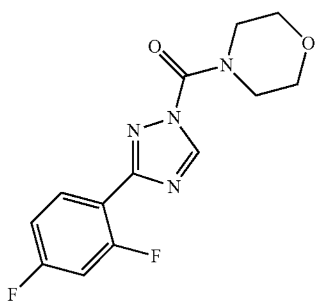 [SMILES: O=C(N1CCOCC1)n1cnc(-c2ccc(F)cc2F)n1] |
| 79 | 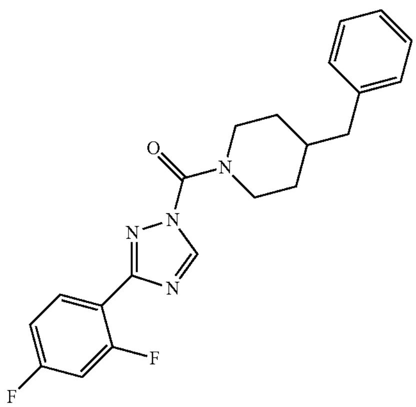 [SMILES: O=C(N1CCC(Cc2ccccc2)CC1)n1cnc(-c2ccc(F)cc2F)n1] |
| 80 | 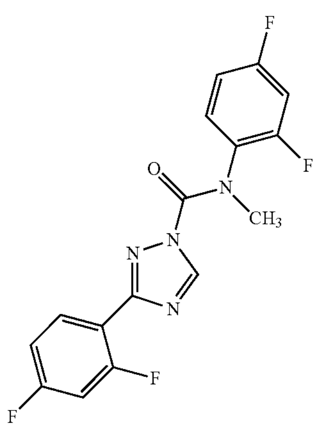 [SMILES: CN(C(=O)n1cnc(-c2ccc(F)cc2F)n1)c1ccc(F)cc1F] |
| 81 | 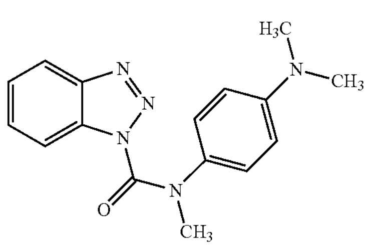 [SMILES: CN(C)c1ccc(N(C)C(=O)n2nnc3ccccc32)cc1] |

-continued
| No. | Structure |
|---|---|
| 82 | 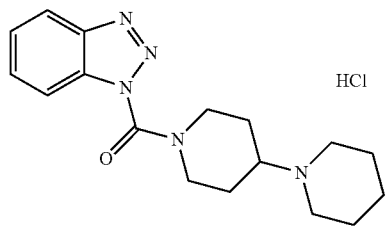 [SMILES: O=C(N1CCC(N2CCCCC2)CC1)n1nnc2ccccc21 ; Cl] |
| 83 | 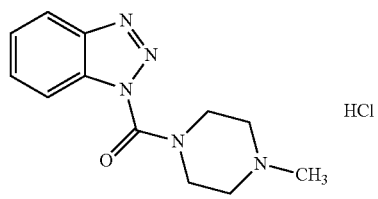 [SMILES: CN1CCN(C(=O)n2nnc3ccccc32)CC1 ; Cl] |
| 84 | 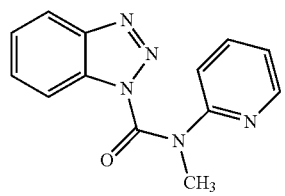 [SMILES: CN(C(=O)n1nnc2ccccc21)c1ccccn1] |
| 85 | 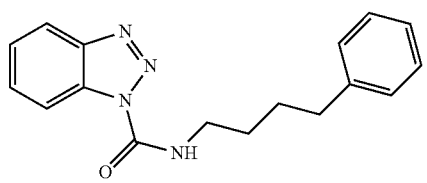 [SMILES: O=C(NCCCCc1ccccc1)n1nnc2ccccc21] |
| 86 | 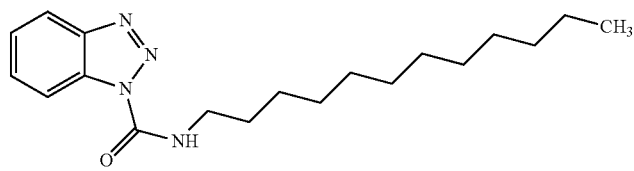 [SMILES: CCCCCCCCCCCCNC(=O)n1nnc2ccccc21] |
| 87 | 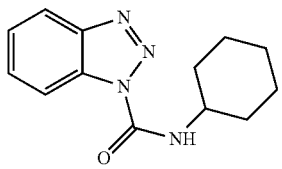 [SMILES: O=C(NC1CCCCC1)n1nnc2ccccc21] |
| 88 | 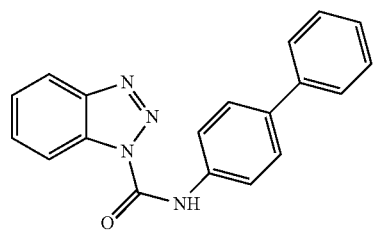 [SMILES: O=C(Nc1ccc(-c2ccccc2)cc1)n1nnc2ccccc21] |

-continued
| No. | Structure |
|---|---|
| 89 | 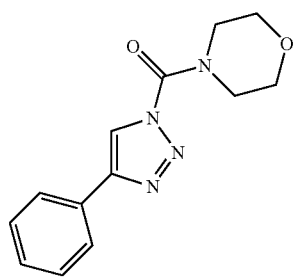 [SMILES: O=C(N1CCOCC1)n1cc(-c2ccccc2)nn1] |
| 90 | 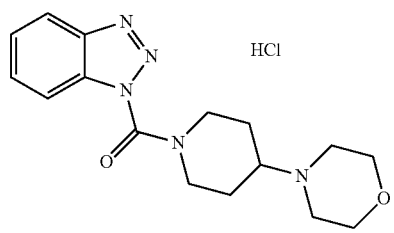 [SMILES: O=C(N1CCC(N2CCOCC2)CC1)n1nnc2ccccc21 ; Cl] HCl |
| 91 | 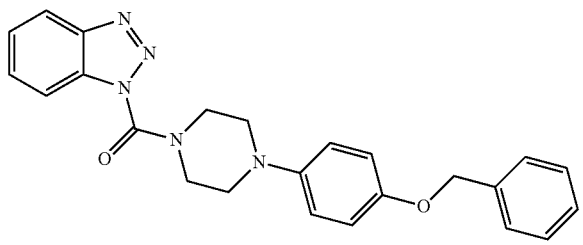 [SMILES: O=C(N1CCN(c2ccc(OCc3ccccc3)cc2)CC1)n1nnc2ccccc21] |
| 92 | 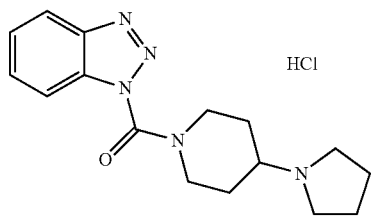 [SMILES: O=C(N1CCC(N2CCCC2)CC1)n1nnc2ccccc21 ; Cl] HCl |
| 93 | 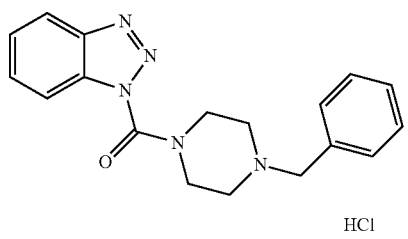 [SMILES: O=C(N1CCN(Cc2ccccc2)CC1)n1nnc2ccccc21 ; Cl] HCl |
| 94 | 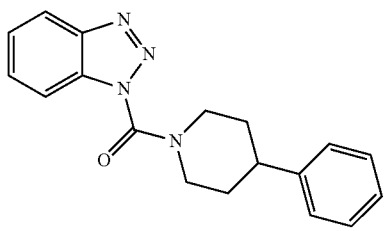 [SMILES: O=C(N1CCC(c2ccccc2)CC1)n1nnc2ccccc21] |

-continued

| No. | Structure |
|---|---|
| 95 | 3-cyanophenyl-substituted benzotriazole-1-carboxamide, N-cyclohexyl-N-methyl |
| 96 | 4-fluorophenyl-substituted benzotriazole-1-carboxamide, N-cyclohexyl-N-methyl |
| 97 | 5-bromo-benzotriazole-1-carboxamide, N-cyclohexyl-N-methyl |
| 98 | benzotriazol-1-yl(pyrrolidin-1-yl)methanone |
| 99 | benzotriazol-1-yl[4-(4-methylphenoxy)piperidin-1-yl]methanone |
| 100 | benzotriazol-1-yl[4-(2-phenylethyl)piperidin-1-yl]methanone |

-continued

| No. | Structure |
|---|---|
| 101 | 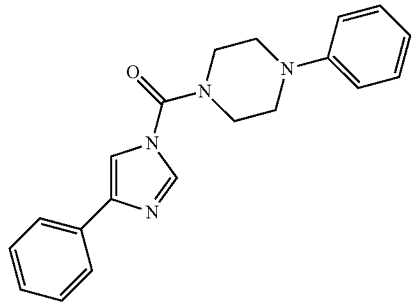 [SMILES: O=C(N1CCN(c2ccccc2)CC1)n1cnc(-c2ccccc2)c1] |
| 102 | 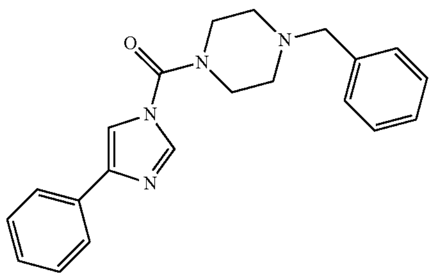 [SMILES: O=C(N1CCN(Cc2ccccc2)CC1)n1cnc(-c2ccccc2)c1] |
| 103 | 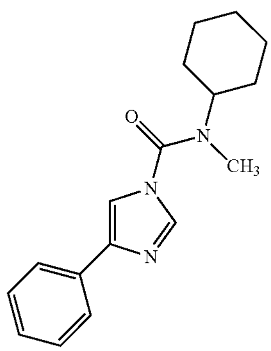 [SMILES: CN(C(=O)n1cnc(-c2ccccc2)c1)C1CCCCC1] |
| 104 | 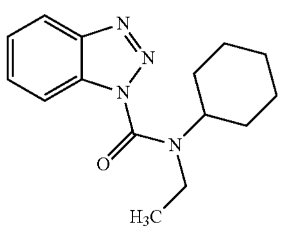 [SMILES: CCN(C(=O)n1nnc2ccccc21)C1CCCCC1] |
| 105 | 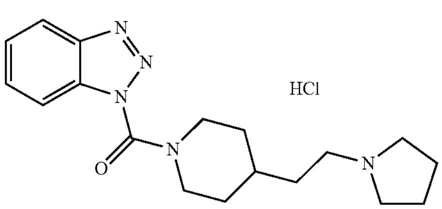 [SMILES: O=C(N1CCC(CCN2CCCC2)CC1)n1nnc2ccccc21 ; Cl] |
| 106 | 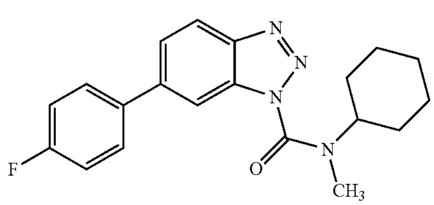 [SMILES: CN(C(=O)n1nnc2ccc(-c3ccc(F)cc3)cc21)C1CCCCC1] |

| No. | Structure |
|---|---|
| 107 | 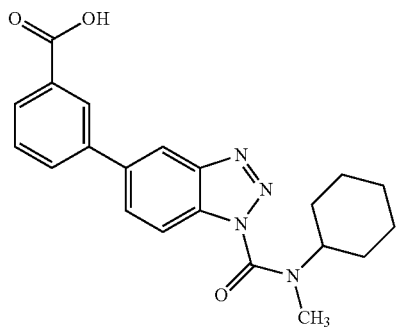 |
| 108 | 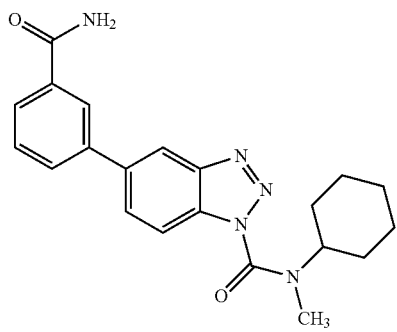 [SMILES: CN(C(=O)n1nnc2cc(-c3cccc(C(=O)O)c3)ccc21)C1CCCCC1] |
| 109 | 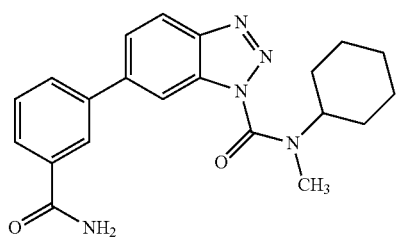 [SMILES: CN(C(=O)n1nnc2ccc(-c3cccc(C(N)=O)c3)cc21)C1CCCCC1] |
| 110 | 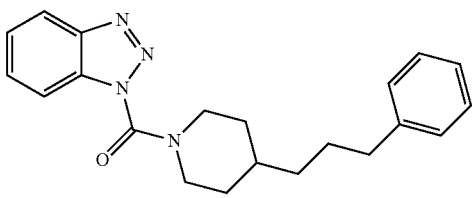 [SMILES: O=C(N1CCC(CCCc2ccccc2)CC1)n1nnc2ccccc21] |
| 111 | 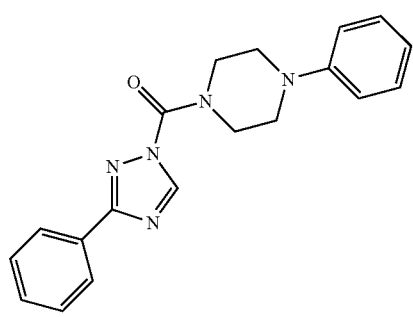 |

-continued
| No. | Structure |
|---|---|
| 112 | 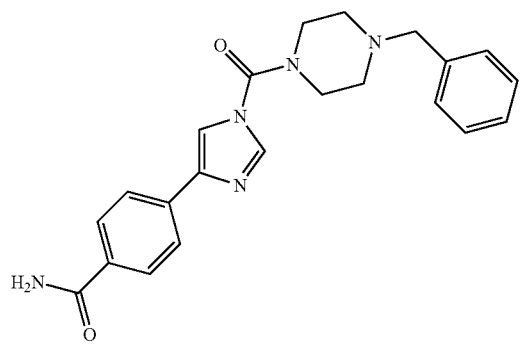 [SMILES: NC(=O)c1ccc(-c2cn(C(=O)N3CCN(Cc4ccccc4)CC3)cn2)cc1] |
| 113 | 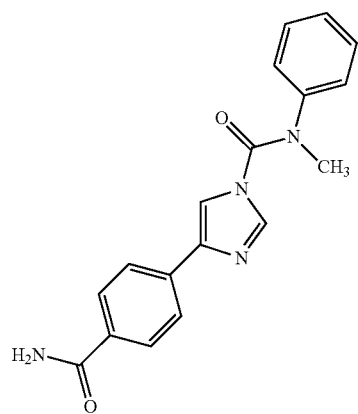 [SMILES: CN(C(=O)n1cnc(-c2ccc(C(N)=O)cc2)c1)c1ccccc1] |
| 114 | 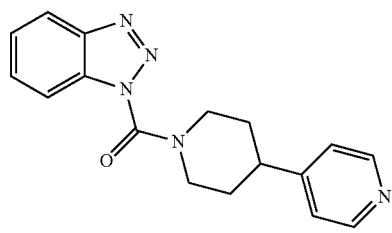 [SMILES: O=C(N1CCC(c2ccncc2)CC1)n1nnc2ccccc21] |
| 115 | 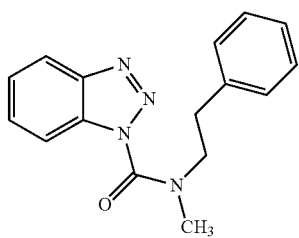 [SMILES: CN(CCc1ccccc1)C(=O)n1nnc2ccccc21] |
| 116 | 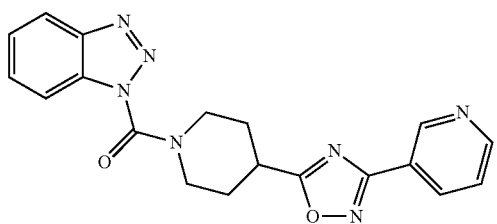 [SMILES: O=C(N1CCC(c2nc(-c3cccnc3)no2)CC1)n1nnc2ccccc21] |

-continued
| No. | Structure |
|---|---|
| 117 | 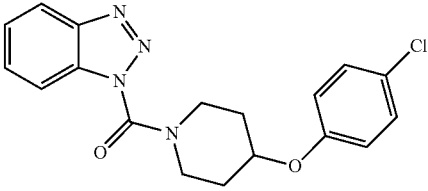 [SMILES: O=C(N1CCC(Oc2ccc(Cl)cc2)CC1)n1nnc2ccccc21] |
| 118 | 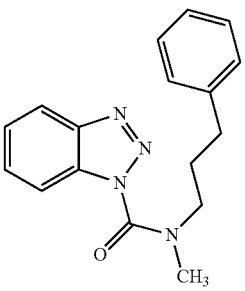 [SMILES: CN(CCCc1ccccc1)C(=O)n1nnc2ccccc21] |
| 119 | 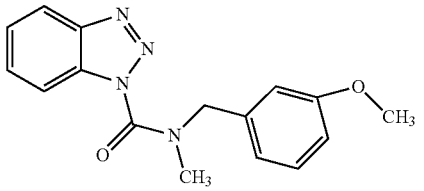 [SMILES: COc1cccc(CN(C)C(=O)n2nnc3ccccc32)c1] |
| 120 | 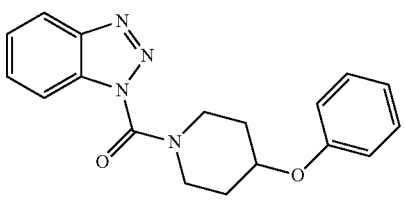 [SMILES: O=C(N1CCC(Oc2ccccc2)CC1)n1nnc2ccccc21] |
| 121 | 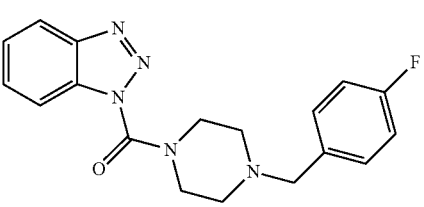 [SMILES: O=C(N1CCN(Cc2ccc(F)cc2)CC1)n1nnc2ccccc21] |
| 122 | 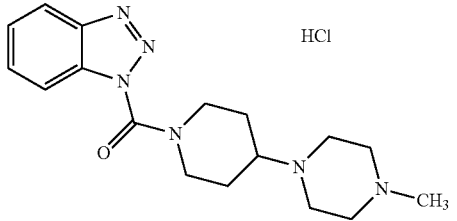 [SMILES: CN1CCN(C2CCN(C(=O)n3nnc4ccccc43)CC2)CC1 ; Cl] HCl |
| 123 | 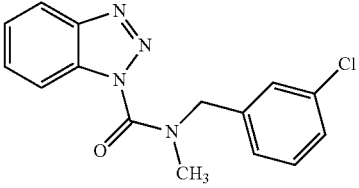 [SMILES: CN(Cc1cccc(Cl)c1)C(=O)n1nnc2ccccc21] |

-continued
| No. | Structure |
|---|---|
| 124 | 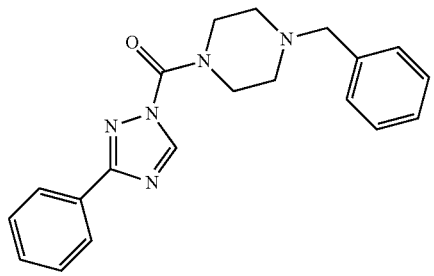 HCl |
| 125 | 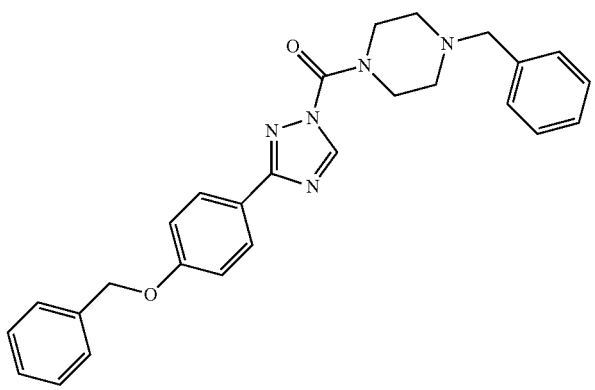 HCl |
| 126 | 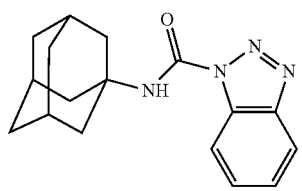 [SMILES: O=C(NC12CC3CC(CC(C3)C1)C2)n1nnc2ccccc21] |
| 127 | 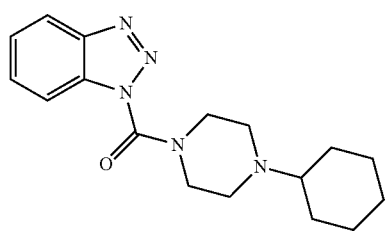 [SMILES: O=C(N1CCN(C2CCCCC2)CC1)n1nnc2ccccc21] |
| 128 | 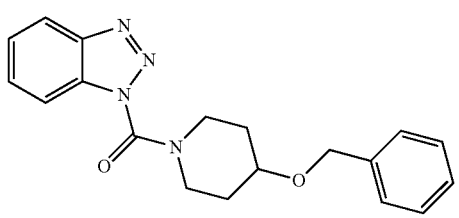 [SMILES: O=C(N1CCC(OCc2ccccc2)CC1)n1nnc2ccccc21] |

-continued
| No. | Structure |
|---|---|
| 129 | 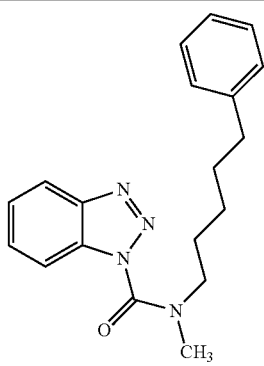 [SMILES: CN(CCCCCc1ccccc1)C(=O)n1nnc2ccccc21] |
| 130 | 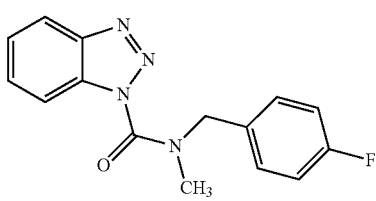 [SMILES: CN(Cc1ccc(F)cc1)C(=O)n1nnc2ccccc21] |
| 131 | 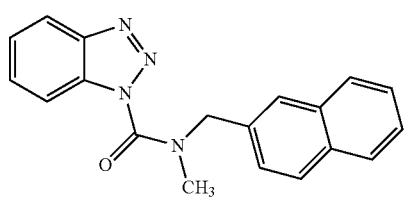 [SMILES: CN(Cc1ccc2ccccc2c1)C(=O)n1nnc2ccccc21] |
| 132 | 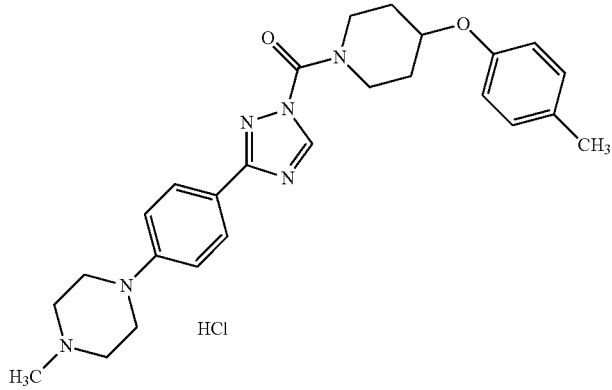 |
| 133 | 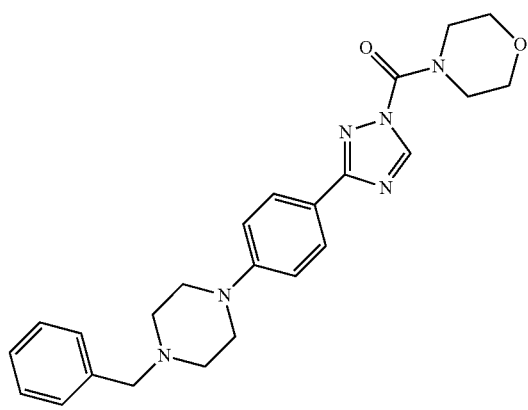 [SMILES: O=C(N1CCOCC1)n1cnc(-c2ccc(N3CCN(Cc4ccccc4)CC3)cc2)n1] |

-continued
| No. | Structure |
|---|---|
| 134 | 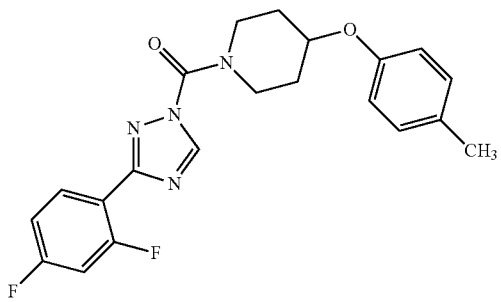 [SMILES: Cc1ccc(OC2CCN(C(=O)n3cnc(-c4ccc(F)cc4F)n3)CC2)cc1] |
| 135 | 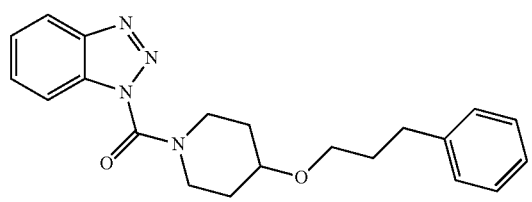 [SMILES: O=C(N1CCC(OCCCc2ccccc2)CC1)n1nnc2ccccc21] |
| 136 | 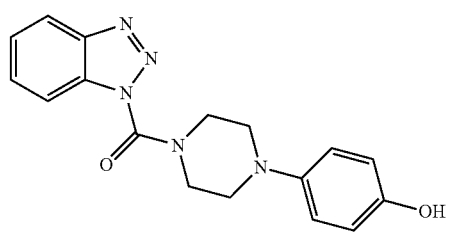 [SMILES: O=C(N1CCN(c2ccc(O)cc2)CC1)n1nnc2ccccc21] |
| 137 | 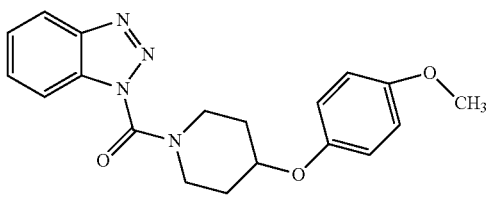 [SMILES: COc1ccc(OC2CCN(C(=O)n3nnc4ccccc43)CC2)cc1] |
| 138 | 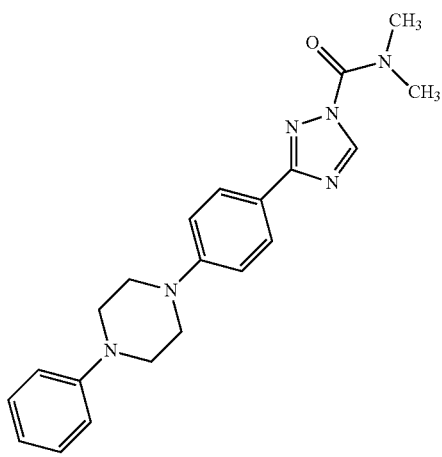 [SMILES: CN(C)C(=O)n1cnc(-c2ccc(N3CCN(c4ccccc4)CC3)cc2)n1] |

| No. | Structure |
|---|---|
| 139 | 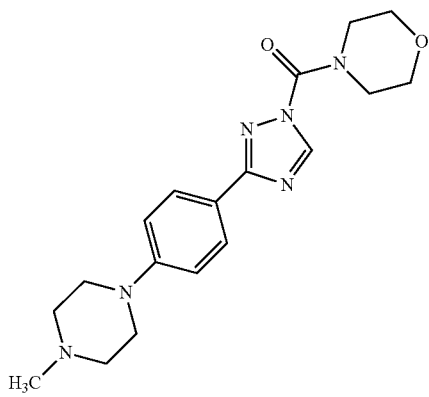 [SMILES: CN1CCN(c2ccc(-c3ncn(C(=O)N4CCOCC4)n3)cc2)CC1] |
| 140 | 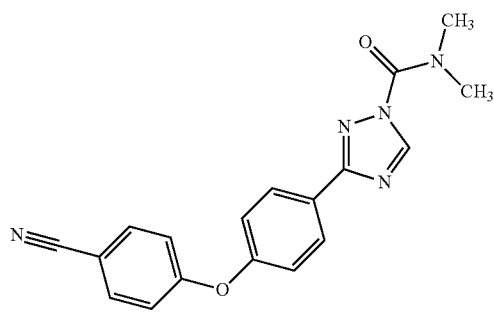 [SMILES: CN(C)C(=O)n1cnc(-c2ccc(Oc3ccc(C#N)cc3)cc2)n1] |
| 141 | 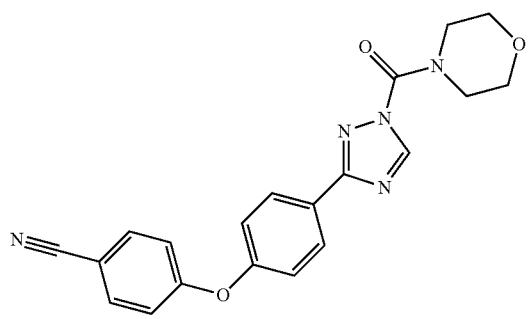 [SMILES: N#Cc1ccc(Oc2ccc(-c3ncn(C(=O)N4CCOCC4)n3)cc2)cc1] |
| 142 | 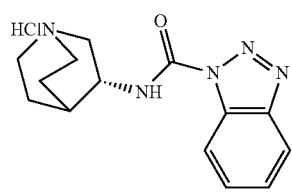 |
| 143 | 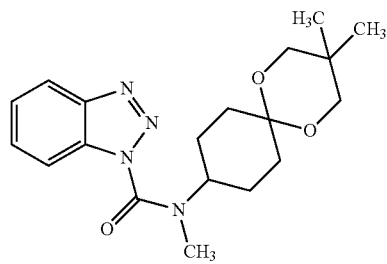 [SMILES: CN(C(=O)n1nnc2ccccc21)C1CCC2(CC1)OCC(C)(C)CO2] |

| No. | Structure |
|---|---|
| 144 | 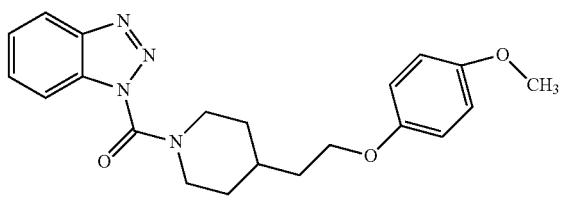 [SMILES: COc1ccc(OCCC2CCN(C(=O)n3nnc4ccccc43)CC2)cc1] |
| 145 | 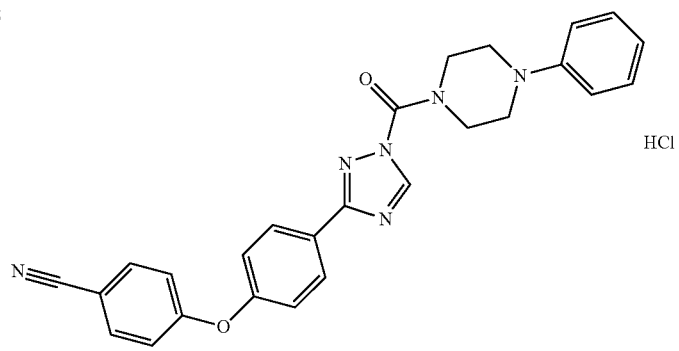 [SMILES: N#Cc1ccc(Oc2ccc(-c3ncn(C(=O)N4CCN(c5ccccc5)CC4)n3)cc2)cc1 ; Cl] |
| 146 | 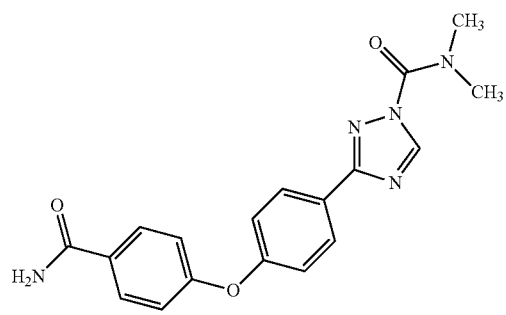 [SMILES: CN(C)C(=O)n1cnc(-c2ccc(Oc3ccc(C(N)=O)cc3)cc2)n1] |
| 147 | 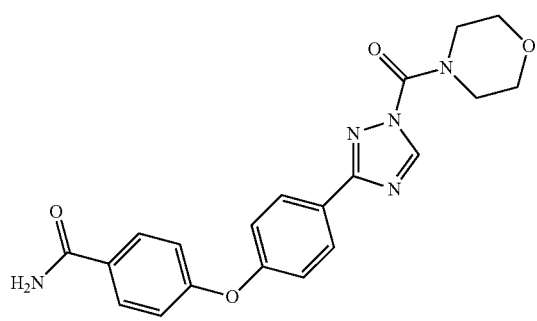 [SMILES: NC(=O)c1ccc(Oc2ccc(-c3ncn(C(=O)N4CCOCC4)n3)cc2)cc1] |
| 148 | 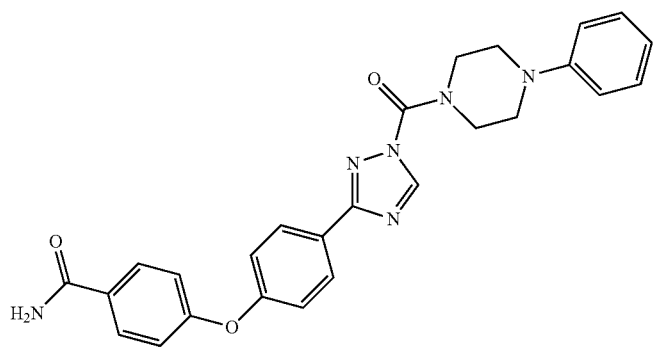 [SMILES: NC(=O)c1ccc(Oc2ccc(-c3ncn(C(=O)N4CCN(c5ccccc5)CC4)n3)cc2)cc1] |

| No. | Structure |
|---|---|
| 149 | 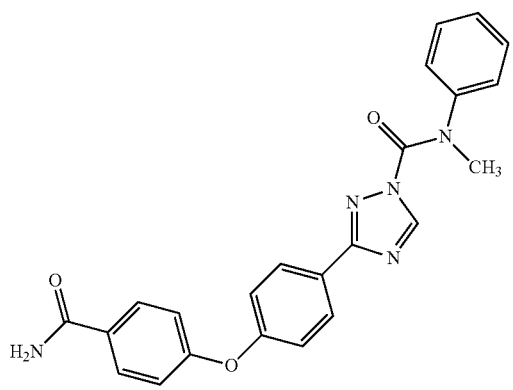 [SMILES: CN(C(=O)n1cnc(-c2ccc(Oc3ccc(C(N)=O)cc3)cc2)n1)c1ccccc1] |
| 150 | 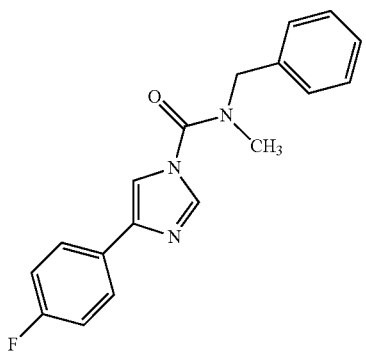 [SMILES: CN(Cc1ccccc1)C(=O)n1cnc(-c2ccc(F)cc2)c1] |
| 151 | 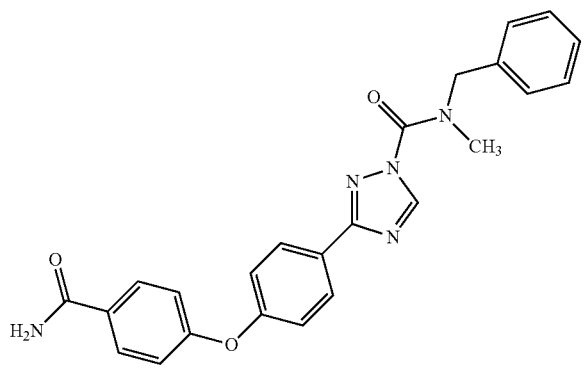 [SMILES: CN(Cc1ccccc1)C(=O)n1cnc(-c2ccc(Oc3ccc(C(N)=O)cc3)cc2)n1] |
| 152 | 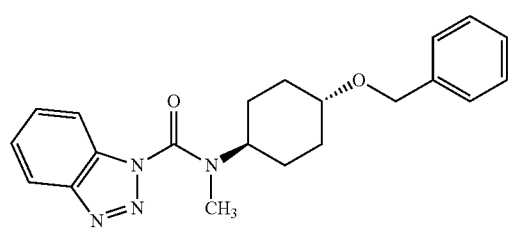 [SMILES: CN(C(=O)n1nnc2ccccc21)[C@H]1CC[C@H](OCc2ccccc2)CC1] |

-continued
| No. | Structure |
|---|---|
| 153 | 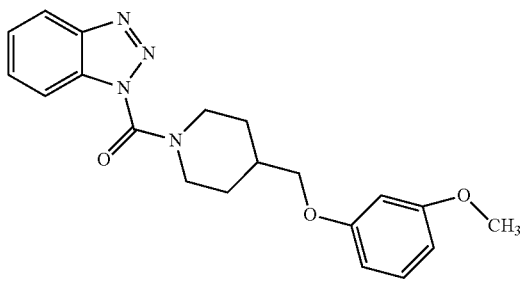 [SMILES: COc1cccc(OCC2CCN(C(=O)n3nnc4ccccc43)CC2)c1] |
| 154 | 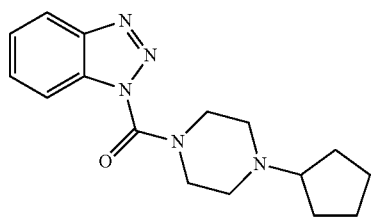 [SMILES: O=C(N1CCN(C2CCCC2)CC1)n1nnc2ccccc21] |
| 155 | 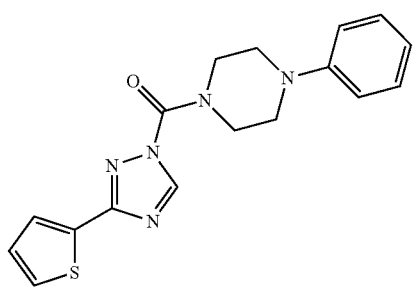 [SMILES: O=C(N1CCN(c2ccccc2)CC1)n1cnc(-c2cccs2)n1] |
| 156 | 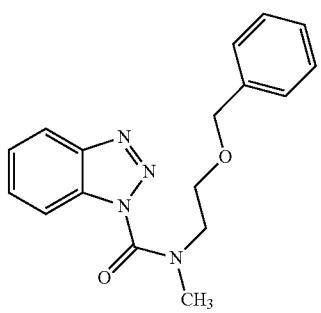 [SMILES: CN(CCOCc1ccccc1)C(=O)n1nnc2ccccc21] |
| 157 | 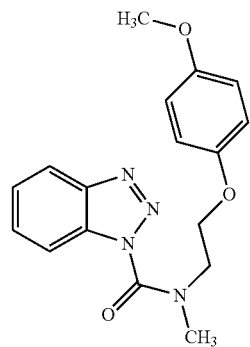 [SMILES: COc1ccc(OCCN(C)C(=O)n2nnc3ccccc32)cc1] |

-continued

| No. | Structure |
|---|---|
| 158 | (structure: 3-(thiophen-2-yl)-1H-1,2,4-triazol-1-yl carbonyl-4-benzylpiperazine, HCl salt) |
| 159 | (structure: 1H-benzotriazol-1-yl carbonyl-4-hydroxypiperidine) |
| 160 | (structure: 3-benzyl-1H-1,2,4-triazole-1-carboxylic acid N-methyl-N-phenylamide) |
| 161 | (structure: 4-phenyl-1H-imidazol-1-yl carbonyl-4,4-dimethyloxazolidine) |
| 162 | (structure: 6-bromo-1H-benzotriazol-1-yl carbonyl-4,4-dimethyloxazolidine) |
| 163 | (structure: 6-(3-carbamoylphenyl)-1H-benzotriazol-1-yl carbonyl-4,4-dimethyloxazolidine) |

-continued
| No. | Structure |
|---|---|
| 164 | 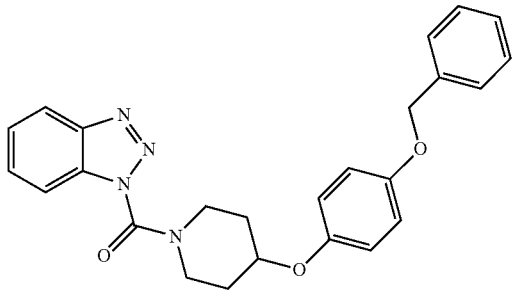 [SMILES: O=C(N1CCC(Oc2ccc(OCc3ccccc3)cc2)CC1)n1nnc2ccccc21] |
| 165 | 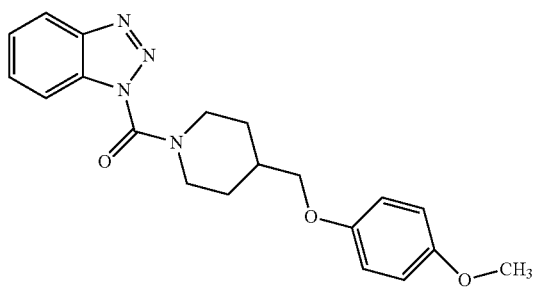 [SMILES: COc1ccc(OCC2CCN(C(=O)n3nnc4ccccc43)CC2)cc1] |
| 166 | 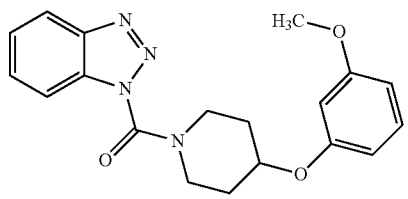 [SMILES: COc1cccc(OC2CCN(C(=O)n3nnc4ccccc43)CC2)c1] |
| 167 | 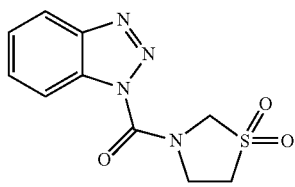 [SMILES: O=C(N1CCS(=O)(=O)C1)n1nnc2ccccc21] |
| 168 | 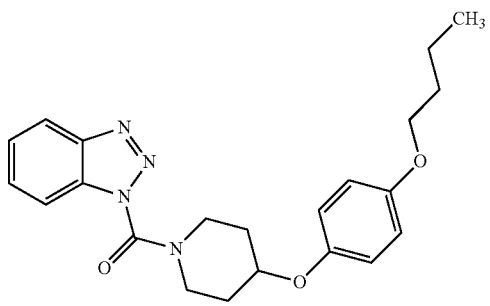 [SMILES: CCCCOc1ccc(OC2CCN(C(=O)n3nnc4ccccc43)CC2)cc1] |
| 169 | 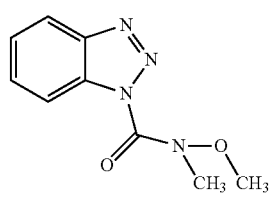 |

-continued

| No. | Structure |
|---|---|
| 170 | 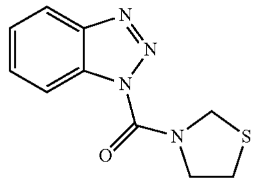 [SMILES: O=C(N1CCSC1)n1nnc2ccccc21] |
| 171 | 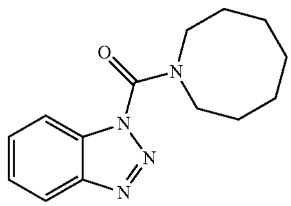 [SMILES: O=C(N1CCCCCCC1)n1nnc2ccccc21] |
| 172 | 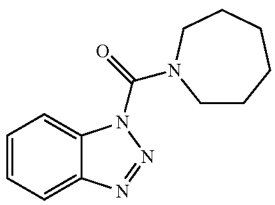 [SMILES: O=C(N1CCCCCC1)n1nnc2ccccc21] |
| 173 | 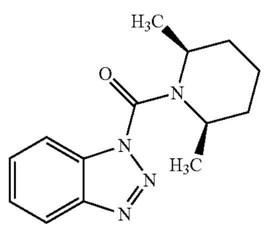 [SMILES: C[C@@H]1CCC[C@H](C)N1C(=O)n1nnc2ccccc21] |
| 174 | 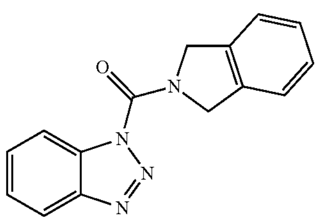 [SMILES: O=C(N1Cc2ccccc2C1)n1nnc2ccccc21] |
| 175 | 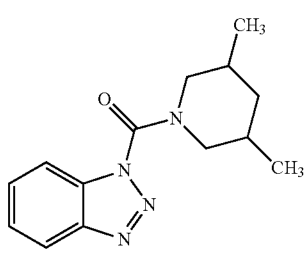 [SMILES: CC1CC(C)CN(C(=O)n2nnc3ccccc32)C1] |
| 176 | 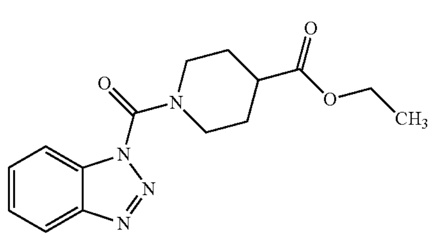 [SMILES: CCOC(=O)C1CCN(C(=O)n2nnc3ccccc32)CC1] |

-continued
| No. | Structure |
|---|---|
| 177 | 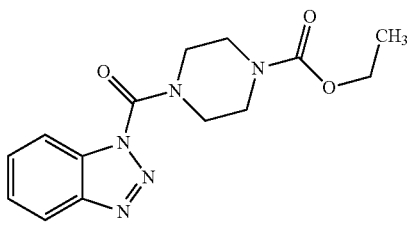 [SMILES: CCOC(=O)N1CCN(C(=O)n2nnc3ccccc32)CC1] |
| 178 | 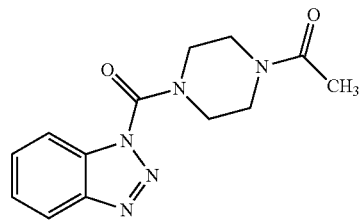 [SMILES: CC(=O)N1CCN(C(=O)n2nnc3ccccc32)CC1] |
| 179 | 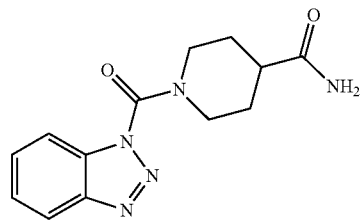 [SMILES: NC(=O)C1CCN(C(=O)n2nnc3ccccc32)CC1] |
| 180 | 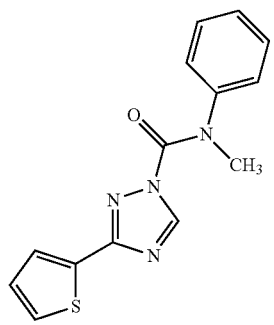 [SMILES: CN(C(=O)n1cnc(-c2cccs2)n1)c1ccccc1] |
| 181 | 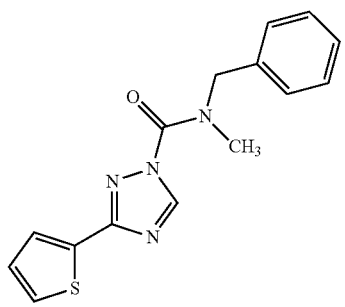 [SMILES: CN(Cc1ccccc1)C(=O)n1cnc(-c2cccs2)n1] |
| 182 | 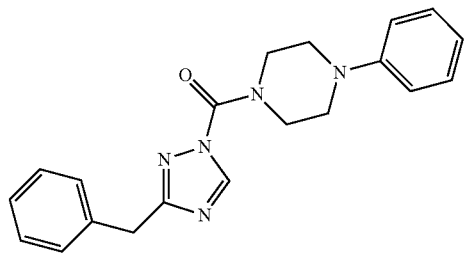 [SMILES: O=C(N1CCN(c2ccccc2)CC1)n1cnc(Cc2ccccc2)n1] |

| No. | Structure |
|---|---|
| 183 | 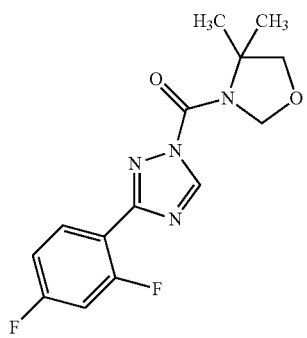 [SMILES: CC1(C)COCN1C(=O)n1cnc(-c2ccc(F)cc2F)n1] |
| 184 | 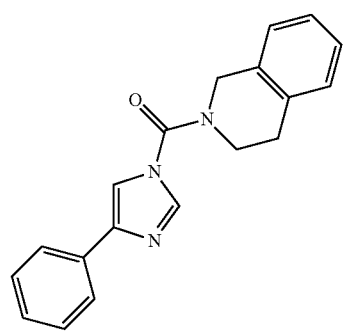 [SMILES: O=C(N1CCc2ccccc2C1)n1cnc(-c2ccccc2)c1] |
| 185 | 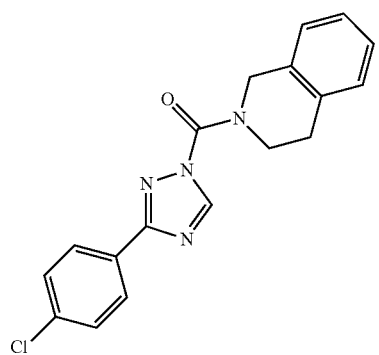 [SMILES: O=C(N1CCc2ccccc2C1)n1cnc(-c2ccc(Cl)cc2)n1] |
| 186 | 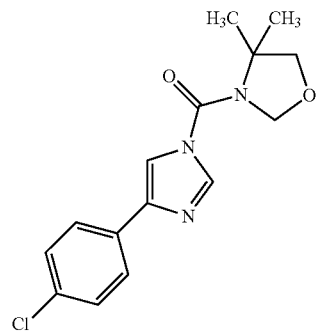 [SMILES: CC1(C)COCN1C(=O)n1cnc(-c2ccc(Cl)cc2)c1] |

| No. | Structure |
|---|---|
| 187 | 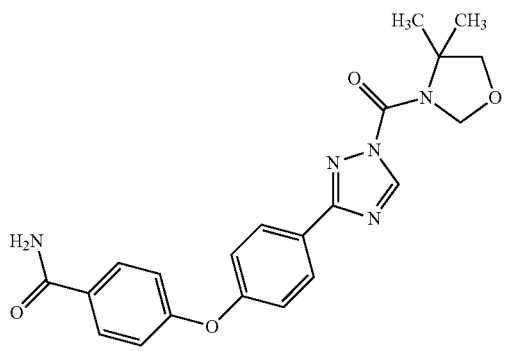 [SMILES: CC1(C)COCN1C(=O)n1cnc(-c2ccc(Oc3ccc(C(N)=O)cc3)cc2)n1] |
| 188 | 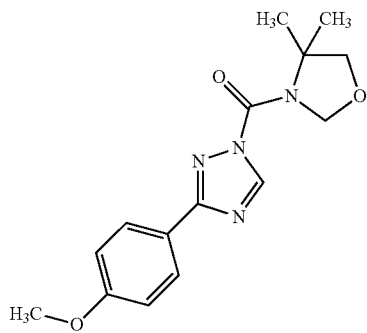 [SMILES: COc1ccc(-c2ncn(C(=O)N3COCC3(C)C)n2)cc1] |
| 189 | 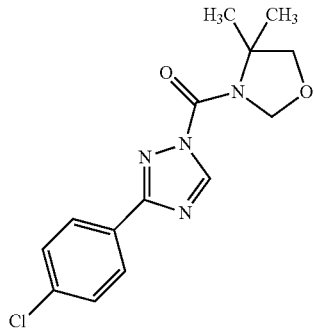 |
| 190 | 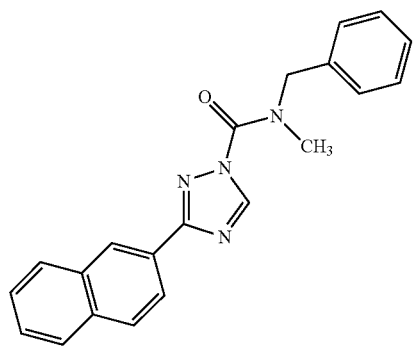 [SMILES: CN(Cc1ccccc1)C(=O)n1cnc(-c2ccc3ccccc3c2)n1] |

-continued
| No. | Structure |
|---|---|
| 191 | 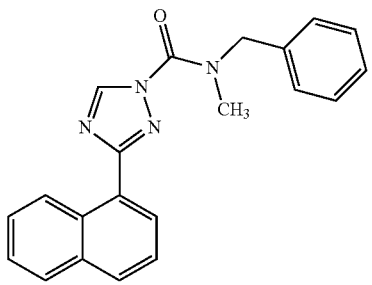 [SMILES: CN(Cc1ccccc1)C(=O)n1cnc(-c2cccc3ccccc23)n1] |
| 192 | 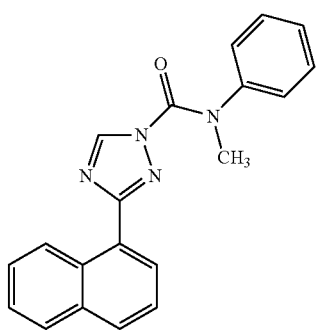 [SMILES: CN(C(=O)n1cnc(-c2cccc3ccccc23)n1)c1ccccc1] |
| 193 | 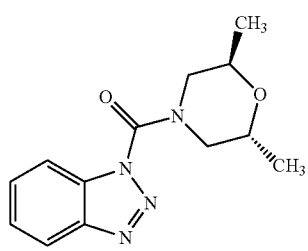 [SMILES: C[C@@H]1CN(C(=O)n2nnc3ccccc32)C[C@@H](C)O1] |
| 194 | 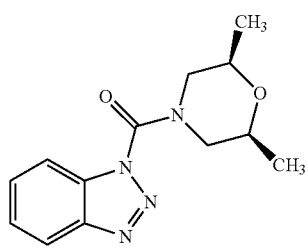 [SMILES: C[C@@H]1CN(C(=O)n2nnc3ccccc32)C[C@H](C)O1] |
| 195 | 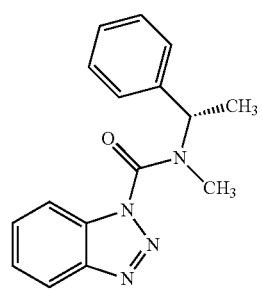 [SMILES: C[C@@H](c1ccccc1)N(C)C(=O)n1nnc2ccccc21] |

| No. | Structure |
|---|---|
| 196 | 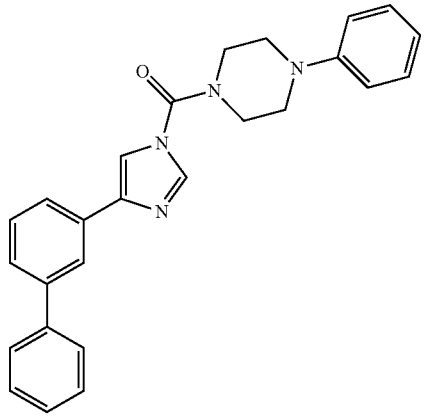 [SMILES: O=C(N1CCN(c2ccccc2)CC1)n1cnc(-c2cccc(-c3ccccc3)c2)c1] |
| 197 | 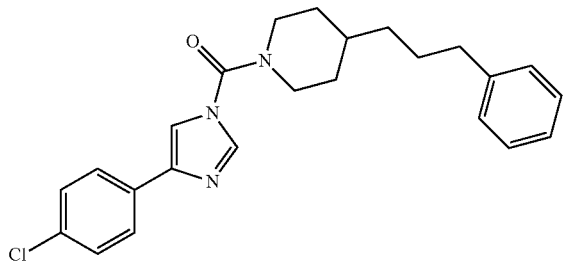 [SMILES: O=C(N1CCC(CCCc2ccccc2)CC1)n1cnc(-c2ccc(Cl)cc2)c1] |
| 198 | 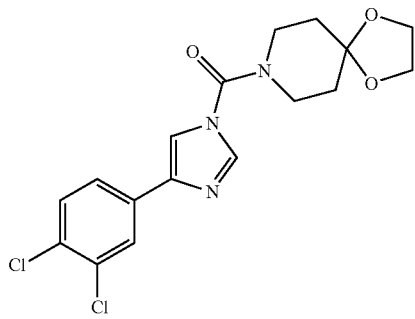 [SMILES: O=C(N1CCC2(CC1)OCCO2)n1cnc(-c2ccc(Cl)c(Cl)c2)c1] |
| 199 | 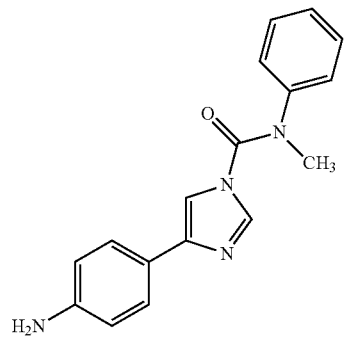 [SMILES: CN(C(=O)n1cnc(-c2ccc(N)cc2)c1)c1ccccc1] |

| No. | Structure |
|---|---|
| 200 | 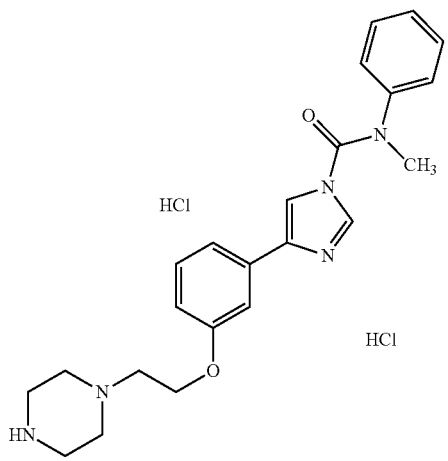 [SMILES: CN(C(=O)n1cnc(-c2cccc(OCCN3CCNCC3)c2)c1)c1ccccc1 ; Cl ; Cl] |
| 201 | 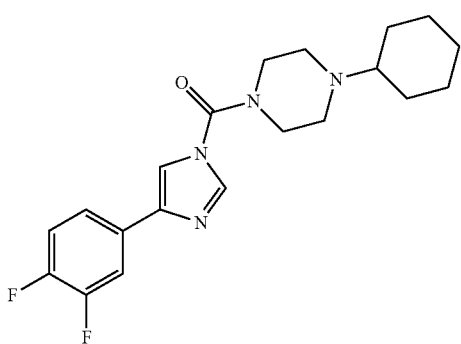 [SMILES: O=C(N1CCN(C2CCCCC2)CC1)n1cnc(-c2ccc(F)c(F)c2)c1] |
| 202 | 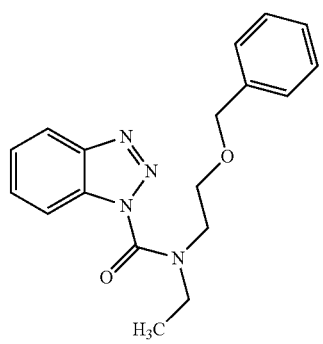 [SMILES: CCN(CCOCc1ccccc1)C(=O)n1nnc2ccccc21] |
| 203 | 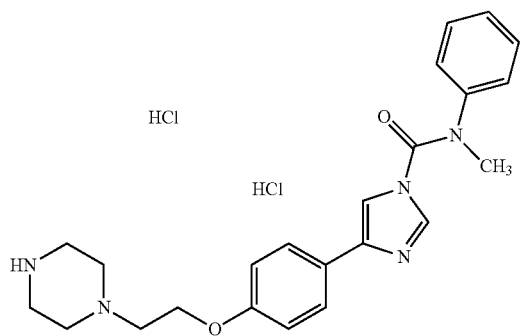 [SMILES: CN(C(=O)n1cnc(-c2ccc(OCCN3CCNCC3)cc2)c1)c1ccccc1 ; Cl ; Cl] |

| No. | Structure |
|---|---|
| 204 | 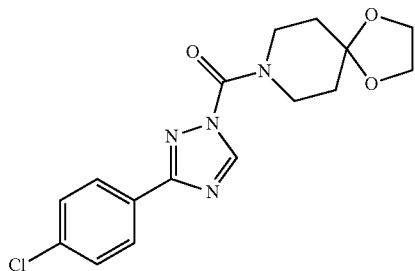 [SMILES: O=C(N1CCC2(CC1)OCCO2)n1cnc(-c2ccc(Cl)cc2)n1] |
| 205 | 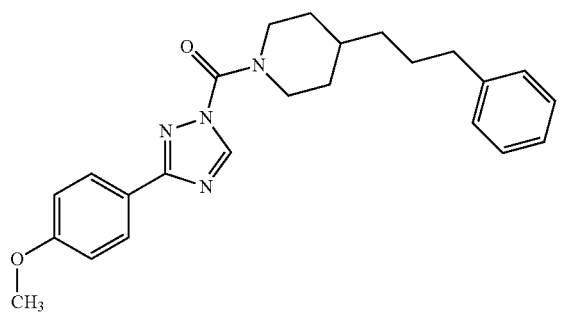 [SMILES: COc1ccc(-c2ncn(C(=O)N3CCC(CCCc4ccccc4)CC3)n2)cc1] |
| 206 | 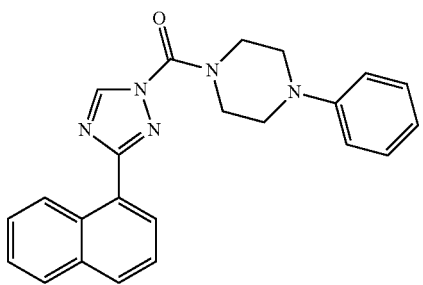 [SMILES: O=C(N1CCN(c2ccccc2)CC1)n1cnc(-c2cccc3ccccc23)n1] |
| 207 | 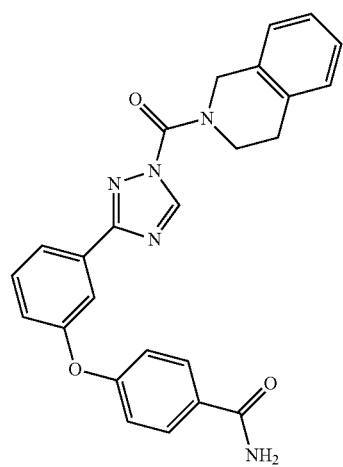 [SMILES: NC(=O)c1ccc(Oc2cccc(-c3ncn(C(=O)N4CCc5ccccc5C4)n3)c2)cc1] |

| No. | Structure |
|-----|-----------|
| 208 | 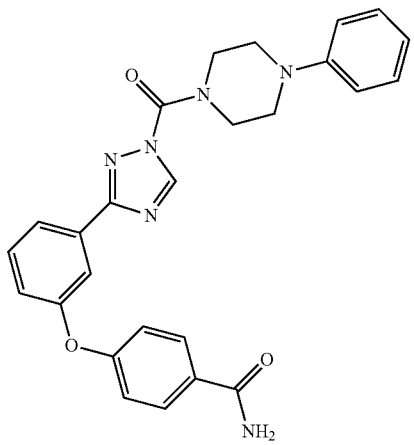 [SMILES: NC(=O)c1ccc(Oc2cccc(-c3ncn(C(=O)N4CCN(c5ccccc5)CC4)n3)c2)cc1] |
| 209 | 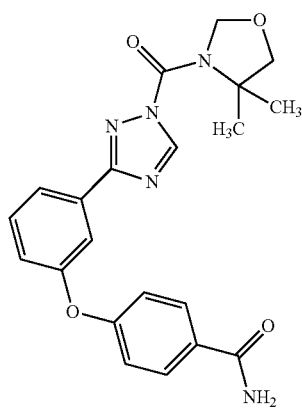 [SMILES: CC1(C)COCN1C(=O)n1cnc(-c2cccc(Oc3ccc(C(N)=O)cc3)c2)n1] |
| 210 | 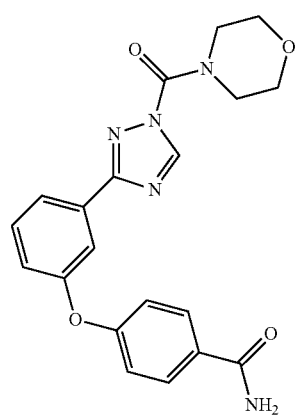 [SMILES: NC(=O)c1ccc(Oc2cccc(-c3ncn(C(=O)N4CCOCC4)n3)c2)cc1] |
| 211 | 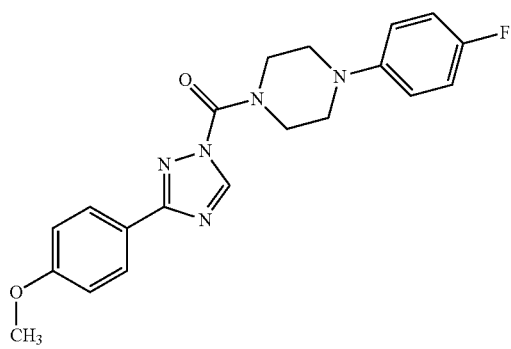 [SMILES: COc1ccc(-c2ncn(C(=O)N3CCN(c4ccc(F)cc4)CC3)n2)cc1] |

| No. | Structure |
|---|---|
| 212 | 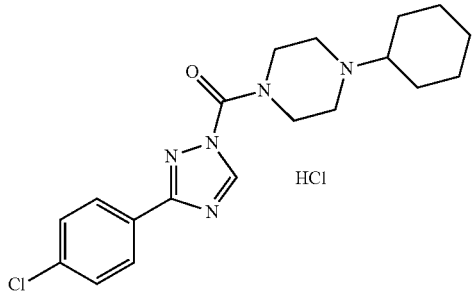 [SMILES: O=C(N1CCN(C2CCCCC2)CC1)n1cnc(-c2ccc(Cl)cc2)n1 ; Cl] HCl |
| 213 | 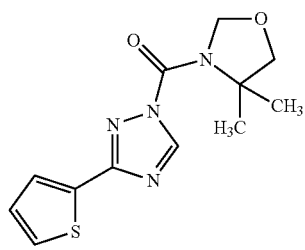 [SMILES: CC1(C)COCN1C(=O)n1cnc(-c2cccs2)n1] |
| 214 | 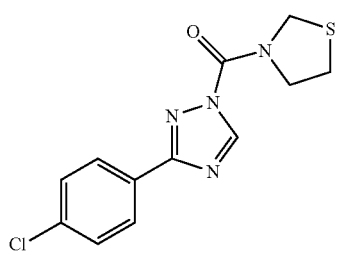 [SMILES: O=C(N1CCSC1)n1cnc(-c2ccc(Cl)cc2)n1] |
| 215 | 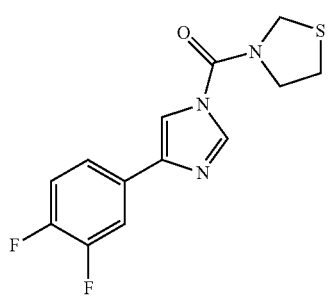 [SMILES: O=C(N1CCSC1)n1cnc(-c2ccc(F)c(F)c2)c1] |
| 216 | 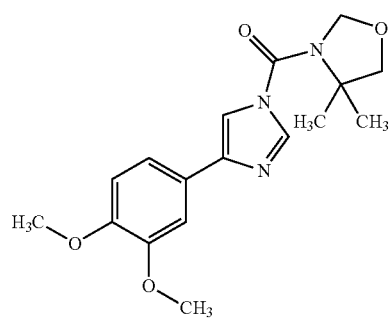 [SMILES: COc1ccc(-c2cn(C(=O)N3COCC3(C)C)cn2)cc1OC] |

| No. | Structure |
|---|---|
| 217 | 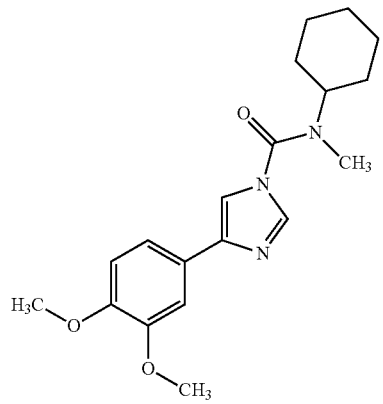 [SMILES: COc1ccc(-c2cn(C(=O)N(C)C3CCCCC3)cn2)cc1OC] |
| 218 | 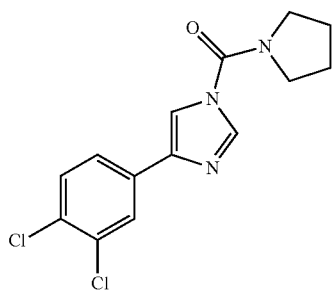 [SMILES: O=C(N1CCCC1)n1cnc(-c2ccc(Cl)c(Cl)c2)c1] |
| 219 | 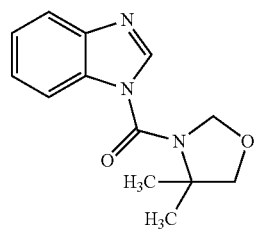 [SMILES: CC1(C)COCN1C(=O)n1cnc2ccccc21] |
| 220 | 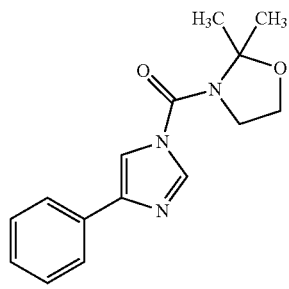 [SMILES: CC1(C)OCCN1C(=O)n1cnc(-c2ccccc2)c1] |
| 221 | 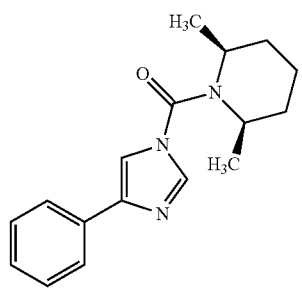 [SMILES: C[C@@H]1CCC[C@H](C)N1C(=O)n1cnc(-c2ccccc2)c1] |

-continued
| No. | Structure |
|---|---|
| 222 | 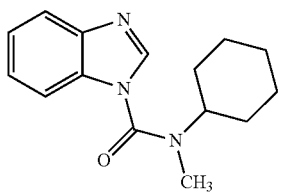 [SMILES: CN(C(=O)n1cnc2ccccc21)C1CCCCC1] |
| 223 | 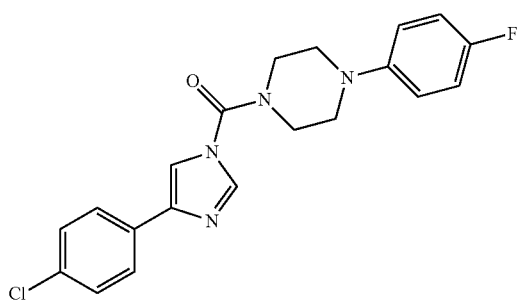 [SMILES: O=C(N1CCN(c2ccc(F)cc2)CC1)n1cnc(-c2ccc(Cl)cc2)c1] |
| 224 | 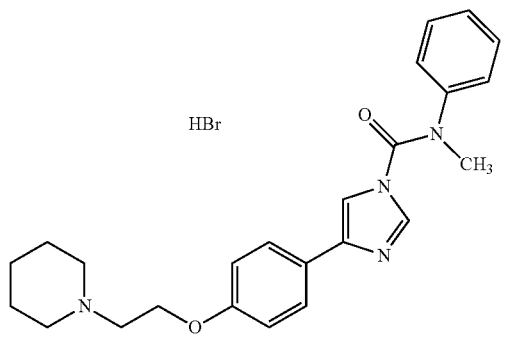 [SMILES: CN(C(=O)n1cnc(-c2ccc(OCCN3CCCCC3)cc2)c1)c1ccccc1 ; Br] |
| 225 | 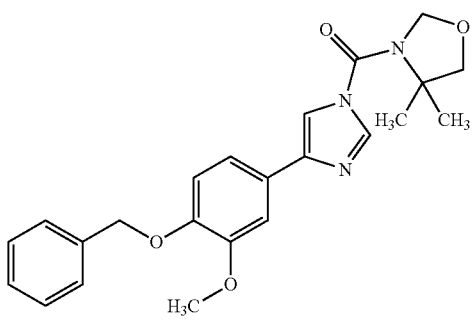 [SMILES: COc1cc(-c2cn(C(=O)N3COCC3(C)C)cn2)ccc1OCc1ccccc1] |
| 226 | 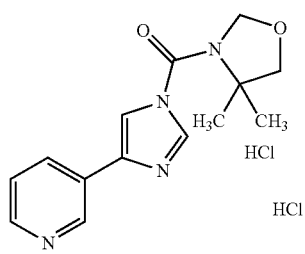 [SMILES: CC1(C)COCN1C(=O)n1cnc(-c2cccnc2)c1 ; Cl ; Cl] |

| No. | Structure |
|---|---|
| 227 | 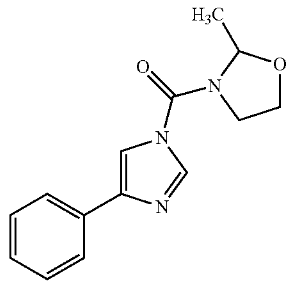 [SMILES: CC1OCCN1C(=O)n1cnc(-c2ccccc2)c1] |
| 228 | 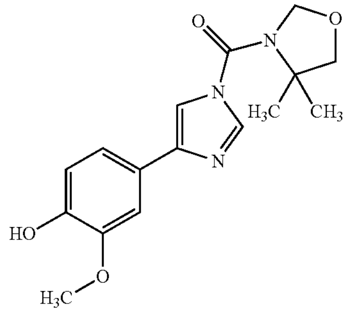 [SMILES: COc1cc(-c2cn(C(=O)N3COCC3(C)C)cn2)ccc1O] |
| 229 | 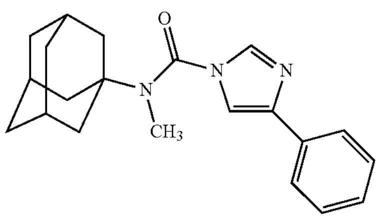 [SMILES: CN(C(=O)n1cnc(-c2ccccc2)c1)C12CC3CC(CC(C3)C1)C2] |
| 230 | 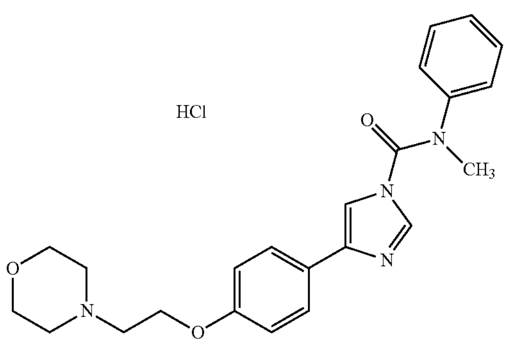 [SMILES: CN(C(=O)n1cnc(-c2ccc(OCCN3CCOCC3)cc2)c1)c1ccccc1 ; Cl] |
| 231 | 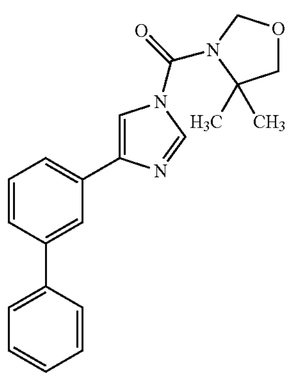 [SMILES: CC1(C)COCN1C(=O)n1cnc(-c2cccc(-c3ccccc3)c2)c1] |

| No. | Structure |
|---|---|
| 232 | 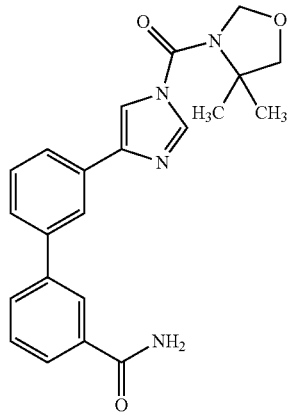 [SMILES: CC1(C)COCN1C(=O)n1cnc(-c2cccc(-c3cccc(C(N)=O)c3)c2)c1] |
| 233 | 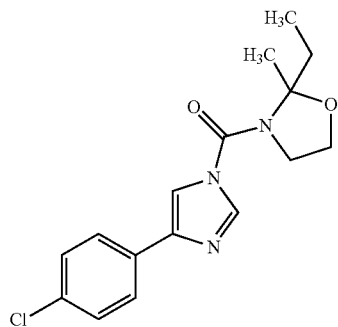 [SMILES: CCC1(C)OCCN1C(=O)n1cnc(-c2ccc(Cl)cc2)c1] |
| 234 | 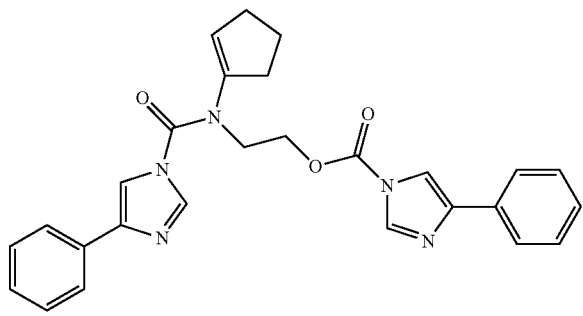 [SMILES: O=C(OCCN(C(=O)n1cnc(-c2ccccc2)c1)C1=CCCC1)n1cnc(-c2ccccc2)c1] |
| 235 | 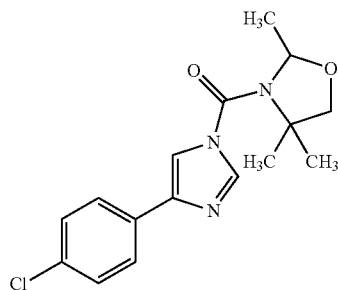 [SMILES: CC1OCC(C)(C)N1C(=O)n1cnc(-c2ccc(Cl)cc2)c1] |

-continued
| No. | Structure |
|---|---|
| 236 | 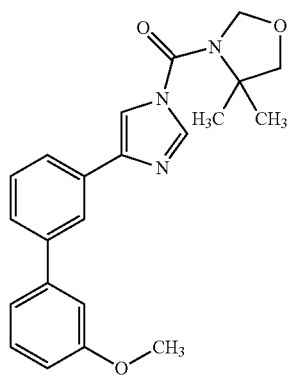 [SMILES: COc1cccc(-c2cccc(-c3cn(C(=O)N4COCC4(C)C)cn3)c2)c1] |
| 237 | 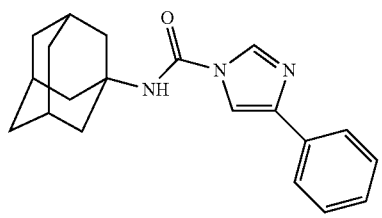 [SMILES: O=C(NC12CC3CC(CC(C3)C1)C2)n1cnc(-c2ccccc2)c1] |
| 238 | 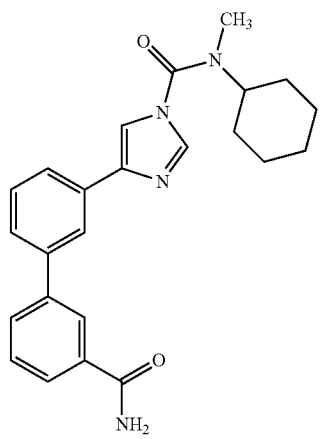 [SMILES: CN(C(=O)n1cnc(-c2cccc(-c3cccc(C(N)=O)c3)c2)c1)C1CCCCC1] |
| 239 | 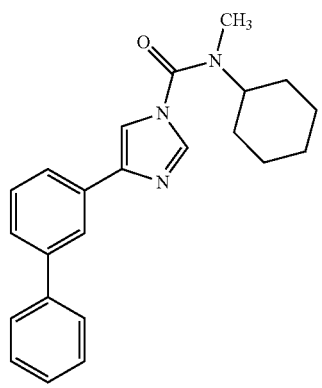 [SMILES: CN(C(=O)n1cnc(-c2cccc(-c3ccccc3)c2)c1)C1CCCCC1] |

| No. | Structure |
|---|---|
| 240 | 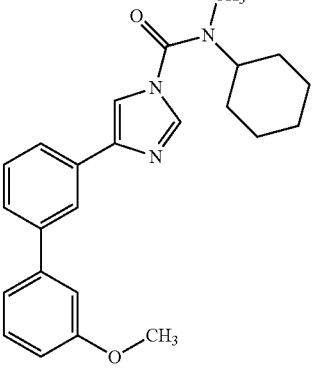 |
| 241 | 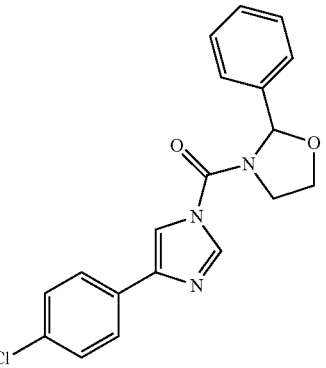 |
| 242 | 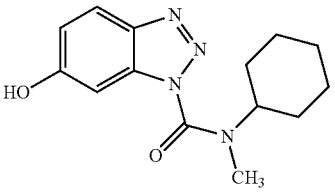 [SMILES: CN(C(=O)n1nnc2ccc(O)cc21)C1CCCCC1] |
| 243 | 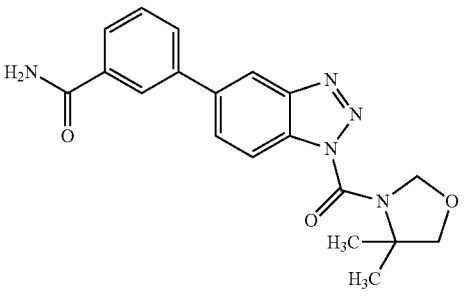 [SMILES: CC1(C)COCN1C(=O)n1nnc2cc(-c3cccc(C(N)=O)c3)ccc21] |
| 244 | 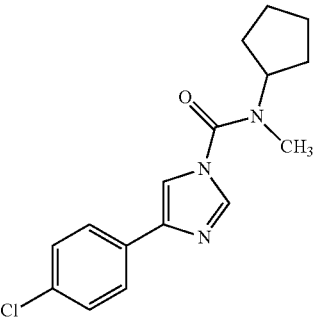 [SMILES: CN(C(=O)n1cnc(-c2ccc(Cl)cc2)c1)C1CCCC1] |

-continued
| No. | Structure |
|---|---|
| 245 | 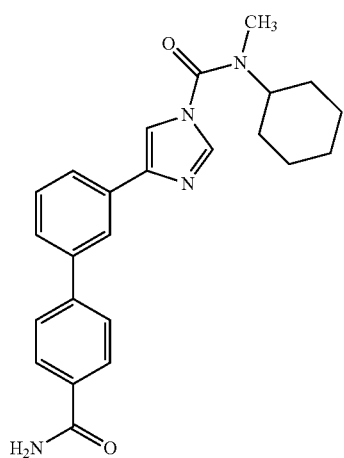 [SMILES: CN(C(=O)n1cnc(-c2cccc(-c3ccc(C(N)=O)cc3)c2)c1)C1CCCCC1] |
| 246 | 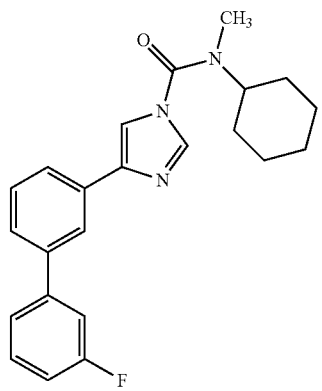 [SMILES: CN(C(=O)n1cnc(-c2cccc(-c3cccc(F)c3)c2)c1)C1CCCCC1] |
| 247 | 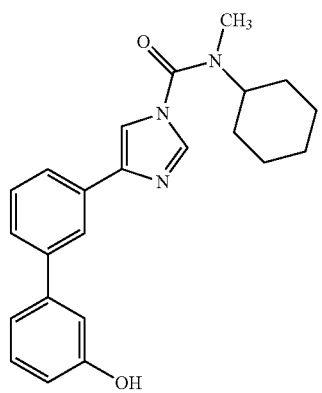 |

-continued
| No. | Structure |
|---|---|
| 248 | 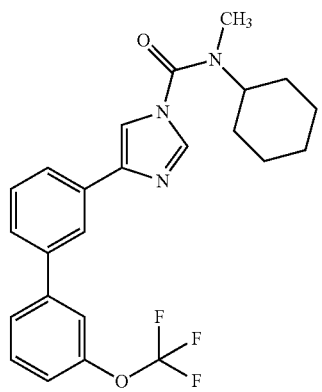 [SMILES: CN(C(=O)n1cnc(-c2cccc(-c3cccc(OC(F)(F)F)c3)c2)c1)C1CCCCC1] |
| 249 | 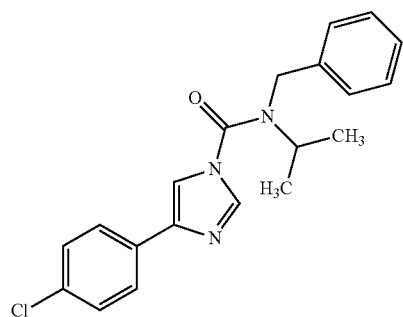 [SMILES: CC(C)N(Cc1ccccc1)C(=O)n1cnc(-c2ccc(Cl)cc2)c1] |
| 250 | 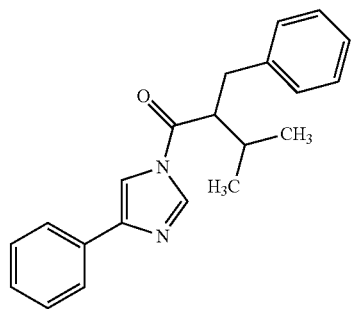 [SMILES: CC(C)C(Cc1ccccc1)C(=O)n1cnc(-c2ccccc2)c1] |
| 251 | 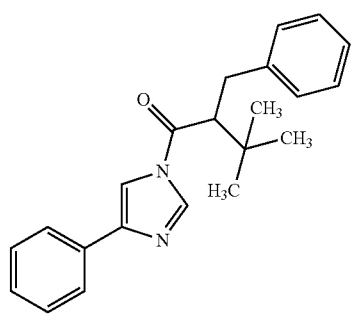 [SMILES: CC(C)(C)C(Cc1ccccc1)C(=O)n1cnc(-c2ccccc2)c1] |

-continued
| No. | Structure |
|---|---|
| 252 | 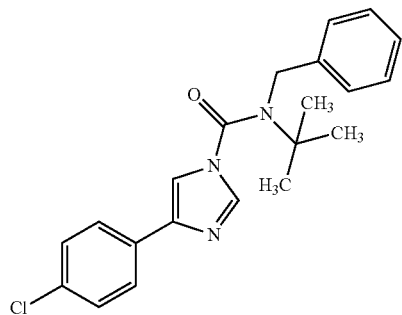 [SMILES: CC(C)(C)N(Cc1ccccc1)C(=O)n1cnc(-c2ccc(Cl)cc2)c1] |
| 253 | 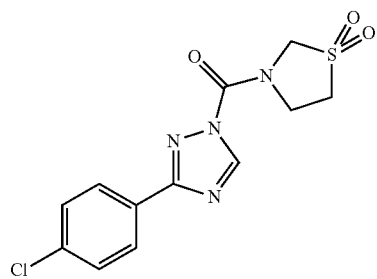 [SMILES: O=C(N1CCS(=O)(=O)C1)n1cnc(-c2ccc(Cl)cc2)n1] |
| 254 | 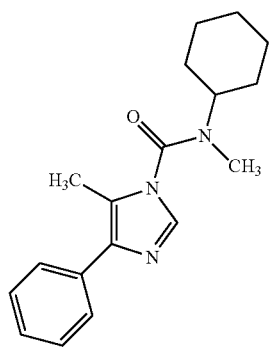 [SMILES: Cc1c(-c2ccccc2)ncn1C(=O)N(C)C1CCCCC1] |
| 255 | 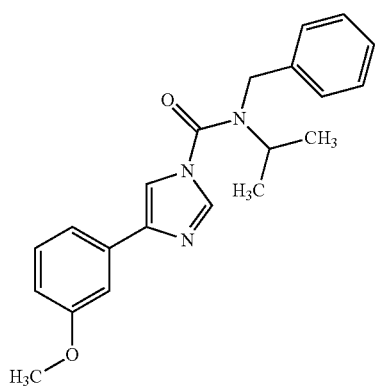 [SMILES: COc1cccc(-c2cn(C(=O)N(Cc3ccccc3)C(C)C)cn2)c1] |

| No. | Structure |
|---|---|
| 256 | 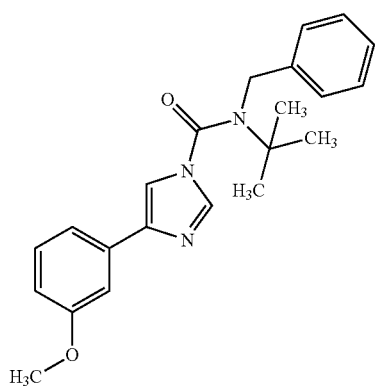 [SMILES: COc1cccc(-c2cn(C(=O)N(Cc3ccccc3)C(C)(C)C)cn2)c1] |
| 257 | 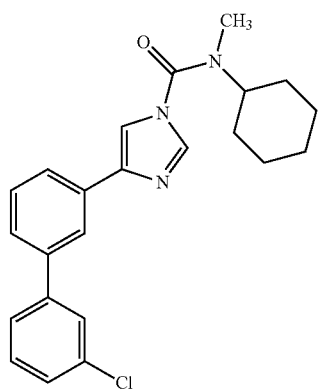 [SMILES: CN(C(=O)n1cnc(-c2cccc(-c3cccc(Cl)c3)c2)c1)C1CCCCC1] |
| 258 | 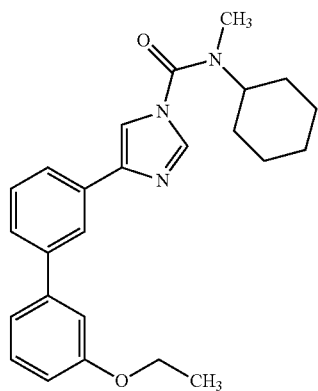 [SMILES: CCOc1cccc(-c2cccc(-c3cn(C(=O)N(C)C4CCCCC4)cn3)c2)c1] |
| 259 | 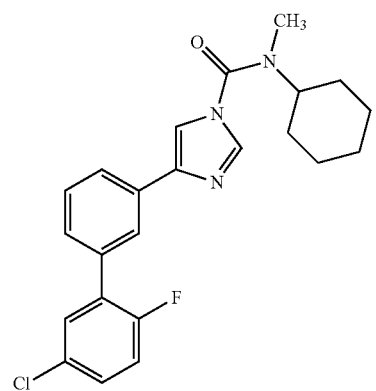 [SMILES: CN(C(=O)n1cnc(-c2cccc(-c3cc(Cl)ccc3F)c2)c1)C1CCCCC1] |

-continued
| No. | Structure |
|---|---|
| 260 | 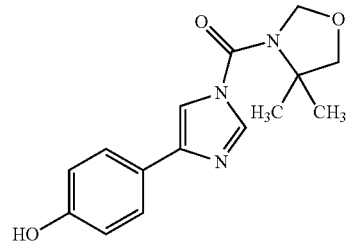 [SMILES: CC1(C)COCN1C(=O)n1cnc(-c2ccc(O)cc2)c1] |
| 261 | 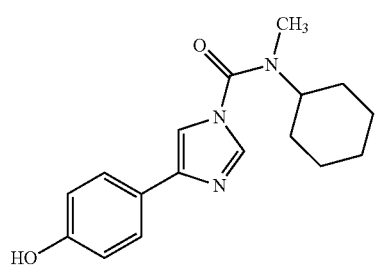 [SMILES: CN(C(=O)n1cnc(-c2ccc(O)cc2)c1)C1CCCCC1] |
| 262 | 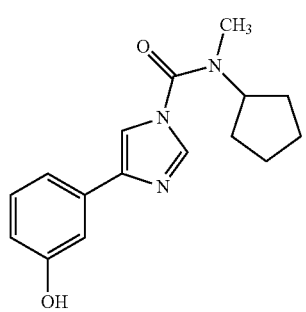 [SMILES: CN(C(=O)n1cnc(-c2cccc(O)c2)c1)C1CCCC1] |
| 263 | 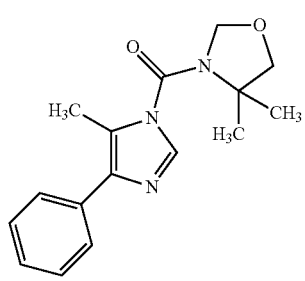 [SMILES: Cc1c(-c2ccccc2)ncn1C(=O)N1COCC1(C)C] |
| 264 | 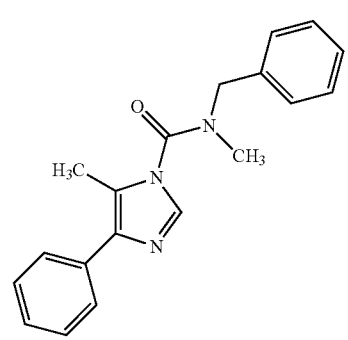 [SMILES: Cc1c(-c2ccccc2)ncn1C(=O)N(C)Cc1ccccc1] |

-continued
| No. | Structure |
|---|---|
| 265 | 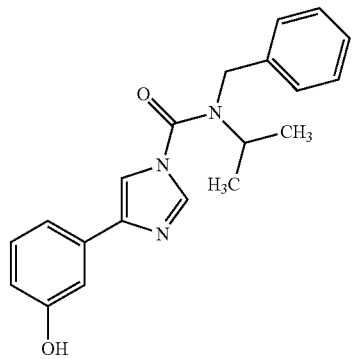 [SMILES: CC(C)N(Cc1ccccc1)C(=O)n1cnc(-c2cccc(O)c2)c1] |
| 266 | 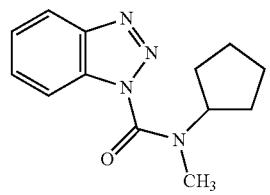 [SMILES: CN(C(=O)n1nnc2ccccc21)C1CCCC1] |
| 267 | 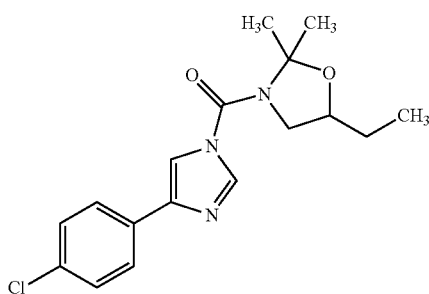 [SMILES: CCC1CN(C(=O)n2cnc(-c3ccc(Cl)cc3)c2)C(C)(C)O1] |
| 268 | 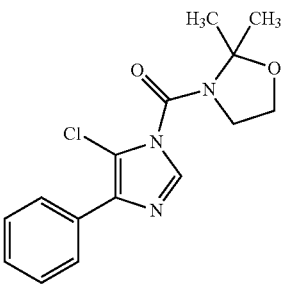 [SMILES: CC1(C)OCCN1C(=O)n1cnc(-c2ccccc2)c1Cl] |
| 269 | 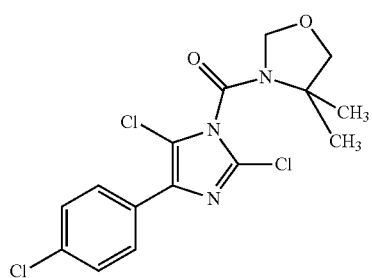 [SMILES: CC1(C)COCN1C(=O)n1c(Cl)nc(-c2ccc(Cl)cc2)c1Cl] |

-continued
| No. | Structure |
|---|---|
| 270 | 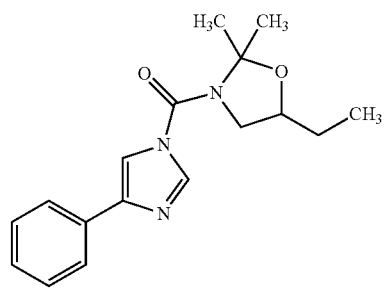 [SMILES: CCC1CN(C(=O)n2cnc(-c3ccccc3)c2)C(C)(C)O1] |
| 271 | 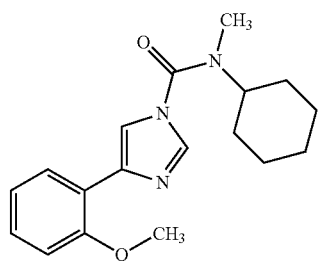 [SMILES: COc1ccccc1-c1cn(C(=O)N(C)C2CCCCC2)cn1] |
| 272 | 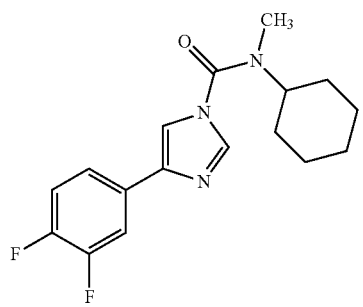 |
| 273 | 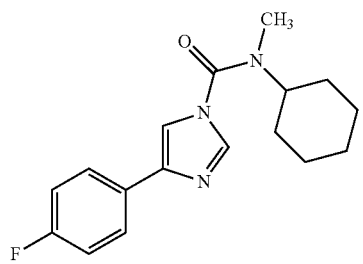 [SMILES: CN(C(=O)n1cnc(-c2ccc(F)cc2)c1)C1CCCCC1] |
| 274 | 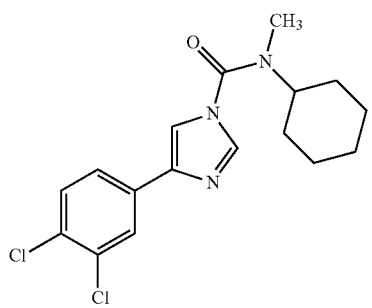 [SMILES: CN(C(=O)n1cnc(-c2ccc(Cl)c(Cl)c2)c1)C1CCCCC1] |

| No. | Structure |
|---|---|
| 275 | 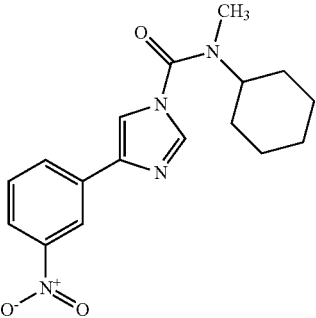 [SMILES: CN(C(=O)n1cnc(-c2cccc([N+](=O)[O-])c2)c1)C1CCCCC1] |
| 276 | 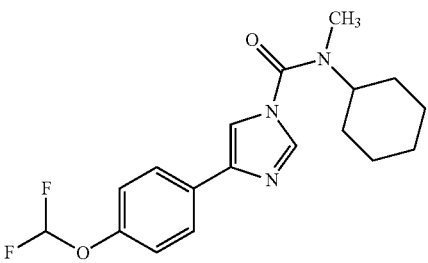 |
| 277 | 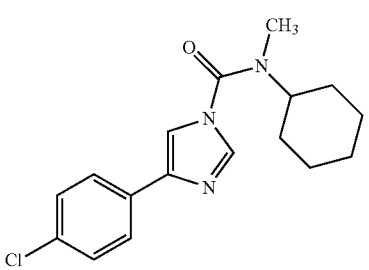 [SMILES: CN(C(=O)n1cnc(-c2ccc(Cl)cc2)c1)C1CCCCC1] |
| 278 | 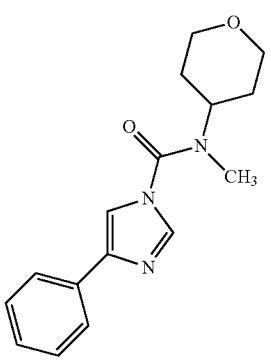 [SMILES: CN(C(=O)n1cnc(-c2ccccc2)c1)C1CCOCC1] |
| 279 | 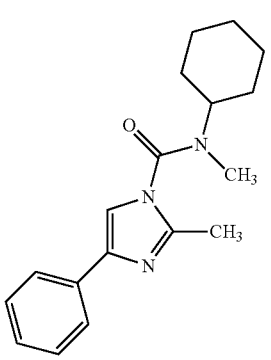 |

| No. | Structure |
|---|---|
| 280 | 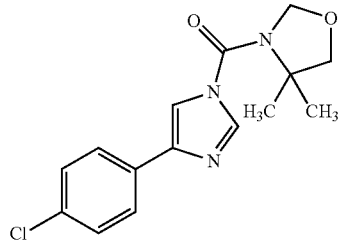 [SMILES: CC1(C)COCN1C(=O)n1cnc(-c2ccc(Cl)cc2)c1] |
| 281 | 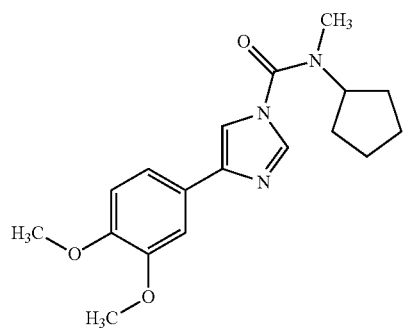 [SMILES: COc1ccc(-c2cn(C(=O)N(C)C3CCCC3)cn2)cc1OC] |
| 282 | 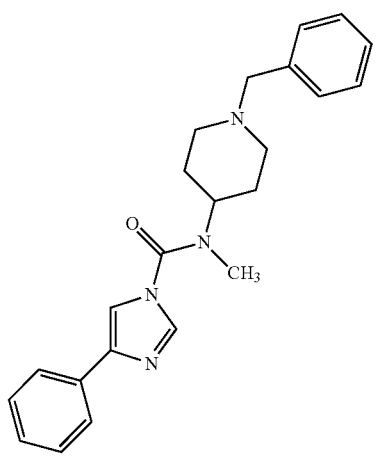 [SMILES: CN(C(=O)n1cnc(-c2ccccc2)c1)C1CCN(Cc2ccccc2)CC1] |
| 283 | 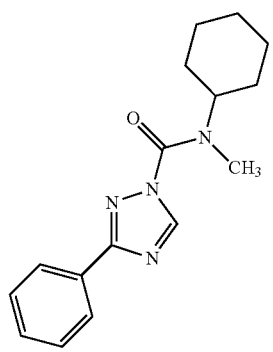 [SMILES: CN(C(=O)n1cnc(-c2ccccc2)n1)C1CCCCC1] |

| No. | Structure |
|---|---|
| 284 | 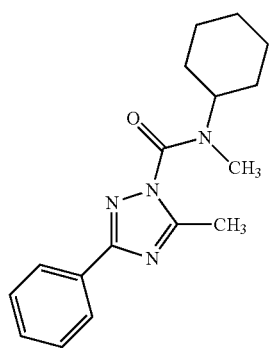 [SMILES: Cc1nc(-c2ccccc2)nn1C(=O)N(C)C1CCCCC1] |
| 285 | 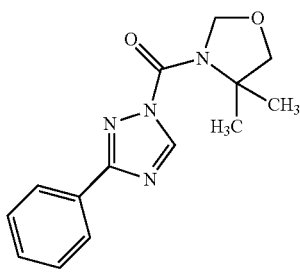 [SMILES: CC1(C)COCN1C(=O)n1cnc(-c2ccccc2)n1] |
| 286 | 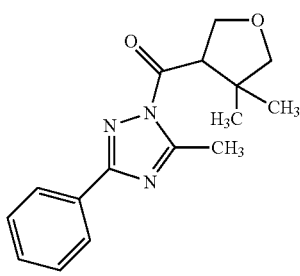 [SMILES: Cc1nc(-c2ccccc2)nn1C(=O)C1COCC1(C)C] |
| 287 | 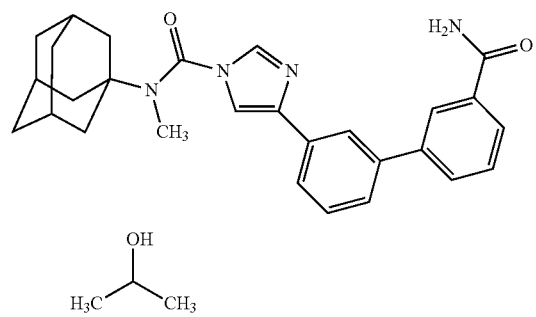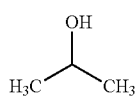 |
| 288 | 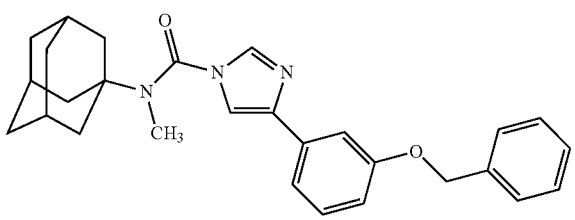 [SMILES: CN(C(=O)n1cnc(-c2cccc(OCc3ccccc3)c2)c1)C12CC3CC(CC(C3)C1)C2] |

-continued
| No. | Structure |
|---|---|
| 289 | 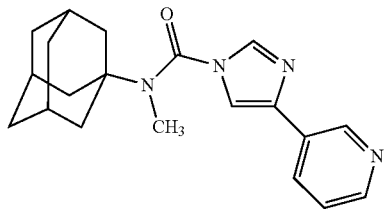 [SMILES: CN(C(=O)n1cnc(-c2cccnc2)c1)C12CC3CC(CC(C3)C1)C2] |
| 290 | 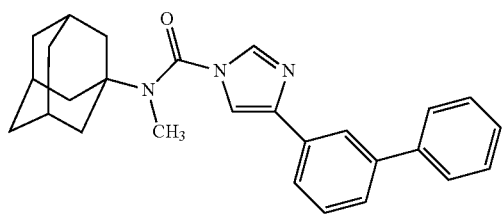 [SMILES: CN(C(=O)n1cnc(-c2cccc(-c3ccccc3)c2)c1)C12CC3CC(CC(C3)C1)C2] |
| 291 | 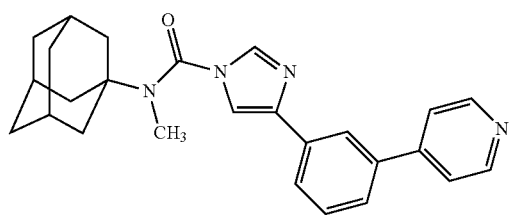 [SMILES: CN(C(=O)n1cnc(-c2cccc(-c3ccncc3)c2)c1)C12CC3CC(CC(C3)C1)C2] |
| 292 | 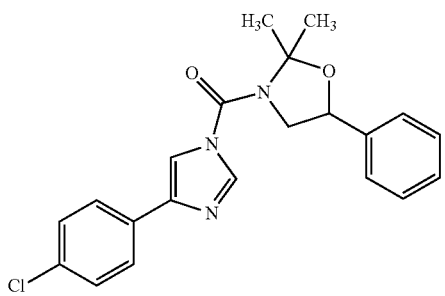 [SMILES: CC1(C)OC(c2ccccc2)CN1C(=O)n1cnc(-c2ccc(Cl)cc2)c1] |
| 293 | 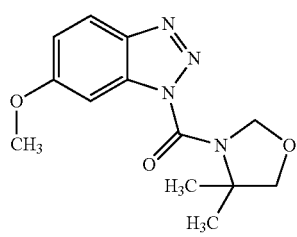 [SMILES: COc1ccc2nnn(C(=O)N3COCC3(C)C)c2c1] |
| 294 | 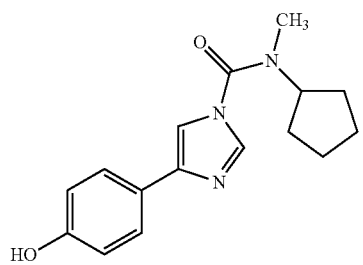 [SMILES: CN(C(=O)n1cnc(-c2ccc(O)cc2)c1)C1CCCC1] |

-continued

| No. | Structure |
|---|---|
| 295 | 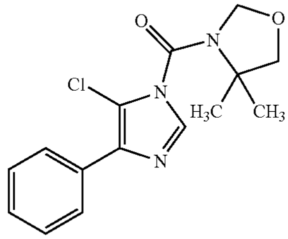 [SMILES: CC1(C)COCN1C(=O)n1cnc(-c2ccccc2)c1Cl] |
| 296 | 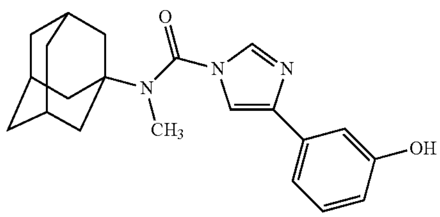 [SMILES: CN(C(=O)n1cnc(-c2cccc(O)c2)c1)C12CC3CC(CC(C3)C1)C2] |
| 297 | 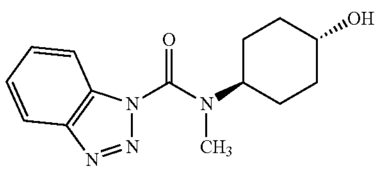 [SMILES: CN(C(=O)n1nnc2ccccc21)[C@H]1CC[C@H](O)CC1] |
| 298 | 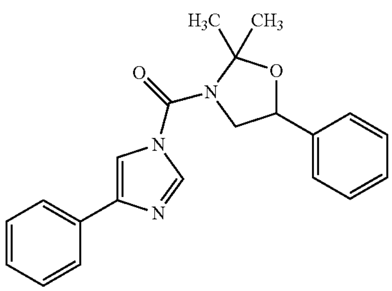 [SMILES: CC1(C)OC(c2ccccc2)CN1C(=O)n1cnc(-c2ccccc2)c1] |
| 299 | 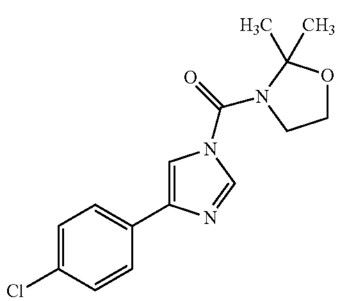 [SMILES: CC1(C)OCCN1C(=O)n1cnc(-c2ccc(Cl)cc2)c1] |
| 300 | 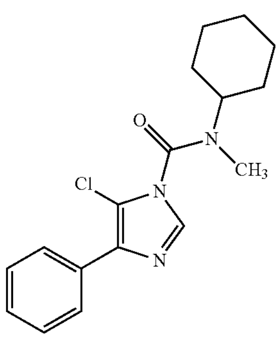 [SMILES: CN(C(=O)n1cnc(-c2ccccc2)c1Cl)C1CCCCC1] |

| No. | Structure |
|---|---|
| 301 | 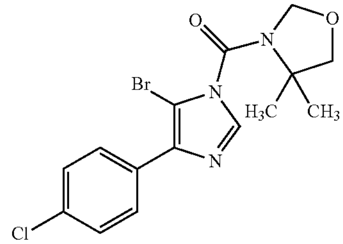 [SMILES: CC1(C)COCN1C(=O)n1cnc(-c2ccc(Cl)cc2)c1Br] |
| 302 | 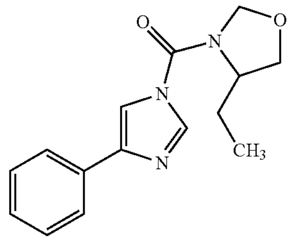 [SMILES: CCC1COCN1C(=O)n1cnc(-c2ccccc2)c1] |
| 303 | 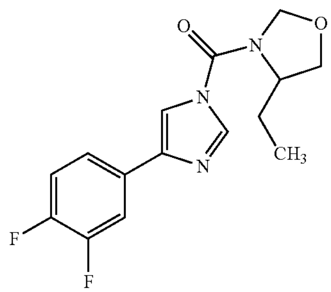 [SMILES: CCC1COCN1C(=O)n1cnc(-c2ccc(F)c(F)c2)c1] |
| 304 | 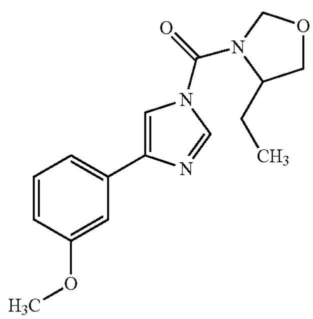 [SMILES: CCC1COCN1C(=O)n1cnc(-c2cccc(OC)c2)c1] |
| 305 | 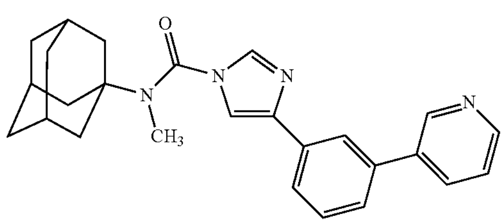 [SMILES: CN(C(=O)n1cnc(-c2cccc(-c3cccnc3)c2)c1)C12CC3CC(CC(C3)C1)C2] |
| 306 | 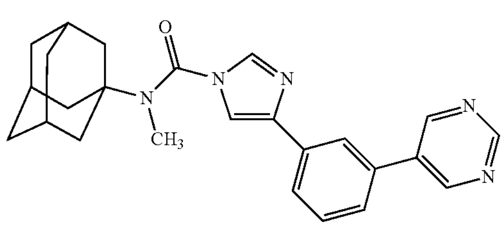 [SMILES: CN(C(=O)n1cnc(-c2cccc(-c3cncnc3)c2)c1)C12CC3CC(CC(C3)C1)C2] |

| No. | Structure |
|---|---|
| 307 | 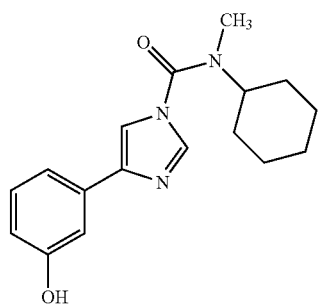 [SMILES: CN(C(=O)n1cnc(-c2cccc(O)c2)c1)C1CCCCC1] |
| 308 | 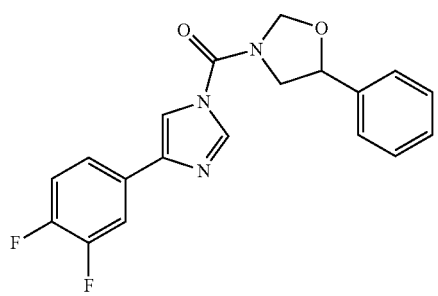 [SMILES: O=C(N1COC(c2ccccc2)C1)n1cnc(-c2ccc(F)c(F)c2)c1] |
| 309 | 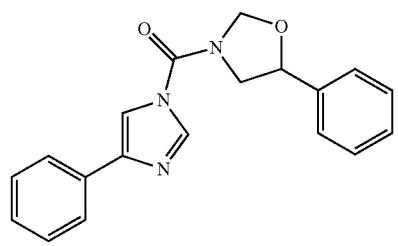 [SMILES: O=C(N1COC(c2ccccc2)C1)n1cnc(-c2ccccc2)c1] |
| 310 | 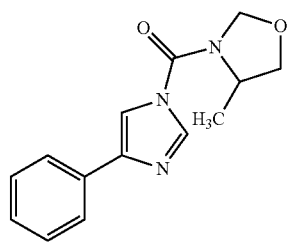 [SMILES: CC1COCN1C(=O)n1cnc(-c2ccccc2)c1] |
| 311 | 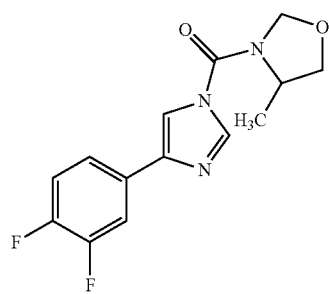 [SMILES: CC1COCN1C(=O)n1cnc(-c2ccc(F)c(F)c2)c1] |

-continued
| No. | Structure |
|---|---|
| 312 | 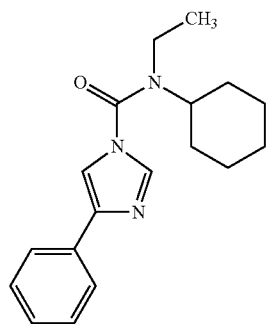 [SMILES: CCN(C(=O)n1cnc(-c2ccccc2)c1)C1CCCCC1] |
| 313 | 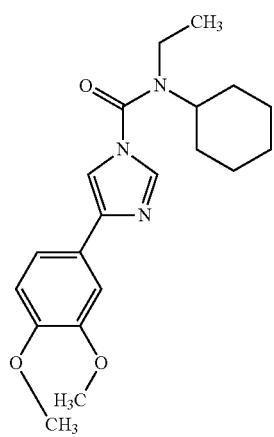 [SMILES: CCN(C(=O)n1cnc(-c2ccc(OC)c(OC)c2)c1)C1CCCCC1] |
| 314 | 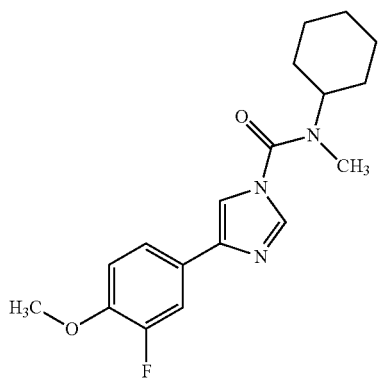 [SMILES: COc1ccc(-c2cn(C(=O)N(C)C3CCCCC3)cn2)cc1F] |
| 315 | 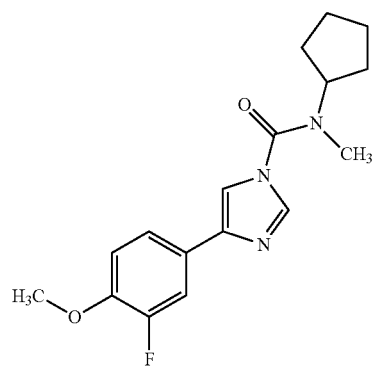 [SMILES: COc1ccc(-c2cn(C(=O)N(C)C3CCCC3)cn2)cc1F] |

| No. | Structure |
|---|---|
| 316 | 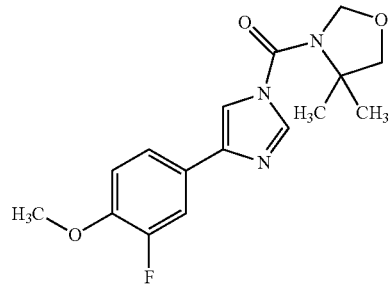 [SMILES: COc1ccc(-c2cn(C(=O)N3COCC3(C)C)cn2)cc1F] |
| 317 | 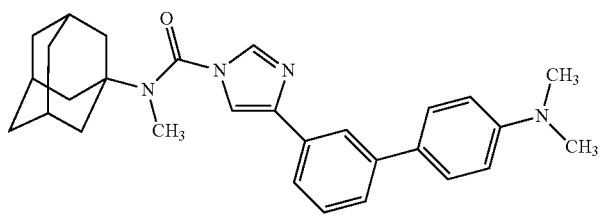 [SMILES: CN(C)c1ccc(-c2cccc(-c3cn(C(=O)N(C)C45CC6CC(CC(C6)C4)C5)cn3)c2)cc1] |
| 318 | 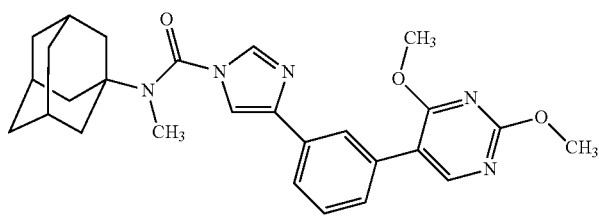 [SMILES: COc1ncc(-c2cccc(-c3cn(C(=O)N(C)C45CC6CC(CC(C6)C4)C5)cn3)c2)c(OC)n1] |
| 319 | 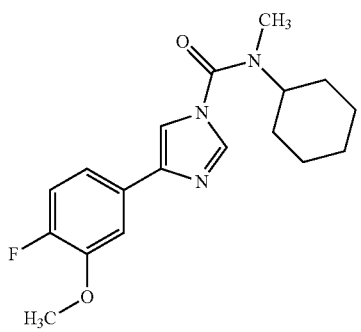 |
| 320 | 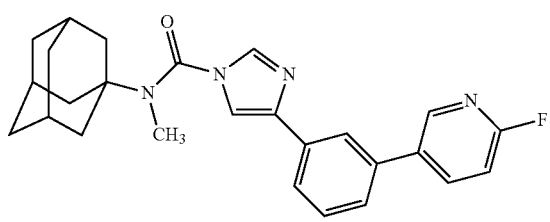 [SMILES: CN(C(=O)n1cnc(-c2cccc(-c3ccc(F)nc3)c2)c1)C12CC3CC(CC(C3)C1)C2] |

-continued
| No. | Structure |
|-----|-----------|
| 321 | 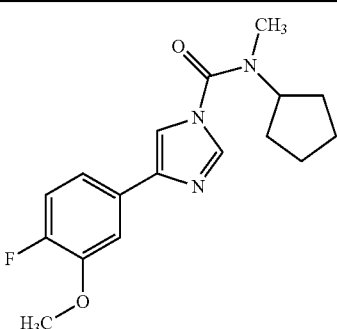 |
| 322 | 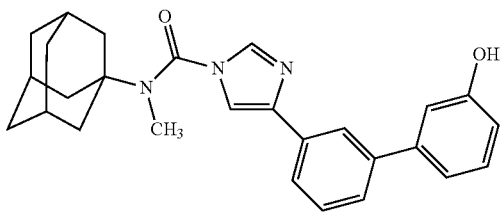 [SMILES: CN(C(=O)n1cnc(-c2cccc(-c3cccc(O)c3)c2)c1)C12CC3CC(CC(C3)C1)C2] |
| 323 | 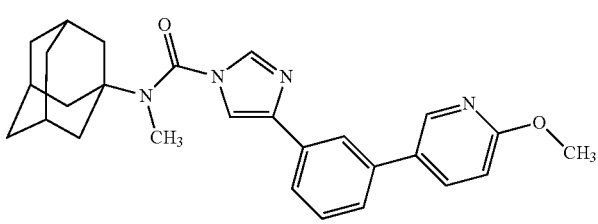 [SMILES: COc1ccc(-c2cccc(-c3cn(C(=O)N(C)C45CC6CC(CC(C6)C4)C5)cn3)c2)cn1] |
| 324 | 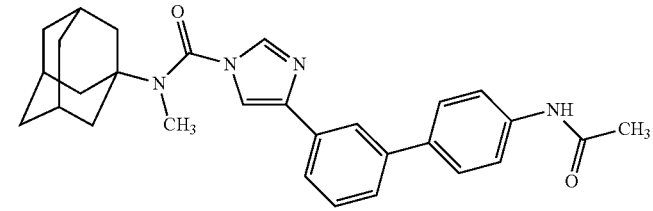 [SMILES: CC(=O)Nc1ccc(-c2cccc(-c3cn(C(=O)N(C)C45CC6CC(CC(C6)C4)C5)cn3)c2)cc1] |
| 325 | 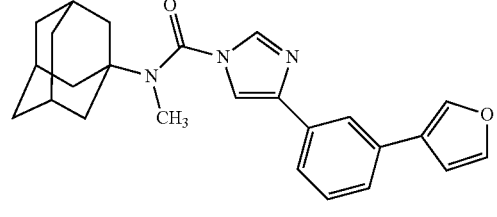 [SMILES: CN(C(=O)n1cnc(-c2cccc(-c3ccoc3)c2)c1)C12CC3CC(CC(C3)C1)C2] |
| 326 | 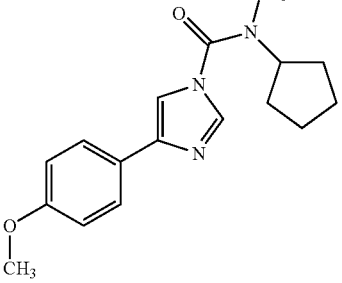 |

-continued
| No. | Structure |
|---|---|
| 327 | 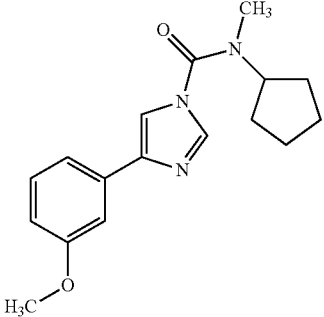 [SMILES: COc1cccc(-c2cn(C(=O)N(C)C3CCCC3)cn2)c1] |
| 328 | 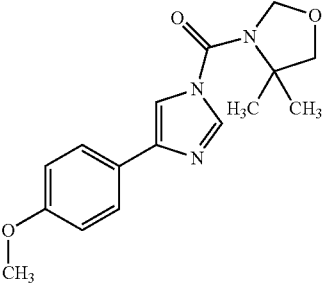 [SMILES: COc1ccc(-c2cn(C(=O)N3COCC3(C)C)cn2)cc1] |
| 329 | 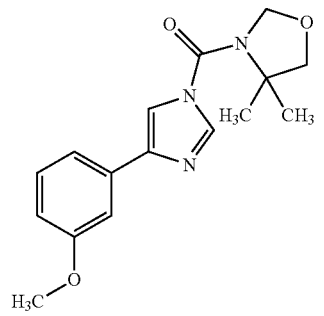 [SMILES: COc1cccc(-c2cn(C(=O)N3COCC3(C)C)cn2)c1] |
| 330 | 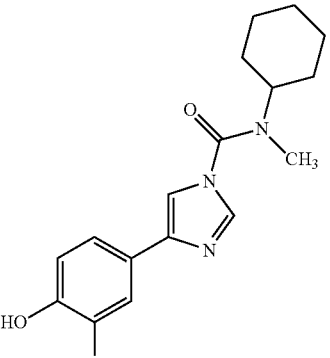 |

-continued
| No. | Structure |
|---|---|
| 331 | 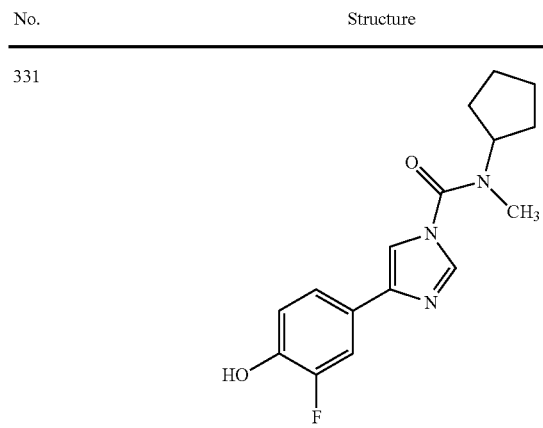 |
| 332 | 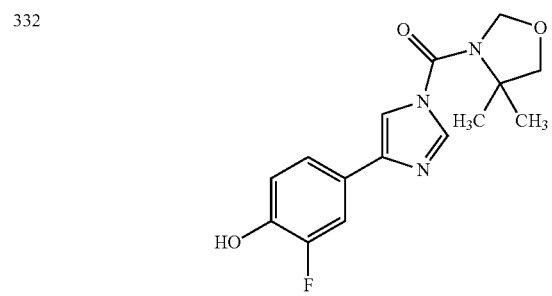 |
| 333 | 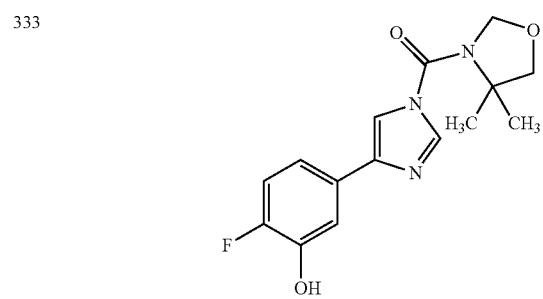 |
| 334 | 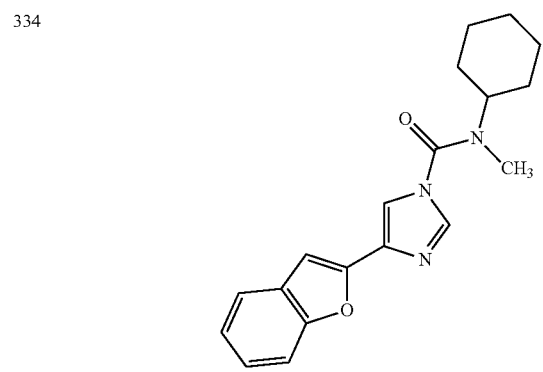 |

-continued
| No. | Structure |
|---|---|
| 335 | 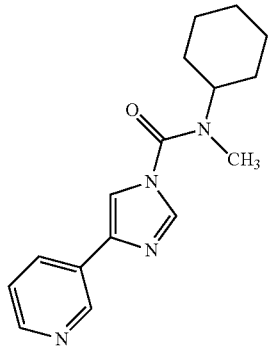 [SMILES: CN(C(=O)n1cnc(-c2cccnc2)c1)C1CCCCC1] |
| 336 | 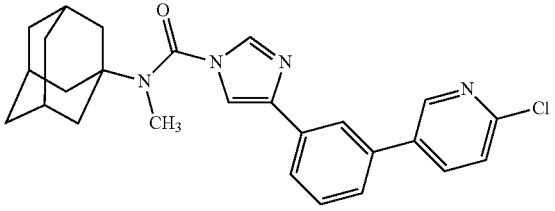 [SMILES: CN(C(=O)n1cnc(-c2cccc(-c3ccc(Cl)nc3)c2)c1)C12CC3CC(CC(C3)C1)C2] |
| 337 | 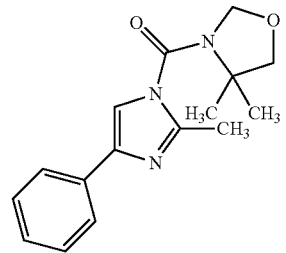 [SMILES: Cc1nc(-c2ccccc2)cn1C(=O)N1COCC1(C)C] |
| 338 | 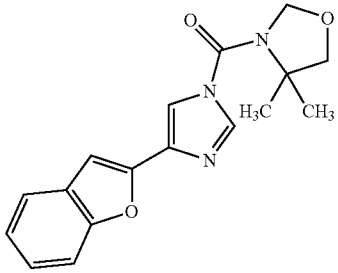 [SMILES: CC1(C)COCN1C(=O)n1cnc(-c2cc3ccccc3o2)c1] |
| 339 | 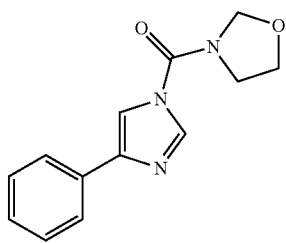 [SMILES: O=C(N1CCOC1)n1cnc(-c2ccccc2)c1] |

| No. | Structure |
|---|---|
| 340 | 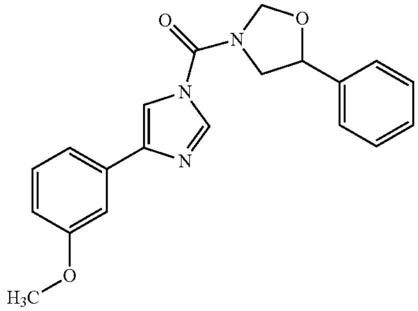 [SMILES: COc1cccc(-c2cn(C(=O)N3COC(c4ccccc4)C3)cn2)c1] |
| 341 | 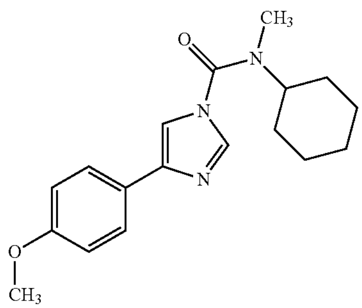 [SMILES: COc1ccc(-c2cn(C(=O)N(C)C3CCCCC3)cn2)cc1] |
| 342 | 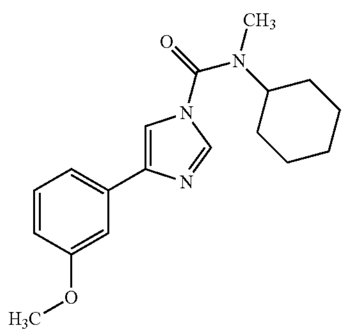 [SMILES: COc1cccc(-c2cn(C(=O)N(C)C3CCCCC3)cn2)c1] |
| 343 | 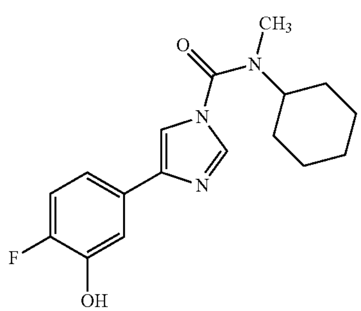 |
| 344 | 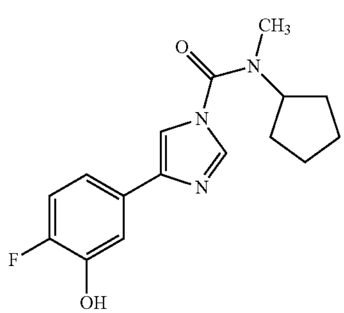 [SMILES: CN(C(=O)n1cnc(-c2ccc(F)c(O)c2)c1)C1CCCC1] |

-continued
| No. | Structure |
|---|---|
| 345 | 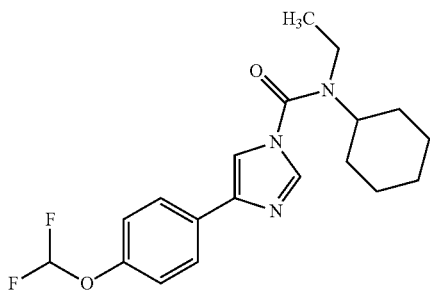 [SMILES: CCN(C(=O)n1cnc(-c2ccc(OC(F)F)cc2)c1)C1CCCCC1] |
| 346 | 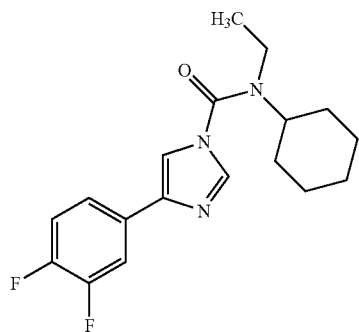 [SMILES: CCN(C(=O)n1cnc(-c2ccc(F)c(F)c2)c1)C1CCCCC1] |
| 347 | 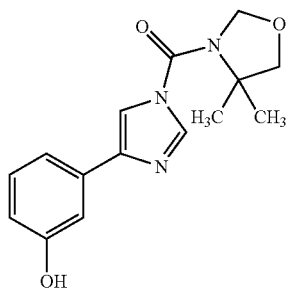 [SMILES: CC1(C)COCN1C(=O)n1cnc(-c2cccc(O)c2)c1] |
| 348 | 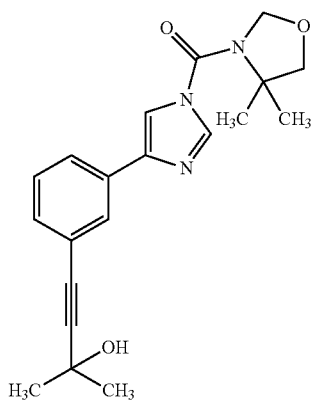 [SMILES: CC(C)(O)C#Cc1cccc(-c2cn(C(=O)N3COCC3(C)C)cn2)c1] |

-continued

| No. | Structure |
|---|---|
| 349 | 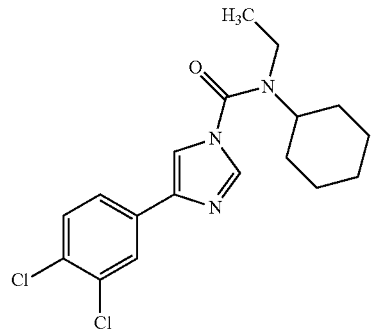 [SMILES: CCN(C(=O)n1cnc(-c2ccc(Cl)c(Cl)c2)c1)C1CCCCC1] |
| 350 | 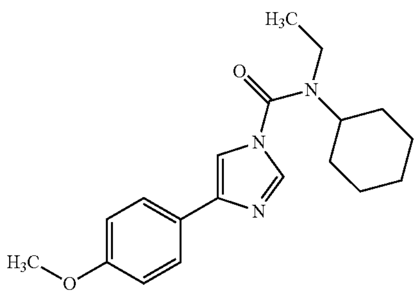 [SMILES: CCN(C(=O)n1cnc(-c2ccc(OC)cc2)c1)C1CCCCC1] |
| 351 | 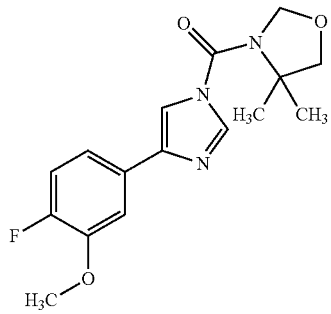 [SMILES: COc1cc(-c2cn(C(=O)N3COCC3(C)C)cn2)ccc1F] |
| 352 | 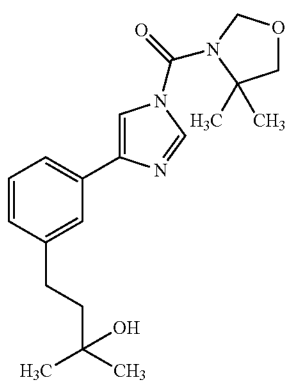 [SMILES: CC(C)(O)CCc1cccc(-c2cn(C(=O)N3COCC3(C)C)cn2)c1] |
| 353 | 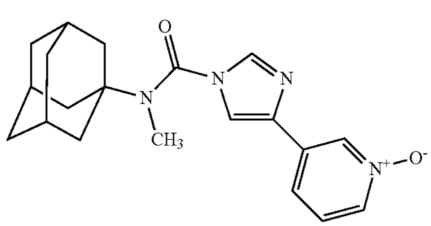 [SMILES: CN(C(=O)n1cnc(-c2ccc[n+]([O-])c2)c1)C12CC3CC(CC(C3)C1)C2] |

-continued
| No. | Structure |
|---|---|
| 354 | 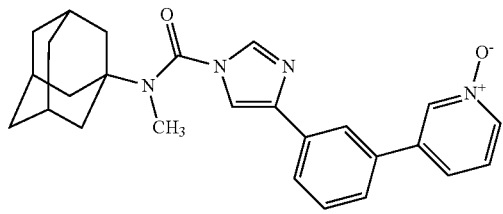 [SMILES: CN(C(=O)n1cnc(-c2cccc(-c3ccc[n+]([O-])c3)c2)c1)C12CC3CC(CC(C3)C1)C2] |
| 355 | 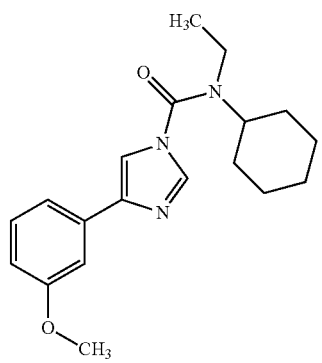 [SMILES: CCN(C(=O)n1cnc(-c2cccc(OC)c2)c1)C1CCCCC1] |
| 356 | 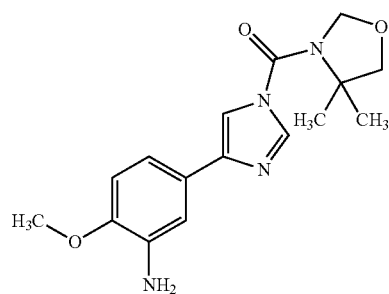 [SMILES: COc1ccc(-c2cn(C(=O)N3COCC3(C)C)cn2)cc1N] |
| 357 | 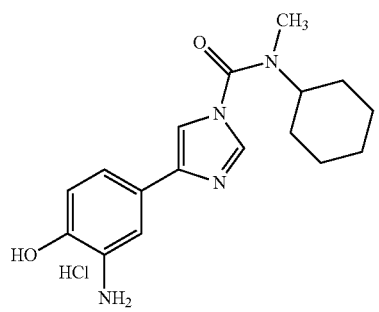 [SMILES: CN(C(=O)n1cnc(-c2ccc(O)c(N)c2)c1)C1CCCCC1 ; Cl] |
| 358 | 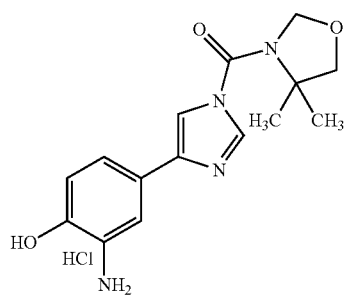 [SMILES: CC1(C)COCN1C(=O)n1cnc(-c2ccc(O)c(N)c2)c1 ; Cl] |

| No. | Structure |
|---|---|
| 359 | 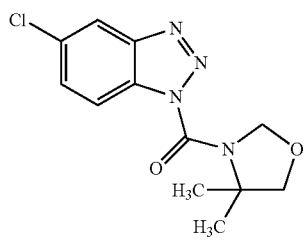 [SMILES: CC1(C)COCN1C(=O)n1nnc2cc(Cl)ccc21] |
| 360 | 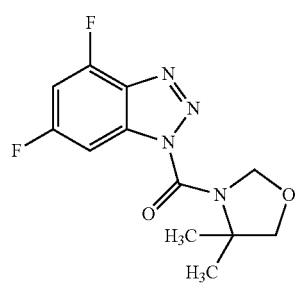 [SMILES: CC1(C)COCN1C(=O)n1nnc2c(F)cc(F)cc21] |
| 361 | 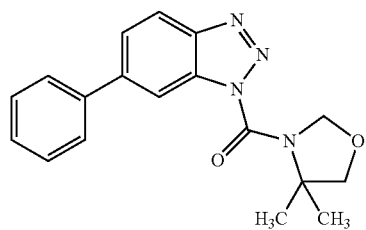 [SMILES: CC1(C)COCN1C(=O)n1nnc2ccc(-c3ccccc3)cc21] |
| 362 | 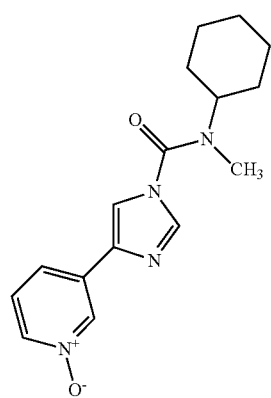 [SMILES: CN(C(=O)n1cnc(-c2ccc[n+]([O-])c2)c1)C1CCCCC1] |

-continued
| No. | Structure |
|---|---|
| 363 | 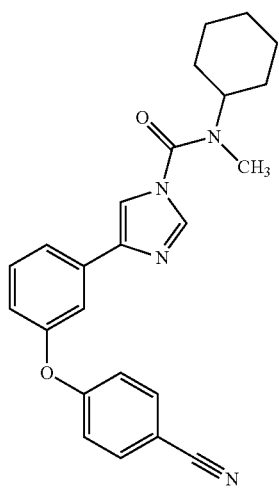 [SMILES: CN(C(=O)n1cnc(-c2cccc(Oc3ccc(C#N)cc3)c2)c1)C1CCCCC1] |
| 364 | 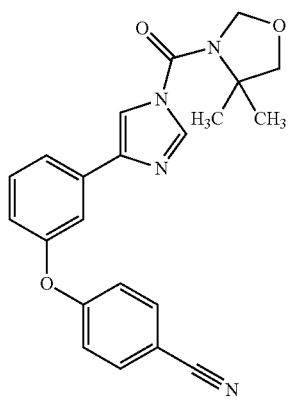 [SMILES: CC1(C)COCN1C(=O)n1cnc(-c2cccc(Oc3ccc(C#N)cc3)c2)c1] |
| 365 | 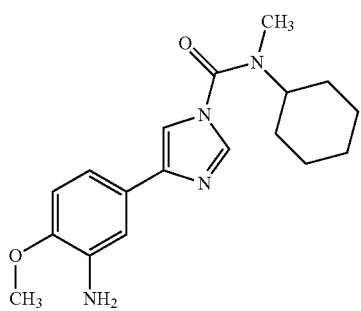 [SMILES: COc1ccc(-c2cn(C(=O)N(C)C3CCCCC3)cn2)cc1N] |
| 366 | 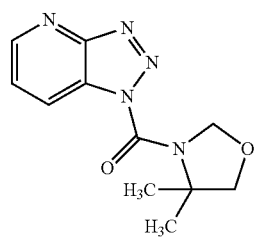 [SMILES: CC1(C)COCN1C(=O)n1nnc2ncccc21] |

| No. | Structure |
|---|---|
| 367 | 6-methyl-benzotriazol-1-yl carbonyl-(4,4-dimethyl-oxazolidin-3-yl) |
| 368 | [1,2,3]triazolo[4,5-b]pyridin-1-yl carbonyl-(4,4-dimethyl-oxazolidin-3-yl) |
| 369 | benzotriazol-1-yl carbonyl-(oxazolidin-3-yl) |
| 370 | 6-(2-methoxyphenyl)-benzotriazol-1-yl carbonyl-(4,4-dimethyl-oxazolidin-3-yl) |
| 371 | 5-trifluoromethyl-benzotriazol-1-yl carbonyl-(4,4-dimethyl-oxazolidin-3-yl) |
| 372 | 4,6-dimethoxy-benzotriazol-1-yl carbonyl-(4,4-dimethyl-oxazolidin-3-yl) |
| 373 | benzotriazol-1-yl carbonyl-(2,2-dimethyl-oxazolidin-3-yl) |

| No. | Structure |
|---|---|
| 374 | 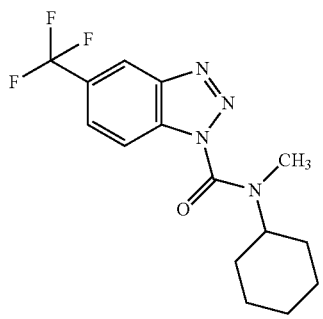 [SMILES: CN(C(=O)n1nnc2cc(C(F)(F)F)ccc21)C1CCCCC1] |
| 375 | 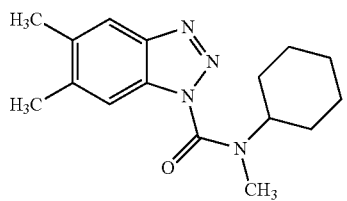 [SMILES: Cc1cc2nnn(C(=O)N(C)C3CCCCC3)c2cc1C] |
| 376 | 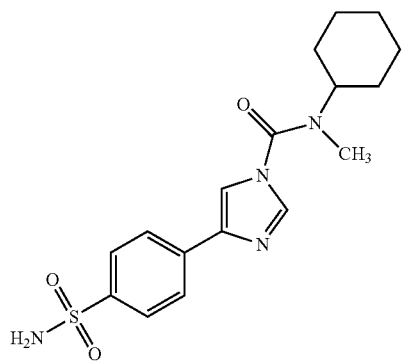 [SMILES: CN(C(=O)n1cnc(-c2ccc(S(N)(=O)=O)cc2)c1)C1CCCCC1] |
| 377 | 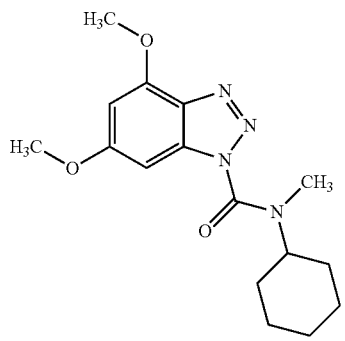 [SMILES: COc1cc(OC)c2nnn(C(=O)N(C)C3CCCCC3)c2c1] |
| 378 | 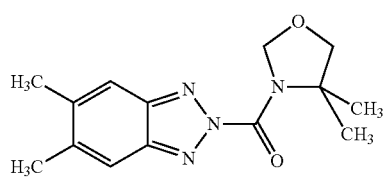 |

| No. | Structure |
|-----|-----------|
| 379 | 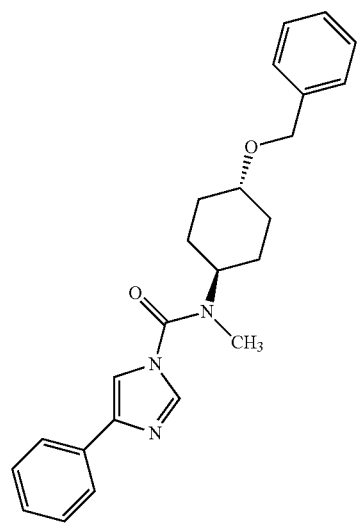 [SMILES: CN(C(=O)n1cnc(-c2ccccc2)c1)[C@H]1CC[C@H](OCc2ccccc2)CC1] |
| 380 | 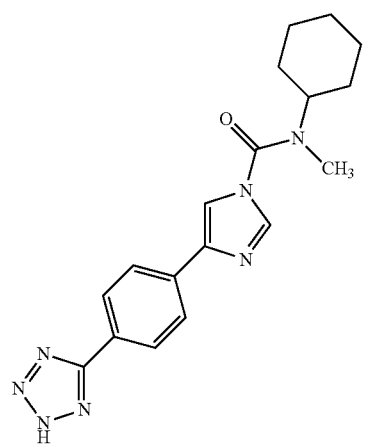 [SMILES: CN(C(=O)n1cnc(-c2ccc(-c3nn[nH]n3)cc2)c1)C1CCCCC1] |
| 381 | 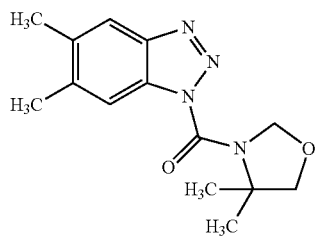 |
| 382 | 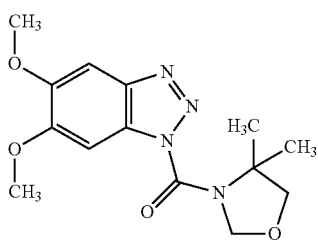 [SMILES: COc1cc2nnn(C(=O)N3COCC3(C)C)c2cc1OC] |

| No. | Structure |
|---|---|
| 383 | 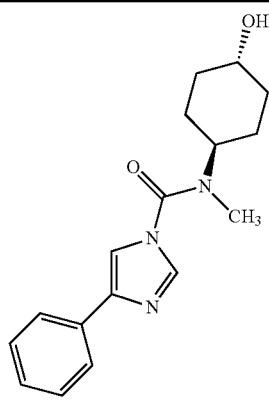 |
| 384 | 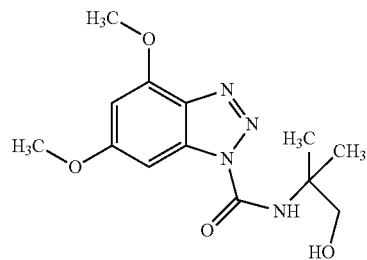 [SMILES: COc1cc(OC)c2nnn(C(=O)NC(C)(C)CO)c2c1] |
| 385 | 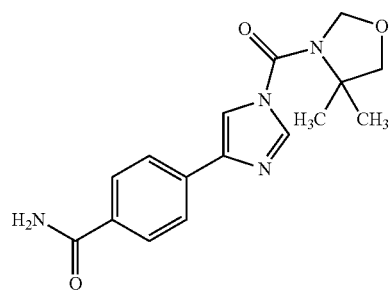 [SMILES: CC1(C)COCN1C(=O)n1cnc(-c2ccc(C(N)=O)cc2)c1] |
| 386 | 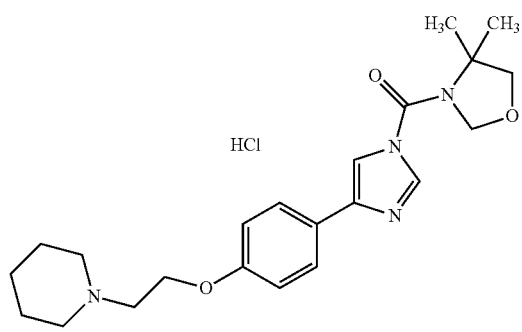 [SMILES: CC1(C)COCN1C(=O)n1cnc(-c2ccc(OCCN3CCCCC3)cc2)c1 ; Cl] |
| 387 | 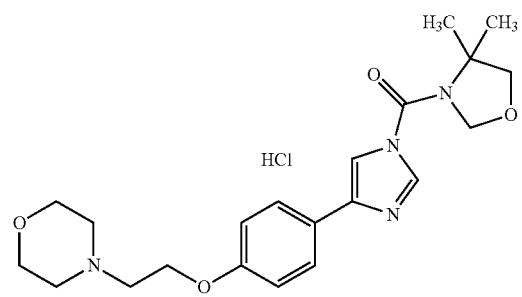 [SMILES: CC1(C)COCN1C(=O)n1cnc(-c2ccc(OCCN3CCOCC3)cc2)c1 ; Cl] |

-continued
| No. | Structure |
|---|---|
| 388 | 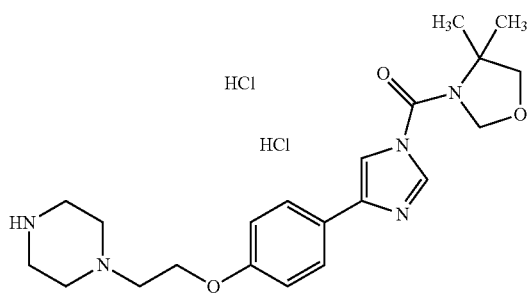 [SMILES: CC1(C)COCN1C(=O)n1cnc(-c2ccc(OCCN3CCNCC3)cc2)c1 ; Cl ; Cl] |
| 389 | 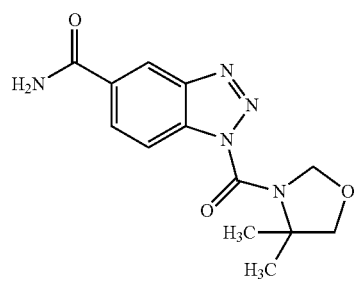 [SMILES: CC1(C)COCN1C(=O)n1nnc2cc(C(N)=O)ccc21] |
| 390 | 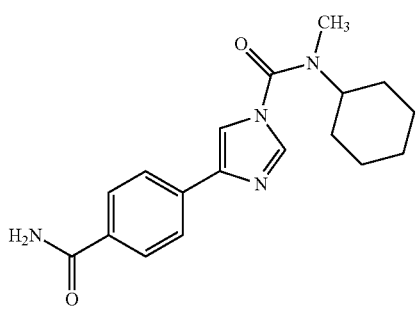 [SMILES: CN(C(=O)n1cnc(-c2ccc(C(N)=O)cc2)c1)C1CCCCC1] |
| 391 | 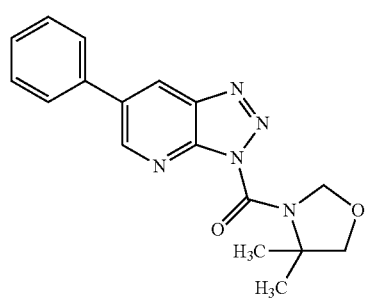 [SMILES: CC1(C)COCN1C(=O)n1nnc2cc(-c3ccccc3)cnc21] |
| 392 | 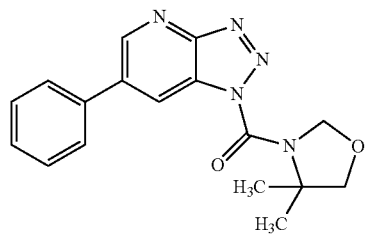 [SMILES: CC1(C)COCN1C(=O)n1nnc2ncc(-c3ccccc3)cc21] |

| No. | Structure |
|---|---|
| 393 | 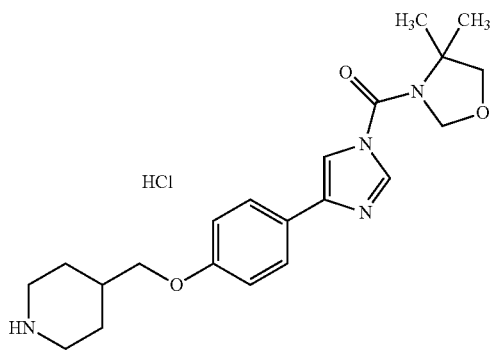 [SMILES: CC1(C)COCN1C(=O)n1cnc(-c2ccc(OCC3CCNCC3)cc2)c1 ; Cl] |
| 394 | 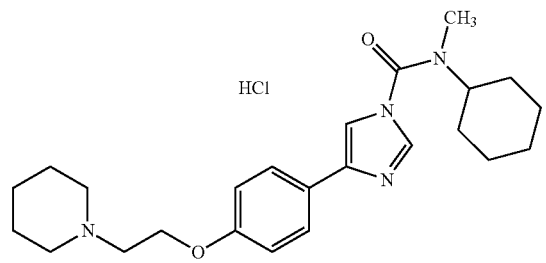 [SMILES: CN(C(=O)n1cnc(-c2ccc(OCCN3CCCCC3)cc2)c1)C1CCCCC1 ; Cl] |
| 395 | 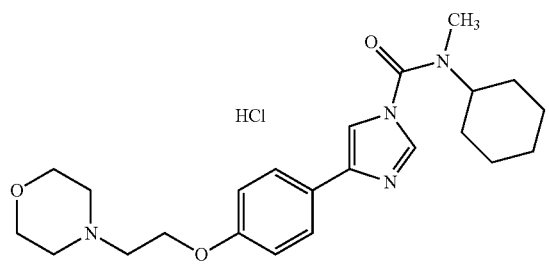 [SMILES: CN(C(=O)n1cnc(-c2ccc(OCCN3CCOCC3)cc2)c1)C1CCCCC1 ; Cl] |
| 396 | 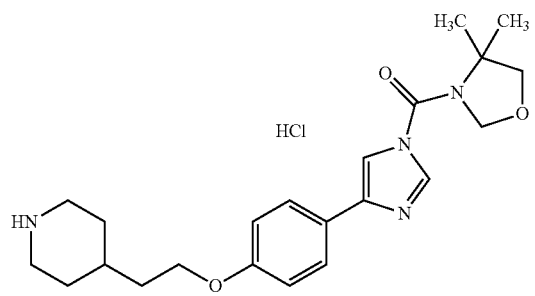 [SMILES: CC1(C)COCN1C(=O)n1cnc(-c2ccc(OCCC3CCNCC3)cc2)c1 ; Cl] |
| 397 | 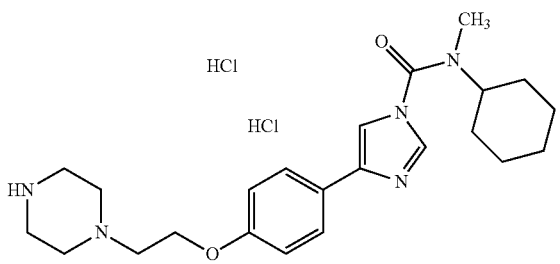 [SMILES: CN(C(=O)n1cnc(-c2ccc(OCCN3CCNCC3)cc2)c1)C1CCCCC1 ; Cl ; Cl] |

| No. | Structure |
|---|---|
| 398 | 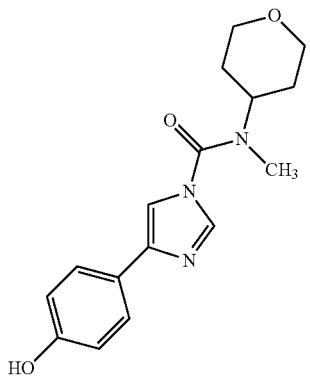 [SMILES: CN(C(=O)n1cnc(-c2ccc(O)cc2)c1)C1CCOCC1] |
| 399 | 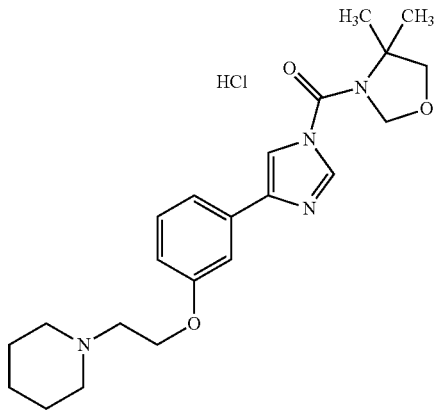 [SMILES: CC1(C)COCN1C(=O)n1cnc(-c2cccc(OCCN3CCCCC3)c2)c1 ; Cl] |
| 400 | 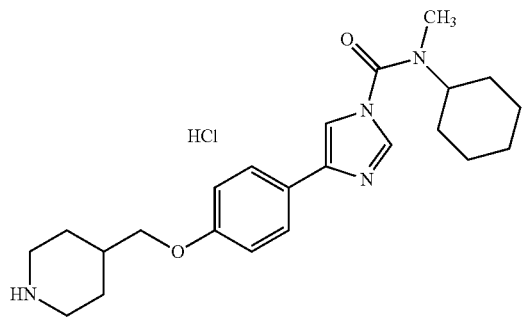 [SMILES: CN(C(=O)n1cnc(-c2ccc(OCC3CCNCC3)cc2)c1)C1CCCCC1 ; Cl] |
| 401 | 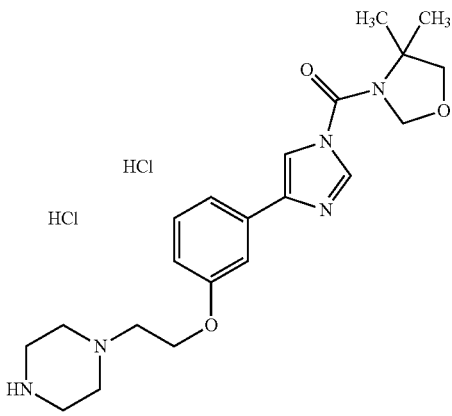 [SMILES: CC1(C)COCN1C(=O)n1cnc(-c2cccc(OCCN3CCNCC3)c2)c1 ; Cl ; Cl] |

| No. | Structure |
|---|---|
| 402 | 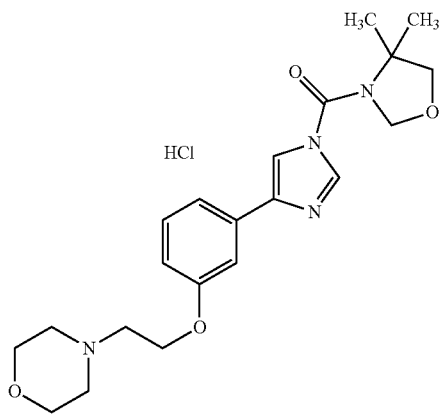 [SMILES: CC1(C)COCN1C(=O)n1cnc(-c2cccc(OCCN3CCOCC3)c2)c1 ; Cl] |
| 403 | 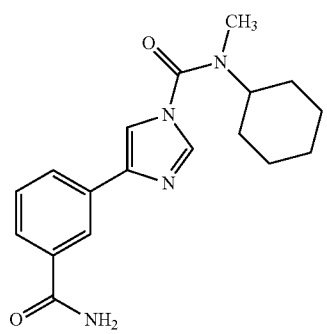 [SMILES: CN(C(=O)n1cnc(-c2cccc(C(N)=O)c2)c1)C1CCCCC1] |
| 404 | 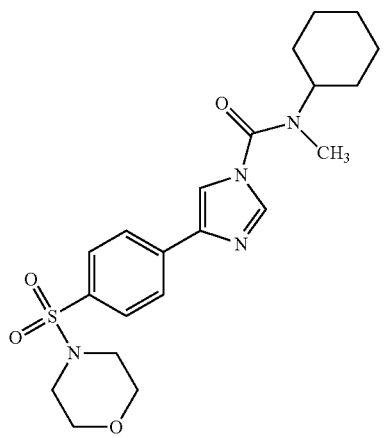 [SMILES: CN(C(=O)n1cnc(-c2ccc(S(=O)(=O)N3CCOCC3)cc2)c1)C1CCCCC1] |
| 405 | 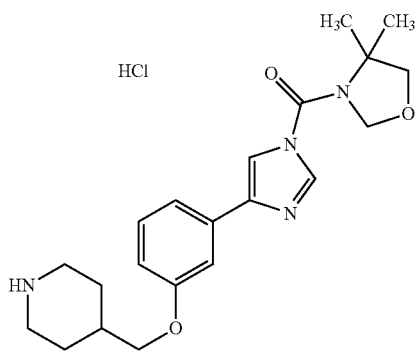 [SMILES: CC1(C)COCN1C(=O)n1cnc(-c2cccc(OCC3CCNCC3)c2)c1 ; Cl] |

| No. | Structure |
|---|---|
| 406 | 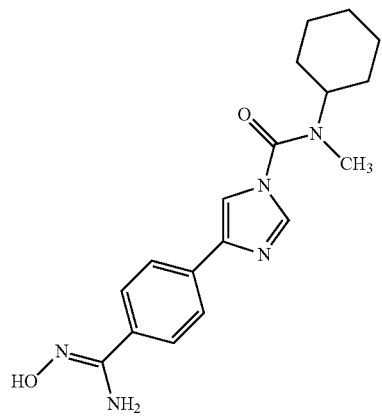 [SMILES: CN(C(=O)n1cnc(-c2ccc(/C(N)=N/O)cc2)c1)C1CCCCC1] |
| 407 | 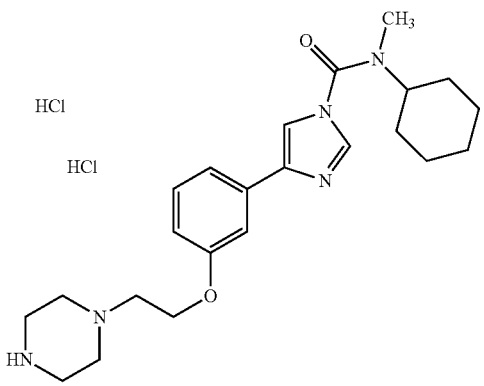 [SMILES: CN(C(=O)n1cnc(-c2cccc(OCCN3CCNCC3)c2)c1)C1CCCCC1 ; Cl ; Cl] |
| 408 | 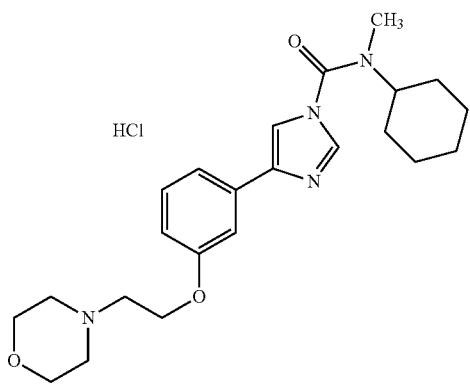 [SMILES: CN(C(=O)n1cnc(-c2cccc(OCCN3CCOCC3)c2)c1)C1CCCCC1 ; Cl] |
| 409 | 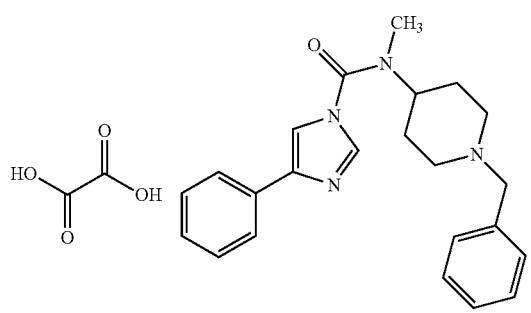 |

| No. | Structure |
|---|---|
| 410 | 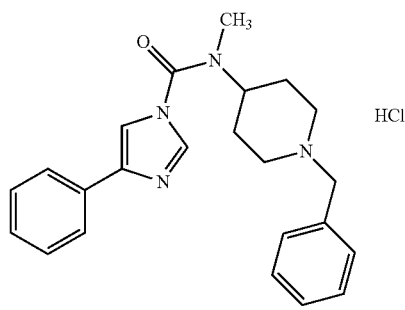 [SMILES: CN(C(=O)n1cnc(-c2ccccc2)c1)C1CCN(Cc2ccccc2)CC1 ; Cl] HCl |
| 411 | 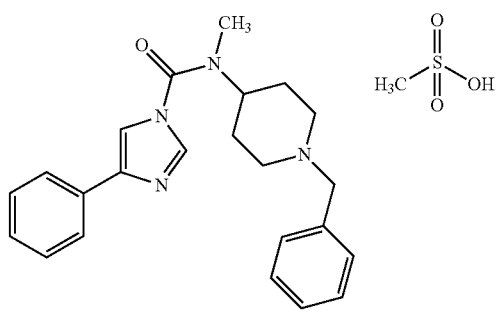 |
| 412 | 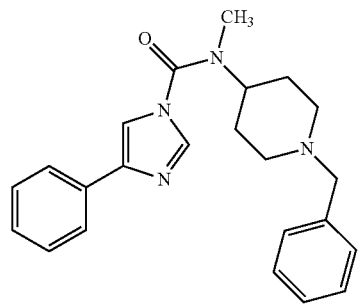 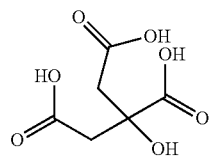 |
| 413 | 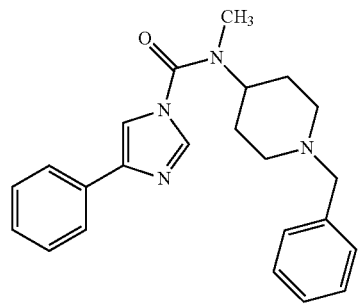 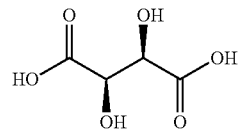 |

-continued
| No. | Structure |
|---|---|
| 414 | 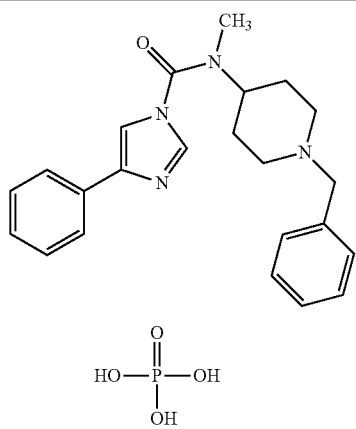 [SMILES: CN(C(=O)n1cnc(-c2ccccc2)c1)C1CCN(Cc2ccccc2)CC1 ; O=P(O)(O)O]<br>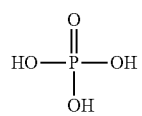 |
| 415 | 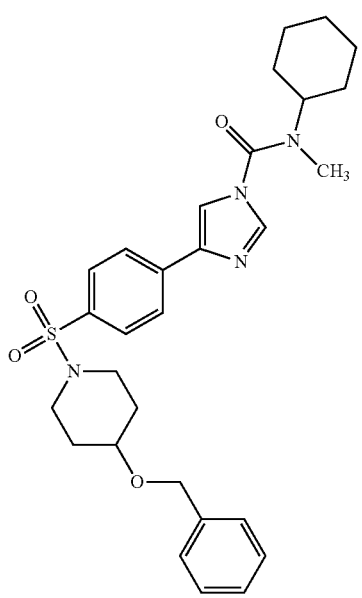 [SMILES: CN(C(=O)n1cnc(-c2ccc(S(=O)(=O)N3CCC(OCc4ccccc4)CC3)cc2)c1)C1CCCCC1] |
| 416 | 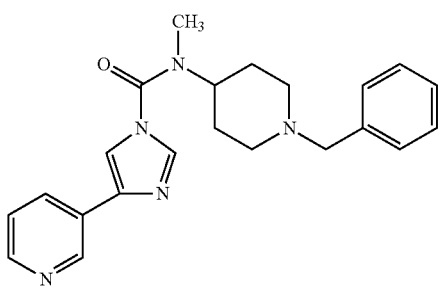 [SMILES: CN(C(=O)n1cnc(-c2cccnc2)c1)C1CCN(Cc2ccccc2)CC1] |
| 417 | 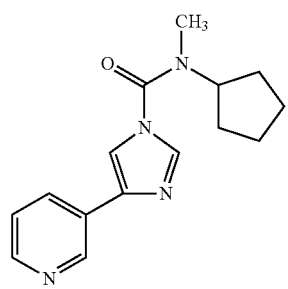 [SMILES: CN(C(=O)n1cnc(-c2cccnc2)c1)C1CCCC1] |

| No. | Structure |
|---|---|
| 418 | 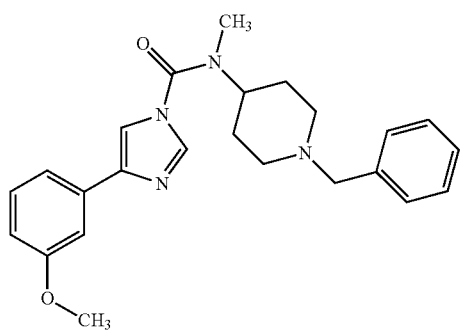 [SMILES: COc1cccc(-c2cn(C(=O)N(C)C3CCN(Cc4ccccc4)CC3)cn2)c1] |
| 419 | 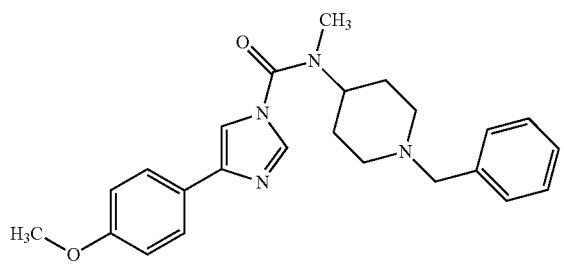 [SMILES: COc1ccc(-c2cn(C(=O)N(C)C3CCN(Cc4ccccc4)CC3)cn2)cc1] |
| 420 | 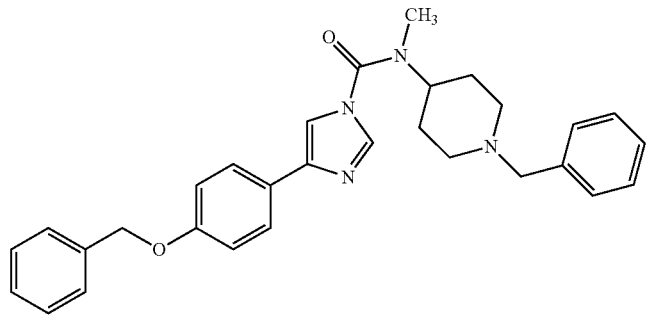 [SMILES: CN(C(=O)n1cnc(-c2ccc(OCc3ccccc3)cc2)c1)C1CCN(Cc2ccccc2)CC1] |
| 421 | 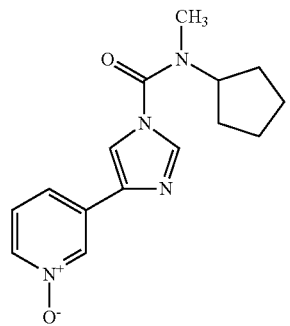 [SMILES: CN(C(=O)n1cnc(-c2ccc[n+]([O-])c2)c1)C1CCCC1] |

-continued
| No. | Structure |
|---|---|
| 422 | 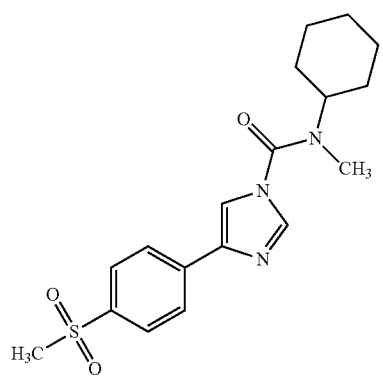 [SMILES: CN(C(=O)n1cnc(-c2ccc(S(C)(=O)=O)cc2)c1)C1CCCCC1] |
| 423 | 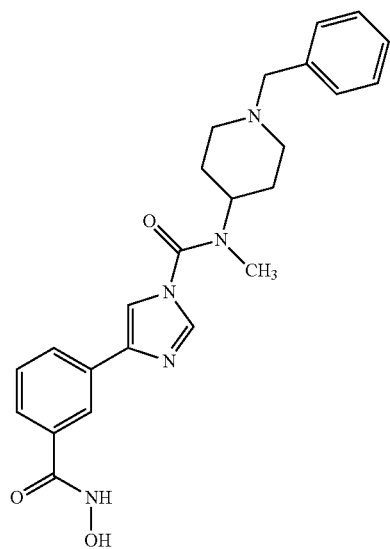 [SMILES: CN(C(=O)n1cnc(-c2cccc(C(=O)NO)c2)c1)C1CCN(Cc2ccccc2)CC1] |
| 424 | 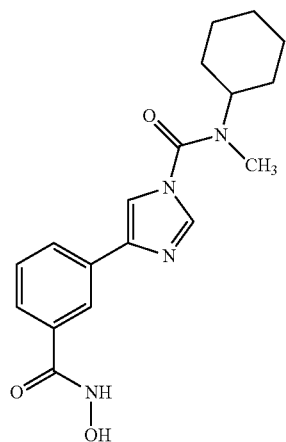 [SMILES: CN(C(=O)n1cnc(-c2cccc(C(=O)NO)c2)c1)C1CCCCC1] |

-continued
| No. | Structure |
|---|---|
| 425 | 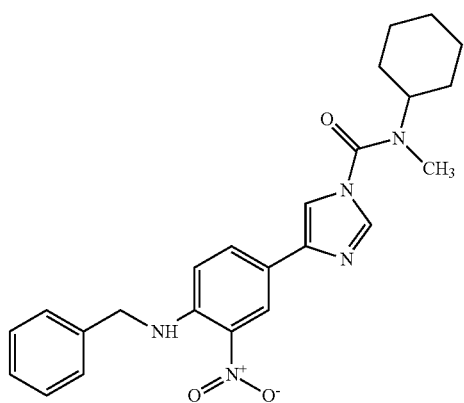 [SMILES: CN(C(=O)n1cnc(-c2ccc(NCc3ccccc3)c([N+](=O)[O-])c2)c1)C1CCCCC1] |
| 426 | 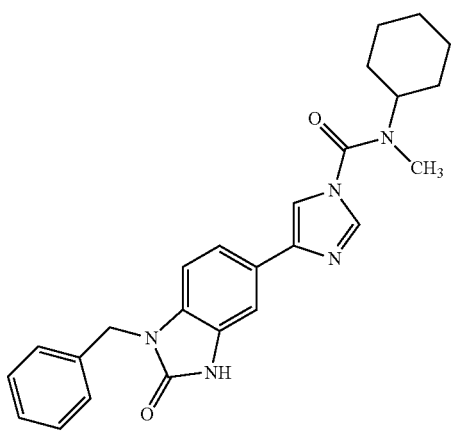 [SMILES: CN(C(=O)n1cnc(-c2ccc3c(c2)[nH]c(=O)n3Cc2ccccc2)c1)C1CCCCC1] |
| 427 | 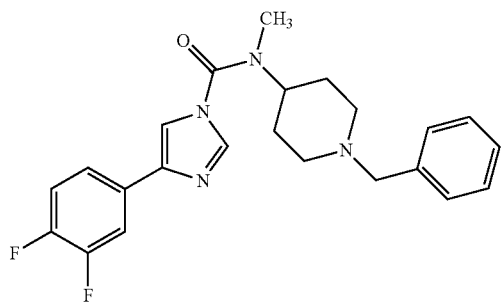 [SMILES: CN(C(=O)n1cnc(-c2ccc(F)c(F)c2)c1)C1CCN(Cc2ccccc2)CC1] |
| 428 | 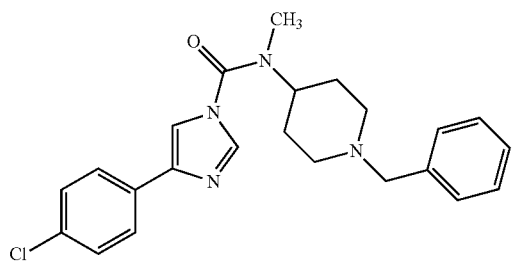 [SMILES: CN(C(=O)n1cnc(-c2ccc(Cl)cc2)c1)C1CCN(Cc2ccccc2)CC1] |

-continued
| No. | Structure |
|---|---|
| 429 | 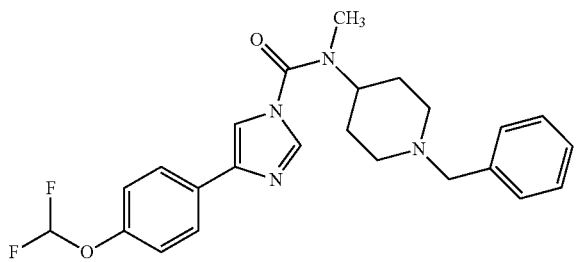 [SMILES: CN(C(=O)n1cnc(-c2ccc(OC(F)F)cc2)c1)C1CCN(Cc2ccccc2)CC1] |
| 430 | 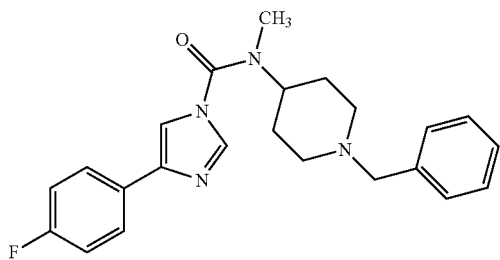 [SMILES: CN(C(=O)n1cnc(-c2ccc(F)cc2)c1)C1CCN(Cc2ccccc2)CC1] |
| 431 | 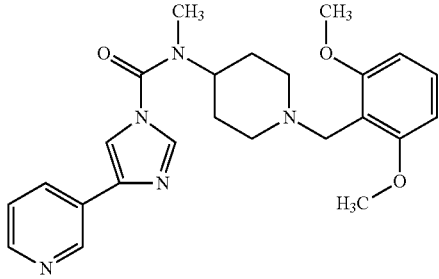 [SMILES: COc1cccc(OC)c1CN1CCC(N(C)C(=O)n2cnc(-c3cccnc3)c2)CC1] |
| 432 | 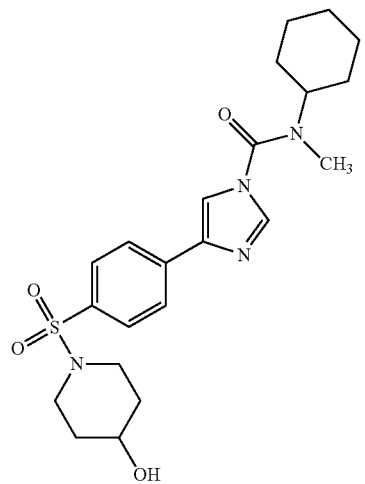 [SMILES: CN(C(=O)n1cnc(-c2ccc(S(=O)(=O)N3CCC(O)CC3)cc2)c1)C1CCCCC1] |

| No. | Structure |
|---|---|
| 433 | 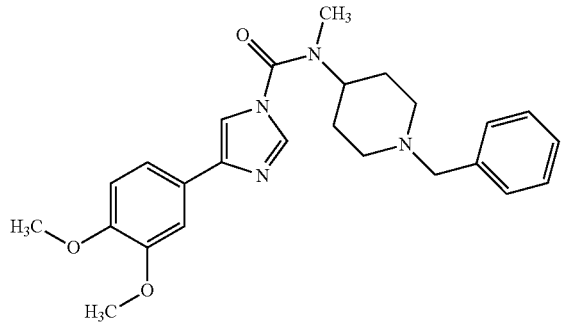 [SMILES: COc1ccc(-c2cn(C(=O)N(C)C3CCN(Cc4ccccc4)CC3)cn2)cc1OC] |
| 434 | 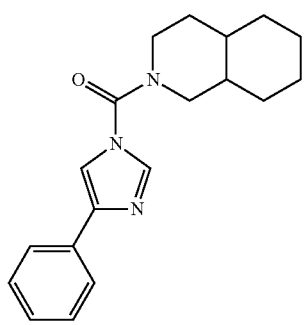 [SMILES: O=C(N1CCC2CCCCC2C1)n1cnc(-c2ccccc2)c1] |
| 435 | 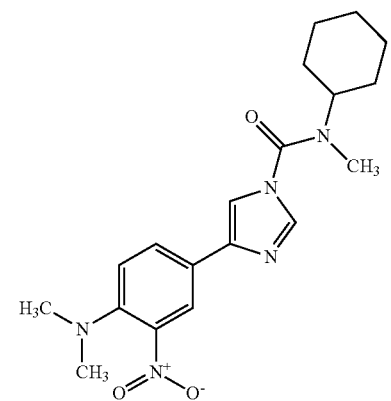 [SMILES: CN(C)c1ccc(-c2cn(C(=O)N(C)C3CCCCC3)cn2)cc1[N+](=O)[O-]] |
| 436 | 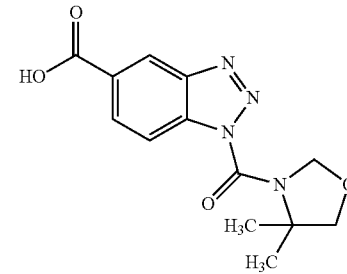 |
| 437 | 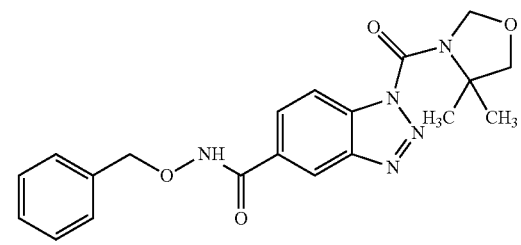 [SMILES: CC1(C)COCN1C(=O)n1nnc2cc(C(=O)NOCc3ccccc3)ccc21] |

| No. | Structure |
|---|---|
| 438 | 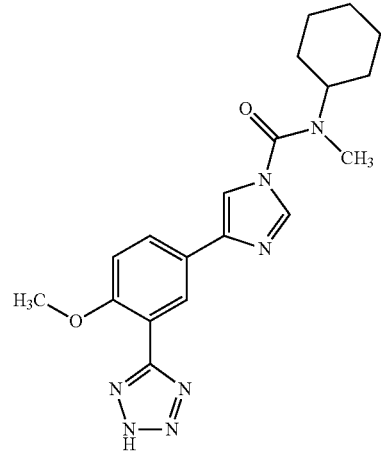 [SMILES: COc1ccc(-c2cn(C(=O)N(C)C3CCCCC3)cn2)cc1-c1nn[nH]n1] |
| 439 | 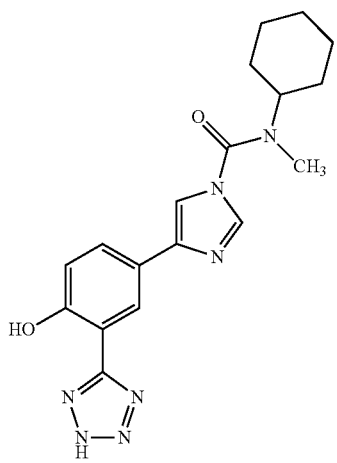 [SMILES: CN(C(=O)n1cnc(-c2ccc(O)c(-c3nn[nH]n3)c2)c1)C1CCCCC1] |
| 440 | 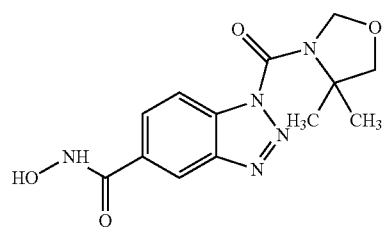 [SMILES: CC1(C)COCN1C(=O)n1nnc2cc(C(=O)NO)ccc21] |
| 441 | 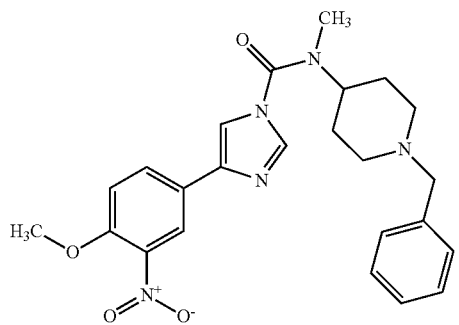 [SMILES: COc1ccc(-c2cn(C(=O)N(C)C3CCN(Cc4ccccc4)CC3)cn2)cc1[N+](=O)[O-]] |

| No. | Structure |
|---|---|
| 442 | 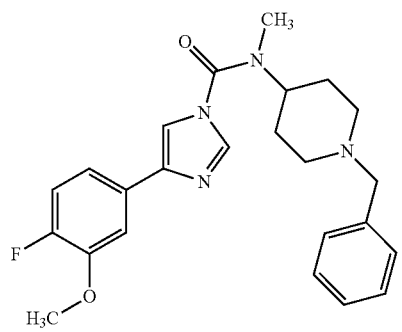 [SMILES: COc1cc(-c2cn(C(=O)N(C)C3CCN(Cc4ccccc4)CC3)cn2)ccc1F] |
| 443 | 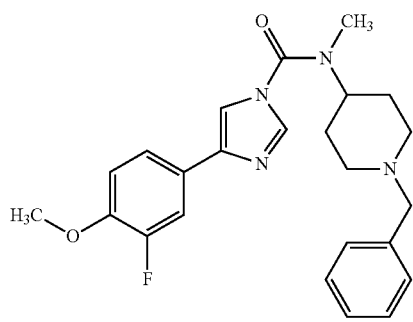 [SMILES: COc1ccc(-c2cn(C(=O)N(C)C3CCN(Cc4ccccc4)CC3)cn2)cc1F] |
| 444 | 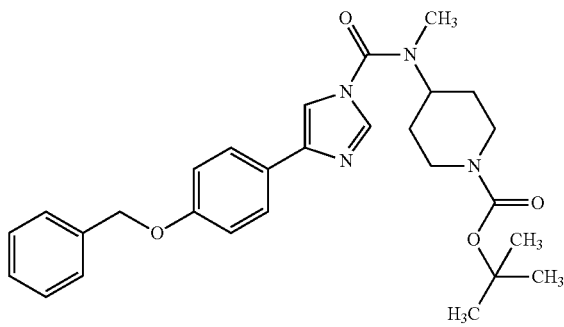 [SMILES: CN(C(=O)n1cnc(-c2ccc(OCc3ccccc3)cc2)c1)C1CCN(C(=O)OC(C)(C)C)CC1] |
| 445 | 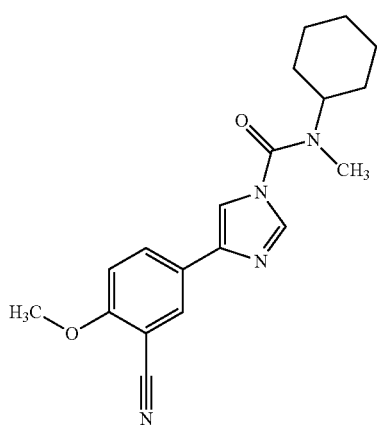 [SMILES: COc1ccc(-c2cn(C(=O)N(C)C3CCCCC3)cn2)cc1C#N] |

| No. | Structure |
|---|---|
| 446 | 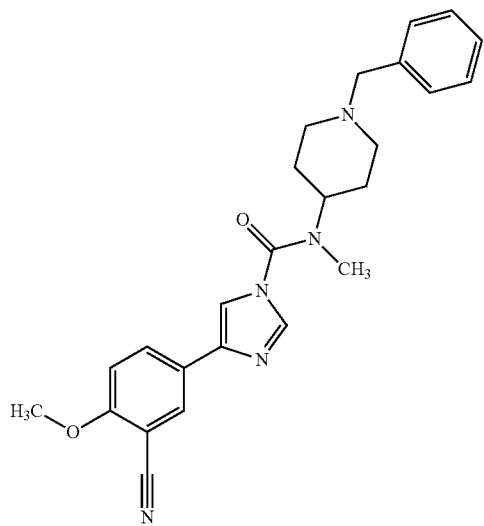 [SMILES: COc1ccc(-c2cn(C(=O)N(C)C3CCN(Cc4ccccc4)CC3)cn2)cc1C#N] |
| 447 | 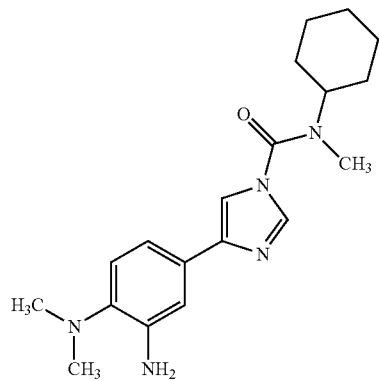 [SMILES: CN(C)c1ccc(-c2cn(C(=O)N(C)C3CCCCC3)cn2)cc1N] |
| 448 | 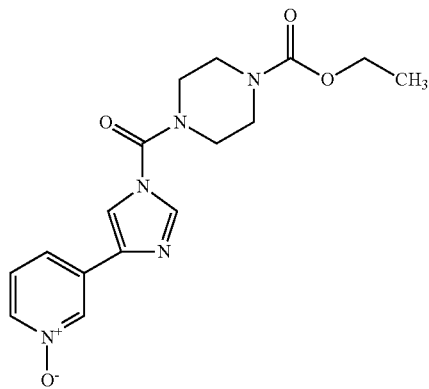 [SMILES: CCOC(=O)N1CCN(C(=O)n2cnc(-c3ccc[n+]([O-])c3)c2)CC1] |

-continued

| No. | Structure |
|---|---|
| 449 | 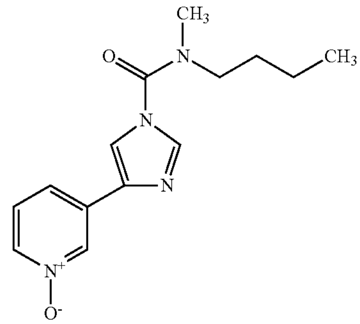 [SMILES: CCCCN(C)C(=O)n1cnc(-c2ccc[n+]([O-])c2)c1] |
| 450 | 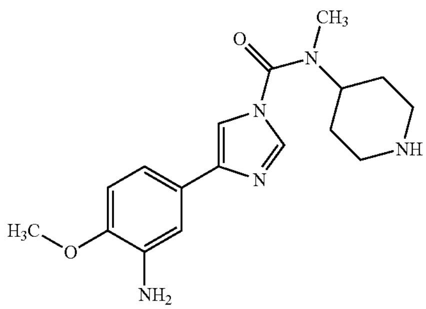 [SMILES: COc1ccc(-c2cn(C(=O)N(C)C3CCNCC3)cn2)cc1N] |
| 451 | 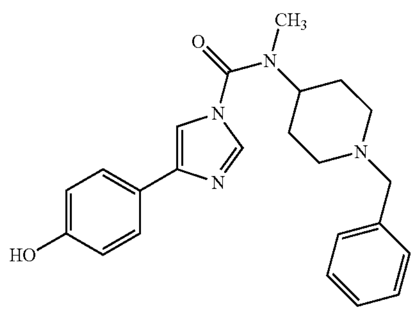 [SMILES: CN(C(=O)n1cnc(-c2ccc(O)cc2)c1)C1CCN(Cc2ccccc2)CC1] |
| 452 | 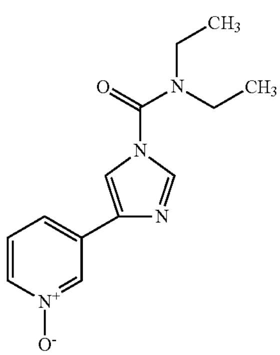 [SMILES: CCN(CC)C(=O)n1cnc(-c2ccc[n+]([O-])c2)c1] |
| 453 | 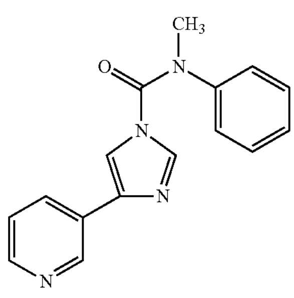 [SMILES: CN(C(=O)n1cnc(-c2cccnc2)c1)c1ccccc1] |

-continued

| No. | Structure |
|---|---|
| 454 | 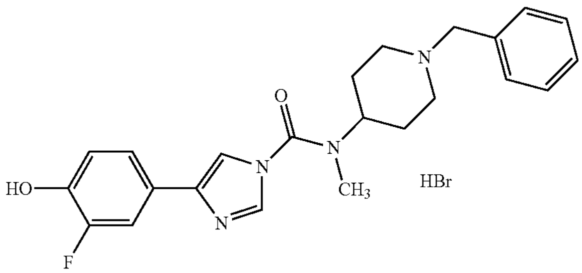 [SMILES: CN(C(=O)n1cnc(-c2ccc(O)c(F)c2)c1)C1CCN(Cc2ccccc2)CC1 ; Br] |
| 455 | 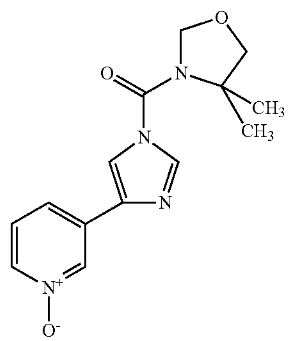 [SMILES: CC1(C)COCN1C(=O)n1cnc(-c2ccc[n+]([O-])c2)c1] |
| 456 | 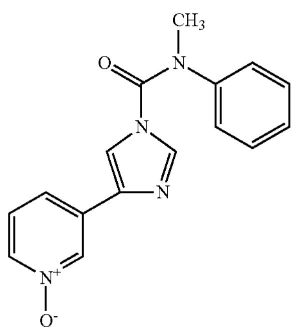 [SMILES: CN(C(=O)n1cnc(-c2ccc[n+]([O-])c2)c1)c1ccccc1] |
| 457 | 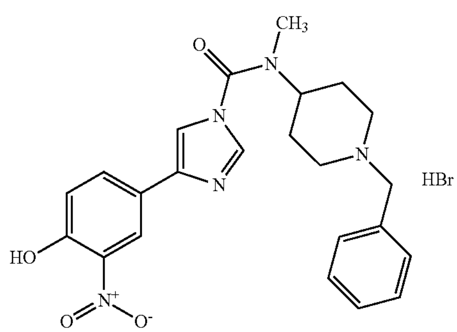 [SMILES: CN(C(=O)n1cnc(-c2ccc(O)c([N+](=O)[O-])c2)c1)C1CCN(Cc2ccccc2)CC1 ; Br] |
| 458 | 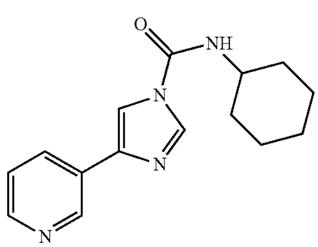 [SMILES: O=C(NC1CCCCC1)n1cnc(-c2cccnc2)c1] |

-continued

| No. | Structure |
|---|---|
| 459 | 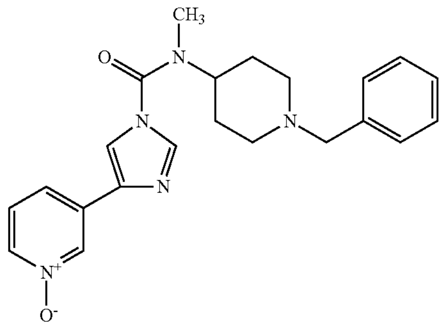 [SMILES: CN(C(=O)n1cnc(-c2ccc[n+]([O-])c2)c1)C1CCN(Cc2ccccc2)CC1] |
| 460 | 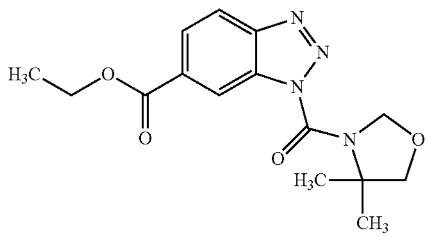 [SMILES: CCOC(=O)c1ccc2nnn(C(=O)N3COCC3(C)C)c2c1] |
| 461 | 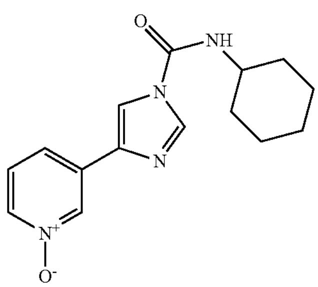 [SMILES: O=C(NC1CCCCC1)n1cnc(-c2ccc[n+]([O-])c2)c1] |
| 462 | 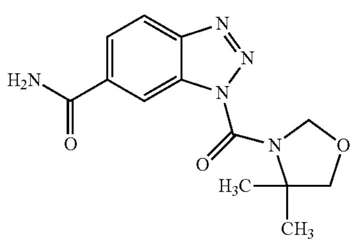 [SMILES: CC1(C)COCN1C(=O)n1nnc2ccc(C(N)=O)cc21] |
| 463 | 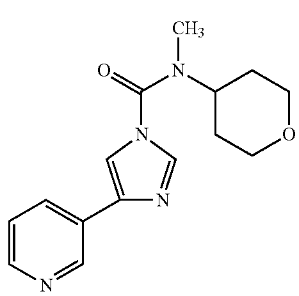 [SMILES: CN(C(=O)n1cnc(-c2cccnc2)c1)C1CCOCC1] |

US 9,353,082 B2
277
-continued
| No. | Structure |
|---|---|
| 464 | 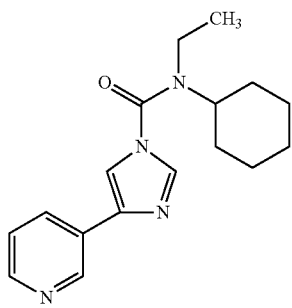 [SMILES: CCN(C(=O)n1cnc(-c2cccnc2)c1)C1CCCCC1] |
| 465 | 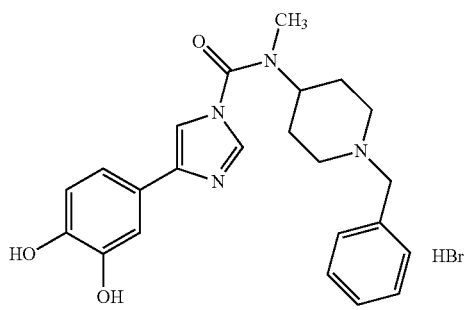 [SMILES: CN(C(=O)n1cnc(-c2ccc(O)c(O)c2)c1)C1CCN(Cc2ccccc2)CC1 ; Br] |
| 466 | 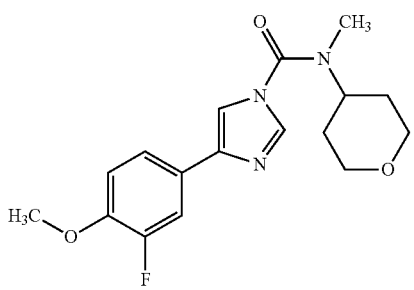 [SMILES: COc1ccc(-c2cn(C(=O)N(C)C3CCOCC3)cn2)cc1F] |
| 467 | 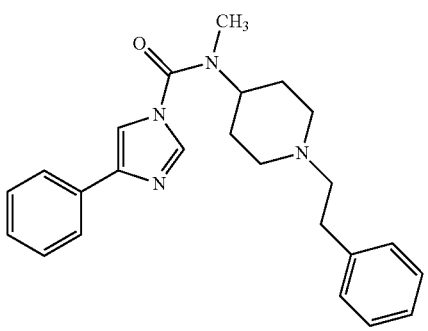 [SMILES: CN(C(=O)n1cnc(-c2ccccc2)c1)C1CCN(CCc2ccccc2)CC1] |
| 468 | 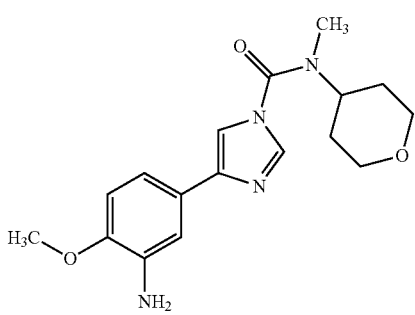 [SMILES: COc1ccc(-c2cn(C(=O)N(C)C3CCOCC3)cn2)cc1N] |
278

| No. | Structure |
|-----|-----------|
| 469 | 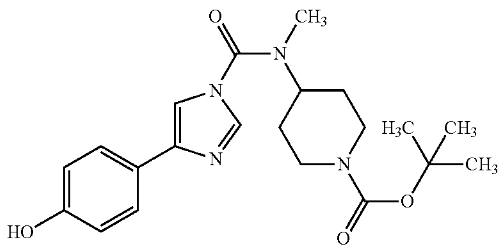 [SMILES: CN(C(=O)n1cnc(-c2ccc(O)cc2)c1)C1CCN(C(=O)OC(C)(C)C)CC1] |
| 470 | 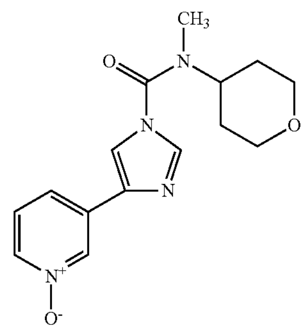 [SMILES: CN(C(=O)n1cnc(-c2ccc[n+]([O-])c2)c1)C1CCOCC1] |
| 471 | 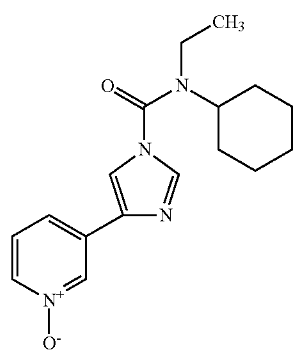 [SMILES: CCN(C(=O)n1cnc(-c2ccc[n+]([O-])c2)c1)C1CCCCC1] |
| 472 | 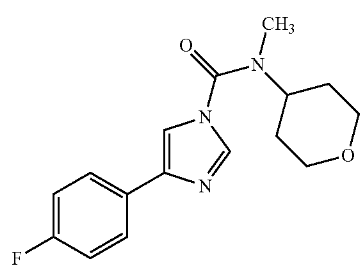 [SMILES: CN(C(=O)n1cnc(-c2ccc(F)cc2)c1)C1CCOCC1] |
| 473 | 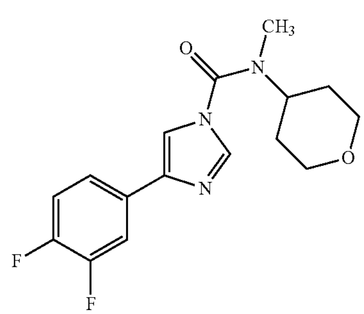 [SMILES: CN(C(=O)n1cnc(-c2ccc(F)c(F)c2)c1)C1CCOCC1] |

-continued
| No. | Structure |
|---|---|
| 474 | 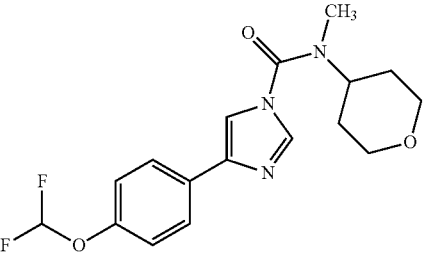 [SMILES: CN(C(=O)n1cnc(-c2ccc(OC(F)F)cc2)c1)C1CCOCC1] |
| 475 | 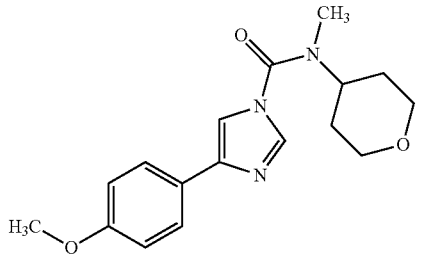 [SMILES: COc1ccc(-c2cn(C(=O)N(C)C3CCOCC3)cn2)cc1] |
| 476 | 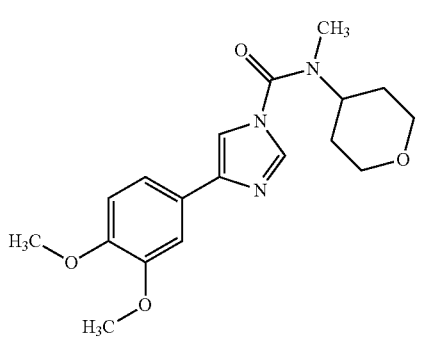 [SMILES: COc1ccc(-c2cn(C(=O)N(C)C3CCOCC3)cn2)cc1OC] |
| 477 | 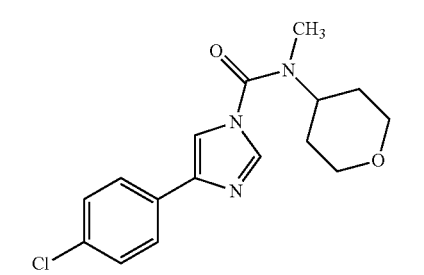 [SMILES: CN(C(=O)n1cnc(-c2ccc(Cl)cc2)c1)C1CCOCC1] |
| 478 | 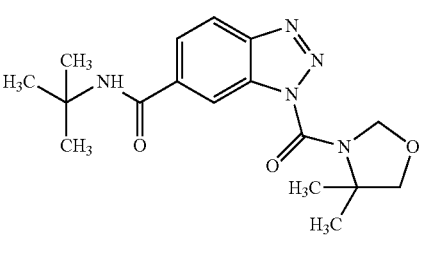 [SMILES: CC(C)(C)NC(=O)c1ccc2nnn(C(=O)N3COCC3(C)C)c2c1] |
| 479 | 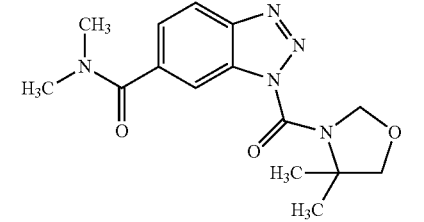 [SMILES: CN(C)C(=O)c1ccc2nnn(C(=O)N3COCC3(C)C)c2c1] |

| No. | Structure |
|---|---|
| 480 | 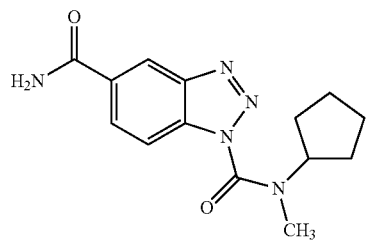 [SMILES: CN(C(=O)n1nnc2cc(C(N)=O)ccc21)C1CCCC1] |
| 481 | 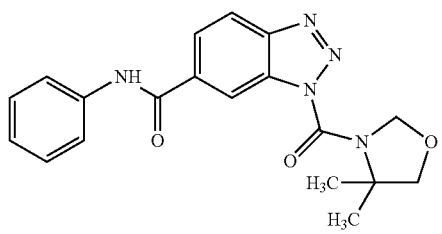 [SMILES: CC1(C)COCN1C(=O)n1nnc2ccc(C(=O)Nc3ccccc3)cc21] |
| 482 | 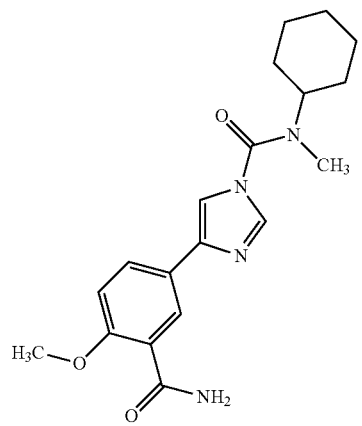 [SMILES: COc1ccc(-c2cn(C(=O)N(C)C3CCCCC3)cn2)cc1C(N)=O] |
| 483 | 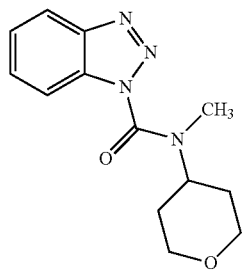 [SMILES: CN(C(=O)n1nnc2ccccc21)C1CCOCC1] |
| 484 | 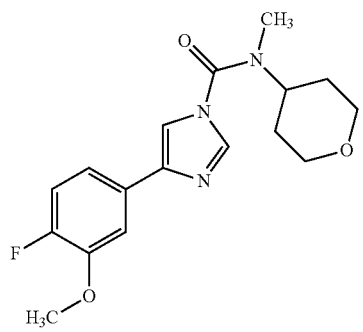 |

-continued
| No. | Structure |
|---|---|
| 485 | 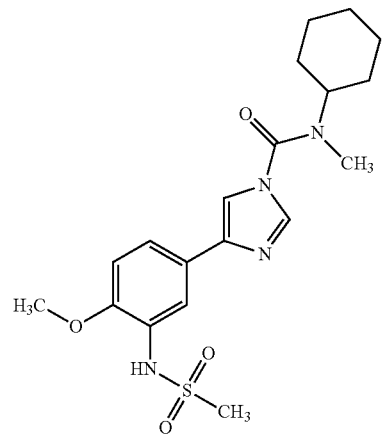 [SMILES: COc1ccc(-c2cn(C(=O)N(C)C3CCCCC3)cn2)cc1NS(C)(=O)=O] |
| 486 | 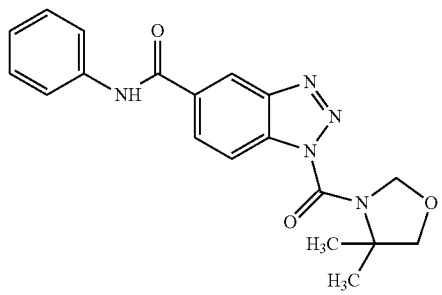 [SMILES: CC1(C)COCN1C(=O)n1nnc2cc(C(=O)Nc3ccccc3)ccc21] |
| 487 | 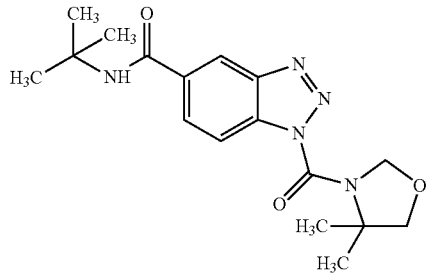 [SMILES: CC(C)(C)NC(=O)c1ccc2c(c1)nnn2C(=O)N1COCC1(C)C] |
| 488 | 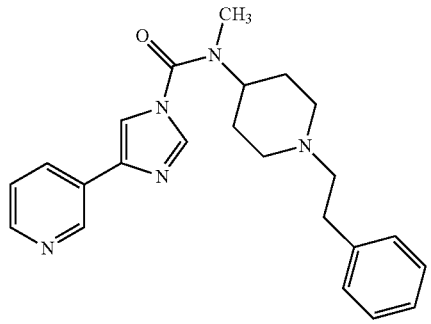 [SMILES: CN(C(=O)n1cnc(-c2cccnc2)c1)C1CCN(CCc2ccccc2)CC1] |

287 288
-continued
| No. | Structure |
|---|---|
| 489 | 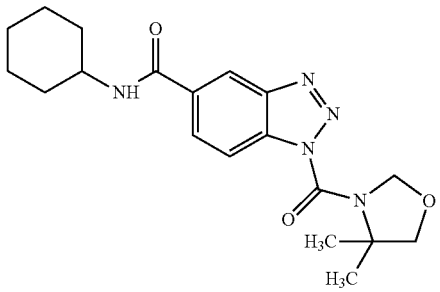 [SMILES: CC1(C)COCN1C(=O)n1nnc2cc(C(=O)NC3CCCCC3)ccc21] |
| 490 | 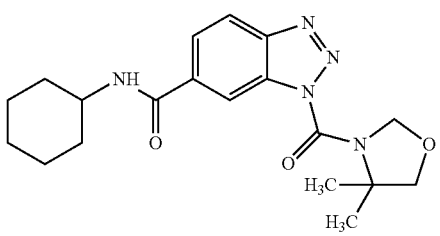 [SMILES: CC1(C)COCN1C(=O)n1nnc2ccc(C(=O)NC3CCCCC3)cc21] |
| 491 | 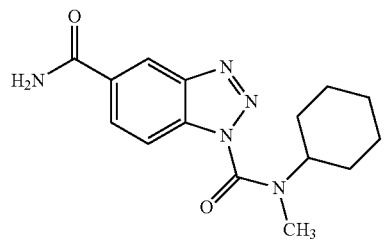 [SMILES: CN(C(=O)n1nnc2cc(C(N)=O)ccc21)C1CCCCC1] |
| 492 | 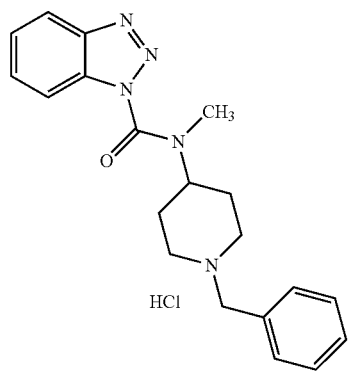 [SMILES: CN(C(=O)n1nnc2ccccc21)C1CCN(Cc2ccccc2)CC1 ; Cl] |
| 493 | 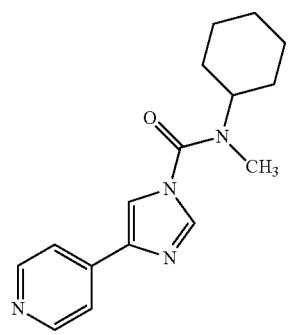 [SMILES: CN(C(=O)n1cnc(-c2ccncc2)c1)C1CCCCC1] |

| No. | Structure |
|---|---|
| 494 | 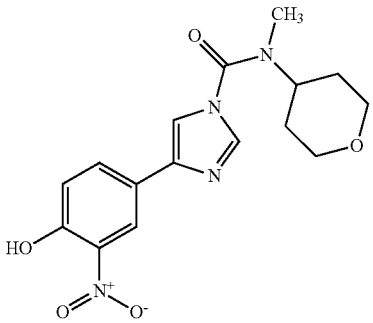 [SMILES: CN(C(=O)n1cnc(-c2ccc(O)c([N+](=O)[O-])c2)c1)C1CCOCC1] |
| 495 | 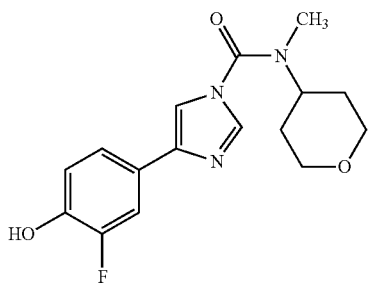 [SMILES: CN(C(=O)n1cnc(-c2ccc(O)c(F)c2)c1)C1CCOCC1] |
| 496 | 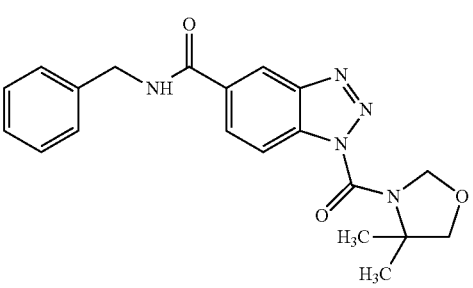 [SMILES: CC1(C)COCN1C(=O)n1nnc2cc(C(=O)NCc3ccccc3)ccc21] |
| 497 | 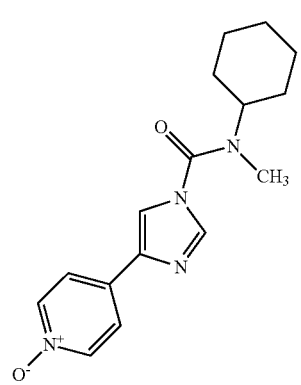 [SMILES: CN(C(=O)n1cnc(-c2cc[n+]([O-])cc2)c1)C1CCCCC1] |
| 498 | 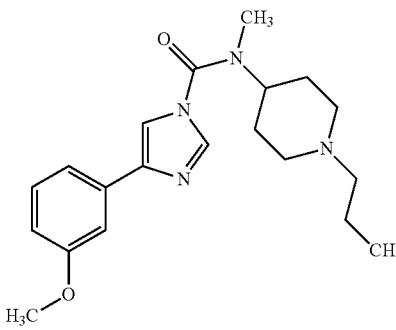 |

-continued
| No. | Structure |
|---|---|
| 499 | 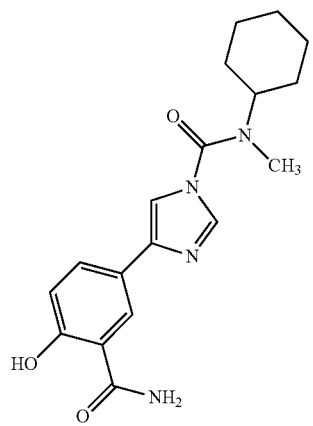 [SMILES: CN(C(=O)n1cnc(-c2ccc(O)c(C(N)=O)c2)c1)C1CCCCC1] |
| 500 | 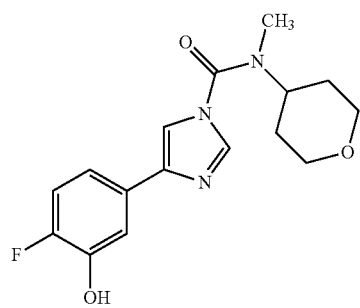 [SMILES: CN(C(=O)n1cnc(-c2ccc(F)c(O)c2)c1)C1CCOCC1] |
| 501 | 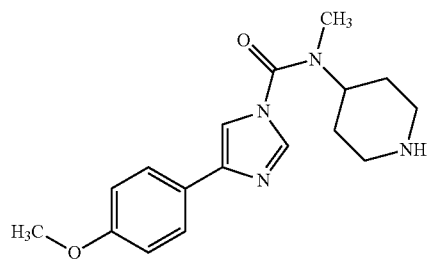 [SMILES: COc1ccc(-c2cn(C(=O)N(C)C3CCNCC3)cn2)cc1] |
| 502 | 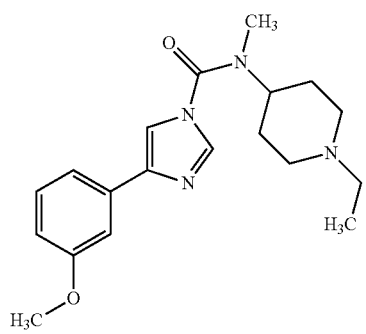 [SMILES: CCN1CCC(N(C)C(=O)n2cnc(-c3cccc(OC)c3)c2)CC1] |

-continued
| No. | Structure |
|---|---|
| 503 | 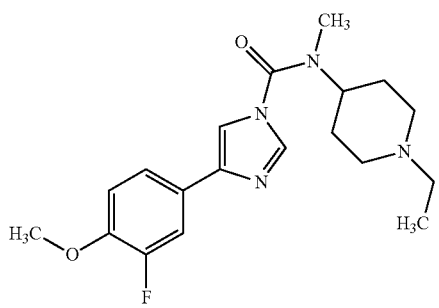 [SMILES: CCN1CCC(N(C)C(=O)n2cnc(-c3ccc(OC)c(F)c3)c2)CC1] |
| 504 | 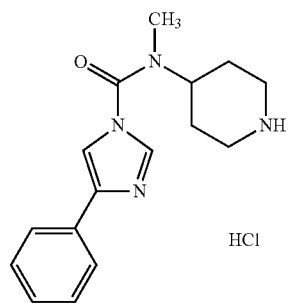 [SMILES: CN(C(=O)n1cnc(-c2ccccc2)c1)C1CCNCC1 ; Cl] |
| 505 | 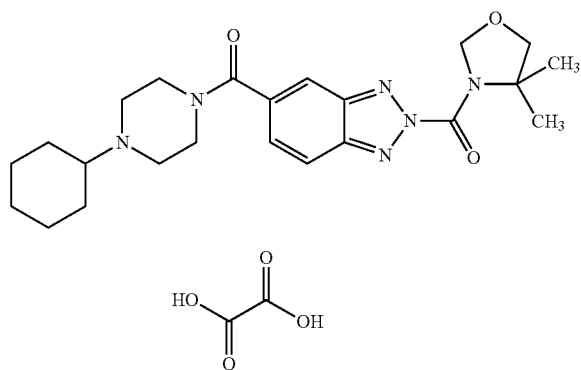 [SMILES: CC1(C)COCN1C(=O)n1nc2ccc(C(=O)N3CCN(C4CCCCC4)CC3)cc2n1 ; O=C(O)C(=O)O] |
| 506 | 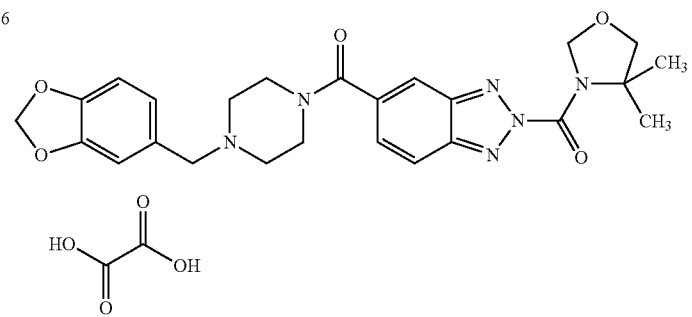 |

-continued
| No. | Structure |
|---|---|
| 507 | 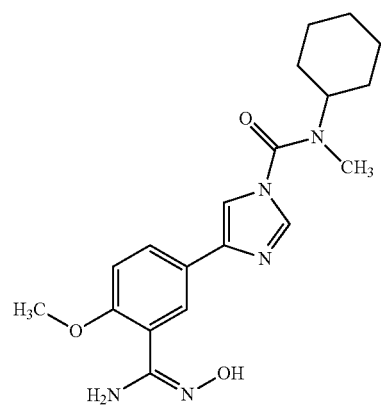 [SMILES: COc1ccc(-c2cn(C(=O)N(C)C3CCCCC3)cn2)cc1/C(N)=N\O] |
| 508 | 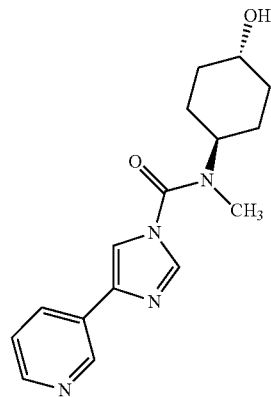 [SMILES: CN(C(=O)n1cnc(-c2cccnc2)c1)[C@H]1CC[C@H](O)CC1] |
| 509 | 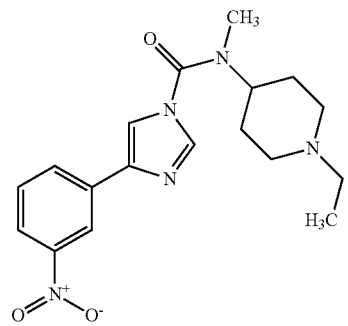 [SMILES: CCN1CCC(N(C)C(=O)n2cnc(-c3cccc([N+](=O)[O-])c3)c2)CC1] |
| 510 | 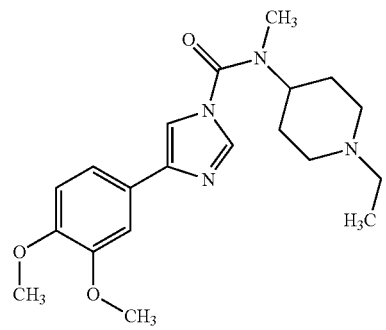 [SMILES: CCN1CCC(N(C)C(=O)n2cnc(-c3ccc(OC)c(OC)c3)c2)CC1] |

-continued
| No. | Structure |
|---|---|
| 511 | 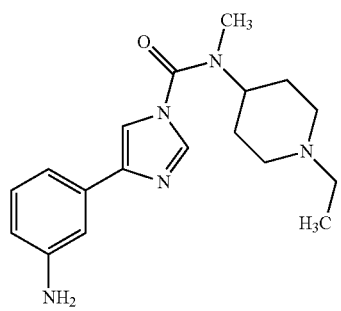 [SMILES: CCN1CCC(N(C)C(=O)n2cnc(-c3cccc(N)c3)c2)CC1] |
| 512 | 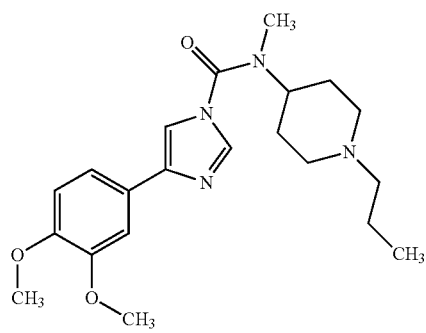 [SMILES: CCCN1CCC(N(C)C(=O)n2cnc(-c3ccc(OC)c(OC)c3)c2)CC1] |
| 513 | 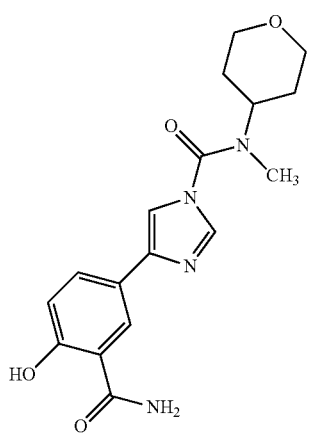 [SMILES: CN(C(=O)n1cnc(-c2ccc(O)c(C(N)=O)c2)c1)C1CCOCC1] |
| 514 | 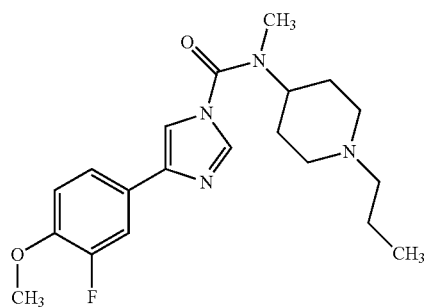 [SMILES: CCCN1CCC(N(C)C(=O)n2cnc(-c3ccc(OC)c(F)c3)c2)CC1] |

| No. | Structure |
|-----|-----------|
| 515 | 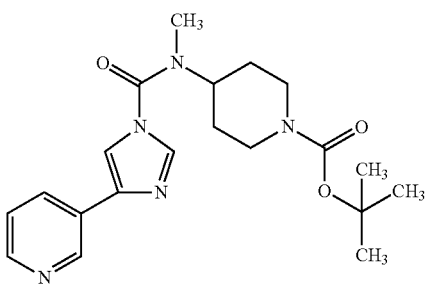 [SMILES: CN(C(=O)n1cnc(-c2cccnc2)c1)C1CCN(C(=O)OC(C)(C)C)CC1] |
| 516 | 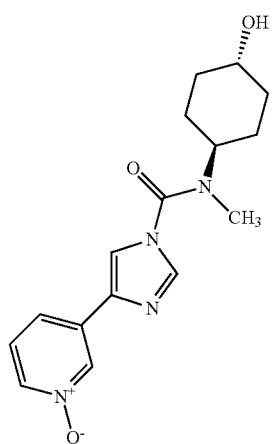 [SMILES: CN(C(=O)n1cnc(-c2ccc[n+]([O-])c2)c1)[C@H]1CC[C@H](O)CC1] |
| 517 | 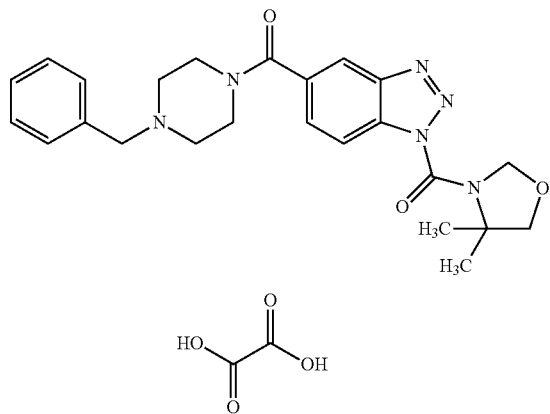 [SMILES: CC1(C)COCN1C(=O)n1nnc2cc(C(=O)N3CCN(Cc4ccccc4)CC3)ccc21 ; O=C(O)C(=O)O] |
| 518 | 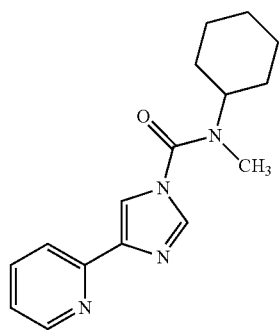 [SMILES: CN(C(=O)n1cnc(-c2ccccn2)c1)C1CCCCC1] |

-continued
| No. | Structure |
|---|---|
| 519 | 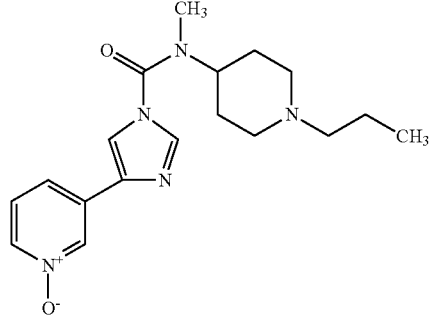 [SMILES: CCCN1CCC(N(C)C(=O)n2cnc(-c3ccc[n+]([O-])c3)c2)CC1] |
| 520 | 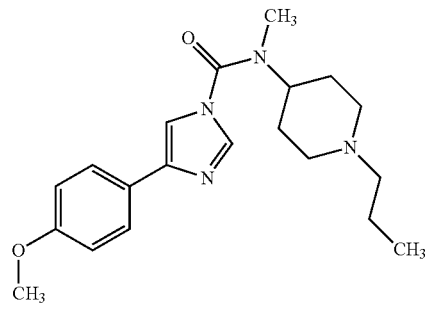 [SMILES: CCCN1CCC(N(C)C(=O)n2cnc(-c3ccc(OC)cc3)c2)CC1] |
| 521 | 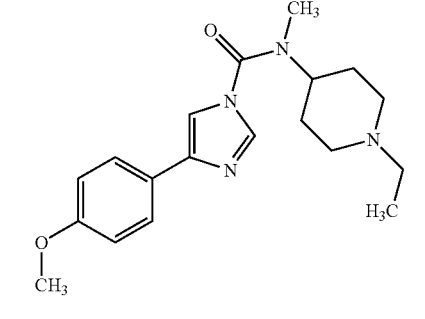 [SMILES: CCN1CCC(N(C)C(=O)n2cnc(-c3ccc(OC)cc3)c2)CC1] |
| 522 | 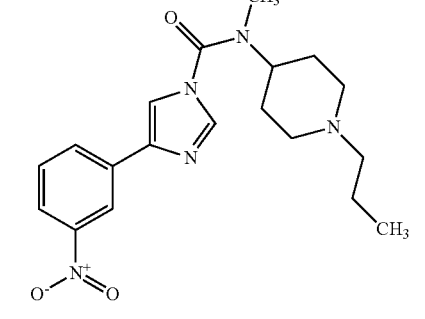 |
| 523 | 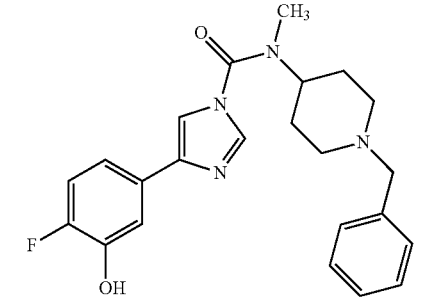 [SMILES: CN(C(=O)n1cnc(-c2ccc(F)c(O)c2)c1)C1CCN(Cc2ccccc2)CC1] |

-continued

| No. | Structure |
|---|---|
| 524 | 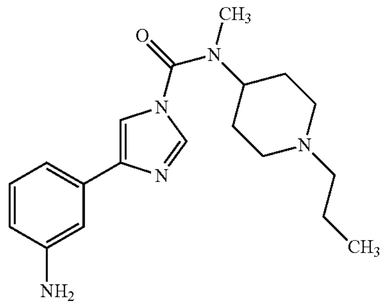 [SMILES: CCCN1CCC(N(C)C(=O)n2cnc(-c3cccc(N)c3)c2)CC1] |
| 525 | 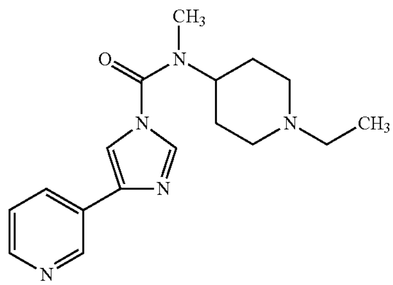 [SMILES: CCN1CCC(N(C)C(=O)n2cnc(-c3cccnc3)c2)CC1] |
| 526 | 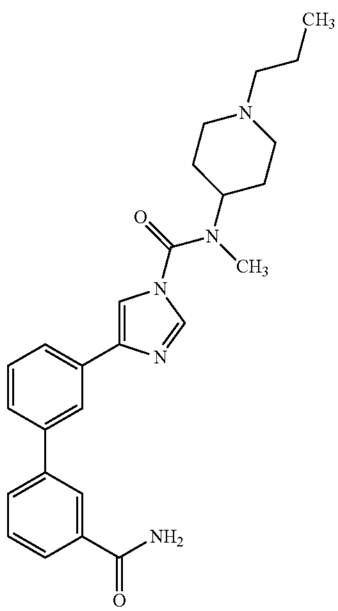 [SMILES: CCCN1CCC(N(C)C(=O)n2cnc(-c3cccc(-c4cccc(C(N)=O)c4)c3)c2)CC1] |
| 527 | 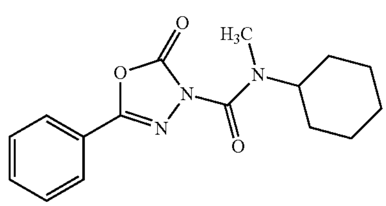 [SMILES: CN(C(=O)n1nc(-c2ccccc2)oc1=O)C1CCCCC1] |
| 528 | 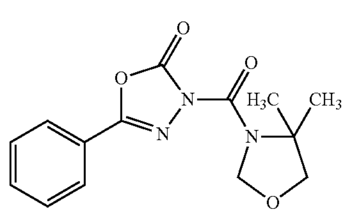 [SMILES: CC1(C)COCN1C(=O)n1nc(-c2ccccc2)oc1=O] |

-continued

| No. | Structure |
|---|---|
| 529 | 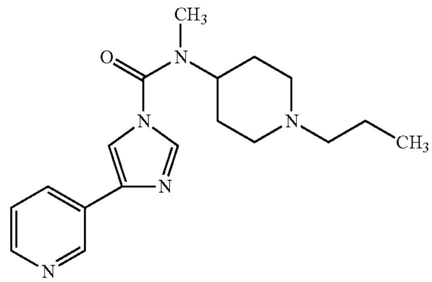 [SMILES: CCCN1CCC(N(C)C(=O)n2cnc(-c3cccnc3)c2)CC1] |
| 530 | 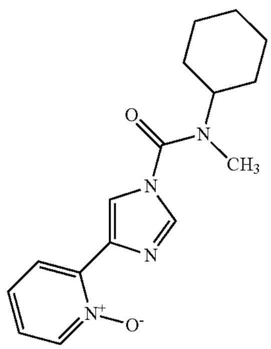 [SMILES: CN(C(=O)n1cnc(-c2cccc[n+]2[O-])c1)C1CCCCC1] |
| 531 | 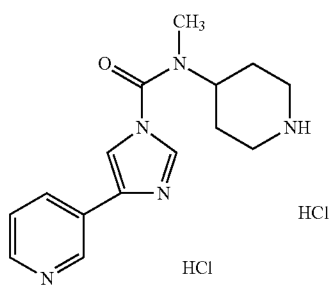 [SMILES: CN(C(=O)n1cnc(-c2cccnc2)c1)C1CCNCC1 ; Cl ; Cl] |
| 532 | 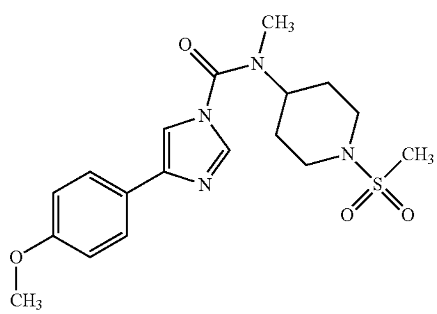 [SMILES: COc1ccc(-c2cn(C(=O)N(C)C3CCN(S(C)(=O)=O)CC3)cn2)cc1] |
| 533 | 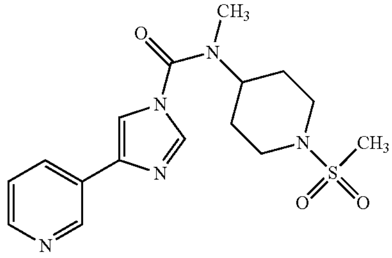 [SMILES: CN(C(=O)n1cnc(-c2cccnc2)c1)C1CCN(S(C)(=O)=O)CC1] |

-continued
| No. | Structure |
|---|---|
| 534 | 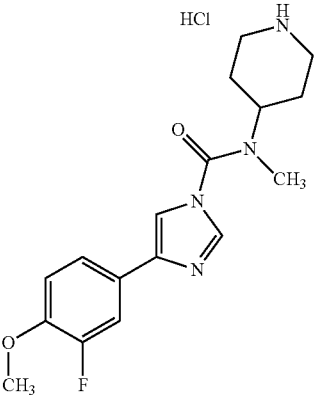 [SMILES: Cl ; COc1ccc(-c2cn(C(=O)N(C)C3CCNCC3)cn2)cc1F] |
| 535 | 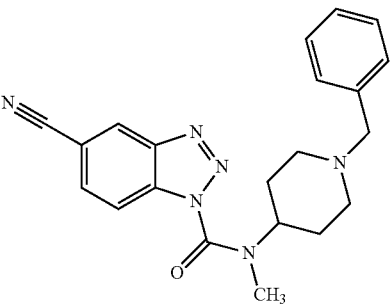 [SMILES: CN(C(=O)n1nnc2cc(C#N)ccc21)C1CCN(Cc2ccccc2)CC1] |
| 536 | 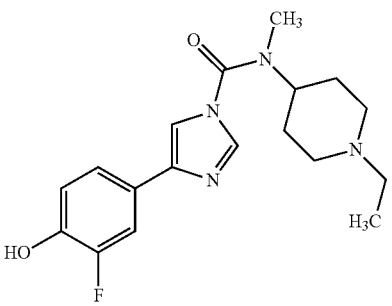 [SMILES: CCN1CCC(N(C)C(=O)n2cnc(-c3ccc(O)c(F)c3)c2)CC1] |
| 537 | 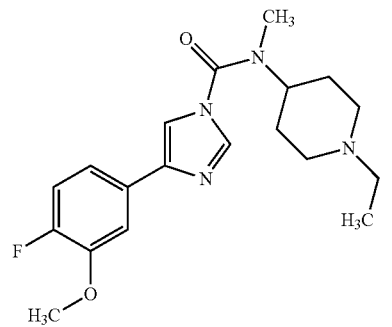 [SMILES: CCN1CCC(N(C)C(=O)n2cnc(-c3ccc(F)c(OC)c3)c2)CC1] |
| 538 | 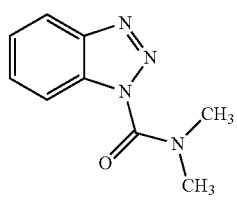 |

-continued
| No. | Structure |
|---|---|
| 539 | 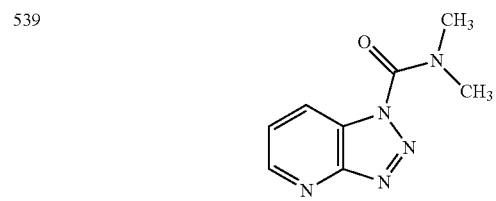 |
| 540 | 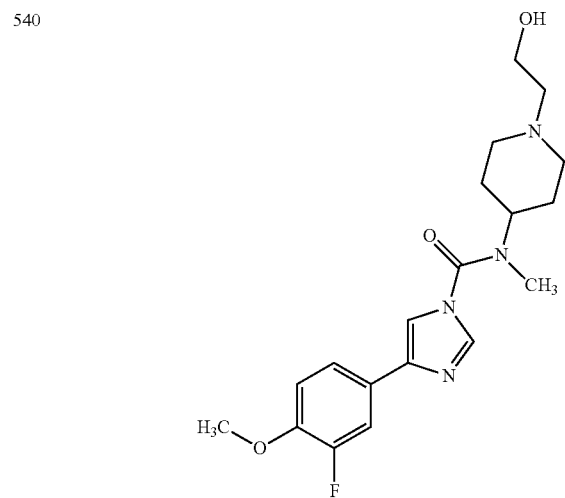 |
| 541 | 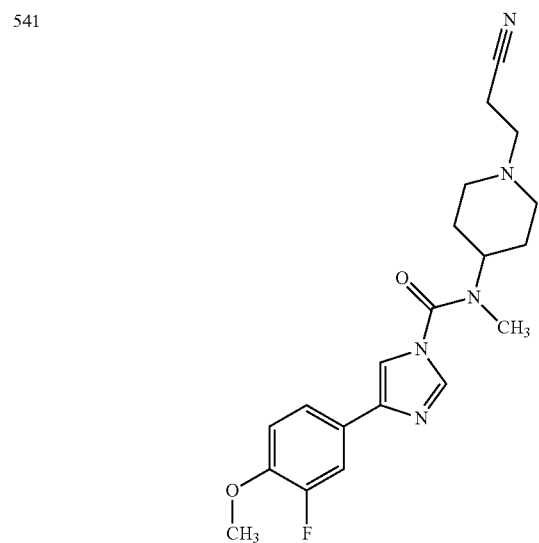 |
| 542 | 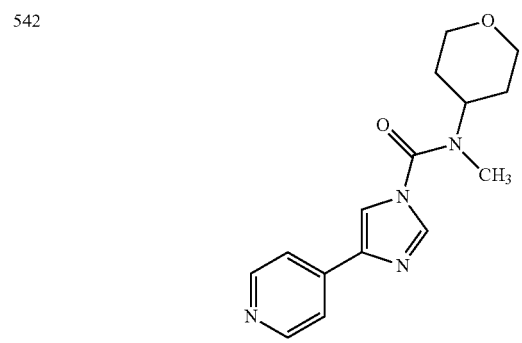 |

-continued
| No. | Structure |
|---|---|
| 543 | 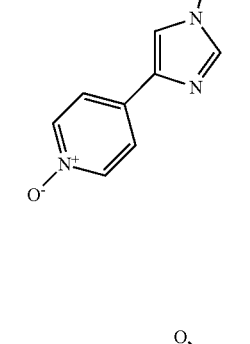 |
| 544 | 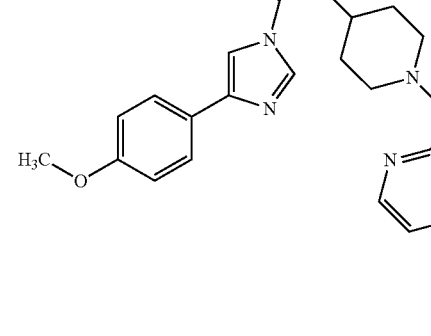 |
| 545 | 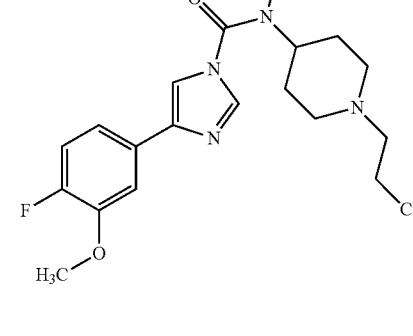 |
| 546 | 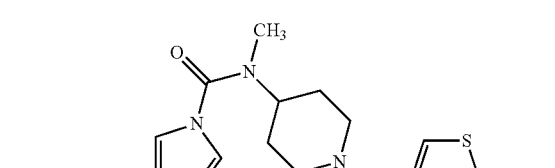 |

| No. | Structure |
|---|---|
| 547 | 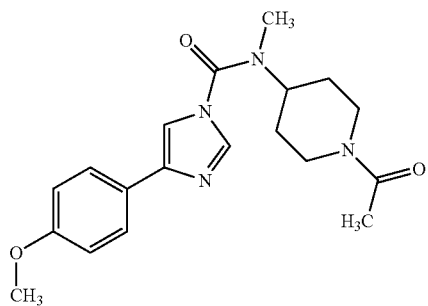 [SMILES: COc1ccc(-c2cn(C(=O)N(C)C3CCN(C(C)=O)CC3)cn2)cc1] |
| 548 | 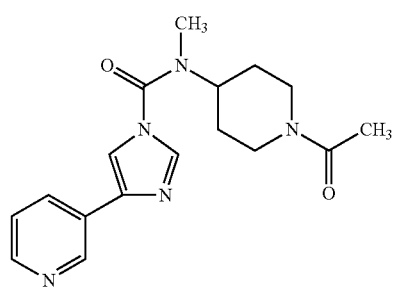 [SMILES: CC(=O)N1CCC(N(C)C(=O)n2cnc(-c3cccnc3)c2)CC1] |
| 549 | 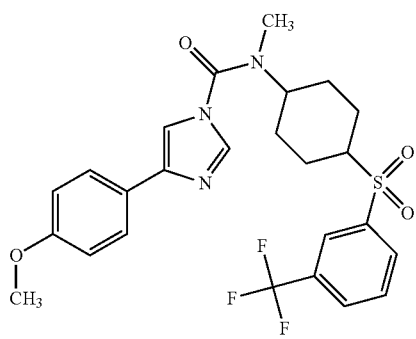 [SMILES: COc1ccc(-c2cn(C(=O)N(C)C3CCC(S(=O)(=O)c4cccc(C(F)(F)F)c4)CC3)cn2)cc1] |
| 550 | 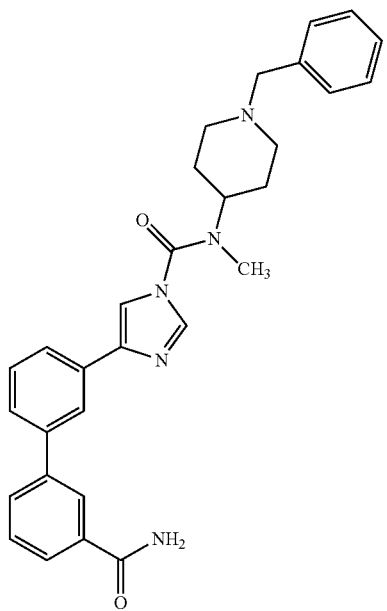 [SMILES: CN(C(=O)n1cnc(-c2cccc(-c3cccc(C(N)=O)c3)c2)c1)C1CCN(Cc2ccccc2)CC1] |

| No. | Structure |
|---|---|
| 551 | 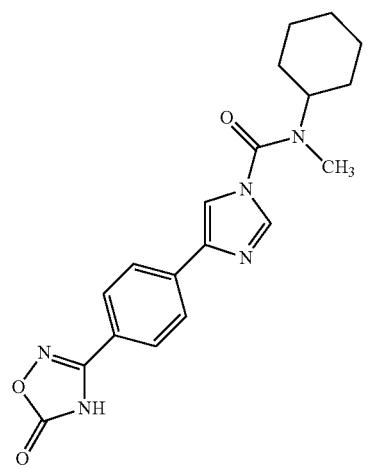 [SMILES: CN(C(=O)n1cnc(-c2ccc(-c3noc(=O)[nH]3)cc2)c1)C1CCCCC1] |
| 552 | 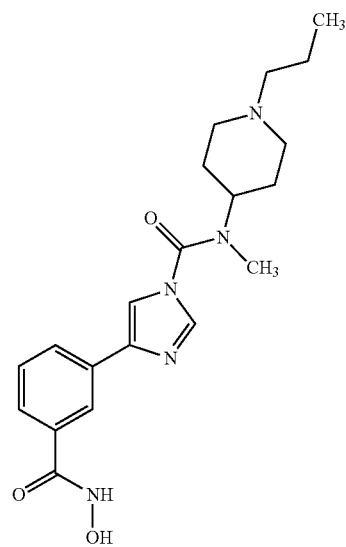 [SMILES: CCCN1CCC(N(C)C(=O)n2cnc(-c3cccc(C(=O)NO)c3)c2)CC1] |
| 553 | 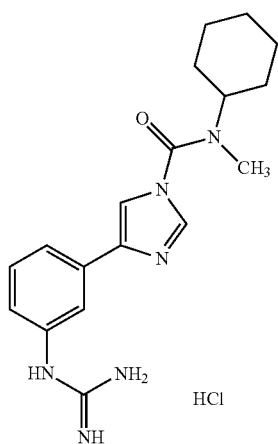 [SMILES: CN(C(=O)n1cnc(-c2cccc(NC(=N)N)c2)c1)C1CCCCC1 ; Cl] |

-continued
| No. | Structure |
|---|---|
| 554 | 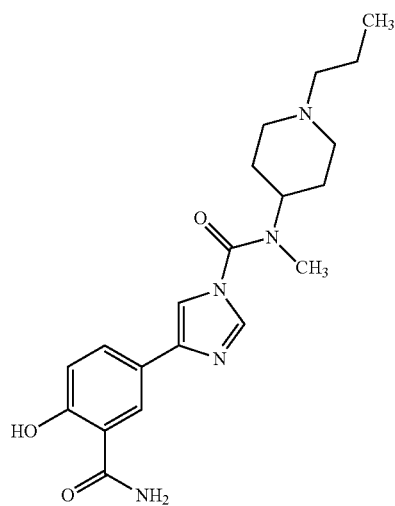 [SMILES: CCCN1CCC(N(C)C(=O)n2cnc(-c3ccc(O)c(C(N)=O)c3)c2)CC1] |
| 555 | 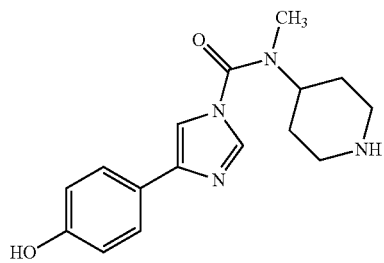\nHBr |
| 556 | 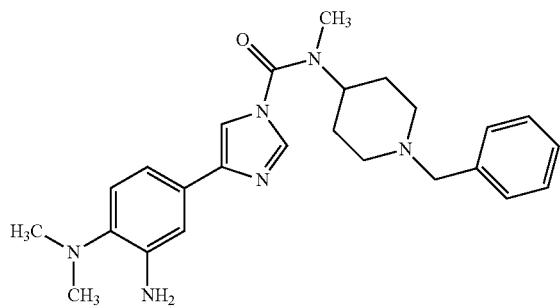 [SMILES: CN(C)c1ccc(-c2cn(C(=O)N(C)C3CCN(Cc4ccccc4)CC3)cn2)cc1N] |
| 557 | 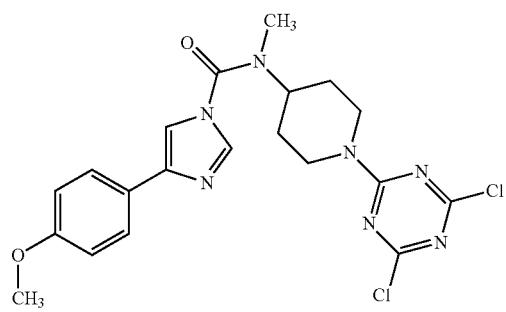 [SMILES: COc1ccc(-c2cn(C(=O)N(C)C3CCN(c4nc(Cl)nc(Cl)n4)CC3)cn2)cc1] |

| No. | Structure |
|---|---|
| 558 | 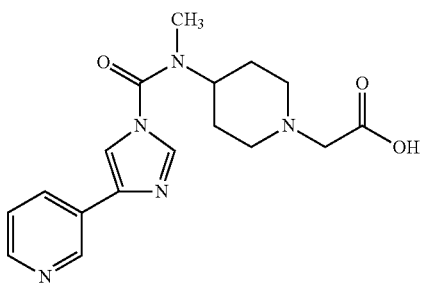 [SMILES: CN(C(=O)n1cnc(-c2cccnc2)c1)C1CCN(CC(=O)O)CC1] |
| 559 | 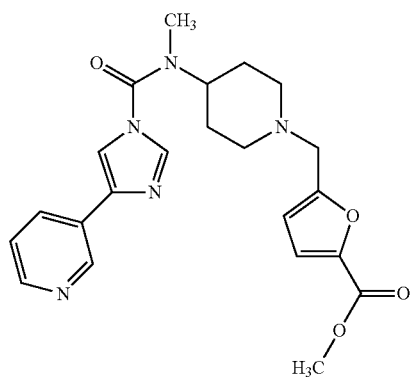 [SMILES: COC(=O)c1ccc(CN2CCC(N(C)C(=O)n3cnc(-c4cccnc4)c3)CC2)o1] |
| 560 | 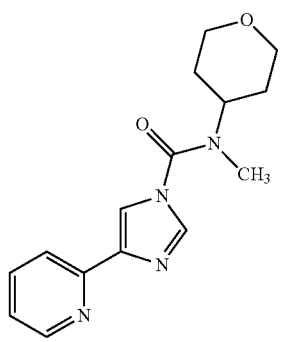 [SMILES: CN(C(=O)n1cnc(-c2ccccn2)c1)C1CCOCC1] |
| 561 | 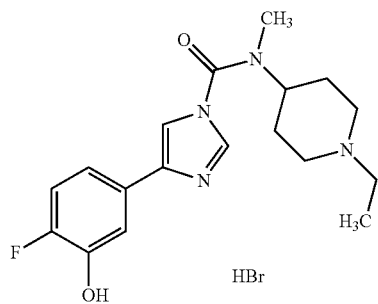 [SMILES: CCN1CCC(N(C)C(=O)n2cnc(-c3ccc(F)c(O)c3)c2)CC1 ; Br] |

-continued
| No. | Structure |
|---|---|
| 562 | 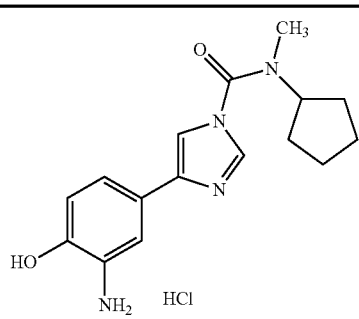 |
| 563 | 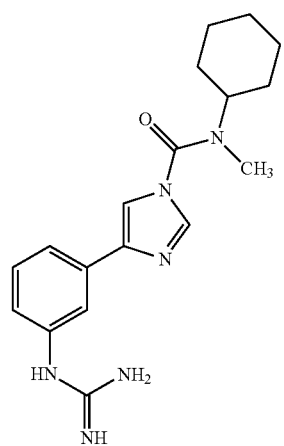 [SMILES: CN(C(=O)n1cnc(-c2cccc(NC(=N)N)c2)c1)C1CCCCC1] |
| 564 | 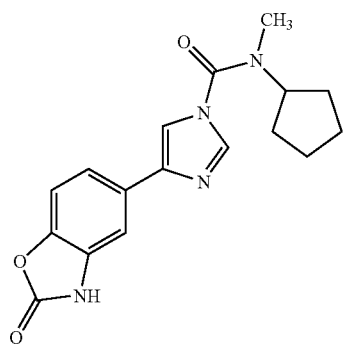 [SMILES: CN(C(=O)n1cnc(-c2ccc3oc(=O)[nH]c3c2)c1)C1CCCC1] |
| 565 | 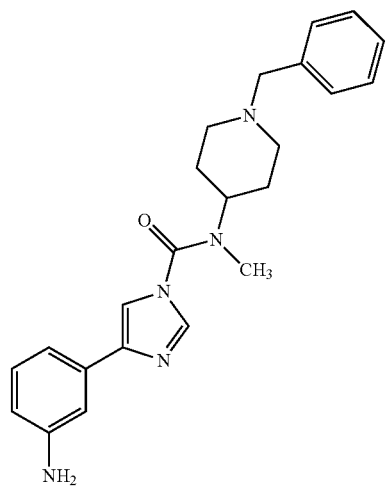 [SMILES: CN(C(=O)n1cnc(-c2cccc(N)c2)c1)C1CCN(Cc2ccccc2)CC1] |

-continued
| No. | Structure |
|-----|-----------|
| 566 | 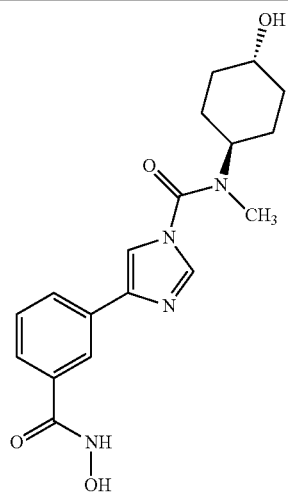 [SMILES: CN(C(=O)n1cnc(-c2cccc(C(=O)NO)c2)c1)[C@H]1CC[C@H](O)CC1] |
| 567 | 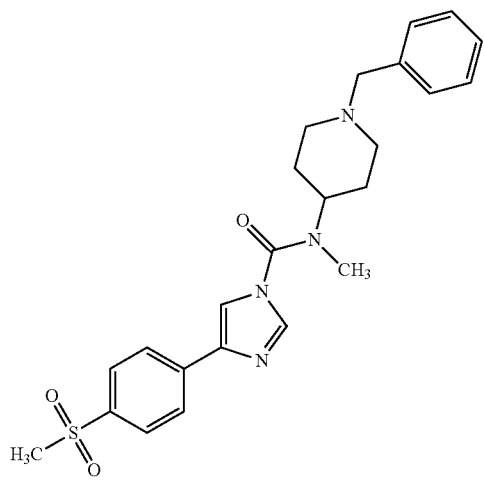 [SMILES: CN(C(=O)n1cnc(-c2ccc(S(C)(=O)=O)cc2)c1)C1CCN(Cc2ccccc2)CC1] |
| 568 | 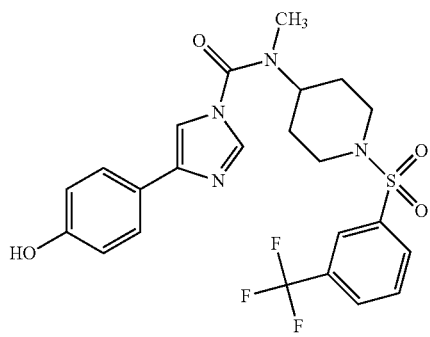 [SMILES: CN(C(=O)n1cnc(-c2ccc(O)cc2)c1)C1CCN(S(=O)(=O)c2cccc(C(F)(F)F)c2)CC1] |
| 569 | 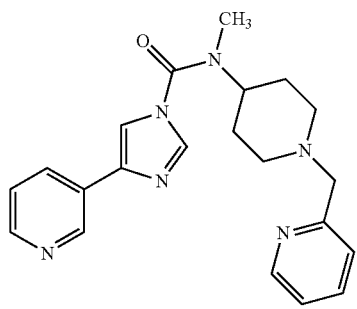 [SMILES: CN(C(=O)n1cnc(-c2cccnc2)c1)C1CCN(Cc2ccccn2)CC1] |

| No. | Structure |
|---|---|
| 570 | 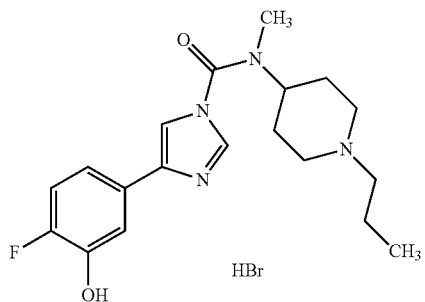 [SMILES: CCCN1CCC(N(C)C(=O)n2cnc(-c3ccc(F)c(O)c3)c2)CC1 ; Br] |
| 571 | 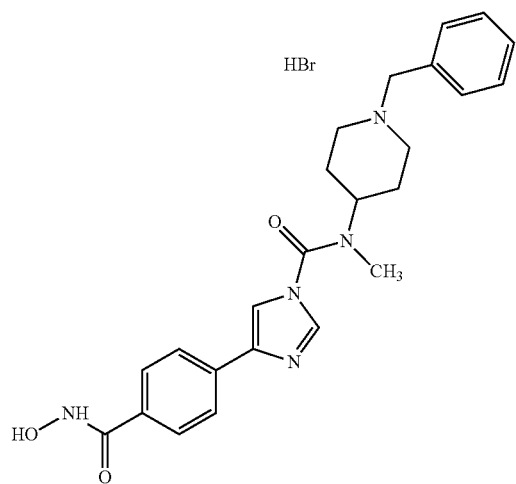 [SMILES: CN(C(=O)n1cnc(-c2ccc(C(=O)NO)cc2)c1)C1CCN(Cc2ccccc2)CC1 ; Br] |
| 572 | 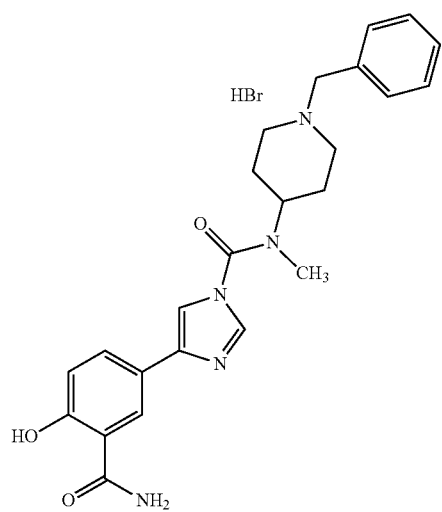 [SMILES: CN(C(=O)n1cnc(-c2ccc(O)c(C(N)=O)c2)c1)C1CCN(Cc2ccccc2)CC1 ; Br] |

| No. | Structure |
|---|---|
| 573 | 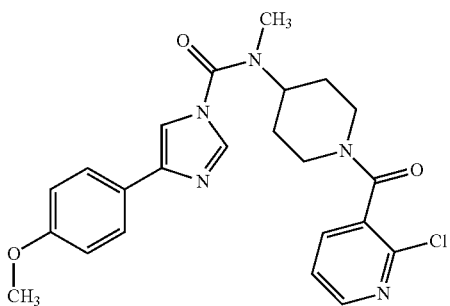 [SMILES: COc1ccc(-c2cn(C(=O)N(C)C3CCN(C(=O)c4cccnc4Cl)CC3)cn2)cc1] |
| 574 | 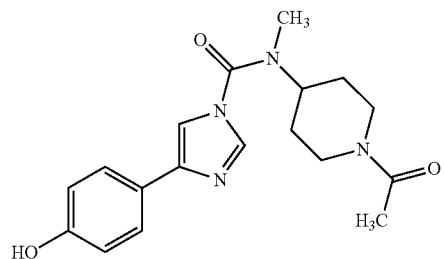 [SMILES: CC(=O)N1CCC(N(C)C(=O)n2cnc(-c3ccc(O)cc3)c2)CC1] |
| 575 | 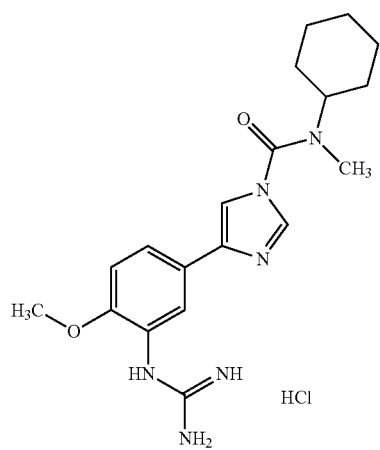 [SMILES: COc1ccc(-c2cn(C(=O)N(C)C3CCCCC3)cn2)cc1NC(=N)N ; Cl] |
| 576 | 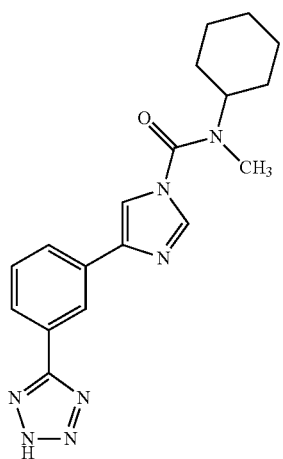 [SMILES: CN(C(=O)n1cnc(-c2cccc(-c3nn[nH]n3)c2)c1)C1CCCCC1] |

-continued
| No. | Structure |
|---|---|
| 577 | 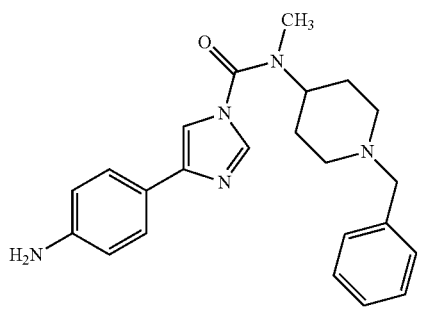 [SMILES: CN(C(=O)n1cnc(-c2ccc(N)cc2)c1)C1CCN(Cc2ccccc2)CC1] |
| 578 | 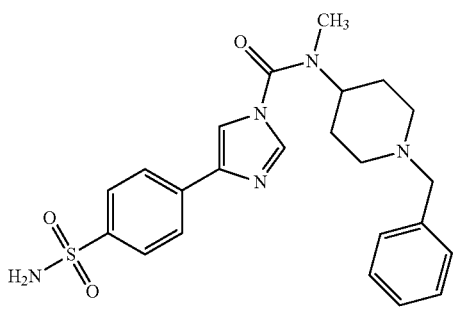 [SMILES: CN(C(=O)n1cnc(-c2ccc(S(N)(=O)=O)cc2)c1)C1CCN(Cc2ccccc2)CC1] |
| 579 | 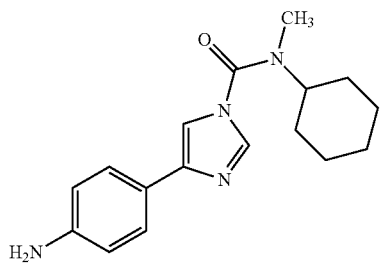 [SMILES: CN(C(=O)n1cnc(-c2ccc(N)cc2)c1)C1CCCCC1] |
| 580 | 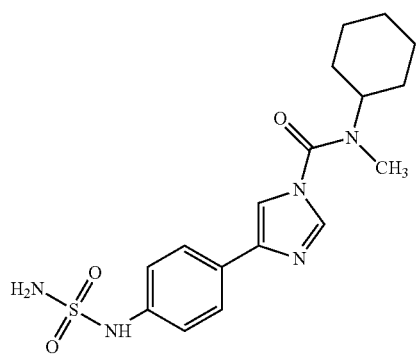 [SMILES: CN(C(=O)n1cnc(-c2ccc(NS(N)(=O)=O)cc2)c1)C1CCCCC1] |

-continued
| No. | Structure |
|---|---|
| 581 | 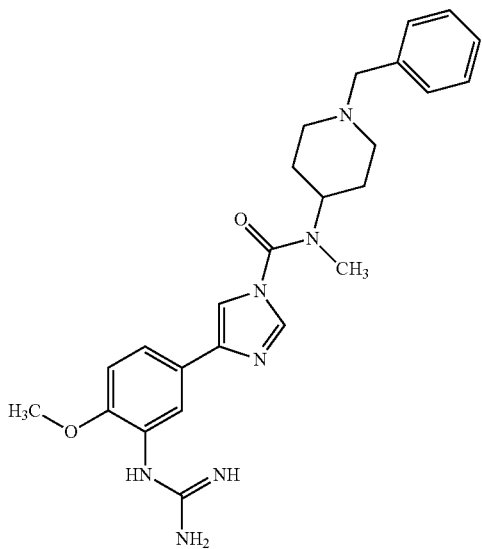 [SMILES: COc1ccc(-c2cn(C(=O)N(C)C3CCN(Cc4ccccc4)CC3)cn2)cc1NC(=N)N] |
| 582 | 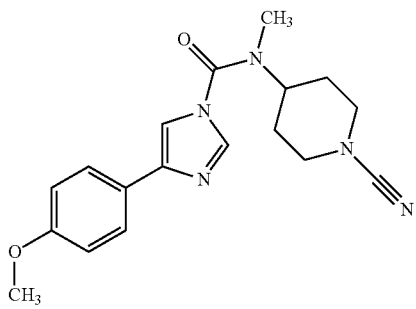 [SMILES: COc1ccc(-c2cn(C(=O)N(C)C3CCN(C#N)CC3)cn2)cc1] |
| 583 | 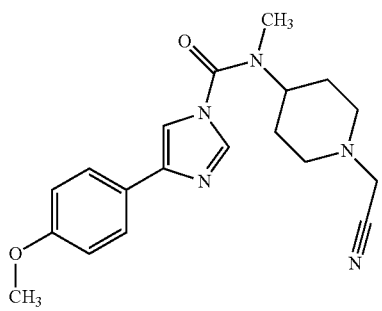 [SMILES: COc1ccc(-c2cn(C(=O)N(C)C3CCN(CC#N)CC3)cn2)cc1] |
| 584 | 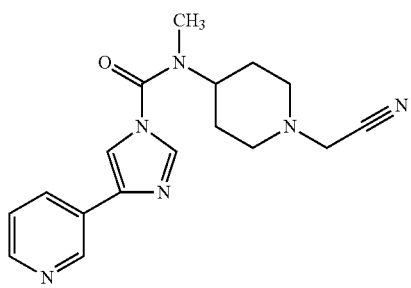 [SMILES: CN(C(=O)n1cnc(-c2cccnc2)c1)C1CCN(CC#N)CC1] |

| No. | Structure |
|---|---|
| 585 | 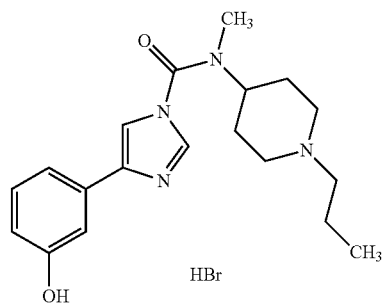 [SMILES: CCCN1CCC(N(C)C(=O)n2cnc(-c3cccc(O)c3)c2)CC1 ; Br] |
| 586 | 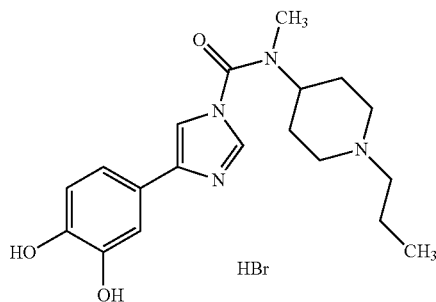 [SMILES: CCCN1CCC(N(C)C(=O)n2cnc(-c3ccc(O)c(O)c3)c2)CC1 ; Br] |
| 587 | 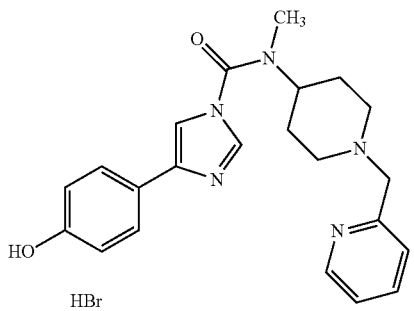 [SMILES: CN(C(=O)n1cnc(-c2ccc(O)cc2)c1)C1CCN(Cc2ccccn2)CC1 ; Br] |
| 588 | 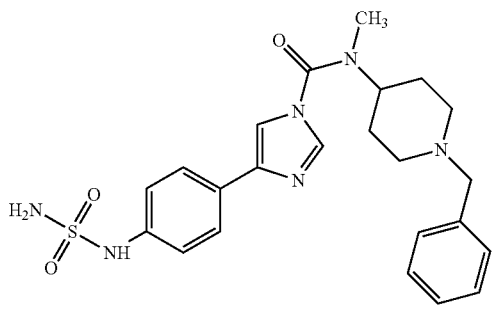 [SMILES: CN(C(=O)n1cnc(-c2ccc(NS(N)(=O)=O)cc2)c1)C1CCN(Cc2ccccc2)CC1] |

| No. | Structure |
|---|---|
| 589 | 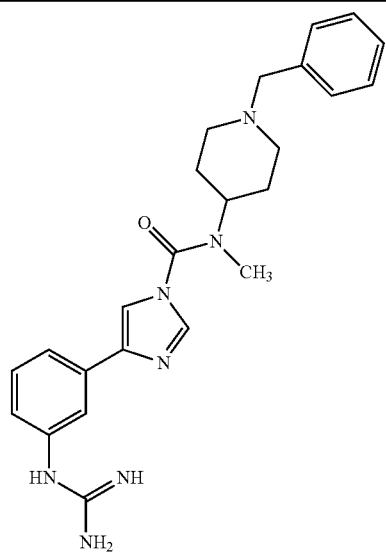 |
| 590 | 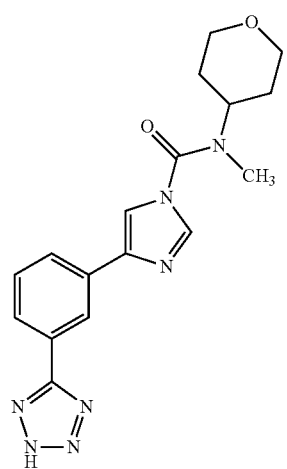 [SMILES: CN(C(=O)n1cnc(-c2cccc(-c3nn[nH]n3)c2)c1)C1CCOCC1] |
| 591 | 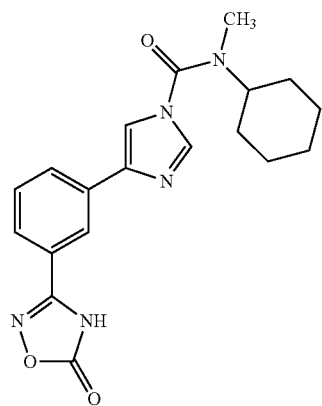 [SMILES: CN(C(=O)n1cnc(-c2cccc(-c3noc(=O)[nH]3)c2)c1)C1CCCCC1] |

| No. | Structure |
|---|---|
| 592 | 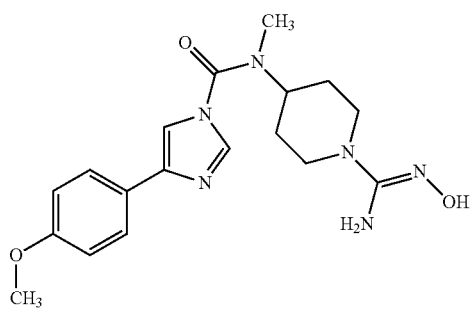 [SMILES: COc1ccc(-c2cn(C(=O)N(C)C3CCN(/C(N)=N/O)CC3)cn2)cc1] |
| 593 | 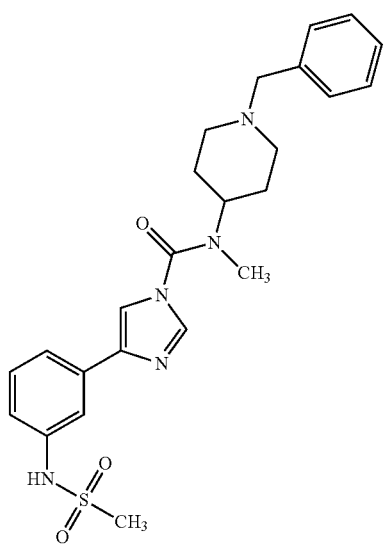 [SMILES: CN(C(=O)n1cnc(-c2cccc(NS(C)(=O)=O)c2)c1)C1CCN(Cc2ccccc2)CC1] |
| 594 | 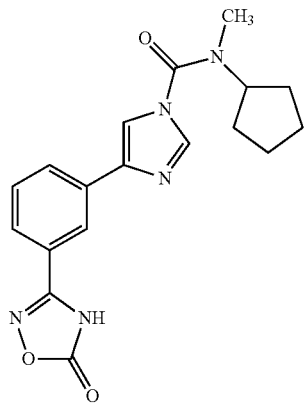 [SMILES: CN(C(=O)n1cnc(-c2cccc(-c3noc(=O)[nH]3)c2)c1)C1CCCC1] |
| 595 | 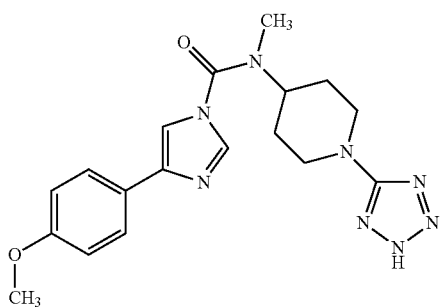 [SMILES: COc1ccc(-c2cn(C(=O)N(C)C3CCN(c4nn[nH]n4)CC3)cn2)cc1] |

| No. | Structure |
|---|---|
| 596 | (4-methoxyphenyl-imidazole linked to N-methyl carbamoyl piperidine with N-carboxamide) |
| 597 | (4-methoxyphenyl-imidazole linked to N-methyl carbamoyl piperidine with N-hydroxyethyl) |

The compounds of the invention above were characterised by melting point and NMR as detailed below. NMR spectra were recorded on a Bruker Avance DPX400 spectrometer with solvent used as internal standard. 13C spectra were recorded at 100 MHz and 1H spectra were recorded at 400 MHz. Data are reported in the following order: approximate chemical shift (ppm), number of protons, multiplicity (br, broad; d, doublet; m, multiplet; s, singlet; t; triplet) and coupling constant (Hz).

Compound no. 1 (MP: 89-91). NMR solvent: DMSO
13C: 150.4, 137.1, 128.9, 118.6, 65.7, 46.1
1H: 8.04 (1H, s), 7.48 (1H, s), 7.03 (1H, s), 3.65 (4H, m, J=5.0 Hz), 3.50 (4H, m, J=5.0 Hz)

Compound no. 2 (MP: 58). NMR solvent: CDCl3
13C: 150.2, 142.9, 137.7, 130.3, 129, 128, 125.9, 118.4, 40.1
1H: 7.57 (1H, s), 7.39 (2H, t, J=7.7 Hz), 7.32 (1H, t, J=7.3 Hz), 7.13 (2H, d, J=7.7 Hz), 6.85 (1H, s), 6.81 (1H, s), 3.50 (3H, s)

Compound no. 3 (MP: 97-99). NMR solvent: CDCl3
13C: 150.8, 142.7, 136.9, 132.7, 128.7, 127.7, 125.2, 112.8, 66.5, 46.8
1H: 7.92 (1H, s), 7.79 (2H, d, J=7.8 Hz), 7.47 (1H, s), 7.41 (2H, t, J=7.6 Hz), 7.30 (1H, m, J=7.6 Hz), 3.78 (4H, m), 3.68 (4H, m)

Compound no. 4 (MP: 104-105). NMR solvent: CDCl3
13C: 150.1, 142.9, 141.4, 137.7, 132.8, 130.4, 128.5, 128.2, 127.4, 126, 125, 113.5, 40.2
1H: 7.60 (2H, d, J=7.7 Hz), 7.53 (1H, s), 7.40 (2H, t, J=7.7 Hz), 7.34 (1H, m), 7.32 (2H, t, J=7.6 Hz), 7.25 (1H, m), 7.19 (2H, m), 7.18 (1H, s), 3.52 (3H, s)

Compound no. 5 (MP: 117). NMR solvent: CDCl3
13C: 154.2, 146.9, 136.6, 131.7, 129.9, 129.2, 129.1, 128.8, 126.3, 124.7, 119.8, 106.7
1H: 9.19 (1H, s), 8.36 (1H, d, J=2.7 Hz), 7.91 (2H, d, J=8.0 Hz), 7.67 (2H, d, J=7.8 Hz), 7.49 (2H, m, J=7.2 Hz), 7.43 (3H, m), 7.19 (1H, t, J=7.4 Hz), 6.79 (1H, d, J=2.7 Hz)

Compound no. 6 (MP: 98-99). NMR solvent: CDCl3
13C: 156.7, 154.1, 147.2, 131.8, 129.9, 129.5, 129.1, 128.8, 126.2, 121.7, 114.4, 106.5, 55.5
1H: 9.05 (1H, s), 8.34 (1H, d, J=2.8 Hz), 7.89 (2H, m, J=8.4 Hz), 7.55 (2H, m, J=8.8 Hz), 7.47 (2H, t, J=7.7 Hz), 7.41 (1H, t, J=7.3 Hz), 6.94 (2H, m, J=8.8 Hz), 6.76 (1H, d, J=2.8 Hz), 3.83 (3H, s)

Compound no. 7 (MP: 62). NMR solvent: CDCl3
13C: 151.7, 149.1, 145.7, 143.1, 129.6, 127.7, 125.8, 40.5
1H: 8.64 (1H, s), 7.73 (1H, s), 7.37 (2H, t, J=7.7 Hz), 7.30 (1H, t, J=7.3 Hz), 7.13 (2H, d, J=7.8 Hz), 3.56 (3H, s)

Compound no. 8 (MP: 64-65). NMR solvent: CDCl3
13C: 151.7, 144.6, 141.8, 131.1, 129.3, 126.6, 125.4, 107.3, 40.4
1H: 8.01 (1H, d br, J=2.7 Hz), 7.40 (1H, br), 7.33 (2H, m, J=8.1 Hz), 7.23 (1H, m, J=7.6 Hz), 7.11 (2H, m, J=8.3 Hz), 6.25 (1H, d d, J=1.7, 2.7 Hz), 3.55 (3H, s)

Compound no. 9 (MP: 71-72). NMR solvent: CDCl3
13C: 146.8, 142.3, 136.6, 129.2, 128.7, 124.7, 119.6, 109
1H: 9.13 (1H, s), 8.33 (1H, d d, J=0.6, 2.7 Hz), 7.69 (1H, d d, J=0.6, 1.6 Hz), 7.63 (2H, m, J=8.7 Hz), 7.40 (2H, m, J=8.0 Hz), 7.18 (1H, m, J=7.5 Hz), 6.47 (1H, d d, J=1.6, 2.7 Hz)

Compound no. 10 (MP: 125-126). NMR solvent: CDCl3
13C: 157.4, 154.3, 154, 147.1, 132, 131.7, 130, 129.8, 129.2, 128.8, 126.3, 123.2, 121.6, 119.7, 118.6, 106.6
1H: 9.14 (1H, s), 8.36 (1H, d, J=2.8 Hz), 7.91 (2H, d, J=8.0 Hz), 7.62 (2H, d, J=9.0 Hz), 7.49 (2H, t, J=7.6 Hz), 7.43 (1H, t, J=7.2 Hz), 7.36 (2H, t, J=8.0 Hz), 7.12 (1H, t, J=7.5 Hz), 7.08 (2H, d, J=9.0 Hz), 7.04 (2H, d, J=8.2 Hz), 6.80 (1H, d, J=2.8 Hz)

Compound no. 11 (MP: 110). NMR solvent: CDCl3
13C: 155.9, 154.1, 147.1, 136.8, 131.8, 129.9, 129.8, 129.1, 128.8, 128.6, 128, 127.5, 126.2, 121.7, 115.4, 106.5, 70.3
1H: 9.06 (1H, s), 8.35 (1H, d, J=2.7 Hz), 7.90 (2H, d, J=8.3 Hz), 7.56 (2H, m, J=9.0 Hz), 7.47 (2H, m), 7.45 (2H, m), 7.43

(1H, m), 7.40 (2H, m), 7.34 (1H, m), 7.03 (2H, m, J=9.0 Hz), 6.78 (1H, d, J=2.7 Hz), 5.09 (2H, s)

Compound no. 12 (MP: 79). NMR solvent: CDCl3
13C: 153, 151.3, 144.9, 132.3 (2 sig.), 129.2, 128.5 (2 sig.), 126.7, 125.9, 125.9, 104.7, 40.5
1H: 8.11 (1H, d, J=2.5 Hz), 7.40 (2H, m), 7.36 (2H, t, J=7.5 Hz), 7.28 (4H, m), 7.17 (2H, d, J=7.8 Hz), 6.55 (1H, d, J=2.5 Hz), 3.59 (3H, s)

Compound no. 13 (MP: 79-80). NMR solvent: CDCl3
13C: 153.7, 151, 133.3, 132.1, 128.8, 128.7, 126, 104.9, 66.8, 47
1H: 8.19 (1H, d, J=2.8 Hz), 7.83 (2H, d, J=8.4 Hz), 7.44 (2H, t, J=7.7 Hz), 7.39 (1H, m, J=7.2 Hz), 6.70 (1H, d, J=2.8 Hz), 4.0 (4H, s br), 3.84 (4H, m)

Compound no. 14 (MP: 132). NMR solvent: CDCl3
13C: 150, 142.9, 141.4, 137.9, 133.5, 132.8, 130.4, 130.1, 128.2, 128.2, 128.1, 127.6, 126.2, 126, 125.7, 123.6, 123.3, 114, 40.2
1H: 8.19 (1H, s), 7.85-7.77 (3H, m), 7.64 (1H, d d, 1.8, 8.7 Hz), 7.56 (1H, d, J=1.3 Hz), 7.44 (4H, m), 7.36 (1H, m, J=7.4 Hz), 7.34 (1H, d, J=1.3 Hz), 7.21 (2H, m, J=8.1 Hz), 3.54 (3H, s)

Compound no. 15 (MP: 134). NMR solvent: Acetone
13C: 154.8, 148.1, 141.2, 138, 137.9, 133, 131.1, 129.9, 129.8, 129.7, 128.2, 128.1, 127.6, 127.1, 121.5, 107.4
1H: 10.05 (1H, s), 8.45 (1H, d, J=3.0 Hz), 8.03 (2H, m, J=8.7 Hz), 7.94 (2H, m, J=8.6 Hz), 7.72 (2H, m, J=8.6 Hz), 7.69 (2H, m, J=8.3 Hz), 7.49 (2H, m), 7.47 (2H, m), 7.43 (1H, m), 7.36 (1H, m, J=7.4 Hz), 7.06 (1H, d, J=3.0 Hz)

Compound no. 16 (MP: 119-120). NMR solvent: CDCl3
13C: 159.2, 150.1, 141.2, 137.9, 135.5, 133.6, 132.8, 130.2, 128.2, 128.1, 127.6, 127.3, 126.2, 125.7, 123.6, 123.3, 115.5, 114.2, 55.5, 40.5
1H: 8.21 (1H, m), 7.82-7.80 (3H, m), 7.67 (1H, d d, J=1.7, 8.6 Hz), 7.49 (1H, d, J=1.3 Hz), 7.45 (2H, m), 7.42 (1H, m), 7.14 (2H, m, J=9.0 Hz), 6.93 (2H, m, J=9.0 Hz), 3.81 (3H, s), 3.50 (3H, s)

Compound no. 17 (MP: 138). NMR solvent: CDCl3
13C: 159.1, 150.1, 141.2, 137.7, 135.5, 132.8, 128.6, 127.4, 127.3, 125, 115.5, 113.7, 55.5, 40.5
1H: 7.64 (2H, d, J=8.1 Hz), 7.47 (1H, s), 7.35 (2H, t, J=7.2 Hz), 7.30 (2H, m, J=8.6 Hz), 7.25 (1H, m, J=7.4 Hz), 7.11 (2H, s, J=8.6 Hz), 6.91 (2H, d, J=8.6 Hz), 3.81 (3H, s), 3.49 (3H, s)

Compound no. 18 (MP: 123-124). NMR solvent: CDCl3
13C: 150.9, 143.4, 142.7, 141.5, 132.4, 130.3, 127.6, 125.4, 124.8, 123.9, 120.2, 114, 39.7
1H: 7.95 (1H, d, J=7.8 Hz), 7.69 (1H, d, J=8.0 Hz), 7.54 (1H, s), 7.38 (1H, m), 7.33 (2H, m), 7.32 (1H, m), 7.25 (1H, m), 7.12 (2H, d, J=7.8 Hz), 3.58 (3H, s)

Compound no. 19 (MP: 104). NMR solvent: CDCl3
13C: 149.4, 145.3, 133.1, 129.5, 125.4, 119.9, 113.6, 66.7, 48.2, 45.6
1H: 8.10 (1H, d, J=8.3 Hz), 8.01 (1H, d, J=8.4 Hz), 7.62 (1H, t, J=7.9 Hz), 7.47 (1H, t, J=7.6 Hz), 3.96 (4H, s br), 3.89 (4H, s br)

Compound no. 20 (MP: 181-183). NMR solvent: DMSO
13C: 153, 147.4, 140.6, 139.5, 137.4, 130.8, 130.7, 129, 128.8, 127.8, 127, 126.8, 126.7, 124.4, 121, 106.8
1H: 10.36 (1H, s), 8.51 (1H, d, J=2.6 Hz), 8.18 (2H, d, J=8.1 Hz), 7.82 (2H, d, J=8.2 Hz), 7.78 (2H, m), 7.76 (2H, d, J=8.7 Hz), 7.50 (2H, t, J=7.8 Hz), 7.41 (2H, m), 7.39 (1H, m), 7.19 (1H, d, J=2.6 Hz), 7.19 (1H, m)

Compound no. 21 (MP: 208-211). NMR solvent: DMSO
13C: 150, 147.8, 143.2, 140.7, 140, 134.5, 130.5, 126.8, 106.1, 66, 46.6
1H: 9.35 (1H, s), 8.86 (2H, m), 8.40 (1H, d, J=2.5 Hz), 8.02 (1H, t br, J=6.3 Hz), 7.31 (1H, d, J=2.5 Hz), 3.77 (4H, br), 3.71 (4H, br)

Compound no. 22 (MP: 168-170). NMR solvent: DMSO
13C: 159.6, 153, 147.3, 140.6, 139.5, 138.6, 130.8, 130.7, 129.6, 129, 127.8, 127, 126.9, 126.7, 113, 109.9, 106.9, 55.2
1H: 10.32 (1H, s), 8.50 (1H, d, J=3.0 Hz), 8.18 (2H, d, J=8.5 Hz), 7.81 (2H, d, J=8.5 Hz), 7.76 (2H, d, J=8.6 Hz), 7.75 (1H, t, J=2.3 Hz), 7.50 (2H, t, J=7.8 Hz), 7.42 (1H, m), 7.39 (1H, m, J=7.2 Hz), 7.31 (1H, t, J=8.5 Hz), 7.19 (1H, d, J=3.0 Hz), 6.76 (1H, m, J=1.0, 2.4, 8.3 Hz), 3.76 (3H, s)

Compound no. 23 (MP: 163). NMR solvent: DMSO
13C: 156.2, 152.9, 147.5, 140.5, 139.5, 130.8, 130.7, 130.2, 129, 127.8, 127, 126.8, 126.7, 122.9, 113.9, 106.6, 55.3
1H: 10.25 (1H, s), 8.49 (1H, d, J=2.6 Hz), 8.18 (2H, d, J=8.1 Hz), 7.82 (2H, d, J=8.1 Hz), 7.77 (2H, d, J=7.4 Hz), 7.66 (2H, d, J=9.0 Hz), 7.50 (2H, t, J=7.8 Hz), 7.40 (1H, t, J=7.3 Hz), 7.16 (1H, d, J=2.6 Hz), 6.98 (2H, d, J=9.0 Hz), 3.77 (3H, s)

Compound no. 24 (MP: 99). NMR solvent: CDCl3
13C: 150.9, 150.1, 149.4, 147.4, 144.7, 133, 132.6, 129.3, 128.1, 126.9, 125.9, 123.4, 104.6, 40.5
1H: 8.61 (1H, s), 8.50 (1H, d, J=4.9 Hz), 8.16 (1H, d, J=2.6 Hz), 7.65 (1H, d, J=7.9 Hz), 7.36 (2H, t, J=7.6 Hz), 7.29 (1H, t, J=7.5 Hz), 7.22 (1H, d d, J=4.9, 7.9 Hz), 7.17 (2H, d, J=7.8 Hz), 6.59 (1H, d, J=2.6 Hz), 3.58 (3H, s)

Compound no. 25 (MP: 137). NMR solvent: DMSO
13C: 151.6, 150.7, 144.5, 140.1, 139.5, 133, 131, 129.1, 129, 127.7, 126.8, 126.6, 126.5, 126.1, 125.8, 105.1, 40
1H: 8.22 (1H, d, J=2.5 Hz), 7.69 (2H, d, J=7.8 Hz), 7.64 (2H, d, J=8.4 Hz), 7.59 (2H, d, J=8.4 Hz), 7.46 (2H, t, J=7.6 Hz), 7.37 (3H, m), 7.26 (3H, m), 6.92 (1H, d, J=2.5 Hz), 3.48 (3H, s)

Compound no. 26 (MP: 123-125). NMR solvent: CDCl3
13C: 151.9, 146.5, 141.4, 130.3, 129.3, 129, 128.9, 128.3, 127.3, 126.9, 124.1, 120, 38.9
1H: 7.43-7.24 (6H, m), 7.14-6.93 (4H, m), 6.33 (2H, br), 3.37 (3H, s br)

Compound no. 27 (MP: 121). NMR solvent: CDCl3
13C: 149.9, 142.8, 140.3, 137.8, 133, 131.3, 130.4, 128.7, 128.2, 126.2, 126, 113.7, 40.2
1H: 7.54 (2H, m, J=8.6 Hz), 7.50 (1H, d, J=1.3 Hz), 7.42 (2H, m, J=7.7 Hz), 7.35 (1H, m, J=7.4 Hz), 7.29 (2H, m, J=8.6 Hz), 7.19 (1H, d, J=1.3 Hz), 7.18 (2H, m), 3.52 (3H, s)

Compound no. 28 (MP: 127). NMR solvent: CDCl3
13C: 159, 150.1, 142.9, 141.2, 137.6, 130.3, 128.1, 126.3, 125.9, 125.5, 113.9, 112.4, 55.2, 40.2
1H: 7.53 (2H, m, J=8.9 Hz), 7.51 (1H, d, J=1.4 Hz), 7.41 (2H, m, J=7.9 Hz), 7.34 (1H, m, J=7.5 Hz), 7.19 (2H, m, J=8.3 Hz), 7.09 (1H, d, J=1.4 Hz), 6.87 (2H, m, J=8.9 Hz), 3.80 (3H, s), 3.52 (3H, s)

Compound no. 29 (MP: 127-129). NMR solvent: CDCl3
13C: 162.2 (d, J=246.0 Hz), 150.0, 142.9, 140.5, 137.8, 130.4, 129.0 (d, J=3.3 Hz), 128.2, 126.7 (d, J=8.0 Hz), 126.0, 111.5 (d, J=21.5 Hz), 113.2, 40.2
1H: 7.57 (2H, m, J=5.4, 9.0 Hz), 7.50 (1H, d, J=1.3 Hz), 7.43 (2H, t, J=7.7 Hz), 7.35 (1H, m, J=7.3 Hz), 7.18 (2H, m), 7.15 (1H, d, J=1.3 Hz), 7.01 (2H, t, J=8.7 Hz), 3.52 (3H, s)

Compound no. 30 (MP: 126). NMR solvent: CDCl3
13C: 159.5 (d, J=249.0 Hz), 150.0, 142.8, 137.3, 135.1 (d, J=2.6 Hz), 130.3, 128.3 (d, J=8.6 Hz), 128.2, 127.7 (d, J=4.0 Hz), 125.9, 124.2 (d, J=3.2 Hz), 120.7 (d, J=12.8 Hz), 117.7 (d, J=16.0 Hz), 115.4 (d, J=22.0 Hz), 40.2
1H: 8.02 (1H, d t, J=2.0, 7.6 Hz), 7.65 (1H, d, J=1.3 Hz), 7.41 (2H, m), 7.34 (1H, m), 7.31 (1H, d d, J=1.3, 3.6 Hz), 7.19

(2H, m), 7.16 (1H, m), 7.15 (1H, m, J=1.6, 7.4), 7.03 (1H, m, J=1.5, 7.8, 11.4 Hz), 3.53 (3H, s)

Compound no. 31 (MP: 128-129). NMR solvent: CDCl3
13C: 159.8, 150, 142.9, 141.2, 137.7, 134.2, 130.4, 129.6, 128.2, 126, 117.4, 113.8, 113.6, 109.9, 55.2, 40.2
1H: 7.52 (1H, d, J=1.4 Hz), 7.41 (2H, m, J=7.8 Hz), 7.34 (1H, m, J=7.4 Hz), 7.23 (1H, t, J=7.8 Hz), 7.21 (1H, m), 7.19 (3H, m), 7.16-7.13 (1H, m), 6.79 (1H, d d d, 1.0, 2.5, 8.0 Hz), 3.81 (3H, s), 3.52 (3H, s)

Compound no. 32 (MP: 144-146). NMR solvent: CDCl3
13C: 149.7, 143.5, 143.4, 136, 133.4, 129.6, 127.6, 126.4, 126, 120.7, 113.3, 40.4
1H: 8.10 (1H, d, J=1.6 Hz), 7.91 (1H, d, J=8.8 Hz), 7.40 (1H, d d, J=1.6, 8.8 Hz), 7.34 (2H, m, J=7.9 Hz), 7.27 (1H, m), 7.17 (2H, d, J=7.6 Hz), 3.67 (3H, s)

Compound no. 33 (MP: 112). NMR solvent: CDCl3
13C: 149.7, 145.6, 143.4, 131.5, 131, 130.1, 129.6, 127.6, 125.9, 119.3, 114.2, 40.4
1H: 8.0 (1H, d, J=8.9 Hz), 7.98 (1H, d, J=1.6 Hz), 7.57 (1H, d d, J=1.6, 8.9 Hz), 7.34 (2H, t, J=8.1 Hz), 7.27 (1H, m), 7.17 (2H, d, J=7.8 Hz), 3.67 (3H, s)

Compound no. 34 (MP: 89-90). NMR solvent: CDCl3
13C: 150.2, 145, 143.6, 132.8, 129.5, 129.3, 127.4, 125.9, 125.1, 119.9, 113.2, 40.3
1H: 8.06 (1H, d, J=8.4 Hz), 8.0 (1H, d, J=8.4 Hz), 7.61 (1H, m, J=7.7 Hz), 7.43 (1H, m, J=7.7 Hz), 7.32 (2H, t, J=7.8 Hz), 7.25 (1H, t, J=7.5 Hz), 7.18 (2H, d, J=7.5 Hz), 3.68 (3H, s)

Compound no. 35 (MP: 166-169). NMR solvent: DMSO
13C: 149.8, 142.9, 139.7, 139.7, 138.7, 137.9, 132.1, 129.9, 129, 127.7, 127.4, 126.9, 126.5, 126.2, 125.2, 114.5, 39.6
1H: 7.73 (2H, d, J=8.2 Hz), 7.69-7.61 (6H, m), 7.48-7.39 (4H, m), 7.39-7.30 (4H, m), 3.44 (3H, s)

Compound no. 36 (MP: oil). NMR solvent: DMSO
13C: 160.8 (d, J=245 Hz), 158.6, 149.9, 140.2, 139.3 (d, J=3 Hz), 137.6, 128.6 (d, J=9 Hz), 126.0, 125.6, 116.7 (d, J=23.5 Hz), 114.1, 113.0, 55.1, 39.5
1H: 7.69 (1H, s), 7.57 (2H, d, J=8.7 Hz), 7.45 (1H, s), 7.41 (2H, m), 7.25 (2H, t, J=8.7 Hz), 6.90 (2H, d, J=8.7 Hz), 3.73 (3H, s), 3.40 (3H, s)

Compound no. 37 (MP: 162-164). NMR solvent: CDCl3
13C: 149.7, 142, 137.6, 137.4, 132.8, 131.7, 128.9, 128.6, 127.5, 127.1, 125.8, 125.1, 123, 113.1, 45.8, 26.6, 23.9
1H: 7.68 (1H, s), 7.68 (2H, d, J=7.7 Hz), 7.36 (2H, t, J=7.7 Hz), 7.28 (1H, s), 7.26 (1H, m), 7.23 (1H, d, J=7.5 Hz), 7.11 (1H, t, J=7.6 Hz), 7.03 (1H, d, J=7.7 Hz), 6.75 (1H, d, J=8.0 Hz), 3.92 (2H, t, J=6.6 Hz), 2.87 (2H, t, J=6.6 Hz), 2.11 (2H, qt, J=6.6 Hz)

Compound no. 38 (MP: 232-233). NMR solvent: DMSO
13C: 158.3, 147.9, 141.9, 137.2, 135.4, 129.9, 128.2, 126.9, 126.3, 118.8, 115.8, 114, 39.9
1H: 8.79 (1H, s), 8.78 (1H, s), 7.67 (1H, s), 7.43 (2H, m, J=8.6 Hz), 7.41 (4H, m), 7.34 (1H, m), 6.80 (2H, m, J=8.6 Hz), 3.74 (3H, s)

Compound no. 39 (MP: 97-98). NMR solvent: CDCl3
13C: 159.9, 149.6, 141.8, 137.6, 137.4, 134.2, 131.8, 129.6, 128.9, 127.1, 125.8, 123, 117.5, 113.7, 113.4, 110.1, 55.3, 45.8, 26.6, 23.9
1H: 7.68 (1H, d, J=1.3 Hz), 7.29 (1H, m), 7.28 (1H, d, J=1.3 Hz), 7.24 (2H, m), 7.23 (1H, m), 7.12 (1H, d t, J=1.2, 7.5 Hz), 7.04 (1H, d t, J=1.5, 8.0 Hz), 6.83 (1H, d d d, 1.5, 2.5, 7.5 Hz), 6.75 (1H, d br, J=8.0 Hz), 3.93 (2H, t, J=6.7 Hz), 3.84 (3H, s), 2.88 (2H, t, J=6.6 Hz), 2.12 (2H, qt, J=6.6 Hz)

Compound no. 40 (MP: 139-141). NMR solvent: DMSO
13C: 157.6, 149.7, 142.8, 139.9, 137.7, 133.9, 129.9, 129.7, 127.7, 126.2, 115.5, 114.3, 114.2, 111.5, 39.6
1H: 9.43 (1H, s), 7.68 (1H, s), 7.43 (1H, s), 7.41 (2H, m), 7.35 (2H, m), 7.32 (1H, m), 7.11 (1H, t), 7.03 (1H, br), 7.02 (1H, m), 6.62 (1H, d, J=8.0 Hz), 3.42 (3H, s)

Compound no. 41 (MP: 152). NMR solvent: DMSO
13C: 150.6, 148.8, 144.7, 132.5, 129.6, 129.1, 125.5, 119.6, 119.5, 115.9, 113.4, 48.3, 47.1, 44.8
1H: 8.21 (1H, d, J=8.5 Hz), 7.97 (1H, d, J=8.3 Hz), 7.71 (1H, m, J=7.8 Hz), 7.55 (1H, m, J=7.6 Hz), 7.25 (2H, t, J=7.5 Hz), 7.0 (2H, d, J=8.2 Hz), 6.83 (1H, t, J=7.3 Hz), 3.92 (4H, m), 3.33 (4H, m)

Compound no. 42 (MP: 79-80). NMR solvent: DMSO
13C: 148.6, 144.7, 140, 132.5, 129.4, 129.1, 128.3, 125.9, 125.4, 119.6, 113.1, 47.6, 45, 41.9, 37.1, 31.6
1H: 8.18 (1H, d, J=8.4 Hz), 7.90 (1H, d, J=8.4 Hz), 7.68 (1H, m, J=8.0 Hz), 7.53 (1H, m, J=7.6 Hz), 7.29 (2H, t, J=7.3 Hz), 7.20 (2H, d, J=7.3 Hz), 7.19 (1H, t, J=7.5 Hz), 4.20 (2H, s br), 3.13 (2H, s br), 2.58 (2H, d, J=7.2 Hz), 1.88 (1H, m), 1.70 (2H, br), 1.34 (2H, m, J=4.0, 12.5 Hz)

Compound no. 43 (MP: 105). NMR solvent: CDCl3
13C: 161.7 (d, J=250.0 Hz), 149.8, 140.5, 138.8 (d, J=3.6 Hz), 137.7, 133.1, 131.2, 128.8, 127.8 (d, J=8.4 Hz), 126.3, 117.4 (d, J=23.2 Hz), 113.6, 40.4
1H: 7.56 (2H, m, J=8.8 Hz), 7.49 (1H, d, J=1.4 Hz), 7.31 (2H, m, J=8.8 Hz), 7.23 (1H, d, J=1.4 Hz), 7.17 (2H, m), 7.12 (2H, m), 3.50 (3H, s)

Compound no. 44 (MP: 145). NMR solvent: CDCl3
13C: 162.3 (d, J=246.5 Hz), 149.6, 141.1, 137.6, 137.5, 131.8, 129.0 (d, J=3.0 Hz), 129, 127.1, 126.8 (d, J=8.0 Hz), 125.9, 123, 115.5 (d, J=21.5 Hz), 112.8 (d, J=1.6 Hz), 45.8, 26.6, 23.9
1H: 7.65 (2H, m), 7.65 (1H, d, J=1.3 Hz), 7.24 (1H, m), 7.23 (1H, d, J=1.3 Hz), 7.12 (1H, m), 7.05 (2H, m, J=8.9 Hz), 7.05 (1H, m, J=1.2, 7.5 Hz), 6.75 (1H, m, J=8.1 Hz), 3.92 (2H, t, J=6.6 Hz), 2.88 (2H, t, J=6.6 Hz), 2.12 (2H, qt, J=6.6 Hz)

Compound no. 45 (MP: 93-96). NMR solvent: CDCl3
13C: 161.7 (d, J=249.5 Hz), 159.6 (d, J=249.0 Hz), 150.0, 138.9 (d, J=3.5 Hz), 137.2, 135.3 (d, J=2.0 Hz), 128.4 (d, J=8.3 Hz), 127.8 (d, J=8.3 Hz), 127.7 (d, J=4.0 Hz), 124.3 (d, J=3.2 Hz), 120.6 (d, J=13.0 Hz), 117.5 (d, J=16.0 Hz), 117.4 (d, J=23.0 Hz), 115.5 (d, J=22.0 Hz), 40.3
1H: 8.03 (1H, d t, J=2.0, 7.8 Hz), 7.68 (1H, d, J=1.4 Hz), 7.30 (1H, d d, J=1.4, 3.5 Hz), 7.19 (2H, m), 7.16 (1H, m), 7.15 (1H, m), 7.10 (2H, m), 7.04 (1H, d d d, J=1.4, 7.9, 11.3 Hz), 3.50 (3H, s)

Compound no. 46 (MP: 90-91). NMR solvent: CDCl3
13C: 158.9 (d, J=238.0 Hz), 154, 131.7, 130.2 (d, J=10.0 Hz), 127.5, 114.2 (d, J=9.5 Hz), 111.9 (d, J=26.0 Hz), 106.3 (d, J=27.5 Hz), 106.2, 66.6, 47.1
1H: 7.66 (1H, d d, J=4.5, 9.1 Hz), 7.34 (1H, d, J=3.5 Hz), 7.25 (1H, d d, J=2.5, 9.0 Hz), 7.05 (1H, d t, J=2.5, 9.1 Hz), 6.58 (1H d d, J=0.7, 3.5 Hz), 3.80 (4H, m, J=5.0, 6.0 Hz), 3.62 (4H, m, J=5.0, 6.0 Hz)

Compound no. 47 (MP: 112-113). NMR solvent: CDCl3
13C: 155.5, 154.4, 130.3, 130, 126.7, 114, 113.2, 106.1, 103.1, 66.7, 55.7, 47.1
1H: 7.60 (1H, d, J=8.9 Hz), 7.30 (1H, d, J=3.5 Hz), 7.06 (1H, d br, J=2.5 Hz), 6.95 (1H, d d, J=2.5, 8.9 Hz), 6.55 (1H, d d, J=0.7, 3.5 Hz), 3.86 (3H, s), 3.79 (4H, m, J=5.0 Hz), 3.61 (4H, m, J=5.0 Hz)

Compound no. 48 (MP: 184). NMR solvent: DMSO
13C: 162.4, 148.7, 147.4, 147, 144.7, 132.5, 129.6, 128.6, 125.5, 123.3, 119.7, 113.4, 109.9, 108.1, 101.1, 60.5, 51.4, 46.5, 43.8
1H: 8.20 (1H, d, J=8.4 Hz), 7.93 (1H, d, J=8.4 Hz), 7.71 (1H, t, J=8.0 Hz), 7.54 (1H, t, J=7.5 Hz), 6.97 (1H, s br), 6.91 (1H, d, J=8.0 Hz), 6.85 (1H, d d, J=1.5, 8.0 Hz), 6.02 (2H, s), 3.84 (4H, m), 3.75 (2H, s), 2.80 (4H, m)

Compound no. 49 (MP: 89). NMR solvent: DMSO
13C: 158.6, 148.9, 147.6, 144.7, 137.8, 132.5, 129.6, 125.5, 119.6, 113.5, 113.4, 107.3, 46.9, 44.4
1H: 8.21 (1H, d, J=8.4 Hz), 8.15 (1H, d d, J=1.5, 4.8 Hz), 7.97 (1H, d, J=8.3 Hz), 7.71 (1H, m), 7.58 (1H, m), 7.55 (1H, m), 6.88 (1H, d, J=8.7 Hz), 6.69 (1H, d d, J=4.8, 7.1 Hz), 3.88 (4H, m), 3.71 (4H, m)

Compound no. 50 (MP: 113-114). NMR solvent: DMSO
13C: 149.2, 144.7, 134.4, 132.6, 129.5, 128.6, 128.6, 126.8, 126.5, 126.3, 125.5, 119.6, 113.5, 48.6, 46.7, 45.5, 42.8, 28.8, 27.2
1H: 8.21 (1H, d t, J=0.8, 8.3 Hz), 7.95 (1H, d, J=8.3 Hz), 7.70 (1H, t, J=7.8 Hz), 7.54 (1H, d d d, J=1.0, 7.1, 8.3 Hz), 7.24 (4H, br), 4.94 (2H, br), 3.96 (2H, t, J=6.0 Hz), 3.04 (2H, t, J=6.0 Hz)

Compound no. 51 (MP: 188). NMR solvent: CDCl3
13C: 158.6, 150.8, 142.6, 138.8, 138.6, 134.8, 133.7, 130.8, 130, 127.8, 127, 124.1, 117.6, 115.8, 114.9, 113, 47.1, 27.5, 24.9
1H: 7.76 (1H, d, J=1.4 Hz), 7.36 (1H, d, J=1.4 Hz), 7.28 (1H, d br, J=7.7 Hz), 7.15 (1H, t, J=7.8 Hz), 7.13 (1H, t), 7.09 (1H, m), 7.07 (1H, m), 7.04 (1H, d t, J=1.5, 8.0 Hz), 6.79 (1H, d br, J=8.2 Hz), 6.69 (1H, d d d, J=1.1, 2.5, 8.0 Hz), 3.91 (2H, t, J=6.5 Hz), 2.90 (2H, t, J=6.5 Hz), 2.10 (2H, qt, J=6.5 Hz)

Compound no. 52 (MP: 174). NMR solvent: DMSO
13C: 153.5, 152.6, 130.2, 129.1, 127.3, 113.8, 112.9, 105.1, 105, 65.9, 46.5
1H: 9.09 (1H, s), 7.47 (1H, d, J=9.0 Hz), 7.44 (1H, d, J=3.5 Hz), 6.91 (1H, d, J=2.0 Hz), 6.74 (1H, d d, J=2.0, 9.0 Hz), 6.50 (1H, d, J=3.5 Hz), 3.67 (4H, m), 3.47 (4H, m)

Compound no. 53 (MP: oil). NMR solvent: CDCl3
13C: 150.9, 145.3, 135.7, 133.2, 129.4, 128.8, 128.1 (br), 128.0, 125.2, 119.8, 113.7, 55.3, 53.8, 37.7
1H: 8.11 (1H, d, J=8.2 Hz), 8.06 (1H, d, J=8.2 Hz), 7.63 (1H, t, J=7.4 Hz), 7.48 (1H, t, J=7.8 Hz), 7.40 (5H, br), 4.94 (2H, br), 3.31 (3H, br)

Compound no. 54 (MP: 218-220). NMR solvent: CDCl3
13C: 161.8 (d, J=251.0 Hz), 159, 146.3, 136.7 (d, J=4.0 Hz), 136, 134.3, 127.9 (d, J=9.0 Hz), 127, 117.2 (d, J=23.0 Hz), 115.9, 115.6, 113.6, 40.1
1H: 8.89 (1H, m), 7.18 (2H, m), 7.09 (2H, m, J=8.7 Hz), 7.05 (1H, m), 6.95 (2H, m, J=8.6 Hz), 6.65 (2H, m, J=8.7 Hz), 3.35 (3H, s)

Compound no. 55 (MP: 116). NMR solvent: CDCl3
13C: 149.3, 145.3, 133.2, 129.3, 125.2, 119.8, 113.5, 106.6, 64.6, 46.1, 43.6, 35.3
1H: 8.09 (1H, d, J=8.5 Hz), 7.99 (1H, d, J=8.3 Hz), 7.61 (1H, t, J=8.1 Hz), 7.46 (1H, t, J=7.4 Hz), 4.03 (4H, s), 3.98 (4H, br), 1.93 (4H, t, J=6.0 Hz)

Compound no. 56 (MP: 134). NMR solvent: CDCl3
13C: 157.1, 154.5, 146.6, 146.5, 131.6, 131.3, 130.3, 129.8, 125.7, 123.4, 121.9, 120.2, 119.7, 118.7, 114
1H: 9.15 (1H, s), 8.35 (1H, d, J=8.4 Hz), 8.15 (1H, d, J=8.3 Hz), 7.69 (1H, t, J=7.6 Hz), 7.65 (2H, m, J=9.2 Hz), 7.52 (1H, t, J=7.7 Hz), 7.37 (2H, t, J=8.1 Hz), 7.14 (1H, t, J=7.3 Hz), 7.10 (2H, m, J=9.2 Hz), 7.05 (2H, m, J=8.5 Hz)

Compound no. 57 (MP: 156-157). NMR solvent: CDCl3
13C: 157.2, 146.6, 146.4, 131.6, 130.2, 128.9, 125.6, 122, 120.2, 114.5, 114, 55.5
1H: 9.06 (1H, s), 8.34 (1H, d, J=8.5 Hz), 8.14 (1H, d, J=8.3 Hz), 7.67 (1H, m, J=7.5 Hz), 7.59 (2H, m, J=9.1 Hz), 7.51 (1H, m, J=7.8 Hz), 6.97 (2H, m, J=9.1 Hz), 3.85 (3H, s)

Compound no. 58 (MP: 101-102). NMR solvent: CDCl3
13C: 150.4, 145.2, 133.2, 129.1, 125, 119.7, 113.5, 57.1, 32.4, 30.4, 29.7, 25.5, 25.3
1H: 8.09 (1H, d, J=8.3 Hz), 7.98 (1H, d, J=8.5 Hz), 7.60 (1H, m, J=7.8 Hz), 7.45 (1H, t, J=7.6 Hz), 4.26 (1H, br), 3.18 (3H, s), 2.0 (2H, d br, J=11.0 Hz), 1.87 (2H, br), 1.67 (1H, br), 1.63 (2H, m, J=3.0, 12.3 Hz), 1.43 (2H, m), 1.16 (1H, m)

Compound no. 59 (MP: 148-150). NMR solvent: CDCl3
13C: 160.6 (d d, J=11.5, 248.0 Hz), 153.4 (d d, J=12.0, 249.0 Hz), 146.5, 146.4, 131.5, 130.5, 125.9, 122.7 (d d, J=2.0, 9.3 Hz), 121.0 (d d, J=3.7, 11.0 Hz), 120.4, 113.8, 111.6 (d d, J=4.0, 22.5 Hz), 104.2 (d d, J=22.5, 27.0 Hz)
1H: 9.28 (1H, s), 8.32 (1H, m, J=8.3 Hz), 8.27 (1H, m, J=6.0, 8.9 Hz), 8.17 (1H, m, J=8.3 Hz), 7.70 (1H, m, J=8.2 Hz), 7.53 (1H, m, J=8.1 Hz), 7.0 (2H, m)

Compound no. 60 (MP: 142-143). NMR solvent: CDCl3
13C: 146.5, 146.4, 136.1, 131.6, 130.3, 129.4, 125.7, 125.3, 120.2, 120, 114
1H: 9.19 (1H, s), 8.35 (1H, d, J=8.3 Hz), 8.15 (1H, d, J=8.4 Hz), 7.70 (2H, d, J=8.0 Hz), 7.69 (1H, m), 7.52 (1H, t, J=7.8 Hz), 7.45 (2H, t, J=8.0 Hz), 7.25 (1H, t, J=7.4 Hz)

Compound no. 61 (MP: 109). NMR solvent: CDCl3
13C: 149.2, 146.3, 136.9, 131.6, 130, 128.9, 128, 127.8, 125.5, 120, 113.9, 44.4
1H: 8.32 (1H, d, J=8.4 Hz), 8.11 (1H, d, J=8.4 Hz), 7.67 (1H, m), 7.65 (1H, t, J=7.8 Hz), 7.49 (1H, t, J=8.0 Hz), 7.43 (2H, m), 7.40 (2H, t, J=7.7 Hz), 7.34 (1H, m), 4.75 (2H, d, J=6.0 Hz)

Compound no. 62 (MP: 195-197). NMR solvent: CDCl3
13C: 146.5, 146.3, 134.7, 131.5, 130.4 (2 sig.), 129.4, 125.9, 121.2, 120.3, 113.9
1H: 9.19 (1H, s), 8.34 (1H, d, J=8.3 Hz), 8.16 (1H, d, J=8.5 Hz), 7.70 (1H, t, J=7.9 Hz), 7.66 (2H, d, J=8.8 Hz), 7.53 (1H, t, J=7.5 Hz), 7.42 (2H, d, J=8.8 Hz)

Compound no. 63 (MP: 62). NMR solvent: CDCl3
13C: 150, 145, 142.2, 133.1, 132.8, 129.7, 129.5, 127.3, 125.3, 119.9, 113.3, 40.3
1H: 8.06 (1H, d, J=8.5 Hz), 8.02 (1H, d, J=8.3 Hz), 7.62 (1H, t, J=7.9 Hz), 7.45 (1H, t, J=7.7 Hz), 7.30 (2H, d, J=8.6 Hz), 7.13 (2H, d, J=8.6 Hz), 3.65 (3H, s)

Compound no. 64 (MP: 84-85). NMR solvent: CDCl3
13C: 161.9, 160.9, 149.1, 146.3, 143.5, 129.5, 128, 127.5, 126.1, 122.4, 113.8, 55.2, 40.4
1H: 8.66 (1H, s), 7.71 (2H, d, J=8.5 Hz), 7.39 (2H, t, J=7.9 Hz), 7.32 (1H, t, J=7.2 Hz), 7.19 (2H, d, J=7.9 Hz), 6.87 (2H, d, J=8.5 Hz), 3.82 (3H, s), 3.58 (3H, s)

Compound no. 65 (MP: 105-106). NMR solvent: CDCl3
13C: 162.6, 161.2, 148.8, 147.3, 128.3, 122.3, 114.1, 66.6, 55.3, 46.9
1H: 8.81 (1H, s), 8.06 (2H, d, J=8.9 Hz), 6.98 (2H, d, J=8.9 Hz), 3.98 (4H, br), 3.87 (3H, s), 3.83 (4H, m br)

Compound no. 66 (MP: 116). NMR solvent: CDCl3
13C: 162.1, 161.5 (d, J=248.0 Hz), 161, 149.1, 146.5, 139.5 (d, J=3.5 Hz), 128.1 (d, J=9.0 Hz), 128, 122.3, 116.3 (d, J=22.5 Hz), 113.9, 55.3, 40.7
1H: 8.74 (1H, s), 7.72 (2H, d, J=8.4 Hz), 7.20 (2H, m, J=5.0, 9.0 Hz), 7.09 (2H, t, J=8.8 Hz), 6.89 (2H, d, J=8.9 Hz), 3.83 (3H, s), 3.56 (3H, s)

Compound no. 67 (MP: 91). NMR solvent: CDCl3
13C: 161.2, 148.8, 146.5, 143.3, 135.8, 129.5, 128.7, 128.3, 127.8, 127.7, 126.1, 40.5
1H: 8.69 (1H, s), 7.69 (2H, m, J=8.3 Hz), 7.39 (2H, t, J=7.8 Hz), 7.32 (1H, m), 7.31 (2H, m, J=, 8.3 Hz), 7.19 (2H, d, J=8.0 Hz), 3.58 (3H, s)

Compound no. 68 (MP: 120-121). NMR solvent: CDCl3
13C: 161.9, 148.5, 147.6, 136.2, 129, 128.2, 128.1, 66.6, 47.5, 46
1H: 8.84 (1H, s), 8.06 (2H, d, J=8.7 Hz), 7.44 (2H, d, J=8.7 Hz), 3.98 (4H, br), 3.84 (4H, s br)

Compound no. 69 (MP: 127-128). NMR solvent: CDCl3

13C: 161.6 (d, J=248.5 Hz), 161.4, 148.8, 146.7, 139.3 (d, J=3.3 Hz), 135.9, 128.8, 128.2, 128.1 (d, J=8.5 Hz), 127.8, 116.3 (d, J=23.0 Hz), 40.7

1H: 8.76 (1H, s), 7.71 (2H, d, J=7.0 Hz), 7.35 (2H, d, J=8.0 Hz), 7.19 (2H, m), 7.09 (2H, t, J=8.5 Hz), 3.56 (3H, s)

Compound no. 70 (MP: 91-92). NMR solvent: CDCl3

13C: 161.8 (d d, J=11.5, 251.0 Hz), 157.7 (d d, J=12.5, 252.0 Hz), 150.1, 144.9, 132.7, 129.6, 129.3 (d d, J=1.5, 10.0 Hz), 127.7 (d d, J=5.0, 12.0 Hz), 125.4, 119.9, 113.5, 112.1 (d d, J=4.0, 23.0 Hz), 105.1 (d d, J=24.0, 26.5 Hz), 39.7

1H: 8.10 (1H, d, J=8.4 Hz), 8.01 (1H, d, J=8.1 Hz), 7.63 (1H, m, J=7.8 Hz), 7.45 (1H, t, J=7.7 Hz), 7.30 (1H, m), 6.88 (1H, m), 6.84 (1H, m), 3.60 (3H, s)

Compound no. 71 (MP: 65-66). NMR solvent: CDCl3

13C: 146.1, 145.3, 132.8, 129.4, 125.5, 119.8, 114.4, 82.5, 79.6, 62.2, 23

1H: 8.23 (1H, d, J=8.4 Hz), 8.10 (1H, d, J=8.3 Hz), 7.62 (1H, t, J=7.8 Hz), 7.48 (1H, t, J=7.7 Hz), 5.54 (2H, s), 3.90 (2H, s), 1.69 (6H, s)

Compound no. 72 (MP: 85). NMR solvent: CDCl3

13C: 152, 142.2, 138.9, 130.1, 124.2, 122.8, 119.8, 115.2, 67.1, 47.2

1H: 8.09 (1H, d, J=8.6 Hz), 7.69 (1H, d, J=8.2 Hz), 7.58 (1H, t, J=7.5 Hz), 7.36 (1H, t, J=7.5 Hz), 3.87 (4H, br), 3.80 (4H, br)

Compound no. 73 (MP: 80). NMR solvent: CDCl3

13C: 162.8, 148.7, 147.4, 130.2, 129.6, 128.7, 126.7, 66.6, 47.3, 46.2

1H: 8.85 (1H, s), 8.12 (2H, m), 7.47 (3H, m), 4.02 (4H, br), 3.84 (4H, m)

Compound no. 74 (MP: 114). NMR solvent: CDCl3

13C: 162.4, 162.0 (d d, J=15.0, 251.0 Hz), 158.0 (d d, J=13.0, 252.0 Hz), 148.9, 146.7, 130.0, 129.6, 129.2 (d d, J=2.0, 10.0 Hz), 128.6, 127.6 (m, J=13.0 Hz), 126.5, 111.8 (d d, J=4.0, 22.5 Hz), 104.8 (t, J=25.0 Hz), 39.9

1H: 8.86 (1H, s), 7.74 (2H, br), 7.38 (3H, m br), 7.28 (1H, m), 6.95 (1H, m), 6.92 (1H, m), 3.52 (3H, s)

Compound no. 75 (MP: oil). NMR solvent: CDCl3

13C: 150.5, 145.2, 133.2, 129.2, 125.1, 119.7, 113.6, 51.7, 50.4, 38.0, 35.7, 30.1, 29.0, 19.8, 13.8

1H: 8.10 (1H, d, J=8.4 Hz), 8.0 (1H, d, J=8.3 Hz), 7.59 (1H, t, J=7.8 Hz), 7.45 (1H, t, J=7.6 Hz), 3.67 (2H, br), 3.31 (3H, m br), 1.78 (2H, m), 1.45-1.30 (2H, m br), 1.0-0.9 (3H, m br)

Compound no. 76 (MP: 130). NMR solvent: CDCl3

13C: 150.3, 150.1, 144.9, 135.3, 132.8, 129.2, 126.8, 125, 119.8, 115.8, 113.2, 66.7, 48.7, 40.5

1H: 8.04 (1H, d, J=8.4 Hz), 8.0 (1H, d, J=8.2 Hz), 7.60 (1H, t, J=7.9 Hz), 7.42 (1H, t, J=7.6 Hz), 7.08 (2H, d, J=7.7 Hz), 6.80 (2H, d, J=8.7 Hz), 3.83 (4H, m), 3.63 (3H, s), 3.13 (4H, m)

Compound no. 77 (MP: 163-138). NMR solvent: CDCl3

13C: 161.2, 150.1, 145.2, 145, 132.8, 129.3, 125.1, 119.8, 113.2, 104.4, 99.1, 55.4, 40.3

1H: 8.05 (1H, d, J=8.7 Hz), 8.02 (1H, d, J=8.9 Hz), 7.61 (1H, t, J=7.7 Hz), 7.44 (1H, t, J=7.7 Hz), 6.34 (1H, t, J=2.0 Hz), 6.31 (2H, d, J=2.0 Hz), 3.70 (6H, s), 3.65 (3H, s)

Compound no. 78 (MP: 155-157). NMR solvent: CDCl3

13C: 163.8 (d d, J=12.0, 253.0 Hz), 160.8 (d d, J=12.0, 258.0 Hz), 158.4 (d, J=6.0 Hz), 148.4, 146.9, 131.5 (d d, J=4.0, 10.0 Hz), 114.3 (d d, J=4.0, 11.5 Hz), 111.8 (d d, J=4.0, 21.5 Hz), 105.0 (t, J=25.0 Hz), 66.6, 47.9, 45.9

1H: 8.87 (1H, s), 8.12 (1H, m, J=6.7, 8.5 Hz), 7.0 (1H, m), 6.95 (1H, m), 4.10 (4H, br), 3.83 (4H, s br)

Compound no. 79 (MP: 86). NMR solvent: CDCl3

13C: 163.8 (d d, J=12.0, 253.0 Hz), 160.8 (d d, J=12.5, 259.0 Hz), 158.2 (d, J=5.5 Hz), 148.5, 146.7, 139.7, 131.5 (d, J=4.0, 10.0 Hz), 129, 128.3, 126.1, 114.6 (d d, J=4.0, 11.0 Hz), 111.7 (d d, J=4.5, 21.0 Hz), 105.0 (t, J=26.0 Hz), 47.7, 46.2, 42.8, 38, 31.9

1H: 8.83 (1H, s), 8.13 (1H, m, J=6.8, 8.3 Hz), 7.31 (2H, t, J=7.5 Hz), 7.23 (1H, m, J=7.3 Hz), 7.17 (2H, d, J=7.8 Hz), 7.0 (1H, m), 6.96 (1H, m), 4.62 (2H, m br), 3.02 (2H, br), 2.61 (2H, d, J=6.9 Hz), 1.87 (1H, m), 1.81 (2H, d br, J=14.0 Hz), 1.43 (2H, m, J=4.0, 13.0 Hz)

Compound no. 80 (MP: 91). NMR solvent: CDCl3

13C: 163.7 (d d, J=12, 253.5 Hz), 162.1 (d d, J=11.0, 250.5 Hz), 160.7 (d d, J=12.0, 260.0 Hz), 158.2, 157.9 (d d, J=12.5, 251.5 Hz), 148.8, 146.2, 131.2 (d d, J=4.0, 10.0 Hz), 129.0 (d br, J=10.5 Hz), 126.4 (d d, J=4.5, 13.0 Hz), 114.2 (d d, J=4.0, 12.0 Hz), 111.8 (d d, J=3.0, 22.5 Hz), 111.6 (d d, J=4.0, 21.5 Hz), 104.9 (t, J=25.3 Hz, 2 Carbons), 40.0

1H: 8.89 (1H, s), 7.84 (1H, br), 7.26 (1H, m), 6.98-6.77 (4H, m), 3.51 (3H, s)

Compound no. 81 (MP: 99-100). NMR solvent: CDCl3

13C: 150.4, 149.4, 144.9, 132.9, 132.2, 129, 126.7, 124.9, 119.7, 113.1, 112.5, 40.5, 40.4

1H: 8.03 (1H, d, J=8.4 Hz), 8.0 (1H, d, J=8.4 Hz), 7.59 (1H, m, J=7.8 Hz), 7.41 (1H, t, J=7.6 Hz), 7.03 (2H, br), 6.59 (2H, d br, J=8.0 Hz), 3.62 (3H, s), 2.92 (6H, s)

Compound no. 82 (MP: 179-182 (dec)). NMR solvent: DMSO

13C: 148.6, 144.7, 132.5, 129.6, 125.5, 119.7, 113.4, 61.7, 49, 46, 43.5, 25.8, 22.5, 21.6

1H: 10.52 (1H, s br), 8.20 (1H, d, J=8.3 Hz), 7.93 (1H, d, J=8.4 Hz), 7.71 (1H, t, J=7.7 Hz), 7.55 (1H, t, J=7.7 Hz), 4.43 (2H, d br, J=13.5 Hz), 3.52 (1H, m), 3.41 (2H, d br, J=11.5 Hz), 3.23 (2H, t br), 2.94 (2H, m, J=12.0 Hz), 2.25 (2H, br), 1.88 (2H, br), 1.86 (4H, m), 1.71 (1H, m, J=14.0 Hz), 1.40 (1H, m)

Compound no. 83 (MP: 259-261 (dec)). NMR solvent: DMSO

13C: 148.8, 144.8, 132.5, 129.8, 125.7, 119.7, 113.6, 51.9, 43.3, 42

1H: 11.59 (1H, s br), 8.22 (1H, d, J=8.3 Hz), 7.96 (1H, d, J=8.3 Hz), 7.73 (1H, t, J=7.8 Hz), 7.56 (1H, t, J=7.6 Hz), 4.47 (2H, m), 3.71 (2H, m), 3.52 (2H, m), 3.29 (2H, m), 2.81 (3H, s)

Compound no. 84 (MP: 92). NMR solvent: CDCl3

13C: 155.9, 150.4, 148.7, 145.2, 138.4, 132.6, 129.5, 125.3, 121.8, 119.9, 119.5, 113.5, 37.8

1H: 8.32 (1H, d d, J=1.6, 5.0 Hz), 8.12 (1H, d, J=8.3 Hz), 8.02 (1H, d, J=8.3 Hz), 7.69 (1H, d t, J=1.9, 7.9 Hz), 7.63 (1H, t, J=7.8 Hz), 7.45 (1H, t, J=7.7 Hz), 7.18 (1H, d, J=8.1 Hz), 7.15 (1H, d d, J=5.0, 7.5 Hz), 3.74 (3H, s)

Compound no. 85 (MP: 66). NMR solvent: CDCl3

13C: 149.2, 146.2, 141.8, 131.6, 129.9, 128.4 (2 sig.), 125.9, 125.4, 120, 113.9, 40.3, 35.4, 29.1, 28.5

1H: 8.29 (1H, m, J=8.3 Hz), 8.10 (1H, m, J=8.4 Hz), 7.63 (1H, m, J=1.0, 7.1 Hz), 7.47 (1H, m, J=1.0, 7.1 Hz), 7.33 (1H, br), 7.30 (2H, m), 7.20 (2H, m), 7.19 (1H, m), 3.58 (2H, m), 2.71 (2H, m, J=7.0 Hz), 1.77 (4H, m)

Compound no. 86 (MP: 60). NMR solvent: CDCl3

13C: 149.2, 146.3, 131.6, 129.9, 125.3, 119.9, 114, 40.5, 31.9, 29.6, 29.6, 29.5, 29.5, 29.3, 29.2, 26.8, 22.7, 14.1

1H: 8.29 (1H, d, J=8.3 Hz), 8.10 (1H, d, J=8.4 Hz), 7.63 (1H, m, J=1.0, 7.1 Hz), 7.47 (1H, m, J=1.0, 7.1 Hz), 7.33 (1H, t br, J=5.0 Hz), 3.55 (2H, m), 1.71 (2H, m), 1.50-1.15 (18H, m), 0.88 (3H, t, J=7.1 Hz)

Compound no. 87 (MP: 73). NMR solvent: CDCl3

13C: 148.4, 146.3, 131.7, 129.8, 125.3, 119.9, 114, 49.8, 33, 25.3, 24.7

1H: 8.28 (1H, d, J=8.4 Hz), 8.09 (1H, d, J=8.4 Hz), 7.63 (1H, t, J=7.8 Hz), 7.47 (1H, t, J=7.6 Hz), 7.21 (1H, d, J=7.5 Hz), 3.95 (1H, m), 2.11 (2H, m), 1.83 (2H, m), 1.69 (1H, m), 1.43 (4H, m), 1.29 (1H, m)

Compound no. 88 (MP: 186-188). NMR solvent: CDCl3
13C: 146.5, 146.4, 140.2, 138.2, 135.3, 131.6, 130.3, 128.8, 128, 127.4, 126.9, 125.8, 120.3, 120.2, 114
1H: 9.24 (1H, s), 8.37 (1H, d, J=8.3 Hz), 8.16 (1H, d, J=8.5 Hz), 7.78 (2H, d, J=8.6 Hz), 7.69 (1H, m), 7.68 (2H, d, J=8.6 Hz), 7.62 (2H, d, J=7.7 Hz), 7.53 (1H, t, J=7.8 Hz), 7.47 (2H, t, J=7.7 Hz), 7.37 (1H, t, J=7.6 Hz)

Compound no. 89 (MP: 167 (dec)). NMR solvent: CDCl3
13C: 148.1, 146.8, 129.3, 129, 128.8, 125.9, 120.9, 66.6, 48.5, 45.8
1H: 8.38 (1H, s), 7.88 (2H, d, J=8.2 Hz), 7.47 (2H, t, J=7.7 Hz), 7.39 (1H, m, J=7.5 Hz), 4.04 (2H, m br), 3.84 (6H, m)

Compound no. 90 (MP: 230-231 (dec)). NMR solvent: DMSO
13C: 148.6, 144.7, 132.5, 129.6, 125.6, 119.7, 113.4, 63.3, 61.9, 48.3, 45.6, 43.6, 25.8
1H: 11.53 (1H, s br), 8.20 (1H, d, J=8.3 Hz), 7.93 (1H, d, J=8.2 Hz), 7.71 (1H, m, J=7.5 Hz), 7.55 (1H, m, J=7.6 Hz), 4.44 (2H, d br, J=12.5 Hz), 3.98 (2H, d br, J=11.5 Hz), 3.90 (2H, t, J=12.0 Hz), 3.54 (1H, m), 3.45 (2H, d br, J=12.0 Hz), 3.22 (2H, br), 3.11 (2H, m), 2.28 (2H, br), 1.90 (2H, m, J=4.0, 12.3 Hz)

Compound no. 91 (MP: 143). NMR solvent: DMSO
13C: 152.5, 148.7, 145.1, 144.7, 137.5, 132.6, 129.6, 128.4, 127.8, 127.6, 125.5, 119.7, 118, 115.4, 113.4, 69.4, 49.8, 47.5, 44.9
1H: 8.21 (1H, d, J=8.4 Hz), 7.96 (1H, d, J=8.4 Hz), 7.71 (1H, t, J=7.6 Hz), 7.55 (1H, t, J=7.5 Hz), 7.43 (2H, d, J=8.0 Hz), 7.38 (2H, t, J=7.7 Hz), 7.31 (1H, m, J=7.1 Hz), 6.94 (4H, m), 5.03 (2H, s), 3.90 (4H, m), 3.19 (4H, br)

Compound no. 92 (MP: 218-220 (dec)). NMR solvent: DMSO
13C: 148.7, 144.8, 132.5, 129.6, 125.5, 119.7, 113.4, 60.2, 50.5, 45.7, 43.2, 27.9, 22.7
1H: 11.24 (1H, s), 8.20 (1H, d, J=8.2 Hz), 7.93 (1H, d, J=8.3 Hz), 7.70 (1H, t, J=7.7 Hz), 7.54 (1H, t, J=7.4 Hz), 4.40 (2H, d br, J=13.0 Hz), 3.49 (2H, br), 3.45 (1H, m), 3.22 (2H, m br), 3.08 (2H, br), 2.20 (2H, br), 1.96 (4H, m), 1.89 (2H, m)

Compound no. 93 (MP: 254-256 (dec)). NMR solvent: DMSO
13C: 148.8, 144.8, 132.5, 131.5, 129.8, 129.6, 129.4, 128.8, 125.7, 119.7, 113.6, 58.6, 50.1, 43.6, 42.1
1H: 11.97 (1H, s br), 8.21 (1H, d, J=8.4 Hz), 7.95 (1H, d, J=8.3 Hz), 7.67 (2H, m), 7.56 (1H, t, J=7.7 Hz), 7.47 (3H, m), 7.33 (1H, t, J=7.6 Hz), 4.47 (2H, d br, J=15.0 Hz), 4.39 (2H, s), 3.79 (2H, m), 3.43 (2H, m), 3.28 (2H, m)

Compound no. 94 (MP: 109-111). NMR solvent: CDCl3
13C: 149.4, 145.4, 144.7, 133.2, 129.3, 128.6, 126.8, 126.6, 125.2, 119.8, 113.5, 48.8, 46.1, 42.6, 33.2
1H: 8.12 (1H, m, J=8.3 Hz), 8.02 (1H, m, J=8.4 Hz), 7.63 (1H, m, J=1.0, 7.1 Hz), 7.47 (1H, m, J=1.0, 7.1 Hz), 7.35 (2H, m, J=7.7 Hz), 7.27 (2H, m), 7.25 (1H, m), 4.70 (2H, d br, J=13.5 Hz), 3.29 (2H, br), 2.89 (1H, m), 2.01 (4H, m)

Compound no. 95 (MP: 157). NMR solvent: CDCl3
13C: 150.2, 145.9, 141.5, 136.4, 133.2, 131.8, 131.1, 131, 129.9, 128.7, 118.6, 118, 114.4, 113.2, 58.6, 57.2, 32.6, 30.8, 29.7, 25.5, 25.3
1H: 8.25 (1H, br), 8.09 (1H, d, J=8.6 Hz), 7.90 (1H, d br, J=7.9 Hz), 7.80 (1H, d d, J=1.6, 8.7 Hz), 7.70 (1H, d, J=7.6 Hz), 7.62 (1H, t, J=7.7 Hz), 4.29 (1H, m br), 3.21 (3H, s), 2.02 (2H, m br), 1.90 (2H, m br), 1.73 (1H, br), 1.64 (2H, m), 1.46 (2H, m), 1.17 (1H, m)

Compound no. 96 (MP: 146-147). NMR solvent: CDCl3
13C: 162.6 (d, J=247.0 Hz), 150.3, 146, 137.9, 136.3 (d, J=3.0 Hz), 132.7, 129.1 (d, J=8.4 Hz), 129.0, 117.4, 115.9 (d, J=22.0 Hz), 113.8, 58.6, 57.2, 32.7, 30.4, 29.6, 25.5, 25.3
1H: 8.21 (1H, br), 8.03 (1H, d, J=8.5 Hz), 7.80 (1H, d d, J=1.5, 8.5 Hz), 7.62 (2H, m d, J=5.3, 8.7 Hz), 7.19 (2H, t, J=8.5 Hz), 4.27 (1H, m br), 3.20 (3H, s br), 2.01 (2H, m), 1.89 (2H, m), 1.73 (1H, m), 1.64 (2H, m), 1.44 (2H, m), 1.17 (1H, m)

Compound no. 97 (MP: 158). NMR solvent: CDCl3
13C: 149.9, 146.3, 132.4, 132.3, 122.4, 118.3, 114.9, 58.8, 57.1, 32.6, 30.9, 29.5, 25.5, 25.3
1H: 8.25 (1H, br, J=2.0 Hz), 7.89 (1H, d, J=8.8 Hz), 7.68 (1H, d d, J=2.0, 8.8 Hz), 4.27 (1H, m br), 3.18 (3H, s), 1.98 (2H, m), 1.89 (2H, m), 1.70 (1H, m), 1.61 (2H, m), 1.45 (2H, m), 1.17 (1H, m)

Compound no. 98 (MP: 93-94). NMR solvent: CDCl3
13C: 148.8, 145.1, 133, 129.2, 125.2, 119.7, 114.3, 50.3, 48.5, 26.6, 24
1H: 8.18 (1H, m, J=8.4 Hz), 8.09 (1H, m, J=8.3 Hz), 7.60 (1H, m, J=1.0, 7.0 Hz), 7.46 (1H, m, J=1.0, 7.0 Hz), 4.08 (2H, m), 3.81 (2H, m), 2.04 (4H, m)

Compound no. 99 (MP: 139-141). NMR solvent: CDCl3
13C: 154.7, 149.4, 145.4, 133.2, 130.7, 130.1, 129.3, 125.2, 119.8, 116.2, 113.5, 70.9, 44.4, 41.9, 30.4, 20.5
1H: 8.11 (1H, d, J=8.3 Hz), 8.0 (1H, d, J=8.4 Hz), 7.62 (1H, t, J=7.8 Hz), 7.46 (1H, t, J=7.6 Hz), 7.12 (2H, m, J=8.5 Hz), 6.87 (2H, m, J=8.5 Hz), 4.66 (1H, m), 4.0 (4H, m), 2.31 (3H, s), 2.10 (4H, m)

Compound no. 100 (MP: 80). NMR solvent: CDCl3
13C: 149.3, 145.3, 142.1, 133.2, 129.2, 128.4, 128.3, 125.8, 125.1, 119.8, 113.4, 48.4, 45.8, 38, 35.4, 32.8, 32.2
1H: 8.10 (1H, d, J=8.2 Hz), 7.98 (1H, d, J=8.3 Hz), 7.61 (1H, t, J=8.0 Hz), 7.46 (1H, t, J=7.8 Hz), 7.31 (2H, t, J=7.1 Hz), 7.21 (1H, m), 7.20 (2H, d, J=7.9 Hz), 4.53 (2H, d br, J=12.0 Hz), 3.15 (2H, br), 2.69 (2H, m, J=7.5 Hz), 1.93 (2H, br), 1.49 (2H, br), 1.67 (3H, m)

Compound no. 101 (MP: 134). NMR solvent: CDCl3
13C: 150.7, 150.5, 142.6, 137, 132.8, 129.3, 128.7, 127.7, 125.2, 121.1, 116.9, 112.9, 49.5, 46.5
1H: 7.91 (1H, s), 7.82 (2H, d, J=7.9 Hz), 7.51 (1H, s), 7.42 (2H, t, J=7.8 Hz), 7.32 (3H, m), 6.96 (3H, m), 3.83 (4H, m, J=5.0 Hz), 3.29 (4H, m, J=5.0 Hz)

Compound no. 102 (MP: 122). NMR solvent: CDCl3
13C: 150.6, 142.4, 137.1, 137, 132.8, 129.1, 128.7, 128.4, 127.6, 127.4, 125.1, 113, 62.7, 52.5, 46.5
1H: 7.91 (1H, d, J=1.3 Hz), 7.80 (2H, d, J=8.0 Hz), 7.47 (1H, d, J=1.3 Hz), 7.41 (2H, t, J=7.8 Hz), 7.34 (4H, m), 7.32 (1H, m), 7.29 (1H, m), 3.67 (4H, m, J=5.0 Hz), 3.58 (2H, s), 2.55 (4H, m, J=5.0 Hz)

Compound no. 103 (MP: 154). NMR solvent: CDCl3
13C: 151.3, 142.1, 136.9, 133, 128.7, 127.5, 125.1, 113.2, 57.5, 31.3, 30, 25.4, 25.2
1H: 7.92 (1H, d, J=1.0 Hz), 7.81 (2H, d, J=8.2 Hz), 7.50 (1H, d, J=1.0 Hz), 7.41 (2H, t, J=8.0 Hz), 7.29 (1H, t, J=7.5 Hz), 3.96 (1H, m), 2.99 (3H, s), 1.86 (4H, m), 1.70 (1H, d br, J=13.5 Hz), 1.58 (2H, m, J=3.5, 13.1 Hz), 1.38 (2H, m), 1.13 (1H, t q, J=3.5, 13.0 Hz)

Compound no. 104 (MP: 83). NMR solvent: CDCl3
13C: 150, 145.2, 133.3, 129, 125, 119.7, 113.5, 58.9, 40, 31.2, 25.7, 25.3, 15.1
1H: 8.10 (1H, d, J=8.3 Hz), 7.97 (1H, d, J=8.3 Hz), 7.59 (1H, m, J=1.0, 7.1 Hz), 7.45 (1H, m, J=1.0, 7.1 Hz), 4.17 (1H, m), 3.63 (2H, m, J=6.6 Hz), 2.02 (2H, d br, J=12.0 Hz), 1.85 (2H, d br, J=12.0 Hz), 1.69 (3H, br), 1.31 (5H, br), 1.17 (1H, m)

Compound no. 105 (MP: 204). NMR solvent: CDCl3
13C: 149.2, 145.3, 133, 129.3, 125.2, 119.7, 113.4, 53.5, 53.1, 48, 45.4, 33.5, 31.7 (2 sig.), 23.3
1H: 12.38 (1H, s br), 8.07 (1H, d, J=8.3 Hz), 7.94 (1H, d, J=8.4 Hz), 7.59 (1H, t, J=7.7 Hz), 7.44 (1H, t, J=7.5 Hz), 4.52 (2H, d br, J=12.0 Hz), 3.79 (2H, br), 3.15 (2H, br), 3.12 (2H, m), 2.79 (2H, m br), 2.24 (2H, m br), 2.08 (2H, m br), 1.90 (5H, m br), 1.50 m br)

Compound no. 106 (MP: oil). NMR solvent: CDCl3
13C: 162.9 (d, J=248 Hz), 150.5, 144.6, 141.7, 136.3 (d, J=3 Hz), 133.9, 129.4 (d, J=8 Hz), 125.1, 119.9, 115.8 (d, J=21.5 Hz), 111.5, 58.9 (br), 57.0 (br), 32.6 (br), 30.6 (br), 29.7 (br), 25.5, 25.3
1H: 8.12 (2H, m), 7.66-7.62 (3H, m), 7.17 (2H, m, J=8.7 Hz), 4.28 (1H, br), 3.19 (3H, s br), 2.0 (2H, m br), 1.88 (2H, br), 1.76-1.56 (3H, br), 1.44 (2H, br), 1.18 (1H, m br)

Compound no. 107 (MP: 232-233). NMR solvent: DMSO
13C: 167.2, 149.6, 145.5, 139.7, 136.9, 132.3, 131.8, 131.7, 129.5, 128.9, 128.6, 127.9, 117.3, 113.9, 56.9, 32.5, 30.2, 29, 25.2, 24.8
1H: 13.19 (1H, s br), 8.49 (1H, s), 8.29 (1H, s), 8.06 (1H, m), 7.98 (3H, m), 7.65 (1H, t, J=7.8 Hz), 4.09 (1H, m br), 3.08 (3H, s), 1.88 (2H, m), 1.80 (2H, m), 1.67 (2H, m), 1.60 (1H, m), 1.33 (2H, m), 1.16 (1H, br)

Compound no. 108 (MP: 183). NMR solvent: CDCl3
13C: 169.2, 150.3, 145.9, 140.8, 137.7, 134.1, 132.9, 131, 129.3, 129, 126.7, 126.3, 117.7, 114, 58.8, 57.1, 32.6, 30.7, 29.6, 25.5, 25.3
1H: 8.27 (1H, s br), 8.15 (1H, s br), 8.04 (1H, d, J=8.5 Hz), 7.85 (1H, br), 7.83 (1H, m), 7.81 (1H, m), 7.56 (1H, t, J=7.8 Hz), 6.42 (1H, s br), 6.12 (1H, s b), 4.30 (1H, br), 3.22 (3H, s), 2.03 (2H, m), 1.91 (2H, m), 1.76 (1H, m), 1.67 (2H, m), 1.47 (2H, m), 1.20 (1H, m)

Compound no. 109 (MP: 209-210). NMR solvent: DMSO
13C: 167.7, 149.7, 144.2, 140.9, 139.3, 135.2, 133.4, 130.3, 129.3, 127.4, 126.5, 125.2, 120, 111, 58.3, 57.2, 32.3, 29.6, 28.8, 25.2, 24.8
1H: 8.28 (1H, d, J=8.6 Hz), 8.26 (1H, s br), 8.22 (1H, s br), 8.17 (1H, br), 7.94 (2H, m), 7.91 (1H, m), 7.61 (1H, t, J=7.7 Hz), 7.53 (1H, s br), 4.03 (1H, br), 3.09 (3H, s), 1.89 (2H, m), 1.80 (2H, m), 1.60 (1H, m), 1.36 (2H, m), 1.67 (2H, m), 1.16 (1H, m)

Compound no. 110 (MP: 66-67). NMR solvent: CDCl3
13C: 149.3, 145.3, 142.3, 133.1, 129.2, 128.3, 128.3, 125.7, 125.1, 119.8, 113.4, 48.4, 45.8, 36, 35.9, 35.8, 32.2, 28.5
1H: 8.10 (1H, d, J=8.4 Hz), 7.97 (1H, d, J=8.3 Hz), 7.60 (1H, t, J=7.5 Hz), 7.45 (1H, t, J=7.7 Hz), 7.30 (2H, t, J=7.8 Hz), 7.20 (1H, m), 7.19 (2H, d, J=7.8 Hz), 4.51 (2H, m, br), 3.14 (2H, br), 2.64 (2H, t, J=7.6 Hz), 1.86 (2H, m), 1.69 (2H, m), 1.64 (1H, m), 1.43 (2H, m), 1.38 (2H, m)

Compound no. 111 (MP: 83). NMR solvent: DMSO
13C: 161.4, 150.6, 148.4, 148.1, 130.2, 129.7, 129.1, 129, 126.4, 119.5, 115.9, 48.2, 45.7
1H: 9.17 (1H, s), 8.09 (2H, m, J=1.5, 7.2 Hz), 7.53 (3H, m), 7.25 (2H, t, J=7.6 Hz), 6.99 (2H, d, J=8.1 Hz), 6.83 (1H, t, J=7.2 Hz), 3.90 (4H, br), 3.30 (4H, m)

Compound no. 112 (MP: 203). NMR solvent: DMSO
13C: 167.6, 149.9, 140.1, 137.9, 137.7, 136, 132.6, 128.9, 128.3, 128, 127.1, 124.4, 115.6, 61.7, 52.1, 45.9
1H: 8.13 (1H, d, J=1.2 Hz), 8.09 (1H, d, J=1.2 Hz), 7.98 (1H, s br), 7.91 (4H, m br), 7.36 (1H, s br), 7.33 (4H, m), 7.26 (1H, m), 3.56 (4H, m, J=5.5 Hz), 3.53 (2H, s), 2.47 (4H, m, J=5.5 Hz)

Compound no. 113 (MP: 231-233 (dec)). NMR solvent: DMSO
13C: 167.6, 149.7, 142.8, 139.3, 138, 135.7, 132.6, 129.9, 128, 127.7, 126.2, 124.2, 115.6, 39.6
1H: 7.95 (1H, s br), 7.84 (2H, d, J=8.5 Hz), 7.74 (1H, d, J=1.0 Hz), 7.72 (2H, d, J=8.5 Hz), 7.60 (1H, d, J=1.0 Hz), 7.41 (2H, t, J=7.6 Hz), 7.35 (1H, s br), 7.35 (2H, m), 7.31 (1H, t, J=7.1 Hz), 3.43 (3H, s)

Compound no. 114 (MP: 135-136). NMR solvent: DMSO
13C: 153.8, 149.8, 148.7, 144.7, 132.6, 129.5, 125.4, 122.4, 119.6, 113.3, 47.7, 45.2, 40.5, 31.8
1H: 8.50 (2H, m, J=5.0 Hz), 8.20 (1H, d, J=8.5 Hz), 7.95 (1H, d, J=8.3 Hz), 7.71 (1H, t, J=7.9 Hz), 7.54 (1H, t, J=7.7 Hz), 7.34 (2H, m, J=5.0 Hz), 4.39 (2H, br), 3.32 (2H, br), 2.96 (1H, m), 1.95 (2H, br), 1.82 (2H, m, J=4.0, 12.3 Hz)

Compound no. 115 (MP: oil). NMR solvent: CDCl3
13C: 150.5, 145.2, 138.1, 133.2, 129.1, 128.7, 128.6, 126.6, 125.1, 119.7, 113.8, 53.1 (br), 38.2 (very broad), 34.3 (br)
1H: 8.08 (1H, d, J=8.3 Hz), 7.91 (1H, br), 7.57 (1H, t, J=7.7 Hz), 7.44 (1H, t, J=7.7 Hz), 7.23 (5H, br), 3.96 (2H, br), 3.31 (3H, s), 3.10 (2H, m, J=7.2 Hz)

Compound no. 116 (MP: 147). NMR solvent: CDCl3
13C: 181.1, 166.4, 152.1, 149.4, 148.6, 145.4, 134.7, 133.1, 129.5, 125.3, 123.7, 122.9, 119.9, 113.5, 46.9, 44.8, 34, 29.2
1H: 9.32 (1H, d, J=1.7 Hz), 8.76 (1H, d d, J=1.6, 4.9 Hz), 8.37 (1H, d t, J=2.0, 8.0 Hz), 8.12 (1H, d, J=8.4 Hz), 8.0 (1H, d, J=8.4 Hz), 7.63 (1H, t, J=7.9 Hz), 7.48 (1H, t, J=7.9 Hz), 7.45 (1H, d d, J=4.9, 8.0 Hz), 4.56 (2H, d br), 3.57 (2H, br), 3.46 (1H, m), 2.37 (2H, m), 2.27 (2H, m)

Compound no. 117 (MP: 138-139). NMR solvent: CDCl3
13C: 155.4, 149.4, 145.4, 133.1, 129.6, 129.4, 126.2, 125.2, 119.9, 117.4, 113.5, 71.2, 44.4, 42, 30.4
1H: 8.11 (1H, d, J=8.4 Hz), 7.99 (1H, d, J=8.2 Hz), 7.62 (1H, t, J=7.8 Hz), 7.47 (1H, t, J=7.8 Hz), 7.27 (2H, m, J=9.0 Hz), 6.89 (2H, m, J=9.0 Hz), 4.67 (1H, m), 4.01 (4H, s br), 2.15 (2H, m), 2.06 (2H, m)

Compound no. 118 (MP: oil). NMR solvent: CDCl3
13C: 150.5, 142.5, 141.0, 133.2, 129.2, 128.5, 128.2, 126.1, 125.1, 119.8, 113.6, 51.4, 50.4, 38.1, 35.8, 32.9, 29.6, 28.6
1H: 8.10 (1H, d, J=8.5 Hz), 8.01 (1H, d, J=8.2 Hz), 7.61 (1H, t, J=7.9 Hz), 7.46 (1H, t, J=7.7 Hz), 7.24 (5H, br), 3.71 (2H, m, J=7.2 Hz), 3.31 (3H, br), 2.71 (2H, br), 2.15 (2H, m, J=7.5 Hz)

Compound no. 119 (MP: oil). NMR solvent: CDCl3
13C: 160.1, 151.0, 145.3, 137.4, 133.3, 129.9, 129.3, 125.2, 120.3, 119.9, 113.7 (2 sig.), 113.4, 55.3, 54.2, 37.5
1H: 8.11 (1H, d, J=8.2 Hz), 8.06 (1H, d, J=8.3 Hz), 7.62 (1H, t, J=7.8 Hz), 7.47 (1H, t, J=7.5 Hz), 7.30 (1H, t, J=7.7 Hz), 6.96 (2H, br), 6.87 (1H, d, J=8.2), 4.89 (2H, br), 3.81 (3H, s), 3.29 (3H, br)

Compound no. 120 (MP: 70-71). NMR solvent: CDCl3
13C: 156.9, 149.4, 145.4, 133.2, 129.7, 129.3, 125.2, 121.3, 119.8, 116.1, 113.5, 70.6, 44.4, 42, 30.4
1H: 8.11 (1H, d, J=8.3 Hz), 8.0 (1H, d, J=8.3 Hz), 7.62 (1H, t, J=7.8 Hz), 7.47 (1H, t, J=7.6 Hz), 7.33 (2H, m, J=8.0 Hz), 7.0 (1H, t, J=7.4 Hz), 6.97 (2H, d, J=8.3 Hz), 4.72 (1H, m), 4.01 (4H, s br), 2.16 (2H, m), 2.10 (2H, m)

Compound no. 121 (MP: 115). NMR solvent: CDCl3
13C: 162.1 (d, J=245.0 Hz), 149.3, 145.3, 133.1, 133.1, 130.6 (d, J=8.0 Hz), 129.4, 125.2, 119.8, 115.2 (d, J=21.0 Hz), 113.5, 61.9, 52.7, 48.1, 45.2
1H: 8.10 (1H, m, J=8.3 Hz), 7.99 (1H, m, J=8.4 Hz), 7.61 (1H, m, J=1.0, 7.0, 8.2 Hz), 7.46 (1H, m, J=1.0, 7.0, 8.2 Hz), 7.32 (2H, m d, J=5.6, 8.7 Hz), 7.06 (2H, m t, J=8.3 Hz), 3.93 (4H, s br), 3.56 (2H, s), 2.63 (4H, s br)

Compound no. 122 (MP: 188 (dec)). NMR solvent: DMSO
13C: 148.6, 144.7, 132.5, 129.5, 125.4, 119.6, 113.3, 59.7, 52.9, 46.5, 45.6, 44.1, 42.1, 27.9
1H: 10.72 (1H, br), 8.19 (1H, d, J=8.4 Hz), 7.91 (1H, d, J=8.3 Hz), 7.70 (1H, t, J=7.9 Hz), 7.53 (1H, t, J=7.8 Hz), 4.28 (2H, s br), 3.21 (4H, m br), 2.96 (4H, m br), 2.68 (6H, m), 1.90 (2H, m br), 1.57 (2H, m br)

Compound no. 123 (MP: oil). NMR solvent: CDCl3
13C: 151.0, 145.2, 137.9, 134.7, 133.2, 130.1, 129.5, 128.2, 127.9, 126.2, 125.3, 119.9, 113.7, 54.8, 53.4, 37.8
1H: 8.11 (1H, d, J=8.5 Hz), 8.07 (1H, d, J=8.3 Hz), 7.63 (1H, d d d, J=1, 7.1, 8.2 Hz), 7.48 (1H, d d d, J=1, 7.0, 8.2 Hz), 7.42 (1H, br), 7.32 (3H, br), 4.90 (2H, br), 3.28 (3H, br)

Compound no. 124 (MP: 258-259 (dec)). NMR solvent: DMSO
13C: 161.6, 148.4, 148.3, 131.5, 130.3, 129.6, 129.5, 129.1, 129, 128.8, 126.5, 58.6, 50, 42.6
1H: 12.03 (1H, s br), 9.16 (1H, s), 8.07 (2H, m), 7.67 (2H, m), 7.51 (3H, m), 7.45 (3H, m), 4.55 (2H, m), 4.38 (2H, s), 3.73 (2H, m, J=12.0 Hz), 3.41 (2H, br, J=11.7 Hz), 3.24 (2H, m)

Compound no. 125 (MP: 232 (dec)). NMR solvent: DMSO
13C: 161.4, 159.9, 148.4, 148.2, 136.8, 131.5, 129.6, 129.5, 128.8, 128.5, 128.1, 128, 127.9, 122.2, 115.2, 69.4, 58.6, 50, 42.6
1H: 11.97 (1H, s), 9.12 (1H, s), 8.0 (2H, d, J=8.6 Hz), 7.66 (2H, m), 7.45 (5H, m), 7.40 (2H, t, J=7.5 Hz), 7.33 (1H, t, J=7.2 Hz), 7.15 (2H, d, J=8.6 Hz), 5.17 (2H, s), 4.55 (2H, m), 4.37 (2H, s), 3.70 (2H, m, J=12.0 Hz), 3.41 (2H, m), 3.24 (2H, m)

Compound no. 126 (MP: 135). NMR solvent: CDCl3
13C: 147.3, 146.3, 131.6, 129.7, 125.2, 119.9, 114.1, 52.8, 41.6, 36.1, 29.4
1H: 8.27 (1H, d, J=8.4 Hz), 8.09 (1H, d, J=8.4 Hz), 7.61 (1H, m, J=1.0, 7.0, 8.0 Hz), 7.45 (1H, m, J=1.0, 7.0, 8.0 Hz), 7.17 (1H, s), 2.20 (9H, s), 1.76 (6H, s)

Compound no. 127 (MP: 101). NMR solvent: DMSO
13C: 148.6, 144.7, 132.5, 129.5, 125.5, 119.7, 113.3, 62.6, 48.4, 45.2, 28.3, 25.9, 25.4
1H: 8.18 (1H, d, J=8.2 Hz), 7.91 (1H, d, J=8.5 Hz), 7.69 (1H, t, J=7.8 Hz), 7.56 (1H, t, J=7.6 Hz), 3.71 (4H, m), 2.63 (4H, s br), 2.30 (1H, m), 1.76 (2H, m), 1.73 (2H, m), 1.56 (1H, d, J=12.4 Hz), 1.20 (4H, m), 1.07 (1H, m)

Compound no. 128 (MP: oil). NMR solvent: CDCl3
13C: 149.4, 145.3, 138.4, 133.1, 129.3, 128.5, 127.7, 127.4, 125.1, 119.8, 113.5, 72.5, 70.1, 44.9, 42.3, 30.9
1H: 8.10 (1H, d, J=8.4 Hz), 7.98 (1H, d, J=8.4 Hz), 7.61 (1H, d d d, J=1, 7.1, 8.2 Hz), 7.46 (1H, d d d, J=1, 7.1, 8.2 Hz), 7.40-7.28 (5H, m), 4.62 (2H, s), 4.06 (2H, m), 3.81 (3H, m), 2.08 (2H, m), 1.94 (2H, br)

Compound no. 129 (MP: oil). NMR solvent: CDCl3
13C: 150.5, 145.2, 142.3, 133.2, 129.2, 128.4, 128.3, 125.7, 125.1, 119.7, 113.6, 51.8, 50.6, 38.0, 35.8, 31.1, 28.0, 26.8, 26.2
1H: 8.11 (1H, d, J=8.3 Hz), 8.0 (1H, d, J=8.4 Hz), 7.61 (1H, d d d, J=1.0, 7.0, 8.2 Hz), 7.46 (1H, d d d, J=1.0, 7.0, 8.2 Hz), 7.27 (2H, t, J=7.7 Hz), 7.17 (3H, m), 3.66 (2H, m), 3.31 (3H, br), 2.64 (2H, br), 1.82 (2H, m, J=7.7 Hz), 1.71 (2H, br), 1.47-1.31 (2H, very broad)

Compound no. 130 (MP: oil). NMR solvent: CDCl3
13C: 162.4 (d, J=247 Hz), 150.9, 145.2, 133.2, 131.5 (d, J=3 Hz), 129.9, 129.4, 125.3, 119.9, 115.8 (d, J=22 Hz), 113.6, 54.5, 53.2, 37.6
1H: 8.11 (1H, d, J=8.4 Hz), 8.05 (1H, d, J=8.3 Hz), 7.63 (1H, d d d, J=1.0, 7.1, 8.2 Hz), 7.48 (1H, d d d, J=1.0, 7.1, 8.2 Hz), 7.41 (2H, br), 7.08 (2H, t, J=8.1 Hz), 4.88 (2H, br), 3.24 (3H, br)

Compound no. 131 (MP: oil). NMR solvent: CDCl3
13C: 150.9, 145.2, 133.9, 133.2, 130.9, 129.4, 128.9, 126.8, 126.1, 125.3 (2 Signa Hzs), 123.1, 119.9, 113.6, 53.1, 51.7, 37.5
1H: 8.24-8.06 (3H, m), 7.98-7.82 (2H, m), 7.65 (1H, d d d, J=1.1, 7.0, 8.0 Hz), 7.60-7.45 (4H, m, br), 7.48 (1H, d d d, J=1.0, 7.0, 8.0 Hz), 5.38 (2H, m br), 3.28 (3H, s br)

Compound no. 132 (MP: 129-130 (dec)). NMR solvent: DMSO
13C: 161.3, 154.6, 150.6, 148.5, 147.6, 130, 129.6, 127.4, 120.8, 115.9, 115.5, 71.1, 51.8, 44.7, 43, 41.9, 30.3, 20.1
1H: 11.17 (1H, s), 9.05 (1H, s), 7.92 (2H, d, J=7.8 Hz), 7.11 (2H, d, J=7.8 Hz), 7.08 (2H, d, J=7.6 Hz), 6.89 (2H, d, J=7.6 Hz), 4.64 (1H, m br), 3.95 (2H, m), 3.93 (2H, m), 3.61 (2H, m), 3.48 (2H, m), 3.17 (4H, m), 2.79 (3H, s), 2.22 (3H, s), 2.05 (2H, s br), 1.74 (2H, br)

Compound no. 133 (MP: 140). NMR solvent: DMSO
13C: 161.7, 152.1, 148.6, 147.7, 138, 129, 128.3, 127.4, 127.1, 119.5, 114.7, 65.9, 62, 52.4, 47.4, 46.2
1H: 9.04 (1H, s), 7.88 (2H, d, J=8.2 Hz), 7.33 (4H, br), 7.27 (1H, br), 7.02 (2H, d, J=8.2 Hz), 3.75 (4H, m br), 3.70 (4H, m br), 3.52 (2H, br), 3.23 (4H, br), 2.50 (4H, br)

Compound no. 134 (MP: oil). NMR solvent: DMSO
13C: 163.1 (d d, J=13.5, 251.5 Hz), 160.1 (d d, J=13.0, 257.5 Hz), 157.1 (d, J=6 Hz), 154.6, 148.2, 147.4, 131.6 (d d, J=4.5, 10.5 Hz), 130.0, 129.6, 116.0, 114.6 (d d, J=4.0, 11.5 Hz), 112.3 (d d, J=4.0, 22.0 Hz), 105.3 (t, J=25.5 Hz), 71.1, 43.1 (br), 30.3, 20.1
1H: 9.17 (1H, s), 8.12 (1H, d t, J=6.7, 8.6 Hz), 7.43 (1H, d d d, J=2.5, 9.4, 11.5 Hz), 7.26 (1H, d t, J=2.5, 8.5 Hz), 7.08 (2H, d, J=8.4 Hz), 6.89 (2H, d, J=8.4 Hz), 4.64 (1H, m, J=3.7 Hz), 3.93 (2H, m br), 3.61 (2H, m br), 2.22 (3H, s br), 2.05 (2H, m), 1.73 (2H, m)

Compound no. 135 (MP: oil). NMR solvent: CDCl3
13C: 149.4, 145.3, 141.8, 133.1, 129.3, 128.4, 128.3, 125.8, 125.1, 119.8, 113.4, 73.0, 67.3, 45.0, 42.4, 32.3, 31.5, 30.9
1H: 8.11 (1H, d, J=8.4 Hz), 7.98 (1H, d, J=8.3 Hz), 7.61 (1H, t, J=7.7 Hz), 7.46 (1H, t, J=7.5 Hz), 7.30 (2H, t, J=7.9 Hz), 7.21 (3H, m), 4.04 (2H, m), 3.77 (2H, m), 3.66 (1H, m, J=3.4 Hz), 3.50 (2H, t, J=6.3 Hz), 2.74 (2H, t, J=7.9 Hz), 2.02 (2H, m), 1.94 (2H, m), 1.85 (2H, m)

Compound no. 136 (MP: 197-198). NMR solvent: DMSO
13C: 151.5, 148.7, 144.7, 143.7, 132.6, 129.6, 125.5, 119.7, 118.6, 115.6, 113.4, 50.3, 47.4, 45.2
1H: 8.95 (1H, s), 8.20 (1H, d, J=8.3 Hz), 7.95 (1H, d, J=8.4 Hz), 7.71 (1H, t, J=7.7 Hz), 7.55 (1H, t, J=7.7 Hz), 6.85 (2H, m, J=9.0 Hz), 6.68 (2H, m, J=9.0 Hz), 3.89 (4H, m br), 3.12 (4H, m)

Compound no. 137 (MP: 100-101). NMR solvent: CDCl3
13C: 154.4, 150.8, 149.4, 145.4, 133.1, 129.3, 125.2, 119.8, 117.8, 114.8, 113.5, 72, 55.7, 44.5, 41.9, 30.5
1H: 8.11 (1H, d, J=8.5 Hz), 8.0 (1H, d, J=8.6 Hz), 7.62 (1H, d, J=7.6 Hz), 7.47 (1H, m, J=7.8 Hz), 6.92 (2H, m, J=9.2 Hz), 6.86 (2H, m, J=9.2 Hz), 4.57 (1H, m), 3.99 (4H, m br), 3.79 (3H, s), 2.09 (4H, m)

Compound no. 138 (MP: 187-188). NMR solvent: DMSO
13C: 161.5, 151.9, 150.9, 149.8, 147.4, 129, 127.4, 120, 119.3, 115.7, 115, 48.2, 47.5, 37.8
1H: 9.02 (1H, s), 7.92 (2H, m, J=9.0 Hz), 7.25 (2H, d d, J=7.3, 8.5 Hz), 7.11 (2H, m, J=9.0 Hz), 7.0 (2H, d, J=8.5 Hz), 6.81 (1H, t, J=7.3 Hz), 3.38 (4H, m), 3.29 (4H, m), 3.16 (6H, s br)

Compound no. 139 (MP: 161-162). NMR solvent: DMSO
13C: 161.7, 152, 148.6, 147.7, 127.4, 119.5, 114.7, 65.9, 54.4, 47.2, 46.3, 45.7

1H: 9.04 (1H, s), 7.89 (2H, m, J=9.0 Hz), 7.03 (2H, m, J=9.0 Hz), 3.75 (4H, br), 3.70 (4H, m), 3.23 (4H, m, J=5.0 Hz), 2.47 (4H, m, J=5.0 Hz), 2.23 (3H, s)

Compound no. 140 (MP: 167-168). NMR solvent: CDCl3
13C: 161.8, 161, 156.4, 149.8, 147.2, 134.2, 128.8, 126.9, 120.3, 118.7, 118.4, 106.3, 39.3, 38.6
1H: 8.84 (1H, s), 8.19 (2H, d, J=8.8 Hz), 7.64 (2H, d, J=9.0 Hz), 7.15 (2H, d, J=8.8 Hz), 7.08 (2H, d, J=9.0 Hz), 3.41 (3H, s), 3.23 (3H, s)

Compound no. 141 (MP: 144-145). NMR solvent: CDCl3
13C: 162, 160.9, 156.6, 148.6, 147.6, 134.2, 128.9, 126.5, 120.3, 118.7, 118.4, 106.4, 66.6, 46.6
1H: 8.85 (1H, s), 8.17 (2H, d, J=8.8 Hz), 7.64 (2H, d, J=8.9 Hz), 7.15 (2H, d, J=8.8 Hz), 7.08 (2H, d, J=8.9 Hz), 4.0 (8H, s br)

Compound no. 142 (MP: 202-203). NMR solvent: DMSO
13C: 149, 145.5, 131.4, 130.2, 125.8, 119.9, 113.6, 49.6, 45.7, 45.4, 45, 24.7, 21.4, 17.2
1H: 10.72 (1H, s br), 9.55 (1H, d, J=6.8 Hz), 8.23 (1H, d, J=8.3 Hz), 8.18 (1H, d, J=8.2 Hz), 7.74 (1H, m, J=8.0 Hz), 7.57 (1H, m, J=7.6 Hz), 4.41 (1H, m), 3.66 (1H, t, J=11.5 Hz), 3.40 (1H, m), 3.20 (4H, m), 2.30 (1H, m), 2.12 (1H, m), 1.94 (1H, m), 1.74 (1H, m)

Compound no. 143 (MP: 108-109). NMR solvent: CDCl3
13C: 150.6, 145.2, 133.2, 129.2, 125.1, 119.8, 113.5, 96.3, 70.3, 70, 57.9, 55.8, 32.6, 31, 30.2, 26.1, 24.8, 22.6
1H: 8.10 (1H, d, J=8.3 Hz), 7.98 (1H, d, J=8.4 Hz), 7.61 (1H, t, J=7.5 Hz), 7.46 (1H, t, J=7.6 Hz), 4.37 (1H, br), 3.53 (4H, s), 3.18 (3H, s), 2.41 (2H, br), 1.91 (4H, m), 1.53 (2H, br), 0.99 (6H, s)

Compound no. 144 (MP: 67-68). NMR solvent: CDCl3
13C: 153.8, 152.9, 149.3, 145.3, 133.1, 129.2, 125.1, 119.8, 115.3, 114.6, 113.4, 65.6, 55.7, 48.4, 45.8, 35.6, 32.9, 32.1
1H: 8.11 (1H, m, J=8.4 Hz), 7.98 (1H, d, J=8.4 Hz), 7.61 (1H, m, J=1.0, 7.1, 8.1 Hz), 7.46 (1H, m, J=1.0, 7.1, 8.1 Hz), 6.85 (4H, s), 4.55 (2H, d br, J=13.0 Hz), 4.01 (2H, t, J=6.2 Hz), 3.78 (3H, s), 3.19 (2H, s br), 1.96 (3H, m), 1.81 (2H, q, J=6.2 Hz), 1.52 (2H, m)

Compound no. 145 (MP: 179-180 (dec)). NMR solvent: DMSO
13C: 160.8, 160.4, 156.2, 148.3, 148.2, 147.9, 134.8, 129.4, 128.6, 126.3, 122.8, 120.4, 118.7, 117.7 (2 sig.), 105.7, 50, 44.9
1H: 9.19 (1H, s), 8.15 (2H, d, J=8.6 Hz), 7.88 (2H, d, J=8.4 Hz), 7.35 (2H, t, J=7.3 Hz), 7.29 (2H, br), 7.28 (2H, d, J=8.6 Hz), 7.19 (2H, d, J=8.4 Hz), 7.05 (1H, t, J=7.0 Hz), 4.05 (4H, br), 3.46 (4H, m br)

Compound no. 146 (MP: 192-193). NMR solvent: DMSO
13C: 167.1, 160.8, 158.8, 157.4, 149.7, 147.7, 129.9, 129.6, 128.4, 125.6, 119.5, 118.1, 37.8
1H: 9.10 (1H, s), 8.10 (2H, d, J=8.8 Hz), 7.97 (1H, s br), 7.93 (2H, d, J=8.9 Hz), 7.35 (1H, s br), 7.20 (2H, d, J=8.8 Hz), 7.11 (2H, d, J=8.9 Hz), 3.16 (6H, s br)

Compound no. 147 (MP: 220-221). NMR solvent: DMSO
13C: 167.1, 160.9, 158.7, 157.5, 148.5, 148.1, 129.9, 129.6, 128.5, 125.5, 119.5, 118, 65.9, 46.2
1H: 9.13 (1H, s), 8.10 (2H, d, J=8.8 Hz), 7.98 (1H, s br), 7.93 (2H, d, J=8.9 Hz), 7.36 (1H, s br), 7.20 (2H, d, J=8.8 Hz), 7.11 (2H, d, J=8.9 Hz), 3.75-3.70 (8H, m)

Compound no. 148 (MP: 187-188). NMR solvent: DMSO
13C: 167.1, 161, 158.7, 157.5, 150.6, 148.4, 148.1, 129.9, 129.6, 129.1, 128.5, 125.5, 119.5, 119.5, 118.1, 115.9, 48.2, 45.6
1H: 9.16 (1H, s), 8.12 (2H, d, J=8.5 Hz), 7.98 (1H, s br), 7.94 (2H, d, J=8.6 Hz), 7.36 (1H, s br), 7.25 (2H, d, J=8.0 Hz), 7.21 (2H, d, J=8.5 Hz), 7.11 (2H, d, J=8.5 Hz), 6.98 (2H, d, J=8.2 Hz), 6.82 (1H, t, J=7.5 Hz), 3.90 (4H, m), 3.29 (4H, m)

Compound no. 149 (MP: 191-192). NMR solvent: DMSO
13C: 167.1, 160.3, 158.6, 157.4, 148.7, 147.4, 143.2, 129.8, 129.6, 129.3, 128.1, 127.3, 126.1, 125.4, 119.2, 118.2, 39.9
1H: 8.95 (1H, s), 7.97 (1H, s br), 7.92 (2H, d, J=8.6 Hz), 7.75 (2H, d, J=8.2 Hz), 7.37 (2H, t, J=7.5 Hz), 7.35 (1H, s br), 7.32 (2H, d, J=8.0 Hz), 7.28 (1H, t, J=7.0 Hz), 7.08 (2H, d, J=8.7 Hz), 7.07 (2H, d, J=8.7 Hz), 3.49 (3H, s)

Compound no. 150 (MP: 91-92). NMR solvent: CDCl3
13C: 162.3 (d, J=246.5 Hz), 151.8, 141.5, 137, 135.2, 129.1, 129.0 (d, J=3.3 Hz), 128.2, 127.5, 126.8 (d, J=8.0 Hz), 115.6 (d, J=21.5 Hz), 112.8, 54.1, 36.5
1H: 7.96 (1H, d, J=1.3 Hz), 7.73 (2H, d d, J=5.3, 8.9 Hz), 7.49 (1H, d, J=1.3 Hz), 7.43 (2H, m, J=7.5 Hz), 7.37 (1H, m, J=7.2 Hz), 7.32 (2H, m, J=8.1 Hz), 7.08 (2H, m t, J=8.9 Hz), 4.69 (2H, s), 3.09 (3H, s)

Compound no. 151 (MP: 143-144). NMR solvent: DMSO
13C: 167, 160.9, 158.6, 157.3, 149.7, 147.7, 136.2, 129.6, 129.6, 128.5, 128.2, 127.5, 127.4, 125.4, 119.2, 117.9, 53.3, 36.3
1H: 9.14 (1H, s), 8.05 (2H, d br, J=8.0 Hz), 7.93 (2H, d, J=8.5 Hz), 7.87 (1H, s br), 7.40 (4H, m), 7.33 (1H, m), 7.21 (1H, s br), 7.17 (2H, d, J=8.0 Hz), 7.10 (2H, d, J=8.5 Hz), 4.82 (2H, s), 3.14 (3H, s)

Compound no. 152 (MP: 95-96). NMR solvent: CDCl3
13C: 150.5, 145.2, 138.7, 133.2, 129.2, 128.4, 127.5, 127.5, 125.1, 119.8, 113.5, 76.1, 70.1, 56.3, 32.6, 31, 27.5
1H: 8.10 (1H, d, J=8.4 Hz), 7.98 (1H, d, J=8.3 Hz), 7.60 (1H, t, J=7.6 Hz), 7.46 (1H, t, J=8.0 Hz), 7.40-7.33 (4H, m), 7.30 (1H, m), 4.58 (2H, s), 4.30 (1H, m), 3.36 (1H, m), 3.16 (3H, s), 2.24 (2H, d br, J=10.0 Hz), 2.06 (2H, d br, J=12.0 Hz), 1.72 (2H, m, J=1.8, 13.0 Hz), 1.51 (2H, s br)

Compound no. 153 (MP: 75). NMR solvent: CDCl3
13C: 160.8, 160, 149.4, 145.4, 133.2, 129.9, 129.3, 125.2, 119.8, 113.5, 106.5, 106.4, 100.9, 71.8, 55.3, 48.1, 45.4, 36.1, 29
1H: 8.11 (1H, m, J=1.0, 8.3 Hz), 7.99 (1H, m, J=1.0, 8.3 Hz), 7.61 (1H, m, J=1.0, 7.1 Hz), 7.47 (1H, m, J=1.0, 7.1 Hz), 7.20 (1H, t, J=8.3 Hz), 6.55-6.49 (2H, m), 6.48 (1H, t, J=2.5 Hz), 4.62 (2H, m br, J=13.5 Hz), 3.88 (21-1, d, J=6.5 Hz), 3.81 (3H, s), 3.24 (2H, br), 2.20 (1H, m), 2.04 (2H, br), 1.66 (2H, m)

Compound no. 154 (MP: 129-130). NMR solvent: DMSO
13C: 148.6, 144.7, 132.5, 129.6, 125.5, 119.7, 113.3, 66.4, 51.4, 47.7, 44.9, 29.8, 23.7
1H: 8.19 (1H, d, J=8.4 Hz), 7.91 (1H, m, J=8.4 Hz), 7.69 (1H, m, J=1.0, 7.0, 8.0 Hz), 7.53 (1H, m, J=1.0, 7.0, 8.0 Hz), 3.73 (4H, m), 2.51 (1H, m), 2.50 (4H, m), 1.79 (2H, m), 1.61 (2H, m), 1.49 (2H, m), 1.34 (2H, m)

Compound no. 155 (MP: 108). NMR solvent: CDCl3
13C: 158.9, 150.7, 148.4, 147.4, 132.4, 129.3, 127.9, 127.8, 127.7, 120.8, 116.7, 49.4, 46.4
1H: 8.83 (1H, s), 7.79 (1H d d, J=1.2, 3.7 Hz), 7.44 (1H, d d, J=1.2, 5.1 Hz), 7.33 (2H, d d, J=7.3, 8.8 Hz), 7.15 (1H, d d, J=3.7, 5.1 Hz), 6.98 (2H, m d, J=8.8 Hz), 6.95 (1H, m, J=7.3 Hz), 4.11 (4H, br), 3.34 (4H, m, J=5.2 Hz)

Compound no. 156 (MP: 66-67). NMR solvent: CDCl3
13C: 150.9, 145.2, 137.8, 133.2, 129.2, 128.4, 127.7, 127.5, 125.1, 119.7, 113.6, 73.2, 68.2, 51.5, 51, 39.7, 37.1
1H: 8.10 (1H, d, J=8.3 Hz), 7.96 (1H, d, J=8.0 Hz), 7.58 (1H, t, J=8.2 Hz), 7.45 (1H, t, J=7.9 Hz), 7.30 (5H, m), 4.53 (2H, s br), 3.93 (2H, s br), 3.85 (2H, s br), 3.41 (3H, s br)

Compound no. 157 (MP: oil). NMR solvent: CDCl3
13C: 154.1, 152.3, 150.9, 150.8, 145.2, 133.2, 129.3, 125.2, 119.8, 115.3, 114.6, 113.7, 66.9, 55.7, 50.9, 40, 37.3

1H: 8.10 (1H, d, J=8.3 Hz), 8.03 (1H, d, J=8.4 Hz), 7.61 (1H, m, J=1.0, 7.1, 8.3 Hz), 7.47 (1H, m, J=1.0, 7.1, 8.3 Hz), 6.81 (4H, m br), 4.33 (2H, t br, J=5.2 Hz), 4.10 (2H, br), 3.76 (3H, s), 3.55-3.42 (3H, m br)

Compound no. 158 (MP: 257-259 (dec)). NMR solvent: DMSO

13C: 157.8, 148.2 (2 sig.), 132, 131.5, 129.6, 129.4, 128.8 (2 sig.), 128.3, 127.7, 58.6, 49.9, 42.6

1H: 11.94 (1H, s br), 9.13 (1H, s), 7.73 (2H, d, J=4.0 Hz), 7.65 (2H, m), 7.46 (3H, m), 7.20 (1H, t, J=4.2 Hz), 4.47 (2H, br), 4.37 (2H, s), 3.70 (2H, m, J=12.5 Hz), 3.40 (2H, d br, J=12.0 Hz), 3.22 (2H, m)

Compound no. 159 (MP: 143). NMR solvent: CDCl3

13C: 149.4, 145.3, 133.1, 129.3, 125.2, 119.8, 113.5, 66.4, 44.9, 42.4, 34

1H: 8.10 (1H, d, J=8.3 Hz), 7.98 (1H, d, J=8.4 Hz), 7.61 (1H, t, J=8.0 Hz), 7.46 (1H, t, J=7.7 Hz), 4.16 (2H, m), 4.12 (1H, m), 3.69 (2H, m), 2.10 (2H, m), 1.80 (2H, m), 1.86 (1H, d, J=3.8 Hz)

Compound no. 160 (MP: 78-80). NMR solvent: CDCl3

13C: 163.6, 149.2, 146.1, 143.3, 136.8, 129.5, 128.7, 128.3, 127.4, 126.5, 125.8, 40.3, 34.4

1H: 8.52 (1H, s), 7.33 (3H, m), 7.21 (2H, m), 7.20 (1H, m), 7.11 (2H, d br, J=8.0 Hz), 7.0 (2H, d br, J=7.0 Hz), 3.86 (2H, s), 3.53 (3H, s)

Compound no. 161 (MP: 89). NMR solvent: CDCl3

13C: 146.5, 142.6, 136.2, 132.7, 128.7, 127.7, 125.2, 112, 81.1, 80.3, 61.8, 22.8

1H: 7.96 (1H, d, J=1.3 Hz), 7.79 (2H, m, J=8.3 Hz), 7.52 (1H, d, J=1.3 Hz), 7.41 (2H, m, J=7.9 Hz), 7.30 (1H, m, J=7.3 Hz), 5.13 (2H, s), 3.88 (2H, s), 1.62 (6H, s)

Compound no. 162 (MP: 119-121). NMR solvent: CDCl3

13C: 145.7, 144.1, 133.7, 129.3, 124.2, 120.8, 117.5, 82.4, 79.5, 62.4, 22.9

1H: 8.48 (1H, s br), 7.96 (1H, d, J=8.7 Hz), 7.59 (1H, d d, J=1.5, 8.7 Hz), 5.53 (2H, s), 3.90 (2H, s), 1.68 (6H, s)

Compound no. 163 (MP: 231-232). NMR solvent: DMSO

13C: 167.6, 145.6, 144.3, 141.2, 139.3, 135.2, 133, 130.3, 129.3, 127.5, 126.5, 125.6, 120.2, 111.7, 81.8, 78.7, 61.6, 22.6

1H: 8.37 (1H, br), 8.30 (1H, d, J=8.5 Hz), 8.26 (1H, br), 8.22 (1H, s br), 7.94 (2H, m), 7.93 (1H, d, J=8.5 Hz), 7.62 (1H, t, J=7.6 Hz), 7.52 (1H, s br), 5.46 (2H, s), 3.91 (2H, s), 1.60 (6H, s)

Compound no. 164 (MP: 102). NMR solvent: CDCl3

13C: 153.5, 150.9, 149.4, 145.3, 137.1, 133.1, 129.3, 128.6, 127.9, 127.5, 125.2, 119.8, 117.7, 115.8, 113.5, 71.8, 70.5, 44.5, 42, 30.5

1H: 8.11 (1H, d, J=8.4 Hz), 8.0 (1H, d, J=8.3 Hz), 7.62 (1H, m, J=1.0, 7.2, 8.2 Hz), 7.47 (1H, m, J=1.0, 7.1, 8.2 Hz), 7.44 (2H, d, J=7.0 Hz), 7.40 (2H, m, J=7.4 Hz), 7.34 (1H, m, J=7.1 Hz), 6.93 (4H, m), 5.04 (2H, s), 4.58 m), 3.99 (4H, br), 2.10 (4H, m br)

Compound no. 165 (MP: 131). NMR solvent: CDCl3

13C: 153.8, 152.9, 149.4, 145.3, 133.1, 129.3, 125.1, 119.8, 115.3, 114.6, 113.4, 72.5, 55.7, 48.1, 45.5, 36.2, 29.1

1H: 8.11 (1H, d, J=8.3 Hz), 7.99 (1H, d, J=8.4 Hz), 7.61 (1H, t, J=7.8 Hz), 7.46 (1H, t, J=7.6 Hz), 6.85 (4H, s), 4.61 (2H, d br, J=13.0 Hz), 3.85 (2H, d, J=6.4 Hz), 3.78 (3H, s), 3.23 (2H, s br), 2.18 (1H, m), 2.03 (2H, m), 1.62 (2H, m)

Compound no. 166 (MP: 87). NMR solvent: CDCl3

13C: 160.9, 158.1, 149.4, 145.4, 133.1, 130.1, 129.4, 125.2, 119.8, 113.5, 108, 106.6, 102.6, 70.6, 55.3, 44.5, 41.9, 30.4

1H: 8.11 (1H, d, J=8.4 Hz), 8.0 (1H, d, J=8.4 Hz), 7.62 (1H, m, J=1.0, 7.1, 8.2 Hz), 7.47 (1H, m, J=1.0, 7.1, 8.1 Hz), 7.22 (1H, t, J=8.2 Hz), 6.58-6.54 (2H, m), 6.52 (1H, t, J=2.2 Hz), 4.70 (1H, m), 4.01 (4H, m), 3.81 (3H, s), 2.12 (4H, m)

Compound no. 167 (MP: 162 (dec.)). NMR solvent: CDCl3

13C: NO DATA

1H: 8.15 (2H, m), 7.69 (1H, m, J=1.0, 7.1, 8.2 Hz), 7.55 (1H, m, J=1.0, 7.1, 8.2 Hz), 5.09 (2H, s br), 4.46 (2H, s br), 3.45 (2H, t, J=7.1 Hz)

Compound no. 168 (MP: 72). NMR solvent: CDCl3

13C: 153.9, 150.6, 149.4, 145.3, 133.1, 129.3, 125.2, 119.8, 117.8, 115.4, 113.5, 71.9, 68.2, 44.5, 41.8, 31.4, 30.5, 19.2, 13.9

1H: 8.11 (1H, d, J=8.4 Hz), 8.0 (1H, d, J=8.3 Hz), 7.62 (1H, m, J=1.0, 7.1, 8.3 Hz), 7.47 (1H, m, J=1.0, 7.1, 8.2 Hz), 6.90 (2H, m, J=9.3 Hz), 6.85 (2H, m, J=9.3 Hz), 4.57 (1H, m), 3.99 (4H, br), 3.93 (2H, t, J=6.5 Hz), 2.11 (2H, m), 2.05 (2H, m), 1.76 (2H, m), 1.49 (2H, m), 0.98 (3H, t, J=7.4 Hz)

Compound no. 169 (MP: 90). NMR solvent: CDCl3

13C: 151, 145.1, 132.9, 129.6, 125.4, 119.9, 113.5, 62.2, 36.4

1H: 8.11 (1H, d, J=8.4 Hz), 8.05 (1H, d, J=8.4 Hz), 7.62 (1H, m, J=1.0, 7.1, 8.3 Hz), 7.47 (1H, m, J=1.0, 7.1, 8.2 Hz), 3.99 (3H, s), 3.55 (3H, s)

Compound no. 170 (MP: 51). NMR solvent: CDCl3

13C: 148.4, 145.2, 132.9, 129.6, 125.6, 119.9, 114.1, 51.8, 51, 31.7, 29.2

1H: 8.14 (1H, d, J=8.5 Hz), 8.11 (1H, d, J=8.4 Hz), 7.63 (1H, t, J=7.8 Hz), 7.49 (1H, t, J=7.4 Hz), 5.0 (2H, s br), 4.28 (2H, s br), 3.19 (2H, t, J=6.3 Hz)

Compound no. 171 (MP: 81). NMR solvent: CDCl3

13C: 150.1, 145.1, 133.1, 129.1, 125, 119.7, 113.4, 51.5, 49.8, 26.9, 26.7, 25.8, 25.2, 24.1

1H: 8.10 (1H, d, J=8.3 Hz), 8.0 (1H, d, J=8.3 Hz), 7.59 (1H, m, J=1.1, 7.1, 8.1 Hz), 7.45 (1H, m, J=1.0, 7.1, 8.2 Hz), 3.86 (2H, m, J=5.3 Hz), 3.79 (2H, m, J=5.3 Hz), 1.95 (2H, m), 1.79 (2H, m), 1.67 (6H, m)

Compound no. 172 (MP: 37-38). NMR solvent: CDCl3

13C: 150.5, 145.1, 133.2, 129.1, 125, 119.7, 113.5, 50.4, 49, 29.1, 27.4, 27.3, 26.6

1H: 8.09 (1H, m d, J=8.3 Hz), 8.01 (1H, m d, J=8.5 Hz), 7.59 (1H, m, J=1.0, 7.0, 8.2 Hz), 7.45 (1H, m, J=1.0, 7.1, 8.2 Hz), 3.87 (2H, t, J=6.0 Hz), 3.79 (2H, t, J=6.0 Hz), 1.94 (2H, m), 1.90 (2H, m), 1.71 (2H, m), 1.68 (2H, m)

Compound no. 173 (MP: oil). NMR solvent: CDCl3

13C: 150.2, 145.1, 133.3, 129, 124.9, 119.7, 113.1, 49, 30.1, 21.4, 13.8

1H: 8.10 (1H, d, J=8.5 Hz), 7.92 (1H, d, J=8.3 Hz), 7.59 (1H, m, J=7.9 Hz), 7.45 (1H, m, J=7.6 Hz), 4.78 (2H, m), 1.94 (1H, m), 1.87 (2H, m), 1.69 (2H, d br, J=13.5 Hz), 1.61 (1H, m), 1.45 (6H, d, J=7.1 Hz)

Compound no. 174 (MP: 193). NMR solvent: CDCl3

13C: 148.9, 145.1, 136.6, 134.4, 133.1, 129.5, 127.9, 127.9, 125.5, 122.6, 122.6, 119.8, 114.5, 56, 54.8

1H: 8.28 (1H, d, J=8.4 Hz), 8.14 (1H, d, J=8.3 Hz), 7.64 (1H, t, J=7.7 Hz), 7.50 (1H, t, J=7.6 Hz), 7.36 (4H, m), 5.53 (2H, s), 5.19 (2H, s)

Compound no. 175 (MP: oil). NMR solvent: CDCl3

13C: 150.1, 149.2, 145.4, 133.3, 129.1, 125, 125, 119.8, 113.5, 113.4, 54.4, 52.6, 42.3, 39.2, 31.6, 27.4, 18.8, 18

1H: 8.10 (1H, d, J=8.3 Hz), 7.97 (1H, d J=8.4 Hz), 7.59 (1H, t, J=7.6 Hz), 7.44 (1H, t, J=7.6 Hz), 4.45 (1.4H, d, J=12.0 Hz), 3.88 (0.6H, br), 3.50 (0.6H, br), 2.63 (1.4H, br), 2.15 (0.6H, m), 1.89 (1.4H, m), 1.0-0.96 (6H, m br), 1.93, 1.57, 0.9 (2H, m)

Compound no. 176 (MP: 48). NMR solvent: CDCl3

13C: 173.9, 149.4, 145.3, 133.1, 129.4, 125.2, 119.8, 113.5, 60.8, 47.4, 44.9, 40.7, 28, 14.2

1H: 8.10 (1H, d, J=8.3 Hz), 7.98 (1H, d, J=8.3 Hz), 7.61 (1H, m J=7.8 Hz), 7.46 (1H, m, J=7.8 Hz), 4.41 (2H, d t, J=4.0, 13.5 Hz), 4.19 (2H, q, J=7.1 Hz), 3.39 (2H, s br), 2.11 (2H, d br, J=12.9 Hz), 1.98 (2H, m), 1.29 (3H, t, J=7.1 Hz)

Compound no. 177 (MP: 75). NMR solvent: CDCl3
13C: 155.3, 149.5, 145.3, 133.1, 129.6, 125.4, 119.9, 113.6, 61.9, 47.8, 45.1, 43.5, 14.6

1H: 8.11 (1H, d, J=8.4 Hz), 8.0 (1H, d, J=8.4 Hz), 7.63 (1H, m, J=8.2 Hz), 7.48 (1H, m, J=7.6 Hz), 4.20 (2H, q, J=7.2 Hz), 3.92 (4H, s br), 3.71 (4H, m), 1.30 (3H, t, J=7.2 Hz)

Compound no. 178 (MP: 143). NMR solvent: CDCl3
13C: 169.2, 149.5, 145.3, 133.1, 129.7, 125.5, 120, 113.6, 47.8, 46.3, 46, 41.2, 21.4

1H: 8.11 (1H, d, J=8.3 Hz), 8.0 (1H, d, J=8.3 Hz), 7.63 (1H, m, J=1.0, 7.1, 8.2 Hz), 7.48 (1H, m, J=1.0, 7.1, 8.2 Hz), 3.94 (4H, s br), 3.85 (2H, m), 3.71 (2H, m), 2.18 (3H, s)

Compound no. 179 (MP: 197 (dec.)). NMR solvent: DMSO
13C: 175.7, 148.7, 144.7, 132.5, 129.5, 125.4, 119.6, 113.2, 47.1, 44.5, 41, 28.4

1H: 8.19 (1H, d, J=8.4 Hz), 7.91 (1H, d, J=8.3 Hz), 7.70 (1H, m, J=7.8 Hz), 7.53 (1H, m, J=7.7 Hz), 7.38 (1H, br), 6.90 (1H, s br), 4.23 (2H, s br), 3.24 (2H, s br), 2.47 (1H, m), 1.85 (2H, s br), 1.69 (2H, m, J=4.2, 12.0 Hz)

Compound no. 180 (MP: oil). NMR solvent: CDCl3
13C: 158.2, 148.8, 146.4, 143.2, 132.5, 129.5, 127.7, 127.7, 127.5, 127.3, 126.1, 40.5

1H: 8.63 (1H, s), 7.47 (1H, d br, J=3.6 Hz), 7.39 (2H, m, J=8.0 Hz), 7.33 (1H, m, J=7.3 Hz), 7.31 (1H, d d, J=1.2, 5.0 Hz), 7.19 (2H, m, J=8.3 Hz), 7.02 (1H, d d, J=3.6, 5.0 Hz), 3.58 (3H, s)

Compound no. 181 (MP: 79). NMR solvent: CDCl3
13C: 158.8, 149.9, 147.3, 135.8, 132.5, 128.8, 128, 127.8, 127.6, 127.6, 54.4, 36.9, 36.2

1H: 8.86 (1H, s), 7.46-7.30 (6H, m), 7.73 (1H, br), 7.11 (1H, t, J=4.0 Hz), 4.93 (2H, br), 3.24 (3H, br)

Compound no. 182 (MP: 87). NMR solvent: CDCl3
13C: 164.3, 150.7, 148.6, 147.3, 137, 129.3, 128.8, 128.6, 126.8, 120.7, 116.7, 49.4, 46.5, 34.7

1H: 8.73 (1H, s), 7.37-7.21 (5H, m), 7.32 (2H, m), 6.95 (2H, m), 6.93 (1H, m), 4.11 (2H, s), 4.03 (4H, br), 3.27 (4H, m)

Compound no. 183 (MP: 144). NMR solvent: CDCl3
13C: 163.8 (d d, J=12.0, 253.0 Hz), 160.8 (d d, J=14.0, 261.0 Hz), 158.5 (d, J=6.0 Hz), 145.6, 144.7, 131.4 (d d, J=4.2, 10.0 Hz), 114.4 (d d, J=4.0, 11.5 Hz), 111.8 (d d, J=4.0, 22.0 Hz), 105.0 (t, J=25.0 Hz), 82.1, 79.2, 62.2, 22.8

1H: 8.96 (1H, s), 8.12 (1H, m, J=7.0, 8.4 Hz), 7.0 (1H, m), 6.95 (1H, m), 5.53 (2H, s), 3.84 (2H, s), 1.62 (6H, s)

Compound no. 184 (MP: 126). NMR solvent: CDCl3
13C: 151, 142.5, 136.9, 133.7, 132.8, 131.7, 128.9, 128.7, 127.6, 127.3, 126.8, 126.3, 125.2, 112.9, 48.5, 44.6, 28.5

1H: 7.99 (1H, d, J=1.3 Hz), 7.82 (2H, m, J=8.2 Hz), 7.55 (1H, d, J=1.3 Hz), 7.42 (2H, t, J=7.8 Hz), 7.31 (1H, m, J=7.4 Hz), 7.27-7.19 (3H, m), 7.12 (1H, m), 4.80 (2H, br), 3.88 (2H, t, J=5.8 Hz), 3.05 (2H, t, J=5.8 Hz)

Compound no. 185 (MP: 125). NMR solvent: DMSO
13C: 160.4, 148.6, 147.8, 134.7, 134.2, 132.4, 129, 128.6, 128.4, 128, 126.7, 126.3, 126.2, 47.3, 44.2, 28

1H: 9.14 (1H, s), 8.10 (2H, m, J=8.6 Hz), 7.59 (2H, m, J=8.6 Hz), 7.23 (4H, br), 4.88 (2H, br), 3.93 (2H, t, J=5.8 Hz), 3.02 (2H, t, J=5.8 Hz)

Compound no. 186 (MP: 136). NMR solvent: CDCl3
13C: 146.3, 141.6, 136.2, 133.3, 131.3, 128.9, 126.4, 112.3, 81.1, 80.4, 61.9, 22.8

1H: 7.94 (1H, d, J=1.3 Hz), 7.72 (2H, m, J=8.7 Hz), 7.51 (1H, d, J=1.3 Hz), 7.37 (2H, m, J=8.7 Hz), 5.13 (2H, s), 3.89 (2H, s), 1.62 (6H, s)

Compound no. 187 (MP: 176-177). NMR solvent: DMSO
13C: 167.1, 161.1, 158.7, 157.5, 147.1, 144.6, 129.8, 129.6, 128.5, 125.5, 119.5, 118, 81.4, 78.4, 61.4, 22.4

1H: 9.21 (1H, s), 8.11 (2H, d, J=8.8 Hz), 7.98 (1H, s br), 7.93 (2H, d, J=8.4 Hz), 7.36 (1H, s br), 7.20 (2H, d, J=8.8 Hz), 7.11 (2H, d, J=8.4 Hz), 5.44 (2H, s), 3.85 (2H, s), 1.52 (6H, s)

Compound no. 188 (MP: 88). NMR solvent: CDCl3
13C: 162.8, 161.1, 146, 145, 128.2, 122.4, 114.1, 82, 79.3, 62.1, 55.3, 22.8

1H: 8.90 (1H, s), 8.05 (2H, m, J=9.0 Hz), 6.98 (2H, m, J=9.0 Hz), 5.56 (2H, s), 3.87 (3H, s), 3.84 (2H, s), 1.62 (6H, s)

Compound no. 189 (MP: 132). NMR solvent: CDCl3
13C: 162.1, 146.3, 144.7, 136.1, 129, 128.3, 128, 81.9, 79.3, 62.3, 22.8

1H: 8.93 (1H, s), 8.05 (2H, m, J=8.6 Hz), 7.44 (2H, m, J=8.6 Hz), 5.55 (2H, s), 3.85 (2H, s), 1.62 (6H, s)

Compound no. 190 (MP: 82). NMR solvent: CDCl3
13C: 162.7, 150.1, 147.4, 136, 134.1, 133.1, 128.8, 128.7, 128.4, 128, 127.8, 127.1, 126.9, 126.7, 126.5, 123.7, 54.5, 36.7

1H: 8.96 (1H, s), 8.64 (1H, br), 8.15 (1H, br), 7.90 (3H, m), 7.53 (2H, m), 7.47-7.31 (5H, m), 5.0 (2H, br), 3.28 (3H, br)

Compound no. 191 (MP: 107). NMR solvent: DMSO
13C: 161.7, 150, 147.3, 136.3, 133.6, 130.6, 128.7, 128.6, 128.5, 127.6, 127.1, 126.1, 125.8, 125.4, 53.6, 37.3, 35.8

1H: 9.34 (1H, s), 8.87 (1H, br), 8.27 (1H, d, J=7.2 Hz), 8.06 (1H, d, J=8.0 Hz), 8.0 (1H, br), 7.63 (1H, t, J=7.5 Hz), 7.55 (1H, br), 7.46-7.26 (6H, m), 4.90 (2H, br), 3.16 (3H, s)

Compound no. 192 (MP: 121-123 (dec.)). NMR solvent: DMSO
13C: 161, 148.7, 146.9, 143.5, 133.4, 130.5, 129.6, 129.5, 128.4, 128.3, 127.2, 127, 126 (2 sig.), 125.8, 125.2, 40.1

1H: 9.21 (1H, s), 8.10 (1H, d d, J=J=1.2, 7.2 Hz), 7.98 (1H, d, J=8.2 Hz), 7.93 (2H, m), 7.60-7.30 (8H, m), 3.52 (3H, s)

Compound no. 193 (MP: 142). NMR solvent: CDCl3
13C: 149.2, 145.3, 133.1, 129.5, 125.3, 119.9, 113.5, 71.8, 53.3, 50.2, 18.6

1H: 8.11 (1H, d, J=8.3 Hz), 8.0 (1H, d, J=8.4 Hz), 7.62 (1H, m, J=1.0, 7.1, 8.1 Hz), 7.47 (1H, m, J=1.0, 7.1, 8.1 Hz), 4.42 (2H, d br, J=13.0 Hz), 3.83 (2H, m), 3.03-2.90 (2H, m br), 1.26 (6H, s br)

Compound no. 194 (MP: 75). NMR solvent: CDCl3
13C: 150, 145.3, 133.1, 129.5, 125.4, 119.9, 113.6, 66.1, 52.8, 49.7, 17.5

1H: 8.11 (1H, d, J=8.3 Hz), 8.01 (1H, d, J=8.3 Hz), 7.63 (1H, t, J=7.8 Hz), 7.48 (1H, t, J=7.8 Hz), 4.22 (2H, s br), 4.06-3.90 (2H, m br), 3.66 (2H, s br), 1.31 (6H, s br)

Compound no. 195 (MP: oil). NMR solvent: CDCl3
13C: 150.9, 145.3, 139.1, 133.3, 129.3, 128.7, 127.9, 127.3, 125.2, 119.8, 113.6, 55, 32.2, 16

1H: 8.12 (1H, m, J=8.3 Hz), 8.07 (1H, m, J=8.4 Hz), 7.63 (1H, m, J=1.0, 7.0, 8.0 Hz), 7.48 (1H, m, J=1.0, 7.1, 8.3 Hz), 7.45 (2H, br), 7.41 (2H, m, J=7.4 Hz), 7.34 (1H, m J=8.0 Hz), 5.95 (1H, q, J=6.8 Hz), 3.0 (3H, s), 1.78 (3H, d, J=7.1 Hz)

Compound no. 196 (MP: 140). NMR solvent: CDCl3
13C: 150.7, 150.5, 142.6, 141.7, 140.9, 137.1, 133.2, 129.3, 129.2, 128.7, 127.4, 127.2, 126.5, 124.1, 124, 121.1, 116.9, 113.2, 49.5, 46.5

1H: 8.07 (1H, t, J=1.7 Hz), 7.99 (1H, d, J=1.2 Hz), 7.80 (1H, d t, J=1.5, 7.6 Hz), 7.67 (2H, d, J=8.2 Hz), 7.57 (1H, d, J=1.2 Hz), 7.56 (1H, d t, J=1.5, 7.7 Hz), 7.49 (1H, t, J=7.5 Hz), 7.47 (2H, m, J=7.7 Hz), 7.37 (1H, m, J=7.2 Hz), 7.32 (2H, m, J=8.2 Hz), 6.96 (3H, m), 3.85 (4H, m, J=5.0 Hz), 3.30 (4H, m, J=5.0 Hz)

Compound no. 197 (MP: 113). NMR solvent: CDCl3
13C: 150.5, 142.2, 141.3, 137, 133.1, 131.5, 128.8, 128.3 (2 sig.), 126.4, 125.8, 113.3, 47, 35.9, 35.8, 35.7, 32.1, 28.4
1H: 7.88 (1H, d, J=1.3 Hz), 7.73 (2H, m), 7.45 (1H, d, J=1.3 Hz), 7.37 (2H, m), 7.30 (2H, m, J=7.5 Hz), 7.20 (1H, m, J=7.6 Hz), 7.19 (2H, m, J=8.0 Hz), 4.14 (2H, d br, J=13.2 Hz), 3.04 (2H, d t, J=2.3, 13.0 Hz), 2.63 (2H, t, J=7.7 Hz), 1.83 (2H, d br, J=13.5 Hz), 1.67 (2H, m), 1.58 (1H, m), 1.36 (2H, m), 1.25 (2H, d q, J=4.2, 13.1 Hz)

Compound no. 198 (MP: 178). NMR solvent: CDCl3
13C: 150.3, 140.3, 137.2, 133, 132.8, 131.2, 130.6, 127, 124.3, 113.9, 106.1, 64.6, 44.8, 35
1H: 7.90 (1H, d, J=2.0 Hz), 7.89 (1H, d, J=1.4 Hz), 7.61 (1H, d d, J=2.1, 8.4 Hz), 7.49 (1H, d, J=1.4 Hz), 7.46 (1H, d, J=8.4 Hz), 4.01 (4H, s), 3.73 (4H, m, J=5.5 Hz), 1.82 (4H, m, J=5.5 Hz)

Compound no. 199 (MP: 174). NMR solvent: CDCl3
13C: 150.2, 145.8, 143, 141.7, 137.5, 130.3, 128, 126.2, 125.9, 123.5, 115.1, 111.7, 40.1
1H: 7.49 (1H, d, J=1.2 Hz), 7.41 (2H, m, J=8.4 Hz), 7.40 (2H, m, J=7.5 Hz), 7.33 (1H, m, J=7.4 Hz), 7.17 (2H, m, J=8.4 Hz), 7.04 (1H, d, J=1.2 Hz), 6.65 (2H, m, J=8.4 Hz), 3.69 (2H, s), 3.51 (3H, s)

Compound no. 200 (MP: Hygroscopic). NMR solvent: DMSO
13C: 157.8, 149, 142.4, 137.5, 130, 129.9, 127.9, 126.2, 118, 115.4, 114.4, 111, 62.3, 54.4, 48.4, 39.7
1H: 12.25 (1H, s br), 9.94 (2H, s), 8.04 (1H, s), 7.82 (1H, s), 7.42 (2H, t, J=8.0 Hz), 7.39 (1H, s), 7.36 (2H, m), 7.32 (1H, m), 7.30 (2H, m), 6.92 (1H, m), 4.46 (2H, m), 3.63 (6H, m), 3.48 (4H, m), 3.45 (3H, s)

Compound no. 201 (MP: 119). NMR solvent: CDCl3
13C: 149.8 (d d, J=13.0, 244.5 Hz), 149.8, 148.5 (d d, J=12.5, 245.0 Hz), 138.9, 137.9, 131.1 (d d, J=4.0, 7.0 Hz), 121.4 (d d, J=3.0, 6.5 Hz), 117.8 (d, J=17.3 Hz), 115.2, 113.5 (d, J=18.7 Hz), 62.7, 48.1, 46.5, 28.3, 25.8, 25.3
1H: 8.12 (1H, s), 8.06 (1H, s), 7.87 (1H, d d d, J=2.0, 7.8, 12.0 Hz), 7.70 (1H, m), 7.46 (1H, d t, J=8.7, 10.7 Hz), 3.51 (4H, m), 2.57 (4H, m), 2.29 (1H, br), 1.74 (4H, m), 1.57 (1H, d br, J=12.0 Hz), 1.20 (4H, m), 1.07 (1H, t br, J=10.0 Hz)

Compound no. 202 (MP: oil). NMR solvent: CDCl3
13C: 150.4, 145.1, 137.8, 133.2, 129.2, 128.4, 127.7, 127.6, 125.1, 119.7, 113.7, 73.3, 69.4, 68.3, 48.7, 45.1, 13.9, 12.6
1H: 8.09 (1H, d, J=8.4 Hz), 7.98 (1H, d, J=8.3 Hz), 7.58 (1H, t, J=7.9 Hz), 7.45 (1H, m, J=1.0, 7.2, 8.2 Hz), 7.31 (5H, m), 4.53 (2H, br), 3.95-3.75 (6H, m), 1.38 (3H, t, J=6.9 Hz)

Compound no. 203 (MP: 132). NMR solvent: DMSO
13C: 157.4, 148.6, 142.2, 137.3, 136.6, 129.9, 128, 126.5, 126.3, 123.2, 115.2, 114.3, 62.4, 54.4, 48.4, 39.7 (2 sig.)
1H: 11.97 (1H, s br), 9.68 (2H, s), 7.88 (1H, s), 7.62 (2H, d, J=8.8 Hz), 7.57 (1H, s), 7.42 (2H, t, J=7.4 Hz), 7.36 (2H, d, J=8.8 Hz), 7.32 (1H, t, J=7.4 Hz), 7.0 (2H, d, J=8.8 Hz), 4.42 (2H, m), 3.61 (6H, m), 3.47 (4H, m), 3.43 (3H, s)

Compound no. 204 (MP: 141). NMR solvent: CDCl3
13C: 161.7, 148.5, 147.3, 136.1, 128.9, 128.4, 128, 106.5, 64.6, 44.7, 35.1
1H: 8.80 (1H, s), 8.07 (2H, d, J=8.8 Hz), 7.43 (2H, d, J=8.8 Hz), 4.02 (4H, s), 3.95 (4H, br), 1.89 (4H, m)

Compound no. 205 (MP: 74-75). NMR solvent: CDCl3
13C: 162.3, 161, 148.8, 147, 142.3, 128.3 (2 sig.), 128.2, 125.7, 122.6, 114, 55.3, 47, 36, 35.8 (2 sig.), 32.1, 28.5

1H: 8.75 (1H, s), 8.07 (2H, d, J=7.7 Hz), 7.28 (2H, m), 7.19 (3H, m), 6.98 (2H, d, J=7.7 Hz), 4.61 (2H, br), 3.03 (2H, br), 3.86 (3H, s), 2.62 (2H, m), 1.84 (2H, m), 1.67 (2H, m), 1.59 (1H, m), 1.30 (4H, m)

Compound no. 206 (MP: 131). NMR solvent: DMSO
13C: 161.8, 150.6, 148.5, 147.3, 133.6, 130.7, 130, 129.1, 128.7, 128.4, 127.3, 126.4, 126.3, 125.8, 125.4, 119.5, 115.9, 48.2, 45.8
1H: 9.29 (1H, s), 9.03 (1H, d, J=8.4 Hz), 8.28 (1H, d d, J=1.0, 7.3 Hz), 8.10 (1H, d, J=8.1 Hz), 8.05_(1H, d, J=8.0 Hz), 7.72-7.57 (3H, m), 7.25 (2H, t, J=7.8 Hz), 6.99 (2H, d, J=8.3 Hz), 6.82 (1H, t, J=7.3 Hz), 3.94 (4H, s br), 3.32 (4H, m, J=5.0 Hz)

Compound no. 207 (MP: 181). NMR solvent: DMSO
13C: 167.1, 160.7, 158.8, 156.6, 148.7, 148, 134.2, 132.6, 131.7, 131.1, 129.9, 129.7, 128.6, 126.8, 126.4, 126.3, 121.8, 120.8, 118.2, 116.1, 46.9, 44.9, 28.2
1H: 9.15 (1H, s), 7.98 (1H, s br), 7.96 (2H, d, J=8.8 Hz), 7.90 (1H, d, J=7.7 Hz), 7.66 (1H, m br), 7.59 (1H, t, J=8.0 Hz), 7.37 (1H, s br), 7.24 (1H, d d, J=2.4, 8.2 Hz), 7.21 (4H, m br), 7.13 (2H, d, J=8.8 Hz), 4.83 (2H, m br), 3.88 (2H, m br), 2.96 (2H, t, J=5.3 Hz)

Compound no. 208 (MP: 217-218). NMR solvent: DMSO
13C: 167.2, 160.7, 159, 156.4, 150.6, 148.3, 148.1, 131.7, 131.1, 129.8, 129.6, 129.1, 122, 121, 119.5, 117.9, 116.6, 115.9, 48.2, 45.8
1H: 9.15 (1H, s), 7.98 (1H, s br), 7.94 (2H, d, J=8.8 Hz), 7.91 (1H, m), 7.69 (1H, m br), 7.59 (1H, t, J=8.0 Hz), 7.36 (1H, s br), 7.24 (2H, t, J=7.7 Hz), 7.23 (1H, m), 7.11 (2H, d, J=8.8 Hz), 6.97 (2H, d, J=8.0 Hz), 6.82 (1H, t, J=7.0 Hz), 3.88 (4H, br), 3.27 (4H, br)

Compound no. 209 (MP: 192-193). NMR solvent: DMSO
13C: 167.1, 160.8, 159, 156.3, 147.2, 144.5, 131.7, 131.1, 129.8, 129.5, 122.1, 121, 117.8, 116.8, 81.3, 78.3, 61.4, 22.3
1H: 9.20 (1H, s), 7.96 (1H, s br), 7.93 (2H, m, J=8.8 Hz), 7.90 (1H, m), 7.69 (1H, d d, J=1.8, 2.4 Hz), 7.57 (1H, t, J=8.0 Hz), 7.35 (1H, s br), 7.22 (1H, d d d, J=0.9, 2.5, 8.2 Hz), 7.09 (2H, m, J=8.8 Hz), 5.39 (2H, s), 3.82 (2H, s), 1.50 (6H, s)

Compound no. 210 (MP: 185). NMR solvent: DMSO
13C: 167.1, 160.7, 158.9, 156.5, 148.3, 148.1, 131.7, 131.1, 129.8, 129.6, 122, 120.9, 118, 116.5, 65.8, 46.2
1H: 9.13 (1H, s), 7.97 (1H, s br), 7.93 (2H, d, J=8.7 Hz), 7.88 (1H, d, J=7.7 Hz), 7.65 (1H, m br), 7.58 (1H, t, J=7.8 Hz), 7.35 (1H, s br), 7.22 (1H, d d, J=1.9, 7.9 Hz), 7.10 (2H, d, J=8.7 Hz), 3.80-3.63 (8H, m)

Compound no. 211 (MP: 116). NMR solvent: CDCl3
13C: 162.6, 161.2, 157.7 (d, J=240.0 Hz), 148.7, 147.4 (d, J=2.0 Hz), 147.3, 128.3, 122.3, 118.7 (d, J=7.8 Hz), 115.8 (d, J=22.0 Hz), 114.1, 55.3, 50.5, 46.4
1H: 8.83 (1H, s), 8.08 (2H, m), 7.01 (2H, t, J=9.4 Hz), 7.0 (2H, m), 6.93 (2H, m), 4.12 (4H, br), 3.88 (3H, s), 3.25 (4H, m)

Compound no. 212 (MP: 281 (dec.)). NMR solvent: DMSO
13C: 160.6, 148.5, 148.1, 135, 129.2, 128.4, 128.2, 64.3, 47.3, 42.9, 26.1, 24.7, 24.5
1H: 11.29 (1H, s), 9.20 (1H, s), 8.10 (2H, m, J=8.8 Hz), 7.60 (2H, m, J=8.8 Hz), 4.55 (2H, m br), 3.75 (2H, t br, J=12.0 Hz), 3.55 (2H, d br, J=11.5 Hz), 3.23 (3H, m), 2.13 (2H, d br, J=10.5 Hz), 1.82 (2H, d br, J=12.8 Hz), 1.61 (1H, d br, J=12.5 Hz), 1.43 (2H, m, J=11.5 Hz), 1.26 (2H, m, J=12.8 Hz), 1.10 (1H, m, J=12.5 Hz)

Compound no. 213 (MP: 99). NMR solvent: CDCl3
13C: 159, 146.2, 144.7, 132.4, 127.9, 127.7, 127.6, 82, 79.2, 62.2, 22.8
1H: 8.89 (1H, s), 7.74 (1H, d, J=3.0 Hz), 7.41 (1H, d, J=4.9 Hz), 7.13 (1H, m), 5.51 (2H, s), 3.84 (2H, s), 1.61 (6H, s)

Compound no. 214 (MP: 121). NMR solvent: CDCl3
13C: 162.1, 147.0 (2 sig.), 136.2, 129, 128.2, 128.1, 51.8, 51.1, 32, 28.9
1H: 8.93 (1H, s), 8.07 (2H, m, J=8.8 Hz), 7.44 (2H, m, J=8.8 Hz), 4.97 (2H, m br), 4.23 (2H, m br), 3.14 (2H, br)

Compound no. 215 (MP: 129). NMR solvent: CDCl3
13C: 150.6 (d d, J=13.0, 248.0 Hz), 149.9 (d d, J=13.0, 249.0 Hz), 149.4, 140.9, 137, 129.9 (d d, J=4.0, 7.0 Hz), 121.2 (d d, J=4.0, 6.5 Hz), 117.6 (d, J=17.7 Hz), 114.3 (d, J=19.0 Hz), 113, 51.3, 50.9, 30.5
1H: 8.02 (1H, d, J=1.4 Hz), 7.61 (1H, d d d, J=2.0, 7.7, 11.5 Hz), 7.55 (1H, d, J=1.4 Hz), 7.50 (1H, m), 7.19 (1H, d t, J=8.3, 10.0 Hz), 4.71 (2H, s), 3.98 (2H, t, J=6.3 Hz), 3.14 (2H, t, J=6.3 Hz)

Compound no. 216 (MP: 115). NMR solvent: CDCl3
13C: 149.3, 149, 144.2, 136.4, 135.8, 121, 118, 114, 112, 109.1, 80.7, 79.3, 61.4, 55.8, 55.6, 22.2
1H: 9.22 (1H, s), 8.36 (1H, s), 7.55 (1H, d, J=1.8 Hz), 7.49 (1H, d d, J=1.8, 8.4 Hz), 7.05 (1H, d, J=8.4 Hz), 5.22 (2H, s), 3.87 (2H, s), 3.83 (3H, s), 3.79 (3H, s), 1.52 (6H, s)

Compound no. 217 (MP: 154-155). NMR solvent: CDCl3
13C: 151.3, 149.1, 148.5, 141.9, 136.7, 126.1, 117.4, 112.4, 111.2, 108.4, 57.5, 55.9 (2 sig.), 31.4, 30, 25.4, 25.2
1H: 7.90 (1H, s), 7.43 (1H, s), 7.40 (1H, s), 7.31 (1H, d br, J=8.6 Hz), 6.91 (1H, d, J=8.3 Hz), 3.97 (3H, s), 3.97 (1H, m), 3.91 (3H, s), 3.0 (3H, s), 1.86 (4H, m), 1.70 (1H, d br, J=13.5 Hz), 1.58 (2H, m), 1.38 (2H, m), 1.13 (1H, m)

Compound no. 218 (MP: 140-141). NMR solvent: CDCl3
13C: 149.2, 139.9, 137, 133.1, 132.8, 131.1, 130.6, 126.9, 124.3, 113.6, 48.9, 25.3
1H: 8.05 (1H, d, J=1.3 Hz), 7.90 (1H, d, J=2.0 Hz), 7.65 (1H, d, J=1.3 Hz), 7.61 (1H, d d, J=2.0, 8.5 Hz), 7.46 (1H, d, J=8.5 Hz), 3.68 (4H, m), 2.03 (4H, m)

Compound no. 219 (MP: 106). NMR solvent: CDCl3
13C: 147, 143.1, 139.8, 131.8, 124.8, 124, 120.7, 113, 81, 80.6, 61.5, 23.1
1H: 8.11 (1H, s), 7.82 (1H, d, J=7.8 Hz), 7.70 (1H, d, J=7.7 Hz), 7.40 (1H, d t, J=1.5, 7.4 Hz), 7.36 (1H, d t, J=1.5, 7.4 Hz), 5.04 (2H, s), 3.92 (2H, s), 1.67 (6H, s)

Compound no. 220 (MP: 114-115). NMR solvent: CDCl3
13C: 146.9, 142.2, 136.6, 132.8, 128.7, 127.6, 125.1, 112.5, 96.3, 63.5, 48.2, 24.1
1H: 8.06 (1H, d, J=1.4 Hz), 7.80 (2H, m, J=8.2 Hz), 7.62 (1H, d, J=1.4 Hz), 7.41 (2H, t, J=7.8 Hz), 7.30 (1H, m, J=7.4 Hz), 4.10 (2H, t, J=6.0 Hz), 3.84 (2H, t, J=6.0 Hz), 1.73 (6H, s)

Compound no. 221 (MP: 120). NMR solvent: CDCl3
13C: 151.4, 142.2, 136.7, 133, 128.7, 127.4, 125.1, 113.2, 49.1, 30, 21.2, 13.6
1H: 7.87 (1H, d, J=1.5 Hz), 7.80 (2H, m, J=8.0 Hz), 7.46 (1H, d, J=1.5 Hz), 7.41 (2H, t, J=8.0 Hz), 7.29 (1H, m, J=7.5 Hz), 4.41 (2H, m), 1.90 (1H, m), 1.77 (2H, m), 1.66 (2H, m), 1.62 (1H, m), 1.39 (6H, d, J=7.2 Hz)

Compound no. 222 (MP: 116). NMR solvent: CDCl3
13C: 151.7, 143.3, 141.4, 132.1, 124.5, 123.6, 120.6, 112.6, 57.4, 31.3, 30, 25.4, 25.3
1H: 8.16 (1H, s), 7.82 (1H, m, J=7.8 Hz), 7.55 (1H, m), 7.38 (1H, d t, J=1.5, 7.3 Hz), 7.35 (1H, d t, J=1.5, 7.3 Hz), 4.0 (1H, m, J=3.4, 12.1 Hz), 2.96 (3H, s), 1.89 (4H, m), 1.70 (1H, d br, J=13.5 Hz), 1.61 (2H, d q, J=4.0, 12.5 Hz), 1.38 (2H, t q, J=4.0, 13.5 Hz), 1.14 (1H, t q, J=3.5, 13.5 Hz)

Compound no. 223 (MP: 155). NMR solvent: CDCl3
13C: 157.9 (d, J=241.0 Hz), 150.5, 147.1 (d, J=2.5 Hz), 141.6, 137, 133.3, 131.3, 128.9, 126.4, 118.9 (d, J=7.7 Hz), 115.8 (d, J=22.0 Hz), 113.2, 50.5, 46.5
1H: 7.94 (1H, d, J=1.2 Hz), 7.74 (2H, m, J=8.6 Hz), 7.50 (1H, d, J=1.2 Hz), 7.38 (2H, m, J=8.6 Hz), 7.01 (2H, m), 6.91 (2H, m), 3.82 (4H, m, J=5.0 Hz), 3.19 (4H, m, J=5.0 Hz)

Compound no. 224 (MP: 201-202). NMR solvent: DMSO
13C: 156.8, 149.8, 143, 139.8, 137.7, 129.9, 127.7, 126.5, 126.3, 126, 114.9, 113.3, 62.2, 54.9, 52.8, 39.6, 22.5, 21.2
1H: 9.28 (1H, s br), 7.60 (2H, d, J=8.9 Hz), 7.55 (1H, d, J=1.0 Hz), 7.48 (1H, d, J=1.0 Hz), 7.41 (2H, t, J=7.4 Hz), 7.34 (2H, d, J=7.3 Hz), 7.32 (1H, m, J=7.2 Hz), 6.98 (2H, d, J=8.9 Hz), 4.32 (2H, t, J=5.0 Hz), 3.50 (2H, br), 3.48 (2H, m), 3.42 (3H, s), 3.0 (2H, br), 1.79 (2H, br), 1.69 (3H, br), 1.39 (1H, br)

Compound no. 225 (MP: 109). NMR solvent: CDCl3
13C: 149.8, 147.8, 146.5, 142.5, 137, 136, 128.5, 127.8, 127.2, 126.4, 117.4, 114.1, 111.3, 108.9, 81.1, 80.4, 71, 61.8, 56, 22.9
1H: 7.93 (1H, d, J=1.5 Hz), 7.46 (2H, d, J=8.0 Hz), 7.42 (1H, d, J=1.5 Hz), 7.41 (1H, d, J=2.0 Hz), 7.38 (2H, t, J=7.7 Hz), 7.31 (1H, m), 7.21 (1H, d d, J=2.0, 8.3 Hz), 6.91 (1H, d, J=8.3 Hz), 5.20 (2H, s), 5.12 (2H, s), 3.97 (3H, s), 3.88 (2H, s), 1.61 (6H, s)

Compound no. 226 (MP: 230-232 (dec.)). NMR solvent: DMSO
13C: 145.4, 140.5, 139.7, 138.3, 137.6, 134.8, 132.6, 127.5, 117.7, 80.7, 79.3, 61.1, 22.4
1H: 9.34 (1H, d, J=1.8 Hz), 8.97 (1H, t d, J=1.5, 8.2 Hz), 8.81 (1H, d br, J=5.2 Hz), 8.59 (1H, d, J=1.3 Hz), 8.41 (1H, d, J=1.3 Hz), 8.11 (1H, d d, J=5.2, 8.2 Hz), 5.20 (2H, s), 3.86 (2H, s), 1.50 (6H, s)

Compound no. 227 (MP: 118-119). NMR solvent: CDCl3
13C: 148.7, 142.6, 136.7, 132.7, 128.7, 127.7, 125.2, 112.3, 88, 66.4, 48, 19.2
1H: 8.08 (1H, d, J=1.2 Hz), 7.81 (2H, d, J=8.4 Hz), 7.62 (1H, d, J=1.2 Hz), 7.42 (2H, t, J=7.9 Hz), 7.31 (1H, m. J=7.4 Hz), 5.49 (1H, q, J=5.2 Hz), 4.27 (1H, m), 3.89 (1H, m), 3.80 (2H, m), 1.57 (3H, d, J=5.2 Hz)

Compound no. 228 (MP: 204-205). NMR solvent: DMSO
13C: 147.7, 146.3, 145.9, 141.3, 136.6, 124.8, 117.5, 115.6, 111.9, 109, 80.6, 79.3, 60.8, 55.6, 22.4
1H: 9.03 (1H, s), 8.09 (1H, d, J=1.0 Hz), 7.87 (1H, d, J=1.0 Hz), 7.38 (1H, d, J=1.7 Hz), 7.26 (1H, d d, J=1.7, 8.1 Hz), 6.77 (1H, d, J=8.1 Hz), 5.17 (2H, s), 3.84 (2H, s), 3.81 (3H, s), 1.50 (6H, s)

Compound no. 229 (MP: 152). NMR solvent: CDCl3
13C: 151.2, 142.1, 137.2, 133.1, 128.6, 127.4, 125.1, 113, 58.4, 38.6, 36.2, 34.1, 29.7
1H: 7.92 (1H, d, J=1.2 Hz), 7.80 (2H, d, J=8.6 Hz), 7.48 (1H, d, J=1.2 Hz), 7.40 (2H, t, J=7.8 Hz), 7.29 (1H, t, J=7.3 Hz), 2.99 (3H, s), 2.20 (9H, s), 1.73 (6H, s)

Compound no. 230 (MP: 67-68). NMR solvent: DMSO
13C: 157.4, 148.7, 142.3, 137.4, 136.8, 129.9, 127.9, 126.5, 126.3, 123.4, 115.1, 114.2, 63.1, 62.3, 54.7, 51.6, 39.7
1H: 11.54 (1H, s br), 8.28 (1H, s), 7.70 (1H, s), 7.66 (2H, d, J=8.9 Hz), 7.43 (2H, t, J=7.9 Hz), 7.40 (2H, d, J=7.7 Hz), 7.34 (1H, m, J=6.9 Hz), 7.03 (2H, d. J=8.9 Hz), 4.46 (2H, m), 3.95 (2H, d br, J=13.0 Hz), 3.85 (2H, t br, J=11.70 Hz), 3.54 (2H, m), 3.48 (2H, m), 3.46 (3H, s), 3.19 (2H, m)

Compound no. 231 (MP: 46-47). NMR solvent: CDCl3
13C: 146.5, 142.5, 141.7, 140.9, 136.3, 133.2, 129.1, 128.7, 127.4, 127.2, 126.5, 124.1, 124, 112.2, 81.1, 80.4, 61.8, 22.9
1H: 8.05 (1H, t, J=1.6 Hz), 7.99 (1H, d, J=1.3 Hz), 7.77 (1H, t d, J=1.3, 7.6 Hz), 7.66 (2H, d, J=8.2 Hz), 7.58 (1H, d, J=1.3 Hz), 7.54 (1H, t d, J=1.3, 7.7 Hz), 7.48 (Hi, t, J=7.7 Hz), 7.46 (2H, t, J=7.8 Hz), 7.37 (1H, m, J=7.4 Hz), 5.15 (2H, s), 3.89 (2H, s), 1.63 (6H, s)

Compound no. 232 (MP: 191-192). NMR solvent: DMSO
13C: 167.9, 146.2, 140.7, 140.1, 140, 137.1, 135, 134, 129.6, 129.4, 129, 126.7, 125.8, 125.7, 124.2, 123.2, 114, 80.6, 79.3, 60.8, 22.4
1H: 8.23-8.17 (4H, m), 8.15 (1H, s br), 7.88 (3H, m), 7.63 (1H, m, J=8.1 Hz), 7.57 (1H, t, J=7.8 Hz), 7.52 (1H, t, J=7.8 Hz), 7.49 (1H, s br), 5.20 (2H, s), 3.86 (2H, s), 1.51 (6H, s)

Compound no. 233 (MP: 130-131). NMR solvent: CDCl3
13C: 146.5, 141.2, 136.7, 133.3, 131.4, 128.9, 126.4, 112.8, 98.6, 63.6, 48.8, 29.2, 22.3, 7.6
1H: 8.05 (1H, d, J=1.3 Hz), 7.73 (2H, m, J=8.6 Hz), 7.61 (1H, d, J=1.3 Hz), 7.38 (2H, m, J=8.6 Hz), 4.16 (1H, m), 4.06 (1H, m), 3.83 (2H, m), 2.21 (1H, m), 2.06 (1H, m), 1.70 (3H, s), 0.95 (3H, t, J=7.4 Hz)

Compound no. 234 (MP: 135-136 (dec.)). NMR solvent: CDCl3
13C: 150.1, 148.4, 143.6, 142.3, 142.2, 137.1, 137, 132.6, 132.3, 128.8, 128.7, 128, 127.7, 125.3, 125.2, 125.1, 112.8, 111.6, 65.2, 48.9, 32.8, 30.2, 22.1
1H: 8.18 (1H, d, J=1.4 Hz), 7.98 (1H, d, J=1.4 Hz), 7.81 (2H, m, J=8.5 Hz), 7.77 (2H, m, J=8.5 Hz), 7.67 (1H, d, J=1.4 Hz), 7.57 (1H, d, J=1.4 Hz), 7.42 (2H, t, J=7.5 Hz), 7.40 (2H, t, J=7.5 Hz), 7.33 (1H, m), 7.30 (1H, m), 5.61 (1H, m), 4.73 (2H, t, J=5.3 Hz), 4.12 (2H, t, J=5.3 Hz), 2.34 (2H, m), 2.30 (2H, m), 1.91 (2H, qt, J=7.6 Hz)

Compound no. 235 (MP: 154-155). NMR solvent: CDCl3
13C: 147.3, 141.7, 136.1, 133.3, 131.3, 128.9, 126.4, 112.3, 88.8, 78.6, 62.5, 24.8, 22, 20.7
1H: 7.92 (1H, d, J=1.2 Hz), 7.74 (2H, d, J=8.6 Hz), 7.50 (1H, d, J=1.2 Hz), 7.38 (2H, d, J=8.6 Hz), 5.48 (1H, q, J=5.2 Hz), 3.93 (1H, d, J=8.6 Hz), 3.72 (1H, d, J=8.6 Hz), 1.62 (3H, s), 1.47 (3H, s), 1.20 (3H, d, J=5.2 Hz)

Compound no. 236 (MP: 114-115). NMR solvent: CDCl3
13C: 159.9, 146.5, 142.5 (2 sig.), 141.6, 136.3, 133.2, 129.7, 129.1, 126.6, 124.2, 124, 119.7, 112.8, 112.8, 112.3, 81.1, 80.4, 61.9, 55.3, 22.9
1H: 8.02 (1H, t, J=1.8 Hz), 7.99 (1H, d, J=1.5 Hz), 7.78 (1H, t d, J=1.5, 7.6 Hz), 7.57 (1H, d, J=1.5 Hz), 7.53 (1H, t d, J=1.5, 7.7 Hz), 7.48 (1H, t, J=7.7 Hz), 7.38 (1H, t, J=8.1 Hz), 7.25 (1H, d d d, J=1.0, 1.5, 7.6 Hz), 7.19 (1H, d d, J=1.8, 2.6 Hz), 6.92 (1H, d d d, J=1.0, 2.6, 8.2 Hz), 5.15 (2H, s), 3.89 (5H, s), 1.63 (6H, s)

Compound no. 237 (MP: 148-149). NMR solvent: CDCl3
13C: 146.8, 143.2, 135.9, 132.9, 128.7, 127.6, 125.2, 110.7, 53.2, 41.5, 36.1, 29.4
1H: 8.10 (1H, s), 7.79 (2H, d, J=8.0 Hz), 7.52 (1H, s), 7.40 (2H, t, J=8.0 Hz), 7.30 (1H, t, J=7.5 Hz), 5.39 (1H, s), 2.17 (3H, s), 2.11 (6H, s), 1.74 (6H, s)

Compound no. 238 (MP: 175). NMR solvent: CDCl3
13C: 169.3, 151.3, 141.8, 141.5, 140.6, 137, 133.8, 133.7, 130.7, 129.3, 129, 126.3, 126.3, 126.1, 124.5, 124, 113.6, 57.5, 31.4, 29.9, 25.4, 25.2
1H: 8.11 (1H, t, J=1.8 Hz), 8.08 (1H, t, J=1.6 Hz), 7.94 (1H, d, J=1.2 Hz), 7.81 (2H, m), 7.78 (1H, m), 7.57 (1H, d, J=1.2 Hz), 7.52 (1H, t, J=7.6 Hz), 7.51 (1H, m), 7.48 (1H, t, J=7.6 Hz), 6.43 (1H, s br), 5.93 (1H, s br), 3.97 (1H, m), 3.0 (3H, s), 1.88 (2H, m), 1.85 (2H, m), 1.70 (1H, d br, J=13.5 Hz), 1.58 (2H, d q, J=3.5, 12.5 Hz), 1.38 (2H, t q, J=3.0, 13.0 Hz), 1.13 (1H, t q, J=3.3, 13.0 Hz)

Compound no. 239 (MP: 129). NMR solvent: CDCl3
13C: 151.3, 142.1, 141.7, 141, 137, 133.5, 129.1, 128.7, 127.3, 127.2, 126.3, 124, 124, 113.4, 57.5, 31.3, 30, 25.4, 25.2
1H: 8.07 (1H, t, J=1.8 Hz), 7.95 (1H, d, J=1.3 Hz), 7.78 (1H, t d, J=1.7, 7.7 Hz), 7.67 (2H, d, J=8.0 Hz), 7.56 (1H, d, J=1.3 Hz), 7.54 (1H, d t, J=1.8, 7.9 Hz), 7.48 (1H, t, J=7.7 Hz), 7.46 (2H, t, J=7.9 Hz), 7.37 (1H, m), 3.97 (1H, m), 3.0 (3H, s), 1.89 (2H, m), 1.85 (2H, m), 1.71 (1H, d br, J=13.0 Hz), 1.59 (2H, d q, J=3.5, 12.5 Hz), 1.38 (2H, t q, J=3.0, 13.0 Hz), 1.13 (1H, t q, J=3.5, 13.0 Hz)

Compound no. 240 (MP: 129-130). NMR solvent: CDCl3
13C: 159.9, 151.3, 142.6, 142, 141.5, 137, 133.5, 129.7, 129.1, 126.4, 124.2, 124, 119.8, 113.4, 112.8, 112.8, 57.5, 55.3, 31.3, 30, 25.4, 25.2
1H: 8.04 (1H, t, J=1.6 Hz), 7.94 (1H, d, J=1.3 Hz), 7.79 (1H, t t, J=1.5, 7.5 Hz), 7.56 (1H, d, J=1.3 Hz), 7.52 (1H, d t, J=2.0, 7.9 Hz), 7.48 (1H, t, J=7.8 Hz), 7.38 (1H, t, J=7.9 Hz), 7.25 (1H, d d d, J=1.0, 1.7, 7.7 Hz), 7.19 (1H, d d, J=1.8, 2.5 Hz), 6.92 (1H, d d d, J=1.0, 2.6, 8.2), 3.97 (1H, m), 3.89 (3H, s), 3.0 (3H, s), 1.88 (2H, m), 1.85 (2H, m), 1.71 (1H, d br, J=13.0 Hz), 1.59 (2H, d q, J=3.5, 12.3 Hz), 1.39 (2H, t q, J=3.0, 13.0 Hz), 1.13 (1H, t q, J=3.3, 13.0 Hz)

Compound no. 241 (MP: 173-174). NMR solvent: CDCl3
13C: 149.1, 141.7, 136.7 (2 sig.), 133.4, 131.2, 129.7, 128.9, 128.8, 126.9, 126.4, 112.5, 91, 66.2, 47.9
1H: 8.01 (1H, br), 7.68 (2H, d, J=8.3 Hz), 7.54 (1H, br), 7.51 (2H, m), 7.42 (3H, m), 7.36 (2H, d, J=8.3 Hz), 6.39 (1H, s), 4.32 (1H, br), 4.12 (1H, m), 4.04 (1H, m), 3.94 (1H, m)

Compound no. 242 (MP: 173-174). NMR solvent: CDCl3
13C: 158.9, 151.8, 140.2, 134.6, 120.8, 117, 97.4, 59.7, 57.3, 33.2, 30.9, 29.6, 25.4, 25.3
1H: 8.61 (1H, s br), 7.94 (1H, d, J=9.0 Hz), 7.53 (1H, d, J=2.0 Hz), 7.06 (1H, d d, J=2.0, 9.0 Hz), 3.21 (3H, s), 2.0 (2H, m), 1.89 (2H, m), 1.70 (2H, m), 1.61 (3H, m), 1.18 (1H, m)

Compound no. 243 (MP: 165-166). NMR solvent: DMSO
13C: 167.7, 145.6, 145.5, 139, 137.4, 135.1, 131.9, 130, 129.2, 129.1, 127.1, 126.1, 117.3, 114.5, 81.8, 78.7, 61.6, 22.6
1H: 8.57 (1H, d d, J=0.7, 1.6 Hz), 8.31 (1H, t, J=1.7 Hz), 8.21 (1H, d d, J=0.7, 8.8 Hz), 8.18 (1H, s br), 8.11 (1H, d d, J=1.6, 8.8 Hz), 7.98 (1H, d t, J=1.5, 7.8 Hz), 7.91 (1H, d t, J=1.4, 7.8 Hz), 7.60 (1H, t, J=7.7 Hz), 7.51 (1H, s br), 5.46 (2H, s), 3.91 (2H, s), 1.60 (6H, s)

Compound no. 244 (MP: 148). NMR solvent: CDCl3
13C: 151.5, 141.1, 137, 133.1, 131.5, 128.8, 126.4, 113.5, 59.3, 31.2, 28.9, 24.4
1H: 7.91 (1H, d, J=1.2 Hz), 7.73 (2H, d, J=8.6 Hz), 7.50 (1H, d, J=1.2 Hz), 7.37 (2H, d, J=8.6 Hz), 4.44 (1H, qt, J=8.2 Hz), 3.0 (3H, s), 1.95 (2H, m), 1.78 (2H, m), 1.68 (2H, m), 1.63 (2H, m)

Compound no. 245 (MP: 213-215). NMR solvent: DMSO
13C: 167.6, 150.9, 142.7, 140.4, 139.6, 137.7, 134.2, 133.2, 129.4, 128.2, 126.6, 125.6, 124.4, 123.1, 115, 56.8, 31.4, 29, 25.2, 24.9
1H: 8.20 (1H, t, J=1.8 Hz), 8.18 (1H, d, J=1.1 Hz), 8.15 (1H, d, J=1.1 Hz), 8.07 (1H, s br), 8.0 (2H, d, J=8.4 Hz), 7.90 (1H, t d, J=1.4, 7.7 Hz), 7.83 (2H, d, J=8.4 Hz), 7.62 (1H, t d, J=1.6, 8.0 Hz), 7.51 (1H, t, J=7.7 Hz), 7.44 (1H, s br), 3.84 (1H, m), 2.95 (3H, s), 1.80 (4H, m), 1.60 (1H, m), 1.57 (2H, m), 1.30 (2H, m, J=12.7 Hz), 1.11 (1H, m, J=13 Hz)

Compound no. 246 (MP: 118-119). NMR solvent: CDCl3
13C: 163.1 (d, J=245.0 Hz), 151.3, 143.3 (d, J=8.0 Hz), 141.8, 140.4 (d, J=2.0 Hz), 137, 133.7, 130.1 (d, J=8.5 Hz), 129.2, 126.2, 124.5, 123.9, 122.8 (d, J=), 114.1 (d, J=22.0 Hz), 114.1 (d, J=21.0 Hz), 113.5, 57.6, 31.4, 30, 25.4, 25.2
1H: 8.05 (1H, m), 7.94 (1H, d, J=1.3 Hz), 7.79 (1H, t d, J=2.0, 6.7 Hz), 7.57 (1H, d, J=1.3 Hz), 7.50 (2H, m), 7.44 (2H, m), 7.37 (1H, d d d, J=1.7, 2.5, 10.5 Hz), 7.06 (1H, m), 3.98 (1H, m), 3.02 (3H, s), 1.89 (2H, m), 1.87 (2H, m), 1.71 (1H, d br, J=11.5 Hz), 1.59 (2H, d q, J=3.6, 12.5 Hz), 1.39 (2H, t q, J=3.2, 13.2 Hz), 1.13 (1H, t q, J=3.3, 13.0 Hz)

Compound no. 247 (MP: 208-209). NMR solvent: DMSO
13C: 157.9, 150.9, 141.6, 140.7, 140.5, 137.7, 134, 130, 129.2, 125.3, 123.8, 122.9, 117.6, 114.8, 114.5, 113.6, 56.8, 31.4, 29, 25.2, 24.9
1H: 9.56 (1H, s, br), 8.14 (2H, s), 8.08 (1H, s), 7.83 (1H, t d, J=2.0, 6.6 Hz), 7.47 (1H, m), 7.45 (1H, t, J=7.7 Hz), 7.27 (1H, t, J=8.0 Hz), 7.13 (1H, d d d, J=1.0, 1.7, 7.6 Hz), 7.08 (1H, t, J=1.9 Hz), 6.78 (1H, d d d, 1.0, 2.4, 8.0 Hz), 3.84 (1H, m), 2.94 (3H, s), 1.79 (4H, m), 1.60 (1H, m), 1.57 (2H, m), 1.30 (2H, q, J=12.7 Hz), 1.13 (1H, m, J=13.0 Hz)

Compound no. 248 (MP: 131-132). NMR solvent: DMSO
13C: 150.9, 149 (m, J=2.0 Hz), 142.5, 140.3, 138.8, 137.7, 134.3, 130.9, 129.5, 126.0, 125.6, 124.6, 123.1, 120.2 (q, J=256.0 Hz), 119.9, 119.4, 115.1, 56.8, 31.4, 29, 25.2, 24.9
1H: 8.20 (1H, d, J=1.2 Hz), 8.17 (1H, t, J=1.6 Hz), 8.15 (1H, d, J=1.2 Hz), 7.91 (1H, t d, J=1.4, 7.8 Hz), 7.79 (1H, d, J=7.9 Hz), 7.71 (1H, br), 7.62 (1H, t, J=8.1 Hz), 7.61 (1H, m), 7.51 (1H, t, J=7.7 Hz), 7.39 (1H, d, J=8.2 Hz), 2.94 (3H, s), 3.84 (1H, m), 1.78 (4H, m), 1.60 (1H, m), 1.56 (2H, m), 1.30 (2H, m, J=12.8 Hz), 1.11 (1H, m)

Compound no. 249 (MP: 162-163). NMR solvent: CDCl3
13C: 151.5, 141.2, 136.9, 136.8, 133.1, 131.4, 128.9, 128.8, 127.7, 126.6, 126.3, 113.1, 51.7, 48.6, 20.4
1H: 7.91 (1H, d, J=1.3 Hz), 7.46 (1H, d, J=1.3 Hz), 7.64 (2H, d, J=8.6 Hz), 7.39 (2H, t, J=7.5 Hz), 7.34 (2H, d, J=8.6 Hz), 7.32 (1H, m), 7.31 (2H, d, J=8.2 Hz), 4.61 (2H, s), 4.20 (1H, m, J=6.8 Hz), 1.37 (6H, d, J=6.8 Hz)

Compound no. 250 (MP: 111). NMR solvent: CDCl3
13C: 151.7, 142.3, 137, 136.7, 132.9, 128.9, 128.6, 127.7, 127.5, 126.6, 125.1, 112.9, 51.7, 48.5, 20.4
1H: 7.93 (1H, d, J=1.3 Hz), 7.72 (2H, d, J=8.2 Hz), 7.48 (1H, d, J=1.3 Hz), 7.39 (2H, m), 7.37 (2H, m), 7.31 (3H, m), 7.27 (1H, m), 4.62 (2H, s), 4.21 (1H, m, J=6.7 Hz), 1.37 (6H, d, J=6.7 Hz)

Compound no. 251 (MP: 132-133). NMR solvent: CDCl3
13C: 152.2, 142, 138.4, 136.8, 133, 129, 128.6, 127.6, 127.3, 126.1, 125, 113, 59.4, 51.3, 28.1
1H: 7.91 (1H, d, J=1.4 Hz), 7.65 (2H, d, J=8.5 Hz), 7.46 (1H, d, J=1.4 Hz), 7.38 (2H, t, J=7.1 Hz), 7.35 (2H, t, J=8.0 Hz), 7.31 (1H, m, J=7.4 Hz), 7.26 (2H, m), 7.25 (1H, m), 4.69 (2H, s), 1.52 (9H, s)

Compound no. 252 (MP: 129-130). NMR solvent: CDCl3
13C: 152.1, 141, 138.4, 136.9, 133, 131.5, 129, 128.8, 127.6, 126.2, 126.1, 113.2, 59.5, 51.3, 28.1
1H: 7.89 (1H, d, J=1.3 Hz), 7.57 (2H, d, J=8.6 Hz), 7.43 (1H, d, J=1.3 Hz), 7.38 (2H, t, J=7.6 Hz), 7.31 (1H, m), 7.31 (2H, d, J=8.6 Hz), 7.24 (1H, d, J=8.0 Hz), 4.68 (2H, s), 1.52 (9H, s)

Compound no. 253 (MP: 147-148). NMR solvent: CDCl3
13C: 162.9, 147.5, 147.3, 136.8, 129.1, 128.2, 127.5, 64.6, 47.3, 44.2
1H: 8.95 (1H, s), 8.07 (2H, d, J=8.7 Hz), 7.47 (2H, d, J=8.7 Hz), 5.15 (2H, br), 4.36 (2H, br), 3.40 (2H, t, J=6.8 Hz)

Compound no. 254 (MP: 141-142). NMR solvent: CDCl3
13C: 151.5, 138.3, 134.2, 133.9, 128.4, 127.1, 126.8, 122.9, 57.2, 30.8, 30.1, 25.4, 25.2, 10.5
1H: 7.68 (2H, d, J=8.1 Hz), 7.62 (1H, s), 7.43 (2H, t, J=7.8 Hz), 7.30 (1H, t, J=7.4 Hz), 3.91 (1H, m), 2.91 (3H, s), 2.46 (3H, s), 1.86 (2H, m), 1.81 (2H, m), 1.70 (1H, d br, J=13.0 Hz), 1.57 (2H, m), 1.36 (2H, m), 1.12 (1H, m)

Compound no. 255 (MP: oil). NMR solvent: CDCl3
13C: 159.9, 151.6, 142.1, 137, 136.7, 134.3, 129.7, 128.9, 127.7, 126.6, 117.5, 113.7, 113.2, 110, 55.3, 51.7, 48.6, 20.4
1H: 7.92 (1H, d, J=1.0 Hz), 7.47 (1H, d, J=1.0 Hz), 7.39 (2H, t, J=7.2 Hz), 7.31 (4H, m), 7.28 (1H, m), 6.84 (1H, m), 4.61 (2H, s), 4.21 (1H, m, J=6.8 Hz), 3.85 (3H, m), 1.37 (6H, d, J=6.8 Hz)

Compound no. 256 (MP: oil). NMR solvent: CDCl3
13C: 159.8, 152.2, 141.8, 138.5, 136.8, 134.4, 129.6, 129, 127.6, 126.1, 117.4, 113.8, 113.3, 109.7, 59.4, 55.2, 51.2, 28.1
1H: 7.91 (1H, d, J=1.2 Hz), 7.45 (1H, d, J=1.2 Hz), 7.39 (2H, t, J=7.6 Hz), 7.30 (1H, m, J=7.3 Hz), 7.26 (2H, m), 7.24 (2H, m), 7.19 (1H, m), 6.81 (1H, d d d, J=1.2, 2.6, 8.0 Hz), 4.69 (2H, s), 3.82 (3H, m), 1.53 (9H, s)

Compound no. 257 (MP: 138-139). NMR solvent: CDCl3
13C: 151.3, 142.8, 141.8, 140.2, 137, 134.6, 133.7, 129.9, 129.2, 127.3, 127.3, 126.2, 125.4, 124.5, 123.9, 113.6, 57.6, 31.4, 30, 25.4, 25.2
1H: 8.04 (1H, m), 7.94 (1H, d, J=1.3 Hz), 7.78 (1H, m), 7.66 (1H, t, J=1.7 Hz), 7.57 (1H, d, J=1.3 Hz), 7.54 (1H, t d, J=1.5, 7.6 Hz), 7.49 (1H, t, J=7.7 Hz), 7.48 (1H, m), 7.39 (1H, t, J=7.6 Hz), 7.34 (1H, d d d, J=1.5, 2.2, 8.1 Hz), 3.98 (1H, m), 3.02 (3H, s), 1.89 (2H, m), 1.87 (2H, m), 1.71 (1H, d br, J=13.3 Hz), 1.60 (2H, m), 1.39 (2H, t q, J=3.0, 12.7 Hz), 1.14 (1H, t q, J=3.3, 13.0 Hz)

Compound no. 258 (MP: 115-118). NMR solvent: CDCl3
13C: 159.2, 151.3, 142.5, 142, 141.6, 137, 133.5, 129.7, 129.1, 126.4, 124.1, 124, 119.6, 113.4 (2 sig.), 113.3, 63.5, 57.5, 31.4, 30, 25.4, 25.2, 14.9
1H: 8.04 (1H, m, J=1.7 Hz), 7.94 (1H, d, J=1.4 Hz), 7.78 (1H, t d, J=1.7, 7.5 Hz), 7.55 (1H, d, J=1.4 Hz), 7.52 (1H, d t, J=1.5, 7.9 Hz), 7.47 (1H, t, J=7.6 Hz), 7.36 (1H, t, J=8.0 Hz), 7.24 (1H, d d d, J=1.0, 1.7, 7.7 Hz), 7.19 (1H, d d, J=1.7, 2.5 Hz), 6.91 (1H, d d d, J=1.0, 2.5, 8.2 Hz), 4.11 (2H, q, J=7.0 Hz), 3.97 (1H, m), 3.01 (3H, s), 1.89 (2H, m), 1.86 (2H, m), 1.71 (1H, d br, J=12.5 Hz), 1.59 (2H, qd, J=3.5, 12.5 Hz), 1.46 (3H, t, J=7.0 Hz), 1.39 (2H, t q, J=3.0, 13.0 Hz), 1.13 (1H, t q, J=3.5, 13.0 Hz)

Compound no. 259 (MP: 137-139). NMR solvent: CDCl3
13C: 158.3 (d, J=248.0 Hz), 151.3, 141.7, 137.0, 135.0 (d, J=1.3 Hz), 133.5, 130.5 (d, J=3.5 Hz), 130.4 (m. J=14.0 Hz), 129.3 (d, J=3.3 Hz), 128.9, 128.7 (d, J=8.5 Hz), 128.0, 125.6 (d, J=2.5 Hz), 124.9, 117.4 (d, J=25.0 Hz), 113.6, 57.5, 31.4, 30, 25.4, 25.2
1H: 7.97 (1H, s br), 7.93 (1H, d, J=1.1 Hz), 7.82 (1H, t d, J=1.7, 7.2 Hz), 7.56 (1H, d, J=1.1 Hz), 7.52-7.43 (3H, m), 7.29 (1H, m), 7.11 (1H, t, J=9.5 Hz), 3.96 (1H, m), 3.0 (3H, s), 1.88 (2H, m), 1.85 (2H, m), 1.71 (1H, d br, J=13.0 Hz), 1.59 (2H, d q, J=3.5, 12.5 Hz), 1.39 (2H, t q, J=3.0, 13.0 Hz), 1.13 (1H, t q, J=3.5, 13.0 Hz)

Compound no. 260 (MP: 190-191). NMR solvent: DMSO
13C: 156.8, 146.3, 141.3, 136.7, 126.2, 124.4, 115.4, 111.6, 80.6, 79.3, 60.8, 22.5
1H: 9.48 (1H, s), 8.09 (1H, d, J=1.3 Hz), 7.80 (1H, d, J=1.3 Hz), 7.64 (2H, m d, J=8.5 Hz), 6.76 (2H, m d, J=8.5 Hz), 5.14 (2H, s), 3.84 (2H, s), 1.49 (6H, s)

Compound no. 261 (MP: 197-199). NMR solvent: DMSO
13C: 156.7, 151, 140.9, 137.3, 126.1, 124.4, 115.4, 112.5, 56.8, 31.3, 29.1, 25.2, 24.9
1H: 9.48 (1H, s), 8.05 (1H, d, J=1.3 Hz), 7.77 (1H, d, J=1.3 Hz), 7.64 (2H, m, J=8.3 Hz), 6.77 (2H, m, J=8.3 Hz), 3.80 (1H, m), 2.91 (3H, s), 1.77 (4H, m), 1.59 (1H, m), 1.55 (2H, m), 1.28 (2H, m), 1.10 (1H, m)

Compound no. 262 (MP: 170 (dec.)). NMR solvent: DMSO
13C: 157.9, 149, 137.3, 135.3, 130.2, 129.5, 116.3, 116, 115.9, 112.3, 58.7, 31.5, 28.2, 24
1H: 9.70 (1H, s), 9.24 (1H, s), 8.32 (1H, s), 7.29 (1H, t, J=7.8 Hz), 7.27 (1H, m), 7.24 (1H, m), 6.83 (1H, m, J=2.2, 6.7 Hz), 4.39 (1H, m), 2.97 (3H, s), 1.89 (2H, m), 1.70 (4H, m), 1.53 (2H, m)

Compound no. 263 (MP: 89-91). NMR solvent: CDCl3
13C: 146.8, 138.7, 134, 133.1, 128.4, 127.2, 126.9, 122.8, 81.2, 80.7, 61, 23, 10.6
1H: 7.66 (2H, d, J=8.4 Hz), 7.63 (1H, s), 7.43 (2H, t, J=7.8 Hz), 7.31 (1H, t, J=7.4 Hz), 4.93 (2H, s), 3.90 (2H, s), 2.49 (3H, s), 1.61 (6H, s)

Compound no. 264 (MP: 118-119). NMR solvent: CDCl3
13C: 152.1, 138.7, 135.3, 134.2, 134.1, 129.1, 128.4, 128.2, 127.7, 127.2, 126.9, 123.2, 53.9, 36, 10.6
1H: 7.69 (1H, s), 7.67 (2H, d, J=8.3 Hz), 7.43 (2H, t, J=7.7 Hz), 7.31 (1H, t, J=7.4 Hz), 7.40-7.27 (5H, m), 4.66 (2H, s), 3.01 (3H, s), 2.49 (3H, s)

Compound no. 265 (MP: 178-180 (dec.)). NMR solvent: DMSO
13C: 157.9, 149.1, 137.3, 136.8, 135.8, 130.2, 129.5, 128.5, 127.2, 126.8, 116.3, 116.1, 115.4, 112.4, 51.4, 47.1, 20.1
1H: 9.73 (1H, s), 9.18 (1H, s), 8.29 (1H, s), 7.36-7.28 (5H, m), 7.27 (1H, t, J=8.0 Hz), 7.21 (1H, m), 7.18 (1H, m), 6.82 (1H, m, J=2.5, 8.1 Hz), 4.65 (2H, s), 4.16 (1H, m), 1.28 (6H, d, J=6.7 Hz)

Compound no. 266 (MP: oil). NMR solvent: CDCl3
13C: 150.7, 145.2, 133.2, 129.1, 125.1, 119.7, 113.5, 59.3, 28.8, 24.3
1H: 8.09 (1H, m d, J=8.3 Hz), 7.98 (1H, m d, J=8.3 Hz), 7.59 (1H, m, J=7.7 Hz), 7.45 (1H, m, J=7.7 Hz), 4.78 (1H, m), 3.17 (3H, s), 2.07 (2H, m), 1.75 (4H, m), 1.63 (2H, m)

Compound no. 267 (MP: 142-143). NMR solvent: CDCl3
13C: 146.6, 141.2, 136.7, 133.2, 131.4, 128.9, 126.4, 112.8, 96.5, 75.9, 53.4, 25.6, 25.4, 23.7, 9.8
1H: 8.03 (1H, br), 7.73 (2H, d, J=8.5 Hz), 7.59 (1H, br), 7.37 (2H, d, J=8.5 Hz), 4.10 (1H, m), 3.81 (1H, d d, J=5.3, 9.0 Hz), 3.43 (1H, t, J=9.2 Hz), 1.74 (3H, s), 1.72 (2H, s), 1.66 (3H, s), 1.0 (3H, t, J=7.5 Hz)

Compound no. 268 (MP: 117-118). NMR solvent: CDCl3
13C: 144.9, 136.5, 133.6, 131.7, 128.5, 127.8, 126.4, 110.8, 95.7, 63.1, 47.7, 23.9
1H: 7.96 (2H, d, J=8.8 Hz), 7.78 (1H, s), 7.45 (2H, t, J=8.0 Hz), 7.35 (1H, t, J=7.5 Hz), 4.07 (2H, t, J=6.2 Hz), 3.58 (2H, t, J=6.2 Hz), 1.74 (6H, s)

Compound no. 269 (MP: 92-93). NMR solvent: CDCl3
13C: 141.6, 135.3, 133.9, 129.4, 128.8, 128.1, 127.5, 111.0, 80.6, 61.3, 29.7, 22.7, 22.5
1H: 7.85 (2H, d, J=8.8 Hz), 7.40 (2H, d, J=8.8 Hz), 4.81 (2H, s), 3.84 (2H, s), 1.65 (6H, s)

Compound no. 270 (MP: oil). NMR solvent: CDCl3
13C: 146.7, 142.2, 136.6, 132.9, 128.7, 127.6, 125.2, 112.5, 96.4, 75.9, 53.4, 25.6, 25.4, 23.7, 9.8
1H: 8.05 (1H, d, J=1.3 Hz), 7.80 (2H, d, J=8.5 Hz), 7.61 (1H, d, J=1.3 Hz), 7.41 (2H, t, J=8.0 Hz), 7.30 (1H, t, J=7.4 Hz), 4.11 (1H, m), 3.81 (1H, d d, J=5.2, 9.0 Hz), 3.44 (1H, t, J=9.5 Hz), 1.75 (3H, s), 1.73 (3H, s), 1.72 (2H, m), 1.0 (3H, t, J=7.7 Hz)

Compound no. 271 (MP: 113-114). NMR solvent: CDCl3
13C: 156, 151.7, 137.4, 136, 128, 127.6, 121.7, 120.9, 117.2, 110.6, 57.5, 55.2, 31.1, 30.1, 25.4, 25.2
1H: 8.23 (1H, d d, J=1.8, 7.7 Hz), 7.94 (1H, d, J=1.3 Hz), 7.82 (1H, d, J=1.3 Hz), 7.28 (1H, d t, J=2.0, 7.6 Hz), 7.07 (1H, J=1.1, 7.6 Hz), 6.97 (1H, d, J=8.3 Hz), 3.95 (3H, s), 3.95 (1H, m), 2.99 (3H, s), 1.87 (4H, m), 1.69 (1H, d br, J=12.3 Hz), 1.59 (2H, d q, J=3.5, 12.5 Hz), 1.37 (2H, t q, J=3.0, 13.0 Hz), 1.13 (1H, t q, J=3.3, 13.1 Hz)

Compound no. 272 (MP: 178-181). NMR solvent: CDCl3
13C: 151.0, 150.5 (d d, J=12.7, 247 Hz), 149.7 (d d, J=13.0, 248.0 Hz), 140.3, 137, 130.3 (d d, J=3.7, 6.6 Hz), 121.0 (d d, J=3.5, 6.3 Hz), 117.5 (d, J=17.5 Hz), 114.1 (d, J=18.5 Hz), 113.5 (d, J=1.0 Hz), 57.6, 31.3, 29.9, 25.4, 25.2
1H: 7.88 (1H, d, J=1.3 Hz), 7.61 (1H, d d d, J=2.2, 7.7, 11.6 Hz), 7.49 (1H, m), 7.45 (1H, d, J=1.3 Hz), 7.17 (1H, d t, J=8.4, 10.5 Hz), 3.93 (1H, m), 2.99 (3H, s), 1.86 (4H, m), 1.70 (1H, d br), 1.58 (2H, d q, J=3.5, 12.3 Hz), 1.37 (2H, t q, 3.0, 13.0 Hz), 1.12 (1H, t q, J=3.5, 13.0 Hz)

Compound no. 273 (MP: 142-143). NMR solvent: CDCl3
13C: 162.3 (d, J=246 Hz), 151.3, 141.3, 136.9, 129.2 (d, J=3.2 Hz), 126.8 (d, J=8.0 Hz), 115.6 (d, J=22.0 Hz), 112.9, 57.5, 31.3, 30, 25.4, 25.2
1H: 7.89 (1H, d, J=1.3 Hz), 7.76 (2H, m, J=5.4, 8.9 Hz), 7.74 (1H, d, J=1.3 Hz), 7.09 (2H, m, J=8.8 Hz), 3.95 (1H, m), 2.99 (3H, s), 1.87 (4H, m), 1.70 (1H, d br, J=13.0 Hz), 1.58 (2H, d q, J=3.5, 12.2 Hz), 1.37 (2H, t q, J=3.5, 13.0 Hz), 1.13 (1H, t q, J=3.5, 13.0 Hz)

Compound no. 274 (MP: 156-158). NMR solvent: CDCl3
13C: 151, 140, 137.1, 133.2, 132.8, 131.1, 130.6, 126.9, 124.3, 114, 57.6, 31.4, 29.9, 25.4, 25.2
1H: 7.91 (1H, d, J=2.0 Hz), 7.90 (1H, d, J=1.4 Hz), 7.61 (1H, d d, J=2.0, 8.4 Hz), 7.51 (1H, d, J=1.4 Hz), 7.45 (1H, d, J=8.4 Hz), 3.94 (1H, m), 3.0 (3H, s), 1.86 (4H, m), 1.71 (1H, m), 1.58 (2H, J=3.5, 12.5 Hz), 1.38 (2H, t q, J=3.0, 13.0 Hz), 1.13 (1H, t q, J=3.5, 13.0 Hz)

Compound no. 275 (MP: 160-162). NMR solvent: CDCl3
13C: 150.9, 148.6, 140, 137.3, 134.9, 130.9, 129.7, 122, 119.9, 114.6, 57.6, 31.4, 29.9, 25.4, 25.2
1H: 8.61 (1H, t, J=2 Hz), 8.14 (2H, m), 7.94 (1H, d, J=1.3 Hz), 7.64 (1H, d, J=1.3 Hz), 7.57 (1H, t, J=8.0 Hz), 3.96 (1H, m, J=12.0 Hz), 3.02 (3H, s), 1.88 (4H, m), 1.72 (1H, m), 1.60 (2H, d q, J=3.5, 12.5 Hz), 1.39 (2H, t q, J=3.0, 13.0 Hz), 1.14 (1H, t q, J=3.5, 13.0 Hz)

Compound no. 276 (MP: 130-131). NMR solvent: CDCl3
13C: 151.2, 150.5 (t, J=2.7 Hz), 141.1, 137, 130.5, 126.5, 119.7, 115.9 (t, J=259.5 Hz), 113.2, 57.6, 31.3, 30, 25.4, 25.2
1H: 7.89 (1H, d, J=1.3 Hz), 7.79 (2H, d, J=8.8 Hz), 7.47 (1H, d, J=1.3 Hz), 7.15 (2H, d, J=8.8 Hz), 6.54 (1H, t, J=74 Hz), 3.95 (1H, m, J=11.0 Hz), 3.0 (3H, s), 1.86 (4H, m), 1.70 (1H, dbr, J=14.0 Hz), 1.58 (2H, d q, J=3.6, 12.2 Hz), 1.37 (2H, J=3.2, 13.0 Hz), 1.13 (1H, J=3.5, 13.0 Hz)

Compound no. 277 (MP: 168-169). NMR solvent: CDCl3
13C: 151.2, 141.1, 137, 133.1, 131.6, 128.8, 126.4, 113.4, 57.6, 31.3, 30, 25.4, 25.2
1H: 7.90 (1H, d, J=1.3 Hz), 7.73 (2H, d. J=8.7 Hz), 7.49 (1H, d, J=1.3 Hz), 7.37 (2H, d, J=8.7 Hz), 3.95 (1H, m, J=11.8 Hz), 2.99 (3H, s), 1.86 (4H, m), 1.70 (1H, d, J=13.5 Hz), 1.58 (2H, d q, J=3.5, 12.3 Hz), 1.38 (2H, t q, J=3.0, 13.0 Hz), 1.13 (1H, t q, J=3.5, 13 Hz)

Compound no. 278 (MP: 160). NMR solvent: CDCl3
13C: 151.5, 142.3, 136.9, 132.8, 128.7, 127.6, 125.1, 113.1, 67, 54.4, 31.8, 29.5
1H: 7.94 (1H, s), 7.80 (2H, d, J=7.6 Hz), 7.51 (1H, s), 7.41 (2H, t, J=7.6 Hz), 7.30 (1H, t, J=7.3 Hz), 4.28 (1H, m), 4.09 (2H, d d, J=4.0, 11.5 Hz), 3.50 (2H, t, J=11.5 Hz), 3.04 (3H, s), 1.94 (2H, d q, J=4.5, 12.3 Hz), 1.77 (2H, d br, J=12.0 Hz)

Compound no. 279 (MP: 157-159). NMR solvent: CDCl3
13C: 152.2, 145.6, 140.7, 133.3, 128.6, 127.1, 125, 112.4, 57, 30.7, 30.1, 25.4, 25.2, 14
1H: 7.76 (2H, d, J=8.2 Hz), 7.38 (2H, t, J=7.9 Hz), 7.26 (1H, t, J=7.5 Hz), 7.21 (1H, s), 3.90 (1H, m br), 2.88 (3H, s), 2.52 (3H, s), 1.81 (4H, m), 1.68 (1H, d br, J=13.0 Hz), 1.55 (2H, d q, J=3.3, 12.2 Hz), 1.35 (2H, q br, J=12.5 Hz), 1.11 (1H, t q, J=3.0, 13.0 Hz)

Compound no. 280 (MP: 137). NMR solvent: CDCl3
13C: 143.9, 135.7, 133.7, 133.7, 130.1, 128.7, 127.7, 111.2, 80.9, 80.6, 61.3, 22.9
1H: 7.90 (2H, d, J=8.6 Hz), 7.73 (1H, s), 7.41 (2H, s, J=8.6 Hz), 4.88 (2H, s), 3.91 (2H, s), 1.62 (6H, s)

Compound no. 281 (MP: 132-134). NMR solvent: CDCl3
13C: 151.7, 149.1, 148.5, 142, 136.7, 126.1, 117.4, 112.4, 111.2, 108.4, 59.3, 55.9, 55.9, 31.2, 28.8, 24.3
1H: 7.91 (1H, d, J=1.3 Hz), 7.44 (1H, d, J=1.3 Hz), 7.40 (1H, d, J=2.0 Hz), 7.30 (1H, d d, J=2.0, 8.3 Hz), 6.90 (1H, d, J=8.3 Hz), 4.44 (1H, m, J=8.2 Hz), 3.96 (3H, s), 3.91 (3H, s), 2.99 (3H, s), 1.95 (2H, m), 1.73 (4H, m), 1.62 (2H, m)

Compound no. 282 (MP: 189-191). NMR solvent: CDCl3
13C: 151.5, 142.2, 138.1, 137, 132.9, 129.1, 128.7, 128.3, 127.6, 127.2, 125.1, 113.1, 62.8, 55.8, 52.5, 31.6, 28.9
1H: 7.92 (1H, d, J=1.3 Hz), 7.80 (2H, m, J=8.0 Hz), 7.50 (1H, d, J=1.3 Hz), 7.41 (2H, t, J=7.6 Hz), 7.37-7.25 (6H, m), 4.03 (1H, m), 3.53 (2H, s), 3.03 (3H, s), 3.01 (2H, m), 2.11 (2H, t br, J=11.2 Hz), 1.90 (2H, q br, J=12.0 Hz), 1.79 (2H, d br, J=12.0 Hz)

Compound no. 283 (MP: 128). NMR solvent: CDCl3
13C: 162.3, 149.8, 147.2, 130.1, 129.9, 128.7, 126.7, 57.6, 30.2 (2 sig.), 25.5, 25.3
1H: 8.82 (1H, s), 8.15 (2H, m), 7.48 (3H, m), 4.32 (1H, m br), 3.14 (3H, s), 1.93 (4H, m), 1.71 (1H, d br, J=13.3 Hz), 1.59 (2H, m), 1.40 (2H, m), 1.15 (1H, t q, J=3.5, 13.0 Hz)

Compound no. 284 (MP: 151-153). NMR solvent: CDCl3
13C: 160.3, 153.3, 151, 130.3, 129.6, 128.6, 126.5, 58.7, 30.8, 29.5, 25.5, 25.2, 13.8
1H: 8.10 (2H, m, J=7.5 Hz), 7.45 (3H, m), 4.21+3.80 (1H, m), 3.03-2.99 (3H, m), 2.69 (3H, s), 1.88 (4H, m), 1.72 (1H, m), 1.58 (2H, m), 1.54 (2H, m), 1.12 (1H, m)

Compound no. 285 (MP: 135-138). NMR solvent: CDCl3
13C: 162.9, 146.2, 144.9, 130.1, 129.8, 128.7, 126.7, 82, 79.3, 62.2, 22.8
1H: 8.94 (1H, s), 8.12 (2H, m), 7.47 (3H, m), 5.57 (2H, s), 3.86 (2H, s), 1.63 (6H, s)

Compound no. 286 (MP: 125-127). NMR solvent: CDCl3
13C: 160, 157.7, 146.4, 129.9, 129.9, 128.6, 126.6, 82.2, 79.6, 61.7, 22.8, 15.1
1H: 8.08 (2H, m), 7.45 (3H, m), 5.40 (2H, s), 3.85 (2H, s), 2.80 (3H, s), 1.62 (6H, s)

Compound no. 287 (MP: 222-224). NMR solvent: DMSO
13C: 167.8, 150.7, 140.5, 140.2, 140, 137.8, 135, 134.2, 129.6, 129.3, 129, 126.7, 125.8, 125.6, 124.1, 123.1, 114.7, 57.5, 37.9, 35.9, 33.8, 29.2
1H: 8.21 (1H, m, J=1.6 Hz), 8.17 (1H, m, J=1.6 Hz), 8.15 (1H, s br), 8.14 (1H, d, J=1.3 Hz), 8.12 (1H, d, J=1.3 Hz), 7.88 (1H, d d, J=1.6, 7.8 Hz), 7.88 (2H, m), 7.62 (1H, m), 7.57 (1H, t, J=7.8 Hz), 7.51 (1H, t, J=7.8 Hz), 7.48 (1H, s br), 2.94 (3H, s), 2.16 (6H, s), 2.11 (3H, s), 1.66 (6H, s)

Compound no. 288 (MP: 138-139). NMR solvent: CDCl3
13C: 159.2, 151.2, 141.9, 137.2, 137, 134.6, 129.7, 128.5, 127.9, 127.5, 117.8, 114.3, 113.3, 111.2, 69.9, 58.4, 38.6, 36.2, 34.1, 29.7
1H, 7.93 (1H, d, J=1.3 Hz), 7.50 (1H, m), 7.47 (2H, m), 7.46 (1H, d, J=1.3 Hz), 7.40 (2H, m), 7.38 (1H, m), 7.34 (1H, m), 7.31 (1H, t, J=7.9 Hz), 6.92 (1H, d d d, J=1.0, 2.5, 8.2 Hz), 5.14 (2H, s), 2.99 (3H, s), 2.20 (9H, s), 1.74 (6H, s)

Compound no. 289 (MP: 165-169 (dec.)). NMR solvent: CDCl3
13C: 150.9, 148.4, 146.7, 139.1, 137.6, 132.4, 129.1, 123.6, 113.8, 58.5, 38.5, 36.2, 34.1, 29.6
1H: 9.0 (1H, d, J=1.5 Hz), 8.52 (1H, d d, J=1.3, 4.7 Hz), 8.11 (1H, d t, J=1.8, 7.8 Hz), 7.94 (1H, s), 7.55 (1H, s), 7.33 (1H, d d, J=4.9, 7.7 Hz), 2.99 (3H, s), 2.19 (9H, s), 1.73 (6H, s)

Compound no. 290 (MP: 149). NMR solvent: CDCl3
13C: 151.2, 142, 141.6, 141, 137.3, 133.6, 129.1, 128.7, 127.3, 127.2, 126.3, 124, 123.9, 113.2, 58.4, 38.6, 36.2, 34.1, 29.7
1H: 8.05 (1H, t br, J=1.8 Hz), 7.95 (1H, d, J=0.13 Hz), 7.78 (1H, d t, J=1.5, 7.5 Hz), 7.67 (2H, m, J=8.5 Hz), 7.53 (1H, d, J=1.3 Hz), 7.53 (1H, m), 7.48 (1H, t, J=7.6 Hz), 7.46 (2H, t, J=7.8 Hz), 7.37 (1H, m, J=7.5 Hz), 3.0 (3H, s), 2.21 (9H, s), 1.74 (6H, s)

Compound no. 291 (MP: 208-210). NMR solvent: CDCl3
13C: 151.1, 150.2, 148.2, 141.5, 138.6, 137.4, 134.1, 129.4, 126, 125.7, 123.8, 121.7, 113.5, 58.5, 38.6, 36.2, 34.1, 29.7
1H: 8.67 (2H, m, J=5.0 Hz), 8.11 (1H, m, J=2.0 Hz), 7.95 (1H, d, J=1.3 Hz), 7.84 (1H, d t, J=1.7, 7.5 Hz), 7.58 (2H, m), 7.55 (1H, d, J=1.3 Hz), 7.55 (1H, m), 7.51 (1H, t, J=7.6 Hz), 3.0 (3H, s), 2.20 (9H, s), 1.73 (6H, s)

Compound no. 292 (MP: 75-77). NMR solvent: CDCl3
13C: 146.4, 141.3, 136.9, 136.3, 133.2, 131.3, 129, 128.9, 128.8, 126.4, 126.2, 112.5, 97, 76.3, 55.5, 25.4, 24
1H: 8.05 (1H, d, J=1.0 Hz), 7.70 (2H, d, J=8.5 Hz), 7.56 (1H, d, J=1.0 Hz), 7.46-7.38 (5H, m), 7.35 (2H, d, J=8.5 Hz), 5.21 (1H, d d, J=5.5, 9.8 Hz), 4.10 (1H, d d, J=5.5, 9.3 Hz), 3.68 (1H, t, J=9.5 Hz), 1.88 (3H, s), 1.87 (3H, s)

Compound no. 293 (MP: 164-165). NMR solvent: CDCl3
13C: 161.4, 146.5, 140.5, 134.4, 120.3, 117.9, 94.7, 82.6, 79.6, 62.1, 56, 23
1H: 7.92 (1H, d d, J=0.5, 9.0 Hz), 7.58 (1H, d, J=2.5 Hz), 7.08 (1H, d d, J=2.5, 9.0 Hz), 5.53 (1H, s), 3.94 (3H, s), 3.90 (2H, s), 1.69 (6H, s)

Compound no. 294 (MP: 190-193 (dec.)). NMR solvent: DMSO
13C: 156.9, 151, 140.3, 137.2, 126.2, 123.8, 115.4, 112.7, 58.4, 31.2, 28.2, 24
1H: 9.53 (1H, s), 8.18 (1H, s), 7.81 (1H, s), 7.65 (2H, d, J=8.7 Hz), 6.79 (2H, d, J=8.7 Hz), 4.36 (1H, m), 2.92 (3H, s), 1.86 (2H, m), 1.67 (4H, m), 1.53 (2H, m)

Compound no. 295 (MP: 91-93). NMR solvent: CDCl3
13C: 144.0, 136.6, 133.6, 131.6, 128.5, 127.9, 126.5, 110.9, 81.0, 80.6, 61.3, 22.9
1H: 7.96 (2H, d, J=8.4 Hz), 7.74 (1H, s), 7.45 (2H, m, J=7.8 Hz), 7.35 (1H, m, J=7.6 Hz), 4.88 (2H, s), 3.91 (2H, s), 1.62 (6H, s)

Compound no. 296 (MP: 106-110). NMR solvent: CDCl3
13C: 156.9, 150.9, 141.6, 137.3, 134, 130, 117.1, 115.1, 113.5, 112.6, 58.5, 38.5, 36.2, 34.1, 29.7
1H: 7.95 (1H, s), 7.46 (1H, m), 7.42 (1H, s), 7.24 (1H, m), 7.23 (1H, m), 6.91 (1H, m), 2.96 (3H, s), 2.18 (9H, s), 1.72 (6H, s)

Compound no. 297 (MP: 119-121). NMR solvent: DMSO
13C: 149.8, 144.6, 132.6, 129.3, 125.3, 119.6, 113.3, 67.9, 57.6, 56.1, 34.2, 27.2
1H: 8.18 (1H, d, J=8.3 Hz), 7.90 (1H, d, J=8.3 Hz), 7.68 (1H, t, J=7.8 Hz), 7.52 (1H, t, J=7.6 Hz), 4.64 (1H, s br), 4.03 (1H, s br), 3.40 (1H, s br), 3.03 (3H, s), 1.90 (2H, s br), 1.82 (2H, s br), 1.75 (2H, s br), 1.26 (2H, s br)

Compound no. 298 (MP: 94-95). NMR solvent: CDCl3
13C: 146.6, 142.4, 136.9, 136.3, 132.8, 129, 128.9, 128.7, 127.6, 126.2, 125.2, 112.3, 96.9, 76.3, 55.5, 25.4, 24
1H: 8.06 (1H, d, J=1.3 Hz), 7.78 (2H, m, J=8.3 Hz), 7.58 (1H, d, J=1.3 Hz), 7.44 (5H, m), 7.39 (2H, m, J=7.8 Hz), 7.29 (1H, m, J=7.4 Hz), 5.21 (1H, d d, J=5.5, 9.8 Hz), 4.11 (1H, d d, J=5.5, 9.3 Hz), 3.69 (1H, t, J=9.5 Hz), 1.89 (3H, s), 1.87 (3H, s)

Compound no. 299 (MP: 140-142). NMR solvent: CDCl3
13C: 146.7, 141.2, 136.7, 133.3, 131.4, 128.9, 126.4, 112.8, 96.4, 63.6, 48.3, 24.1
1H: 8.06 (1H, br), 7.73 (2H, m, J=8.6 Hz), 7.61 (1H, br), 7.38 (2H, m, J=8.6 Hz), 4.12 (2H, t, J=6.0 Hz), 3.85 (2H, t, J=6.0 Hz), 1.74 (6H, s)

Compound no. 300 (MP: 149-150). NMR solvent: CDCl3
13C: 149.1, 136.3, 134.3, 131.9, 128.5, 127.7, 126.4, 111.6, 57, 30.6, 29.8, 25.3, 25.2
1H: 7.98 (2H, d, J=8.2 Hz), 7.72 (1H, br), 7.45 (2H, m, J=7.6 Hz), 7.34 (1H, m, J=7.5 Hz), 4.24 (1H, m br), 2.88 (3H, br), 1.86 (4H, m), 1.70 (1H, m), 1.56 (2H, m), 1.40 (2H, m), 1.13 (1H, m)

Compound no. 301 (MP: 136-137). NMR solvent: CDCl3
13C: 144.3, 138.8, 135.2, 133.8, 130.5, 128.6, 128.1, 96.1, 81.1, 80.7, 61.3, 22.9
1H: 7.91 (2H, d, J=8.5 Hz), 7.82 (1H, s), 7.41 (2H, d, J=8.5 Hz), 4.84 (2H, s), 3.91 (2H, s), 1.63 (6H, s)

Compound no. 302 (MP: 108). NMR solvent: CDCl3
13C: 149.4, 143.0, 136.4, 132.6, 128.7, 127.8, 125.2, 112.2, 80.7, 71.4, 57.8, 24.9, 9.8
1H: 7.98 (1H, br), 7.81 (2H, d, J=8.2 Hz), 7.54 (1H, br), 7.42 (2H, t, J=7.4 Hz), 7.31 (1H, t, J=7.3 Hz), 5.13 (1H, d, J=4.5 Hz), 5.0 (1H, d, J=4.5 Hz), 4.32 (2H, m), 3.73 (1H, m), 1.91 (1H, m), 1.64 (1H, m), 0.98 (3H, t, J=7.5 Hz)

Compound no. 303 (MP: 80-81). NMR solvent: CDCl3
13C: 150.6 (d d, J=13.0, 247.5 Hz), 149.9 (d d, J=13.0, 249.0 Hz), 149.1, 141.1, 136.5, 129.9 (d d, J=3.8, 7.0 Hz), 121.2 (d d, J=3.5, 6.2 Hz), 117.6 (d, J=17.5 Hz), 114.3 (d, J=18.6 Hz), 112.5, 80.7, 71.5, 57.8, 24.9, 9.8
1H: 7.95 (1H, d, J=1.3 Hz), 7.62 (1H, d d d, J=2.0, 7.5, 11.5 Hz), 7.50 (1H, d, J=1.3 Hz), 7.49 (1H, m), 7.19 (1H, d t, J=8.4, 10.2 Hz), 5.12 (1H, d, J=4.5 Hz), 4.99 (1H, d, J=4.5 Hz), 4.33 (2H, m), 3.74 (1H, m), 1.90 (1H, m), 1.64 (1H, m), 0.98 (3H, t, J=7.4 Hz)

Compound no. 304 (MP: 100-101). NMR solvent: CDCl3
13C: 159.9, 149.3, 142.8, 136.4, 134, 129.7, 117.6, 113.9, 112.4, 110.3, 80.7, 71.4, 57.8, 55.3, 24.9, 9.8
1H: 7.98 (1H, d, J=1.2 Hz), 7.52 (1H, d, J=1.2 Hz), 7.39 (1H, m), 7.36 (1H, d t, J=1.5, 7.7 Hz), 7.31 (1H, t, J=7.7 Hz), 6.88 (1H, d d d, J=1.4, 2.6, 8.0 Hz), 5.13 (1H, d, J=4.5 Hz), 5.0 (1H, d, J=4.5 Hz), 4.32 (2H, m), 3.88 (3H, s), 3.73 (1H, m), 1.90 (1H, m), 1.63 (1H, m), 0.98 (3H, t, J=7.5 Hz)

Compound no. 305 (MP: 131-132). NMR solvent: CDCl3
13C: 151.1, 148.5, 148.3, 141.6, 138.3, 137.3, 136.5, 134.5, 134, 129.4, 126.2, 124.8, 123.9, 123.5, 113.4, 58.4, 38.6, 36.2, 34.1, 29.7
1H: 8.91 (1H, d, J=2.5 Hz), 8.61 (1H, d d, J=1.7, 4.8 Hz), 8.05 (1H, m), 7.95 (1H, d, J=1.3 Hz), 7.95 (1H, m), 7.82 (1H, m), 7.55 (1H, d, J=1.3 Hz), 7.51 (1H, m), 7.50 (1H, m), 7.38 (1H, d d d, J=0.8, 4.8, 7.9 Hz), 3.0 (3H, s), 2.10 (9H, s), 1.73 (6H, s)

Compound no. 306 (MP: 195-196). NMR solvent: CDCl3
13C: 157.5, 155, 151, 141.2, 137.4, 134.7, 134.4, 134.2, 129.7, 125.9, 125.6, 123.7, 113.6, 58.5, 38.5, 36.2, 34.1, 29.6
1H: 9.22 (1H, s), 9.01 (2H, s), 8.05 (1H, s), 7.95 (1H, s), 7.85 (1H, d, J=7.5 Hz), 7.56 (1H, s), 7.54 (1H, t, J=7.5 Hz), 7.48 (1H, d, J=7.5 Hz), 3.0 (3H, s), 2.19 (9H, s), 1.73 (6H, s)

Compound no. 307 (MP: 150-151). NMR solvent: DMSO
13C: 157.6, 150.8, 140.7, 137.5, 134.6, 129.6, 115.7, 114.3, 114.1, 111.7, 56.8, 31.3, 29.1, 25.2, 24.9
1H: 9.43 (1H, s), 8.09 (1H, d, J=1.0 Hz), 7.90 (1H, d, J=1.0 Hz), 7.26 (2H, m), 7.16 (1H, t, J=8.0 Hz), 6.65 (1H, d d d, J=1.0, 2.2, 8.0 Hz), 3.80 (1H, m), 2.92 (3H, s), 1.77 (4H, m), 1.59 (1H, m), 1.55 (2H, m), 1.29 (2H, m, J=11.5 Hz), 1.10 (1H, q, J=13.0 Hz)

Compound no. 308 (MP: 139-140). NMR solvent: CDCl3
13C: 150.6 (d d, J=13.0, 248.0 Hz), 149.9 (d d, J=13.0, 249.0 Hz), 148.1, 141.1, 136.7, 136.1, 129.8 (d d, J=3.9, 6.5 Hz), 129.1, 128.9, 126.1, 121.2 (d d, J=3.5, 6.2 Hz), 117.6 (d, J=17.8 Hz), 114.3 (d, J=18.5 Hz), 112.4, 80.4, 80.1, 53.0
1H: 8.05 (1H, d, J=1.3 Hz), 7.62 (1H, d d d, J=2.0, 7.6, 11.5 Hz), 7.56 (1H, d, J=1.3 Hz), 7.45 (1H, m), 7.42-7.37 (5H, m), 7.18 (1H, d t, J=8.3, 10.0 Hz), 5.44 (1H, d, J=4.5 Hz), 5.26 (1H, d, J=4.5 Hz), 5.18 (1H, d d, J=6.1, 8.8 Hz), 4.16 (1H, d d, J=6.1, 10.0 Hz), 3.68 (1H, d d, J=9.0, 10.0 Hz)

Compound no. 309 (MP: 155-157). NMR solvent: CDCl3
13C: 148.4, 142.9, 136.6, 136.2, 132.5, 129.0, 128.9, 128.7, 127.8, 126.1, 125.2, 112.1, 80.4, 80.0, 53.0
1H: 8.08 (1H, br), 7.80 (2H, d, J=8.0 Hz), 7.60 (1H, br), 7.42 (7H, m), 7.31 (1H, t, J=7.5 Hz), 5.44 (1H, d, J=4.8 Hz), 5.27 (1H, d, J=4.8 Hz), 5.16 (1H, d d, J=6.3, 8.8 Hz), 4.16 (1H, d d, J=6.3, 10.1 Hz), 3.68 (1H, t, J=9.6 Hz)

Compound no. 310 (MP: 126-127). NMR solvent: CDCl3
13C: 148.9, 142.9, 136.4, 132.6, 128.7, 127.8, 125.2, 112.1, 80.4, 73.4, 52.9, 17
1H: 7.99 (1H, d, J=1.3 Hz), 7.80 (2H, m d, J=8.4 Hz), 7.54 (1H, d, J=1.3 Hz), 7.42 (2H, m t, J=7.8 Hz), 7.31 (1H, m t, J=7.5 Hz), 5.14 (1H, d, J=4.5 Hz), 5.04 (1H, d, J=4.5 Hz), 4.39 (1H, m), 4.36 (1H, m), 3.63 (1H, d d, J=6.9, 8.4 Hz), 1.37 (3H, d, J=6.0 Hz)

Compound no. 311 (MP: 127). NMR solvent: CDCl3
13C: 150.6 (d d, J=12.5, 247.5 Hz), 149.9 (d d, J=13.0, 248.5 Hz), 148.6, 141.1, 136.4, 129.9 (d d, J=3.5, 7.0 Hz), 121.2 (d d, J=3.5, 6.3 Hz), 117.6 (d, J=17.5 Hz), 114.3 (d, J=18.6 Hz), 112.5, 80.4, 73.4, 53, 17.0
1H: 7.96 (1H, d, J=1.3 Hz), 7.62 (1H, d d d, J=2.1, 7.7, 11.5 Hz), 7.51 (1H, d, J=1.3 Hz), 7.49 (1H, m), 7.19 (1H, d t, J=8.3, 10.1 Hz), 5.13 (1H, d, J=4.5 Hz), 5.04 (1H, d, J=4.5 Hz), 4.39 (1H, m), 4.36 (1H, m), 3.65 (1H, m), 1.37 (3H, d, J=6.0 Hz)

Compound no. 312 (MP: 118). NMR solvent: CDCl3
13C: 150.9, 142.2, 136.5, 133, 128.7, 127.4, 125.1, 113, 58.9, 39.4, 31.4, 25.6, 25.1, 14.9
1H: 7.89 (1H, d, J=1.3 Hz), 7.81 (2H, m d, J=8.3 Hz), 7.48 (1H, d, J=1.3 Hz), 7.41 (2H, m t, J=7.9 Hz), 7.30 (1H, m t, J=7.5 Hz), 3.77 (1H, t t, J=3.5, 12.0 Hz), 3.43 (2H, q, J=7.1 Hz), 1.82 (4H, m), 1.66 (3H, m), 1.30 (2H, m), 1.25 (3H, t, J=7.1 Hz), 1.13 (1H, m)

Compound no. 313 (MP: 121-122). NMR solvent: CDCl3
13C: 150.9, 149.1, 148.5, 142, 136.2, 126.2, 117.3, 112.3, 111.2, 108.4, 58.9, 55.9, 55.9, 39.4, 31.4, 25.6, 25.1, 14.9
1H: 7.86 (1H, d, J=1.3 Hz), 7.41 (1H, s), 7.41 (1H, d, J=1.3 Hz), 6.91 (1H, d, J=8.4 Hz), 7.30 (1H, d d, J=2.0, 8.4 Hz), 3.96 (3H, s), 3.91 (3H, s), 3.77 (1H, t t, J=3.5, 12.0 Hz), 3.43 (2H, q, J=7.1 Hz), 1.84 (4H, m), 1.68 (3H, m), 1.29 (2H, m), 1.25 (3H, t, J=7.1 Hz), 1.12 (1H, m)

Compound no. 314 (MP: 208). NMR solvent: DMSO
13C: 151.6 (d, J=243.0 Hz), 150.6, 146.1 (d, J=11.0 Hz), 139.5 (d, J=2.5 Hz), 137.2, 126.8 (d, J=7.0 Hz), 120.8 (d, J=3.4 Hz), 114.1 (d, J=2.0 Hz), 113.7, 112.1 (d, J=19.5 Hz), 56.8, 56, 31, 28.9, 25, 24.6
1H: 8.04 (1H, d, J=1.3 Hz), 7.90 (1H, d, J=1.3 Hz), 7.64 (1H, d d, J=2.0, 8.3 Hz), 7.61 (1H, m), 7.18 (1H, t, J=9.3 Hz), 3.86 (3H, s), 3.80 (1H, m), 2.92 (3H, s), 1.79 (4H, m), 1.62 (1H, m), 1.59 (2H, m), 1.30 (2H, m), 1.12 (1H, m)

Compound no. 315 (MP: 162-163). NMR solvent: DMSO
13C: 151.6 (d, J=242.5 Hz), 150.7, 146.4 (d, J=10.5 Hz), 138.5, 137.5, 125.7 (d, J=7.6 Hz), 121.2 (d, J=3.0 Hz), 114.3, 114.1 (d, J=2.0 Hz), 112.4 (d, J=19.5 Hz), 58.5, 56.1, 31.3, 28.2, 24
1H: 8.31 (1H, s br), 8.03 (1H, d, J=1.2 Hz), 7.69 (1H, d d, J=2.0, 12.5 Hz), 7.65 (1H, m), 7.21 (1H, t, J=8.8 Hz), 4.37 (1H, m), 3.86 (3H, s), 2.93 (3H, s), 1.88 (2H, m), 1.68 (4H, m), 1.53 (2H, m)

Compound no. 316 (MP: 205). NMR solvent: DMSO
13C: 151.6 (d, J=243.5 Hz), 147.2 (d, J=10.5 Hz), 144.6, 136.8, 136, 122.9, 121.8 (d, J=3.3 Hz), 114.3, 114.3, 112.9 (d, J=20.0 Hz), 80.7, 79.3, 61.3, 56.1, 22.3

1H: 9.05 (1H, s br), 8.31 (1H, d, J=1.3 Hz), 7.82 (1H, d d, J=2.2, 12.7 Hz), 7.74 (1H, d, J=8.5 Hz), 7.28 (1H, t, J=8.7 Hz), 5.21 (2H, s), 3.87 (3H, s), 3.86 (2H, s), 1.51 (6H, s)

Compound no. 317 (MP: 173-174). NMR solvent: CDCl3
13C: 151.3, 150, 142.3, 141.5, 137.2, 133.4, 129 (2 sig.), 127.7, 125.4, 123, 122.8, 113.1, 112.7, 58.3, 40.6, 38.6, 36.2, 34.1, 29.7

1H: 8.01 (1H, s), 7.95 (1H, s), 7.69 (1H, d, J=7.5 Hz), 7.59 (2H, m, J=8.8 Hz), 7.51 (1H, s), 7.50 (1H, d, J=8.0 Hz), 7.43 (1H, t, J=7.7 Hz), 6.82 (2H, m, J=8.8 Hz), 3.01 (6H, s), 3.0 (3H, s), 2.21 (9H, s), 1.74 (6H, s)

Compound no. 318 (MP: 181-182). NMR solvent: CDCl3
13C: 168.1, 164.5, 157.6, 151.1, 141.7, 137.2, 133.7, 133.4, 128.7, 128, 125.5, 124.4, 116.1, 113.3, 58.4, 54.8, 54.2, 38.5, 36.2, 34.1, 29.6

1H: 8.31 (1H, s), 7.93 (1H, s), 7.91 (1H, s), 7.78 (1H, d, J=7.6 Hz), 7.50 (1H, s), 7.46 (1H, t, J=7.5 Hz), 7.40 (1H, d, J=7.5 Hz), 4.04 (3H, s), 4.03 (3H, s), 2.99 (3H, s), 2.19 (9H, s), 1.73 (6H, s)

Compound no. 319 (MP: 109-111). NMR solvent: CDCl3
13C: 151.9 (d, J=246.0 Hz), 151.2, 147.8 (d, J=11.0 Hz), 141.3, 136.8, 129.6 (d, J=3.5 Hz), 117.3 (d, J=7.0 Hz), 116.1 (d, J=19.0 Hz), 113.1, 110.3 (d, J=1.5 Hz), 57.6, 56.2, 31.3, 30, 25.4, 25.2

1H: 7.89 (1H, d, J=1.2 Hz), 7.50 (1H, d d, J=2.0, 8.2 Hz), 7.45 (1H, d, J=1.2 Hz), 7.24 (1H, d d d, J=2.0, 4.3, 8.3 Hz), 7.09 (1H, d d, J=8.3, 11.0 Hz), 3.96 (3H, s), 3.95 (1H, m), 2.99 (3H, s), 1.86 (4H, m), 1.70 (1H, d br, J=13.0 Hz), 1.58 (2H, d q, J=4.5, 13.5 Hz), 1.37 (2H, t q, J=3.0, 13.0 Hz), 1.13 (1H, t q, J=3.4, 13.0 Hz)

Compound no. 320 (MP: 170-171). NMR solvent: CDCl3
13C: 163.1 (d, J=240.0 Hz), 151.1, 145.9 (d, J=15.0 Hz), 141.5, 139.9 (d, J=8.0 Hz), 137.4, 137.2, 134.7 (d, J=4.5 Hz), 134.1, 129.5, 126.1, 124.8, 123.8, 113.5, 109.4 (d, J=37.5 Hz), 58.5, 38.6, 36.2, 34.1, 29.7

1H: 8.49 (1H, m, J=2.5 Hz), 8.05 (1H, m, J=2.5, 7.5 Hz), 8.02 (1H, m, J=1.6 Hz), 7.95 (1H, d, J=1.3 Hz), 7.81 (1H, d t, J=1.5, 7.5 Hz), 7.55 (1H, d, J=1.3 Hz), 7.51 (1H, t, J=7.5 Hz), 7.46 (1H, d t, J=1.5, 7.8 Hz), 7.03 (1H, m, J=3.0, 8.5 Hz), 3.0 (3H, s), 2.20 (9H, s), 1.74 (6H, s)

Compound no. 321 (MP: 100-103). NMR solvent: CDCl3
13C: 151.9 (d, J=246.0 Hz), 151.5, 147.8 (d, J=11.0 Hz), 141.3, 136.8, 129.5 (d, J=3.5 Hz), 117.3 (d, J=7.0 Hz), 116.2 (d, J=19.0 Hz), 113.2, 110.3, 59.3, 56.2, 31.2, 28.9, 24.3

1H: 7.94 (1H, d, J=1.0 Hz), 7.50 (1H, d d, J=2.0, 7.50 Hz), 7.47 (1H, d, J=1.0 Hz), 7.24 (1H, d d d, J=2.0, 4.3, 8.3 Hz), 7.09 (1H, d d, J=8.3, 11.0 Hz), 4.44 (1H, qt, J=8.0 Hz), 3.97 (3H, s), 3.0 (3H, s), 1.96 (2H, m), 1.75 (4H, m), 1.63 (2H, m)

Compound no. 322 (MP: 216-217). NMR solvent: CDCl3
13C: 156.9, 151, 142.4, 141.9, 141.4, 137.3, 132.9, 129.7, 129, 126.3, 124.2, 124.1, 118.8, 114.7, 114.5, 113.4, 58.5, 38.6, 36.2, 34.1, 29.7

1H: 8.07 (1H, br), 8.03 (1H, d, J=1.3 Hz), 7.90 (1H, s br), 7.70 (1H, d t, J=1.7, 7.4 Hz), 7.52 (1H, d, J=1.3 Hz), 7.44 (1H, d t, J=1.8, 7.8 Hz), 7.40 (1H, t, J=7.6 Hz), 7.24 (1H, t, J=7.9 Hz), 7.17 (1H, s br), 7.13 (1H, m), 6.85 (1H, d d d, J=0.9, 2.5, 8.0 Hz), 3.0 (3H, s), 2.20 (9H, s), 1.74 (6H, s)

Compound no. 323 (MP: 184-185). NMR solvent: CDCl3
13C: 163.6, 151.2, 145, 141.8, 138.3, 137.6, 137.3, 133.8, 130, 129.3, 125.7, 124, 123.5, 113.3, 110.7, 58.4, 53.5, 38.6, 36.2, 34.1, 29.7

1H: 8.44 (1H, d d, J=0.6, 2.5 Hz), 7.98 (1H, m), 7.95 (1H, d, J=1.3 Hz), 7.87 (1H, d d, J=2.5, 8.6 Hz), 7.77 (1H, d t, J=1.8, 7.0 Hz), 7.53 (1H, d, J=1.3 Hz), 7.48 (1H, t, J=7.5 Hz), 7.45 (1H, m), 6.83 (1H, d d, J=0.6, 8.6 Hz), 3.99 (3H, s), 3.0 (3H, s), 2.20 (9H, s), 1.73 (6H, s)

Compound no. 324 (MP: 138-140). NMR solvent: CDCl3
13C: 168.4, 151.2, 142, 140.9, 137.3, 137.3, 136.8, 133.5, 129.1, 127.6, 126, 123.8, 123.6, 120, 113.3, 58.4, 38.6, 36.2, 34.1, 29.7, 24.6

1H: 8.01 (1H, t, J=1.7 Hz), 7.95 (1H, d, J=1.2 Hz), 7.74 (1H, d t, J=1.7, 7.3 Hz), 7.60 (4H, br), 7.52 (1H, d, J=1.2 Hz), 7.49 (1H, d t, J=1.9, 7.8 Hz), 7.44 (1H, t, J=7.6 Hz), 3.0 (3H, s), 2.20 (9H, s), 2.19 (3H, s), 1.73 (6H, s)

Compound no. 325 (MP: 150-152). NMR solvent: CDCl3
13C: 151.1, 143.6, 141.8, 138.7, 137.2, 133.6, 132.8, 129.1, 126.3, 124.9, 123.7, 122.5, 113.2, 108.9, 58.4, 38.5, 36.2, 34.1, 29.6

1H: 7.96 (1H, s), 7.94 (1H, s), 7.81 (1H, s), 7.66 (1H, m), 7.51 (1H, s), 7.49 (1H, m), 7.40 (2H, m), 6.78 (1H, m), 2.99 (3H, s), 2.20 (9H, s), 1.73 (6H, s)

Compound no. 326 (MP: 105-107). NMR solvent: CDCl3
13C: 159.1, 151.8, 142, 136.8, 126.4, 125.8, 114, 112.1, 59.3, 55.3, 31.1, 28.8, 24.3

1H: 7.91 (1H, d, J=1.2 Hz), 7.73 (2H, d, J=8.8 Hz), 7.41 (1H, d, J=1.2 Hz), 6.95 (2H, d, J=8.8 Hz), 4.45 (1H, qt, J=8.0 Hz), 3.85 (3H, s), 3.0 (3H, s), 1.95 (2H, m), 1.76 (2H, m), 1.67 (2H, m), 1.63 (2H, m)

Compound no. 327 (MP: 92-94). NMR solvent: CDCl3
13C: 159.9, 151.6, 142, 136.9, 134.4, 129.7, 117.5, 113.6, 113.5, 110.1, 59.3, 55.3, 31.2, 28.9, 24.3

1H: 7.93 (1H, d, J=1.3 Hz), 7.51 (1H, d, J=1.3 Hz), 7.40 (1H, d d, J=1.4, 2.4 Hz), 7.36 (1H, td, J=1.2, 7.6 Hz), 7.32 (1H, t, J=7.7 Hz), 6.86 (1H, d d d, J=1.3, 2.7, 8.0 Hz), 4.45 (1H, m), 3.88 (3H, s), 3.0 (3H, s), 1.96 (2H, m), 1.78 (2H, m), 1.68 (2H, m), 1.60 (2H, m)

Compound no. 328 (MP: 153-154). NMR solvent: CDCl3
13C: 159.2, 146.6, 142.5, 136.1, 126.4, 125.5, 114.1, 110.9, 81.1, 80.3, 61.8, 55.3, 22.9

1H: 7.93 (1H, d, J=1.5 Hz), 7.71 (2H, d, J=8.9 Hz), 7.41 (1H, d, J=1.5 Hz), 6.94 (2H, d, J=8.9 Hz), 5.13 (2H, s), 3.88 (2H, s), 3.84 (3H, s), 1.61 (6H, s)

Compound no. 329 (MP: 100-101). NMR solvent: CDCl3
13C: 159.9, 146.4, 142.4, 136.1, 134.1, 129.7, 117.5, 113.8, 112.3, 110.2, 81, 80.3, 61.8, 55.3, 22.8

1H: 7.95 (1H, d, J=1.3 Hz), 7.51 (1H, d, J=1.3 Hz), 7.40 (1H, d d, J=1.5, 2.5 Hz), 7.34 (1H, t d, J=1.5, 7.6 Hz), 7.30 (1H, t, J=7.8 Hz), 6.85 (1H, d d d, J=1.5, 2.7, 7.9 Hz), 5.12 (2H, s), 3.87 (2H, s), 3.86 (3H, s), 1.61 (6H, s)

Compound no. 330 (MP: 164-166). NMR solvent: DMSO
13C: 151.2 (d, J=240.0 Hz), 150.8, 144.0 (d, J=12.3 Hz), 139.9 (d, J=2.0 Hz), 137.4, 125.4 (d, J=7.0 Hz), 121.0 (d, J=3.0 Hz), 117.9 (d, J=3.2 Hz), 113.5, 112.5 (d, J=19.5 Hz), 56.8, 31.3, 29, 25.1, 24.8

1H: 9.89 (1H, s), 8.06 (1H, d, J=1.3 Hz), 7.88 (1H, d, J=1.3 Hz), 7.58 (1H, d d, J=2.0, 12.7 Hz), 7.48 (1H, m, J=2.0, 8.4 Hz), 6.95 (1H, d d, J=8.4, 9.0 Hz), 3.80 (1H, m), 2.91 (3H, s), 1.76 (4H, m), 1.60 (1H, m), 1.55 (2H, m), 1.29 (2H, m), 1.10 (1H, m)

Compound no. 331 (MP: 170-171). NMR solvent: DMSO
13C: 151.2 (d, J=240.0 Hz), 151.2, 144.0 (d, J=12.5 Hz), 139.9 (d, J=2.6 Hz), 137.4, 125.4 (d, J=6.9 Hz), 121.0 (d, J=3.0 Hz), 117.9 (d, J=3.3 Hz), 113.5, 112.5 (d, J=19.5 Hz), 58.4, 31.2, 28.2, 24

1H: 9.89 (1H, s), 8.06 (1H, d, J=1.3 Hz), 7.88 (1H, d, J=1.3 Hz), 7.58 (1H, d d, J=2.0, 12.7 Hz), 7.48 (1H, d d d, J=1.0, 2.0, 8.4 Hz), 6.95 (1H, d d, J=8.4, 9.1 Hz), 4.35 (1H, m), 2.92 (3H, s), 1.87 (2H, m), 1.67 (4H, m), 1.53 (2H, m)

Compound no. 332 (MP: 194-196). NMR solvent: DMSO
13C: 151.2 (d, J=240.0 Hz), 146.2, 144.1 (d, J=12.0 Hz), 140.2 (d, J=2.3 Hz), 136.9, 125.3 (d, J=6.8 Hz), 121.1 (d, J=3.0 Hz), 117.9 (d, J=3.7 Hz), 112.5 (d, J=20.0 Hz), 112.5, 80.6, 79.3, 60.8, 22.4

1H: 9.91 (1H, s), 8.11 (1H, d, J=1.3 Hz), 7.91 (1H, d, J=1.3 Hz), 7.59 (1H, d d, J=2.1, 12.5 Hz), 7.48 (1H, m, J=2.1, 8.6 Hz), 6.95 (1H, d d, J=8.6, 9.1 Hz), 5.16 (2H, s), 3.84 (2H, s), 1.49 (6H, s)

Compound no. 333 (MP: 173-176). NMR solvent: DMSO
13C: 150.4 (d, J=240.0 Hz), 146.1, 145.0 (d, J=12.5 Hz), 140.2, 136.9, 130.1 (d, J=3.0 Hz), 116.2 (d, J=18.5 Hz), 115.9 (d, J=6.3 Hz), 114.3 (d, J=2.7 Hz), 113.1, 80.6, 79.3, 60.8, 22.4

1H: 9.93 (1H, s), 8.13 (1H, d, J=1.3 Hz), 7.92 (1H, d, J=1.3 Hz), 7.46 (1H, d d, J=2.1, 8.8 Hz), 7.24 (1H, d d d, J=2.1, 4.4, 8.5 Hz), 7.13 (1H, d d, J=8.5, 11.2 Hz), 5.16 (2H, s), 3.84 (2H, s), 1.49 (6H, s)

Compound no. 334 (MP: 154-155). NMR solvent: CDCl3
13C: 154.6, 150.9, 150.7, 137.8, 134.3, 128.9, 124.2, 122.9, 121, 114.6, 110.9, 101.9, 57.6, 31.4, 29.9, 25.4, 25.2

1H: 7.97 (1H, d, J=1.3 Hz), 7.61 (1H, d, J=1.3 Hz), 7.60 (1H, m), 7.49 (1H, d, J=8.0 Hz), 7.28 (1H, d t, J=0.15, 7.5 Hz), 7.24 (1H, d t, J=1.1, 7.3 Hz), 7.10 (1H, s), 3.97 (1H, m), 3.01 (3H, s), 1.87 (4H, m), 1.71 (1H, d br, J=13.0 Hz), 1.59 (2H, d q, J=3.5, 12.5 Hz), 1.39 (2H, q, J=13.0 Hz), 1.14 (1H, t q, J=3.5, 13.0 Hz)

Compound no. 335 (MP: 161-163). NMR solvent: CDCl3
13C: 151, 148.5, 146.7, 139.2, 137.3, 132.4, 129, 123.6, 114, 57.6, 31.4, 30, 25.4, 25.2

1H: 9.01 (1H, d d, J=0.8, 2.3 Hz), 8.53 (1H, d d, J=1.7, 4.8 Hz), 8.12 (1H, d d d, J=1.8, 2.2, 8.0 Hz), 7.94 (1H, d, J=1.3 Hz), 7.58 (1H, d, J=1.3 Hz), 7.34 (1H, d d d, J=0.8, 4.9, 8.0 Hz), 3.95 (1H, m), 3.01 (3H, s), 1.87 (4H, m), 1.71 (1H, d br, J=13.5 Hz), 1.59 (2H, d q, J=3.5, 12.5 Hz), 1.38 (2H, t q, J=3.5, 13.0 Hz), 1.13 (1H, t q, J=3.5, 13.5 Hz)

Compound no. 336 (MP: 211-213). NMR solvent: CDCl3
13C: 151, 150.4, 148, 141.4, 137.4, 137.3, 137, 135.5, 134.2, 129.5, 126, 125.1, 124.2, 123.8, 113.6, 58.5, 38.6, 36.2, 34.1, 29.7

1H: 8.66 (1H, d, J=2.0 Hz), 8.02 (1H, s), 7.95 (1H, s), 7.92 (1H, d d, J=2.5, 8.3 Hz), 7.81 (1H, d, J=7.3 Hz), 7.55 (1H, s), 7.51 (1H, t, J=7.51 Hz), 7.46 (1H, d, J=8.0 Hz), 7.41 (1H, d, J=8.3 Hz), 3.0 (3H, s), 2.20 (9H, s), 1.73 (6H, s)

Compound no. 337 (MP: oil). NMR solvent: CDCl3
13C: 147.5, 145.8, 140.9, 133, 128.6, 127.3, 125, 111.1, 81, 80.6, 61, 22.9, 14.3

1H: 7.74 (2H, d, J=8.3 Hz), 7.38 (2H, t, J=7.9 Hz), 7.27 (1H, t, J=7.6 Hz), 7.20 (1H, s), 4.90 (2H, s), 3.88 (2H, s), 2.56 (3H, s), 1.61 (6H, s)

Compound no. 338 (MP: 129-130). NMR solvent: CDCl3
13C: 154.6, 150.4, 146.1, 137.3, 134.9, 128.8, 124.3, 123, 121.1, 113.2, 110.9, 102.3, 81.1, 80.3, 62, 22.8

1H: 8.04 (1H, d, J=1.3 Hz), 7.61 (1H, d, 1.3 Hz), 7.60 (1H, m), 7.48 (1H, m, J=7.8 Hz), 7.30 (1H, d t, J=1.5, 7.3 Hz), 7.24 (1H, d t, J=1.2, 7.4 Hz), 7.10 (1H, s), 5.16 (2H, s), 3.89 (2H, s), 1.62 (6H, s)

Compound no. 339 (MP: 154-155). NMR solvent: CDCl3
13C: 148.6, 142.8, 136.5, 132.6, 128.7, 127.8, 125.2, 112.2, 80.3, 67.1, 46.0

1H: 8.05 (1H, d, J=1.3 Hz), 7.80 (2H, m d, J=8.4 Hz), 7.60 (1H, d, J=1.3 Hz), 7.41 (2H, m t, J=7.5 Hz), 7.31 (1H, m t, J=7.3 Hz), 5.12 (2H, s), 4.15 (2H, t, J=6.5 Hz), 3.80 (2H, t, J=6.5 Hz)

Compound no. 340 (MP: 122-123). NMR solvent: CDCl3
13C: 159.9, 148.4, 142.8, 136.6, 136.2, 133.9, 129.7, 129, 128.9, 126.1, 117.6, 113.9, 112.3, 110.3, 80.4, 80, 55.3, 1H: 8.97 (1H, d, J=1.3 Hz), 7.59 (1H, d, J=1.3 Hz), 7.47-7.37 (5H, m), 7.40 (1H, m), 7.36 (1H, m), 7.31 (1H, t, J=7.7 Hz), 6.87 (1H, d d d, J=1.3, 2.6, 7.9 Hz), 5.43 (1H, d, J=4.5 Hz), 5.26 (1H, d, J=4.5 Hz), 5.16 (1H, d d, J=6.1, 8.8 Hz), 4.16 (1H, d d, J=6.2, 10.0 Hz), 3.87 (3H, s), 3.68 (1H, t, J=9.5 Hz)

Compound no. 341 (MP: 164-165). NMR solvent: CDCl3
13C: 159.1, 151.4, 142, 136.8, 126.4, 125.8, 114, 112.1, 57.5, 55.3, 31.3, 30, 25.4, 25.2

1H: 7.89 (1H, d, J=1.3 Hz), 7.40 (1H, d, J=1.3 Hz), 7.33 (2H, m d, J=9.0 Hz), 6.95 (2H, m d, J=9.0 Hz), 3.95 (1H, m), 3.84 (3H, s), 2.99 (3H, s), 1.86 (4H, m), 1.70 (1H, d br, J=13.0 Hz), 1.58 (2H, d q, J=3.5, 12.5 Hz), 1.37 (2H, t q, J=3.2, 13.0 Hz), 1.12 (1H, t q, J=3.5, 13.0 Hz)

Compound no. 342 (MP: 122-123). NMR solvent: CDCl3
13C: 159.9, 151.3, 141.9, 136.8, 134.4, 129.7, 117.5, 113.6, 113.5, 110.1, 57.5, 55.3, 31.3, 30, 25.4, 25.2

1H: 7.92 (1H, d, J=1.3 Hz), 7.49 (1H, d, J=1.3 Hz), 7.40 (1H, d d, J=1.4, 2.5 Hz), 7.36 (1H, t d, J=1.4, 7.7 Hz), 7.31 (1H, 1H, t, J=8.0 Hz), 6.85 (1H, d d d, J=1.2, 2.5, 7.9 Hz), 3.95 (1H, m), 3.88 (3H, s), 3.0 (3H, s), 1.86 (2H, m), 1.84 (2H, m), 1.70 (1H, d br, J=13.0 Hz), 1.58 (2H, d q, J=4.5, 13.3 Hz), 1.38 (2H, t q, J=3.2, 13.0 Hz), 1.13 (1H, t q, J=3.5, 13.0 Hz)

Compound no. 343 (MP: 150-152). NMR solvent: DMSO
13C: 150.3 (d, J=240.0 Hz), 150.8, 144.9 (d, J=12.5 Hz), 139.9, 137.5, 130.2 (d, J=3.5 Hz), 116.2 (d, J=18.7 Hz), 115.9 (d, J=6.3 Hz), 114.2 (d, J=3.0 Hz), 114.1, 56.8, 31.3, 29, 25.1, 24.8

1H: 9.89 (1H, s br), 8.08 (1H, s), 7.89 (1H, s), 7.45 (1H, d, J=8.3 Hz), 7.24 (1H, s br), 7.13 (1H, m, J=9.0, 11.0 Hz), 3.79 (1H, s br), 2.91 (3H, s), 1.76 (4H, m), 1.58 (3H, m), 1.29 (2H, m), 1.10 (1H, m)

Compound no. 344 (MP: 144-145). NMR solvent: DMSO
13C: 151.1, 150.3 (d, J=241.0 Hz), 144.9 (d, J=12.5 Hz), 140.0, 137.5, 130.2 (d, J=3.2 Hz), 116.3 (d, J=18.5 Hz), 115.9 (d, J=6.5 Hz), 114.2 (d, J=3.0 Hz), 114.1, 58.4, 31.2, 28.2, 24.0

1H: 9.91 (1H, s), 8.08 (1H, s), 7.88 (1H, d, J=1.3 Hz), 7.45 (1H, d d, J=2.0, 8.7 Hz), 7.24 (1H, m), 7.13 (1H, dd, J=8.6, 11.2 Hz), 4.35 (1H, m), 2.92 (3H, s), 1.87 (2H, m), 1.68 (4H, m), 1.53 (2H, In)

Compound no. 345 (MP: 113-114). NMR solvent: CDCl3
13C: 150.8, 150.5 (t, J=3.0 Hz), 141.2, 136.6, 130.5, 126.5, 119.7, 115.9 (t, J=259.5 Hz), 113.1, 58.9, 39.4, 31.4, 25.6, 25.1, 14.9

1H: 7.87 (1H, d, J=1.3 Hz), 7.80 (2H, m d, J=8.8 Hz), 7.45 (1H, d, J=1.3 Hz), 7.16 (2H, m d, J=8.8 Hz), 6.54 (1H, t, J=74 Hz), 3.75 (1H, t t, J=3.5, 12.0 Hz), 3.43 (2H, q, J=7.1 Hz), 1.85 (4H, m), 1.68 (2H, m), 1.64 (1H, m), 1.29 (2H, m), 1.25 (3H, t, J=7.1 Hz), 1.12 (1H, m)

Compound no. 346 (MP: 129-131). NMR solvent: CDCl3
13C: 150.6 (d d, J=13.0, 247.5 Hz), 150.6, 149.7 (d d, J=12.5, 248.0 Hz), 140.4 (d, J=2.0 Hz), 136.6, 130.3 (d d, J=3.5, 7.0 Hz), 121.0 (d d, J=3.6, 6.1 Hz), 117.5 (d, J=17.5 Hz), 114.1 (d, J=18.5 Hz), 113.4, 59, 39.5, 31.4, 25.6, 25.1, 14.9

1H: 7.85 (1H, d, J=1.3 Hz), 7.61 (1H, d d d, J=2.2, 7.6, 11.6 Hz), 7.49 (1H, m), 7.44 (1H, d, J=1.3 Hz), 7.18 (1H, d t, J=8.4, 10.2 Hz), 3.74 (1H, t t, J=3.5, 12.0 Hz), 3.43 (2H, q, J=7.1 Hz), 1.85 (4H, m), 1.67 (2H, m), 1.64 (1H, m), 1.30 (2H, m), 1.25 (3H, t, J=7.1 Hz), 1.13 (1H, m)

Compound no. 347 (MP: 144-145). NMR solvent: DMSO
13C: 157.6, 146.2, 141, 136.9, 134.6, 129.6, 115.7, 114.2, 113.4, 111.7, 80.6, 79.3, 60.8, 22.4

1H: 9.43 (1H, s), 8.13 (1H, d, J=1.3 Hz), 7.93 (1H, d, J=1.3 Hz), 7.26 (2H, m), 7.16 (1H, t, J=7.8 Hz), 6.66 (1H, d d d, J=1.5, 2.0, 8.0 Hz), 5.17 (2H, s), 3.83 (2H, s), 1.50 (6H, s)

Compound no. 348 (MP: 129-130). NMR solvent: CDCl3
13C: 146.4, 141.8, 136.4, 132.9, 130.6, 128.7, 128.5, 125, 123.1, 112.4, 94, 81.9, 81.1, 80.3, 65.5, 61.9, 31.5, 22.8

1H: 7.97 (1H, d, J=1.3 Hz), 7.85 (1H, br), 7.74 (1H, m), 7.51 (1H, d, J=1.3 Hz), 7.34 (2H, m), 5.12 (2H, s), 3.88 (2H, s), 1.63 (6H, s), 1.61 (6H, s)

Compound no. 349 (MP: 129-131). NMR solvent: DMSO
13C: 150.3, 138.4, 137.5, 134.2, 131.5, 130.9, 129.1, 126.3, 124.8, 115.7, 58.3, 39.1, 30.2, 25.3, 24.7, 14.7
1H: 8.15 (1H, d, J=1.3 Hz), 8.11 (1H, d, J=1.3 Hz), 8.09 (1H, d, J=2.0 Hz), 7.84 (1H, d d, J=2.0, 8.4 Hz), 7.65 (1H, d, J=8.4 Hz), 3.57 (1H, t br, J=10.5 Hz), 3.38 (2H, q, J=7.1 Hz), 1.79 (2H, m), 1.75 (2H, m), 1.64 (2H, m), 1.55 (1H, m), 1.17 (2H, m), 1.1 (3H, t, J=7.1 Hz), 1.10 (1H, m)

Compound no. 350 (MP: 92-93). NMR solvent: CDCl3
13C: 159.1, 151, 142, 136.4, 126.4, 125.8, 114.1, 111.9, 58.9, 55.3, 39.3, 31.4, 25.6, 25.1, 14.9
1H: 7.87 (1H, d, J=1.3 Hz), 7.73 (2H, m d, J=8.8 Hz), 7.38 (1H, d, J=1.3 Hz), 6.85 (2H, m d, J=8.8 Hz), 3.84 (3H, s), 3.77 (1H, t t, J=3.5, 12.0 Hz), 3.43 (2H, t, J=7.1 Hz), 1.85 (4H, m), 1.68 (2H, m), 1.64 (1H, m), 1.30 (2H, m), 1.25 (3H, t, J=7.1 Hz), 1.12 (1H, m)

Compound no. 351 (MP: 100-101). NMR solvent: CDCl3
13C: 152.0 (d, J=246.5 Hz), 147.8 (d, J=11.0 Hz), 146.4, 141.8, 136.1, 129.4 (d, J=3.5 Hz), 117.4 (d, J=7.0 Hz), 116.2 (d, J=18.5 Hz), 112, 110.4 (d, J=1.5 Hz), 81.1, 80.3, 61.9, 56.2, 22.8
1H: 7.94 (1H, d, J=1.3 Hz), 7.48 (1H, d d, J=2.0, 8.2 Hz), 7.47 (1H, d, J=1.3 Hz), 7.23 (1H, d d d, J=2.0, 4.3, 8.3 Hz), 7.09 (1H, d d, J=8.3, 11.0 Hz), 5.13 (2H, s), 3.96 (3H, s), 3.89 (2H, s), 1.61 (6H, s)

Compound no. 352 (MP: 113-114). NMR solvent: CDCl3
13C: 146.5, 143.1, 142.6, 136.2, 132.8, 128.8, 127.8, 125.2, 122.6, 112, 81.1, 80.4, 70.9, 61.8, 45.7, 30.7, 29.3, 22.9
1H: 7.97 (1H, d, J=, 1.3 Hz), 7.68 (1H, t br, J=2.0 Hz), 7.58 (1H, m d, J=7.7 Hz), 7.50 (1H, d, J=1.3 Hz), 7.32 (1H, t, J=7.6 Hz), 7.15 (1H, m d, J=7.7 Hz), 5.13 (2H, s), 3.89 (2H, s), 2.75 (2H, m), 1.84 (2H, m), 1.62 (6H, s), 1.30 (6H, s)

Compound no. 353 (MP: 192 (dec.)). NMR solvent: CDCl3
13C: 150.4, 137.9, 137.5, 136.7, 136, 132.9, 125.9, 122.7, 115.2, 58.7, 38.5, 36.1, 34.1, 29.6
1H: 8.68 (1H, s), 8.13 (1H, d, J=6.3 Hz), 7.92 (1H, d, J=0.9 Hz), 7.70 (1H, d, J=8.1 Hz), 7.56 (1H, d, J=0.9 Hz), 7.30 (1H, d d, J=6.3, 8.1 Hz), 2.98 (3H, s), 2.18 (9H, m), 1.72 (6H, m)

Compound no. 354 (MP: 217 (dec.)). NMR solvent: CDCl3
13C: 151, 141.1, 140.2, 137.6, 137.6, 137.5, 135.5, 134.4, 129.7, 125.9, 125.8, 125.7, 124.8, 123.7, 113.6, 58.5, 38.6, 36.2, 34.1, 29.6
1H: 8.54 (1H, t, J=1.5 Hz), 8.21 (1H, d d d, J=1.0, 1.6, 6.4 Hz), 8.0 (1H, t, J=1.8 Hz), 7.95 (1H, d, J=1.3 Hz), 7.86 (1H, td, J=1.5, 7.8 Hz), 7.56 (1H, d d d, J=1.0, 1.5, 8.0 Hz), 7.55 (1H, d, J=1.3 Hz), 7.52 (1H, t, J=7.8 Hz), 7.44 (1H, d d d, J=1.5, 1.8, 7.8 Hz), 7.36 (1H, d d, J=6.5, 8.0 Hz), 3.0 (3H, s), 2.20 (9H, s), 1.73 (6H, s)

Compound no. 355 (MP: 144-147). NMR solvent: CDCl3
13C: 160, 149.9, 140.6, 135.9, 132.5, 129.9, 117.6, 114.5, 113.5, 110.3, 59.2, 55.5, 39.7, 31.3, 25.5, 25, 14.9
1H: 8.13 (1H, br), 7.50 (1H, m), 7.50 (1H, d, J=1.3 Hz), 7.38 (1H, m, J=7.7 Hz), 7.34 (1H, t, J=7.8 Hz), 6.90 (1H, d d d, J=1.3, 2.6, 8.0 Hz), 3.90 (3H, s), 3.72 (1H, tt, J=3.5, 12 Hz), 3.44 (2H, q, J=7.1 Hz), 1.86 (4H, m), 1.69 (2H, m), 1.65 (1H, m), 1.30 (2H, m), 1.27 (3H, t, J=7.1 Hz), 1.13 (1H, m)

Compound no. 356 (MP: 120-121). NMR solvent: DMSO
13C: 146.3, 145.9, 141.7, 137.5, 136.5, 126.1, 113.2, 111.7, 110.7, 110.6, 80.6, 79.3, 60.8, 55.3, 22.5
1H: 8.07 (1H, d, J=1.3 Hz), 7.71 (1H, d, J=1.3 Hz), 7.14 (1H, d, J=2.0 Hz), 7.0 (1H, d d, J=2.0, 8.5 Hz), 6.79 (1H, d, J=8.5 Hz), 5.16 (2H, s), 4.72 (2H, s), 3.83 (3H, s), 3.77 (3H, s), 1.49 (6H, s)

Compound no. 357 (MP: 176 (dec.)). NMR solvent: DMSO
13C: 150.8, 149.5, 137.3, 136.7, 126.1, 122, 121, 119.7, 116.6, 114.3, 57, 31.4, 28.9, 25, 24.8
1H: 11.13 (1H, s), 10.0 (3H, br), 8.75 (1H, s br), 8.05 (1H, s br), 7.81 (1H, s br), 7.70 (1H, d, J=7.7 Hz), 7.13 (1H, d, J=7.7 Hz), 3.85 (1H, m), 2.93 (3H, s), 1.78 (4H, m), 1.55 (3H, m), 1.30 (2H, m), 1.16 (1H, m)

Compound no. 358 (MP: 209 (dec.)). NMR solvent: DMSO
13C: 150.7, 145.2, 137.8, 136.9, 126.1, 122.8, 121, 119.6, 116.6, 113.3, 80.6, 79.3, 61.1, 22.4
1H: 11.08 (1H, s), 9.98 (3H, s br), 8.62 (1H, s br), 8.04 (1H, s br), 7.81 (1H, d, J=2.0 Hz), 7.70 (1H, d d, J=2.0, 8.5 Hz), 7.11 (1H, d, J=8.5 Hz), 5.18 (2H, s), 3.85 (2H, s), 1.50 (6H, s)

Compound no. 359 (MP: 97-98). NMR solvent: CDCl3
13C: 145.9, 145.6, 131.5, 131.3, 130.3, 119.2, 115.4, 82.4, 79.5, 62.4, 22.9
1H: 8.18 (1H, d, J=8.8 Hz), 8.08 (1H, d, J=1.4 Hz), 7.58 (1H, d d, J=1.4, 8.8 Hz), 5.53 (2H, s), 3.90 (2H, s), 1.68 (6H, s)

Compound no. 360 (MP: 138-140). NMR solvent: CDCl3
13C: 163.3 (d d, J=10.0, 252.0 Hz), 152.9 (d d, J=15.0, 262.5 Hz), 145.3, 135.1 (d d, J=7.2, 16.8 Hz), 132.7 (d, J=19.0 Hz), 101.7 (d d, J=20.0, 30.0 Hz), 97.2 (d d, J=5.5, 29.5 Hz), 82.4, 79.5, 62.5, 22.9
1H: 7.75 (1H, d d d, J=0.9, 2.1, 8.0 Hz), 6.97 (1H, d t, J=2.1, 9.4 Hz), 5.52 (2H, s), 3.90 (2H, s), 1.67 (6H, s)

Compound no. 361 (MP: 146-147). NMR solvent: CDCl3
13C: 146.2, 144.7, 143.1, 140.2, 133.5, 128.9, 128.1, 127.9, 125.7, 119.9, 112.4, 82.5, 79.6, 62.2, 23
1H: 8.44 (1H, d d, J=1.7, 1.6 Hz), 8.14 (1H, d d, J=0.7, 8.7 Hz), 7.74 (1H, d d, J=1.6, 8.7 Hz), 7.71 (2H, m, J=8.2 Hz), 7.50 (2H, m, J=7.9 Hz), 7.42 (1H, m, J=7.5 Hz), 5.57 (2H, s), 3.92 (2H, s), 1.70 (6H, s)

Compound no. 362 (MP: 225 (dec.)). NMR solvent: DMSO
13C: 150.4, 138.3, 137.1, 135.7, 134.7, 132.8, 126.7, 121.2, 117, 56.8, 31.4, 29, 25.1, 24.8
1H: 8.70 (1H, t, J=1.5 Hz), 8.28 (1H, s), 8.20 (1H, s), 8.11 (1H, d, J=6.5 Hz), 7.78 (1H, d, J=8.1 Hz), 7.45 (1H, dd, J=6.5, 8.1 Hz), 3.80 (1H, m), 2.92 (3H, s), 1.77 (4H, m), 1.56 (3H, m), 1.30 (2H, m), 1.11 (1H, m)

Compound no. 363 (MP: 171). NMR solvent: CDCl3
13C: 161.6, 155.2, 151.1, 141, 137, 135.5, 134.1, 130.5, 121.8, 119.3, 118.9, 117.9, 117, 113.9, 105.7, 57.6, 31.3, 29.9, 25.4, 25.2
1H: 7.89 (1H, d, J=1.3 Hz), 7.64 (1H, t d, J=1.2, 7.9 Hz), 7.60 (2H, m d, J=8.9 Hz), 7.53 (1H, t br, J=2.0 Hz), 7.51 (1H, d, J=1.3 Hz), 7.43 (1H, t, J=7.9 Hz), 7.05 (2H, m d, J=8.9 Hz), 7.0 (1H, d d d, J=1.0, 2.5, 7.9 Hz), 3.94 (1H, m), 2.99 (3H, s), 1.87 (2H, m), 1.84 (2H, m), 1.70 (1H, d br, J=13.5 Hz), 1.58 (2H, d q, J=3.4, 12.3 Hz), 1.37 (2H, t q, J=3.0, 12.7 Hz), 1.12 (1H, t q, J=3.2, 13.2 Hz)

Compound no. 364 (MP: 173). NMR solvent: CDCl3
13C: 161.6, 155.3, 146.2, 141.5, 136.2, 135.2, 134.1, 130.5, 121.8, 119.5, 118.9, 118, 117.1, 112.8, 105.8, 81, 80.3, 61.9, 22.8
1H: 7.93 (1H, d, J=1.3 Hz), 7.64 (1H, m), 7.61 (2H, m d, J=9.0 Hz), 7.53 (1H, d, J=1.3 Hz), 7.52 (1H, t br, J=2.0 Hz), 7.44 (1H, t, J=8.0 Hz), 7.05 (2H, m d, J=9.0 Hz), 7.0 (1H, d d, J=1.0, 2.5, 8.0 Hz), 5.11 (2H, s), 3.88 (2H, s), 1.61 (6H, s)

Compound no. 365 (MP: 154 (dec.)). NMR solvent: DMSO
13C: 150.6, 148.4, 139.9, 137.4, 130, 125.9, 118.8, 114.9, 113.4, 111.6, 56.8, 55.8, 31.3, 29, 25.2, 24.8
1H: 8.19 (1H, s br), 7.84 (1H, s br), 7.44 (1H, d, J=2.0 Hz), 7.38 (1H, d d, J=2.0, 8.6 Hz), 7.01 (1H, d, J=8.6 Hz), 3.84

(3H, s), 3.80 (1H, br), 2.92 (3H, s), 1.77 (4H, m), 1.57 (3H, m br), 1.29 (2H, q br, J=13.0 Hz), 1.11 (1H, q bbr, J=13.0 Hz)

Compound no. 366 (MP: 135-136). NMR solvent: CDCl3
13C: 156.8, 149.5, 145.4, 125.7, 124, 123.6, 82.4, 79.4, 62.5, 22.9
1H: 8.82 (1H, d d, J=1.6, 4.5 Hz), 8.60 (1H, d d, J=1.6, 8.4 Hz), 7.57 (1H, d d, J=4.5, 8.4 Hz), 5.58 (2H, s), 3.90 (2H, s), 1.68 (6H, s)

Compound no. 367 (MP: 67-68). NMR solvent: CDCl3
13C: 146.1, 144, 140.4, 133.3, 127.6, 119.1, 113.7, 82.5, 79.6, 62.1, 23, 22
1H: 8.02 (1H, br), 7.95 (1H, d, J=8.5 Hz), 7.29 (1H, d d, J=1.0, 8.5 Hz), 5.53 (2H, s), 3.89 (2H, s), 2.55 (3H, s), 1.68 (6H, s)

Compound no. 368 (MP: 111-112). NMR solvent: CDCl3
13C: 152.2, 145.9, 144.3, 136.8, 129, 121, 81.9, 80, 62.1, 22.9
1H: 8.88 (1H, d d, J=1.0, 4.4 Hz), 8.46 (1H, d d, J=1.0, 8.3 Hz), 7.48 (1H, d d, J=4.4, 8.3 Hz), 5.37 (2H, s), 3.93 (2H, s), 1.72 (6H, s)

Compound no. 369 (MP: 84-85). NMR solvent: CDCl3
13C: 147.4, 145.4, 132.6, 129.7, 125.6, 119.8, 114.3, 81.3, 80.5, 68.5, 65.8, 47.7, 45.7
1H: 8.24 (1H, d, J=8.3 Hz), 8.11 (1H, m, J=1.0, 8.3 Hz), 7.63 (1H, m, J=1.0, 7.2, 8.3 Hz), 7.49 (1H, m, J=1.2, 7.2, 8.3 Hz), 5.50-5.30 (2H, 2 s), 4.20-3.91 (4H, 2 s)

Compound no. 370 (MP: 121-123). NMR solvent: CDCl3
13C: 156.4, 146.2, 144.4, 140.7, 133, 131.2, 129.6, 129.5, 128.1, 120.9, 118.7, 114.6, 111.1, 82.5, 79.6, 62.1, 55.6,
1H: 8.33 (1H, m), 8.09 (1H, d d, J=0.7, 8.5 Hz), 7.67 (1H, d d, J=1.5, 8.5 Hz), 7.39 (1H, d, J=7.6 Hz), 7.38 (1H, m), 7.06 (1H, d t, J=1.0, 7.5 Hz), 7.02 (1H, d, J=8.4 Hz), 5.54 (2H, s), 3.90 (2H, s), 3.83 (3H, s), 1.68 (6H, s)

Compound no. 371 (MP: 134-136). NMR solvent: CDCl3
13C: 145.5, 144.6, 134.4, 128.2 (q, J=33.0 Hz), 126.0 (q, J=3.3 Hz), 123.7 (q, J=273.0 Hz), 117.9 (q, J=5.0 Hz), 115.5, 82.5, 79.6, 62.5, 22.9
1H: 8.42 (1H, m), 8.38 (1H, d, J=8.8 Hz), 7.85 (1H, d d, J=1.5, 8.8 Hz), 5.55 (2H, s), 3.92 (2H, s), 1.69 (6H, s)

Compound no. 372 (MP: 157-159). NMR solvent: CDCl3
13C: 162.9, 151.6, 146.5, 135.7, 133, 97.8, 87.1, 82.6, 79.6, 62.1, 56.2, 56.1, 23
1H: 7.14 (1H, s), 6.42 (1H, s), 5.50 (2H, s), 4.05 (3H, s), 3.91 (3H, s), 3.88 (2H, s), 1.67 (6H, s)

Compound no. 373 (MP: 118-119). NMR solvent: CDCl3
13C: 146.5, 145.1, 133.1, 129.4, 125.4, 119.8, 114.3, 96.5, 64, 49, 24.2
1H: 8.18 (1H, m. J=8.3 Hz), 8.11 (1H, m, J=8.3 Hz), 7.62 (1H, m, J=7.7 Hz), 7.48 (1H, m, J=7.7 Hz), 4.29 (2H, m, J=6.2 Hz), 4.15 (2H, m, J=6.2 Hz), 1.81 (6H, s)

Compound no. 374 (MP: 143-144). NMR solvent: CDCl3
13C: 149.8, 144.5, 134.9, 127.8 (q, J=33.0 Hz), 125.7 (q, J=3.3 Hz), 123.8 (q, J=272.5 Hz), 117.9 (q, J=4.5 Hz), 114.7, 58.9, 57.2, 32.5, 30.7, 30.2, 29.5, 25.5, 25.3
1H: 8.41 (1H, m), 8.12 (1H, d, J=8.8 Hz), 7.83 (1H, d d, J=1.5, 8.8 Hz), 4.28 (1H, m), 3.19 (3H, s), 2.0 (2H, d, br), 1.90 (2H, br), 1.73 (1H, br), 1.64 (2H, m), 1.46 (2H, br), 1.18 (1H, br)

Compound no. 375 (MP: 102-104). NMR solvent: CDCl3
13C: 150.7, 144.4, 139.6, 134.8, 132.2, 118.8, 113, 57.6, 32.4, 29.9, 25.5, 25.3, 20.9, 20.4
1H: 7.81 (1H, s), 7.75 (1H, s), 4.24 (1H, m), 3.15 (3H, s), 2.43 (3H, s), 2.41 (3H, s), 1.98 (2H, d br, J=11.5 Hz), 1.87 (2H, br), 1.70 (1H, m), 1.61 (2H, d q, J=3.7, 12.5 Hz), 1.40 (2H, br), 1.16 (1H, m)

Compound no. 376 (MP: 220-221 (dec)). NMR solvent: DMSO
13C: 150.6, 142.3, 139.3, 138.1, 136.7, 126.2, 124.9, 116.2, 56.9, 31.4, 29, 25.2, 24.9
1H: 8.19 (2H, s), 8.04 (2H, d, J=8.5 Hz), 7.83 (2H, d, J=8.5 Hz), 7.37 (2H, s), 3.83 (1H, m br), 2.95 (3H, s), 1.80 (4H, m), 1.60 (3H, m), 1.31 (2H, m), 1.14 (1H, m)

Compound no. 377 (MP: 93-95). NMR solvent: CDCl3
13C: 162.6, 151.6, 150.9, 136.1, 132.9, 97.3, 86.2, 58.9, 56.8, 56.2, 56, 32.7, 30.8, 29.5, 25.5, 25.3
1H: 6.89 (1H, d, J=2.0 Hz), 6.39 (1H, d, J=2.0 Hz), 4.25 (1H, m), 4.05 (3H, s), 3.88 (3H, s), 3.15 (3H, s), 1.98 (2H, d br, J=12.0 Hz), 1.87 (2H, br), 1.69 (1H, br), 1.60 (2H, d q, J=3.4, 12.2 Hz), 1.43 (2H, br), 1.15 (1H, m)

Compound no. 378 (MP: 118-119). NMR solvent: CDCl3
13C: 145.4, 143.8, 139.8, 117.1, 82.4, 79.6, 62.3, 22.6, 21.1
1H: 7.61 (2H, s), 5.41 (2H, s), 3.88 (2H, s), 2.40 (6H, s), 1.67 (6H, s)

Compound no. 379 (MP: 175). NMR solvent: DMSO
13C: 150.9, 140.6, 139.2, 137.7, 133.4, 128.6, 128.3, 127.4, 127.3, 127.1, 124.7, 114.4, 75.6, 69.1, 56.1, 31.5, 30.8, 26.6
1H: 8.12 (1H, d, J=1.3 Hz), 8.0 (1H, d, J=1.3 Hz), 7.85 (2H, m d, J=8.5 Hz), 7.39 (2H, t, J=7.6 Hz), 7.35-7.29 (4H, m), 7.27 (1H, m), 7.25 (1H, m t, J=7.3 Hz), 4.51 (2H, s), 3.86 (1H, m), 3.33 (1H, m), 2.91 (3H, s), 2.13 (2H, d br, J=11.5 Hz), 1.81 (2H, d br, J=12.5 Hz), 1.68 (2H, d q, J=2.5, 12.5 Hz), 1.30 (2H, q br, J=12.5 Hz)

Compound no. 380 (MP: 207). NMR solvent: DMSO
13C: 155.1, 150.7, 139.6, 138, 136.7, 127.4, 125.5, 122.4, 115.9, 56.9, 31.4, 29, 25.2, 24.8
1H: 16.76 (1H, br), 8.18 (2H, m), 8.07 (4H, m), 3.83 (1H, m), 2.94 (3H, s), 1.78 (4H, m), 1.60 (1H, m), 1.58 (2H, m), 1.30 (2H, q br, J=13.0 Hz), 1.11 (1H, m, J=12.9 Hz)

Compound no. 381 (MP: 102-103). NMR solvent: CDCl3
13C: 146.4, 144.5, 140.1, 135.3, 131.7, 118.9, 113.8, 82.5, 79.6, 62.1, 23, 20.9, 20.4
1H: 7.99 (1H, s), 7.82 (1H, s), 5.53 (2H, s), 3.89 (2H, s), 2.44 (3H, s), 2.42 (3H, s), 1.68 (6H, s)

Compound no. 382 (MP: 112-114). NMR solvent: CDCl3
13C: 152.5, 149.2, 146.4, 139.7, 128.4, 98.6, 94.7, 82.6, 79.5, 62.1, 56.6, 56.2, 23
1H: 7.63 (1H, s), 7.39 (1H, s,), 5.55 (2H, s), 4.04 (3H, s), 4.0 (3H, s), 3.89 (2H, s), 1.68 (6H, s)

Compound no. 383 (MP: 139). NMR solvent: CDCl3
13C: 151.4, 142.2, 137, 132.8, 128.7, 127.6, 125.1, 113.1, 69.6, 56.4, 34.1, 31.7, 27.4
1H: 7.92 (1H, d, J=1.3 Hz), 7.80 (2H, m d, J=8.0 Hz), 7.49 (1H, d, J=1.3 Hz), 7.41 (2H, m t, J=7.9 Hz), 7.30 (1H, m t, J=7.5 Hz), 4.01 (1H, m), 3.62 (1H, m), 2.99 (3H, s), 2.11 (2H, d br, J=12.5 Hz), 1.90 (2H, d br, J=12.5 Hz), 1.71 (2H, d q, J=3.0, 12.5 Hz), 1.46 (2H, d q, J=3.5, 13.0 Hz)

Compound no. 384 (MP: 158-160). NMR solvent: CDCl3
13C: 163.3, 151.7, 149.2, 134.4, 133.9, 97.6, 86.7, 69.5, 56.3, 56.2, 56.1, 24.3
1H: 7.43 (1H, s), 7.13 (1H, d, J=2.0 Hz), 6.40 (1H, d, J=2.0 Hz), 4.05 (3H, s), 3.90 (3H, s), 3.82 (2H, d, J=5.5 Hz), 3.34 (1H, t, J=5.5 Hz), 1.51 (6H, s)

Compound no. 385 (MP: 224-226). NMR solvent: DMSO
13C: 167.6, 146.1, 140.1, 137.3, 136, 132.6, 128, 124.4, 114.7, 80.6, 79.3, 60.9, 22.4
1H: 8.20 (1H, d, J=1.3 Hz), 8.15 (1H, d, J=1.3 Hz), 7.98 (1H, s br), 7.91 (4H, m), 7.36 (1H, s br), 5.19 (2H, s), 3.85 (2H, s), 1.50 (6H, s)

Compound no. 386 (MP: 183-185). NMR solvent: DMSO
13C: 157.8, 144.5, 136.6, 136.3, 126.9, 122.5, 115.2, 113.8, 80.7, 79.3, 62.5, 61.3, 54.6, 52.6, 22.3, 22.3, 21.3

1H: 10.83 (1H, s), 9.05 (1H, s br), 8.27 (1H, s), 7.89 (2H, d, J=8.6 Hz), 7.10 (2H, d, J=8.6 Hz), 5.21 (2H, s), 4.48 (2H, t, J=5.0 Hz), 3.87 (2H, s), 3.49 (2H, m), 3.45 (2H, m), 2.99 (2H, m), 1.80 (4H, m), 1.69 (1H, d, J=15.0 Hz), 1.51 (6H, s), 1.38 (1H, m)

Compound no. 387 (MP: 172-175). NMR solvent: DMSO
13C: 157.9, 144.2, 136.6, 135.7, 127, 122, 115.2, 114, 80.7, 79.3, 63.2, 62.4, 61.3, 54.7, 51.7, 22.3

1H: 11.69 (1H, s), 9.18 (1H, s), 8.31 (1H, s), 7.91 (2H, d, J=8.6 Hz), 7.12 (2H, d, J=8.6 Hz), 5.22 (2H, s), 4.51 (2H, t, J=5.0 Hz), 3.96 (2H, d br, J=12.6 Hz), 3.87 (2H, m), 3.87 (2H, s), 3.56 (2H, m), 3.49 (2H, d br, J=12.4 Hz), 3.20 (2H, m), 1.51 (6H, s)

Compound no. 388 (MP: 218-220). NMR solvent: DMSO
13C: 157.6, 144.6, 136.6, 136.6, 126.8, 122.9, 115.3, 113.7, 80.7, 79.3, 62.4, 61.3, 54.5, 48.5, 39.5, 22.3

1H: 12.18 (1H, br), 9.89 (2H, s), 8.98 (1H, s), 8.24 (1H, s), 7.88 (2H, d, J=8.9 Hz), 7.11 (2H, d, J=8.9 Hz), 5.20 (2H, s), 4.48 (2H, t, J=5.0 Hz), 3.86 (2H, s), 3.64 (2H, t, J=5.0 Hz), 3.75 (4H, m), 2.50 (4H, br), 1.50 (6H, s)

Compound no. 389 (MP: 216-218). NMR solvent: DMSO
13C: 166.9, 145.4, 144.6, 133.7, 131.9, 129.1, 119, 113.9, 81.7, 78.7, 61.7, 22.5

1H: 8.71 (1H, d d, J=0.8, 1.3 Hz), 8.26 (1H, s br), 8.21 (1H, d, J=1.3, 8.6 Hz), 8.16 (1H, d d, J=0.8, 8.6 Hz), 7.63 (1H, s br), 5.43 (2H, s), 3.90 (2H, s), 1.58 (6H, s)

Compound no. 390 (MP: 245-247). NMR solvent: DMSO
13C: 167.6, 150.7, 139.8, 137.9, 136.1, 132.5, 128, 124.3, 115.6, 56.8, 31.3, 29, 25.1, 24.8

1H: 8.15 (1H, d, J=1.3 Hz), 8.13 (1H, d, J=1.3 Hz), 7.97 (1H, s), 7.92 (2H, m), 7.89 (2H, m), 7.35 (1H, s), 3.82 (1H, m), 2.93 (3H, s), 1.78 (4H, m), 1.59 (3H, m), 1.30 (2H, q br, J=12.7 Hz), 1.11 (1H, q br, J=13.0 Hz)

Compound no. 391 (MP: 165 (dec)). NMR solvent: CDCl3
13C: 155.9, 154.1, 144.5, 137.7, 137.1, 136.9, 129.4, 128.9, 127.7, 124.7, 82.5, 79.6, 62.8, 22.6

1H: 9.21 (1H, d, J=2.2 Hz), 8.40 (1H, d, J=2.2 Hz), 7.68 (2H, d, J=8.2 Hz), 7.56 (2H, t, J=7.8 Hz), 7.50 (1H, t, J=7.3 Hz), 5.50 (2H, s), 3.93 (2H, s), 1.71 (6H, s)

Compound no. 392 (MP: 120). NMR solvent: CDCl3
13C: 156.2, 149.4, 145.6, 137.8, 136.8, 129.3, 128.9, 127.9, 126.1, 121, 82.5, 79.4, 62.6, 22.9

1H: 9.07 (1H, d, J=2.2 Hz), 8.75 (1H, d, J=2.2 Hz), 7.71 (2H, d, J=8.2 Hz), 7.54 (2H, t, J=7.6 Hz), 7.49 (1H, t, J=7.4 Hz), 5.61 (2H, s), 3.92 (2H, s), 1.70 (6H, s)

Compound no. 393 (MP: 179-180). NMR solvent: DMSO
13C: 158.9, 144.2, 136.5, 135.9, 127, 121.3, 115, 113.7, 80.7, 79.3, 71.4, 61.3, 42.6, 33.1, 25.1, 22.2

1H: 9.25 (1H, d, J=11.0 Hz), 9.17 (1H, s), 8.93 (1H, q, J=9.5 Hz), 8.29 (1H, s), 7.88 (2H, d, J=8.6 Hz), 7.06 (2H, d, J=8.6 Hz), 5.22 (2H, s), 3.91 (2H, d, J=6.2 Hz), 3.88 (2H, s), 3.28 (2H, d, J=12.0 Hz), 2.89 (2H, q, J=11.5 Hz), 2.08 (1H, m), 1.92 (2H, d, J=13.0 Hz), 1.54 (2H, q, J=12.5 Hz), 1.52 (6H, s)

Compound no. 394 (MP: 189-190). NMR solvent: DMSO
13C: 157.9, 148.9, 137, 135.5, 127, 122, 115.2, 114.7, 62.5, 57.2, 54.6, 52.6, 31.5, 28.8, 25, 24.8, 22.3, 21.2

1H: 10.86 (1H, br), 9.14 (1H, s), 8.28 (1H, s), 7.91 (2H, d, J=9.0 Hz), 7.11 (2H, d, J=9.0 Hz), 4.49 (2H, t, J=5.2 Hz), 3.84 (1H, m), 3.48 (2H, m), 3.46 (2H, m), 2.99 (2H, m), 2.96 (3H, s), 1.80 (8H, m), 1.69 (1H, m), 1.58 (3H, m), 1.39 (1H, m), 1.30 (2H, m), 1.12 (1H, m)

Compound no. 395 (MP: 74-76). NMR solvent: DMSO
13C: 158, 148.7, 136.9, 134.8, 127.1, 121.3, 115.3, 115, 63.2, 62.5, 57.2, 54.7, 51.7, 31.5, 28.8, 25, 24.8

1H: 11.72 (1H, br), 9.32 (1H, s), 8.35 (1H, s), 7.94 (2H, d, J=8.6 Hz), 7.15 (2H, d, J=8.6 Hz), 4.53 (2H, t, J=5.0 Hz), 3.97 (2H, d br, J=13.0 Hz), 3.90 (1H, m), 3.88 (2H, t br, J=11.8 Hz), 3.57 (2H, m), 3.50 (2H, d br, J=12.4 Hz), 3.21 (2H, m), 2.98 (3H, s), 1.80 (4H, m), 1.61 (3H, m), 1.33 (2H, m, J=12.5 Hz), 1.14 (1H, m)

Compound no. 396 (MP: 180-181). NMR solvent: DMSO
13C: 159, 144.3, 136.5, 136, 127, 121.3, 115, 113.6, 80.7, 79.4, 65.3, 61.4, 43, 34.7, 30.4, 28.3, 22.3

1H: 9.13 (1H, d, J=1.3 Hz), 9.04 (1H, m), 8.82 (1H, m), 8.25 (1H, d, J=1.3 Hz), 7.85 (2H, d, J=9.0 Hz), 7.03 (2H, d, J=9.0 Hz), 5.21 (2H, s), 4.06 (2H, t, J=6.1 Hz), 3.87 (2H, s), 3.22 (2H, d br, J=12.5 Hz), 2.83 (2H, q br, J=11.5 Hz), 1.85 (2H, d br, J=14.0 Hz), 1.76 (1H, m), 1.68 (2H, m), 1.51 (6H, s), 1.41 (2H, d q, J=4.0, 13.8 Hz)

Compound no. 397 (MP: 205-207). NMR solvent: DMSO
13C: 157.8, 148.8, 137, 135.3, 127, 121.9, 115.3, 114.8, 62.4, 57.2, 54.4, 48.4, 39.7, 31.5, 28.8, 25, 24.8

1H: 12.35 (1H, s br), 10.02 (2H, s), 9.21 (1H, s), 8.31 (1H, s), 7.92 (2H, d, J=8.6 Hz), 7.14 (2H, d, J=8.6 Hz), 4.50 (2H, t, J=4.8 Hz), 3.81 (1H, m), 3.65 (2H, t, J=4.8 Hz), 3.50 (8H, s br), 2.96 (3H, s), 1.79 (4H, m), 1.59 (3H, m), 1.31 (2H, q, J=12.5 Hz), 1.12 (1H, q, J=13.0 Hz)

Compound no. 398 (MP: 201 (dec.)). NMR solvent: DMSO
13C: 156.7, 151.2, 141, 137.3, 126.1, 124.5, 115.3, 112.5, 66.3, 54.1, 31.5, 29.1

1H: 9.46 (1H, s), 8.06 (1H, d, J=1.3 Hz), 7.79 (1H, d, J=1.3 Hz), 7.64 (2H, m d, J=8.8 Hz), 6.77 (2H, m d, J=8.8 Hz), 4.09 (1H, m), 3.93 (2H, d d, J=4.3, 11.1 Hz), 3.73 (2H, t br, J=12.0 Hz), 2.94 (3H, s), 1.85 (2H, d q, J=4.5, 12.2 Hz), 1.69 (2H, m d, J=12.3 Hz)

Compound no. 399 (MP: 176-178). NMR solvent: DMSO
13C: 157.9, 144.9, 137.4, 136.9, 131.9, 130.2, 118.2, 114.9, 114.8, 111.1, 80.7, 79.3, 62.5, 61.2, 54.6, 52.6, 22.3, 22.3, 21.2

1H: 10.80 (1H, s), 8.83 (1H, s), 8.35 (1H, s), 7.59 (1H, br), 7.54 (1H, d br, J=7.5 Hz), 7.39 (1H, t, J=7.9 Hz), 6.96 (1H, d d, J=2.0, 8.2 Hz), 5.21 (2H, s), 4.50 (2H, t, J=5.2 Hz), 3.87 (2H, s), 3.46 (4H, m), 3.0 (2H, m), 1.80 (4H, m), 1.69 (1H, m), 1.51 (6H, s), 1.38 (1H, m)

Compound no. 400 (MP: 200-202). NMR solvent: DMSO
13C: 159, 148.8, 136.9, 135.3, 127, 121, 115, 114.6, 71.4, 57.2, 42.6, 33.1, 31.5, 28.8, 25.1, 25, 24.8

1H: 9.24 (1H, m), 9.22 (1H, m), 8.93 (1H, m), 8.29 (1H, s), 7.88 (2H, d, J=8.9 Hz), 7.06 (2H, d, J=8.9 Hz), 3.91 (2H, d, J=6.3 Hz), 3.85 (1H, m), 3.27 (2H, d br, J=12.4 Hz), 2.96 (3H, s), 2.88 (2H, q, J=11.0 Hz), 2.07 (1H, m), 1.91 (2H, d br, J=13.0 Hz), 1.79 (4H, m), 1.58 (3H, m), 1.55 (2H, m), 1.31 (2H, m, J=13.0 Hz), 1.12 (1H, m, J=13.0 Hz)

Compound no. 401 (MP: 160-162). NMR solvent: DMSO
13C: 157.8, 145.1, 138.1, 136.9, 132.5, 130.1, 118.2, 114.7, 114.6, 111.1, 80.6, 79.3, 62.4, 61.1, 54.4, 48.5, 25.5, 22.3

1H: 12.23 (1H, s br), 9.84 (2H, s), 8.69 (1H, br), 8.29 (1H, s), 7.58 (1H, br), 7.53 (1H, d, J=7.6 Hz), 7.38 (1H, t, J=7.9 Hz), 6.97 (1H, d d, J=1.8, 8.0 Hz), 5.20 (2H, s), 4.50 (2H, m), 3.86 (2H, s), 3.66 (2H, m), 3.50 (8H, br), 1.51 (6H, s)

Compound no. 402 (MP: 137-140). NMR solvent: DMSO
13C: 157.9, 144.6, 136.8, 136.6, 131.1, 130.2, 118.3, 115.2, 115.1, 111.2, 80.7, 79.3, 63.2, 62.5, 61.3, 54.7, 51.7, 22.3

1H: 11.70 (1H, s), 9.0 (1H, s), 8.41 (1H, s), 7.62 (1H, br), 7.56 (1H, d, J=7.8 Hz), 7.40 (1H, t, J=8.0 Hz), 7.0 (1H, dd, J=2.0, 8.2 Hz), 5.22 (2H, s), 4.54 (2H, t, J=4.7 Hz), 3.96 (2H, d br, J=13.0 Hz), 3.87 (2H, s), 3.87 (2H, m), 3.57 (2H, m), 3.51 (2H, d br, J=13.0 Hz), 3.22 (2H, m), 1.51 (6H, s)

Compound no. 403 (MP: 204-206). NMR solvent: DMSO
13C: 167.9, 150.8, 140.1, 137.7, 134.7, 133.5, 128.6, 127.3, 126.1, 123.9, 114.9, 56.8, 31.4, 29, 25.2, 24.8
1H: 8.35 (1H, t, J=1.5 Hz), 8.15 (1H, d, J=1.2 Hz), 8.06 (1H, d, J=1.2 Hz), 8.03 (1H, s br), 7.98 (1H, d t, J=1.5, 7.9 Hz), 7.75 (1H, d t, J=1.5, 7.9 Hz), 7.47 (1H, t, J=7.7 Hz), 7.42 (1H, s br), 3.83 (1H, m), 2.94 (3H, s), 1.78 (4H, m), 1.58 (3H, m), 1.29 (2H, m), 1.11 (1H, m)

Compound no. 404 (MP: 198-200). NMR solvent: CDCl3
13C: 150.9, 140.3, 137.9, 137.3, 133.3, 128.4, 125.5, 115.2, 66.1, 57.7, 46, 31.4, 30, 25.4, 25.2
1H: 7.97 (2H, d, J=8.5 Hz), 7.93 (1H, d, J=1.3 Hz), 7.78 (2H, d, J=8.5 Hz), 7.64 (1H, d, J=1.3 Hz), 3.95 (1H, m, J=11.5 Hz), 3.75 (4H, m, J=5.0 Hz), 3.02 (4H, m, J=5.0 Hz), 3.01 (3H, s), 1.87 (4H, m), 1.72 (1H, m), 1.59 (2H, d q, J=3.5, 12.3 Hz), 1.38 (2H, t q, J=3.3, 13.0 Hz), 1.14 (1H, t q, J=3.5, 13.2 Hz)

Compound no. 405 (MP: 152-154). NMR solvent: DMSO
13C: 159, 144.7, 137.2, 136.8, 131.5, 130.1, 117.6, 114.9, 114.9, 110.9, 80.7, 79.3, 71.4, 61.2, 42.6, 33.2, 25.2, 22.3
1H: 9.14 (1H, m), 8.89 (1H, s), 8.85 (1H, m), 8.34 (1H, s), 7.52 (1H, br), 7.49 (1H, m), 7.35 (1H, t, J=7.8 Hz), 6.91 (1H, d d, J=2.0, 8.3 Hz), 5.20 (2H, s), 3.92 (2H, d, J=6.5 Hz), 3.86 (2H, s), 3.28 (2H, d br, J=12.2 Hz), 2.89 (2H, q br, J=11.5 Hz), 2.08 (1H, m), 1.93 (2H, d br, J=13.0 Hz), 1.52 (2H, m), 1.51 (6H, s)

Compound no. 406 (MP: 190-191). NMR solvent: DMSO
13C: 150.8, 150.6, 140.2, 137.7, 133.9, 131.8, 125.6, 124.4, 114.8, 56.8, 31.3, 29, 25.2, 24.8
1H: 9.64 (1H, s), 8.12 (1H, d, J=1.3 Hz), 8.04 (1H, d, J=1.3 Hz), 7.84 (2H, m d, J=8.5 Hz), 7.69 (2H, m d, J=8.5 Hz), 5.82 (2H, s), 3.81 (1H, m), 2.93 (3H, s), 1.78 (4H, m), 1.59 (2H, m), 1.57 (1H, m), 1.29 (2H, q br, J=12.8 Hz), 1.11 (1H, q br, J=12.9 Hz)

Compound no. 407 (MP: hygroscopic). NMR solvent: DMSO
13C: 157.9, 149.3, 137.4, 136.4, 131.1, 130.3, 118.4, 116, 115.2, 111.4, 62.6, 57.2, 54.5, 48.5, 39.7, 31.6, 28.9, 25.1, 24.8
1H: 12.09 (1H, br), 9.87 (2H, s), 8.97 (1H, s), 8.37 (1H, s), 7.62 (1H, br), 7.55 (1H, d, J=8.0 Hz), 7.41 (1H, t, J=8.0 Hz), 7.01 (1H, d d, J=2.0, 8.2 Hz), 4.50 (2H, m), 3.90 (1H, m), 3.70 (4H, br), 3.67 (2H, m), 3.50 (4H, m), 2.96 (3H, s), 1.79 (4H, m), 1.58 (3H, m), 1.31 (2H, m), 1.14 (1H, m)

Compound no. 408 (MP: 124-127). NMR solvent: DMSO
13C: 158, 148.8, 137.3, 135.4, 130.3, 130.2, 118.4, 116.3, 115.5, 111.4, 63.2, 62.6, 57.2, 54.7, 51.7, 31.6, 28.8, 25, 24.8
1H: 11.80 (1H, s), 9.21 (1H, s br), 8.48 (1H, s), 7.67 (1H, br), 7.58 (1H, d, J=7.5 Hz), 7.42 (1H, t, J=8.0 Hz), 7.02 (1H, d d, J=1.5, 8.1 Hz), 4.55 (2H, m), 3.96 (2H, d br, J=12.5 Hz), 3.90 (1H, m), 3.87 (2H, t br, J=12.0 Hz), 3.58 (2H, m), 3.51 (2H, d br, J=12.1 Hz), 3.22 (2H, m), 2.97 (3H, s), 1.79 (4H, m), 1.59 (3H, m), 1.32 (2H, m), 1.12 (1H, m)

Compound no. 409 (MP: 183). NMR solvent: DMSO
13C: 164, 151.1, 140.7, 137.8, 133.3, 132.4, 130.6, 128.8, 128.7, 128.7, 127.1, 124.8, 114.4, 59.5, 53.1, 50.8, 31.6, 25.8
1H: 8.13 (1H, d, J=1.3 Hz), 8.0 (1H, d, J=1.3 Hz), 7.85 (2H, m d, J=8.5 Hz), 7.49-7.40 (5H, m), 7.39 (2H, t, J=7.7 Hz), 7.26 (1H, m t, J=7.5 Hz), 4.05 (2H, s), 4.05 (1H, m), 3.26 (2H, d br, J=12.0 Hz), 2.94 (3H, s), 2.81 (2H, t br, J=12.0 Hz), 2.08 (2H, d q, J=3.3, 12.7 Hz), 1.90 (2H, d br, J=12.0 Hz)

Compound no. 410 (MP: 177-178). NMR solvent: DMSO
13C: 149.6, 137.6, 136.6, 131.4, 129.9, 129.6, 129.5, 129, 128.8, 128.5, 125.3, 115.6, 58.7, 52.3, 50.2, 31.6, 24.6
1H: 11.36 (1H, s br), 9.0 (1H, s), 8.31 (1H, s), 7.92 (2H, m d, J=8.5 Hz), 7.64 (2H, m), 7.50-7.43 (5H, m), 7.37 (1H, m t, J=7.7 Hz), 4.26 (2H, d, J=5.0 Hz), 4.20 (1H, m), 3.39 (2H, d br, J=12.0 Hz), 3.09 (2H, q br, J=12.0 Hz), 2.97 (3H, s), 2.43 (2H, d q, J=3.3, 13.0 Hz), 1.95 (2H, d br, J=13.0 Hz)

Compound no. 411 (MP: 191-192). NMR solvent: DMSO
13C: 151.2, 140.7, 137.8, 133.3, 131.3, 129.7, 129, 128.7, 127.2, 124.8, 114.4, 59.2, 52.2, 50.7, 39.8, 31.8, 25.2
1H: 9.42 (1H, s br), 8.14 (1H, d, J=1.3 Hz), 8.0 (1H, d, J=1.3 Hz), 7.85 (2H, m d, J=8.3 Hz), 7.50 (5H, m), 7.39 (2H, t, J=8.0 Hz), 7.26 (1H, m t, J=7.3 Hz), 4.29 (1H, m), 4.29 (2H, s br), 3.44 (2H, m, J=12.3 Hz), 3.13 (2H, m), 2.93 (3H, s), 2.35 (3H, s), 2.12 (2H, q br, J=13.5 Hz), 2.0 (2H, d br, J=12.5 Hz)

Compound no. 412 (MP: 178). NMR solvent: DMSO
13C: 175.7, 171.4, 151.1, 140.7, 137.7, 135.7, 133.4, 129.7, 128.7, 128.5, 127.9, 127.2, 124.8, 114.4, 72, 60.8, 54.5, 51.7, 43.4, 31.6, 27.2
1H: 8.13 (1H, s br), 8.00 (1H, s, br), 7.84 (2H, d, J=7.9 Hz), 7.43-7.30 (7H, m), 7.26 (1H, t, J=7.5 Hz), 3.93 (1H, m), 3.73 (2H, s), 3.07 (2H, d br, J=11.0 Hz), 2.93 (3H, s), 2.68 (2H, d br, J=15.3 Hz), 2.58 (2H, d, J=15.3 Hz), 2.37 (2H, t br, J=12.5 Hz), 1.92 (2H, q br, J=12.5 Hz), 1.80 (2H, d br, J=12.0 Hz)

Compound no. 413 (MP: 195). NMR solvent: DMSO
13C: 173.4, 151, 140.6, 137.7, 137.3, 133.4, 129.2, 128.6, 128.3, 127.3, 127.1, 124.7, 114.4, 72.1, 61.4, 55, 52, 31.5, 27.8
1H: 8.12 (1H, s), 8.0 (1H, s), 7.84 (2H, d br, J=7.7 Hz), 7.38 (2H, t, J=7.6 Hz), 7.35-7.28 (5H, m), 7.25 (1H, m t, J=7.5 Hz), 4.24 (2H, s), 3.87 (1H, m), 3.58 (2H, s), 2.96 (2H, m), 2.94 (3H, s), 2.15 (2H, t br, J=11.0 Hz), 1.87 (2H, q br, J=12.3 Hz), 1.76 (2H, d br, J=11.0 Hz)

Compound no. 414 (MP: 192). NMR solvent: DMSO
13C: 151, 140.6, 137.7, 136.8, 133.4, 129.3, 128.6, 128.4, 127.5, 127.1, 124.8, 114.4, 61.2, 54.9, 51.8, 31.5, 27.6
1H: 8.12 (1H, d, J=1.3 Hz), 8.0 (1H, d, J=1.3 Hz), 7.85 (2H, m d, J=8.3 Hz), 7.39 (2H, t, J=7.5 Hz), 7.36-7.27 (5H, m), 7.23 (1H, m t, J=7.4 Hz), 3.89 (1H, m), 3.62 (2H, s), 2.99 (2H, d br, J=12.0 Hz), 2.94 (3H, s), 2.21 (2H, t br, J=12.0 Hz), 1.91 (2H, d q, J=3.3, 12.2 Hz), 1.77 (2H, d br, J=11.8 Hz)

Compound no. 415 (MP: 175). NMR solvent: CDCl3
13C: 151, 140.5, 138.3, 137.4, 137.3, 134.5, 128.4, 128.2, 127.6, 127.4, 125.4, 115, 71.9, 69.8, 57.7, 43.3, 31.4, 30.2, 30, 25.4, 25.2
1H: 7.95 (2H, m, J=8.0 Hz), 7.93 (1H, d, J=1.3 Hz), 7.78 (2H, m, J=8.0 Hz), 7.62 (1H, d, J=1.3 Hz), 7.34-7.21 (5H, m), 4.46 (2H, s), 3.95 (1H, m), 3.46 (1H, m), 3.29 (2H, m), 3.0 (3H, s), 2.96 (2H, m), 1.90 (2H, m), 1.87 (4H, m), 1.80 (2H, m), 1.71 (1H, d br, J=13.3 Hz), 1.60 (2H, d q, J=3.5, 13.5 Hz), 1.38 (2H, t q, J=3.5, 13.3 Hz), 1.14 (1H, t q, J=3.5, 13.2 Hz)

Compound no. 416 (MP: 176-177). NMR solvent: CDCl3
13C: 151.2, 148.6, 146.7, 139.3, 138, 137.3, 132.4, 129.1, 129, 128.3, 127.2, 123.6, 113.9, 62.8, 55.9, 52.5, 31.7, 28.9
1H: 9.0 (1H, d d, J=0.7, 2.2 Hz), 8.53 (1H, d d, J=1.7, 4.9 Hz), 8.12 (1H, d t, J=1.7, 7.9 Hz), 7.94 (1H, d, J=1.3 Hz), 7.58 (1H, d, J=1.3 Hz), 7.35 (1H, m), 7.34-7.24 (5H, m), 4.02 (1H, m), 3.52 (2H, s), 3.03 (3H, s), 3.0 (2H, m), 2.11 (2H, t br, J=12.0 Hz), 1.94 (2H, d q, J=3.5, 12.0 Hz), 1.79 (2H, d br, J=12.0 Hz)

Compound no. 417 (MP: 112-113). NMR solvent: CDCl3
13C: 151.4, 148.5, 146.6, 139.2, 137.3, 132.4, 129, 123.6, 114, 59.4, 31.2, 28.9, 24.3
1H: 9.01 (1H, d, J=1.7 Hz), 8.53 (1H, d d, J=1.5, 4.8 Hz), 8.12 (1H, t d, J=2.0, 7.9 Hz), 7.96 (1H, d, J=1.3 Hz), 7.59 (1H, d, J=1.3 Hz), 7.34 (1H, d d, J=4.8, 7.9 Hz), 4.44 (1H, qt, J=8.2 Hz), 3.0 (3H, s), 1.96 (2H, m), 1.77 (2H, m), 1.70 (2H, m), 1.63 (2H, m)

Compound no. 418 (MP: 138-140). NMR solvent: CDCl3
13C: 159.9, 151.5, 142.1, 138, 136.9, 134.3, 129.7, 129.1, 128.3, 127.2, 117.5, 113.7, 113.4, 110.1, 62.8, 55.8, 55.3, 52.5, 31.6, 28.9

1H: 7.92 (1H, d, J=1.3 Hz), 7.49 (1H, d, J=1.3 Hz), 7.40 (1H, d d, J=1.4, 2.4 Hz), 7.38-7.24 (6H, m), 7.31 (1H, t, J=7.6 Hz), 6.86 (1H, d d d, J=1.2, 2.5, 7.9 Hz), 4.02 (1H, m), 3.88 (3H, s), 3.52 (2H, s), 3.02 (3H, s), 3.0 (2H, m), 2.10 (2H, t br, J=11.5 Hz), 1.94 (2H, d q, J=3.3, 12.0 Hz), 1.79 (2H, d br, J=12.0 Hz)

Compound no. 419 (MP: 190-191). NMR solvent: CDCl3
13C: 159.2, 151.6, 142.1, 138, 136.8, 129.1, 128.3, 127.2, 126.4, 125.8, 114.1, 112, 62.8, 55.8, 55.3, 52.5, 31.6, 28.9
1H: 7.90 (1H, d, J=1.3 Hz), 7.73 (2H, m d, J=9.0 Hz), 7.39 (1H, d, J=1.3 Hz), 7.37-7.23 (5H, m), 6.85 (2H, m d, J=9.0 Hz), 4.03 (1H, m), 3.84 (3H, s), 3.52 (2H, s), 3.02 (3H, s), 3.0 (2H, m), 2.10 (2H, t br, J=12.0 Hz), 1.93 (2H, d q, J=3.6, 12.0 Hz), 1.78 (2H, d br, J=13.0 Hz)

Compound no. 420 (MP: 190-191). NMR solvent: CDCl3
13C: 158.4, 151.6, 142.1, 138, 136.9, 136.8, 129.1, 128.6, 128.3, 128, 127.5, 127.2, 126.4, 126, 115, 112.1, 70, 62.8, 55.8, 52.5, 31.6, 28.9
1H: 7.89 (1H, s), 7.72 (2H, m d, J=8.6 Hz), 7.45 (2H, d, J=7.5 Hz), 7.40 (2H, m), 7.38 (1H, s), 7.37-7.23 (6H, m), 7.02 (2H, m d, J=8.6 Hz), 5.10 (2H, s), 4.01 (1H, m), 3.52 (2H, s), 3.01 (3H, s), 2.99 (2H, m), 2.09 (2H, t br, J=10.7 Hz), 1.93 (2H, q br, J=12.5 Hz), 1.78 (2H, d br, J=12.5 Hz)

Compound no. 421 (MP: 165-166). NMR solvent: CDCl3
13C: 150.9, 137.6, 137.6, 136.9, 136, 132.8, 125.9, 122.6, 115.3, 59.4, 31.2, 28.9, 24.3
1H: 8.67 (1H, t br, J=1.5 Hz), 8.13 (1H, d d d, J=1.7, 6.5 Hz), 7.98 (1H, d, J=1.3 Hz), 7.71 (1H, t d, J=1.2, 8.0 Hz), 7.59 (1H, d, J=1.3 Hz), 7.31 (1H, d d, J=6.5, 8.0 Hz), 4.40 (1H, qt, J=8.0 Hz), 3.0 (3H, s), 1.95 (2H, m), 1.77 (2H, m), 1.69 (2H, m), 1.63 (2H, m)

Compound no. 422 (MP: 197). NMR solvent: DMSO
13C: 150.6, 139.0, 138.8, 138.4, 138.2, 127.5, 125.2, 116.8, 56.8, 43.6, 31.3, 29.0, 25.1, 24.8
1H: 8.26 (1H, s), 8.20 (1H, s), 8.11 (2H, d, J=8.5 Hz), 7.93 (2H, d, J=8.5 Hz), 3.81 (1H, m), 3.22 (3H, s), 2.93 (3H, s), 1.78 (4H, m), 1.58 (3H, m), 1.30 (2H, q br, J=12.7 Hz), 1.12 (1H, m)

Compound no. 423 (MP: 179). NMR solvent: DMSO
13C: 164.1, 150.9, 140.1, 138.5, 137.8, 133.6, 133.5, 128.8, 128.7, 128.2, 127, 127, 125.4, 123.2, 114.9, 61.9, 55.5, 52.2, 31.5, 28.2
1H: 11.20 (1H, br), 9.15 (1H, br), 8.23 (1H, br), 8.15 (1H, d, J=1.3 Hz), 8.05 (1H, d, J=1.3 Hz), 7.95 (1H, m d, J=7.8 Hz), 7.62 (1H, d, J=7.8 Hz), 7.45 (1H, t, J=7.7 Hz), 7.36-7.21 (5H, m), 3.83 (1H, m), 3.47 (2H, s), 2.95 (3H, s), 2.90 (2H, d br, J=11.2 Hz), 2.0 (2H, t br, J=11.0 Hz), 1.83 (2H, d q, J=3.3, 11.9 Hz), 1.73 (2H, d br, J=12.3 Hz)

Compound no. 424 (MP: 176). NMR solvent: DMSO
13C: 163.8, 149.2, 137.8, 136.1, 133.6, 130, 129.2, 127.8, 126.6, 124, 116.1, 57.1, 31.5, 28.8, 25.1, 24.8
1H: 11.31 (1H, br), 9.0 (1H, s), 8.37 (1H, s), 8.27 (1H, t br, J=1.5 Hz), 8.0 (1H, t d, J=1.5, 7.7 Hz), 7.73 (1H, t d, J=1.4, 7.8 Hz), 7.56 (1H, t, J=7.7 Hz), 3.86 (1H, m), 2.98 (3H, s), 1.81 (4H, m), 1.60 (3H, m), 1.32 (2H, q br, J=12.8 Hz), 1.13 (1H, q br, J=13.0 Hz)

Compound no. 425 (MP: 140-142). NMR solvent: CDCl3
13C: 151.1, 144.6, 140.2, 137.2, 137, 133.6, 132.1, 129, 127.8, 127.1, 122.9, 121.2, 114.7, 112.5, 57.6, 47.2, 31.5, 30, 25.4, 25.2
1H: 8.61 (1H, d, J=2.2 Hz), 8.50 (1H, t, J=5.7 Hz), 7.90 (1H, d, J=1.3 Hz), 7.89 (1H, d d, J=2.2, 9.0 Hz), 7.43 (1H, d, J=1.3 Hz), 7.42-7.29 (5H, m), 6.89 (1H, d, J=9.0 Hz), 4.61 (2H, d, J=5.7 Hz), 3.96 (1H, m), 3.0 (3H, s), 1.87 (4H, m), 1.71 (1H, d br, J=13.0 Hz), 1.60 (2H, m), 1.39 (2H, q br, J=13.0 Hz), 1.13 (1H, m, J=3.5, 13.2 Hz)

Compound no. 426 (MP: 261). NMR solvent: CDCl3
13C: 155.4, 151.1, 141.6, 137.1, 136.2, 130, 128.8, 128.4, 127.7, 127.3, 126.8, 118.5, 112.6, 108.6, 106.4, 57.6, 44.5, 31.5, 29.9, 25.4, 25.2
1H: 9.87 (1H, s), 8.17 (1H, d, J=1.3 Hz), 7.74 (1H, d, J=1.4 Hz), 7.45 (1H, d, J=1.3 Hz), 7.39 (1H, d d, J=1.4, 8.2 Hz), 7.36-7.25 (5H, m), 6.87 (1H, d, J=8.2 Hz), 5.10 (2H, s), 3.97 (1H, m), 3.02 (3H, s), 1.87 (4H, m), 1.70 (1H, m), 1.58 (2H, q br, J=13.0 Hz), 1.38 (2H, q br, J=13.0 Hz), 1.13 (1H, q br, J=12.8 Hz)

Compound no. 427 (MP: 204-205). NMR solvent: CDCl3
13C: 150.6 (d d, J=13.0, 247.5 Hz), 151.2, 149.8 (d d, J=12.0, 248.0 Hz), 140.4, 138, 137, 130.2 (d d, J=4.0, 6.5 Hz), 129.1, 128.3, 127.2, 121.0 (d d, J=3.5, 6.2 Hz), 117.5 (d, J=17.5 Hz), 114.2 (d, J=19.0 Hz), 113.5, 62.8, 55.9, 52.5, 31.7, 28.9
1H: 7.89 (1H, d, J=1.3 Hz), 7.61 (1H, d d d, J=2.2, 7.2, 11.5 Hz), 7.50 (1H, m), 7.46 (1H, d, J=1.3 Hz), 7.37-7.25 (5H, m), 7.18 (1H, d t, J=8.4, 10.2 Hz), 4.02 (1H, m), 3.53 (2H, s), 3.03 (3H, s), 3.01 (2H, m), 2.11 (2H, t br, J=12.0 Hz), 1.93 (2H, d q, J=3.5, 12.0 Hz), 1.78 (2H, d br, J=12.0 Hz)

Compound no. 428 (MP: 222-223). NMR solvent: CDCl3
13C: 151.3, 141.2, 138, 137, 133.1, 131.5, 129.1, 128.8, 128.3, 127.2, 126.4, 113.4, 62.8, 55.8, 52.5, 31.6, 28.9
1H: 7.91 (1H, d, J=1.3 Hz), 7.49 (1H, d, J=1.3 Hz), 7.73 (2H, m d, J=8.5 Hz), 7.37 (2H, m d, J=8.5 Hz), 7.35-7.25 (5H, m), 4.02 (1H, m), 3.52 (2H, s), 3.02 (3H, s), 3.0 (2H, m), 2.10 (2H, t br, J=11.5 Hz), 1.93 (2H, d, J=3.5, 12.0 Hz), 1.78 (2H, d br, J=12.0 Hz)

Compound no. 429 (MP: 203-204). NMR solvent: CDCl3
13C: 151.4, 150.5, 141.2, 138, 137, 130.4, 129.1, 128.3, 127.2, 126.6, 119.7, 115.9, 113.2, 62.8, 55.9, 52.5, 31.6, 28.9
1H: 7.91 (1H, d, J=1.3 Hz), 7.79 (2H, m d, J=8.8 Hz), 7.47 (1H, d, J=1.3 Hz), 7.37-7.25 (5H, m), 7.16 (2H, m d, J=8.8 Hz), 6.54 (1H, t, J=74.0 Hz), 4.03 (1H, m), 3.53 (2H, s), 3.03 (3H, s), 3.01 (2H, m), 2.11 (2H, t br, J=12.0 Hz), 1.93 (2H, d q, J=3.5, 12.0 Hz), 1.79 (2H, d br, J=12.5 Hz)

Compound no. 430 (MP: 211-212). NMR solvent: CDCl3
13C: 162.3 (d, J=247.0 Hz), 151.4, 141.4, 138, 136.9, 129.2 (d, J=3.5 Hz), 129.1, 128.3, 127.2, 126.8 (d, J=8.0 Hz), 115.6 (d, J=21.5 Hz), 112.9, 62.8, 55.8, 52.5, 31.6, 28.9
1H: 7.90 (1H, d, J=1.3 Hz), 7.76 (2H, m, J=5.3, 8.8 Hz), 7.45 (1H, d, J=1.3 Hz), 7.37-7.25 (5H, m), 7.10 (2H, m t, J=8.9 Hz), 4.03 (1H, m), 3.52 (2H, s), 3.02 (3H, s), 3.0 (2H, m), 2.10 (2H, t br, J=12.0 Hz), 1.93 (2H, d q, J=3.5, 12.0 Hz), 1.78 (2H, d br, J=10.5 Hz)

Compound no. 431 (MP: 190-191). NMR solvent: CDCl3
13C: 159.3, 151.2, 148.5, 146.7, 139.2, 137.2, 132.4, 129, 128.7, 123.6, 114, 113.7, 103.8, 56.2, 55.8, 52.1, 48.9, 31.5, 29.1
1H: 9.0 (1H, d, J=1.8 Hz), 8.53 (1H, d d, J=1.5, 4.8 Hz), 8.11 (1H, t d, J=1.8, 7.9 Hz), 7.92 (1H, d, J=1.0 Hz), 7.57 (1H, d, J=1.0 Hz), 7.34 (1H, d d, J=4.8, 7.9 Hz), 7.22 (1H, t, J=8.3 Hz), 6.57 (2H, d, J=8.3 Hz), 3.91 (1H, m), 3.81 (6H, s), 3.71 (2H, s), 3.09 (2H, d br, J=12.0 Hz), 3.0 (3H, s), 2.20 (2H, t br, J=11.6 Hz), 1.94 (2H, d q, J=3.2, 12.0 Hz), 1.72 (2H, d br, J=12.0 Hz)

Compound no. 432 (MP: 190 (dec)). NMR solvent: DMSO
13C: 150.4, 139.1, 137.9, 137.7, 133.4, 127.8, 125, 116.3, 63.8, 56.7, 43.1, 32.8, 31.2, 29, 25.1, 24.8
1H: 8.24 (1H, d, J=1.3 Hz), 8.19 (1H, d, J=1.3 Hz), 8.09 (2H, m d, J=8.5 Hz), 7.73 (2H, m d, J=8.5 Hz), 4.68 (1H, d, J=4.0 Hz), 3.81 (1H, m br), 3.51 (1H, m), 3.16 (2H, m), 2.93 (3H, s), 2.71 (2H, m), 1.78 (4H, m), 1.73 (2H, m), 1.58 (3H, m), 1.42 (2H, m), 1.30 (2H, q br, J=12.8 Hz), 1.12 (1H, q br, J=12.5 Hz)

Compound no. 433 (MP: 161-162). NMR solvent: CDCl3
13C: 151.6, 149.1, 148.6, 142.1, 138, 136.7, 129.1, 128.3, 127.2, 126.1, 117.4, 112.3, 111.3, 108.4, 62.8, 55.9, 55.9, 55.8, 52.5, 31.6, 28.9
1H: 7.90 (1H, d, J=1.3 Hz), 7.42 (1H, d, J=1.3 Hz), 7.40 (1H, d, J=1.9 Hz), 7.37-7.24 (5H, m), 7.30 (1H, d d, J=1.9, 8.3 Hz), 6.91 (1H, d, J=8.3 Hz), 4.03 (1H, m), 3.97 (3H, s), 3.92 (3H, s), 3.53 (2H, s), 3.03 (3H, s), 3.01 (2H, m), 2.11 (2H, t br, J=11.5 Hz), 1.94 (2H, d q, J=3.2, 11.8 Hz), 1.79 (2H, d br, J=11.8 Hz)

Compound no. 434 (MP: 126-128). NMR solvent: CDCl3
13C: 150.7, 142.2, 136.8, 133, 128.7, 127.5, 125.1, 113.1, 56.2, 42.2, 35.3, 31, 25.9, 25.4, 24.4, 23.7, 19.9
1H: 7.88 (1H, s), 7.81 (2H, d, J=7.8 Hz), 7.46 (1H, s), 7.41 (2H, t, J=7.7 Hz), 7.30 (1H, t, J=7.4 Hz), 4.19 (1H, s br), 3.91 (1H, s br), 3.14 (1H, t, J=12.7 Hz), 2.10-1.20 (13H, m)

Compound no. 435 (MP: 127-128). NMR solvent: CDCl3
13C: 151.2, 145.3, 140.4, 139.1, 137, 130, 123.4, 123.2, 118.3, 112.6, 57.5, 42.5, 31.4, 29.9, 25.4, 25.2
1H: 8.18 (1H, d, J=2.2 Hz), 7.89 (1H, d, J=1.3 Hz), 7.85 (1H, d d, J=2.2, 8.8 Hz), 7.43 (1H, d, J=1.3 Hz), 7.06 (1H, d, J=8.8 Hz), 3.95 (1H, m), 3.0 (3H, s), 2.93 (6H, s), 1.88 (2H, m), 1.85 (2H, m), 1.70 (1H, d br, J=13.0 Hz), 1.58 (2H, d q, J=3.4, 12.2 Hz), 1.38 (2H, t q, J=3.0, 13.0 Hz), 1.13 (1H, t q, J=3.5, 13.2 Hz)

Compound no. 436 (MP: 215-217). NMR solvent: DMSO
13C: 166.6, 145.3, 144.6, 134.6, 130, 128.6, 121.5, 114.3, 81.7, 78.7, 61.7, 22.5
1H: 13.38 (1H, br), 8.70 (1H, s), 8.24 (1H, d, J=9.0 Hz), 8.19 (1H, d, J=9.0 Hz), 5.43 (2H, s), 3.90 (2H, s), 1.58 (6H, s)

Compound no. 437 (MP: 181). NMR solvent: DMSO
13C: 163.6, 144.4, 144.3, 142.8, 135.9, 132.7, 129.1, 128.4, 128.4, 127.3, 119.5, 118.7, 81.6, 78.7, 77.1, 61.8, 22.2
1H: 12.06 (1H, br), 8.39 (1H, s), 8.11 (1H, d, J=9.0 Hz), 7.87 (1H, d, J=9.0 Hz), 7.49 (2H, d, J=7.0 Hz), 7.41 (3H, m), 5.29 (2H, s), 4.98 (2H, s), 3.92 (2H, s), 1.57 (6H, s)

Compound no. 438 (MP: 194). NMR solvent: DMSO
13C: 155.6, 151.2, 150.8, 139.6, 137.7, 129.3, 126.7, 125.6, 114, 112.5, 112.4, 56.8, 56, 31.4, 29, 25.2, 24.9
1H: 16.04 (1H, br), 8.58 (1H, d, J=2.2 Hz), 8.13 (1H, d, J=1.3 Hz), 8.05 (1H, d, J=1.3 Hz), 8.04 (1H, d d, J=2.2, 8.9 Hz), 7.31 (1H, d, J=8.9 Hz), 3.99 (3H, s), 3.82 (1H, m), 2.94 (3H, s), 1.78 (4H, m), 1.58 (3H, m), 1.30 (2H, q, J=12.5 Hz), 1.11 (1H, q, J=13.0 Hz)

Compound no. 439 (MP: 226-228 (DEC.)). NMR solvent: DMSO
13C: 154.5, 151.9, 150.9, 139.9, 137.6, 129.1, 125.4, 125.2, 116.7, 113.4, 110.8, 56.8, 31.3, 29, 25.2, 24.9
1H: 16.0 (1H, br), 11.14 (1H, br), 8.48 (1H, d, J=2.2 Hz), 8.12 (1H, d, J=1.3 Hz), 7.95 (1H, s br), 7.87 (1H, d d, J=2.2, 8.5 Hz), 7.09 (1H, d, J=8.5 Hz), 3.82 (1H, m), 2.94 (3H, s), 1.78 (4H, m), 1.57 (3H, m), 1.30 (2H, q, J=12.5 Hz), 1.11 (1H, q, J=13.0 Hz)

Compound no. 440 (MP: 104-105). NMR solvent: DMSO
13C: 163.3, 144.4, 144.2, 142.9, 133.2, 127.4, 119.3, 118.1, 81.6, 78.7, 61.8, 22.2
1H: 11.56 (1H, br), 9.27 (1H, s br), 8.39 (1H, s), 8.10 (1H, d, J=9.1 Hz), 7.89 (1H, d, J=9.1 Hz), 5.29 (2H, s), 3.92 (2H, s), 1.57 (6H, s)

Compound no. 441 (MP: 169-170). NMR solvent: CDCl3
13C: 152.2, 151.2, 139.9, 139.6, 138, 137.2, 130.7, 129.1, 128.3, 127.2, 126, 122.3, 113.8, 113.3, 62.8, 56.6, 55.9, 52.5, 31.7, 28.8
1H: 8.24 (1H, d, J=2.2 Hz), 8.0 (1H, d d, J=2.2, 8.8 Hz), 7.91 (1H, d, J=1.3 Hz), 7.49 (1H, d, J=1.3 Hz), 7.37-7.25 (5H, m), 7.13 (1H, d, J=8.8 Hz), 4.03 (1H, m), 4.0 (3H, m), 3.53 (2H, s), 3.03 (3H, s), 3.01 (2H, m), 2.11 (2H, t br, J=11.5 Hz), 1.93 (2H, d q, J=3.5, 12.0 Hz), 1.79 (2H, d br, J=12.0 Hz)

Compound no. 442 (MP: 162). NMR solvent: CDCl3
13C: 151.9 (d, J=246.0 Hz), 151.4, 147.8 (d, J=11.2 Hz), 141.5, 138, 136.8, 129.6 (d, J=4.0 Hz), 129.1, 128.3, 127.2, 117.3 (d, J=7.0 Hz), 116.2 (d, J=18.5 Hz), 113.1, 110.4 (d, J=1.7 Hz), 62.8, 56.2, 55.9, 52.5, 31.7, 28.9
1H: 7.90 (1H, d, J=1.3 Hz), 7.50 (1H, d d, J=1.8, 8.3 Hz), 7.46 (1H, d, J=1.3 Hz), 7.37-7.27 (5H, m), 7.24 (1H, m), 7.09 (1H, d d, J=8.5, 11.0 Hz), 4.03 (1H, m), 3.97 (3H, s), 3.53 (2H, s), 3.03 (3H, s), 3.01 (2H, m), 2.10 (2H, t br, J=11.8 Hz), 1.94 (2H, d q, J=3.0, 12.0 Hz), 1.79 (2H, d br, J=11.5 Hz)

Compound no. 443 (MP: 188-189). NMR solvent: CDCl3
13C: 152.5 (d, J=245.0 Hz), 151.4, 147.1 (d, J=11.0 Hz), 141.1 (d, J=2.5 Hz), 138, 136.9, 129.1, 128.3, 127.2, 126.5 (d, J=7.2 Hz), 120.9 (d, J=3.5 Hz), 113.5 (d, J=2.5 Hz), 113.1 (d, J=19.7 Hz), 112.6, 62.8, 56.3, 55.8, 52.5, 31.6, 28.9
1H: 7.89 (1H, d, J=1.3 Hz), 7.53 (1H, m), 7.50 (1H, d d, J=2.5, 8.5 Hz), 7.40 (1H, d, J=1.3 Hz), 7.37-7.23 (5H, m), 6.99 (1H, t, J=8.4 Hz), 4.02 (1H, m), 3.92 (3H, s), 3.52 (2H, s), 3.02 (3H, s), 3.0 (2H, m), 2.10 (2H, t br, J=11.8 Hz), 1.93 (2H, d q, J=3.5, 12.0 Hz), 1.78 (2H, m)

Compound no. 444 (MP: 168). NMR solvent: DMSO
13C: 157.6, 153.8, 151.1, 140.6, 137.5, 137.1, 128.5, 127.9, 127.8, 126.3, 126.1, 114.9, 113.2, 78.8, 69.2, 55.1, 43, 42.2, 31.7, 28.1 (2 sig.)
1H: 8.09 (1H, d, J=1.3 Hz), 7.88 (1H, d, J=1.3 Hz), 7.77 (2H, m d, J=8.7 Hz), 7.46 (2H, d, J=8.4 Hz), 7.40 (2H, t, J=7.4 Hz), 7.33 (1H, t, J=7.3 Hz), 7.03 (2H, m d, J=8.7 Hz), 5.12 (2H, s), 4.03 (3H, m), 2.92 (3H, s), 2.79 (2H, br), 1.76 (2H, d br, J=11.5 Hz), 1.66 (2H, d q, J=4.3, 12.1 Hz), 1.41 (9H, s)

Compound no. 445 (MP: 170-171). NMR solvent: CDCl3
13C: 160.4, 151.1, 140, 137.1, 131.1, 130.3, 126.5, 116.3, 113, 111.6, 102, 57.6, 56.2, 31.4, 30, 25.4, 25.2
1H: 7.98 (1H, d d, J=2.2, 8.5 Hz), 7.97 (1H, d, J=2.2 Hz), 7.89 (1H, d, J=1.3 Hz), 7.44 (1H, d, J=1.3 Hz), 7.02 (1H, d, J=8.5 Hz), 3.96 (3H, s), 3.95 (1H, m), 3.0 (3H, s), 1.87 (4H, m), 1.71 (1H, m), 1.58 (2H, d q, J=3.5, 12.5 Hz), 1.38 (2H, t q, J=3.0, 13.0 Hz), 1.13 (1H, t q, J=3.5, 13 Hz)

Compound no. 446 (MP: 176-177). NMR solvent: CDCl3
13C: 160.5, 151.2, 140.1, 138, 137.1, 131.1, 130.3, 129.1, 128.3, 127.2, 126.4, 116.3, 112.9, 111.6, 102, 62.8, 56.2, 55.9, 52.5, 31.7, 28.9
1H: 7.98 (1H, d d, J=2.2, 8.5 Hz), 7.97 (1H, d, J=2.2 Hz), 7.90 (1H, d, J=1.3 Hz), 7.44 (1H, d, J=1.3 Hz), 7.37-7.23 (5H, m), 7.01 (1H, d, J=8.5 Hz), 4.01 (1H, m), 3.96 (3H, s), 3.53 (2H, s), 3.03 (3H, s), 3.01 (2H, m), 2.10 (2H, t br, J=12.0 Hz), 1.94 (2H, d q, J=3.5, 12.0 Hz), 1.79 (2H, d br, J=12.0 Hz)

Compound no. 447 (MP: 103-105). NMR solvent: CDCl3
13C: 151.5, 142.3, 141.4, 140.3, 136.8, 128.9, 119.4, 115.4, 112.4, 112, 57.5, 43.6, 31.3, 30, 25.4, 25.2
1H: 7.89 (1H, d, J=1.3 Hz), 7.38 (1H, d, J=1.3 Hz), 7.22 (1H, d, J=2.2 Hz), 7.15 (1H, d d, J=2.2, 8.1 Hz), 7.03 (1H, d, J=8.1 Hz), 4.03 (2H, br), 3.94 (1H, m), 2.99 (3H, s), 2.69 (6H, s), 1.85 (4H, m), 1.70 (1H, d br, J=14.0 Hz), 1.58 (2H, d q, J=3.5, 12.5 Hz), 1.37 (2H, m q, J=13.0 Hz), 1.13 (1H, m q, J=13.0 Hz)

Compound no. 448 (MP: 180-182). NMR solvent: CDCl3
13C: 155.1, 150.2, 137.9, 137.6, 137.5, 136.2, 132.5, 126, 122.7, 115, 62.1, 46.4, 43.3, 14.6
1H: 8.68 (1H, s br), 8.15 (1H, d, J=6.3 Hz), 7.94 (1H, d, J=1.3 Hz), 7.71 (1H, d, J=8.0 Hz), 7.57 (1H, d, J=1.3 Hz), 7.33 (1H, d d, J=6.3, 8.0 Hz), 4.20 (2H, q. J=7.2 Hz), 3.64 (8H, m), 1.30 (3H, t, J=7.2 Hz)

Compound no. 449 (MP: 110-112). NMR solvent: CDCl3
13C: 150.8, 137.6, 137.6, 136.9, 136, 132.7, 125.9, 122.7, 115.3, 50.6, 36.4, 29.3, 19.8, 13.7

1H: 8.67 (1H, t, J=1.5 Hz), 8.14 (1H, d d d, J=1.0, 1.6, 6.4 Hz), 7.94 (1H, d, J=1.3 Hz), 7.71 (1H, t d, J=1.3, 8.1 Hz), 7.58 (1H, d, J=1.3 Hz), 7.32 (1H, d d, J=6.4, 8.1 Hz), 3.46 (2H, t, J=7.6 Hz), 3.13 (3H, s), 1.68 (2H, m), 1.37 (2H, m), 0.97 (3H, t, J=7.4 Hz)

Compound no. 450 (MP: 122-123). NMR solvent: DMSO
13C: 151.1, 145.9, 141.4, 137.6, 137.2, 126.2, 113.2, 112.6, 110.7, 110.6, 55.7, 55.4, 45.4, 31.4, 29.5
1H: 8.03 (1H, s), 7.68 (1H, s), 7.14 (1H, d, J=1.8 Hz), 7.0 (1H, d d, J=1.8, 8.2 Hz), 6.79 (1H, d, J=8.2 Hz), 4.73 (2H, s br), 3.88 (1H, m), 3.76 (3H, s), 3.01 (2H, d br, J=12.0 Hz), 2.93 (3H, s), 2.47 (2H, m), 1.67 (4H, m)

Compound no. 451 (MP: 170-172). NMR solvent: DMSO
13C: 157.6, 150.2, 138.3, 137.3, 131.4, 129.7, 129.7, 129, 126.7, 121.6, 115.7, 113.3, 59.1, 52.3, 50.6, 31.9, 25
1H: 9.62 (2H, m br), 8.67 (1H, s), 8.0 (1H, s), 7.65 (2H, d, J=8.2 Hz), 7.55 (2H, m), 7.49 (3H, m), 6.82 (2H, d, J=8.2 Hz), 4.32 (2H, m), 4.18 (1H, m), 3.45 (2H, m), 3.16 (2H, m), 2.94 (3H, s), 2.19 (2H, q br, J=12.0 Hz), 2.0 (2H, d br, J=12.0 Hz)

Compound no. 452 (MP: 74-76). NMR solvent: CDCl3
13C: 150.3, 137.6, 137.3, 136.9, 136, 132.7, 125.9, 122.8, 115.1, 42.8, 13.2
1H: 8.67 (1H, t br, J=1.3 Hz), 8.14 (1H, d, J=6.4 Hz), 7.93 (1H, d, J=1.3 Hz), 7.72 (1H, d, J=8.0 Hz), 7.57 (1H, d, J=1.3 Hz), 7.32 (1H, d d, J=6.4, 8.0 Hz), 3.49 (4H, q, J=7.2 Hz), 1.31 (6H, t, J=7.2 Hz)

Compound no. 453 (MP: 130-132). NMR solvent: DMSO
13C: 149.6, 147.8, 145.7, 142.8, 138.2, 137.1, 132.2, 129.9, 129, 127.7, 126.3, 124, 115.6, 39.6
1H: 8.87 (1H, d d, J=0.8, 2.2 Hz), 8.43 (1H, d d, J=1.7, 4.9 Hz), 8.04 (1H, t d, J=1.9, 8.0 Hz), 7.81 (1H, d, J=1.3 Hz), 7.61 (1H, d, J=1.3 Hz), 7.45-7.28 (6H, m), 3.43 (3H, s)

Compound no. 454 (MP: 170-172). NMR solvent: DMSO
13C: 151.2 (d, J=240.0 Hz), 151.1, 144.0 (d, J=12.2 Hz), 140.0 (d, J=2.5 Hz), 137.6, 131.4, 129.7 (2 sig.), 128.9, 125.2 (d, J=7.0 Hz), 121.1 (d, J=2.5 Hz), 117.9 (d, J=3.0 Hz), 113.5, 112.5 (d, J=20.0 Hz), 59.0, 52.1, 50.6, 31.7, 25.1
1H: 9.91 (1H, s), 9.57 (Hi, m), 8.10 (1H, s), 7.90 (1H, s), 7.58 (1H, m), 7.55 (2H, m), 7.48 (4H, m), 6.96 (1H, t, J=8.8 Hz), 4.31 (2H, s br), 4.16 (1H, m), 3.45 (2H, m), 3.15 (2H, m), 2.92 (3H, s), 2.17 (2H, q, J=12.5 Hz), 1.98 (21-1, d br, J=12.5 Hz)

Compound no. 455 (MP: 171-173). NMR solvent: CDCl3
13C: 145.8, 137.7, 137.2, 136.8, 136.1, 132.6, 126, 122.7, 114.3, 81, 80.3, 62.1, 22.8
1H: 8.69 (1H, t br, J=1.5 Hz), 8.14 (1H, d d d, J=1.0, 1.5, 6.4 Hz), 7.96 (1H, d, J=1.3 Hz), 7.70 (1H, t d, J=1.2, 8.2 Hz), 7.63 (1H, d, J=1.3 Hz), 7.31 (1H, d d, J=6.4, 8.2 Hz), 5.12 (2H, s), 3.90 (2H, d), 1.62 (6H, s)

Compound no. 456 (MP: 181-182). NMR solvent: DMSO
13C: 149.4, 142.6, 138.3, 137.1, 135.2, 134.6, 132.4, 129.9, 127.7, 126.6, 126.2, 121.1, 117.1, 39.6
1H: 8.50 (1H, t br, J=1.5 Hz), 8.08 (1H, d d d, J=1.0, 1.8, 6.4 Hz), 7.96 (1H, d, J=1.3 Hz), 7.61 (1H, d, J=1.3 Hz), 7.60 (1H, m), 7.38 (1H, m), 7.50-7.29 (5H, m), 3.43 (3H, s)

Compound no. 457 (MP: 179 (dec.)). NMR solvent: DMSO
13C: 151.4, 150.6, 137.9, 137.7, 137, 131.7, 131.4, 129.7, 129.1, 128.9, 123.9, 121, 119.6, 114.7, 59, 52.2, 50.5, 31.9, 25
1H: 11.13 (1H, s br), 9.59 (1H, s), 8.39 (1H, s), 8.33 (1H, d, J=2.0 Hz), 8.14 (1H, s), 8.02 (1H, d d, J=2.0, 8.6 Hz), 7.55 (2H, m), 7.49 (3H, m), 7.19 (1H, d, J=8.6 Hz), 4.32 (2H, d, J=4.9 Hz), 4.18 (1H, m), 3.46 (2H, d br, J=11.5 Hz), 3.16 (2H, m), 2.93 (3H, s), 2.18 (2H, q br, J=12.5 Hz), 1.99 (2H, d br, J=12.3 Hz)

Compound no. 458 (MP: 163-164). NMR solvent: DMSO
13C: 148.1, 147.7, 146.1, 138.3, 136.8, 131.9, 129.1, 123.9, 113.6, 50, 32.2, 25.1, 24.8
1H: 9.02 (1H, d d, J=0.8, 2.2 Hz), 8.46 (1H, d d, J=1.7, 4.7 Hz), 8.38 (1H, d, J=1.3 Hz), 8.33 (1H, d br, J=7.3 Hz), 8.30 (1H, d, J=1.3 Hz), 8.15 (1H, t d, J=1.9, 7.9 Hz), 7.42 (1H, d d d, J=0.8, 4.7, 7.9 Hz), 3.63 (1H, m), 1.90 (2H, m), 1.75 (2H, m), 1.61 (1H, d br, J=12.7 Hz), 1.32 (4H, m), 1.14 (1H, m)

Compound no. 459 (MP: 199-201). NMR solvent: CDCl3
13C: 150.8, 137.9, 137.6, 137.6, 136.9, 136, 132.7, 129.1, 128.3, 127.2, 125.9, 122.6, 115.3, 62.8, 56, 52.4, 31.7, 28.9
1H: 8.66 (1H, s br), 8.13 (1H, d, J=6.3 Hz), 7.93 (1H, s br), 7.70 (1H, d, J=8.1 Hz), 7.58 (1H, s br), 7.30 (1H, d, J=6.6 Hz), 3.99 (1H, m), 3.52 (2H, s), 3.02 (3H, s), 3.01 (2H, m), 2.10 (2H, t br, J=10.9 Hz), 1.93 (2H, m), 1.78 (2H, d br, J=10.9 Hz)

Compound no. 460 (MP: 148). NMR solvent: CDCl3
13C: 165.8, 147.2, 145.6, 132.6, 131.5, 126.5, 119.6, 116.6, 82.4, 79.6, 62.4, 61.7, 23, 14.3
1H: 8.91 (1H, d d, J=0.8, 1.4 Hz), 8.17 (1H, d d, J=1.4, 8.7 Hz), 8.12 (1H, d d, J=0.8, 8.7 Hz), 5.53 (2H, s), 4.45 (2H, q, J=7.2 Hz), 3.91 (2H, s), 1.70 (6H, s), 1.44 (3H, t, J=7.2 Hz)

Compound no. 461 (MP: 186). NMR solvent: MeOD
13C: 149.5, 138.8, 138.8, 137.7, 136.9, 135, 128.4, 127.1, 116.7, 52.2, 33.8, 26.7, 26.5
1H: 8.75 (1H, br), 8.36 (1H, d, J=1.2 Hz), 8.25 (1H, m), 8.24 (1H, m), 7.98 (1H, d, J=8.2 Hz), 7.58 (1H, d d, J=6.6, 8.2 Hz), 3.73 (1H, m), 2.02 (2H, m), 1.87 (2H, m), 1.70 (1H, d br, J=13.5 Hz), 1.45 (2H, m), 1.38 (2H, m), 1.24 (1H, m)

Compound no. 462 (MP: 125 (dec.)). NMR solvent: DMSO
13C: 167.1, 145.8, 145.4, 135.3, 132.2, 124.9, 119.4, 113.9, 81.7, 78.7, 61.6, 22.5
1H: 8.63 (1H, s), 8.34 (1H, s br), 8.25 (1H, d, J=8.5 Hz), 8.01 (1H, d d, J=1.5, 8.7 Hz), 7.65 (1H, s br), 5.43 (2H, s), 3.91 (2H, s), 1.60 (6H, s)

Compound no. 463 (MP: 181-183). NMR solvent: CDCl3
13C: 151.2, 148.6, 146.7, 139.4, 137.3, 132.5, 128.9, 123.6, 113.9, 66.9, 54.5, 31.8, 29.5
1H: 9.00 (1H, d d, J=1.0, 2.2 Hz), 8.53 (1H, d d, J=1.7, 4.8 Hz), 8.11 (1H, d d d, J=1.8, 2.3, 7.9 Hz), 7.96 (1H, d, J=1.3 Hz), 7.59 (1H, d, J=1.3 Hz), 7.34 (1H, d d d, J=1.0, 4.8, 7.9 Hz), 4.29 (1H, m), 4.09 (2H, d d, J=4.6, 11.5 Hz), 3.50 (2H, d t, J=2.2, 12.0 Hz), 3.04 (3H, s), 1.95 (2H, m), 1.78 (2H, m)

Compound no. 464 (MP: 143-144). NMR solvent: CDCl3
13C: 150.6, 148.5, 146.7, 139.3, 136.9, 132.4, 129.1, 123.6, 113.8, 59, 39.5, 31.4, 25.6, 25.1, 14.9
1H: 9.01 (1H, d, J=2.3 Hz), 8.53 (1H, d d, J=1.7, 4.8 Hz), 8.12 (1H, t d, J=2.0, 8.0 Hz), 7.91 (1H, d, J=1.3 Hz), 7.56 (1H, d, J=1.3 Hz), 7.34 (1H, d d d, J=0.8, 4.8, 8.0 Hz), 3.75 (1H, m), 3.44 (2H, q, J=7.0 Hz), 1.84 (4H, m), 1.66 (3H, m), 1.30 (2H, m, J=13.0 Hz), 1.26 (3H, t, J=7.0 Hz), 1.13 (1H, m, J=13.0 Hz)

Compound no. 465 (MP: 184-185). NMR solvent: MeOD
13C: 151.9, 147.7, 147.1, 140.6, 138.4, 132.6, 131.6, 130.6, 130.4, 123, 118.8, 116.9, 114.7, 114.1, 61.8, 54.7, 52.8, 33.5, 26.8
1H: 8.64 (1H, s br), 7.82 (1H, s br), 7.58 (2H, m), 7.52 (3H, m), 7.18 (1H, d, J=2.0 Hz), 7.11 (1H, d d, J=2.0, 8.3 Hz), 6.83 (1H, d, J=8.3 Hz), 4.36 (2H, s), 4.28 (1H, m), 3.63 (2H, d br, J=12.5 Hz), 3.24 (2H, m, J=12.5 Hz), 3.06 (3H, s), 2.30 (2H, m, J=13.0 Hz), 2.17 (2H, d br, J=13.0 Hz)

Compound no. 466 (MP: 221-222). NMR solvent: DMSO
13C: 151.7 (d, J=242.5 Hz), 151.0, 146.2 (d, J=10.8 Hz), 139.6 (d, J=2.5 Hz), 137.7, 126.7 (d, J=7.5 Hz), 120.9 (d, J=3.5 Hz), 114.1 (2 sig.), 112.3 (d, J=19.7 Hz), 66.3, 56.0, 54.2, 31.6, 29.1
1H: 8.11 (1H, d, J=1.3 Hz), 7.98 (1H, d, J=1.3 Hz), 7.66 (1H, m), 7.63 (1H, m), 7.19 (1H, t, J=8.7 Hz), 4.09 (1H, m), 3.93 (2H, d d, J=4.5, 12.3 Hz), 3.85 (3H, s), 3.38 (2H, m), 2.94 (3H, s), 1.85 (2H, d q, J=4.5, 12.3 Hz), 1.69 (2H, d br, J=12.3 Hz)

Compound no. 467 (MP: 177). NMR solvent: CDCl3
13C: 151.5, 142.3, 140, 137, 132.9, 128.7, 128.6, 128.4, 127.6, 126.1, 125.1, 113.1, 60.2, 55.7, 52.6, 33.8, 31.6, 28.9
1H: 7.93 (1H, d, J=1.3 Hz), 7.81 (2H, m d, J=8.2 Hz), 7.51 (1H, d, J=1.3 Hz), 7.41 (2H, t, J=7.9 Hz), 7.30 (3H, t, J=7.4 Hz), 7.22 (1H, m), 7.21 (2H, d, J=7.4 Hz), 4.06 (1H, m), 3.13 (2H, d br, J=11.8 Hz), 3.04 (3H, s), 2.82 (2H, m), 2.63 (2H, m), 2.17 (2H, d t, J=2.4, 12.0 Hz), 1.96 (2H, d q, J=3.6, 12.1 Hz), 1.85 (2H, d br, J=12.0 Hz)

Compound no. 468 (MP: 186-187). NMR solvent: DMSO
13C: 151.2, 145.9, 141.4, 137.5, 137.2, 126.2, 113.2, 112.6, 110.7, 110.6, 66.3, 55.3, 54.1, 31.6, 29.1
1H: 8.05 (1H, d, J=1.3 Hz), 7.69 (1H, d, J=1.3 Hz), 7.15 (1H, d, J=2.2 Hz), 7.0 (1H, d d, J=2.2, 8.4 Hz), 6.79 (1H, d, J=8.4 Hz), 4.73 (2H, s), 4.09 (1H, m), 3.93 (2H, d d, J=4.3, 11.3 Hz), 3.77 (3H, s), 3.38 (2H, d t, J=1.5, 12.0 Hz), 2.94 (3H, s), 1.84 (2H, d q, J=4.5, 12.3 Hz), 1.69 (2H, d d, J=2.8, 12.3 Hz)

Compound no. 469 (MP: 111 (dec.)). NMR solvent: DMSO
13C: 156.7, 153.8, 151.1, 141, 137.3, 126.1, 124.4, 115.3, 112.5, 78.8, 55, 43, 42.2, 31.7, 28.1, 28.1
1H: 9.46 (1H, s), 8.06 (1H, s), 7.78 (1H, s), 7.64 (2H, d, J=8.7 Hz), 6.77 (2H, d, J=8.7 Hz), 4.03 (3H, m), 2.91 (3H, s), 2.79 (2H, s br), 1.75 (2H, d br, J=12.0 Hz), 1.66 (2H, d q, J=4.1, 12.2 Hz), 1.41 (9H, s)

Compound no. 470 (MP: 217 (dec.)). NMR solvent: CDCl3
13C: 150.8, 137.7, 137.6, 137, 136.1, 132.7, 126, 122.8, 115.3, 66.9, 54.6, 31.9, 29.5
1H: 8.68 (1H, t, J=1.3 Hz), 8.15 (1H, d d d, J=1.0, 1.6, 6.4 Hz), 7.95 (1H, d, J=1.3 Hz), 7.73 (1H, t d, J=1.2, 8.1 Hz), 7.60 (1H, d, J=1.3 Hz), 7.33 (1H, d d, J=6.4, 8.1 Hz), 4.28 (1H, m), 4.10 (2H, d d, J=4.5, 11.6 Hz), 3.51 (2H, d t, J=1.8, 12.0 Hz), 3.04 (3H, s), 1.96 (2H, d q, J=4.4, 12.2 Hz), 1.79 (2H, m)

Compound no. 471 (MP: 205-207). NMR solvent: CDCl3
13C: 150.1, 137.6, 137.2, 136.9, 136, 132.8, 125.9, 122.8, 115.1, 59.1, 39.6, 31.3, 25.5, 25, 14.9
1H: 8.67 (1H, t, J=1.6 Hz), 8.14 (1H, d d d, J=1.0, 1.6, 6.4 Hz), 7.89 (1H, d, J=1.3 Hz), 7.72 (1H, t d, J=1.3, 8.1 Hz), 7.55 (1H, d, J=1.3 Hz), 7.31 (1H, d d, J=6.4, 8.1 Hz), 3.69 (1H, m), 3.42 (2H, q, J=7.0 Hz), 1.84 (4H, m), 1.68 (3H, m), 1.27 (2H, m, J=13.0 Hz), 1.25 (3H, t, J=7.0 Hz), 1.12 (1H, m, J=12.8 Hz)

Compound no. 472 (MP: 153-154). NMR solvent: CDCl3
13C: 162.3 (d, J=246.7 Hz), 151.4, 141.5, 136.9, 129.1 (d, J=3.6 Hz), 126.8 (d, J=8.5 Hz), 115.6 (d, J=21.7 Hz), 112.8, 67, 54.4, 31.8, 29.5
1H: 7.91 (1H, d, J=1.3 Hz), 7.76 (2H, m, J=5.5, 8.9 Hz), 7.46 (1H, d, J=1.3 Hz), 7.10 (2H, m t, J=8.8 Hz), 4.28 (1H, m), 4.09 (2H, d d, J=4.6, 11.6 Hz), 3.50 (2H, d t, J=1.7, 11.9 Hz), 3.04 (3H, s), 1.95 (2H, d q, J=4.6, 12.3 Hz), 1.77 (2H, d br, J=11.0 Hz)

Compound no. 473 (MP: 146-147). NMR solvent: CDCl3
13C: 151.2, 150.6 (d d, J=13.1, 247.3 Hz), 149.8 (d d, J=12.8, 248.2 Hz), 140.5, 137.0, 130.1 (d d, J=4.0, 6.5 Hz), 121.1 (d d, J=3.8, 6.3 Hz), 117.5 (d, J=17.6 Hz), 114.2 (d, J=18.8 Hz), 113.4, 67.0, 54.5, 31.8, 29.5
1H: 7.91 (1H, d, J=1.1 Hz), 7.61 (1H, d d d, J=2.1, 7.8, 11.6 Hz), 7.50 (1H, s), 7.46 (1H, s), 7.18 (1H, d t, J=8.5, 10.0 Hz), 4.28 (1H, m), 4.09 (2H, d d, J=4.5, 11.5 Hz), 3.50 (2H, d t, J=1.3, 12.0 Hz), 3.04 (3H, s), 1.95 (2H, d q, J=4.4, 12.2 Hz), 1.77 (2H, d br, J=13.5 Hz)

Compound no. 474 (MP: 148-149). NMR solvent: CDCl3
13C: 151.4, 150.6 (t, J=2.7 Hz), 141.3, 137, 130.3, 126.6, 119.7, 115.9 (t, J=260.0 Hz), 113.1, 67, 54.4, 31.8, 29.5
1H: 7.92 (1H, d, J=1.3 Hz), 7.79 (2H, m d, J=8.8 Hz), 7.48 (1H, d, J=1.3 Hz), 7.16 (2H, m d, J=8.8 Hz), 6.54 (1H, t, J=74.0 Hz), 4.29 (1H, m), 4.09 (2H, d d, J=4.5, 11.5 Hz), 3.50 (2H, d t, J=2.0, 12.0 Hz), 3.04 (3H, s), 1.95 (2H, d q, J=4.5, 12.3 Hz), 1.78 (2H, m)

Compound no. 475 (MP: 183-184). NMR solvent: CDCl3
13C: 159.2, 151.6, 142.2, 136.8, 126.4, 125.6, 114.1, 112, 67, 55.3, 54.3, 31.8, 29.5
1H: 7.91 (1H, d, J=1.3 Hz), 7.72 (2H, m d, J=8.9 Hz), 7.40 (1H, d, J=1.3 Hz), 6.94 (2H, m d, J=8.9 Hz), 4.28 (1H, m), 4.08 (2H, d d, J=4.4, 11.5 Hz), 3.84 (3H, s), 3.50 (2H, d t, J=1.9, 11.8 Hz), 3.03 (3H, s), 1.94 (2H, d q, J=4.5, 12.2 Hz), 1.76 (2H, m d, J=12.3 Hz)

Compound no. 476 (MP: 130). NMR solvent: CDCl3
13C: 151.5, 149.1, 148.6, 142.2, 136.7, 125.9, 117.4, 112.3, 111.2, 108.4, 67, 55.9, 55.9, 54.4, 31.8, 29.5
1H: 7.91 (1H, d, J=1.3 Hz), 7.43 (1H, d, J=1.3 Hz), 7.39 (1H, d, J=2.0 Hz), 7.30 (1H, d d, J=2.0, 8.3 Hz), 6.90 (1H, d, J=8.3 Hz), 4.29 (1H, m), 4.09 (2H, d d, J=4.3, 11.6 Hz), 3.96 (3H, s), 3.92 (3H, s), 3.50 (2H, d t, J=1.7, 12.0 Hz), 3.04 (3H, s), 1.95 (2H, d q, J=4.5, 12.4 Hz), 1.77 (2H, d br, J=12.3 Hz)

Compound no. 477 (MP: 174-176). NMR solvent: CDCl3
13C: 151.3, 141.3, 137, 133.2, 131.4, 128.9, 126.4, 113.3, 67, 54.4, 31.8, 29.5
1H: 7.92 (1H, s), 7.73 (2H, d, J=8.5 Hz), 7.50 (1H, s), 7.37 (2H, d, J=8.5 Hz), 4.28 (1H, m), 4.09 (2H, d d, J=4.5, 11.5 Hz), 3.50 (2H, t. J=11.5 Hz), 3.03 (3H, s), 1.95 (2H, d q, J=4.5, 12.2 Hz), 1.77 (2H, d br, J=12.5 Hz)

Compound no. 478 (MP: 222-225). NMR solvent: CDCl3
13C: 166.1, 146.3, 145.9, 137.5, 132.5, 125.2, 120, 112.4, 82.5, 79.5, 62.4, 52.1, 28.8, 23
1H: 8.46 (1H, d d, J=0.8, 1.5 Hz), 8.10 (1H, d d, J=0.8, 8.7 Hz), 7.91 (1H, d d, J=1.5, 8.7 Hz), 6.12 (1H, s), 5.53 (2H, s), 3.91 (2H, s), 1.69 (6H, s), 1.51 (9H, s)

Compound no. 479 (MP: 193-195). NMR solvent: CDCl3
13C: 170.3, 145.7, 145.3, 137.7, 132.4, 124.7, 120.2, 113.2, 82.4, 79.6, 62.3, 39.6, 35.4, 22.9
1H: 8.30 (1H, s br), 8.14 (1H, d, J=8.6 Hz), 7.53 (1H, d d, J=1.4, 8.6 Hz), 5.53 (2H, s), 3.91 (2H, s), 3.16 (3H, s), 3.0 (3H, s), 1.68 (6H, s)

Compound no. 480 (MP: 233-234). NMR solvent: DMSO
13C: 167, 149.8, 144.5, 134, 131.6, 128.8, 119, 113.1, 59, 31.9, 28.4, 24
1H: 8.71 (1H, s), 8.25 (Hi, s br), 8.18 (1H, d d, J=1.4, 8.3 Hz), 7.94 (1H, d, J=8.3 Hz), 7.61 (1H, s br), 4.57 (1H, br), 3.07 (3H, s), 1.93 (2H, m), 1.78 (2H, m), 1.72 (2H, m), 1.54 (2H, m)

Compound no. 481 (MP: 171-172). NMR solvent: CDCl3
13C: 165, 145, 144.6, 143.5, 137.6, 135.9, 129.1, 127.5, 124.9, 120.4, 119.9, 118.7, 82.4, 79.6, 62.7, 22.6
1H: 8.39 (1H, s), 8.21 (1H, s br), 7.95 (2H, m), 7.69 (2H, d, J=7.9 Hz), 7.39 (2H, t, J=7.9 Hz), 7.19 (1H, t, J=7.3 Hz), 5.40 (2H, s), 3.92 (2H, s), 1.69 (6H, s)

Compound no. 482 (MP: 185-186). NMR solvent: DMSO
13C: 166.4, 156.3, 150.9, 140, 137.6, 128.6, 127.1, 126, 123, 113.6, 112.3, 56.7, 56, 31.3, 29, 25.2, 24.9
1H: 8.25 (1H, d, J=2.3 Hz), 8.09 (1H, s br), 7.95 (1H, s br), 7.92 (1H, d d, J=2.3, 8.7 Hz), 7.67 (1H, s br), 7.56 (1H, s br), 7.16 (1H, d, J=8.7 Hz), 3.90 (3H, s), 3.81 (1H, m), 2.93 (3H, s), 1.78 (4H, m), 1.60 (1H, m), 1.56 (2H, m), 1.30 (2H, m, J=13.0 Hz), 1.11 (1H, m)

Compound no. 483 (MP: 117). NMR solvent: CDCl3
13C: 150.6, 145.3, 133.2, 129.3, 125.2, 119.8, 113.6, 67.1, 54.6, 29.9 (2 sig.)

1H: 8.10 (1H, m d, J=8.4 Hz), 7.99 (1H, m d, J=8.4 Hz), 7.61 (1H, m, J=1.0, 7.0, 8.2 Hz), 7.47 (1H, m, J=1.0, 7.1, 8.2 Hz), 4.54 (1H, m), 4.10 (2H, d br, J=11.5 Hz), 3.51 (2H, s br), 3.21 (3H, s), 2.03 (2H, d q, J=4.6, 12.3 Hz), 1.91 (2H, d br, J=11.5 Hz)

Compound no. 484 (MP: 119-120). NMR solvent: CDCl3
13C: 151.9 (d, J=246.5 Hz), 151.4, 147.8 (d, J=11.2 Hz), 141.5, 136.8, 129.5 (d, J=3.8 Hz), 117.3 (d, J=6.9 Hz), 116.2 (d, J=18.7 Hz), 113, 110.3 (d, J=2.0 Hz), 67, 56.2, 54.4, 31.8, 29.5

1H: 7.92 (1H, d, J=1.3 Hz), 7.50 (1H, d d, J=2.0, 8.3 Hz), 7.47 (1H, d, J=1.3 Hz), 7.24 (1H, m), 7.09 (1H, d d, J=8.3, 11.0 Hz), 4.29 (1H, m), 4.10 (2H, d d, J=4.5, 11.5 Hz), 3.96 (3H, s), 3.50 (2H, d t, J=1.8, 12.0 Hz), 3.04 (3H, s), 1.95 (2H, d q, J=4.6, 12.4 Hz), 1.78 (2H, d br, J=12.5 Hz)

Compound no. 485 (MP: 181). NMR solvent: DMSO
13C: 153.2, 148.8, 137.1, 135, 126.4, 124.2, 123.2, 121.1, 115, 112.4, 57.2, 56.1, 40.7, 31.5, 28.8, 25, 24.8

1H: 9.20 (1H, s br), 9.10 (1H, s), 8.31 (1H, s), 7.77 (1H, d d, J=2.3, 8.2 Hz), 7.76 (1H, s), 7.20 (1H, d, J=8.2 Hz), 3.87 (3H, s), 3.84 (1H, br), 3.03 (3H, s), 2.96 (3H, s), 1.79 (4H, m), 1.61 (1H, m), 1.57 (2H, m), 1.32 (2H, m), 1.12 (1H, m)

Compound no. 486 (MP: 200-203 (dec.)). NMR solvent: CDCl3
13C: 164.7, 145.6, 145, 137.7, 134.5, 132.8, 129.2, 128.6, 124.9, 120.4, 118.8, 115, 82.4, 79.5, 62.5, 23

1H: 8.61 (1H, s), 8.30 (1H, d, J=8.6 Hz), 8.19 (1H, s br), 8.15 (1H, d d, J=1.3, 8.6 Hz), 7.70 (2H, d, J=8.0 Hz), 7.41 (2H, t, J=8.3 Hz), 7.20 (1H, t, J=7.5 Hz), 5.53 (2H, s), 3.92 (2H, s), 1.70 (6H, s)

Compound no. 487 (MP: 175-177). NMR solvent: CDCl3
13C: 165.7, 145.7, 145.1, 134.2, 133.8, 128.4, 118.3, 114.6, 82.5, 79.5, 62.4, 52, 28.8, 23

1H: 8.42 (1H, d d, J=0.5, 1.6 Hz), 8.25 (1H, d d, J=0.5, 8.7 Hz), 8.03 (1H, d d, J=1.6, 8.7 Hz), 6.09 (1H, s br), 5.54 (2H, s), 3.91 (2H, s), 1.69 (6H, s), 1.53 (9H, s)

Compound no. 488 (MP: 175). NMR solvent: CDCl3
13C: 151.2, 148.6, 146.7, 140, 139.3, 137.3, 132.4, 128.9, 128.6, 128.4, 126.1, 123.6, 113.9, 60.2, 55.8, 52.6, 33.8, 31.7, 28.8

1H: 9.01 (1H, d d, J=0.7, 2.2 Hz), 8.53 (1H, d d, J=1.6, 4.8 Hz), 8.12 (1H, d d d, J=1.7, 2.6, 8.0 Hz), 7.96 (1H, d, J=1.3 Hz), 7.59 (1H, d, J=1.3 Hz), 7.34 (1H, d d d, J=1.0, 4.8, 8.0 Hz), 7.30 (2H, m, J=7.5 Hz), 7.21 (1H, m), 7.20 (2H, m, J=7.1 Hz), 4.05 (1H, m), 3.14 (2H, d br, J=12.0 Hz), 3.05 (3H, s), 2.81 (2H, m), 2.63 (2H, m), 2.17 (2H, d t, J=2.0, 11.6 Hz), 1.97 (2H, d q, J=3.7, 12.0 Hz), 1.85 (2H, d br, J=12.0 Hz)

Compound no. 489 (MP: 197). NMR solvent: DMSO
13C: 164.3, 145.4, 144.5, 133.6, 132.4, 129, 118.7, 113.9, 81.7, 78.7, 61.7, 48.7, 32.5, 25.3, 25, 22.5

1H: 8.68 (1H, s), 8.49 (1H, d, J=8.0 Hz), 8.18 (1H, d d, J=1.4, 8.7 Hz), 8.15 (1H, d, J=8.7 Hz), 5.44 (2H, s), 3.90 (2H, s), 3.80 (1H, m), 1.86 (2H, m), 1.75 (2H, m), 1.61 (1H, m), 1.58 (6H, s), 1.35 (2H, m), 1.30 (2H, m), 1.15 (1H, m)

Compound no. 490 (MP: 194-196). NMR solvent: DMSO
13C: 164.6, 144.4, 144.2, 143, 135.2, 128, 118.9, 118.4, 81.7, 78.7, 61.8, 48.7, 32.4, 25.3, 25, 22.2

1H: 8.52 (1H, s), 8.50 (1H, m), 8.07 (1H, d, J=8.0 Hz), 7.97 (1H, d d, J=1.4, 9.0 Hz), 5.31 (2H, s), 3.92 (2H, s), 3.79 (1H, m), 1.85 (2H, m), 1.75 (2H, m), 1.62 (1H, m), 1.58 (6H, s), 1.34 (2H, m), 1.31 (2H, m), 1.15 (1H, m)

Compound no. 491 (MP: 254-256). NMR solvent: DMSO
13C: 167, 149.5, 144.5, 134.1, 131.6, 128.8, 119, 113.1, 58.4, 56.8, 32.3, 30.1, 28.9, 25.1, 24.8

1H: 8.71 (1H, s), 8.24 (1H, s), 8.18 (1H, d, J=8.8 Hz), 7.93 (1H, d, J=8.8 Hz), 7.60 (1H, s), 4.0 (1H, m br), 3.06 (3H, s), 1.97-1.00 (10H, m)

Compound no. 492 (MP: 223-224). NMR solvent: DMSO
13C: 150, 144.7, 132.6, 131.4, 129.9, 129.5, 129.5, 128.8, 125.5, 119.6, 113.5, 58.7, 52.8, 50.3, 32.5, 25.4

1H: 11.21 (1H, s br), 8.19 (1H, m, J=8.3 Hz), 7.91 (1H, m d, J=8.3 Hz), 7.70 (1H, m, J=1.0, 7.0 Hz), 7.63 (2H, m), 7.54 (1H, m, J=1.0, 7.0 Hz), 7.45 (3H, m), 4.39 (1H, m br), 4.26 (2H, m br), 3.40 (2H, m), 3.06 (3H, s), 3.05 (2H, m br), 2.47 (2H, m), 2.05 (2H, d br, J=12.0 Hz)

Compound no. 493 (MP: 140). NMR solvent: CDCl3
13C: 150.8, 150.2, 140.4, 139.6, 137.3, 119.4, 115.7, 57.7, 31.4, 30, 25.4, 25.2

1H: 8.62 (2H, m), 7.93 (1H, d, J=1.3 Hz), 7.68 (1H, d, J=1.3 Hz), 7.67 (2H, m), 3.94 (1H, m), 3.0 (3H, s), 1.86 (4H, m), 1.71 (1H, d br, J=13.0 Hz), 1.59 (2H, d q, J=3.4, 12.3 Hz), 1.38 (2H, m q, J=13.0 Hz), 1.13 (1H, t q, J=3.4, 13.0 Hz)

Compound no. 494 (MP: 193-194). NMR solvent: CDCl3
13C: 154.4, 151.2, 139.9, 137.2, 134.5, 133.7, 126, 121, 120.3, 113.4, 67, 54.5, 31.9, 29.5

1H: 10.61 (1H, s), 8.51 (1H, d, J=2.2 Hz), 8.02 (1H, d d, J=2.2, 8.7 Hz), 7.93 (1H, d, J=1.3 Hz), 7.52 (1H, d, J=1.3 Hz), 7.21 (1H, d, J=8.7 Hz), 4.29 (1H, m), 4.10 (2H, d d, J=4.5, 11.5 Hz), 3.51 (2H, d t, J=1.8, 12.0 Hz), 3.05 (3H, s), 1.95 (2H, d q, J=4.6, 12.4 Hz), 1.78 (2H, d br, J=12.5 Hz)

Compound no. 495 (MP: 185-187). NMR solvent: DMSO
13C: 151.1 (d, J=241.0 Hz), 149.2, 145.5 (d, J=12.2 Hz), 137.2, 135.3, 122.0 (d, J=3.0 Hz), 120.5, 118.2 (d, J=3.5 Hz), 114.8, 113.4 (d, J=20.5 Hz), 66.2, 54.5, 31.7, 28.9

1H: 10.36 (1H, s br), 9.08 (1H, s), 8.23 (1H, s), 7.74 (1H, d d, J=2.0, 12.4 Hz), 7.56 (1H, d d, J=1.5, 8.3 Hz), 7.07 (1H, t, J=8.7 Hz), 4.11 (1H, m), 3.94 (2H, d d, J=4.0, 11.5 Hz), 3.39 (2H, t, J=11.5 Hz), 2.97 (3H, s), 1.86 (2H, d q, J=4.2, 12.2 Hz), 1.70 (2H, d br, J=12.0 Hz)

Compound no. 496 (MP: 116-118). NMR solvent: CDCl3
13C: 166.2, 145.6, 145.1, 137.8, 134.4, 132.2, 128.9, 128.4, 128, 127.8, 118.8, 114.8, 82.5, 79.5, 62.4, 44.5, 23

1H: 8.52 (1H, s), 8.28 (1H, d, J=8.8 Hz), 8.09 (1H, d d, J=1.5, 8.7 Hz), 7.40-7.30 (5H, m), 6.56 (1H, t, J=5.3 Hz), 5.54 (2H, s), 4.72 (2H, d, J=5.3 Hz), 3.91 (2H, s), 1.69 (6H, s)

Compound no. 497 (MP: 173 (dec.)). NMR solvent: CDCl3
13C: 150.6, 139.3, 138.2, 137.5, 131.5, 121.8, 115.4, 57.7, 31.4, 29.9, 25.4, 25.1

1H: 8.22 (2H, d, J=7.0 Hz), 7.90 (1H, s), 7.68 (2H, d, J=7.0 Hz), 7.61 (1H, s), 3.93 (1H, m), 3.0 (3H, s), 1.86 (4H, m), 1.71 (1H, d, J=13.0 Hz), 1.59 (2H, d q, J=2.8, 12.2 Hz), 1.38 (2H, q, J=13.0 Hz), 1.13 (1H, q, J=13.0 Hz)

Compound no. 498 (MP: 109-110). NMR solvent: CDCl3
13C: 159.6, 151.1, 141.7, 136.5, 133.9, 129.4, 117.2, 113.3, 113, 109.8, 60, 55.4, 54.9, 52.3, 31.2, 28.4, 19.8, 11.6

1H: 7.92 (1H, d, J=1.3 Hz), 7.49 (1H, d, J=1.3 Hz), 7.39 (1H, d d, J=1.4, 2.6 Hz), 7.35 (1H, d t, J=1.4, 7.7 Hz), 7.31 (1H, t, J=7.7 Hz), 6.85 (1H, d d d, J=1.4, 2.6, 8.0 Hz), 4.02 (1H, m), 3.87 (3H, s), 3.06 (2H, d br, J=11.7 Hz), 3.02 (3H, s), 2.32 (2H, m), 2.06 (2H, t br, J=11.5 Hz), 1.95 (2H, d q, J=3.4, 12.2 Hz), 1.80 (2H, d br, J=12.0 Hz), 1.52 (2H, m), 0.91 (3H, t, J=7.4 Hz)

Compound no. 499 (MP: 170-171). NMR solvent: DMSO
13C: 171.2, 160.9, 149, 137.2, 135.4, 130.8, 125.9, 119.6, 118, 115.2, 114.7, 57.2, 31.6, 28.8, 25, 24.8

1H: 12.99 (1H, s br), 9.11 (1H, s), 8.42 (1H, s), 8.40 (1H, d, J=2.2 Hz), 8.19 (1H, s), 8.06 (1H, s), 7.87 (1H, d d, J=2.0, 8.6 Hz), 7.02 (1H, d, J=8.5 Hz), 3.86 (1H, m), 2.98 (3H, s), 1.79 (4H, m), 1.60 (3H, m), 1.33 (2H, q, J=12.8 Hz), 1.12 (1H, q, J=13.0 Hz)

Compound no. 500 (MP: 191-193 (dec.)). NMR solvent: DMSO

13C: 151.0, 150.3 (d, J=240.0 Hz), 144.9 (d, J=12.5 Hz), 140.0, 137.6, 130.1, 116.2 (d, J=18.0 Hz), 115.9 (d, J=6.3 Hz), 114.2 (d, J=1.5 Hz), 114.1, 66.3, 54.2, 31.6, 29.1

1H: 9.89 (1H, s), 8.10 (1H, s), 7.90 (1H, s), 7.46 (1H, d, J=8.5 Hz), 7.24 (1H, m), 7.13 (1H, m, J=9.2 Hz), 4.08 (1H, m), 3.93 (2H, d br, J=10.0 Hz), 3.36 (2H, m), 2.94 (3H, s), 1.84 (2H, d q, J=12.0 Hz), 1.69 (2H, d br, J=11.0 Hz)

Compound no. 501 (MP: 138-140). NMR solvent: DMSO

13C: 158.5, 151, 140.6, 137.4, 126.1, 126, 114, 113.1, 55.1, 55.1, 44.9, 31.5, 28.7

1H: 8.08 (1H, s), 7.87 (1H, s), 7.77 (2H, d, J=8.3 Hz), 6.96 (2H, d, J=8.3 Hz), 3.95 (1H, m), 3.77 (3H, s), 3.07 (2H, d, J=12.0 Hz), 2.93 (3H, s), 2.56 (2H, m), 1.73 (4H, m)

Compound no. 502 (MP: 120-121). NMR solvent: CDCl3

13C: 159.9, 151.5, 142.1, 136.9, 134.3, 129.7, 117.5, 113.7, 113.4, 110.2, 55.7, 55.3, 52.2, 52.1, 31.6, 28.8, 12.1

1H: 7.92 (1H, s), 7.49 (1H, s), 7.39 (1H, t br), 7.36 (1H, d, J=7.6 Hz), 7.30 (1H, t, J=7.9 Hz), 6.85 (1H, d br, J=8.1 Hz), 4.03 (1H, m), 3.87 (3H, s), 3.08 (2H, d br, J=11.0 Hz), 3.02 (3H, s), 2.45 (2H, q, J=7.3 Hz), 2.05 (2H, t br, J=11.4 Hz), 1.96 (2H, d q, J=2.5, 11.8 Hz), 1.85 (2H, d br, J=11.0 Hz), 1.11 (3H, t, J=7.3 Hz)

Compound no. 503 (MP: 158-159). NMR solvent: CDCl3

13C: 152.5 (d, J=245.0 Hz), 151.4, 147.1 (d, J=11.0 Hz), 141.1 (d, J=2.5 Hz), 136.9, 126.4 (d, J=7.0 Hz), 120.9 (d, J=3.6 Hz), 113.5 (d, J=2.5 Hz), 113.0 (d, J=20.0 Hz), 112.6, 56.3, 55.7, 52.2, 52.1, 31.6, 28.7, 12.1

1H, 7.88 (1H, d, J=1.3 Hz), 7.50 (2H, m), 7.40 (1H, d, J=1.3 Hz), 6.99 (1H, t, J=8.3 Hz), 4.03 (1H, m), 3.91 (3H, s), 3.09 (2H, d br, J=11.5 Hz), 3.02 (3H, s), 2.45 (2H, q, J=7.3 Hz), 2.06 (2H, t, J=12.0 Hz), 1.96 (2H, d q, J=3.5, 12.0 Hz), 1.83 (2H, d br, J=12.0 Hz), 1.11 (3H, t, J=7.3 Hz)

Compound no. 504 (MP: 183-184). NMR solvent: DMSO

13C: 149.3, 137.5, 136.1, 129.1, 129, 128.7, 125.4, 115.8, 52.6, 42.3, 31.8, 24.6

1H: 9.33 (1H, q br, J=10.0 Hz), 9.20 (1H, d br, J=10.0 Hz), 9.13 (1H, s), 8.37 (1H, s), 7.94 (2H, d, J=8.2 Hz), 7.48 (2H, t, J=7.8 Hz), 7.39 (1H, t, J=7.3 Hz), 4.23 (1H, m), 3.34 (2H, d br, J=12.0 Hz), 3.0 (2H, m), 2.98 (3H, s), 2.19 (2H, d q, J=3.5, 12.8 Hz), 1.92 (2H, d br, J=12.4 Hz)

Compound no. 505 (MP: 143-144). NMR solvent: DMSO

13C: 167.9, 163.8, 144.4, 143.5, 142.8, 135.5, 128, 119.7, 118, 81.6, 78.7, 63.9, 61.8, 47.7, 45.2, 26.8, 25.1, 24.8, 22.2

1H: 8.16 (1H, s br), 8.11 (1H, d, J=9.0 Hz), 7.59 (1H, d d, J=1.2, 8.9 Hz), 5.29 (2H, s), 3.92 (2H, m), 3.84 (2H, br), 3.59 (2H, br), 3.08 (4H, br), 2.93 (1H, m), 1.96 (2H, d br, J=10.8 Hz), 1.80 (2H, d, J=12.4 Hz), 1.58 (1H, m), 1.57 (6H, s), 1.29 (4H, m), 1.09 (1H, m)

Compound no. 506 (MP: 133-135). NMR solvent: DMSO

13C: 168, 162.4, 147.4, 147, 144.4, 143.4, 142.8, 135.9, 128.5, 127.9, 123.3, 119.7, 117.7, 109.8, 108.1, 101.1, 81.6, 78.7, 61.8, 60.6, 51.6, 46.1, 40.7, 22.2

1H: 8.10 (1H, d, J=9.3 Hz), 8.09 (1H, s), 7.54 (1H, d, J=9.3 Hz), 6.94 (1H, s), 6.90 (1H, d, J=8.0 Hz), 6.83 (1H, d, J=8.0 Hz), 6.01 (2H, s), 5.29 (2H, s), 3.92 (2H, d, J=8.0 Hz), 3.75 (2H, m), 3.72 (2H, s), 3.47 (2H, m), 2.69 (4H, m), 1.57 (6H, s)

Compound no. 507 (MP: 213-214). NMR solvent: DMSO

13C: 156.3, 150.9, 150.7, 140.2, 137.5, 126.5, 126.3, 125.7, 122.9, 113.3, 111.9, 56.7, 55.7, 31.3, 29, 25.2, 24.8

1H: 9.38 (1H, s), 8.07 (1H, d, J=1.3 Hz), 7.91 (1H, d, J=1.3 Hz), 7.84 (1H, d, J=2.2 Hz), 7.82 (1H, d d, J=2.2, 8.6 Hz), 7.08 (1H, d, J=8.6 Hz), 5.63 (2H, s), 3.81 (1H, m), 3.81 (3H, s), 2.92 (3H, s), 1.78 (4H, m), 1.58 (3H, m), 1.29 (2H, q, J=12.7 Hz), 1.11 (1H, q, J=13.0 Hz)

Compound no. 508 (MP: 172-173). NMR solvent: DMSO

13C: 150.7, 147.4, 145.5, 138.1, 137.5, 132.5, 129.4, 124.1, 115.7, 67.9, 56.3, 34.2, 31.4, 26.8

1H: 9.08 (1H, s), 8.49 (1H, d, J=4.8 Hz), 8.24 (1H, t d, J=1.7, 8.0 Hz), 8.19 (1H, s), 8.18 (1H, s), 7.47 (1H, d d, J=5.0, 8.0 Hz), 4.62 (1H, br), 3.79 (1H, m), 3.38 (1H, m), 2.92 (3H, s), 1.89 (2H, d br, J=12.0 Hz), 1.80-1.60 (4H, m), 1.23 (2H, q, J=11.3 Hz)

Compound no. 509 (MP: 137-139 (dec.)). NMR solvent: DMSO

13C: 150.7, 148.4, 138.5, 138.2, 135.2, 131, 130.3, 121.6, 118.9, 116.3, 55.6, 51.9, 51.4, 31.5, 28.1, 12.2

1H: 8.66 (1H, t, J=1.8 Hz), 8.31 (1H, s), 8.29 (1H, d t, J=1.8, 8.0 Hz), 8.20 (1H, d, J=1.3 Hz), 8.10 (1H, d br, J=8.0 Hz), 7.69 (1H, t, J=8.0 Hz), 3.83 (1H, m), 2.96 (2H, m), 2.95 (3H, s), 2.32 (2H, q, J=7.1 Hz), 1.93 (2H, t br, J=10.5 Hz), 1.82 (2H, d q, J=3.0, 12.0 Hz), 1.73 (2H, d br, J=12.0 Hz), 0.99 (3H, t, J=10.5 Hz)

Compound no. 510 (MP: 133-134). NMR solvent: CDCl3

13C: 151.5, 149.1, 148.6, 142.1, 136.7, 126, 117.4, 112.3, 111.2, 108.4, 55.9, 55.9, 55.6, 52.2, 52.1, 31.6, 28.7, 12.1

1H: 7.89 (1H, d, J=1.3 Hz), 7.42 (1H, d, J=1.3 Hz), 7.39 (1H, d, J=2.0 Hz), 7.30 (1H, d d, J=2.0, 8.4 Hz), 6.90 (1H, d, J=8.4 Hz), 4.04 (1H, m), 3.96 (3H, s), 3.91 (3H, s), 3.08 (2H, d br, J=11.5 Hz), 3.02 (3H, s), 2.44 (2H, q, J=7.4 Hz), 2.05 (2H, t br, J=11.5 Hz), 1.96 (2H, d q, J=3.0, 11.8 Hz), 1.82 (2H, d br, J=11.8 Hz), 1.10 (3H, t, J=7.4 Hz)

Compound no. 511 (MP: 142-144). NMR solvent: DMSO

13C: 151.6, 146.7, 142.3, 136.8, 133.9, 129.6, 115.5, 114.4, 113.1, 111.9, 55.7, 52.2, 52.1, 31.6, 28.7, 12.1

1H: 7.90 (1H, s), 7.45 (1H, s), 7.20 (1H, s), 7.16 (1H, t, J=7.8 Hz), 7.13 (1H, d, J=7.8 Hz), 6.63 (1H, d, J=7.0 Hz), 4.03 (1H, m), 3.73 (2H, s br), 3.08 (2H, d br, J=11.0 Hz), 3.01 (3H, s), 2.45 (2H, t, J=7.1 Hz), 2.05 (2H, t br, J=11.5 Hz), 1.96 (2H, q, J=12.0 Hz), 1.82 (2H, d br, J=12.0 Hz), 1.11 (3H, t, J=7.1 Hz)

Compound no. 512 (MP: 153-154). NMR solvent: CDCl3

13C: 151.5, 149.1, 148.6, 142.1, 136.7, 126.1, 117.4, 112.3, 111.3, 108.4, 60.4, 55.9, 55.9, 55.8, 52.6, 31.6, 28.9, 20.3, 11.9

1H: 7.89 (1H, d, J=1.3 Hz), 7.42 (1H, d, J=1.3 Hz), 7.40 (1H, d, J=2.0 Hz), 7.30 (1H, d d, J=2.0, 8.3 Hz), 6.90 (1H, d, J=8.3 Hz), 4.02 (1H, m), 3.96 (3H, s), 3.91 (3H, s), 3.04 (2H, d, J=11.0 Hz), 3.02 (3H, s), 2.31 (2H, m), 2.05 (2H, d t, J=1.8, 11.8 Hz), 1.93 (2H, d q, J=3.7, 12.0 Hz), 1.80 (2H, d br, J=12.0 Hz), 1.51 (2H, m), 0.9 (3H, t, J=7.3 Hz)

Compound no. 513 (MP: 215-216 (dec.)). NMR solvent: DMSO

13C: 172.1, 160.3, 151, 140.2, 137.5, 130.5, 124.4, 124.2, 117.7, 114.4, 113.3, 66.3, 54.2, 31.7, 29.1

1H: 13.02 (1H, s), 8.48 (1H, s), 8.32 (1H, d, J=2.0 Hz), 8.14 (1H, s), 7.96 (1H, s), 7.89 (1H, d d, J=2.2, 8.5 Hz), 7.86 (1H, s), 6.92 (1H, d, J=8.5 Hz), 4.11 (1H, m), 3.94 (2H, d d, J=3.5, 11.0 Hz), 3.38 (2H, m), 2.96 (3H, s), 1.96 (2H, d q, J=4.6, 12.4 Hz), 1.70 (2H, d br, J=12.3 Hz)

Compound no. 514 (MP: 185-186). NMR solvent: CDCl3

13C: 152.5 (d, J=245.0 Hz), 151.4, 147.0 (d, J=11.0 Hz), 141.1 (d, J=2.6 Hz), 136.9, 126.4 (d, J=7.3 Hz), 120.9 (d, J=3.5 Hz), 113.4 (d, J=2.0 Hz), 113.0 (d, J=20.0 Hz), 112.6, 60.4, 56.2, 55.8, 52.6, 31.6, 28.9, 20.3, 11.9

1H: 7.88 (1H, d, J=1.3 Hz), 7.50 (2H, m), 7.40 (1H, d, J=1.3 Hz), 6.99 (1H, t, J=8.4 Hz), 4.0 (1H, m), 3.91 (3H, s), 3.04 (2H, d br, J=11.7 Hz), 3.01 (3H, s), 2.31 (2H, m), 2.05 (2H, d t, J=2.0, 12.0 Hz), 1.93 (2H, d q, J=3.5, 12.0 Hz), 1.80 (2H, d br, J=12.0 Hz), 1.51 (2H, m), 0.9 (3H, t, J=7.5 Hz)

Compound no. 515 (MP: 171-172). NMR solvent: CDCl3

13C: 154.5, 151.2, 148.6, 146.7, 139.4, 137.4, 132.5, 128.9, 123.6, 113.9, 80, 55.7, 42.9, 31.9, 28.7, 28.4

1H: 9.01 (1H, d, J=2.2 Hz), 8.54 (1H, d d, J=1.7, 4.8 Hz), 8.12 (1H, d d d, J=1.7, 2.2, 8.0 Hz), 7.96 (1H, d, J=1.3 Hz), 7.59 (1H, d, J=1.3 Hz), 7.35 (1H, d d d, J=0.9, 4.8, 8.0 Hz), 4.28 (2H, br), 4.20 (1H, m), 3.02 (3H, s), 2.81 (2H, br), 1.88-1.69 (4H, m), 1.48 (9H, s)

Compound no. 516 (MP: hygroscopic). NMR solvent: DMSO

13C: 150.1, 138.7, 137.4, 135.1, 134.4, 133, 127.6, 127.4, 118.1, 67.9, 56.4, 34.2, 31.5, 26.8

1H: 9.0 (1H, t, J=1.5 Hz), 8.47 (1H, m d, J=6.3 Hz), 8.42 (1H, s), 8.40 (1H, s), 8.19 (1H, m d, J=8.1 Hz), 7.74 (1H, d d, J=6.3, 8.1 Hz), 3.79 (1H, m br), 3.40 (1H, m), 2.91 (3H, s), 1.88 (2H, d br, J=12.0 Hz), 1.70 (4H, m), 1.23 (2H, q br, J=12.0 Hz)

Compound no. 517 (MP: 130-132). NMR solvent: DMSO

13C: 168, 162.4, 145.4, 144.2, 135.1, 133, 132.7, 129.7, 128.8, 128.5, 128, 118.4, 114.5, 81.7, 78.7, 61.6, 61, 51.8, 46.3, 40.8, 22.5

1H: 8.21 (1H, s), 8.16 (1H, d, J=8.5 Hz), 7.71 (1H, d d, J=1.5, 8.5 Hz), 7.40-7.25 (5H, m), 5.42 (2H, s), 3.91 (2H, s), 3.65 (2H, s br), 3.43 (4H, m), 2.55 (4H, m), 1.60 (6H, s)

Compound no. 518 (MP: 122). NMR solvent: CDCl3

13C: 152.2, 151.2, 149.3, 142.3, 137.5, 136.8, 122.2, 119.7, 115.9, 57.4, 31.4, 29.8, 25.4, 25.2

1H: 8.56 (1H, d d d, J=1.0, 1.8, 4.8 Hz), 8.0 (1H, t d, J=1.1, 8.0 Hz), 7.97 (1H, d, J=1.5 Hz), 7.88 (1H, d, J=1.5 Hz), 7.75 (1H, d t, J=1.9, 7.7 Hz), 7.19 (1H, d d d, J=1.2, 4.8, 7.6 Hz), 3.98 (1H, m), 3.0 (3H, s), 1.88 (2H, m), 1.85 (2H, m), 1.69 (1H, d, J=13.0 Hz), 1.56 (2H, d q, J=3.7, 12.2 Hz), 1.38 (2H, t q, J=3.0, 13.0 Hz), 1.12 (1H, t q, J=3.5, 13.0 Hz)

Compound no. 519 (MP: 158-159). NMR solvent: CDCl3

13C: 150.8, 137.6, 137.6, 136.9, 136, 132.7, 125.9, 122.8, 115.3, 60.4, 56, 52.6, 31.7, 28.8, 20.2, 11.9

1H: 8.66 (1H, t, J=1.6 Hz), 8.13 (1H, d d d, J=1.0, 1.7, 6.4 Hz), 7.93 (1H, d, J=1.3 Hz), 7.71 (1H, t d, J=1.2, 7.9 Hz), 7.59 (1H, d, J=1.3 Hz), 7.31 (1H, d d, J=6.4, 7.9 Hz), 3.98 (1H, m), 3.04 (2H, m d, J=12.0 Hz), 3.01 (3H, s), 2.30 (2H, m), 2.04 (2H, d t, J=2.0, 12.0 Hz), 1.93 (2H, d q, J=3.5, 12.0 Hz), 1.80 (2H, d br, J=11.5 Hz), 1.50 (2H, m), 0.9 (3H, t, J=7.4 Hz)

Compound no. 520 (MP: 170). NMR solvent: CDCl3

13C: 159.2, 151.6, 142.1, 136.8, 126.4, 125.7, 114.1, 112, 60.4, 55.8, 55.3, 52.6, 31.5, 28.9, 20.2, 11.9

1H: 7.90 (1H, d, J=1.3 Hz), 7.72 (2H, m d, J=8.9 Hz), 7.40 (1H, d, J=1.3 Hz), 6.94 (2H, m d, J=8.9 Hz), 4.01 (1H, m), 3.84 (3H, s), 3.04 (2H, m), 3.01 (3H, s), 2.30 (2H, m), 2.04 (2H, d t, J=2.0, 12.0 Hz), 1.94 (2H, d q, J=3.7, 12.0 Hz), 1.80 (2H, d br, J=12.0 Hz), 1.50 (2H, m), 0.9 (3H, t, J=7.4 Hz)

Compound no. 521 (MP: 163-164). NMR solvent: CDCl3

13C: 159.1, 151.6, 142.1, 136.8, 126.4, 125.7, 114.1, 112, 55.7, 55.3, 52.2, 52.1, 31.5, 28.8, 12.2

1H: 7.89 (1H, d, J=1.3 Hz), 7.72 (2H, m d, J=8.9 Hz), 7.39 (1H, d, J=1.3 Hz), 6.94 (2H, m d, J=8.9 Hz), 4.02 (1H, m), 3.84 (3H, s), 3.07 (2H, m d, J=11.7 Hz), 3.01 (3H, s), 2.43 (2H, q, J=7.3 Hz), 2.03 (2H, d t, J=2.0, 12.0 Hz), 1.93 (2H, d q, J=3.5, 12.0 Hz), 1.82 (2H, d br, J=12.0 Hz), 1.09 (3H, t, J=7.2 Hz)

Compound no. 522 (MP: 127). NMR solvent: DMSO

13C: 150.7, 148.4, 138.5, 138.2, 135.2, 131, 130.3, 121.6, 118.9, 116.4, 59.6, 55.6, 52.4, 31.6, 28.2, 19.8, 11.9

1H: 8.66 (1H, t, J=1.8 Hz), 8.32 (1H, s), 8.30 (1H, d br, J=7.9 Hz), 8.20 (1H, s), 8.11 (1H, d d, J=2.2, 8.1 Hz), 7.69 (1H, t, J=8.1 Hz), 3.82 (1H, m), 2.95 (3H, s), 2.93 (2H, m), 2.21 (2H, t br, J=7.5 Hz), 1.91 (2H, t br, J=11.2 Hz), 1.81 (2H, d q, J=3.0, 12.0 Hz), 1.72 (2H, d br, J=12.0 Hz), 1.41 (2H, m), 0.84 (3H, t, J=7.5 Hz)

Compound no. 523 (MP: 163-164 (dec.)). NMR solvent: DMSO

13C: 151, 150.4 (d, J=240.5 Hz), 144.9 (d, J=12.5 Hz), 140, 138.5, 137.6, 130.2 (d, J=3.2 Hz), 128.9, 128.3, 127, 116.3 (d, J=19.0 Hz), 115.9 (d, J=6.5 Hz), 114.2 (d, J=2.5 Hz), 114.1, 61.8, 55.4, 52.2, 31.5, 28.2

1H: 9.20 (1H, s), 8.08 (1H, s), 7.89 (1H, s), 7.45 (1H, d d, J=1.7, 8.7 Hz), 7.39-7.19 (6H, m), 7.13 (1H, d d, J=8.7, 11.2 Hz), 3.82 (1H, m br), 3.47 (2H, s), 2.93 (3H, s), 2.90 (2H, m br), 2.0 (2H, m br), 1.83 (2H, m br), 1.72 (2H, m br)

Compound no. 524 (MP: 124-125). NMR solvent: DMSO

13C: 151.1, 148.8, 141.4, 137.3, 133.8, 129.1, 113.7, 113, 112.8, 110.4, 59.6, 55.6, 52.4, 31.4, 28.2, 19.8, 11.9

1H: 8.06 (1H, d, J=1.3 Hz), 7.79 (1H, d, J=1.3 Hz), 7.08 (1H, t, J=2.0 Hz), 7.0 (1H, t, J=7.6 Hz), 6.95 (1H, t d, J=1.2, 7.5 Hz), 6.45 (1H, d d d, J=1.4, 2.4, 7.8 Hz), 5.08 (2H, s), 3.79 (1H, m), 2.95 (2H, m), 2.92 (3H, s), 2.23 (2H, t, br, J=7.5 Hz), 1.92 (2H, t br, J=11.0 Hz), 1.81 (2H, d q, J=3.0, 11.7 Hz), 1.71 (2H, d br, J=12.0 Hz), 1.42 (2H, m), 0.84 (3H, t, J=7.3 Hz)

Compound no. 525 (MP: 167-168). NMR solvent: CDCl3

13C: 151.2, 148.6, 146.7, 139.3, 137.3, 132.4, 128.9, 123.6, 113.9, 55.9, 52.2, 52.1, 31.6, 28.8, 12.2

1H: 9.0 (1H, d d, J=1.0, 2.3 Hz), 8.52 (1H, d d, J=1.7, 4.9 Hz), 8.11 (1H, d d d, J=1.7, 2.2, 7.9 Hz), 7.94 (1H, d, J=1.3 Hz), 7.58 (1H, d, J=1.3 Hz), 7.34 (1H, d d d, J=1.0, 4.9, 8.0 Hz), 4.03 (1H, m), 3.07 (2H, m d, J=11.5 Hz), 3.03 (3H, s), 2.43 (2H, q, J=7.3 Hz), 2.03 (2H, d t, J=2.0, 11.7 Hz), 1.94 (2H, d q, J=3.5, 12.0 Hz), 1.83 (2H, d br, J=12.0 Hz), 1.09 (3H, t, J=7.3 Hz)

Compound no. 526 (MP: 117). NMR solvent: DMSO

13C: 167.9, 151, 140.5, 140.2, 140, 137.7, 135, 134.1, 129.6, 129.4, 129, 126.8, 125.8, 125.7, 124.2, 123.1, 115, 59.3, 55.2, 52.2, 31.6, 27.9, 19.5, 11.8

1H: 8.21 (1H, t, J=1.7 Hz), 8.19 (1H, t, J=1.7 Hz), 8.16 (3H, m), 7.88 (3H, m), 7.63 (1H, d d d, J=1.2, 2.0, 7.8 Hz), 7.57 (1H, t, J=7.7 Hz), 7.52 (1H, t, J=7.8 Hz), 7.49 (1H, s br), 3.87 (1H, m br), 3.0 (2H, m br), 2.96 (3H, s), 2.31 (2H, m br), 2.05 (2H, m br), 1.86 (2H, q br, J=12.0 Hz), 1.46 (2H, d br, J=10.5 Hz), 1.45 (2H, m), 0.85 (3H, t, J=7.4 Hz)

Compound no. 527 (MP: 85-87). NMR solvent: CDCl3

13C: 154.4, 150.3, 148.9, 132.3, 129, 126.2, 123, 58.8, 56.6, 31.1, 30.6, 29.4, 25.4, 25.3

1H: 7.90 (2H, m d, J=8.4 Hz), 7.56 (1H, m t, J=7.3 Hz), 7.49 (1H, m t, J=7.8 Hz), 4.13, 3.70 (1H, 2 s br), 3.0 (3H, s), 1.87 (4H, m), 1.68 (1H, d, J=12.0 Hz), 1.52 (2H, q, J=12.0 Hz), 1.40 (2H, s br), 1.12 (1H, t q, J=, 3.2, 13.0 Hz)

Compound no. 528 (MP: 138-140). NMR solvent: CDCl3

13C: 153.3, 149.8, 144.2, 132.5, 129.1, 126.2, 122.7, 81, 79.8, 61.8, 22.8

1H: 7.87 (2H, m d, J=8.7 Hz), 7.57 (1H, m t, J=7.3 Hz), 7.50 (2H, m t, J=7.2 Hz), 5.23 (2H, s), 3.83 (2H, s), 1.59 (6H, s)

Compound no. 529 (MP: 154-155). NMR solvent: CDCl3

13C: 151.2, 148.6, 146.7, 139.3, 137.3, 132.4, 128.9, 123.6, 113.9, 60.4, 55.9, 52.6, 31.6, 28.9, 20.3, 11.9

1H: 9.0 (1H, d, J=2.0 Hz), 8.52 (1H, d d, J=1.6, 4.8 Hz), 8.11 (1H, t d, J=2.0, 8.1 Hz), 7.94 (1H, d, J=1.3 Hz), 7.57 (1H, d, J=1.3 Hz), 7.33 (1H, d d, J=4.8, 8.1 Hz), 4.01 (1H, m), 3.05 (2H, m), 3.02 (3H, s), 2.30 (2H, m), 2.04 (2H, t br, J=11.5 Hz), 1.93 (2H, d q, J=3.1, 12.0 Hz), 1.81 (2H, d br, J=11.2 Hz), 1.50 (2H, m), 0.9 (3H, t, J=7.4 Hz)

Compound no. 530 (MP: 185-186 (dec.)). NMR solvent: DMSO

13C: 151, 143.1, 140, 137.5, 132.9, 125.7, 124.2, 122.8, 121.8, 57.4, 31.4, 29.9, 25.4, 25.2

1H: 8.87 (1H, d, J=1.3 Hz), 3.37 (1H, d d, J=2.0, 8.3 Hz), 8.31 (1H, d, J=6.0 Hz), 8.06 (1H, d, J=1.3 Hz), 7.37 (1H, d t,

J=1.2, 8.4 Hz), 7.17 (1H, d t, J=2.2, 7.1 Hz), 4.0 (1H, m), 3.0 (3H, s), 1.87 (4H, m), 1.69 (1H, d, J=13.0 Hz), 1.57 (2H, d q, J=3.5, 13.0 Hz), 1.39 (2H, m q, J=13.0 Hz), 1.12 (1H, m q, J=13.0 Hz)

Compound no. 531 (MP: slow dec.>160). NMR solvent: DMSO

13C: 150.4, 140.2, 139.9, 139, 137.9, 134.8, 132.6, 127.4, 118.6, 52.4, 42.4, 31.8, 24.7

1H: 9.33 (1H, s), 9.25 (1H, q, J=10.0 Hz), 9.10 (1H, d, J=10.0 Hz), 8.94 (1H, d, J=8.2 Hz), 8.80 (1H, d, J=5.3 Hz), 8.55 (1H, s), 8.38 (1H, s), 8.08 (1H, d d, J=5.3, 8.2 Hz), 4.22 (1H, m), 3.34 (2H, d, J=12.0 Hz), 3.01 (2H, q, J=13.0 Hz), 2.96 (3H, s), 2.17 (2H, q, J=13.2 Hz), 1.92 (2H, d, J=12.0 Hz)

Compound no. 532 (MP: 245-246 (dec.)). NMR solvent: DMSO

13C: 158.5, 151.2, 140.6, 137.5, 126.1, 126, 114, 113.1, 55.1, 54.5, 44.9, 34.3, 31.6, 27.7

1H: 8.10 (1H, d, J=1.3 Hz), 7.88 (1H, d, J=1.3 Hz), 7.77 (2H, m d, J=8.9 Hz), 6.96 (2H, m d, J=8.9 Hz), 3.98 (1H, m), 3.77 (3H, s), 3.66 (2H, d br, J=12.0 Hz), 2.95 (3H, s), 2.88 (3H, s), 2.84 (2H, m), 1.87 (4H, m)

Compound no. 533 (MP: 259-260). NMR solvent: DMSO

13C: 150.9, 148.1, 146.2, 138.2, 137.8, 131.9, 129.1, 123.8, 115.5, 54.5, 44.9, 34.4, 31.7, 27.7

1H: 9.07 (1H, s), 8.46 (1H, s), 8.19 (3H, m), 7.42 (1H, s br), 3.98 (1H, m br), 3.66 (2H, m d, J=10.0 Hz), 2.96 (3H, s), 2.88 (3H, s), 2.85 (2H, m br), 1.88 (4H, m br)

Compound no. 534 (MP: 162). NMR solvent: DMSO

13C: 151.5 (d, J=243.0 Hz), 149.4, 147.3 (d, J=10.6 Hz), 137.4, 135.4, 122.4 (m), 121.9 (d, J=2.8 Hz), 115.2, 114.3 (d, J=1.5 Hz), 113.0 (d, J=20.2 Hz), 56.2, 52.5, 42.3, 31.7, 24.6

1H: 8.91 (2H, m), 8.49 (1H, s), 8.11 (1H, s), 7.71 (1H, d d, J=2.0, 12.7 Hz), 7.67 (1H, m d, J=8.8 Hz), 7.23 (1H, t, J=8.8 Hz), 4.21 (1H, m), 3.86 (3H, s), 3.36 (2H, d br, J=12.5 Hz), 3.02 (2H, m br), 2.95 (3H, s), 2.11 (2H, d q, J=4.0, 12.8 Hz), 1.92 (2H, d br, J=12.8 Hz)

Compound no. 535 (MP: 141-142). NMR solvent: CDCl3

13C: 149.6, 144.4, 137.9, 135.2, 131.4, 129.1, 128.3, 127.2, 125.6, 118.1, 115.3, 109.1, 62.8, 57.6, 55.6, 52.5, 32.8, 29.8, 28.5

1H: 8.49 (1H, d d, J=1.0, 1.4 Hz), 8.12 (1H, d d, J=1.0, 8.7 Hz), 7.82 (1H, d d, J=1.4, 8.7 Hz), 7.43-7.20 (5H, m), 4.32-4.20 (1H, 2s br), 3.54 (2H, s), 3.21 (3H, s), 3.03 (2H, s br), 2.18 (2H, s br), 2.01 (2H, m br), 1.94 (2H, m br)

Compound no. 536 (MP: 173-174). NMR solvent: DMSO

13C: 151.2 (d, J=240.0 Hz), 151, 144 (d, J=12.5 Hz), 139.9 (d, J=2.4 Hz), 137.5, 125.4 (d, J=7.0 Hz), 121 (d, J=3.0 Hz), 117.9 (d, J=3.5 Hz), 113.4, 112.5 (d, J=19.4 Hz), 55.2, 51.7, 51.3, 31.5, 27.8, 12

1H: 9.88 (1H, s), 8.08 (1H, d, J=1.3 Hz), 7.89 (1H, d, J=1.3 Hz), 7.59 (1H, d d, J=2.0, 12.5 Hz), 7.48 (1H, d d d, J=1.0, 2.0, 8.5 Hz), 6.95 (1H, d d, J=8.5, 9.2 Hz), 3.85 (1H, m br), 3.02 (2H, m br), 2.93 (3H, s), 2.40 (2H, m br), 1.98 (2H, m br), 1.85 (2H, m br), 1.77 (2H, m br), 1.02 (3H, m br)

Compound no. 537 (MP: 144-146). NMR solvent: CDCl3

13C: 151.9 (d, J=246.2 Hz), 151.4, 147.8 (d, J=11.0 Hz), 141.5, 136.8, 129.6 (d, J=3.8 Hz), 117.3 (d, J=6.8 Hz), 116.1 (d, J=19.0 Hz), 113.1, 110.3 (d, J=1.5 Hz), 56.2, 55.8, 52.2, 52.1, 31.6, 28.8, 12.2

1H: 7.90 (1H, s), 7.49 (1H, d d, J=1.7, 8.5 Hz), 7.45 (1H, s), 7.24 (1H, m), 7.08 (1H, d d, J=8.6, 11.1 Hz), 4.03 (1H, m), 3.96 (3H, s), 3.08 (2H, d br, J=11.2 Hz), 3.02 (3H, s), 2.44 (2H, q, J=7.4 Hz), 2.05 (2H, t br, J=11.0 Hz), 1.95 (2H, d q, J=2.6, 11.9 Hz), 1.83 (2H, d br, J=10.5 Hz), 1.10 (3H, t, J=7.4 Hz)

Compound no. 538 (MP: 44-46). NMR solvent: CDCl3

13C: 150.7, 145.2, 133.1, 129.3, 125.2, 119.8, 113.6, 40, 38

1H: 8.11 (1H, d, J=8.4 Hz), 8.0 (1H, d, J=8.4 Hz), 7.60 (1H, m t, J=7.6 Hz), 7.46 (1H, m t, J=7.7 Hz), 3.34 (6H, 2 s br)

Compound no. 539 (MP: 90-91). NMR solvent: CDCl3

13C: 156.8, 149.9, 149.2, 126, 123.9, 123, 40, 38.3

1H: 8.82 (1H, d d, J=1.6, 4.4 Hz), 8.42 (1H, d d, J=1.6, 8.5 Hz), 7.57 (1H, d d, J=4.4, 8.5 Hz), 3.49, 3.31 (6H, 2s)

Compound no. 540 (MP: 164). NMR solvent: DMSO

13C: 151.7 (d, J=242.5 Hz), 151, 146.2 (d, J=10.5 Hz), 139.5 (d, J=2.5 Hz), 137.6, 126.7 (d, J=7.3 Hz), 120.9 (d, J=3.0 Hz), 114 (2C), 112.2 (d, J=9.4 Hz), 60, 58.8, 56, 55.5, 52.8, 31.5, 28.2

1H: 8.09 (1H, d, J=1.3 Hz), 7.96 (1H, d, J=1.3 Hz), 7.66 (1H, d d, J=2.0, 13.5 Hz), 7.63 (1H, m), 7.19 (1H, t, J=8.7 Hz), 4.41 (1H, t, J=5.3 Hz), 3.85 (3H, s), 3.80 (1H, m), 3.48 (2H, m), 2.95 (2H, d br, J=11.5 Hz), 2.93 (3H, s), 2.38 (2H, t, J=6.4 Hz), 2.01 (2H, t br, J=11.5 Hz), 1.81 (2H, d q, J=3.6, 12.1 Hz), 1.69 (2H, d br, 12.0 Hz)

Compound no. 541 (MP: 220-221). NMR solvent: CDCl3

13C: 152.5 (d, J=245.0 Hz), 151.5, 147.1 (d, J=10.0 Hz), 141.2 (d, J=3.0 Hz), 136.9, 126.4 (d, J=7.0 Hz), 120.9 (d, J=3.5 Hz), 118.7, 113.5 (d, J=2.0 Hz), 113.1 (d, J=19.0 Hz), 112.6, 56.3, 55.3, 53, 52.2, 31.7, 28.7, 16.3

1H: 7.90 (1H, d, J=1.3 Hz), 7.50 (2H, m), 7.40 (1H, d, J=1.3 Hz), 7.0 (1H, t, J=8.5 Hz), 4.04 (1H, m), 3.93 (3H, s), 3.03 (3H, s), 3.02 (2H, m), 2.71 (2H, t, J=7.0 Hz), 2.52 (2H, t, J=7.0 Hz), 2.22 (2H, d t, J=2.0, 11.5 Hz), 1.94 (2H, d q, J=3.5, 12.2 Hz), 1.83 (2H, d br, J=12.2 Hz)

Compound no. 542 (MP: 175). NMR solvent: CDCl3

13C: 151, 150.3, 140.2, 139.8, 137.3, 119.4, 115.6, 66.9, 54.5, 31.9, 29.5

1H: 8.63 (2H, m d, J=4.6 Hz), 7.95 (1H, d, J=1.3 Hz), 7.69 (1H, d, J=1.3 Hz), 7.67 (2H, m d, J=4.6 Hz), 4.28 (1H, m), 4.09 (2H, d d, J=4.7, 11.5 Hz), 3.50 (2H, d t, J=2.1, 12.0 Hz), 3.04 (3H, s), 1.95 (2H, d q, J=4.9, 12.5 Hz), 1.78 (2H, m d, J=12.3 Hz)

Compound no. 543 (MP: 173-174 (dec.)). NMR solvent: CDCl3

13C: 150.8, 139.3, 138.5, 137.5, 131.3, 121.8, 115.3, 66.9, 54.6, 31.9, 29.5

1H: 8.22 (2H, d, J=6.8 Hz), 7.93 (1H, s), 7.68 (2H, d, J=6.8 Hz), 7.62 (1H, s), 4.28 (1H, m), 4.10 (2H, d d, J=4.0, 11.7 Hz), 3.51 (2H, t, J=11.7 Hz), 3.04 (3H, s), 1.95 (2H, d q, J=4.5, 12.2 Hz), 1.78 (2H, d br, J=12.0 Hz)

Compound no. 544 (MP: 163-164). NMR solvent: CDCl3

13C: 159.1, 158.2, 151.6, 149.4, 142.1, 136.8, 136.4, 126.4, 125.7, 123.2, 122.1, 114.1, 112, 64.3, 55.6, 55.3, 52.8, 31.6, 28.8

1H: 8.59 (1H, m d, J=4.9 Hz), 7.89 (1H, d, J=1.3 Hz), 7.72 (2H, m d, J=8.9 Hz), 7.66 (1H, d t, J=1.8, 7.7 Hz), 7.39 (1H, d, J=1.3 Hz), 7.36 (1H, d, J=8.0 Hz), 7.18 (1H, d d d, J=1.0, 4.9, 7.4 Hz), 6.94 (2H, m d, J=8.9 Hz), 4.04 (1H, m), 3.84 (3H, s), 3.66 (2H, s), 3.02 (2H, m), 3.01 (3H, s), 2.20 (2H, d t, J=1.8, 12.0 Hz), 1.97 (2H, d q, J=3.8, 12.2 Hz), 1.78 (2H, d br, J=12.0 Hz)

Compound no. 545 (MP: 127-128). NMR solvent: CDCl3

13C: 151.9 (d, J=246.5 Hz), 151.4, 147.8 (d, J=11.0 Hz), 141.4, 136.8, 129.6 (d, J=4.0 Hz), 117.3 (d, J=7.0 Hz), 116.1 (d, J=18.8 Hz), 113.1, 110.3 (d, J=2.0 Hz), 60.4, 56.2, 55.8, 52.6, 31.6, 28.8, 20.2, 11.9

1H: 7.89 (1H, d, J=1.3 Hz), 7.49 (1H, d d, J=2.0, 8.2 Hz), 7.45 (1H, d, J=1.3 Hz), 7.24 (1H, m), 7.09 (1H, d d, J=8.3, 11.0 Hz), 4.02 (1H, m), 3.96 (3H, s), 3.05 (2H, d br, J=12.0 Hz), 3.02 (3H, s), 2.31 (2H, m), 2.05 (2H, d t, J=2.0, 12.0 Hz), 1.94 (2H, d q, J=3.5, 12.0 Hz), 1.80 (2H, d br, J=12.0 Hz), 1.51 (2H, m), 0.91 (3H, t, J=7.5 Hz)

Compound no. 546 (MP: 240-241). NMR solvent: DMSO
13C: 163.6, 161.9, 158.5, 151.3, 151.1, 151, 147.1, 140.6, 137.5, 133.9, 128.6, 126.1, 126, 125, 124.4, 114, 113.1, 55.1, 55, 45.9, 41.3, 31.8, 28.9, 28.1

1H: 9.18 (1H, d, J=2.0 Hz), 8.71 (1H, d d, J=1.6, 4.9 Hz), 8.35 (1H, t d, J=1.8, 7.9 Hz), 8.27 (1H, s), 8.11 (1H, d, J=1.0 Hz), 7.90 (1H, d, J=1.0 Hz), 7.77 (2H, m d, J=8.8 Hz), 7.58 (1H, d d, J=4.9, 7.9 Hz), 6.96 (2H, m d, J=8.8 Hz), 4.64 (1H, d br, J=12.0 Hz), 4.37 (1H, d br, J=12.0 Hz), 4.22 (1H, m), 3.77 (3H, s), 3.25 (1H, m), 2.97 (3H, s), 2.92 (1H, m), 1.88 (4H, m)

Compound no. 547 (MP: 204-205). NMR solvent: CDCl3
13C: 168.8, 159.2, 151.6, 142.3, 136.9, 126.4, 125.6, 114.1, 111.9, 55.3 (2 sig.), 45.5, 40.7, 31.9, 29.1, 28.4, 21.4

1H: 7.91 (1H, d, J=1.3 Hz), 7.72 (2H, m d, J=8.8 Hz), 7.40 (1H, d, J=1.3 Hz), 6.94 (2H, m d, J=8.8 Hz), 4.82 (1H, m d, J=13.5 Hz), 4.27 (1H, m), 3.95 (1H, m d, J=14.0 Hz), 3.84 (3H, s), 3.18 (1H, d t, J=2.5, 13.5 Hz), 3.0 (3H, s), 2.61 (1H, d t, J=2.5, 13.0 Hz), 2.13 (3H, s), 1.93 (1H, m), 1.88 (1H, m), 1.74 (2H, m)

Compound no. 548 (MP: 196-197). NMR solvent: CDCl3
13C: 168.8, 151.2, 148.6, 146.7, 139.4, 137.4, 132.5, 128.8, 123.6, 113.8, 55.4, 45.4, 40.6, 32, 29.1, 28.3, 21.4

1H: 9.0 (1H, d, J=2.0 Hz), 8.53 (1H, d d, J=1.6, 4.9 Hz), 8.11 (1H, d d d, J=1.8, 2.2, 7.9 Hz), 7.96 (1H, d, J=1.3 Hz), 7.59 (1H, d, J=1.3 Hz), 7.34 (1H, d d d, J=0.9, 4.9, 8.0 Hz), 4.83 (1H, m d, J=13.5 Hz), 4.28 (1H, m), 3.96 (1H, m d, J=14.0 Hz), 3.19 (1H, m t, J=2.7, 13.5 Hz), 3.01 (3H, s), 2.61 (1H, d t, J=2.8, 13.2 Hz), 2.13 (3H, s), 1.94 (1H, m), 1.89 (1H, m), 1.75 (2H, m)

Compound no. 549 (MP: 206-207). NMR solvent: CDCl3
13C: 159.2, 151.6, 142.3, 137.3, 136.8, 132.0 (q, J=34.0 Hz), 130.7, 130.1, 129.7 (q, J=3.8 Hz), 126.4, 125.5, 124.5 (q, J=3.8 Hz), 123.1 (q, J=273.0 Hz), 114.1, 111.9, 55.3, 54.2, 45.6, 31.9, 28.0

1H: 8.03 (1H, t br), 7.97 (1H, d, J=7.9 Hz), 7.90 (1H, d, J=8.0 Hz), 7.87 (1H, d, J=1.3 Hz), 7.73 (1H, t, J=7.9 Hz), 7.70 (2H, m d, J=8.9 Hz), 7.36 (1H, d, J=1.3 Hz), 6.93 (2H, m d, J=8.9 Hz), 4.01 (3H, m), 3.84 (3H, s), 3.02 (3H, s), 2.42 (2H, d t, J=2.8, 11.8 Hz), 2.0 (2H, d q, J=4.0, 12.3 Hz), 1.93 (2H, d br)

Compound no. 550 (MP: 89-101 (dec)). NMR solvent: DMSO
13C: 167.9, 151, 140.5, 140.1, 140, 138.5, 137.7, 135, 134.1, 129.6, 129.4, 129, 128.8, 128.2, 127, 126.7, 125.8, 125.6, 124.2, 123.1, 114.9, 61.9, 55.5, 52.2, 31.6, 28.2

1H: 8.20 (1H, t, J=1.6 Hz), 8.18 (1H, t, J=1.7 Hz), 8.15 (2H, s), 8.14 (1H, s br), 7.88 (3H, m), 7.62 (1H, d d d, J=1.2, 1.8, 7.8 Hz), 7.57 (1H, t, J=7.8 Hz), 7.51 (1H, t, J=7.8 Hz), 7.47 (1H, s br), 7.37-7.20 (5H, m), 3.85 (1H, m), 3.47 (2H, s), 2.96 (3H, s), 2.90 (2H, d br, J=12.0 Hz), 2.01 (2H, t br, J=12.0 Hz), 1.84 (2H, d q, J=3.5, 12.0 Hz), 1.73 (2H, d br, J=12.0 Hz)

Compound no. 551 (MP: 258-260 (dec)). NMR solvent: DMSO
13C: 160.1, 157.3, 150.6, 139.4, 138.1, 137.1, 126.5, 125.3, 121.5, 116.2, 56.9, 31.4, 29, 25.2, 24.8

1H: 12.94 (1H, s br), 8.19 (1H, s), 8.18 (1H, s), 8.04 (2H, m d, J=8.4 Hz), 7.83 (2H, m d, J=8.4 Hz), 3.82 (1H, m br), 2.93 (3H, s), 1.78 (4H, m), 1.58 (3H, m), 1.30 (2H, q, J=13.0 Hz), 1.11 (1H, q, J=13.0 Hz)

Compound no. 552 (MP: 126 (dec.)). NMR solvent: DMSO
13C: 164.2, 150.9, 140, 137.8, 133.6, 133.3, 128.7, 127.3, 125.4, 123.3, 115, 59.6, 55.6, 52.4, 31.5, 28.2, 19.8, 11.9

1H: 11.25 (1H, s br), 9.09 (1H, s br), 8.23 (1H, t, J=1.7 Hz), 8.15 (1H, d, J=1.3 Hz), 8.05 (1H, d, J=1.3 Hz), 7.97 (1H, m d, J=7.9 Hz), 7.62 (1H, m d, J=7.8 Hz), 7.46 (1H, t, J=7.7 Hz), 3.81 (1H, m), 2.94 (3H, s), 2.93 (2H, m), 2.22 (2H, m), 1.91 (2H, t br, J=11.0 Hz), 1.81 (2H, d q, J=3.2, 11.7 Hz), 1.72 (2H, d br, J=11.7 Hz), 1.42 (2H, m), 0.84 (3H, t, J=7.5 Hz)

Compound no. 553 (MP: 271-272). NMR solvent: DMSO
13C: 156.2, 150.7, 139.7, 137.8, 135.7, 134.9, 130, 123.1, 122.8, 120.7, 115.2, 56.8, 31.4, 29, 25.2, 24.8

1H: 10.12 (1H, s), 8.16 (1H, s), 8.10 (1H, s), 7.77 (1H, d, J=8.0 Hz), 7.71 (1H, t br), 7.60 (4H, s br), 7.45 (1H, t, J=7.8 Hz), 7.11 (1H, d d, J=1.3, 7.9 Hz), 3.81 (1H, m br), 2.93 (3H, s), 1.78 (4H, m), 1.58 (3H, m), 1.29 (2H, q, J=12.5 Hz), 1.11 (1H, q, J=13.0 Hz)

Compound no. 554 (MP: 187-188). NMR solvent: DMSO
13C: 172.1, 160.3, 151, 140.2, 137.4, 130.5, 124.4, 124.2, 117.7, 114.4, 113.3, 59.5, 55.4, 52.3, 31.6, 28, 19.7, 11.9

1H: 13.03 (1H, s), 8.50 (1H, s br), 8.32 (1H, d, J=2.0 Hz), 8.12 (1H, d, J=1.3 Hz), 7.97 (1H, s br), 7.88 (1H, d d, J=2.0, 8.5 Hz), 7.86 (1H, d, J=1.3 Hz), 6.91 (1H, d, J=8.5 Hz), 3.84 (1H, m), 2.98 (2H, m), 2.95 (3H, s), 2.26 (2H, m), 1.97 (2H, br), 1.84 (2H, q, J=12.5 Hz), 1.73 (2H, d, J=11.5 Hz), 1.44 (2H, m), 0.84 (3H, t, J=7.3 Hz)

Compound no. 555 (MP: 219-222). NMR solvent: DMSO
13C: 158.4, 149, 137, 135.4, 127.2, 118.7, 115.9, 114.2, 52.7, 42.5, 32, 24.8

1H: 9.89 (1H, br), 9.3 (1H, s), 8.7 (1H, d, J=10.5 Hz), 8.42 (1H, q, J=10.5 Hz), 8.24 (1H, s), 7.68 (2H, m d, J=8.7 Hz), 6.88 (2H, m d, J=8.7 Hz), 4.22 (1H, m), 3.40 (2H, d br, J=12.0 Hz), 3.06 (2H, q br, J=11.5 Hz), 2.97 (3H, s), 2.09 (2H, d q, J=3.5, 12.5 Hz), 1.96 (2H, d br, J=12.5 Hz)

Compound no. 556 (MP: 141). NMR solvent: CDCl3
13C: 151.7, 142.4, 141.4, 140.3, 138.1, 136.8, 129.1, 128.8, 128.3, 127.1, 119.4, 115.4, 112.3, 111.9, 62.8, 55.8, 52.5, 43.5, 31.6, 28.9

1H: 7.89 (1H, d, J=1.3 Hz), 7.38 (1H, d, J=1.3 Hz), 7.36-7.23 (5H, m), 7.21 (1H, d, J=2.0 Hz), 7.15 (1H, d d, J=2.0, 8.2 Hz), 7.03 (1H, d, J=8.2 Hz), 4.01 (3H, m), 3.52 (2H, s), 3.0 (3H, s), 2.99 (2H, m), 2.69 (6H, s), 2.09 (2H, t br, J=12.0 Hz), 1.92 (2H, d q, J=3.5, 12.0 Hz), 1.77 (2H, d br, J=12.0 Hz)

Compound no. 557 (MP: 183-184). NMR solvent: CDCl3
13C: 170.5, 163.9, 159.3, 151.7, 142.4, 136.9, 126.5, 125.5, 114.1, 111.9, 55.3, 54.9, 43.4, 32.1, 28.3

1H: 7.93 (1H, d, J=1.3 Hz), 7.72 (2H, m d, J=8.9 Hz), 7.41 (1H, d, J=1.3 Hz), 6.95 (2H, m d, J=8.9 Hz), 4.97 (2H, m d, J=13.5 Hz), 4.38 (1H, m), 3.84 (3H, s), 3.05 (2H, d t, J=2.7, 13.5 Hz), 3.02 (3H, s), 2.02 (2H, d br, J=13.0 Hz), 1.82 (2H, d q, J=4.5, 12.5 Hz)

Compound no. 558 (MP: 179 (dec.)). NMR solvent: DMSO
13C: 169.4, 150.9, 148.1, 146.2, 138.2, 137.8, 131.9, 129.1, 123.8, 115.5, 58.1, 54.1, 51.5, 31.5, 26.9

1H: 9.07 (1H, s), 8.46 (1H, m), 8.18 (3H, m), 7.43 (1H, m), 3.95 (1H, m), 3.31 (2H, s), 3.18 (2H, m), 2.96 (3H, s), 2.58 (2H, m), 2.0 (2H, q br, J=12.0 Hz), 1.81 (2H, d br, J=11.0 Hz)

Compound no. 559 (MP: 194-195). NMR solvent: CDCl3
13C: 159.1, 156.1, 151.2, 148.6, 146.7, 144, 139.3, 137.3, 132.4, 128.9, 123.6, 118.8, 113.9, 110.9, 55.4, 54.5, 52.2, 51.9, 31.7, 28.6

1H: 9.0 (1H, d, J=1.8 Hz), 8.52 (1H, d d, J=1.5, 4.7 Hz), 8.10 (1H, t d, J=1.8, 7.9 Hz), 7.93 (1H, d, J=1.3 Hz), 7.57 (1H, d, J=1.3 Hz), 7.33 (1H, d d, J=4.9, 7.9 Hz), 7.14 (1H, d, J=3.5 Hz), 6.35 (1H, d, J=3.5 Hz), 4.0 (1H, m), 3.88 (3H, s), 3.64 (2H, s), 3.04 (2H, m), 3.02 (3H, s), 2.21 (2H, t br, J=12.0 Hz), 1.96 (2H, d q, J=3.6, 12.0 Hz), 1.81 (2H, d br, J=12.0 Hz)

Compound no. 560 (MP: 165). NMR solvent: CDCl3
13C: 152.1, 151.5, 149.3, 142.6, 137.6, 136.9, 122.4, 119.8, 115.8, 67, 54.4, 31.8, 29.5

1H: 8.57 (1H, d d d, J=1.0, 2.0, 4.8 Hz), 8.01 (1H, t d, J=1.1, 8.1 Hz), 8.0 (1H, d, J=1.5 Hz), 7.89 (1H, d, J=1.5 Hz), 7.76

(1H, t d, J=1.8, 7.7 Hz), 7.20 (1H, d d d, J=1.1, 4.8, 7.4 Hz), 4.31 (1H, m), 4.09 (2H, d d, J=4.7, 11.6 Hz), 3.51 (2H, d t, J=2.1, 12.0 Hz), 3.05 (3H, s), 1.94 (2H, d q, J=4.5, 12.0 Hz), 1.78 (2H, m d, J=12.3 Hz)

Compound no. 561 (MP: 201-202). NMR solvent: DMSO

13C: 151.1, 150.4 (d, J=240.5 Hz), 144.9 (d, J=12.5 Hz), 140, 137.7, 130.1 (d, J=3.5 Hz), 116.3 (d, J=18.5 Hz), 116.0 (d, J=6.5 Hz), 114.3 (d, J=2.5 Hz), 114.1, 52.1, 50.9, 50.2, 31.8, 25.3, 9.2

1H: 9.90 (1H, s), 9.36 (1H, s br), 8.13 (1H, s), 7.92 (1H, s), 7.46 (1H, d d, J=2.0, 8.7 Hz), 7.25 (1H, m), 7.14 (1H, dd, J=8.5, 11.3 Hz), 4.19 (1H, m), 3.58 (2H, m d, J=11.5 Hz), 3.10 (4H, m), 2.94 (3H, s), 2.18 (2H, m q, J=12.5 Hz), 2.0 (2H, d br, J=12.5 Hz), 1.24 (3H, t, J=7.2 Hz)

Compound no. 562 (MP: 190-192 (dec.)). NMR solvent: DMSO

13C: 151.3, 149.5, 137.2, 135.8, 126.5, 121.4, 121, 119.7, 116.7, 114.6, 58.7, 31.4, 28.2, 24.1

1H: 11.26 (1H, s br), 10.14 (3H, br), 8.96 (1H, s), 8.10 (1H, s), 7.84 (1H, d, J=2.2 Hz), 7.74 (1H, d d, J=2.2, 8.5 Hz), 7.19 (1H, d, J=8.6 Hz), 4.36 (1H, m), 2.95 (3H, s), 1.88 (2H, m), 1.69 (4H, m), 1.53 (2H, m)

Compound no. 563 (MP: 250-252). NMR solvent: DMSO

13C: 155.3, 150.8, 140.1, 138.9, 137.7, 134.8, 129.8, 122.9, 121.7, 120.5, 114.9, 56.8, 31.3, 29, 25.2, 24.8

1H: 8.12 (1H, s), 8.03 (1H, s), 7.63 (1H, d, J=7.8 Hz), 7.57 (1H, t br), 7.37 (1H, t, J=7.8 Hz), 7.0 (3H, br), 6.98 (1H, d, J=8.2 Hz), 3.8 (1H, m), 2.93 (3H, s), 1.78 (4H, m), 1.58 (3H, m), 1.29 (2H, m q, J=12.5 Hz), 1.11 (1H, m q, J=12.5 Hz)

Compound no. 564 (MP: 250). NMR solvent: DMSO

13C: 154.7, 151.1, 142.6, 140.3, 137.6, 130.8, 129.6, 118.6, 114.2, 109.6, 106, 58.4, 31.3, 28.2, 24

1H: 11.71 (1H, br), 8.10 (1H, d, J=1.2 Hz), 8.0 (1H, d, J=1.2 Hz), 7.59 (1H, d d, J=1.7, 8.3 Hz), 7.53 (1H, d, J=1.7 Hz), 7.29 (1H, d, J=8.3 Hz), 4.36 (1H, m), 2.93 (3H, s), 1.87 (2H, m), 1.68 (4H, m), 1.53 (2H, m)

Compound no. 565 (MP: 188-189). NMR solvent: CDCl3

13C: 151.5, 146.7, 142.2, 138, 136.8, 133.9, 129.6, 129.1, 128.3, 127.2, 115.5, 114.4, 113.1, 111.9, 62.8, 55.8, 52.5, 31.6, 28.9

1H: 7.90 (1H, s), 7.45 (1H, s), 7.38-7.24 (5H, m), 7.21 (1H, t br), 7.17 (1H, m), 7.16 (1H, m), 6.63 (1H, m d, J=7.5 Hz), 4.02 (1H, m), 3.74 (2H, s), 3.52 (2H, s), 3.01 (3H, s), 3.0 (2H, m), 2.10 (2H, t br, J=11.5 Hz), 1.93 (2H, d q, J=3.3, 12.0 Hz), 1.78 (2H, d br, J=11.0 Hz)

Compound no. 566 (MP: 196). NMR solvent: DMSO

13C: 163.9, 149.6, 137.8, 136.9, 133.5, 130.7, 129.1, 127.7, 126.4, 123.9, 115.9, 67.9, 56.5, 34.1, 31.5, 26.7

1H: 11.30 (1H, br), 8.81 (1H, s), 8.29 (1H, s), 8.25 (1H, s), 7.98 (1H, t d, J=1.4, 7.9 Hz), 7.70 (1H, t d, J=1.2, 7.9 Hz), 7.54 (1H, t, J=7.8 Hz), 3.85 (1H, m), 3.41 (1H, m), 2.94 (3H, s), 1.90 (2H, d br, J=12.0 Hz), 7.71 (4H, m), 1.25 (2H, q br, J=12.3 Hz)

Compound no. 567 (MP: 219-220). NMR solvent: DMSO

13C: 150.7, 139, 138.8, 138.5, 138.4, 138.3, 128.8, 128.2, 127.6, 127, 125.2, 116.8, 61.9, 55.6, 52.2, 43.7, 31.6, 28.2

1H: 8.25 (1H, d, J=1.1 Hz), 8.20 (1H, d, J=1.1 Hz), 8.10 (2H, m d, J=8.7 Hz), 7.93 (2H, m d, J=8.7 Hz), 7.36-7.20 (5H, m), 3.83 (1H, m), 3.46 (2H, s), 3.22 (3H, s), 2.95 (3H, s), 2.90 (2H, m d, J=11.0 Hz), 2.0 (2H, t br, J=11.0 Hz), 1.83 (2H, d q, J=3.5, 12.0 Hz), 1.72 (2H, d br, J=12.0 Hz)

Compound no. 568 (MP: 193-194). NMR solvent: DMSO

13C: 158.3, 148.9, 137.0, 136.9, 135.3, 131.6, 131.3, 130.1 (q, J=33.0 Hz), 130.0 (q, J=3.5 Hz), 127.1, 123.8 (q, J=4.2 Hz), 123.4 (q, J=273.0 Hz), 118.8, 115.9, 114.2, 54.3, 45.2, 31.9, 27.3

1H: 9.88 (1H, br), 9.21 (1H, s), 8.17 (1H, s), 8.14 (1H, d br, J=7.8 Hz), 8.10 (1H, d br, J=8.0 Hz), 7.99 (1H, t br), 7.92 (1H, t, J=7.9 Hz), 7.64 (2H, m d, J=8.7 Hz), 6.86 (2H, m d, J=8.7 Hz), 3.91 (1H, m), 3.84 (2H, m), 2.94 (3H, s), 2.48 (2H, m), 1.86 (4H, m)

Compound no. 569 (MP: 157-158). NMR solvent: CDCl3

13C: 157.9, 151.2, 149.5, 148.5, 146.7, 139.3, 137.3, 136.4, 132.4, 128.9, 123.6, 123.3, 122.2, 113.9, 64.2, 55.7, 52.7, 31.7, 28.7

1H: 9.0 (1H, d, J=2.2 Hz), 8.59 (1H, d d d, J=1.0, 1.8, 4.9 Hz), 8.53 (1H, d d, J=1.6, 4.8 Hz), 8.11 (1H, d d d, J=1.8, 2.2, 7.9 Hz), 7.94 (1H, d, J=1.3 Hz), 7.67 (1H, d t, J=1.9, 7.7 Hz), 7.57 (1H, d, J=1.3 Hz), 7.37 (1H, d, J=7.7 Hz), 7.34 (1H, d d d, J=0.8, 4.8, 7.9 Hz), 7.19 (1H, d d d, J=1.0, 4.9, 7.7 Hz), 4.05 (1H, m), 3.68 (2H, s), 3.04 (2H, m d, J=12.0 Hz), 3.03 (3H, s), 2.23 (2H, t br, J=11.5 Hz), 2.01 (2H, d q, J=3.5, 12.0 Hz), 1.79 (2H, d br, J=12.0 Hz)

Compound no. 570 (MP: 206-207). NMR solvent: MeOD

13C: 153.2, 152.8 (d, J=241.0 Hz), 146.6 (d, J=13.5 Hz), 142.5, 139.2, 131.0 (d, J=3.5 Hz), 118.0 (d, J=6.5 Hz), 117.3 (d, J=19.3 Hz), 116.0 (d, J=3.0 Hz), 115.1, 60.0, 55.2, 53.3, 33.3, 27.4, 19.5, 11.6

1H: 8.12 (1H, d, J=1.4 Hz), 7.75 (1H, d, J=1.4 Hz), 7.36 (1H, d d, J=2.3, 8.5 Hz), 7.22 (1H, m), 7.06 (1H, d d, J=8.4, 11.0 Hz), 4.22 (1H, m), 3.60 (2H, d br, J=12.0 Hz), 3.07 (3H, s), 2.98 (4H, m), 2.25 (2H, d q, J=3.0, 13.0 Hz), 2.12 (2H, d br, J=13.0 Hz), 1.76 (2H, m), 1.02 (3H, t, J=7.5 Hz)

Compound no. 571 (MP: 182). NMR solvent: DMSO

13C: 163.7, 150.3, 138.1, 138, 134.1, 131.7, 131.4, 129.7, 129.7, 129, 127.5, 124.8, 116.1, 59, 52.3, 50.5, 31.9, 25

1H: 11.29 (1H, br), 9.65 (1H, s br), 8.59 (1H, s), 8.27 (1H, s), 7.93 (2H, m d, J=8.5 Hz), 7.81 (2H, m d, J=8.6 Hz), 7.56 (2H, m), 7.48 (3H, m), 4.32 (2H, d, J=5.0 Hz), 4.19 (1H, m), 3.46 (2H, d br, J=12.0 Hz), 3.17 (2H, m), 3.95 (3H, s), 2.21 (2H, q br, J=13.0 Hz), 2.0 (2H, d br, J=12.5 Hz)

Compound no. 572 (MP: 223). NMR solvent: DMSO

13C: 171.3, 160.9, 149.5, 137.4, 136, 131.5, 130.8, 129.7, 129.7, 128.9, 125.9, 120, 118, 115.1, 114.7, 59, 52.4, 50.5, 32, 24.9

1H: 13.0 (1H, br), 9.77 (1H, s), 9.06 (1H, s), 8.47 (1H, s), 8.44 (1H, s), 8.23 (1H, s), 8.08 (1H, s), 7.89 (1H, d, J=8.5 Hz), 7.59 (2H, m), 7.49 (3H, m), 7.02 (1H, d, J=8.5 Hz), 4.35 (2H, d, J=4.0 Hz), 4.26 (1H, m), 3.48 (2H, d br, J=11.0 Hz), 3.18 (2H, m), 3.0 (3H, s), 2.26 (2H, q br, J=12.0 Hz), 2.02 (2H, d br, J=12.5 Hz)

Compound no. 573 (MP: 173-174). NMR solvent: CDCl3

13C: 165.1, 164.9, 159.2, 151.7, 151.6, 150.4, 150.2, 147.1, 146.8, 142.3, 142.3, 136.9, 136.9, 136.8, 132, 131.8, 126.4, 125.5, 125.5, 122.8, 122.8, 114.1, 111.9, 111.8, 55.3, 55.2, 54.9, 46.4, 45.6, 41, 40.9, 32.3, 32, 28.9, 28.9, 28.3, 28.2

1H: 8.48 (1H, d d, J=1.8, 4.8 Hz), 7.91 (1H, m), 7.71 (2H, m d, J=8.8 Hz), 7.71 and 7.64 (1H: 2 m), 7.40 (1H, m), 7.35 (1H, d d, J=4.9, 7.5 Hz), 6.94 (2H, m d, J=8.8 Hz), 4.98 (1H, m), 4.32 (1H, m), 3.84 (3H, s), 3.54 (1H, m), 3.34 and 3.15 (1H, 2 m), 3.04 and 3.03 (3H, 2 s), 2.89 (1H, m), 2.11-1.58 (4H, m)

Compound no. 574 (MP: 242-243). NMR solvent: DMSO

13C: 168.1, 156.7, 151.2, 141, 137.4, 126.1, 124.5, 115.4, 112.5, 55.1, 44.9, 40, 31.6, 28.6, 28, 21.4

1H: 9.46 (1H, s), 8.07 (1H, s), 7.79 (1H, s), 7.64 (2H, d, J=8.0 Hz), 6.77 (2H, d, J=8.0 Hz), 4.50 (1H, d, J=12.5 Hz), 4.09 (1H, m br), 3.90 (1H, d, J=12.5 Hz), 3.10 (1H, m), 2.91 (3H, s), 2.50 (1H, m), 2.01 (3H, m), 1.78 (1H, m), 1.61 (1H, m)

Compound no. 575 (MP: 233-234). NMR solvent: DMSO

13C: 156.2, 153.3, 150.9, 139.8, 137.6, 126.6, 125.2, 124.2, 123.1, 113.8, 112.8, 56.8, 55.9, 31.3, 29, 25.2, 24.8

1H: 9.13 (1H,$), 8.10 (1H, d, J=1.3 Hz), 7.97 (1H, d, J=1.3 Hz), 7.83 (1H, d d, J=2.3, 8.6 Hz), 7.69 (1H, d, J=2.3 Hz), 7.21 (3H, s br), 7.19 (1H, d, J=8.6 Hz), 3.85 (3H, s), 3.80 (1H, m), 2.92 (3H, s), 1.77 (4H, m), 1.59 (3H, m), 1.29 (2H, q br, J=12.5 Hz), 1.11 (1H, q br, J=12.5 Hz)

Compound no. 576 (MP: 137-138). NMR solvent: DMSO
13C: 155.8, 150.7, 139.7, 137.9, 134.5, 129.7, 127.1, 125.4, 125.2, 123.1, 115.3, 56.8, 31.4, 29, 25.2, 24.9
1H: 8.56 (1H, s br), 8.19 (1H, s), 8.13 (1H, s), 8.02 (1H, m d, J=7.9 Hz), 7.91 (1H, m d, J=7.8 Hz), 7.61 (1H, t, J=7.9 Hz), 3.83 (1H, m), 2.95 (3H, s), 1.79 (4H, m), 1.58 (3H, m), 1.30 (2H, q br, J=13.0 Hz), 1.12 (1H, q br, J=13.0 Hz)

Compound no. 577 (MP: 146-147). NMR solvent: DMSO
13C: 151.3, 148, 141.7, 138.5, 137.1, 128.8, 128.2, 127, 125.8, 121.2, 113.9, 111.4, 61.9, 55.5, 52.3, 31.4, 28.3
1H: 8.0 (1H, s), 7.65 (1H, s), 7.49 (2H, m d, J=8.5 Hz), 7.36-7.21 (5H, m), 6.56 (2H, m d, J=8.5 Hz), 5.13 (2H, s), 3.80 (1H, m), 3.46 (2H, s), 2.92 (3H, s), 2.88 (2H, d br, J=13.0 Hz), 1.99 (2H, t br, J=11.0 Hz), 1.81 (2H, d q, J=3.0, 12.0 Hz), 1.70 (2H, d br, J=11.5 Hz)

Compound no. 578 (MP: 167-168). NMR solvent: DMSO
13C: 150.8, 142.3, 139.3, 138.1, 136.6, 129, 128.7, 128.3, 127.1, 126.2, 124.9, 116.2, 61.8, 55.4, 52.1, 31.6, 28
1H: 8.18 (2H, 2 s), 8.03 (2H, m d, J=8.6 Hz), 7.83 (2H, m d, J=8.6 Hz), 7.40-7.20 (5H, m), 7.28 (2H, s br), 3.86 (1H, m br), 3.49 (2H, br), 2.95 (5H, m), 2.02 (2H, br), 1.87 (2H, br), 1.76 (2H, br)

Compound no. 579 (MP: 168). NMR solvent: DMSO
13C: 151.1, 148, 141.7, 137, 125.8, 121.3, 113.9, 111.4, 56.8, 31.3, 29.1, 25.2, 24.9
1H: 8.0 (1H, d, J=1.3 Hz), 7.64 (1H, d, J=1.3 Hz), 7.48 (2H, m d, J=8.5 Hz), 6.56 (2H, m d, J=8.5 Hz), 5.13 (2H, s), 3.80 (1H, m), 2.91 (3H, s), 1.77 (4H, m), 1.58 (3H, m), 1.29 (2H, m, J=12.6 Hz), 1.11 (1H, m, J=12.6 Hz)

Compound no. 580 (MP: 183-184). NMR solvent: DMSO
13C: 150.9, 140.6, 138.5, 137.4, 127.3, 125.3, 118, 113.4, 56.8, 31.3, 29, 25.2, 24.9
1H: 9.55 (1H, s br), 8.07 (1H, d, J=1.3 Hz), 7.88 (1H, d, J=1.3 Hz), 7.73 (2H, m d, J=8.7 Hz), 7.16 (2H, m d, J=8.7 Hz), 7.13 (2H, s br), 3.81 (1H, m), 2.92 (3H, s), 1.78 (4H, m), 1.57 (3H, m), 1.29 (2H, q br, J=12.7 Hz), 1.11 (1H, m q, J=12.5 Hz)

Compound no. 581 (MP: 182 (dec.)). NMR solvent: DMSO
13C: 155.7, 153, 151, 140.1, 138.5, 137.5, 128.8, 128.2, 127, 126.5, 123.6 (2 sig.), 113.5, 112.6, 61.9, 55.5, 52.2, 31.5, 28.2
1H: 8.09 (1H, d, J=1.3 Hz), 7.93 (1H, d, J=1.3 Hz), 7.72 (1H, d d, J=1.7, 8.6 Hz), 7.59 (1H, s br), 7.36-7.21 (5H, m), 7.12 (1H, d, J=8.6 Hz), 7.01 (4H, br), 3.81 (1H, m), 3.81 (3H, s), 3.47 (2H, s), 2.93 (3H, s), 2.90 (2H, d br, J=11.5 Hz), 1.99 (2H, t br, J=11.2 Hz), 1.83 (2H, d q, J=3.5, 12.1 Hz), 1.71 (2H, d br, J=12.5 Hz)

Compound no. 582 (MP: 199-200). NMR solvent: CDCl3
13C: 159.3, 151.7, 142.4, 136.9, 126.5, 125.5, 117.4, 114.1, 111.8, 55.3, 53.8, 49, 32.2, 27.7
1H: 7.91 (1H, d, J=1.3 Hz), 7.72 (2H, m d, J=8.8 Hz), 7.39 (1H, d, J=1.3 Hz), 6.95 (2H, m d, J=8.8 Hz), 4.19 (1H, m), 3.85 (3H, s), 3.59 (2H, d, J=13.5 Hz), 3.19 (2H, d t, J=2.9, 12.9 Hz), 3.06 (3H, s), 2.0 (2H, d q, J=4.4, 12.3 Hz), 1.91 (2H, d br, J=12.0 Hz)

Compound no. 583 (MP: 166-167). NMR solvent: CDCl3
13C: 159.2, 151.6, 142.2, 136.8, 126.5, 125.6, 114.5, 114.1, 112, 55.3, 54.5, 51.5, 46, 31.9, 28.3
1H: 7.90 (1H, d, J=1.3 Hz), 7.72 (2H, m d, J=9.0 Hz), 7.40 (1H, d, J=1.3 Hz), 6.94 (2H, m d, J=9.0 Hz), 4.07 (1H, m), 3.84 (3H, s), 3.54 (2H, s), 3.03 (3H, s), 2.94 (2H, m d, J=11.5 Hz), 2.51 (2H, d t, J=3.0, 11.5 Hz), 1.97 (2H, d q, J=4.0, 12.0 Hz), 1.90 (2H, m)

Compound no. 584 (MP: 189-191). NMR solvent: CDCl3
13C: 151.2, 148.6, 146.7, 139.4, 137.3, 132.5, 128.9, 123.6, 114.5, 113.8, 54.7, 51.4, 45.9, 32, 28.3
1H: 9.02 (1H, d, J=2.0 Hz), 8.55 (1H, d d, J=1.7, 4.9 Hz), 8.13 (1H, t d, J=1.9, 8.0 Hz), 7.96 (1H, d, J=1.3 Hz), 7.59 (1H, d, J=1.3 Hz), 7.35 (1H, d d, J=4.9, 8.0 Hz), 4.08 (1H, m), 3.55 (2H, s), 3.05 (3H, s), 2.96 (2H, d br, J=11.4 Hz), 2.53 (2H, d t, J=3.0, 11.5 Hz), 1.98 (2H, d q, J=3.9, 12.0 Hz), 1.92 (2H, m)

Compound no. 585 (MP: 197-198 (dec)). NMR solvent: DMSO
13C: 157.8, 149.8, 137.6, 137.1, 131.1, 130, 116.1, 115.4, 115.3, 112.1, 57.3, 52.3, 50.7, 31.9, 25.1, 17, 11
1H: 9.39 (1H, s), 8.90 (1H, s), 8.21 (1H, s), 7.26 (3H, m), 6.78 (1H, m), 4.22 (1H, m), 3.59 (2H, d br, J=11.5 Hz), 3.12 (2H, q br, J=11.5 Hz), 3.0 (2H, m), 2.97 (3H, s), 2.23 (2H, d q, J=3.0, 13.0 Hz), 2.0 (2H, d br, J=12.5 Hz), 1.70 (2H, m), 0.91 (3H, t, J=7.5 Hz)

Compound no. 586 (MP: 183 (dec.)). NMR solvent: MeOD
13C: 150.1, 149.1, 147.6, 137.9, 136.6, 119.3, 118.8, 117.1, 116, 114.4, 59.8, 55.1, 53, 33.7, 26.9, 18.9, 11.4
1H: 9.31 (1H, d, J=1.3 Hz), 8.09 (1H, d, J=1.3 Hz), 7.17 (1H, d, J=2.2 Hz), 7.10 (1H, d d, J=2.2, 8.2 Hz), 6.90 (1H, d, J=8.2 Hz), 4.33 (1H, m), 3.74 (2H, d br, J=12.5 Hz), 3.19 (2H, d t, J=2.8, 13.0 Hz), 3.11 (3H, s), 3.11 (2H, m), 2.36 (2H, d q, J=3.2, 12.8 Hz), 2.23 (2H, d br, J=13.5 Hz), 1.82 (2H, m), 1.04 (3H, t, J=7.5 Hz)

Compound no. 587 (MP: 153-156 (dec.)). NMR solvent: MeOD
13C: 158.7, 153.4, 152.4, 151.1, 143.5, 139.3, 139, 127.9, 125.6, 125.6, 125.5, 116.6, 113.8, 61.5, 54.8, 53.6, 33.3, 26.9
1H: 8.69 (1H, d, J=5.0 Hz), 8.11 (1H, d, J=1.3 Hz), 7.92 (1H, d t, J=1.7, 7.6 Hz), 7.67 (1H, d, J=1.3 Hz), 7.61 (2H, m d, J=8.7 Hz), 7.52 (1H, d, J=7.9 Hz), 7.47 (1H, d d, J=5.0, 7.6 Hz), 6.81 (2H, m d, J=8.7 Hz), 4.45 (2H, s), 4.28 (1H, m), 3.65 (2H, d br, J=11.5 Hz), 3.25 (2H, m), 3.09 (3H, s), 2.31 (2H, q br, J=13.0 Hz), 2.14 (2H, d br, J=12.5 Hz), Compound no. 588 (MP: 184). NMR solvent: DMSO
13C: 151.1, 140.6, 138.5, 137.4, 128.8, 128.2, 127.3, 127, 125.3, 118, 113.3, 61.9, 55.5, 52.2, 31.5, 28.2
1H, 9.55 (1H, s br), 8.08 (1H, d, J=1.3 Hz), 7.88 (1H, d, J=1.3 Hz), 7.73 (2H, m d, J=8.7 Hz), 7.36-7.20 (5H, m), 7.16 (2H, m d, J=8.7 Hz), 7.13 (2H, s br), 3.81 (1H, m), 3.46 (2H, s), 2.94 (3H, s), 2.89 (2H, m d, J=11.0 Hz), 2.0 (2H, t br, J=11.0 Hz), 1.83 (2H, d q, J=3.0, 12.0 Hz), 1.71 (2H, d br, J=12.0 Hz)

Compound no. 589 (MP: 126-129 (dec.)). NMR solvent: DMSO
13C: 152.8, 151.1, 148.9, 141.1, 138.5, 137.5, 134, 129.1, 128.8, 128.2, 127, 122, 119.6, 117.8, 114.1, 61.9, 55.5, 52.2, 31.5, 28.3
1H: 8.08 (1H, d, J=1.3 Hz), 7.91 (1H, d, J=1.3 Hz), 7.37 (1H, t d, J=1.3, 7.8 Hz), 7.33-7.23 (6H, m), 7.21 (1H, t, J=7.7 Hz), 6.72 (1H, d, J=7.9 Hz), 5.58 (4H, s br), 3.81 (1H, m), 3.46 (2H, s), 2.93 (3H, s), 2.89 (2H, m d, J=11.5 Hz), 2.0 (2H, t br, J=11.5 Hz), 1.82 (2H, d q, J=3.3, 12.0 Hz), 1.71 (2H, d br, J=12.0 Hz)

Compound no. 590 (MP: 179-180). NMR solvent: DMSO
13C: 155.6, 150.9, 139.7, 138, 134.5, 129.8, 127.2, 125.5, 125, 123.1, 115.3, 66.3, 54.2, 31.7, 29.1
1H: 8.57 (1H, s), 8.22 (1H, s), 8.16 (1H, s), 8.04 (1H, d, J=7.7 Hz), 7.92 (1H, d, J=7.8 Hz), 7.62 (1H, t, J=7.6 Hz), 4.12

(1H, m), 3.94 (2H, d d, J=3.7, 11.2 Hz), 3.39 (2H, t, J=11.5 Hz), 2.98 (3H, s), 1.87 (2H, d q, J=4.3, 12.2 Hz), 1.71 (2H, d br, J=12.0 Hz)

Compound no. 591 (MP: 187-188). NMR solvent: DMSO
13C: 160.1, 157.5, 150.7, 139.4, 138, 134.5, 129.7, 128.2, 124.5, 123.8, 122.2, 115.5, 56.8, 31.4, 29, 25.1, 24.8
1H: 13.0 (1H, s br), 8.32 (1H, t, J=1.5 Hz), 8.19 (1H, d, J=1.3 Hz), 8.11 (1H, d, J=1.3 Hz), 8.06 (1H, t d, J=1.5, 7.8 Hz), 7.68 (1H, t d, J=1.5, 7.8 Hz), 7.59 (1H, t, J=7.8 Hz), 3.83 (1H, m), 2.94 (3H, s), 1.79 (4H, m), 1.58 (3H, m), 1.30 (2H, q br, J=13.5 Hz), 1.58 (1H, m)

Compound no. 592 (MP: 148-149). NMR solvent: DMSO
13C: 158.5, 155.6, 151, 140.6, 137.5, 126.1, 126, 114, 113.1, 55.5, 55.1, 45.7, 31.6, 27.6
1H: 8.31 (1H, s), 8.09 (1H, s), 7.88 (1H, s), 7.77 (2H, m d, J=8.5 Hz), 6.95 (2H, m d, J=8.5 Hz), 5.20 (2H, s), 3.95 (1H, m br), 3.78 (3H, s), 3.69 (2H, d br, J=12.0 Hz), 2.92 (3H, s), 2.53 (2H, m), 1.78 (2H, q br, J=12.5 Hz), 1.70 (2H, m)

Compound no. 593 (MP: 100-103 (dec.)). NMR solvent: DMSO
13C: 150.9, 140.2, 138.8, 138.4, 137.7, 134.5, 129.6, 128.9, 128.2, 127, 120.5, 118.6, 116.2, 114.8, 61.8, 55.5, 52.2, 39.2, 31.5, 28.1
1H: 9.78 (1H, s), 8.12 (1H, d, J=1.3 Hz), 7.96 (1H, d, J=1.3 Hz), 7.73 (1H, t br, J=1.8 Hz), 7.56 (1H, m d, J=8.0 Hz), 7.33 (1H, t, J=8.0 Hz), 7.38-7.20 (5H, m), 7.11 (1H, m d, J=8.0 Hz), 3.83 (1H, m br), 3.48 (2H, br), 3.0 (3H, s), 2.94 (3H, s), 2.90 (2H, m br), 2.01 (2H, m br), 1.84 (2H, q br, J=11.0 Hz), 1.73 (2H, d br, J=11.0 Hz)

Compound no. 594 (MP: 138-140). NMR solvent: DMSO
13C: 160.1, 157.6, 151, 139.4, 138, 134.4, 129.7, 128.2, 124.5, 123.9, 122.2, 115.4, 58.4, 31.3, 28.2, 24
1H: 13.02 (1H, s br), 8.32 (1H, t br, J=1.6 Hz), 8.19 (1H, d, J=1.3 Hz), 8.10 (1H, d, J=1.3 Hz), 8.08 (1H, m d, J=8.0 Hz), 7.69 (1H, m d, J=8.0 Hz), 7.60 (1H, t, J=8.0 Hz), 4.38 (1H, m), 2.94 (3H, s), 1.88 (2H, m), 1.69 (4H, m), 1.54 (2H, m)

Compound no. 595 (MP: 228-229). NMR solvent: DMSO
13C: 159.1, 158.5, 151.1, 140.6, 137.5, 126.1, 126.0, 114.0, 113.1, 55.1, 54.6, 46.4, 31.7, 27.2
1H: 14.96 (1H, br), 8.10 (1H, d, J=1.3 Hz), 7.89 (1H, d, J=1.3 Hz), 7.77 (2H, m d, J=9.0 Hz), 6.96 (2H, m d, J=9.0 Hz), 4.12 (1H, m br), 3.95 (2H, m d, J=13.0 Hz), 3.77 (3H, s), 3.13 (2H, d t, J=3.5, 12.5 Hz), 2.93 (3H, s), 1.90 (2H, m), 1.86 (2H, m)

Compound no. 596 (MP: 178-180 (dec.)). NMR solvent: DMSO
13C: No data
1H: 8.09 (1H, d, J=1.3 Hz), 7.88 (1H, d, J=1.3 Hz), 7.77 (2H, m d, J=9.0 Hz), 6.95 (2H, m d, J=9.0 Hz), 5.99 (2H, s), 4.06 (2H, d br, J=13.5 Hz), 4.02 (1H, m), 3.77 (3H, s), 2.91 (3H, s), 2.71 (2H, t br, J=12.0 Hz), 1.71 (2H, m), 1.64 (2H, d q, J=4.0, 12.0 Hz)

Compound no. 597 (MP: 162-163). NMR solvent: DMSO
13C: No data
1H: 8.08 (1H, d, J=1.3 Hz), 7.87 (1H, d, J=1.3 Hz), 7.76 (2H, m d, J=9.0 Hz), 6.95 (2H, m d, J=9.0 Hz), 4.51 (1H, s br), 3.85 (1H, m br), 3.77 (3H, s), 3.51 (2H, s br), 3.05 (2H, br), 2.93 (3H, s), 2.48 (2H, m), 2.10 (2H, br), 1.88 (2H, s br), 1.75 (2H, s br)

3. Biological Efficacy of Compounds of the Invention The in vitro test was performed according to the protocol described below. The controls for both in vitro and in vivo were the reaction mix minus the test compounds. Therefore, a low value in Table 1 below for the test compounds indicates a strong inhibitor. A value of 100 indicates that no measurable inhibition took place.

The in vivo test was performed according to the protocol described below. BRh indicates inhibition in central nervous tissue and LVh indicates inhibition in peripheral tissue, in this case liver.

In vitro Protocol

The in vitro pharmaceutical FAAH activity was determined according to the following method:

Frozen brains (without cerebellum) from Wistar rats were used, and each brain was homogenized in 15 ml 1 mM $MgCL_2$, 20 nM HEPES pH 7.0 with Potter Elvejhem (8 strokes at 500 rpm). Homogenates were centrifuged for 20 min at 36000 g at 4° C. (Beckman, 70Ti rotor). Pellets were resuspended in 15 ml of the same buffer and centrifuged under the same conditions. Pellets were resuspended in 15 ml of the same buffer and incubated for 15 min at 37° C. after which they were centrifuged for 20 min at 36000 g at 4° C. Each pellet was then resuspended in 15 ml 3 mM $MgCl_2$, 1 mM EDTA, 50 mM Tris pH 7.4 and protein determined with BioRad Protein Assay (BioRad) using a standard curve of BSA (50-250 µg/ml). The membrane suspensions were aliquoted and stored at −80° C.

The FAAH activity was determined using AEA (labelled with 3H in the ethanolamine part of the molecule) as substrate and measuring the 3H-ethanolamine formed. Reaction mix (total volume of 200 up contained: 2 µM AEA (2 µM AEA+5 nM 3H-AEA), 0.1% fatty acid free BSA, 5 µg protein, in 1 mM EDTA, 10 mM Tris pH 7.6 and 10 µM or 0.1 µM compounds. Stock solutions of the compounds to test (10 mM) were prepared in 100% DMSO and the DMSO concentration in the assay was 0.1%. After a 15 min preincubation period at 37° C., reaction was started by the addition of the substrate solution (cold EAE+radiolabelled EAE+BSA). Reaction was carried out for 10 min before termination by the addition of 400 µl activated charcoal suspension (8 g charcoal in 32 ml 0.5 M HCl in continuous agitation). After a 30 min incubation period at room temperature with agitation, charcoal was sedimented by centrifugation in microfuge (10 min at 13000 rpm). 200 µl of the supernatant were added to 800 µl Optiphase Supermix scintillation cocktail previously distributed in 24-well plates. Counts per minute (cpm) were determined in Microbeta TriLux scintillation counter (10 min counting or until s=2).

In each assay blanks (no protein, usually below 200 cpm) and controls (no compound) were present. The results are reported in Table 1 as % of control after blank subtraction.

In vivo Protocol

Animal Treatment

The animals used for experiments were male NMRI mice (weighing 27-44 g) obtained from Interfauna Ibérica (Spain). Mice were kept 5 per cage, under controlled environmental conditions (12 hr light/dark cycle and room temperature 22±1° C.). Food and tap water were allowed ad libitum and the experiments were all carried out during daylight hours.

Animals were administered 30 mg/kg or 3 mg/kg compounds of the invention via oral route (8 ml/kg; compound suspended in 0.5% carboxymethylcellulose (CMC) or solubilized in water) or vehicle (controls) using animal feeding stainless steel curve needles (Perfectum, U.S.A.). Fifteen minutes before sacrifice animal were anesthetized with pentobarbital 60 mg/kg administered intraperitoneally. A fragment of liver, left lung lobe and brain without cerebellum were removed and put in plastic vials containing membrane buffer (3 mM $MgCl_2$, 1 mM EDTA, 50 mM Tris HCl pH 7.4). Tissues were stored at −30° C. until analysis.

Animals were always fasted overnight before administration of compounds except for time points of >18 h, where food was removed on the morning of day of administration and the compound was administered in the afternoon of the same day. Animals were then given water but nothing else.

All animal procedures were conducted in the strict adherence to the European Directive for Protection of Vertebrate Animals Used for Experimental and Other Scientific Purposes (86/609CEE) and Portuguese legislation (Decreto-Lei 129/92, Portarias 1005/92 e 1131/97). The number of animals used was the minimum possible in compliance with current regulations and scientific integrity Reagents and Solutions Anandamide [ethanolamine-1-$^3$H-] (40-60Ci/mmol) was obtained from American Radiochemicals. All other reagents were obtained from Sigma-Aldrich. Optiphase Supermix was obtained from Perkin Elmer and activated charcoal were obtained from Sigma-Aldrich.

Tissue Preparation

Tissues were thawed on ice and were homogenized in 10 volumes of membrane buffer (3 mM $MgCl_2$, 1 mM EDTA, 50 mM Tris HCl pH 7.4) with either Potter-Elvejhem (brains—8 strokes at 500 rpm) or Heidolph Diax (livers—2 strokes at position 5 for 20 sec with 30 sec pauses).

Total protein in tissues was determined with the BioRad Protein Assay (BioRad) using a standard curve of BSA (50-250 μg/ml).

Enzymatic Assay

Reaction mix (total volume of 200 μl) contained: 2 μl M AEA (2 μM AEA+5 nM $^3$H-AEA), 0.1% fatty acid free BSA, 15 μg (brain), 5 μg (liver) or 50 μg (lung) protein, in 1 mM EDTA, 10 mM Tris pH 7.6. After a 15 mM pre-incubation period at 37° C., reaction was started by the addition of the substrate solution (cold AEA+radiolabelled AEA+BSA). Reaction was carried out for 10 min (brain and lung) or 7 mM (liver) before termination by the addition of 400 μl activated charcoal suspension (8 g charcoal in 32 ml 0.5 M HCl in continuous agitation). After a 30 mM incubation period at room temperature with agitation, charcoal was sedimented by centrifugation in microfuge (10 min at 13000 rpm). 200 μl of the supernatant were added to 800 μl Optiphase Supermix scintillation cocktail previously distributed in 24-well plates. Counts per minute (cpm) were determined in a MicrobetaTri-Lux scintillation counter.

In each assay blanks (without protein) were prepared.

The percentage of remaining enzymatic activity was calculated in respect to controls and after blank subtraction.

TABLE 1

| | Name | Class | In Vitro 10 uM | In Vitro 100 nM | In Vivo BRh 30 mg · kg · 1 h | In Vivo LVh 30 mg · kg · 1 h | In Vivo BRh mg · 3 kg · 8 h | In Vivo LVh mg · 3 kg · 8 h |
|---|---|---|---|---|---|---|---|---|
| 1 | (1H-imidazol-1-yl)(morpholino)methanone | Imidazoles | 62.6 | | | | | |
| 2 | N-methyl-N-phenyl-1H-imidazole-1-carboxamide | Imidazoles | 11.7 | | | | | |
| 3 | morpholino(4-phenyl-1H-imidazol-1-yl)methanone | Imidazoles | 4.8 | | | | | |
| 4 | N-methyl-N,4-diphenyl-1H-imidazole-1-carboxamide | Imidazoles | 0.1 | 83.6 | 14.3 | 10.6 | | |
| 5 | N,3-diphenyl-1H-pyrazole-1-carboxamide | Pyrazoles | 91.3 | | | | | |
| 6 | N-(4-methoxyphenyl)-3-phenyl-1H-pyrazole-1-carboxamide | Pyrazoles | 91.1 | | | | | |
| 7 | N-methyl-N-phenyl-1H-1,2,4-triazole-1-carboxamide | 1,2,4-Triazoles | 0 | 17 | | | | |
| 8 | N-methyl-N-phenyl-1H-pyrazole-1-carboxamide | Pyrazoles | 13.2 | | | | | |
| 9 | N-phenyl-1H-pyrazole-1-carboxamide | Pyrazoles | 78.6 | | | | | |
| 10 | N-(4-phenoxyphenyl)-3-phenyl-1H-pyrazole-1-carboxamide | Pyrazoles | 55 | | | | | |
| 11 | N-(4-(benzyloxy)phenyl)-3-phenyl-1H-pyrazole-1-carboxamide | Pyrazoles | 82.6 | | | | | |
| 12 | N-methyl-N,3-diphenyl-1H-pyrazole-1-carboxamide | Pyrazoles | 86 | | | | | |
| 13 | morpholino(3-phenyl-1H-pyrazol-1-yl)methanone | Pyrazoles | 89.7 | | | | | |
| 14 | N-methyl-4-(naphthalen-2-yl)-N-phenyl-1H-imidazole-1-carboxamide | Imidazoles | 0 | 68.3 | 96.7 | 77.3 | | |
| 15 | N-(biphenyl-4-yl)-3-phenyl-1H-pyrazole-1-carboxamide | Pyrazoles | 66.9 | 103.8 | | | | |
| 16 | N-(4-methoxyphenyl)-N-methyl-(naphthalen-2-yl)-1H-imidazole-1-carboxamide | Imidazoles | 24.7 | | | | | |
| 17 | N-(4-methoxyphenyl)-N-methyl-4-phenyl-1H-imidazole-1-carboxamide | Imidazoles | 65 | | | | | |
| 18 | N-methyl-N-phenyl-1H-benzo[d]imidazole-1-carboxamide | Imidazoles | 67.9 | | | | | |
| 19 | (1H-benzo[d][1,2,3]triazol-1-yl)(morpholino)methanone | Benzotriazoles | 0.1 | 3.1 | 46.6 | 41.1 | | |
| 20 | 3-(biphenyl-4-yl)-N-phenyl-1H-pyrazole-1-carboxamide | Pyrazoles | 97.3 | | | | | |
| 21 | morpholino(3-(pyridin-3-yl)-1H-pyrazol-1-yl)methanone hydrochloride | Pyrazoles | 79.1 | | | | | |
| 22 | 3-(biphenyl-4-yl)-N-(3-methoxyphenyl)-1H-pyrazole-1-carboxamide | Pyrazoles | 95.8 | | | | | |
| 23 | 3-(biphenyl-4-yl)-N-(4-methoxyphenyl)-1H-pyrazole-1-carboxamide | Pyrazoles | 93 | | | | | |
| 24 | N-methyl-N-phenyl-3-(pyridin-3-yl)-1H-pyrazole-1-carboxamide | Pyrazoles | 22.9 | | | | | |
| 25 | 3-(biphenyl-4-yl)-N-methyl-N-phenyl-1H-pyrazole-1-carboxamide | Pyrazoles | 99 | | | | | |
| 26 | N-methyl-N,2-diphenyl-1H-imidazole-1-carboxamide | Imidazoles | 92.6 | | | | | |
| 27 | 4-(4-chlorophenyl)-N-methyl-N-phenyl-1H-imidazole-1-carboxamide | Imidazoles | 0.2 | 71.4 | | | | |
| 28 | 4-(4-methoxyphenyl)-N-methyl-N-phenyl-1H-imidazole-1-carboxamide | Imidazoles | 0.7 | 85.1 | | | | |
| 29 | 4-(4-fluorophenyl)-N-methyl-N-phenyl-1H-imidazole-1-carboxamide | Imidazoles | 0 | 52.5 | 10.7 | 17.2 | | |
| 30 | 4-(2-fluorophenyl)-N-methyl-N-phenyl-1H-imidazole-1-carboxamide | Imidazoles | 0.1 | 72.5 | | | | |
| 31 | 4-(3-methoxyphenyl)-N-methyl-N-phenyl-1H-imidazole-1-carboxamide | Imidazoles | 0 | 69 | | | | |
| 32 | 6-chloro-N-methyl-N-phenyl-1H-benzo[d][1,2,3]triazole-1-carboxamide | Benzotriazoles | 0 | 0.1 | 85.9 | 64.9 | | |
| 33 | 5-chloro-N-methyl-N-phenyl-1H-benzo[d][1,2,3]triazole-1-carboxamide | Benzotriazoles | 0 | 6.2 | 82.3 | 76.7 | | |
| 34 | N-methyl-N-phenyl-1H-benzo[d][1,2,3]triazole-1-carboxamide | Benzotriazoles | 0 | 0.6 | 33.6 | 34.3 | | |
| 35 | 4-(biphenyl-4-yl)-N-methyl-N-phenyl-1H-imidazole-1-carboxamide | Imidazoles | 103.1 | | | | | |
| 36 | N-(4-fluorophenyl)-4-(4-methoxyphenyl)-N-methyl-1H-imidazole-1-carboxamide | Imidazoles | 5 | | | | | |
| 37 | (3,4-dihydroquinolin-1(2H)-yl)(4-phenyl-1H-imidazol-1-yl)methanone | Imidazoles | 51.7 | | | | | |
| 38 | 4-(4-hydroxyphenyl)-N-methyl-N-phenyl-1H-imidazole-1-carboxamide | Imidazoles | 0 | 83.9 | | | | |
| 39 | (3,4-dihydroquinolin-1(2H)-yl)(4-(3-methoxyphenyl)-1H-imidazol-1-yl)methanone | Imidazoles | 16 | | | | 120.6 | 101.1 |

TABLE 1-continued

| | | | In Vitro | | In Vivo | | | |
|---|---|---|---|---|---|---|---|---|
| | | | | | BRh 30 mg · kg · 1 h | LVh 30 mg · kg · 1 h | BRh mg · 3 kg · 8 h | LVh mg · 3 kg · 8 h |
| | Name | Class | 10 uM | 100 nM | | | | |
| 40 | 4-(3-hydroxyphenyl)-N-methyl-N-phenyl-1H-imidazole-1-carboxamide | Imidazoles | 0.1 | 88.8 | 81.5 | 4.5 | 102.8 | 25.6 |
| 41 | (1H-benzo[d][1,2,3]triazol-1-yl)(4-phenylpiperazin-1-yl)methanone | Benzotriazoles | 0 | 0 | 87.6 | 30 | | |
| 42 | (1H-benzo[d][1,2,3]triazol-1-yl)(4-benzylpiperidin-1-yl)methanone | Benzotriazoles | 0 | 0 | 8.4 | 6.4 | | |
| 43 | 4-(4-chlorophenyl)-N-(4-fluorophenyl)-N-methyl-1H-imidazole-1-carboxamide | Imidazoles | 0.1 | 88 | | | | |
| 44 | (3,4-dihydroquinolin-1(2H)-yl)(4-(4-fluorophenyl)-1H-imidazol-1-yl)methanone | Imidazoles | | 97.8 | | | | |
| 45 | 4-(2-fluorophenyl)-N-(4-fluorophenyl)-N-methyl-1H-imidazole-1-carboxamide | Imidazoles | | 83 | | | | |
| 46 | (5-fluoro-1H-indol-1-yl)(morpholino)methanone | Indoles | | 104.3 | | | | |
| 47 | (5-methoxy-1H-indol-1-yl)(morpholino)methanone | Indoles | | 97.2 | | | | |
| 48 | (1H-benzo[d][1,2,3]triazol-1-yl)(4-(benzo[d][1,3]dioxol-5-ylmethyl)piperazin-1-yl)methanone oxalate | Benzotriazoles | | 0.1 | 21.8 | 20.1 | | |
| 49 | (1H-benzo[d][1,2,3]triazol-1-yl)(4-(pyridin-2-yl)piperazin-1-yl)methanone | Benzotriazoles | | 0.1 | 16.9 | 14.9 | | |
| 50 | (1H-benzo[d][1,2,3]triazol-1-yl)(3,4-dihydroisoquinolin-2(1H)-yl)methanone | Benzotriazoles | | 0 | 32.6 | 7.8 | | |
| 51 | (3,4-dihydroquinolin-1(2H)-yl)(4-(3-hydroxyphenyl)-1H-imidazol-1-yl)methanone | Imidazoles | | 100.8 | | | 130.4 | 132.3 |
| 52 | (5-hydroxy-1H-indol-1-yl)(morpholino)methanone | Indoles | | 102.7 | | | | |
| 53 | N-benzyl-N-methyl-1H-benzo[d][1,2,3]triazole-1-carboxamide | Benzotriazoles | | 0 | 1.4 | 6.3 | | |
| 54 | N-(4-fluorophenyl)-4-(4-hydroxyphenyl)-N-methyl-1H-imidazole-1-carboxamide | Imidazoles | | 91 | | | | |
| 55 | 1H-benzo[d][1,2,3]triazol-1-yl(1,4-dioxa-8-azaspiro[4.5]dec-8-yl)methanone | Benzotriazoles | | 0.2 | 2.2 | 2.5 | 42.6 | 37.8 |
| 56 | N-(4-phenoxyphenyl)-1H-benzo[d][1,2,3]triazole-1-carboxamide | Benzotriazoles | | 90.7 | | | | |
| 57 | N-(4-methoxyphenyl)-1H-benzo[d][1,2,3]triazole-1-carboxamide | Benzotriazoles | | 96.9 | | | | |
| 58 | N-cyclohexyl-N-methyl-1H-benzo[d][1,2,3]triazole-1-carboxamide | Benzotriazoles | | 1 | 0.3 | 0.9 | 0.5 | 0.3 |
| 59 | N-(2,4-difluorophenyl)-1H-benzo[d][1,2,3]triazole-1-carboxamide | Benzotriazoles | | 100.4 | | | | |
| 60 | N-phenyl-1H-benzo[d][1,2,3]triazole-1-carboxamide | Benzotriazoles | | 93.8 | | | | |
| 61 | N-benzyl-1H-benzo[d][1,2,3]triazole-1-carboxamide | Benzotriazoles | | 2.2 | 87.5 | 83.9 | | |
| 62 | N-(4-chlorophenyl)-1H-benzo[d][1,2,3]triazole-1-carboxamide | Benzotriazoles | | 93.7 | | | | |
| 63 | N-(4-chlorophenyl)-N-methyl-1H-benzo[d][1,2,3]triazole-1-carboxamide | Benzotriazoles | | 12.6 | 57 | 49.7 | | |
| 64 | 3-(4-methoxyphenyl)-N-methyl-N-phenyl-1H-1,2,4-triazole-1-carboxamide | 1,2,4-Triazoles | | 67.9 | | | | |
| 65 | (3-(4-methoxyphenyl)-1H-1,2,4-triazol-1-yl)(morpholino)methanone | 1,2,4-Triazoles | | 86.5 | | | | |
| 66 | N-(4-fluorophenyl)-3-(4-methoxyphenyl)-N-methyl-1H-1,2,4-triazole-1-carboxamide | 1,2,4-Triazoles | | 80.9 | | | | |
| 67 | 3-(4-chlorophenyl)-N-methyl-N-phenyl-1H-1,2,4-triazole-1-carboxamide | 1,2,4-Triazoles | | 61 | | | | |
| 68 | (3-(4-chlorophenyl)-1H-1,2,4-triazol-1-yl)(morpholino)methanone | 1,2,4-Triazoles | | 73.5 | | | | |
| 69 | 3-(4-chlorophenyl)-N-(4-fluorophenyl)-N-methyl-1H-1,2,4-triazole-1-carboxamide | 1,2,4-Triazoles | | 80.8 | | | | |
| 70 | N-(2,4-difluorophenyl)-N-methyl-1H-benzo[d][1,2,3]triazole-1-carboxamide | Benzotriazoles | | 1.9 | 52 | 42.5 | | |
| 71 | (1H-benzo[d][1,2,3]triazol-1-yl)(4,4-dimethyloxazolidin-3-yl)methanone | Benzotriazoles | 0.1 | 2.3 | 0.3 | 2.2 | 1.8 | 2.5 |
| 72 | (3-chloro-1H-indazol-1-yl)(morpholino)methanone | Indazol | | 87.6 | | | | |
| 73 | morpholino(3-phenyl-1H-1,2,4-triazol-1-yl)methanone | 1,2,4-Triazoles | | 85.8 | | | | |
| 74 | N-(2,4-difluorophenyl)-N-methyl-3-phenyl-1H-1,2,4-triazole-1-carboxamide | 1,2,4-Triazoles | | 73.2 | | | | |
| 75 | N-butyl-N-methyl-1H-benzo[d][1,2,3]triazole-1-carboxamide | Benzotriazoles | | 0 | 0.4 | 2.7 | | |
| 76 | N-methyl-N-(4-morpholinophenyl)-1H-benzo[d][1,2,3]triazole-1-carboxamide | Benzotriazoles | | 97.1 | | | | |
| 77 | N-(3,5-dimethoxyphenyl)-N-methyl-1H-benzo[d][1,2,3]triazole-1-carboxamide | Benzotriazoles | | 76.3 | | | | |
| 78 | (3-(2,4-difluorophenyl)-1H-1,2,4-triazol-1-yl)(morpholino)methanone | 1,2,4-Triazoles | | 81.9 | | | | |
| 79 | (4-benzylpiperidin-1-yl)(3-(2,4-difluorophenyl)-1H-1,2,4-triazol-1-yl)methanone | 1,2,4-Triazoles | | 0.8 | 10.3 | 9.8 | 70 | 45.2 |
| 80 | N,3-bis(2,4-difluorophenyl)-N-methyl-1H-1,2,4-triazole-1-carboxamide | 1,2,4-Triazoles | | 89.5 | | | | |
| 81 | N-(4-(dimethylamino)phenyl)-N-methyl-1H-benzo[d][1,2,3]triazole-1-carboxamide | Benzotriazoles | | 49.2 | | | | |
| 82 | 1,4'-bipiperidin-1'-yl(1H-benzo[d][1,2,3]triazol-1-yl)methanone hydrochloride | Benzotriazoles | | 69.3 | | | | |
| 83 | (1H-benzo[d][1,2,3]triazol-1-yl)(4-methylpiperazin-1-yl)methanone hydrochloride | Benzotriazoles | | 2.5 | | | | |
| 84 | N-methyl-N-(pyridin-2-yl)-1H-benzo[d][1,2,3]triazole-1-carboxamide | Benzotriazoles | | 62.5 | | | | |
| 85 | N-(4-phenylbutyl)-1H-benzo[d][1,2,3]triazole-1-carboxamide | Benzotriazoles | | 0.1 | | | | |
| 86 | N-dodecyl-1H-benzo[d][1,2,3]triazole-1-carboxamide | Benzotriazoles | | 0 | | | | |
| 87 | N-cyclohexyl-1H-benzo[d][1,2,3]triazole-1-carboxamide | Benzotriazoles | | 0 | | | 3.4 | 4 |
| 88 | N-(biphenyl-4-yl)-1H-benzo[d][1,2,3]triazole-1-carboxamide | Benzotriazoles | | 105.4 | | | | |
| 89 | morpholino(4-phenyl-1H-1,2,3-triazol-1-yl)methanone | 1,2,3-Triazoles | | 4.5 | | | | |
| 90 | (1H-benzo[d][1,2,3]triazol-1-yl)(4-morpholinopiperidin-1-yl)methanone hydrochloride | Benzotriazoles | | 38.6 | | | | |
| 91 | (1H-benzo[d][1,2,3]triazol-1-yl)(4-(4-(benzyloxy)phenyl)piperazin-1-yl)methanone | Benzotriazoles | | 0 | | | | |
| 92 | (1H-benzo[d][1,2,3]triazol-1-yl)(4-(pyrrolidin-1-yl)piperidin-1-yl)methanone hydrochloride | Benzotriazoles | | 96 | | | | |

TABLE 1-continued

|  | Name | Class | In Vitro 10 uM | In Vitro 100 nM | In Vivo BRh 30 mg·kg·1 h | In Vivo LVh 30 mg·kg·1 h | In Vivo BRh mg·3 kg·8 h | In Vivo LVh mg·3 kg·8 h |
|---|---|---|---|---|---|---|---|---|
| 93 | (1H-benzo[d][1,2,3]triazol-1-yl)(4-benzylpiperazin-1-yl)methanone hydrochloride | Benzotriazoles |  | 0 |  |  |  |  |
| 94 | (1H-benzo[d][1,2,3]triazol-1-yl)(4-phenylpiperidin-1-yl)methanone | Benzotriazoles |  | 0 |  |  |  |  |
| 95 | 5-(3-cyanophenyl)-N-cyclohexyl-N-methyl-1H-benzo[d][1,2,3]triazole-1-carboxamide | Benzotriazoles |  | 0.7 |  |  |  |  |
| 96 | N-cyclohexyl-5-(4-fluorophenyl)-N-methyl-1H-benzo[d][1,2,3]triazole-1-carboxamide | Benzotriazoles |  | 14.3 |  |  |  |  |
| 97 | 5-bromo-N-cyclohexyl-N-methyl-1H-benzo[d][1,2,3]triazole-1-carboxamide | Benzotriazoles |  | 0 |  |  |  |  |
| 98 | (1H-benzo[d][1,2,3]triazol-1-yl)(pyrrolidin-1-yl)methanone | Benzotriazoles |  | 0.6 |  |  |  |  |
| 99 | (1H-benzo[d][1,2,3]triazol-1-yl)(4-(p-tolyloxy)piperidin-1-yl)methanone | Benzotriazoles |  | 0.2 |  |  | 99.1 | 71.4 |
| 100 | (1H-benzo[d][1,2,3]triazol-1-yl)(4-phenethylpiperidin-1-yl)methanone | Benzotriazoles |  | 0.2 |  |  | 68.1 | 40.5 |
| 101 | (4-phenyl-1H-imidazol-1-yl)(4-phenylpiperazin-1-yl)methanone | Imidazoles |  | 0.5 |  |  |  |  |
| 102 | (4-benzylpiperazin-1-yl)(4-phenyl-1H-imidazol-1-yl)methanone | Imidazoles |  | 0.9 |  |  |  |  |
| 103 | N-cyclohexyl-N-methyl-4-phenyl-1H-imidazole-1-carboxamide | Imidazoles | 0 | 37.5 |  |  |  |  |
| 104 | N-cyclohexyl-N-ethyl-1H-benzo[d][1,2,3]triazole-1-carboxamide | Benzotriazoles |  | 94.2 |  |  |  |  |
| 105 | (1H-benzo[d][1,2,3]triazol-1-yl)(4-(2-(pyrrolidin-1-yl)ethyl)piperidin-1-yl)methanone hydrochloride | Benzotriazoles |  | 64.7 |  |  |  |  |
| 106 | N-cyclohexyl-6-(4-fluorophenyl)-N-methyl-1H-benzo[d][1,2,3]triazole-1-carboxamide | Benzotriazoles |  | 2.3 |  |  |  |  |
| 107 | 3-(1-(cyclohexyl(methyl)carbamoyl)-1H-benzo[d][1,2,3]triazol-5-yl)benzoic acid | Benzotriazoles |  | 13.5 |  |  |  |  |
| 108 | 5-(3-carbamoylphenyl)-N-cyclohexyl-N-methyl-1H-benzo[d][1,2,3]triazole-1-carboxamide | Benzotriazoles |  | 7.4 |  |  |  |  |
| 109 | 6-(3-carbamoylphenyl)-N-cyclohexyl-N-methyl-1H-benzo[d][1,2,3]triazole-1-carboxamide | Benzotriazoles |  | 0 |  |  |  |  |
| 110 | (1H-benzo[d][1,2,3]triazol-1-yl)(4-(3-phenylpropyl)piperidin-1-yl)methanone | Benzotriazoles |  | 0.1 |  |  | 51.7 | 10.2 |
| 111 | (3-phenyl-1H-1,2,4-triazol-1-yl)(4-phenylpiperazin-1-yl)methanone | 1,2,4-Triazoles |  | 1.5 |  |  |  |  |
| 112 | 4-(1-(4-benzylpiperazine-1-carbonyl)-1H-imidazol-4-yl)benzamide | Imidazoles |  | 7.2 |  |  |  |  |
| 113 | 4-(4-carbamoylphenyl)-N-methyl-N-phenyl-1H-imidazole-1-carboxamide | Imidazoles |  | 90.3 |  |  | 84.1 | 32.3 |
| 114 | (1H-benzo[d][1,2,3]triazol-1-yl)(4-(pyridin-4-yl)piperidin-1-yl)methanone | Benzotriazoles |  | 0.1 |  |  | 102.9 | 109.9 |
| 115 | N-methyl-N-phenethyl-1H-benzo[d][1,2,3]triazole-1-carboxamide | Benzotriazoles |  | 0 |  |  |  |  |
| 116 | (1H-benzo[d][1,2,3]triazol-1-yl)(4-(3-(pyridin-3-yl)-1,2,4-oxadiazol-5-yl)piperidin-1-yl)methanone | Benzotriazoles |  | 0.5 |  |  | 126.2 | 113.2 |
| 117 | (1H-benzo[d][1,2,3]triazol-1-yl)(4-(4-chlorophenoxy)piperidin-1-yl)methanone | Benzotriazoles |  | 0.1 |  |  |  |  |
| 118 | N-methyl-N-(3-phenylpropyl)-1H-benzo[d][1,2,3]triazole-1-carboxamide | Benzotriazoles |  | 0 |  |  |  |  |
| 119 | N-(3-methoxybenzyl)-N-methyl-1H-benzo[d][1,2,3]triazole-1-carboxamide | Benzotriazoles |  | 0 |  |  |  |  |
| 120 | (1H-benzo[d][1,2,3]triazol-1-yl)(4-phenoxypiperidin-1-yl)methanone | Benzotriazoles |  | 0.1 |  |  |  |  |
| 121 | (1H-benzo[d][1,2,3]triazol-1-yl)(4-(4-fluorobenzyl)piperazin-1-yl)methanone | Benzotriazoles |  | 0 |  |  | 118.6 | 116.1 |
| 122 | (1H-benzo[d][1,2,3]triazol-1-yl)(4-(4-methylpiperazin-1-yl)piperidin-1-yl)methanone hydrochloride | Benzotriazoles |  | 93 |  |  |  |  |
| 123 | N-(3-chlorobenzyl)-N-methyl-1H-benzo[d][1,2,3]triazole-1-carboxamide | Benzotriazoles |  | 0 |  |  |  |  |
| 124 | (4-benzylpiperazin-1-yl)(3-phenyl-1H-1,2,4-triazol-1-yl)methanone hydrochloride | 1,2,4-Triazoles |  | 1.5 |  |  |  |  |
| 125 | (3-(4-(benzyloxy)phenyl)-1H-1,2,4-triazol-1-yl)(4-benzylpiperazin-1-yl)methanone hydrochloride | 1,2,4-Triazoles |  | 53.5 |  |  |  |  |
| 126 | N-adamantyl-1H-benzo[d][1,2,3]triazole-1-carboxamide | Benzotriazoles |  | 0 |  |  | 0.2 | 2.2 |
| 127 | (1H-benzo[d][1,2,3]triazol-1-yl)(4-cyclohexylpiperazin-1-yl)methanone | Benzotriazoles |  | 0.1 |  |  | 111.5 | 107.3 |
| 128 | (1H-benzo[d][1,2,3]triazol-1-yl)(4-(benzyloxy)piperidin-1-yl)methanone | Benzotriazoles |  | 0 |  |  |  |  |
| 129 | N-methyl-N-(5-phenylpentyl)-1H-benzo[d][1,2,3]triazole-1-carboxamide | Benzotriazoles |  | 0 |  |  | 2.5 | 2 |
| 130 | N-(4-fluorobenzyl)-N-methyl-1H-benzo[d][1,2,3]triazole-1-carboxamide | Benzotriazoles |  | 0 |  |  |  |  |
| 131 | N-methyl-N-(naphthalen-2-ylmethyl)-1H-benzo[d][1,2,3]triazole-1-carboxamide | Benzotriazoles |  | 0 |  |  |  |  |
| 132 | (3-(4-(4-methylpiperazin-1-yl)phenyl)-1H-1,2,4-triazol-1-yl)(4-(p-tolyloxy)piperidin-1-yl)methanone hydrochloride | 1,2,4-Triazoles |  | 85.1 |  |  |  |  |
| 133 | (3-(4-(4-benzylpiperazin-1-yl)phenyl)-1H-1,2,4-triazol-1-yl)(morpholino)methanone | 1,2,4-Triazoles |  | 90.7 |  |  |  |  |
| 134 | (3-(2,4-difluorophenyl)-1H-1,2,4-triazol-1-yl)(4-(p-tolyloxy)piperidin-1-yl)methanone | 1,2,4-Triazoles |  | 34.5 |  |  |  |  |
| 135 | (1H-benzo[d][1,2,3]triazol-1-yl)(4-(3-phenylpropoxy)piperidin-1-yl)methanone | Benzotriazoles |  | 0.1 |  |  | 26.5 | 30.1 |
| 136 | (1H-benzo[d][1,2,3]triazol-1-yl)(4-(4-hydroxyphenyl)piperazin-1-yl)methanone | Benzotriazoles |  | 0.2 |  |  |  |  |
| 137 | (1H-benzo[d][1,2,3]triazol-1-yl)(4-(4-methoxyphenoxy)piperidin-1-yl)methanone | Benzotriazoles |  | 0.1 |  |  |  |  |
| 138 | N,N-dimethyl-3-(4-(4-phenylpiperazin-1-yl)phenyl)-1H-1,2,4-triazole-1-carboxamide | 1,2,4-Triazoles |  | 83.8 |  |  |  |  |
| 139 | (3-(4-(4-methylpiperazin-1-yl)phenyl)-1H-1,2,4-triazol-1-yl)(morpholino)methanone | 1,2,4-Triazoles |  | 80.2 |  |  | 97.1 | 105.7 |

TABLE 1-continued

| | | | In Vitro | | In Vivo | | | |
|---|---|---|---|---|---|---|---|---|
| | | | | | BRh 30 mg·kg·1 h | LVh 30 mg·kg·1 h | BRh mg·3 kg·8 h | LVh mg·3 kg·8 h |
| | Name | Class | 10 uM | 100 nM | | | | |
| 140 | 3-(4-(4-cyanophenoxy)phenyl)-N,N-dimethyl-1H-1,2,4-triazole-1-carboxamide | 1,2,4-Triazoles | | 58.6 | | | | |
| 141 | 4-(4-(1-(morpholine-4-carbonyl)-1H-1,2,4-triazol-3-yl)phenoxy)benzonitrile | 1,2,4-Triazoles | | 15.9 | | | | |
| 142 | (R)—N-(quinuclidin-3-yl)-1H-benzo[d][1,2,3]triazole-1-carboxamide hydrochloride | Benzotriazoles | | 101.8 | | | | |
| 143 | N-(3,3-dimethyl-1,5-dioxaspiro[5.5]undec-9-yl)-N-methyl-1H-benzotriazole-1-carboxamide | Benzotriazoles | | 2.5 | | | 0.4 | 0.7 |
| 144 | (1H-benzo[d][1,2,3]triazol-1-yl)(4-(2-(4-methoxyphenoxy)ethyl)piperidin-1-yl)methanone | Benzotriazoles | | 0.1 | | | 68.2 | 17.6 |
| 145 | 4-(4-(1-(4-phenylpiperazine-1-carbonyl)-1H-1,2,4-triazol-3-yl)phenoxy)benzonitrile hydrochloride | 1,2,4-Triazoles | | 0.3 | | | 89.9 | 116.5 |
| 146 | 3-(4-(4-carbamoylphenoxy)phenyl)-N,N-dimethyl-1H-1,2,4-triazole-1-carboxamide | 1,2,4-Triazoles | | 77.1 | | | | |
| 147 | 4-(4-(1-(morpholine-4-carbonyl)-1H-1,2,4-triazol-3-yl)phenoxy)benzamide | 1,2,4-Triazoles | | 55.1 | | | 124.4 | 103 |
| 148 | 4-(4-(1-(4-phenylpiperazine-1-carbonyl)-1H-1,2,4-triazol-3-yl)phenoxy)benzamide | 1,2,4-Triazoles | | 0.3 | | | 113.7 | 87.6 |
| 149 | 3-(4-(carbamoylphenoxy)phenyl)-N-methyl-N-phenyl-1H-1,2,4-triazole-1-carboxamide | 1,2,4-Triazoles | | 49.9 | | | | |
| 150 | N-benzyl-4-(4-fluorophenyl)-N-methyl-1H-imidazole-1-carboxamide | Imidazoles | | 1.2 | | | 5.6 | 3.8 |
| 151 | N-benzyl-3-(4-(4-carbamoylphenoxy)phenyl)-N-methyl-1H-1,2,4-triazole-1-carboxamide | 1,2,4-Triazoles | | 0.4 | | | 116.7 | 65.8 |
| 152 | N-((1r,4r)-4-(benzyloxy)cyclohexyl)-N-methyl-1H-benzo[d][1,2,3]triazole-1-carboxamide | Benzotriazoles | | 1.3 | | | | |
| 153 | (1H-benzo[d][1,2,3]triazol-1-yl)(4-((3-methoxyphenoxy)methyl)piperidin-1-yl)methanone | Benzotriazoles | | 0 | | | | |
| 154 | (1H-benzo[d][1,2,3]triazol-1-yl)(4-cyclopentylpiperazin-1-yl)methanone | Benzotriazoles | | 0.2 | | | | |
| 155 | (4-phenylpiperazin-1-yl)(3-(thiophen-2-yl)-1H-1,2,4-triazol-1-yl)methanone | 1,2,4-Triazoles | | 0.4 | | | 144.1 | 108.2 |
| 156 | N-(2-(benzyloxy)ethyl)-N-methyl-1H-benzo[d][1,2,3]triazole-1-carboxamide | Benzotriazoles | | 0.1 | | | 67.2 | 24.4 |
| 157 | N-(2-(4-methoxyphenoxy)ethyl)-N-methyl-1H-benzo[d][1,2,3]triazole-1-carboxamide | Benzotriazoles | | 0 | | | 5.2 | 3.5 |
| 158 | (4-benzylpiperazin-1-yl)(3-(thiophen-2-yl)-1H-1,2,4-triazol-1-yl)methanone hydrochloride | 1,2,4-Triazoles | | 0.3 | | | 92 | 85.6 |
| 159 | (1H-benzo[d][1,2,3]triazol-1-yl)(4-hydroxypiperidin-1-yl)methanone | Benzotriazoles | | 4.8 | | | | |
| 160 | 3-benzyl-N-methyl-N-phenyl-1H-1,2,4-triazole-1-carboxamide | 1,2,4-Triazoles | | 18.8 | | | | |
| 161 | (4,4-dimethyloxazolidin-3-yl)(4-phenyl-1H-imidazol-1-yl)methanone | Imidazoles | 3.3 | 93.6 | | | | |
| 162 | (6-bromo-1H-benzo[d][1,2,3]triazol-1-yl)(4,4-dimethyloxazolidin-3-yl)methanone | Benzotriazoles | | 0 | | | 0.9 | 3.1 |
| 163 | 3-(3-(4,4-dimethyloxazolidine-3-carbonyl)-3H-benzo[d][1,2,3]triazol-5-yl)benzamide | Benzotriazoles | | 0.6 | | | 6.3 | 2.4 |
| 164 | (1H-benzo[d][1,2,3]triazol-1-yl)(4-(4-(benzyloxy)phenoxy)piperidin-1-yl)methanone | Benzotriazoles | | 0.3 | | | | |
| 165 | (1H-benzo[d][1,2,3]triazol-1-yl)(4-((4-methoxyphenoxy)methyl)piperidin-1-yl)methanone | Benzotriazoles | | 0 | | | | |
| 166 | (1H-benzo[d][1,2,3]triazol-1-yl)(4-(3-methoxyphenoxy)piperidin-1-yl)methanone | Benzotriazoles | | 0 | | | | |
| 167 | 1-[(1,1-dioxido-1,3-thiazolidin-3-yl)carbonyl]-1H-benzotriazole | Benzotriazoles | | 96.2 | | | 99.9 | 104 |
| 168 | (1H-benzo[d][1,2,3]triazol-1-yl)(4-(4-butoxyphenoxy)piperidin-1-yl)methanone | Benzotriazoles | | 0 | | | | |
| 169 | N-methoxy-N-methyl-1H-benzo[d][1,2,3]triazole-1-carboxamide | Benzotriazoles | | 73.6 | | | | |
| 170 | (1H-benzo[d][1,2,3]triazol-1-yl)(thiazolidin-3-yl)methanone | Benzotriazoles | | 2.1 | | | | |
| 171 | azocan-1-yl(1H-benzo[d][1,2,3]triazol-1-yl)methanone | Benzotriazoles | | 15.2 | | | | |
| 172 | azepan-1-yl(1H-benzo[d][1,2,3]triazol-1-yl)methanone | Benzotriazoles | | 0.3 | | | | |
| 173 | (1H-benzo[d][1,2,3]triazol-1-yl)((2R,6S)-2,6-dimethylpiperidin-1-yl)methanone | Benzotriazoles | | 70.6 | | | | |
| 174 | (1H-benzo[d][1,2,3]triazol-1-yl)(isoindolin-2-yl)methanone | Benzotriazoles | | 0.7 | | | | |
| 175 | (1H-benzo[d][1,2,3]triazol-1-yl)(3,5-dimethylpiperidin-1-yl)methanone | Benzotriazoles | | 21 | | | | |
| 176 | ethyl 1-(1H-benzo[d][1,2,3]triazole-1-carbonyl)piperidine-4-carboxylate | Benzotriazoles | | 0.2 | | | | |
| 177 | ethyl 4-(1H-benzo[d][1,2,3]triazole-1-carbonyl)piperazine-1-carboxylate | Benzotriazoles | | 6.9 | | | | |
| 178 | 1-(4-(1H-benzo[d][1,2,3]triazole-1-carbonyl)piperazin-1-yl)ethanone | Benzotriazoles | | 94.5 | | | | |
| 179 | 1-(1H-benzo[d][1,2,3]triazole-1-carbonyl)piperidine-4-carboxamide | Benzotriazoles | | 49 | | | | |
| 180 | N-methyl-N-phenyl-3-(thiophen-2-yl)-1H-1,2,4-triazole-1-carboxamide | 1,2,4-Triazoles | | 57.5 | | | | |
| 181 | N-benzyl-N-methyl-3-(thiophen-2-yl)-1H-1,2,4-triazole-1-carboxamide | 1,2,4-Triazoles | | 0.9 | | | | |
| 182 | (3-benzyl-1H-1,2,4-triazol-1-yl)(4-phenylpiperazin-1-yl)methanone | 1,2,4-Triazoles | | 0.6 | | | 90.6 | 111 |
| 183 | (3-(2,4-difluorophenyl)-1H-1,2,4-triazol-1-yl)(4,4-dimethyloxazolidin-3-yl)methanone | 1,2,4-Triazoles | | 102 | | | 92.4 | 78.1 |
| 184 | (3,4-dihydroisoquinolin-2(1H)-yl)(4-phenyl-1H-imidazol-1-yl)methanone | Imidazoles | | 30.2 | | | | |
| 185 | (3-(4-chlorophenyl)-1H-1,2,4-triazol-1-yl)(3,4-dihydroisoquinolin-2(1H)-yl)methanone | 1,2,4-Triazoles | | 71.8 | | | | |
| 186 | (4-(4-chlorophenyl)-1H-imidazol-1-yl)(4,4-dimethyloxazolidin-3-yl)methanone | Imidazoles | | 96.5 | | | 78.7 | 37.7 |
| 187 | 4-(4-(1-(4,4-dimethyloxazolidine-3-carbonyl)-1H-1,2,4-triazol-3-yl)phenoxy)benzamide | 1,2,4-Triazoles | | 92.8 | | | 85.6 | 108.6 |

TABLE 1-continued

| | Name | Class | In Vitro 10 uM | In Vitro 100 nM | BRh 30 mg·kg·1 h | LVh 30 mg·kg·1 h | BRh mg·3 kg·8 h | LVh mg·3 kg·8 h |
|---|---|---|---|---|---|---|---|---|
| 188 | (4,4-dimethyloxazolidin-3-yl)(3-(4-methoxyphenyl)-1H-1,2,4-triazol-1-yl)methanone | 1,2,4-Triazoles | | 103.3 | | | 78.7 | 89 |
| 189 | (3-(4-chlorophenyl)-1H-1,2,4-triazol-1-yl)(4,4-dimethyloxazolidin-3-yl)methanone | 1,2,4-Triazoles | | 98.5 | | | 105.9 | 87.6 |
| 190 | N-benzyl-N-methyl-3-(naphthalen-2-yl)-1H-1,2,4-triazole-1-carboxamide | 1,2,4-Triazoles | | 20.7 | | | | |
| 191 | N-benzyl-N-methyl-3-(naphthalen-1-yl)-1H-1,2,4-triazole-1-carboxamide | 1,2,4-Triazoles | | 21 | | | 60 | 20.8 |
| 192 | N-methyl-3-(naphthalen-1-yl)-N-phenyl-1H-1,2,4-triazole-1-carboxamide | 1,2,4-Triazoles | | 64.6 | | | | |
| 193 | (1H-benzo[d][1,2,3]triazol-1-yl)((2R,6R)-2,6-dimethylmorpholino)methanone | Benzotriazoles | | 110.2 | | | | |
| 194 | (1H-benzo[d][1,2,3]triazol-1-yl)((2S,6R)-2,6-dimethylmorpholino)methanone | Benzotriazoles | | 64.2 | | | | |
| 195 | (S)—N-methyl-N-(1-phenylethyl)-1H-benzo[d][1,2,3]triazole-1-carboxamide | Benzotriazoles | | 15.7 | | | 9.1 | 5.7 |
| 196 | (4-(biphenyl-3-yl)-1H-imidazol-1-yl)(4-phenylpiperazin-1-yl)methanone | Imidazoles | | 2.5 | | | 88.1 | 78.3 |
| 197 | (4-(4-chlorophenyl)-1H-imidazol-1-yl)(4-(3-phenylpropyl)piperidin-1-yl)methanone | Imidazoles | | 0.3 | | | | |
| 198 | (4-(3,4-dichlorophenyl)-1H-imidazol-1-yl)(1,4-dioxa-8-azaspiro[4.5]decan-8-yl)methanone | Imidazoles | | 33 | | | | |
| 199 | 4-(4-aminophenyl)-N-methyl-N-phenyl-1H-imidazole-1-carboxamide | Imidazoles | | 89 | | | 45.9 | 19.7 |
| 200 | N-methyl-N-phenyl-4-(4-(2-(piperazin-1-yl)ethoxy)phenyl)-1H-imidazole-1-carboxamide dihydrochloride | Imidazoles | | 100.1 | | | | |
| 201 | (4-cyclohexylpiperazin-1-yl)(4-(3,4-difluorophenyl)-1H-imidazol-1-yl)methanone | Imidazoles | | 0.3 | | | | |
| 202 | N-(2-(benzyloxy)ethyl)-N-ethyl-1H-benzo[d][1,2,3]triazole-1-carboxamide | Benzotriazoles | | 0.1 | | | | |
| 203 | N-methyl-N-phenyl-4-(4-(2-(piperazin-1-yl)ethoxy)phenyl)-1H-imidazole-1-carboxamide dihydrochloride | Imidazoles | | 93.5 | | | 101.8 | 64.3 |
| 204 | (3-(4-chlorophenyl)-1H-1,2,4-triazol-1-yl)(1,4-dioxa-8-azaspiro[4.5]decan-8-yl)methanone | 1,2,4-Triazoles | | 15.8 | | | | |
| 205 | (3-(4-methoxyphenyl)-1H-1,2,4-triazol-1-yl)(4-(3-phenylpropyl)piperidin-1-yl)methanone | 1,2,4-Triazoles | | 0.2 | | | | |
| 206 | (3-(naphthalen-1-yl)-1H-1,2,4-triazol-1-yl)(4-phenylpiperazin-1-yl)methanone | 1,2,4-Triazoles | | 3.3 | | | | |
| 207 | 4-(3-(1-(1,2,3,4-tetrahydroisoquinoline-2-carbonyl)-1H-1,2,4-triazol-3-yl)phenoxy)benzamide | 1,2,4-Triazoles | | 31.6 | | | | |
| 208 | 4-(3-(1-(4-phenylpiperazine-1-carbonyl)-1H-1,2,4-triazol-3-yl)phenoxy)benzamide | 1,2,4-Triazoles | | 0.2 | | | 97.2 | 96.7 |
| 209 | 4-(3-(1-(4,4-dimethyloxazolidine-3-carbonyl)-1H-1,2,4-triazol-3-yl)phenoxy)benzamide | 1,2,4-Triazoles | | 101.5 | | | 99.8 | 70.1 |
| 210 | 4-(3-(1-(morpholine-4-carbonyl)-1H-1,2,4-triazol-3-yl)phenoxy)benzamide | 1,2,4-Triazoles | | 73.3 | | | | |
| 211 | (4-(4-fluorophenyl)piperazin-1-yl)(3-(4-methoxyphenyl)-1H-1,2,4-triazol-1-yl)methanone | 1,2,4-Triazoles | | 1.9 | | | | |
| 212 | (3-(4-chlorophenyl)-1H-1,2,4-triazol-1-yl)(4-cyclohexylpiperazin-1-yl)methanone hydrochloride | 1,2,4-Triazoles | | 0.8 | | | | |
| 213 | (4,4-dimethyloxazolidin-3-yl)(3-(thiophen-2-yl)-1H-1,2,4-triazol-1-yl)methanone | 1,2,4-Triazoles | | 105.6 | | | 53.7 | 6.9 |
| 214 | (3-(4-chlorophenyl)-1H-1,2,4-triazol-1-yl)(thiazolidin-3-yl)methanone | 1,2,4-Triazoles | | 23.7 | | | | |
| 215 | (4-(3,4-difluorophenyl)-1H-imidazol-1-yl)(thiazolidin-3-yl)methanone | Imidazoles | | 16.7 | | | | |
| 216 | (4-(3,4-dimethoxyphenyl)-1H-imidazol-1-yl)(4,4-dimethyloxazolidin-3-yl)methanone | Imidazoles | 38.3 | 108.6 | | | 29.3 | 13.3 |
| 217 | N-cyclohexyl-4-(3,4-dimethoxyphenyl)-N-methyl-1H-imidazole-1-carboxamide | Imidazoles | 0 | 80.5 | | | 6 | 4.2 |
| 218 | (4-(3,4-dichlorophenyl)-1H-imidazol-1-yl)(pyrrolidin-1-yl)methanone | Imidazoles | | 31.6 | | | | |
| 219 | (1H-benzo[d]imidazol-1-yl)(4,4-dimethyloxazolidin-3-yl)methanone | Imidazoles | 50.6 | 111.6 | | | 86.8 | 89 |
| 220 | (2,2-dimethyloxazolidin-3-yl)(4-phenyl-1H-imidazol-1-yl)methanone | Imidazoles | | 103.7 | | | 31.5 | 20 |
| 221 | ((2R,6S)-2,6-dimethylpiperidin-1-yl)(4-phenyl-1H-imidazol-1-yl)methanone | Imidazoles | | 105.8 | | | 104.5 | 44.9 |
| 222 | N-cyclohexyl-N-methyl-1H-benzo[d]imidazole-1-carboxamide | Imidazoles | | 102.9 | | | 111.5 | 59.2 |
| 223 | (4-(4-chlorophenyl)-1H-imidazol-1-yl)(4-(4-fluorophenyl)piperazin-1-yl)methanone | Imidazoles | | 1.1 | | | | |
| 224 | N-methyl-N-phenyl-4-(4-(2-(piperidin-1-yl)ethoxy)phenyl)-1H-imidazole-1-carboxamide hydrobromide | Imidazoles | | 90 | | | | |
| 225 | (4-(4-(benzyloxy)-3-methoxyphenyl)-1H-imidazol-1-yl)(4,4-dimethyloxazolidin-3-yl)methanone | Imidazoles | | 79 | | | | |
| 226 | (4,4-dimethyloxazolidin-3-yl)(4-(pyridin-3-yl)-1H-imidazol-1-yl)methanone dihydrochloride | Imidazoles | | 76.6 | | | 8.4 | 5.1 |
| 227 | (2-methyloxazolidin-3-yl)(4-phenyl-1H-imidazol-1-yl)methanone | Imidazoles | | 64.7 | | | | |
| 228 | (4,4-dimethyloxazolidin-3-yl)(4-(4-hydroxy-3-methoxyphenyl)-1H-imidazol-1-yl)methanone | Imidazoles | | 78.1 | | | 56.4 | 31.9 |
| 229 | N-ADAMANTYL-N-METHYL-4-PHENYL-1H-IMIDAZOLE-1-CARBOXAMIDE | Imidazoles | | 99.2 | | | | |
| 230 | N-methyl-4-(4-(2-morpholinoethoxy)phenyl)-N-phenyl-1H-imidazole-1-carboxamide hydrochloride | Imidazoles | | 96.1 | | | | |
| 231 | (4-(biphenyl-3-yl)-1H-imidazol-1-yl)(4,4-dimethyloxazolidin-3-yl)methanone | Imidazoles | | 54.2 | | | 3.9 | 3.6 |

TABLE 1-continued

| | | | In Vitro | | In Vivo | | | |
|---|---|---|---|---|---|---|---|---|
| | | | | | BRh 30 mg · kg · 1 h | LVh 30 mg · kg · 1 h | BRh mg · 3 kg · 8 h | LVh mg · 3 kg · 8 h |
| | Name | Class | 10 uM | 100 nM | | | | |
| 232 | 3'-(1-(4,4-dimethyloxazolidine-3-carbonyl)-1H-imidazol-4-yl)biphenyl-3-carboxamide | Imidazoles | 0 | 84.7 | | | 82.8 | 6.5 |
| 233 | (4-(4-chlorophenyl)-1H-imidazol-1-yl)(2-ethyl-2-methyloxazolidin-3-yl)methanone | Imidazoles | | 74.1 | | | 33.5 | 21.1 |
| 234 | 2-(N-cyclopentenyl-4-phenyl-1H-imidazole-1-carboxamido)ethyl 4-phenyl-1H-imidazole-1-carboxylate | Imidazoles | | 78.2 | | | | |
| 235 | (4-(4-chlorophenyl)-1H-imidazol-1-yl)(2,4,4-trimethyloxazolidin-3-yl)methanone | Imidazoles | | 76.2 | | | 108.5 | 80.1 |
| 236 | (4,4-dimethyloxazolidin-3-yl)(4-(3'-methoxybiphenyl-3-yl)-1H-imidazol-1-yl)methanone | Imidazoles | | 75.4 | | | 67.7 | 37.7 |
| 237 | N-ADAMANTYL-4-PHENYL-1H-IMIDAZOLE-1-CARBOXAMIDE | Imidazoles | | 91.6 | | | | |
| 238 | 4-(3'-carbamoylbiphenyl-3-yl)-N-cyclohexyl-N-methyl-1H-imidazole-1-carboxamide | Imidazoles | | 1.2 | | | 67.9 | 2.8 |
| 239 | 4-(biphenyl-3-yl)-N-cyclohexyl-N-methyl-1H-imidazole-1-carboxamide | Imidazoles | | 4 | | | 16.4 | 4.6 |
| 240 | N-cyclohexyl-4-(3'-methoxybiphenyl-3-yl)-N-methyl-1H-imidazole-1-carboxamide | Imidazoles | | 22.4 | | | 99 | 39.5 |
| 241 | (4-(4-chlorophenyl)-1H-imidazol-1-yl)(2-phenyloxazolidin-3-yl)methanone | Imidazoles | | 76.5 | | | | |
| 242 | N-cyclohexyl-6-hydroxy-N-methyl-1H-benzo[d][1,2,3]triazole-1-carboxamide | Benzotriazoles | | 0 | | | | |
| 243 | 3-(1-(4,4-dimethyloxazolidine-3-carbonyl)-1H-benzo[d][1,2,3]triazol-5-yl)benzamide | Benzotriazoles | | 39.7 | | | | |
| 244 | 4-(4-chlorophenyl)-N-cyclopentyl-N-methyl-1H-imidazole-1-carboxamide | Imidazoles | | 5.4 | | | | |
| 245 | 4-(4'-carbamoylbiphenyl-3-yl)-N-cyclohexyl-N-methyl-1H-imidazole-1-carboxamide | Imidazoles | | 0.4 | | | 90.6 | 15.8 |
| 246 | N-cyclohexyl-4-(3'-fluorobiphenyl-3-yl)-N-methyl-1H-imidazole-1-carboxamide | Imidazoles | | 2.9 | | | | |
| 247 | N-cyclohexyl-4-(3'-hydroxybiphenyl-3-yl)-N-methyl-1H-imidazole-1-carboxamide | Imidazoles | | 0.5 | | | 131.7 | 85.5 |
| 248 | N-cyclohexyl-N-methyl-4-(3'-(trifluoromethoxy)biphenyl-3-yl)-1H-imidazole-1-carboxamide | Imidazoles | | 68.9 | | | 104.2 | 57 |
| 249 | N-benzyl-4-(4-chlorophenyl)-N-isopropyl-1H-imidazole-1-carboxamide | Imidazoles | | 95.8 | | | | |
| 250 | N-benzyl-N-isopropyl-4-phenyl-1H-imidazole-1-carboxamide | Imidazoles | | 90.5 | | | 102.1 | 52.6 |
| 251 | N-benzyl-N-tert-butyl-4-phenyl-1H-imidazole-1-carboxamide | Imidazoles | | 91.7 | | | | |
| 252 | N-benzyl-N-tert-butyl-4-(4-chlorophenyl)-1H-imidazole-1-carboxamide | Imidazoles | | 83.6 | | | | |
| 253 | 3-(4-chlorophenyl)-1-[(1,1-dioxido-1,3-thiazolidin-3-yl)carbonyl]-1H-1,2,4-triazole | 1,2,4-Triazoles | | 107.7 | | | | |
| 254 | N-cyclohexyl-N,5-dimethyl-4-phenyl-1H-imidazole-1-carboxamide | Imidazoles | 109 | 81 | | | 98.3 | 89.9 |
| 255 | N-benzyl-N-isopropyl-4-(3-methoxyphenyl)-1H-imidazole-1-carboxamide | Imidazoles | | 96.7 | | | | |
| 256 | N-benzyl-N-tert-butyl-4-(3-methoxyphenyl)-1H-imidazole-1-carboxamide | Imidazoles | | 105.6 | | | | |
| 257 | 4-(3'-chlorobiphenyl-3-yl)-N-cyclohexyl-N-methyl-1H-imidazole-1-carboxamide | Imidazoles | | 65.6 | | | 60.1 | 12.2 |
| 258 | N-cyclohexyl-4-(3'-ethoxybiphenyl-3-yl)-N-methyl-1H-imidazole-1-carboxamide | Imidazoles | | 39.9 | | | | |
| 259 | 4-(5'-chloro-2'-fluorobiphenyl-3-yl)-N-cyclohexyl-N-methyl-1H-imidazole-1-carboxamide | Imidazoles | | 33.7 | | | | |
| 260 | (4,4-dimethyloxazolidin-3-yl)(4-(4-hydroxyphenyl)-1H-imidazol-1-yl)methanone | Imidazoles | 37.3 | 95.3 | | | 8.1 | 7.8 |
| 261 | N-cyclohexyl-4-(4-hydroxyphenyl)-N-methyl-1H-imidazole-1-carboxamide | Imidazoles | 0 | 54.1 | | | 1.2 | 1.2 |
| 262 | N-cyclopentyl-4-(3-hydroxyphenyl)-N-methyl-1H-imidazole-1-carboxamide | Imidazoles | | 7.5 | | | | |
| 263 | (4,4-dimethyloxazolidin-3-yl)(5-methyl-4-phenyl-1H-imidazol-1-yl)methanone | Imidazoles | | 92.1 | | | 98.1 | 98.8 |
| 264 | N-benzyl-N,5-dimethyl-4-phenyl-1H-imidazole-1-carboxamide | Imidazoles | | 88 | | | 115 | 76.6 |
| 265 | N-benzyl-4-(3-hydroxyphenyl)-N-isopropyl-1H-imidazole-1-carboxamide | Imidazoles | | 99.6 | | | | |
| 266 | N-cyclopentyl-N-methyl-1H-benzo[d][1,2,3]triazole-1-carboxamide | Benzotriazoles | | 0.2 | | | | |
| 267 | (4-(4-chlorophenyl)-1H-imidazol-1-yl)(5-ethyl-2,2-dimethyloxazolidin-3-yl)methanone | Imidazoles | | 84.1 | | | 79.4 | 83.7 |
| 268 | (5-chloro-4-phenyl-1H-imidazol-1-yl)(2,2-dimethyloxazolidin-3-yl)methanone | Imidazoles | | 104.1 | | | | |
| 269 | (2,5-dichloro-4-(4-chlorophenyl)-1H-imidazol-1-yl)(4,4-dimethyloxazolidin-3-yl)methanone | Imidazoles | | 106.2 | | | | |
| 270 | (5-ethyl-2,2-dimethyloxazolidin-3-yl)(4-phenyl-1H-imidazol-1-yl)methanone | Imidazoles | | 113.1 | | | | |
| 271 | N-cyclohexyl-4-(2-methoxyphenyl)-N-methyl-1H-imidazole-1-carboxamide | Imidazoles | | 55.8 | | | | |
| 272 | N-cyclohexyl-4-(3,4-difluorophenyl)-N-methyl-1H-imidazole-1-carboxamide | Imidazoles | | 63.6 | | | 19 | 7.1 |
| 273 | N-cyclohexyl-4-(4-fluorophenyl)-N-methyl-1H-imidazole-1-carboxamide | Imidazoles | | 65.1 | | | 3.4 | 2.6 |
| 274 | N-cyclohexyl-4-(3,4-dichlorophenyl)-N-methyl-1H-imidazole-1-carboxamide | Imidazoles | | 85 | | | | |
| 275 | N-cyclohexyl-N-methyl-4-(3-nitrophenyl)-1H-imidazole-1-carboxamide | Imidazoles | | 43.8 | | | 12.8 | 2.4 |
| 276 | N-cyclohexyl-4-(4-(difluoromethoxy)phenyl)-N-methyl-1H-imidazole-1-carboxamide | Imidazoles | | 71.5 | | | 1.4 | 2 |
| 277 | 4-(4-chlorophenyl)-N-cyclohexyl-N-methyl-1H-imidazole-1-carboxamide | Imidazoles | | 72.1 | | | | |

TABLE 1-continued

| | | | | In Vivo | | | |
|---|---|---|---|---|---|---|---|
| | | | | BRh 30 mg · kg · 1 h | LVh 30 mg · kg · 1 h | BRh mg · 3 kg · 8 h | LVh mg · 3 kg · 8 h |
| | | In Vitro | | | | | |
| | Name | Class | 10 uM | 100 nM | | | | |
| 278 | N-methyl-4-phenyl-N-(tetrahydro-2H-pyran-4-yl)-1H-imidazole-1-carboxamide | Imidazoles | | 103.5 | | | 1.6 | 1.8 |
| 279 | N-cyclohexyl-N,2-dimethyl-4-phenyl-1H-imidazole-1-carboxamide | Imidazoles | | 87.3 | | | 91.6 | 94.1 |
| 280 | (5-chloro-4-(4-chlorophenyl)-1H-imidazol-1-yl)(4,4-dimethyloxazolidin-3-yl)methanone | Imidazoles | | 111.8 | | | | |
| 281 | N-cyclopentyl-4-(3,4-dimethoxyphenyl)-N-methyl-1H-imidazole-1-carboxamide | Imidazoles | | 25.5 | | | | |
| 282 | N-(1-benzylpiperidin-4-yl)-N-methyl-4-phenyl-1H-imidazole-1-carboxamide | Imidazoles | | 40.9 | | | 0.5 | 1.6 |
| 283 | N-cyclohexyl-N-methyl-3-phenyl-1H-1,2,4-triazole-1-carboxamide | 1,2,4-Triazoles | | 75.1 | | | | |
| 284 | N-cyclohexyl-N,5-dimethyl-3-phenyl-1H-1,2,4-triazole-1-carboxamide | 1,2,4-Triazoles | | 146.2 | | | 130.7 | 145.6 |
| 285 | (4,4-dimethyloxazolidin-3-yl)(3-phenyl-1H-1,2,4-triazol-1-yl)methanone | 1,2,4-Triazoles | | 85.4 | | | | |
| 286 | (4,4-dimethyloxazolidin-3-yl)(5-methyl-3-phenyl-1H-1,2,4-triazol-1-yl)methanone | 1,2,4-Triazoles | | 112.8 | | | 104 | 93 |
| 287 | 4-(3'-carbamoylbiphenyl-3-yl)-N-methyl-N-tricyclo[3.3.1.13,7]dec-1-yl-1H-imidazole-1-carboxamide-propan-2-ol (1:1) | Imidazoles | | 127.3 | | | 105.8 | 85.7 |
| 288 | 4-[3-(benzyloxy)phenyl]-N-methyl-N-tricyclo[3.3.1.13,7]dec-1-yl-1H-imidazole-1-carboxamide | Imidazoles | | 114.8 | | | | |
| 289 | N-methyl-4-pyridin-3-yl-N-tricyclo[3.3.1.13,7]dec-1-yl-1H-imidazole-1-carboxamide | Imidazoles | | 109.8 | | | 113.2 | 96.1 |
| 290 | 4-biphenyl-3-yl-N-methyl-N-tricyclo[3.3.1.13,7]dec-1-yl-1H-imidazole-1-carboxamide | Imidazoles | | | | | 115 | 112.4 |
| 291 | N-methyl-4-(3-pyridin-4-ylphenyl)-N-tricyclo[3.3.1.13,7]dec-1-yl-1H-imidazole-1-carboxamide | Imidazoles | | | | | | |
| 292 | (4-(4-chlorophenyl)-1H-imidazol-1-yl)(2,2-dimethyl-5-phenyloxazolidin-3-yl)methanone | Imidazoles | | | | | | |
| 293 | (4,4-dimethyloxazolidin-3-yl)(6-methoxy-1H-benzo[d][1,2,3]triazol-1-yl)methanone | Benzotriazoles | | | | | 3.5 | 1.7 |
| 294 | N-cyclopentyl-4-(4-hydroxyphenyl)-N-methyl-1H-imidazole-1-carboxamide | Imidazoles | | | | | 1.4 | 1.4 |
| 295 | (5-chloro-4-phenyl-1H-imidazol-1-yl)(4,4-dimethyloxazolidin-3-yl)methanone | Imidazoles | | 99.2 | | | 77.9 | 32.4 |
| 296 | 4-(3-hydroxyphenyl)-N-methyl-N-tricyclo[3.3.1.13,7]dec-1-yl-1H-imidazole-1-carboxamide | Imidazoles | | | | | | |
| 297 | N-((1r,4r)-4-hydroxycyclohexyl)-N-methyl-1H-benzo[d][1,2,3]triazole-1-carboxamide | Benzotriazoles | | | | | | |
| 298 | (2,2-dimethyl-5-phenyloxazolidin-3-yl)(4-phenyl-1H-imidazol-1-yl)methanone | Imidazoles | | | | | 74.4 | 59.2 |
| 299 | (4-(4-chlorophenyl)-1H-imidazol-1-yl)(2,2-dimethyloxazolidin-3-yl)methanone | Imidazoles | | | | | | |
| 300 | 5-chloro-N-cyclohexyl-N-methyl-4-phenyl-1H-imidazole-1-carboxamide | Imidazoles | | | | | | |
| 301 | (5-bromo-4-(4-chlorophenyl)-1H-imidazol-1-yl)(4,4-dimethyloxazolidin-3-yl)methanone | Imidazoles | | | | | | |
| 302 | (4-ethyloxazolidin-3-yl)(4-phenyl-1H-imidazol-1-yl)methanone | Imidazoles | | | | | | |
| 303 | (4-(3,4-difluorophenyl)-1H-imidazol-1-yl)(4-ethyloxazolidin-3-yl)methanone | Imidazoles | | | | | | |
| 304 | (4-ethyloxazolidin-3-yl)(4-(3-methoxyphenyl)-1H-imidazol-1-yl)methanone | Imidazoles | | | | | | |
| 305 | N-methyl-4-(3-pyridin-3-ylphenyl)-N-tricyclo[3.3.1.13,7]dec-1-yl-1H-imidazole-1-carboxamide | Imidazoles | | | | | | |
| 306 | N-methyl-4-(3-pyrimidin-5-ylphenyl)-N-tricyclo[3.3.1.13,7]dec-1-yl-1H-imidazole-1-carboxamide | Imidazoles | | | | | | |
| 307 | N-cyclohexyl-4-(3-hydroxyphenyl)-N-methyl-1H-imidazole-1-carboxamide | Imidazoles | | 56.2 | | | 137.6 | 10.1 |
| 308 | (4-(3,4-difluorophenyl)-1H-imidazol-1-yl)(5-phenyloxazolidin-3-yl)methanone | Imidazoles | | 2.5 | | | | |
| 309 | (4-phenyl-1H-imidazol-1-yl)(5-phenyloxazolidin-3-yl)methanone | Imidazoles | | | | | | |
| 310 | (4-methyloxazolidin-3-yl)(4-phenyl-1H-imidazol-1-yl)methanone | Imidazoles | | | | | | |
| 311 | (4-(3,4-difluorophenyl)-1H-imidazol-1-yl)(4-methyloxazolidin-3-yl)methanone | Imidazoles | | | | | | |
| 312 | N-cyclohexyl-N-ethyl-4-phenyl-1H-imidazole-1-carboxamide | Imidazoles | | | | | | |
| 313 | N-cyclohexyl-4-(3,4-dimethoxyphenyl)-N-ethyl-1H-imidazole-1-carboxamide | Imidazoles | | | | | | |
| 314 | N-cyclohexyl-4-(3-fluoro-4-methoxyphenyl)-N-methyl-1H-imidazole-1-carboxamide | Imidazoles | | 84.3 | | | 84.3 | 48 |
| 315 | N-cyclopentyl-4-(3-fluoro-4-methoxyphenyl)-N-methyl-1H-imidazole-1-carboxamide | Imidazoles | | | | | | |
| 316 | (4,4-dimethyloxazolidin-3-yl)(4-(3-fluoro-4-methoxyphenyl)-1H-imidazol-1-yl)methanone | Imidazoles | | | | | | |
| 317 | 4-[4'-(dimethylamino)biphenyl-3-yl]-N-methyl-N-tricyclo[3.3.1.13,7]dec-1-yl-1H-imidazole-1-carboxamide | Imidazoles | | | | | | |
| 318 | 4-[3-(2,4-dimethoxypyrimidin-5-yl)phenyl]-N-methyl-N-tricyclo[3.3.1.13,7]dec-1-yl-1H-imidazole-1-carboxamide | Imidazoles | | | | | | |

TABLE 1-continued

| | | | In Vitro | | In Vivo | | | |
|---|---|---|---|---|---|---|---|---|
| | | | | | BRh 30 mg · kg · 1 h | LVh 30 mg · kg · 1 h | BRh 3 mg · kg · 8 h | LVh 3 mg · kg · 8 h |
| | Name | Class | 10 uM | 100 nM | | | | |
| 319 | N-cyclohexyl-4-(4-fluoro-3-methoxyphenyl)-N-methyl-1H-imidazole-1-carboxamide | Imidazoles | | 19.2 | | | 5.9 | 2 |
| 320 | 4-[3-(6-fluoropyridin-3-yl)phenyl]-N-methyl-N-tricyclo[3.3.1.13,7]dec-1-yl-1H-imidazole-1-carboxamide | Imidazoles | | | | | | |
| 321 | N-cyclopentyl-4-(4-fluoro-3-methoxyphenyl)-N-methyl-1H-imidazole-1-carboxamide | Imidazoles | | | | | 1.4 | 1.2 |
| 322 | 4-(3'-hydroxybiphenyl-3-yl)-N-methyl-N-tricyclo[3.3.1.13,7]dec-1-yl-1H-imidazole-1-carboxamide | Imidazoles | | | | | | |
| 323 | 4-[3-(6-methoxypyridin-3-yl)phenyl]-N-methyl-N-tricyclo[3.3.1.13,7]dec-1-yl-1H-imidazole-1-carboxamide | Imidazoles | | | | | | |
| 324 | 4-[4'-(acetylamino)biphenyl-3-yl]-N-methyl-N-tricyclo[3.3.1.13,7]dec-1-yl-1H-imidazole-1-carboxamide | Imidazoles | | | | | | |
| 325 | 4-(3-furan-3-ylphenyl)-N-methyl-N-tricyclo[3.3.1.13,7]dec-1-yl-1H-imidazole-1-carboxamide | Imidazoles | | | | | | |
| 326 | N-cyclopentyl-4-(4-methoxyphenyl)-N-methyl-1H-imidazole-1-carboxamide | Imidazoles | | | | | | |
| 327 | N-cyclopentyl-4-(3-methoxyphenyl)-N-methyl-1H-imidazole-1-carboxamide | Imidazoles | | | | | | |
| 328 | (4,4-dimethyloxazolidin-3-yl)(4-(4-methoxyphenyl)-1H-imidazol-1-yl)methanone | Imidazoles | | | | | | |
| 329 | (4,4-dimethyloxazolidin-3-yl)(4-(3-methoxyphenyl)-1H-imidazol-1-yl)methanone | Imidazoles | | 99.5 | | | 83.3 | 18.5 |
| 330 | N-cyclohexyl-4-(3-fluoro-4-hydroxyphenyl)-N-methyl-1H-imidazole-1-carboxamide | Imidazoles | | 29.7 | | | 22.8 | 11.1 |
| 331 | N-cyclopentyl-4-(3-fluoro-4-hydroxyphenyl)-N-methyl-1H-imidazole-1-carboxamide | Imidazoles | | 3.6 | | | 4 | 4.9 |
| 332 | (4,4-dimethyloxazolidin-3-yl)(4-(3-fluoro-4-hydroxyphenyl)-1H-imidazol-1-yl)methanone | Imidazoles | | 88.5 | | | 60 | 19.5 |
| 333 | (4,4-dimethyloxazolidin-3-yl)(4-(4-fluoro-3-hydroxyphenyl)-1H-imidazol-1-yl)methanone | Imidazoles | | 81.9 | | | 119 | 81.5 |
| 334 | 4-(benzofuran-2-yl)-N-cyclohexyl-N-methyl-1H-imidazole-1-carboxamide | Imidazoles | | 58.2 | | | 9.9 | 5.1 |
| 335 | N-cyclohexyl-N-methyl-4-(pyridin-3-yl)-1H-imidazole-1-carboxamide | Imidazoles | | 75.4 | | | 3.1 | 1 |
| 336 | 4-[3-(6-chloropyridin-3-yl)phenyl]-N-methyl-N-tricyclo[3.3.1.13,7]dec-1-yl-1H-imidazole-1-carboxamide | Imidazoles | | | | | | |
| 337 | (4,4-dimethyloxazolidin-3-yl)(2-methyl-4-phenyl-1H-imidazol-1-yl)methanone | Imidazoles | | | | | | |
| 338 | (4-(benzofuran-2-yl)-1H-imidazol-1-yl)(4,4-dimethyloxazolidin-3-yl)methanone | Imidazoles | | | | | | |
| 339 | oxazolidin-3-yl(4-phenyl-1H-imidazol-1-yl)methanone | Imidazoles | | | | | | |
| 340 | (4-(3-methoxyphenyl)-1H-imidazol-1-yl)(5-phenyloxazolidin-3-yl)methanone | Imidazoles | | | | | | |
| 341 | N-cyclohexyl-4-(4-methoxyphenyl)-N-methyl-1H-imidazole-1-carboxamide | Imidazoles | | | | | | |
| 342 | N-cyclohexyl-4-(3-methoxyphenyl)-N-methyl-1H-imidazole-1-carboxamide | Imidazoles | | | | | | |
| 343 | N-cyclohexyl-4-(4-fluoro-3-hydroxyphenyl)-N-methyl-1H-imidazole-1-carboxamide | Imidazoles | | 44.7 | | | 95.5 | 19.7 |
| 344 | N-cyclopentyl-4-(4-fluoro-3-hydroxyphenyl)-N-methyl-1H-imidazole-1-carboxamide | Imidazoles | | 1.7 | | | 121.1 | 2.1 |
| 345 | N-cyclohexyl-4-(4-(difluoromethoxy)phenyl)-N-ethyl-1H-imidazole-1-carboxamide | Imidazoles | | | | | | |
| 346 | N-cyclohexyl-4-(3,4-difluorophenyl)-N-ethyl-1H-imidazole-1-carboxamide | Imidazoles | | | | | | |
| 347 | (4,4-dimethyloxazolidin-3-yl)(4-(3-hydroxyphenyl)-1H-imidazol-1-yl)methanone | Imidazoles | | 109.6 | | | 76.6 | 24.5 |
| 348 | (4,4-dimethyloxazolidin-3-yl)(4-(3-(3-hydroxy-3-methylbut-1-ynyl)phenyl)-1H-imidazol-1-yl)methanone | Imidazoles | | | | | | |
| 349 | N-cyclohexyl-4-(3,4-dichlorophenyl)-N-ethyl-1H-imidazole-1-carboxamide | Imidazoles | | | | | | |
| 350 | N-cyclohexyl-N-ethyl-4-(4-methoxyphenyl)-1H-imidazole-1-carboxamide | Imidazoles | | | | | | |
| 351 | (4,4-dimethyloxazolidin-3-yl)(4-(4-fluoro-3-methoxyphenyl)-1H-imidazol-1-yl)methanone | Imidazoles | | 95.6 | | | 7.1 | 11.7 |
| 352 | (4,4-dimethyloxazolidin-3-yl)(4-(3-(3-hydroxy-3-methylbutyl)phenyl)-1H-imidazol-1-yl)methanone | Imidazoles | | | | | | |
| 353 | N-methyl-4-(1-oxidopyridin-3-yl)-N-tricyclo[3.3.1.13,7]dec-1-yl-1H-imidazole-1-carboxamide | Imidazoles | | | | | | |
| 354 | N-methyl-4-[3-(1-oxidopyridin-3-yl)phenyl]-N-tricyclo[3.3.1.13,7]dec-1-yl-1H-imidazole-1-carboxamide | Imidazoles | | | | | | |
| 355 | N-cyclohexyl-N-ethyl-4-(3-methoxyphenyl)-1H-imidazole-1-carboxamide | Imidazoles | | | | | | |
| 356 | (4-(3-amino-4-methoxyphenyl)-1H-imidazol-1-yl)(4,4-dimethyloxazolidin-3-yl)methanone | Imidazoles | | | | | 6.5 | 9.4 |
| 357 | 4-(3-amino-4-hydroxyphenyl)-N-cyclohexyl-N-methyl-1H-imidazole-1-carboxamide hydrochloride | Imidazoles | | 93.9 | | | 111.9 | 10.4 |
| 358 | (4-(3-amino-4-hydroxyphenyl)-1H-imidazol-1-yl)(4,4-dimethyloxazolidin-3-yl)methanone hydrochloride | Imidazoles | | | | | 117.1 | 81.2 |

TABLE 1-continued

| | | | In Vitro | | In Vivo | | | |
|---|---|---|---|---|---|---|---|---|
| | | | | | BRh 30 mg · kg · 1 h | LVh 30 mg · kg · 1 h | BRh mg · 3 kg · 8 h | LVh mg · 3 kg · 8 h |
| | Name | Class | 10 uM | 100 nM | | | | |
| 359 | (5-chloro-1-benzo[d][1,2,3]triazol-1-yl)(4,4-dimethyloxazolidin-3-yl)methanone | Benzotriazoles | | 1.4 | | | 2.5 | 1.7 |
| 360 | (4,6-difluoro-1H-benzo[d][1,2,3]triazol-1-yl)(4,4-dimethyloxazolidin-3-yl)methanone | Benzotriazoles | | 1.6 | | | 3.1 | 3.7 |
| 361 | (4,4-dimethyloxazolidin-3-yl)(6-phenyl-1H-benzo[d][1,2,3]triazol-1-yl)methanone | Benzotriazoles | | 1.3 | | | 6.3 | 1.4 |
| 362 | 3-(1-(cyclohexyl(methyl)carbamoyl)-1H-imidazol-4-yl)pyridine 1-oxide | Imidazoles | | 78.2 | | | 1.6 | 1.7 |
| 363 | 4-(3-(4-cyanophenoxy)phenyl)-N-cyclohexyl-N-methyl-1H-imidazole-1-carboxamide | Imidazoles | | | | | | |
| 364 | 4-(3-(1-(4,4-dimethyloxazolidine-3-carbonyl)-1H-imidazol-4-yl)phenoxy)benzonitrile | Imidazoles | | | | | | |
| 365 | 4-(3-amino-4-methoxyphenyl)-N-cyclohexyl-N-methyl-1H-imidazole-1-carboxamide | Imidazoles | | | | | | |
| 366 | (1H-[1,2,3]triazolo[4,5-b]pyridin-1-yl)(4,4-dimethyloxazolidin-3-yl)methanone | Triazolopyridine | | | | | | |
| 367 | (4,4-dimethyloxazolidin-3-yl)(6-methyl-1H-benzo[d][1,2,3]triazol-1-yl)methanone | Benzotriazoles | | | | | | |
| 368 | (3H-[1,2,3]triazolo[4,5-b]pyridin-3-yl)(4,4-dimethyloxazolidin-3-yl)methanone | Triazolopyridine | | | | | 4.9 | 9.6 |
| 369 | (1H-benzo[d][1,2,3]triazol-1-yl)(oxazolidin-3-yl)methanone | Benzotriazoles | | | | | | |
| 370 | (4,4-dimethyloxazolidin-3-yl)(6-(2-methoxyphenyl)-1H-benzo[d][1,2,3]triazol-1-yl)methanone | Benzotriazoles | | | | | | |
| 371 | (4,4-dimethyloxazolidin-3-yl)(5-(trifluoromethyl)-1H-benzo[d][1,2,3]triazol-1-yl)methanone | Benzotriazoles | | | | | | |
| 372 | (4,6-dimethoxy-1H-benzo[d][1,2,3]triazol-1-yl)(4,4-dimethyloxazolidin-3-yl)methanone | Benzotriazoles | | | | | | |
| 373 | (1H-benzo[d][1,2,3]triazol-1-yl)(2,2-dimethyloxazolidin-3-yl)methanone | Benzotriazoles | | | | | | |
| 374 | N-cyclohexyl-N-methyl-5-(trifluoromethyl)-1H-benzo[d][1,2,3]triazole-1-carboxamide | Benzotriazoles | | | | | | |
| 375 | N-cyclohexyl-N,5,6-trimethyl-1H-benzo[d][1,2,3]triazole-1-carboxamide | Benzotriazoles | | | | | | |
| 376 | N-cyclohexyl-N-methyl-4-(4-sulfamoylphenyl)-1H-imidazole-1-carboxamide | Imidazoles | | | | | 95.3 | 5.7 |
| 377 | N-cyclohexyl-4,6-dimethoxy-N-methyl-1H-benzo[d][1,2,3]triazole-1-carboxamide | Benzotriazoles | | | | | | |
| 378 | (5,6-dimethyl-2H-benzo[d][1,2,3]triazol-2-yl)(4,4-dimethyloxazolidin-3-yl)methanone | Benzotriazoles | | | | | | |
| 379 | N-((1r,4r)-4-(benzyloxy)cyclohexyl)-N-methyl-4-phenyl-1H-imidazole-1-carboxamide | Imidazoles | | | | | | |
| 380 | 4-(4-(2H-tetrazol-5-yl)phenyl)-N-cyclohexyl-N-methyl-1H-imidazole-1-carboxamide | Imidazoles | | | | | 77.3 | 51.3 |
| 381 | (5,6-dimethyl-1H-benzo[d][1,2,3]triazol-1-yl)(4,4-dimethyloxazolidin-3-yl)methanone | Benzotriazoles | | | | | | |
| 382 | (5,6-dimethoxy-1H-benzo[d][1,2,3]triazol-1-yl)(4,4-dimethyloxazolidin-3-yl)methanone | Benzotriazoles | | | | | | |
| 383 | N-((1r,4r)-4-hydroxycyclohexyl)-N-methyl-4-phenyl-1H-imidazole-1-carboxamide | Imidazoles | | | | | | |
| 384 | N-(1-hydroxy-2-methylpropan-2-yl)-4,6-dimethoxy-1H-benzo[d][1,2,3]triazole-1-carboxamide | Benzotriazoles | | | | | | |
| 385 | 4-(1-(4,4-dimethyloxazolidine-3-carbonyl)-1H-imidazol-4-yl)benzamide | Imidazoles | | | | | | |
| 386 | (4,4-dimethyloxazolidin-3-yl)(4-(4-(2-(piperidin-1-yl)ethoxy)phenyl)-1H-imidazol-1-yl)methanone hydrochloride | Imidazoles | | | | | | |
| 387 | (4,4-dimethyloxazolidin-3-yl)(4-(4-(2-morpholinoethoxy)phenyl)-1H-imidazol-1-yl)methanone hydrochloride | Imidazoles | | | | | | |
| 388 | (4,4-dimethyloxazolidin-3-yl)(4-(4-(2-(piperazin-1-yl)ethoxy)phenyl)-1H-imidazol-1-yl)methanone dihydrochloride | Imidazoles | | | | | | |
| 389 | 1-(4,4-dimethyloxazolidine-3-carbonyl)-1H-benzo[d][1,2,3]triazole-5-carboxamide | Benzotriazoles | | | | | | |
| 390 | 4-(4-carbamoylphenyl)-N-cyclohexyl-N-methyl-1H-imidazole-1-carboxamide | Imidazoles | | | | | | |
| 391 | (4,4-dimethyloxazolidin-3-yl)(6-phenyl-3H-[1,2,3]triazolo[4,5-b]pyridin-3-yl)methanone | Triazolopyridine | | | | | | |
| 392 | (4,4-dimethyloxazolidin-3-yl)(6-phenyl-1H-[1,2,3]triazolo[4,5-b]pyridin-1-yl)methanone | Triazolopyridine | | | | | | |
| 393 | (4,4-dimethyloxazolidin-3-yl)(4-(4-(piperidin-4-ylmethoxy)phenyl)-1H-imidazol-1-yl)methanone hydrochloride | Imidazoles | | | | | | |
| 394 | N-cyclohexyl-N-methyl-4-(4-(2-(piperidin-1-yl)ethoxy)phenyl)-1H-imidazole-1-carboxamide hydrochloride | Imidazoles | | | | | | |
| 395 | N-cyclohexyl-N-methyl-4-(4-(2-morpholinoethoxy)phenyl)-1H-imidazole-1-carboxamide hydrochloride | Imidazoles | | | | | | |
| 396 | (4,4-dimethyloxazolidin-3-yl)(4-(4-(2-(piperidin-4-yl)ethoxy)phenyl)-1H-imidazol-1-yl)methanone hydrochloride | Imidazoles | | | | | | |

TABLE 1-continued

| | | | | In Vivo | | | |
|---|---|---|---|---|---|---|---|
| | | In Vitro | | BRh 30 mg·kg·1 h | LVh 30 mg·kg·1 h | BRh mg·3 kg·8 h | LVh mg·3 kg·8 h |
| Name | Class | 10 uM | 100 nM | | | | |
| 397 N-cyclohexyl-N-methyl-4-(4-(2-(piperazin-1-yl)ethoxy)phenyl)-1H-imidazole-1-carboxamide dihydrochloride | Imidazoles | | | | | | |
| 398 4-(4-hydroxyphenyl)-N-methyl-N-(tetrahydro-2H-pyran-4-yl)-1H-imidazole-1-carboxamide | Imidazoles | | | | | | |
| 399 (4,4-dimethyloxazolidin-3-yl)(4-(3-(2-(piperidin-1-yl)ethoxy)phenyl)-1H-imidazol-1-yl)methanone hydrochloride | Imidazoles | | | | | | |
| 400 N-cyclohexyl-N-methyl-4-(4-(piperidin-4-ylmethoxy)phenyl)-1H-imidazole-1-carboxamide hydrochloride | Imidazoles | | | | | | |
| 401 (4,4-dimethyloxazolidin-3-yl)(4-(3-(2-(piperazin-1-yl)ethoxy)phenyl)-1H-imidazol-1-yl)methanone dihydrochloride | Imidazoles | | | | | | |
| 402 (4,4-dimethyloxazolidin-3-yl)(4-(3-(2-morpholinoethoxy)phenyl)-1H-imidazol-1-yl)methanone hydrochloride | Imidazoles | | | | | | |
| 403 4-(3-carbamoylphenyl)-N-cyclohexyl-N-methyl-1H-imidazole-1-carboxamide | Imidazoles | | | | | | |
| 404 N-cyclohexyl-N-methyl-4-(4-(morpholinosulfonyl)phenyl)-1H-imidazole-1-carboxamide | Imidazoles | | | | | | |
| 405 (4,4-dimethyloxazolidin-3-yl)(4-(3-(piperidin-4-ylmethoxy)phenyl)-1H-imidazol-1-yl)methanone hydrochloride | Imidazoles | | | | | | |
| 406 (Z)—N-cyclohexyl-4-(4-(N'-hydroxycarbamimidoyl)phenyl)-N-methyl-1H-imidazole-1-carboxamide | Imidazoles | | | | | 66.8 | 16.3 |
| 407 N-cyclohexyl-N-methyl-4-(3-(2-(piperazin-1-yl)ethoxy)phenyl)-1H-imidazole-1-carboxamide dihydrochloride | Imidazoles | | | | | | |
| 408 N-cyclohexyl-N-methyl-4-(3-(2-morpholinoethoxy)phenyl)-1H-imidazole-1-carboxamide hydrochloride | Imidazoles | | | | | | |
| 409 N-(1-benzylpiperidin-4-yl)-N-methyl-4-phenyl-1H-imidazole-1-carboxamide oxalate | Imidazoles | | | | | | |
| 410 N-(1-benzylpiperidin-4-yl)-N-methyl-4-phenyl-1H-imidazole-1-carboxamide hydrochloride | Imidazoles | | | | | | |
| 411 N-(1-benzylpiperidin-4-yl)-N-methyl-4-phenyl-1H-imidazole-1-carboxamide methanesulfonate | Imidazoles | | | | | | |
| 412 N-(1-benzylpiperidin-4-yl)-N-methyl-4-phenyl-1H-imidazole-1-carboxamide 2-hydroxypropane-1,2,3-tricarboxylate | Imidazoles | | | | | | |
| 413 N-(1-benzylpiperidin-4-yl)-N-methyl-4-phenyl-1H-imidazole-1-carboxamide (2R,3R)-2,3-dihydroxysuccinate | Imidazoles | | | | | | |
| 414 N-(1-benzylpiperidin-4-yl)-N-methyl-4-phenyl-1H-imidazole-1-carboxamide phosphate | Imidazoles | | | | | | |
| 415 4-(4-(4-(benzyloxy)piperidin-1-ylsulfonyl)phenyl)-N-cyclohexyl-N-methyl-1H-imidazole-1-carboxamide | Imidazoles | | | | | 109.1 | 95.4 |
| 416 N-(1-benzylpiperidin-4-yl)-N-methyl-4-(pyridin-3-yl)-1H-imidazole-1-carboxamide | Imidazoles | | | | | | |
| 417 N-cyclopentyl-N-methyl-4-(pyridin-3-yl)-1H-imidazole-1-carboxamide | Imidazoles | | | | | | |
| 418 N-(1-benzylpiperidin-4-yl)-4-(3-methoxyphenyl)-N-methyl-1H-imidazole-1-carboxamide | Imidazoles | | | | | | |
| 419 N-(1-benzylpiperidin-4-yl)-4-(4-methoxyphenyl)-N-methyl-1H-imidazole-1-carboxamide | Imidazoles | | | | | 0.8 | 1 |
| 420 4-(4-(benzyloxy)phenyl)-N-(1-benzylpiperidin-4-yl)-N-methyl-1H-imidazole-1-carboxamide | Imidazoles | | | | | | |
| 421 3-(1-(cyclopentyl(methyl)carbamoyl)-1H-imidazol-4-yl)pyridine 1-oxide | Imidazoles | | | | | | |
| 422 N-cyclohexyl-N-methyl-4-(4-(methylsulfonyl)phenyl)-1H-imidazole-1-carboxamide | Imidazoles | | | | | 1.7 | 2.7 |
| 423 N-(1-benzylpiperidin-4-yl)-4-(3-(hydroxycarbamoyl)phenyl)-N-methyl-1H-imidazole-1-carboxamide | Imidazoles | | | | | 90 | 2.1 |
| 424 N-cyclohexyl-4-(3-(hydroxycarbamoyl)phenyl)-N-methyl-1H-imidazole-1-carboxamide | Imidazoles | | | | | 1 | 0.5 |
| 425 4-(4-(benzylamino)-3-nitrophenyl)-N-cyclohexyl-N-methyl-1H-imidazole-1-carboxamide | Imidazoles | | | | | 111.4 | 104.6 |
| 426 4-(1-benzyl-2-oxo-2,3-dihydro-1H-benzo[d]imidazol-5-yl)-N-cyclohexyl-N-methyl-1H-imidazole-1-carboxamide | Imidazoles | | | | | 96.9 | 115.8 |
| 427 N-(1-benzylpiperidin-4-yl)-4-(3,4-difluorophenyl)-N-methyl-1H-imidazole-1-carboxamide | Imidazoles | | | | | | |
| 428 N-(1-benzylpiperidin-4-yl)-4-(4-chlorophenyl)-N-methyl-1H-imidazole-1-carboxamide | Imidazoles | | | | | | |
| 429 N-(1-benzylpiperidin-4-yl)-4-(4-(difluoromethoxy)phenyl)-N-methyl-1H-imidazole-1-carboxamide | Imidazoles | | | | | | |
| 430 N-(1-benzylpiperidin-4-yl)-4-(4-fluorophenyl)-N-methyl-1H-imidazole-1-carboxamide | Imidazoles | | | | | | |
| 431 N-(1-(2,6-dimethoxybenzyl)piperidin-4-yl)-N-methyl-4-(pyridin-3-yl)-1H-imidazole-1-carboxamide | Imidazoles | | | | | | |
| 432 N-cyclohexyl-4-(4-(4-hydroxypiperidin-1-ylsulfonyl)phenyl)-N-methyl-1H-imidazole-1-carboxamide | Imidazoles | | | | | 96.1 | 65.5 |
| 433 N-(1-benzylpiperidin-4-yl)-4-(3,4-dimethoxyphenyl)-N-methyl-1H-imidazole-1-carboxamide | Imidazoles | | | | | | |

TABLE 1-continued

| | | | In Vitro | | In Vivo | | | |
|---|---|---|---|---|---|---|---|---|
| | | | | | BRh 30 mg·kg·1 h | LVh 30 mg·kg·1 h | BRh mg·3 kg·8 h | LVh mg·3 kg·8 h |
| | Name | Class | 10 uM | 100 nM | | | | |
| 434 | (octahydroisoquinolin-2(1H)-yl)(4-phenyl-1H-imidazol-1-yl)methanone | Imidazoles | | | | | | |
| 435 | N-cyclohexyl-4-(4-(dimethylamino)-3-nitrophenyl)-N-methyl-1H-imidazole-1-carboxamide | Imidazoles | | | | | 4.3 | 4.9 |
| 436 | 1-(4,4-dimethyloxazolidine-3-carbonyl)-1H-benzo[d][1,2,3]triazole-5-carboxylic acid | Benzotriazoles | | | | | | |
| 437 | N-(benzyloxy)-1-(4,4-dimethyloxazolidine-3-carbonyl)-1H-benzo[d][1,2,3]triazole-5-carboxamide | Benzotriazoles | | | | | | |
| 438 | N-cyclohexyl-4-(4-methoxy-3-(2H-tetrazol-5-yl)phenyl)-N-methyl-1H-imidazole-1-carboxamide | Imidazoles | | | | | 92.4 | 6.1 |
| 439 | N-cyclohexyl-4-(4-hydroxy-3-(2H-tetrazol-5-yl)phenyl)-N-methyl-1H-imidazole-1-carboxamide | Imidazoles | | | | | 94.4 | 58.6 |
| 440 | 1-(4,4-dimethyloxazolidine-3-carbonyl)-N-hydroxy-1H-benzo[d][1,2,3]triazole-5-carboxamide | Benzotriazoles | | | | | 23.2 | 3.3 |
| 441 | N-(1-benzylpiperidin-4-yl)-4-(4-methoxy-3-nitrophenyl)-N-methyl-1H-imidazole-1-carboxamide | Imidazoles | | | | | | |
| 442 | N-(1-benzylpiperidin-4-yl)-4-(4-fluoro-3-methoxyphenyl)-N-methyl-1H-imidazole-1-carboxamide | Imidazoles | | | | | | |
| 443 | N-(1-benzylpiperidin-4-yl)-4-(3-fluoro-4-methoxyphenyl)-N-methyl-1H-imidazole-1-carboxamide | Imidazoles | | | | | | |
| 444 | tert-butyl 4-(4-(4-(benzyloxy)phenyl)-N-methyl-1H-imidazole-1-carboxamido)piperidine-1-carboxylate | Imidazoles | | | | | | |
| 445 | 4-(3-cyano-4-methoxyphenyl)-N-cyclohexyl-N-methyl-1H-imidazole-1-carboxamide | Imidazoles | | | | | | |
| 446 | N-(1-benzylpiperidin-4-yl)-4-(3-cyano-4-methoxyphenyl)-N-methyl-1H-imidazole-1-carboxamide | Imidazoles | | | | | | |
| 447 | 4-(3-amino-4-(dimethylamino)phenyl)-N-cyclohexyl-N-methyl-1H-imidazole-1-carboxamide | Imidazoles | | | | | 11.8 | 6.5 |
| 448 | 3-(1-(4-(ethoxycarbonyl)piperazine-1-carbonyl)-1H-imidazol-4-yl)pyridine 1-oxide | Imidazoles | | | | | | |
| 449 | 3-(1-(butyl(methyl)carbamoyl)-1H-imidazol-4-yl)pyridine 1-oxide | Imidazoles | | | | | | |
| 450 | 4-(3-amino-4-methoxyphenyl)-N-methyl-N-(piperidin-4-yl)-1H-imidazole-1-carboxamide | Imidazoles | | | | | 114.2 | 65.4 |
| 451 | N-(1-benzylpiperidin-4-yl)-4-(4-hydroxyphenyl)-N-methyl-1H-imidazole-1-carboxamide hydrobromide | Imidazoles | | | | | 1.1 | 0.3 |
| 452 | 3-(1-(diethylcarbamoyl)-1H-imidazol-4-yl)pyridine 1-oxide | Imidazoles | | | | | | |
| 453 | N-methyl-N-phenyl-4-(pyridin-3-yl)-1H-imidazole-1-carboxamide | Imidazoles | | | | | | |
| 454 | N-(1-benzylpiperidin-4-yl)-4-(3-fluoro-4-hydroxyphenyl)-N-methyl-1H-imidazole-1-carboxamide hydrobromide | Imidazoles | | | | | 3.1 | 3 |
| 455 | 3-(1-(4,4-dimethyloxazolidine-3-carbonyl)-1H-imidazol-4-yl)pyridine 1-oxide | Imidazoles | | | | | | |
| 456 | 3-(1-(methyl(phenyl)carbamoyl)-1H-imidazol-4-yl)pyridine 1-oxide | Imidazoles | | | | | | |
| 457 | N-(1-benzylpiperidin-4-yl)-4-(4-hydroxy-3-nitrophenyl)-N-methyl-1H-imidazole-1-carboxamide hydrobromide | Imidazoles | | | | | 28.1 | 10.6 |
| 458 | N-cyclohexyl-4-(pyridin-3-yl)-1H-imidazole-1-carboxamide | Imidazoles | | | | | | |
| 459 | 3-(1-((1-benzylpiperidin-4-yl)(methyl)carbamoyl)-1H-imidazol-4-yl)pyridine 1-oxide | Imidazoles | | | | | 1.3 | 1.9 |
| 460 | ethyl 1-(4,4-dimethyloxazolidine-3-carbonyl)-1H-benzo[d][1,2,3]triazole-6-carboxylate | Benzotriazoles | | | | | | |
| 461 | 3-(1-(cyclohexylcarbamoyl)-1H-imidazol-4-yl)pyridine 1-oxide | Imidazoles | | | | | | |
| 462 | 1-(4,4-dimethyloxazolidine-3-carbonyl)-1H-benzo[d][1,2,3]triazole-6-carboxamide | Benzotriazoles | | | | | | |
| 463 | N-methyl-4-(pyridin-3-yl)-N-(tetrahydro-2H-pyran-4-yl)-1H-imidazole-1-carboxamide | Imidazoles | | | | | | |
| 464 | N-cyclohexyl-N-ethyl-4-(pyridin-3-yl)-1H-imidazole-1-carboxamide | Imidazoles | | | | | | |
| 465 | N-(1-benzylpiperidin-4-yl)-4-(3,4-dihydroxyphenyl)-N-methyl-1H-imidazole-1-carboxamide hydrobromide | Imidazoles | | | | | 3.8 | 3.1 |
| 466 | 4-(3-fluoro-4-methoxyphenyl)-N-methyl-N-(tetrahydro-2H-pyran-4-yl)-1H-imidazole-1-carboxamide | Imidazoles | | | | | | |
| 467 | N-methyl-N-(1-phenethylpiperidin-4-yl)-4-phenyl-1H-imidazole-1-carboxamide | Imidazoles | | | | | | |
| 468 | 4-(3-amino-4-methoxyphenyl)-N-methyl-N-(tetrahydro-2H-pyran-4-yl)-1H-imidazole-1-carboxamide | Imidazoles | | | | | 4.7 | 4.3 |
| 469 | tert-butyl 4-(4-(4-hydroxyphenyl)-N-methyl-1H-imidazole-1-carboxamido)piperidine-1-carboxylate | Imidazoles | | | | | 1.4 | 0.7 |
| 470 | 3-(1-(methyl(tetrahydro-2H-pyran-4-yl)carbamoyl)-1H-imidazol-4-yl)pyridine 1-oxide | Imidazoles | | | | | | |
| 471 | 3-(1-(cyclohexyl(ethyl)carbamoyl)-1H-imidazol-4-yl)pyridine 1-oxide | Imidazoles | | | | | | |
| 472 | 4-(4-fluorophenyl)-N-methyl-N-(tetrahydro-2H-pyran-4-yl)-1H-imidazole-1-carboxamide | Imidazoles | | | | | | |
| 473 | 4-(3,4-difluorophenyl)-N-methyl-N-(tetrahydro-2H-pyran-4-yl)-1H-imidazole-1-carboxamide | Imidazoles | | | | | | |

TABLE 1-continued

| | Name | Class | In Vitro 10 uM | In Vitro 100 nM | In Vivo BRh 30 mg·kg·1 h | In Vivo LVh 30 mg·kg·1 h | In Vivo BRh mg·3 kg·8 h | In Vivo LVh mg·3 kg·8 h |
|---|---|---|---|---|---|---|---|---|
| 474 | 4-(4-(difluoromethoxy)phenyl)-N-methyl-N-(tetrahydro-2H-pyran-4-yl)-1H-imidazole-1-carboxamide | Imidazoles | | | | | | |
| 475 | 4-(4-methoxyphenyl)-N-methyl-N-(tetrahydro-2H-pyran-4-yl)-1H-imidazole-1-carboxamide | Imidazoles | | | | | | |
| 476 | 4-(3,4-dimethoxyphenyl)-N-methyl-N-(tetrahydro-2H-pyran-4-yl)-1H-imidazole-1-carboxamide | Imidazoles | | | | | | |
| 477 | 4-(4-chlorophenyl)-N-methyl-N-(tetrahydro-2H-pyran-4-yl)-1H-imidazole-1-carboxamide | Imidazoles | | | | | | |
| 478 | N-tert-butyl-1-(4,4-dimethyloxazolidine-3-carbonyl)-1H-benzo[d][1,2,3]triazole-6-carboxamide | Benzotriazoles | | | | | | |
| 479 | 1-(4,4-dimethyloxazolidine-3-carbonyl)-N,N-dimethyl-1H-benzo[d][1,2,3]triazole-6-carboxamide | Benzotriazoles | | | | | | |
| 480 | N1-cyclopentyl-N1-methyl-1H-benzo[d][1,2,3]triazole-1,5-dicarboxamide | Benzotriazoles | | | | | | |
| 481 | 1-(4,4-dimethyloxazolidine-3-carbonyl)-N-phenyl-1H-benzo[d][1,2,3]triazole-6-carboxamide | Benzotriazoles | | | | | | |
| 482 | 4-(3-carbamoyl-4-methoxyphenyl)-N-cyclohexyl-N-methyl-1H-imidazole-1-carboxamide | Imidazoles | | | | | 83.2 | 16.7 |
| 483 | N-methyl-N-(tetrahydro-2H-pyran-4-yl)-1H-benzo[d][1,2,3]triazole-1-carboxamide | Benzotriazoles | | | | | | |
| 484 | 4-(4-fluoro-3-methoxyphenyl)-N-methyl-N-(tetrahydro-2H-pyran-4-yl)-1H-imidazole-1-carboxamide | Imidazoles | | | | | | |
| 485 | N-cyclohexyl-4-(4-methoxy-3-(methylsulfonamido)phenyl)-N-methyl-1H-imidazole-1-carboxamide | Imidazoles | | | | | 92.1 | 15.1 |
| 486 | 1-(4,4-dimethyloxazolidine-3-carbonyl)-N-phenyl-1H-benzo[d][1,2,3]triazole-5-carboxamide | Benzotriazoles | | | | | | |
| 487 | N-tert-butyl-1-(4,4-dimethyloxazolidine-3-carbonyl)-1H-benzo[d][1,2,3]triazole-5-carboxamide | Benzotriazoles | | | | | | |
| 488 | N-methyl-N-(1-phenethylpiperidin-4-yl)-4-(pyridin-3-yl)-1H-imidazole-1-carboxamide | Imidazoles | | | | | 3.8 | 2 |
| 489 | N-cyclohexyl-1-(4,4-dimethyloxazolidine-3-carbonyl)-1H-benzo[d][1,2,3]triazole-5-carboxamide | Benzotriazoles | | | | | | |
| 490 | N-cyclohexyl-1-(4,4-dimethyloxazolidine-3-carbonyl)-1H-benzo[d][1,2,3]triazole-6-carboxamide | Benzotriazoles | | | | | | |
| 491 | N1-cyclohexyl-N1-methyl-1H-benzo[d][1,2,3]triazole-1,5-dicarboxamide | Benzotriazoles | | | | | | |
| 492 | N-(1-benzylpiperidin-4-yl)-N-methyl-1H-benzo[d][1,2,3]triazole-1-carboxamide hydrochloride | Benzotriazoles | | | | | 0.9 | 0.7 |
| 493 | N-cyclohexyl-N-methyl-4-(pyridin-4-yl)-1H-imidazole-1-carboxamide | Imidazoles | | | | | | |
| 494 | 4-(4-hydroxy-3-nitrophenyl)-N-methyl-N-(tetrahydro-2H-pyran-4-yl)-1H-imidazole-1-carboxamide | Imidazoles | | | | | 48.9 | 22.9 |
| 495 | 4-(3-fluoro-4-hydroxyphenyl)-N-methyl-N-(tetrahydro-2H-pyran-4-yl)-1H-imidazole-1-carboxamide | Imidazoles | | | | | 2.1 | 2.3 |
| 496 | N-benzyl-1-(4,4-dimethyloxazolidine-3-carbonyl)-1H-benzo[d][1,2,3]triazole-5-carboxamide | Benzotriazoles | | | | | | |
| 497 | 4-(1-(cyclohexyl(methyl)carbamoyl)-1H-imidazol-4-yl)pyridine 1-oxide | Imidazoles | | | | | | |
| 498 | 4-(3-methoxyphenyl)-N-methyl-N-(1-propylpiperidin-4-yl)-1H-imidazole-1-carboxamide | Imidazoles | | | | | 21.4 | 12.6 |
| 499 | 4-(3-carbamoyl-4-hydroxyphenyl)-N-cyclohexyl-N-methyl-1H-imidazole-1-carboxamide | Imidazoles | | | | | 120.6 | 44.1 |
| 500 | 4-(4-fluoro-3-hydroxyphenyl)-N-methyl-N-(tetrahydro-2H-pyran-4-yl)-1H-imidazole-1-carboxamide | Imidazoles | | | | | 75.1 | 21.8 |
| 501 | 4-(4-methoxyphenyl)-N-methyl-N-(piperidin-4-yl)-1H-imidazole-1-carboxamide | Imidazoles | | | | | 108.5 | 67.4 |
| 502 | N-(1-ethylpiperidin-4-yl)-4-(3-methoxyphenyl)-N-methyl-1H-imidazole-1-carboxamide | Imidazoles | | | | | 50.2 | 11.5 |
| 503 | N-(1-ethylpiperidin-4-yl)-4-(3-fluoro-4-methoxyphenyl)-N-methyl-1H-imidazole-1-carboxamide | Imidazoles | | | | | 78.8 | 25.1 |
| 504 | N-methyl-4-phenyl-N-(piperidin-4-yl)-1H-imidazole-1-carboxamide hydrochloride | Imidazoles | | | | | 112.5 | 51.2 |
| 505 | (4-cyclohexylpiperazin-1-yl)(2-(4,4-dimethyloxazolidine-3-carbonyl)-2H-benzo[d][1,2,3]triazol-5-yl)methanone oxalate | Benzotriazoles | | | | | | |
| 506 | (4-(benzo[d][1,3]dioxol-5-ylmethyl)piperazin-1-yl)(2-(4,4-dimethyloxazolidine-3-carbonyl)-2H-benzo[d][1,2,3]triazol- | Benzotriazoles | | | | | | |
| 507 | (E)—N-cyclohexyl-4-(3-(N'-hydroxycarbamimidoyl)-4-methoxyphenyl)-N-methyl-1H-imidazole-1-carboxamide | Imidazoles | | | | | 101.7 | 34 |
| 508 | N-((1r,4r)-4-hydroxycyclohexyl)-N-methyl-4-(pyridin-3-yl)-1H-imidazole-1-carboxamide | Imidazoles | | | | | | |
| 509 | N-(1-ethylpiperidin-4-yl)-N-methyl-4-(3-nitrophenyl)-1H-imidazole-1-carboxamide | Imidazoles | | | | | 78.3 | 17.2 |
| 510 | 4-(3,4-dimethoxyphenyl)-N-(1-ethylpiperidin-4-yl)-N-methyl-1H-imidazole-1-carboxamide | Imidazoles | | | | | | |
| 511 | 4-(3-aminophenyl)-N-(1-ethylpiperidin-4-yl)-N-methyl-1H-imidazole-1-carboxamide | Imidazoles | | | | | | |

TABLE 1-continued

| | | | | | In Vivo | | |
| | | | | BRh 30 mg · kg · 1 h | LVh 30 mg · kg · 1 h | BRh mg · 3 kg · 8 h | LVh mg · 3 kg · 8 h |
| | | In Vitro | | | | | |
| Name | Class | 10 uM | 100 nM | | | | |
|---|---|---|---|---|---|---|---|
| 512 4-(3,4-dimethoxyphenyl)-N-methyl-N-(1-propylpiperidin-4-yl)-1H-imidazole-1-carboxamide | Imidazoles | | | | | | |
| 513 4-(3-carbamoyl-4-hydroxyphenyl)-N-methyl-N-(tetrahydro-2H-pyran-4-yl)-1H-imidazole-1-carboxamide | Imidazoles | | | | | 90.3 | 14.4 |
| 514 4-(3-fluoro-4-methoxyphenyl)-N-methyl-N-(1-propylpiperidin-4-yl)-1H-imidazole-1-carboxamide | Imidazoles | | | | | | |
| 515 tert-butyl 4-(N-methyl-4-(pyridin-3-yl)-1H-imidazole-1-carboxamido)piperidine-1-carboxylate | Imidazoles | | | | | | |
| 516 3-(1-(((1r,4r)-4-hydroxycyclohexyl)(methyl)carbamoyl)-1H-imidazol-4-yl)pyridine 1-oxide | Imidazoles | | | | | | |
| 517 (4-benzylpiperazin-1-yl)(1-(4,4-dimethyloxazolidine-3-carbonyl)-1H-benzo[d][1,2,3]triazol-5-yl)methanone oxalate | Benzotriazoles | | | | | | |
| 518 N-cyclohexyl-N-methyl-4-(pyridin-2-yl)-1H-imidazole-1-carboxamide | Imidazoles | | | | | | |
| 519 3-(1-(methyl(1-propylpiperidin-4-yl)carbamoyl)-1H-imidazol-4-yl)pyridine 1-oxide | Imidazoles | | | | | 82 | 4.4 |
| 520 4-(4-methoxyphenyl)-N-methyl-N-(1-propylpiperidin-4-yl)-1H-imidazole-1-carboxamide | Imidazoles | | | | | | |
| 521 N-(1-ethylpiperidin-4-yl)-4-(4-methoxyphenyl)-N-methyl-1H-imidazole-1-carboxamide | Imidazoles | | | | | | |
| 522 N-methyl-4-(3-nitrophenyl)-N-(1-propylpiperidin-4-yl)-1H-imidazole-1-carboxamide | Imidazoles | | | | | | |
| 523 N-(1-benzylpiperidin-4-yl)-4-(4-fluoro-3-hydroxyphenyl)-N-methyl-1H-imidazole-1-carboxamide | Imidazoles | | | | | | |
| 524 4-(3-aminophenyl)-N-methyl-N-(1-propylpiperidin-4-yl)-1H-imidazole-1-carboxamide | Imidazoles | | | | | | |
| 525 N-(1-ethylpiperidin-4-yl)-N-methyl-4-(pyridin-3-yl)-1H-imidazole-1-carboxamide | Imidazoles | | | | | | |
| 526 4-(3'-carbamoylbiphenyl-3-yl)-N-methyl-N-(1-propylpiperidin-4-yl)-1H-imidazole-1-carboxamide | Imidazoles | | | | | | |
| 527 N-cyclohexyl-N-methyl-2-oxo-5-phenyl-1,3,4-oxadiazole-3(2H)-carboxamide | oxadiazole | | | | | | |
| 528 3-(4,4-dimethyloxazolidine-3-carbonyl)-5-phenyl-1,3,4-oxadiazol-2(3H)-one | oxadiazole | | | | | | |
| 529 N-methyl-N-(1-propylpiperidin-4-yl)-4-(pyridin-3-yl)-1H-imidazole-1-carboxamide | Imidazoles | | | | | | |
| 530 2-(1-(cyclohexyl(methyl)carbamoyl)-1H-imidazol-4-yl)pyridine 1-oxide | Imidazoles | | | | | | |
| 531 N-methyl-N-(piperidin-4-yl)-4-(pyridin-3-yl)-1H-imidazole-1-carboxamide dihydrochloride | Imidazoles | | | | | | |
| 532 4-(4-methoxyphenyl)-N-methyl-N-(1-(methylsulfonyl)piperidin-4-yl)-1H-imidazole-1-carboxamide | Imidazoles | | | | | | |
| 533 N-methyl-N-(1-(methylsulfonyl)piperidin-4-yl)-4-(pyridin-3-yl)-1H-imidazole-1-carboxamide | Imidazoles | | | | | 12 | 0.2 |
| 534 4-(3-fluoro-4-methoxyphenyl)-N-methyl-N-(piperidin-4-yl)-1H-imidazole-1-carboxamide hydrochloride | Imidazoles | | | | | | |
| 535 N-(1-benzylpiperidin-4-yl)-5-cyano-N-methyl-1H-benzo[d][1,2,3]triazole-1-carboxamide | Benzotriazoles | | | | | | |
| 536 N-(1-ethylpiperidin-4-yl)-4-(3-fluoro-4-hydroxyphenyl)-N-methyl-1H-imidazole-1-carboxamide | Imidazoles | | | | | 74.6 | 18.3 |
| 537 N-(1-ethylpiperidin-4-yl)-4-(4-fluoro-3-methoxyphenyl)-N-methyl-1H-imidazole-1-carboxamide | Imidazoles | | | | | | |
| 538 N,N-dimethyl-1H-benzo[d][1,2,3]triazole-1-carboxamide | Benzotriazoles | | | | | | |
| 539 N,N-dimethyl-1H-[1,2,3]triazolo[4,5-b]pyridine-1-carboxamide | Benzotriazoles | | | | | | |
| 540 4-(3-fluoro-4-methoxyphenyl)-N-(1-(2-hydroxyethyl)piperidin-4-yl)-N-methyl-1H-imidazole-1-carboxamide | Imidazoles | | | | | 89.7 | 33.7 |
| 541 N-(1-(2-cyanoethyl)piperidin-4-yl)-4-(3-fluoro-4-methoxyphenyl)-N-methyl-1H-imidazole-1-carboxamide | Imidazoles | | | | | | |
| 542 N-methyl-4-(pyridin-4-yl)-N-(tetrahydro-2H-pyran-4-yl)-1H-imidazole-1-carboxamide | Imidazoles | | | | | | |
| 543 4-(1-(methyl(tetrahydro-2H-pyran-4-yl)carbamoyl)-1H-imidazol-4-yl)pyridine 1-oxide | Imidazoles | | | | | | |
| 544 4-(4-methoxyphenyl)-N-methyl-N-(1-(pyridin-2-ylmethyl)piperidin-4-yl)-1H-imidazole-1-carboxamide | Imidazoles | | | | | | |
| 545 4-(4-fluoro-3-methoxyphenyl)-N-methyl-N-(1-propylpiperidin-4-yl)-1H-imidazole-1-carboxamide | Imidazoles | | | | | | |
| 546 4-(4-methoxyphenyl)-N-methyl-N-(1-(2-(pyridin-3-yl)thiazole-4-carbonyl)piperidin-4-yl)-1H-imidazole-1-carboxamide | Imidazoles | | | | | | |
| 547 N-(1-acetylpiperidin-4-yl)-4-(4-methoxyphenyl)-N-methyl-1H-imidazole-1-carboxamide | Imidazoles | | | | | | |
| 548 N-(1-acetylpiperidin-4-yl)-N-methyl-4-(pyridin-3-yl)-1H-imidazole-1-carboxamide | Imidazoles | | | | | | |
| 549 4-(4-methoxyphenyl)-N-methyl-N-(1-(3-(trifluoromethyl)phenylsulfonyl)piperidin-4-yl)-1H-imidazole-1-carboxamide | Imidazoles | | | | | | |

TABLE 1-continued

| | | | In Vitro | | In Vivo | | | |
|---|---|---|---|---|---|---|---|---|
| | | | | | BRh 30 mg·kg·1 h | LVh 30 mg·kg·1 h | BRh mg·3 kg·8 h | LVh mg·3 kg·8 h |
| | Name | Class | 10 uM | 100 nM | | | | |
| 550 | N-(1-benzylpiperidin-4-yl)-4-(3'-carbamoylbiphenyl-3-yl)-N-methyl-1H-imidazole-1-carboxamide | Imidazoles | | | | | 94.3 | 5.7 |
| 551 | N-cyclohexyl-N-methyl-4-(4-(5-oxo-4,5-dihydro-1,2,4-oxadiazol-3-yl)phenyl)-1H-imidazole-1-carboxamide | Imidazoles | | | | | 85.2 | 3.8 |
| 552 | 4-(3-(hydroxycarbamoyl)phenyl)-N-methyl-N-(1-propylpiperidin-4-yl)-1H-imidazole-1-carboxamide | Imidazoles | | | | | 90.2 | 45 |
| 553 | N-cyclohexyl-4-(3-guanidinophenyl)-N-methyl-1H-imidazole-1-carboxamide hydrochloride | Imidazoles | | | | | 72.3 | 15.4 |
| 554 | 4-(3-carbamoyl-4-hydroxyphenyl)-N-methyl-N-(1-propylpiperidin-4-yl)-1H-imidazole-1-carboxamide | Imidazoles | | | | | 102.2 | 85.6 |
| 555 | 4-(4-hydroxyphenyl)-N-methyl-N-(piperidin-4-yl)-1H-imidazole-1-carboxamide hydrobromide | Imidazoles | | | | | | |
| 556 | 4-(3-amino-4-(dimethylamino)phenyl)-N-(1-benzylpiperidin-4-yl)-N-methyl-1H-imidazole-1-carboxamide | Imidazoles | | | | | | |
| 557 | N-(1-(4,6-dichloro-1,3,5-triazin-2-yl)piperidin-4-yl)-4-(4-methoxyphenyl)-N-methyl-1H-imidazole-1-carboxamide | Imidazoles | | | | | | |
| 558 | 2-(4-(N-methyl-4-(pyridin-3-yl)-1H-imidazole-1-carboxamido)piperidin-1-yl)acetic acid | Imidazoles | | | | | 83.1 | 91.1 |
| 559 | methyl 5-((4-(N-methyl-4-(pyridin-3-yl)-1H-imidazole-1-carboxamido)piperidin-1-yl)methyl)furan-2-carboxylate | Imidazoles | | | | | | |
| 560 | N-methyl-4-(pyridin-2-yl)-N-(tetrahydro-2H-pyran-4-yl)-1H-imidazole-1-carboxamide | Imidazoles | | | | | | |
| 561 | N-(1-ethylpiperidin-4-yl)-4-(4-fluoro-3-hydroxyphenyl)-N-methyl-1H-imidazole-1-carboxamide hydrobromide | Imidazoles | | | | | 82.2 | 78.6 |
| 562 | 4-(3-amino-4-hydroxyphenyl)-N-cyclopentyl-N-methyl-1H-imidazole-1-carboxamide hydrochloride | Imidazoles | | | | | | |
| 563 | N-cyclohexyl-4-(3-guanidinophenyl)-N-methyl-1H-imidazole-1-carboxamide | Imidazoles | | | | | | |
| 564 | N-cyclopentyl-N-methyl-4-(2-oxo-2,3-dihydrobenzo[d]oxazol-5-yl)-1H-imidazole-1-carboxamide | Imidazoles | | | | | 37.6 | 2.3 |
| 565 | 4-(3-aminophenyl)-N-(1-benzylpiperidin-4-yl)-N-methyl-1H-imidazole-1-carboxamide | Imidazoles | | | | | | |
| 566 | 4-(3-(hydroxycarbamoyl)phenyl)-N-((1r,4r)-4-hydroxycyclohexyl)-N-methyl-1H-imidazole-1-carboxamide | Imidazoles | | | | | 88.5 | 69.8 |
| 567 | N-(1-benzylpiperidin-4-yl)-N-methyl-4-(4-(methylsulfonyl)phenyl)-1H-imidazole-1-carboxamide | Imidazoles | | | | | 87.8 | 6.3 |
| 568 | 4-(4-hydroxyphenyl)-N-methyl-N-(1-(3-(trifluoromethyl)phenylsulfonyl)piperidin-4-yl)-1H-imidazole-1-carboxamide | Imidazoles | | | | | | |
| 569 | N-methyl-N-(1-(pyridin-2-ylmethyl)piperidin-4-yl)-4-(pyridin-3-yl)-1H-imidazole-1-carboxamide | Imidazoles | | | | | | |
| 570 | 4-(4-fluoro-3-hydroxyphenyl)-N-methyl-N-(1-propylpiperidin-4-yl)-1H-imidazole-1-carboxamide hydrobromide | Imidazoles | | | | | | |
| 571 | N-(1-benzylpiperidin-4-yl)-4-(4-(hydroxycarbamoyl)phenyl)-N-methyl-1H-imidazole-1-carboxamide hydrobromide | Imidazoles | | | | | | |
| 572 | N-(1-benzylpiperidin-4-yl)-4-(3-carbamoyl-4-hydroxyphenyl)-N-methyl-1H-imidazole-1-carboxamide hydrobromide | Imidazoles | | | | | | |
| 573 | N-(1-(2-chloronicotinoyl)piperidin-4-yl)-4-(4-methoxyphenyl)-N-methyl-1H-imidazole-1-carboxamide | Imidazoles | | | | | | |
| 574 | N-(1-acetylpiperidin-4-yl)-4-(4-hydroxyphenyl)-N-methyl-1H-imidazole-1-carboxamide | Imidazoles | | | | | | |
| 575 | N-cyclohexyl-4-(3-guanidino-4-methoxyphenyl)-N-methyl-1H-imidazole-1-carboxamide hydrochloride | Imidazoles | | | | | | |
| 576 | 4-(3-(2H-tetrazol-5-yl)phenyl)-N-cyclohexyl-N-methyl-1H-imidazole-1-carboxamide | Imidazoles | | | | | | |
| 577 | 4-(4-aminophenyl)-N-(1-benzylpiperidin-4-yl)-N-methyl-1H-imidazole-1-carboxamide | Imidazoles | | | | | | |
| 578 | N-(1-benzylpiperidin-4-yl)-N-methyl-4-(4-sulfamoylphenyl)-1H-imidazole-1-carboxamide | Imidazoles | | | | | | |
| 579 | 4-(4-aminophenyl)-N-cyclohexyl-N-methyl-1H-imidazole-1-carboxamide | Imidazoles | | | | | | |
| 580 | N-cyclohexyl-N-methyl-4-(4-(sulfamoylamino)phenyl)-1H-imidazole-1-carboxamide | Imidazoles | | | | | | |
| 581 | N-(1-benzylpiperidin-4-yl)-4-(3-guanidino-4-methoxyphenyl)-N-methyl-1H-imidazole-1-carboxamide | Imidazoles | | | | | | |
| 582 | N-(1-cyanopiperidin-4-yl)-4-(4-methoxyphenyl)-N-methyl-1H-imidazole-1-carboxamide | Imidazoles | | | | | | |
| 583 | N-(1-(cyanomethyl)piperidin-4-yl)-4-(4-methoxyphenyl)-N-methyl-1H-imidazole-1-carboxamide | Imidazoles | | | | | | |
| 584 | N-(1-(cyanomethyl)piperidin-4-yl)-N-methyl-4-(pyridin-3-yl)-1H-imidazole-1-carboxamide | Imidazoles | | | | | | |
| 585 | 4-(3-hydroxyphenyl)-N-methyl-N-(1-propylpiperidin-4-yl)-1H-imidazole-1-carboxamide hydrobromide | Imidazoles | | | | | | |

TABLE 1-continued

| | | | In Vitro | | In Vivo | | | |
|---|---|---|---|---|---|---|---|---|
| | | | | | BRh 30 mg · kg · 1 h | LVh 30 mg · kg · 1 h | BRh mg · 3 kg · 8 h | LVh mg · 3 kg · 8 h |
| | Name | Class | 10 uM | 100 nM | | | | |
| 586 | 4-(3,4-dihydroxyphenyl)-N-methyl-N-(1-propylpiperidin-4-yl)-1H-imidazole-1-carboxamide hydrobromide | Imidazoles | | | | | | |
| 587 | 4-(4-hydroxyphenyl)-N-methyl-N-(1-(pyridin-2-ylmethyl)piperidin-4-yl)-1H-imidazole-1-carboxamide hydrobromide | Imidazoles | | | | | | |
| 588 | N-(1-benzylpiperidin-4-yl)-N-methyl-4-(4-(sulfamoylamino)phenyl)-1H-imidazole-1-carboxamide | Imidazoles | | | | | | |
| 589 | N-(1-benzylpiperidin-4-yl)-4-(3-guanidinophenyl)-N-methyl-1H-imidazole-1-carboxamide | Imidazoles | | | | | | |
| 590 | 4-(3-(2H-tetrazol-5-yl)phenyl)-N-methyl-N-(tetrahydro-2H-pyran-4-yl)-1H-imidazole-1-carboxamide | Imidazoles | | | | | | |
| 591 | N-cyclohexyl-N-methyl-4-(3-(5-oxo-4,5-dihydro-1,2,4-oxadiazol-3-yl)phenyl)-1H-imidazole-1-carboxamide | Imidazoles | | | | | | |
| 592 | (E)—N-(1-(N'-hydroxycarbamimidoyl)piperidin-4-yl)-4-(4-methoxyphenyl)-N-methyl-1H-imidazole-1-carboxamide | Imidazoles | | | | | | |
| 593 | N-(1-benzylpiperidin-4-yl)-N-methyl-4-(3-(methylsulfonamido)phenyl)-1H-imidazole-1-carboxamide | Imidazoles | | | | | | |
| 594 | N-cyclopentyl-N-methyl-4-(3-(5-oxo-4,5-dihydro-1,2,4-oxadiazol-3-yl)phenyl)-1H-imidazole-1-carboxamide | Imidazoles | | | | | | |
| 595 | N-(1-(2H-tetrazol-5-yl)piperidin-4-yl)-4-(4-methoxyphenyl)-N-methyl-1H-imidazole-1-carboxamide | Imidazoles | | | | | | |
| 596 | 4-(4-(4-methoxyphenyl)-N-methyl-1H-imidazole-1-carboxamido)piperidine-1-carboxamide | Imidazoles | | | | | | |
| 597 | N-(1-(2-hydroxyethyl)piperidin-4-yl)-4-(4-methoxyphenyl)-N-methyl-1H-imidazole-1-carboxamide | Imidazoles | | | | | | |

4. Biological Selectivity of Compounds of the Invention

FAAH inhibition was determined as described above. Inhibition of monoacylglycerol lipase (MAGL) and carboxylesterase (CE) was performed according to the protocols described below. The controls for both in vitro and in vivo were the reaction mix minus the test compounds. Therefore, a low value in Table 2 below for the test compounds indicates a strong inhibitor. A value of 100 indicates that no measurable inhibition took place.

MAGL

MAGL activity measurement was based on rate of hydrolysis of [$^3$H] 2-OG (glycerol labeled) as substrate. Briefly, cerebella cytosol (CRBcyt) fractions, previously obtained from adult WISTAR rats, were diluted to appropriate assay protein concentrations in Tris-HCl buffer (10 mM, pH 7.2) containing 1 mM EDTA, and were added to assay tubes containing test compound. Blanks contained assay buffer instead of cytosol samples were used as control. Substrate (final concentration 2 µM OG) was then added and the samples incubated for 10 mM at 37° C. The final assay contained 0.125% w v$^{-1}$ fatty acid-free BSA. After the incubation phase, reactions were stopped by adding 400 µL chloroform:methanol (1/1 v v$^{-1}$), vortex mixing the tubes two times and placing them on ice. Phases were separated by centrifugation and 200 µL aliquots of the methanol/buffer phase were taken and tritium content assayed by liquid scintillation spectroscopy with quench correction.

CE

CE activity measurement is based on the formation of p-nitrophenol from p-nitrophenyl acetate. Briefly, in 96-well plates 8 µg/ml of rat or mouse liver microsomes (LVms) were incubated with 10 µM FAAH inhibitors for 15 min and then the substrate, p-nitrophenyl acetate, was added to a final concentration of 1 mM. The plate was read at 405 nm 10 min after substrate addition for the appearance of p-nitrophenol using a spectrophotometer. The carboxylesterase activity in microsome extracts without inhibitor added were set at 100% as control and the remaining CE activities after incubation with inhibitors were calculated relative to the control.

TABLE 2

| | | In Vitro | | In Vivo | | In Vitro | | |
|---|---|---|---|---|---|---|---|---|
| | Name | FAAH 10 uM | FAAH 100 nM | FAAH BRh 3 mg · kg · 8 h | FAAH LVh 3 mg · kg · 8 h | CE Mou LVms 10 uM 10 min | CE Rat LVms 10 uM 10 min | MAGL Rat CRBcyto 12.5 uM 8 min |
| 16 | N-(4-methoxyphenyl)-N-methyl-4-(naphthalen-2-yl)-1H-imidazole-1-carboxamide | 24.7 | | | | 95.4 | 87.5 | |
| 39 | (3,4-dihydroquinolin-1(2H)-yl)(4-(3-methoxyphenyl)-1H-imidazol-1-yl)methanone | 16 | | 120.6 | 101.1 | 84.3 | 94.7 | 87 |
| 85 | N-(4-phenylbutyl)-1H-benzo[d][1,2,3]triazole-1-carboxamide | | 0.1 | | | 31 | 33 | |
| 97 | 5-bromo-N-cyclohexyl-N-methyl-1H-benzo[d][1,2,3]triazole-1-carboxamide | | 0 | | | 50.7 | 41.1 | |
| 564 | N-cyclopentyl-N-methyl-4-(2-oxo-2,3-dihydrobenzo[d]oxazol-5-yl)-1H-imidazole-1-carboxamide | | | 37.6 | 2.3 | 87.4 | 96.1 | 91.6 |

| Name | In Vitro FAAH 10 uM | FAAH 100 nM | In Vivo FAAH BRh 3 mg·kg·8 h | FAAH LVh 3 mg·kg·8 h | In Vitro CE Mou LVms 10 uM 10 min | CE Rat LVms 10 uM 10 min | MAGL Rat CRBcyto 12.5 uM 8 min |
|---|---|---|---|---|---|---|---|
| 567 N-(1-benzylpiperidin-4-yl)-N-methyl-4-(4-(methylsulfonyl)phenyl)-1H-imidazole-1-carboxamide | | | 87.8 | 6.3 | 88.6 | 97.8 | 94.2 |

The invention claimed is:
1. A compound having Formula IIa:

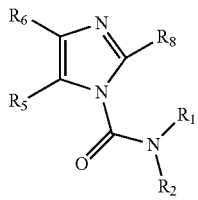

Formula IIa wherein:
R$_1$ is C$_1$-C$_4$ alkyl,
R$_2$ is selected from H, C$_{1-20}$ alkyl, aryl, heteroaryl, partially or fully saturated heterocyclyl, C$_{3-10}$ cycloalkyl, substituted C$_{1-6}$ alkyl, halogen, OH, OR$_{1a}$, OCOR$_{1a}$, SH, SR$_{1a}$, SCOR$_{1a}$, NH$_2$, NHR$_{1a}$, NHSO$_2$NH$_2$, NHSO$_2$R$_{1a}$, NR$_{1a}$COR$_{1b}$, NHCOR$_{1a}$, NR$_{1a}$R$_{1b}$, COR$_{1a}$, CSR$_{1a}$, CN, COOH, COOR$_{1a}$, CONH$_2$, CONHOH, CONHR$_{1a}$, CONHOR$_{1a}$, SO$_2$R$_{1a}$, SO$_3$H, SO$_2$NH$_2$, CONR$_{1a}$R$_{1b}$, and SO$_2$NR$_{1a}$R$_{1b}$, wherein R$_{1a}$ and R$_{1b}$ are independently selected from C$_{1-6}$ alkyl, substituted C$_{1-6}$ alkyl, aryl, heteroaryl, C$_{3-8}$ cycloalkyl and heterocyclyl, or R$_{1a}$ and R$_{1b}$, together with the heteroatom to which they are joined, can form heterocyclyl,
wherein, when R$_2$ is a moiety selected from the group consisting of (a) C$_{1-20}$ alkyl, (b) OR$_{1a}$, wherein R$_{1a}$ is C$_{1-6}$ alkyl, (c) aryl, (d) heteroaryl, (e) heterocyclyl, (f) C$_{3-10}$ cycloalkyl, (g) a substituted C$_{1-6}$ alkyl selected from the group consisting of aryl C$_{1-6}$ alkyl, heteroaryl C$_{1-6}$ alkyl, heterocyclyl C$_{1-6}$ alkyl, and C$_{3-10}$ cycloalkyl C$_{1-6}$ alkyl, or is a group containing at least one moiety selected from the group consisting of (a), (b), (c), (d), (e), (f), and (g), each moiety (a), (b), (c), (d), (e), (f), and (g) may optionally be substituted with one or more groups selected from C$_{1-6}$ alkyl, C$_{3-8}$ cycloalkyl, halogen, aryl, heteroaryl, heterocyclyl, aryloxy, heteroaryloxy, heterocyclyloxy, substituted C$_{1-6}$ alkyl, aryl C$_{1-6}$ alkoxy, heteroaryl C$_{1-6}$ alkoxy, heterocyclyl C$_{1-6}$ alkoxy, C$_{1-6}$ alkylamino, C$_{1-6}$ dialkylamino, C$_{1-10}$ alkyl, OH, OR$_{1c}$, OCOR$_{1c}$, SH, SR$_{1c}$, SCOR$_{1c}$, NH$_2$, NO$_2$, NHR$_{1c}$, NHSO$_2$NH$_2$, NHSO$_2$R$_{1c}$, NR$_{1c}$COR$_{1d}$, NHC(NH)NH$_2$, NHCOR$_{1c}$, NR$_{1c}$R$_{1d}$, COR$_{1c}$, CSR$_{1c}$, CN, COOH, COOR$_{1c}$, CONH$_2$, CONHOH, CONHR$_{1c}$, CONHOR$_{1c}$, C(NOH)NH$_2$, CONR$_{1c}$R$_{1d}$, SO$_2$R$_{1c}$, SO$_3$H, SO$_2$NH$_2$, SO$_2$NR$_{1c}$R$_{1d}$, wherein R$_{1c}$ and R$_{1d}$ are independently selected from C$_{1-6}$ alkyl, substituted C$_{1-6}$ alkyl, aryl, heteroaryl, C$_{3-8}$ cycloalkyl and heterocyclyl, or R$_{1c}$ and R$_{1d}$, together with the heteroatom to which they are joined, can form heterocyclyl,
wherein, when the substituent of R$_2$ is a moiety selected from the group consisting of (a) C$_{1-10}$ alkyl, (b) aryl, (c) heteroaryl, (d) heterocyclyl, (e) OR$_{1c}$, wherein R$_{1c}$ is C$_{1-6}$ alkyl, (f) aryloxy, (g) heteroaryloxy, (h) heterocyclyloxy, (i) a substituted C$_{1-6}$ alkyl selected from the group consisting of aryl C$_{1-6}$ alkyl, heteroaryl C$_{1-6}$ alkyl, and heterocyclyl C$_{1-6}$ alkyl, (j) aryl C$_{1-6}$ alkoxy, (k) heteroaryl C$_{1-6}$ alkoxy, (l) heterocyclyl C$_{1-6}$ alkoxy, (m) C$_{1-6}$ alkylamino, (n) C$_{1-6}$ dialkylamino, and (o) C$_{3-8}$ cycloalkyl or is a group containing at least one moiety selected from the group consisting of (a), (b), (c), (d), (e), (f), (g), (h), (i), (j), (k), (l), (m), (n), and (o), each moiety (a), (b), (c), (d), (e), (f), (g), (h), (i), (j), (k), (l), (m), (n), and (o) may optionally be substituted with one or more groups selected from substituted C$_{1-6}$ alkyl, aryl, heteroaryl, C$_{3-8}$ cycloalkyl, heterocyclyl, halogen, C$_{1-10}$ alkyl, OH, OR$_{1e}$, OCOR$_{1e}$, SH, SR$_{1e}$, SCOR$_{1e}$, NH$_2$, NO$_2$, NHR$_{1e}$, NHSO$_2$NH$_2$, NHSO$_2$R$_{1e}$, NR$_{1e}$COR$_{1f}$, NHC(NH)NH$_2$, NHCOR$_{1e}$, NR$_{1e}$R$_{1f}$, COR$_{1e}$, CSR$_{1e}$, CN, COOH, COOR$_{1e}$, CONH$_2$, CONHOH, CONHR$_{1e}$, CONHOR$_{1e}$, C(NOH)NH$_2$, CONR$_{1e}$R$_{1f}$, SO$_2$R$_{1e}$, SO$_3$H, SO$_2$NH$_2$, SO$_2$NR$_{1e}$R$_{1f}$, wherein R$_{1e}$ and R$_{1f}$ are independently selected from C$_{1-6}$ alkyl, substituted C$_{1-6}$ alkyl, aryl, heteroaryl, C$_{3-8}$ cycloalkyl and heterocyclyl, or R$_{1e}$ and R$_{1f}$, together with the heteroatom to which they are joined, can form heterocyclyl,
with the exception that R$_1$ and R$_2$ are not both methyl, or
R$_1$ and R$_2$, together with the N to which they are attached, can form a heterocyclyl group which may optionally be substituted with one or more anionic oxygen atoms or one or more groups selected from aryl, heteroaryl, partially or fully saturated heterocyclyl, C$_{3-8}$ cycloalkyl, C$_{1-6}$ alkyl, substituted C$_{1-6}$ alkyl, C$_{1-6}$ alkoxy, aryloxy, heteroaryloxy, heterocyclyloxy, halogen, OH, OR$_{2a}$, OCOR$_{2a}$, SH, SR$_{2a}$, SCOR$_{2a}$, NH$_2$, NO$_2$, NHR$_{2a}$, NHSO$_2$NH$_2$, NHSO$_2$R$_{2a}$, NR$_{2a}$COR$_{2b}$, NHC(NH)NH$_2$, NHCOR$_{2a}$, NR$_{2a}$R$_{2b}$, COR$_{2a}$, CSR$_{2a}$, CN, COOH, COOR$_{2a}$, CONH$_2$, CONHOH, CONHR$_{2a}$, CONHOR$_{2a}$, C(NOH)NH$_2$, CONR$_{2a}$R$_{2b}$, SO$_2$R$_{2a}$, SO$_3$H, SO$_2$NH$_2$, SO$_2$NR$_{2a}$R$_{2b}$, wherein R$_{2a}$ and R$_{2b}$ are independently selected from C$_{1-6}$ alkyl, substituted C$_{1-6}$ alkyl, aryl, heteroaryl, C$_{3-8}$ cycloalkyl and heterocyclyl, or R$_{2a}$ and R$_{2b}$, together with the heteroatom to which they are joined, can form heterocyclyl,
wherein, when the substituent of the heterocyclyl formed by R$_1$ and R$_2$ together is a moiety selected from the group consisting of (a) aryl, (b) heteroaryl, (c) heterocyclyl, (d) C$_{3-8}$ cycloalkyl, (e) C$_{1-6}$ alkyl, (f) a substituted C$_{1-6}$ alkyl selected from the group consisting of aryl C$_{1-6}$ alkyl, heteroaryl C$_{1-6}$ alkyl, heterocyclyl C$_{1-6}$ alkyl, and C$_{3-8}$ cycloalkyl C$_{1-6}$ alkyl, (g) OR$_{1a}$, wherein R$_{1a}$ is C$_{1-6}$ alkyl, (h) aryloxy, (i) heteroaryloxy, and (j) heterocyclyloxy, or is a group containing at least one moiety selected from the group consisting of (a), (b), (c), (d), (e), (f), (g), (h), (i), and (j), each moiety (a), (b), (c), (d), (e), (f), (g), (h), (i), and (j) may optionally be substituted with one or more groups selected from halogen, hydroxyl, $C_{1-6}$ alkyl, aryl, heteroaryl, heterocyclyl, $C_{3-8}$ cycloalkyl, aryloxy, heteroaryloxy, heterocyclyloxy, $C_{3-8}$ cycloalkyloxy, aryl $C_{1-4}$ alkoxy, heteroaryl $C_{1-6}$ alkoxy, heterocyclyl $C_{1-4}$ alkoxy, $C_{3-8}$ cycloalkyl $C_{1-4}$ alkoxy, substituted $C_{1-6}$ alkyl, $OR_{2c}$, $OCOR_{2c}$, SH, $SR_{2c}$, $SCOR_{2c}$, $NH_2$, $NO_2$, $NHR_{2c}$, $NHSO_2NH_2$, $NHSO_2R_{2c}$, $NR_{2c}COR_{2d}$, $NHC(NH)NH_2$, $NHCOR_{2c}$, $NR_{2c}R_{2d}$, $COR_{2c}$, $CSR_{2c}$, CN, COOH, $COOR_{2c}$, $CONH_2$, CONHOH, $CONHR_{2c}$, $CONHOR_{2c}$, $C(NOH)NH_2$, $CONR_{2c}R_{2d}$, $SO_2R_{2c}$, $SO_3H$, $SO_2NH_2$, $SO_2NR_{2c}R_{2d}$, wherein $R_{2c}$ and $R_{2d}$ are independently selected from $C_{1-6}$ alkyl, substituted $C_{1-6}$ alkyl, aryl, heteroaryl, $C_{3-8}$ cycloalkyl and heterocyclyl, or $R_{2c}$ and $R_{2d}$, together with the heteroatom to which they are joined, can form heterocyclyl, wherein, when the substituent of the substituent of the heterocyclyl formed by $R_1$ and $R_2$ together is a moiety selected from the group consisting of (a) $C_{1-6}$ alkyl, (b) aryl, (c) heteroaryl, (d) heterocyclyl, (e) $C_{3-8}$ cycloalkyl, (f) $OR_{2e}$, wherein $R_{2e}$ is $C_{1-6}$ alkyl, (g) aryloxy, (h) heteroaryloxy, (i) heterocyclyloxy, (j) $C_{3-8}$ cycloalkyloxy, (k) aryl $C_{1-4}$ alkoxy, (l) heteroaryl $C_{1-4}$ alkoxy, (m) heterocyclyl $C_{1-4}$ alkoxy, and (n) $C_{3-8}$ cycloalkyl $C_{1-4}$ alkoxy, or is a group containing at least one moiety selected from the group consisting of (a), (b), (c), (d), (e), (f), (g), (h), (i), (j), (k), (l), (m), and (n), each moiety (a), (b), (c), (d), (e), (f), (g), (h), (i), (j), (k), (l), (m), and (n) may optionally be substituted with one or more groups selected from $C_{1-6}$ alkyl, substituted $C_{1-6}$ alkyl, aryl, heteroaryl, $C_{3-8}$ cycloalkyl, heterocyclyl, halogen, OH, $OR_{2e}$, $OCOR_{2e}$, SH, $SR_{2e}$, $SCOR_{2e}$, $NH_2$, $NO_2$, $NHR_{2e}$, $NHSO_2NH_2$, $NHSO_2R_{2e}$, $NR_{2e}COR_{2f}$, $NHC(NH)NH_2$, $NR_{2e}R_{2f}$, $NHCOR_{2e}$, $COR_{2e}$, $CSR_{2e}$, CN, COOH, $COOR_{2e}$, $CONH_2$, CONHOH, $CONHR_{2e}$, $CONHOR_{2e}$, $C(NOH)NH_2$, $CONR_{2e}R_{2f}$, $SO_2R_{2e}$, $SO_3H$, $SO_2NH_2$, $SO_2NR_{2e}R_{2f}$, wherein $R_{2e}$ and $R_{2f}$ are independently selected from $C_{1-6}$ alkyl, substituted $C_{1-6}$ alkyl, aryl, heteroaryl, $C_{3-8}$ cycloalkyl and heterocyclyl, or $R_{2e}$ and $R_{2f}$, together with the heteroatom to which they are joined, can form heterocyclyl;

or $R_1$ and $R_2$, together with the N to which they are attached, can form a heteroaryl or heterocyclyl group, each of which may optionally be substituted with one or more anionic oxygen atoms or one or more groups selected from heteroaryl, partially or fully saturated heterocyclyl, $C_{3-8}$ cycloalkyl, $C_{1-6}$ alkyl, substituted $C_{1-6}$ alkyl, $C_{1-6}$ alkoxy, aryloxy, heteroaryloxy, heterocyclyloxy, halogen, OH, $OR_{2a}$, $OCOR_{2a}$, SH, $SR_{2a}$, $SCOR_{2a}$, $NH_2$, $NO_2$, $NHR_{2a}$, $NHSO_2NH_2$, $NHSO_2R_{2a}$, $NR_{2a}COR_{2b}$, $NHC(NH)NH_2$, $NHCOR_{2a}$, $NR_{2a}R_{2b}$, $COR_{2a}$, $CSR_{2a}$, CN, COOH, $COOR_{2a}$, $CONH_2$, CONHOH, $CONHR_{2a}$, $CONHOR_{2a}$, $C(NOH)NH_2$, $CONR_{2a}R_{2b}$, $SO_2R_{2a}$, $SO_3H$, $SO_2NH_2$, $SO_2NR_{2a}R_{2b}$, wherein $R_{2a}$ and $R_{2b}$ are independently selected from $C_{1-6}$ alkyl, substituted $C_{1-6}$ alkyl, aryl, heteroaryl, $C_{3-8}$ cycloalkyl and heterocyclyl, or $R_{2a}$ and $R_{2b}$, together with the heteroatom to which they are joined, can form heterocyclyl, wherein, when the substituent of the heteroaryl or heterocyclyl formed by $R_1$ and $R_2$ together is a moiety selected from the group consisting of (a) heteroaryl, (b) heterocyclyl, (c) $C_{3-8}$ cycloalkyl, (d) $C_{1-6}$ alkyl, (e) a substituted $C_{1-6}$ alkyl selected from the group consisting of aryl $C_{1-6}$ alkyl, heteroaryl $C_{1-6}$ alkyl, heterocyclyl $C_{1-6}$ alkyl, and $C_{3-8}$ cycloalkyl $C_{1-6}$ alkyl, (f) $OR_{1a}$, wherein $R_{1a}$ is $C_{1-6}$ alkyl, (g) aryloxy, (h) heteroaryloxy, and (i) heterocyclyloxy, or is a group containing at least one moiety selected from the group consisting of (a), (b), (c), (d), (e), (f), (g), (h), and (i), each moiety (a), (b), (c), (d), (e), (f), (g), (h), and (i) may optionally be substituted with one or more groups selected from halogen, hydroxyl, $C_{1-6}$ alkyl, aryl, heteroaryl, heterocyclyl, $C_{3-8}$ cycloalkyl, aryloxy, heteroaryloxy, heterocyclyloxy, $C_{3-8}$ cycloalkyloxy, aryl $C_{1-4}$ alkoxy, heteroaryl $C_{1-6}$ alkoxy, heterocyclyl $C_{1-4}$ alkoxy, $C_{3-8}$ cycloalkyl $C_{1-4}$ alkoxy, substituted $C_{1-6}$ alkyl, $OR_{2c}$, $OCOR_{2c}$, SH, $SR_{2c}$, $SCOR_{2c}$, $NH_2$, $NO_2$, $NHR_{2c}$, $NHSO_2NH_2$, $NHSO_2R_{2c}$, $NR_{2c}COR_{2d}$, $NHC(NH)NH_2$, $NHCOR_{2c}$, $NR_{2c}R_{2d}$, $COR_{2c}$, $CSR_{2c}$, CN, COOH, $COOR_{2c}$, $CONH_2$, CONHOH, CONHR, $CONHOR_{2c}$, $C(NOH)NH_2$, $CONR_{2c}R_{2d}$, $SO_2R_{2c}$, $SO_3H$, $SO_2NH_2$, $SO_2NR_{2c}R_{2d}$, wherein $R_{2c}$ and $R_{2d}$ are independently selected from $C_{1-6}$ alkyl, substituted $C_{1-6}$ alkyl, aryl, heteroaryl, $C_{3-8}$ cycloalkyl and heterocyclyl, or $R_{2c}$ and $R_{2d}$, together with the heteroatom to which they are joined, can form heterocyclyl, wherein, when the substituent of the substituent of the heteroaryl or heterocyclyl formed by $R_1$ and $R_2$ together is a moiety selected from the group consisting of (a) $C_{1-6}$ alkyl, (b) heteroaryl, (c) heterocyclyl, (d) $C_{3-8}$ cycloalkyl, (e) $OR_{2e}$, wherein $R_{2e}$ is $C_{1-6}$ alkyl, (f) aryloxy, (g) heteroaryloxy, (h) heterocyclyloxy, (i) $C_{3-8}$ cycloalkyloxy, (j) aryl $C_{1-4}$ alkoxy, (k) heteroaryl $C_{1-4}$ alkoxy, (l) heterocyclyl $C_{1-4}$ alkoxy, and (m) $C_{3-8}$ cycloalkyl $C_{1-4}$ alkoxy, or is a group containing at least one moiety selected from the group consisting of (a), (b), (c), (d), (e), (f), (g), (h), (i), (j), (k), (l), and (m), each moiety (a), (b), (c), (d), (e), (f), (g), (h), (i), (j), (k), (l), and (m) may optionally be substituted with one or more groups selected from $C_{1-6}$ alkyl, substituted $C_{1-6}$ alkyl, aryl, heteroaryl, $C_{3-8}$ cycloalkyl, heterocyclyl, halogen, OH, $OR_{2e}$, $OCOR_{2e}$, SH, $SR_{2e}$, $SCOR_{2e}$, $NH_2$, $NO_2$, $NHR_{2e}$, $NHSO_2NH_2$, $NHSO_2R_{2e}$, $NR_{2e}COR_{2f}$, $NHC(NH)NH_2$, $NR_{2e}R_{2f}$, $NHCOR_{2e}$, $COR_{2e}$, $CSR_{2e}$, CN, COOH, $COOR_{2e}$, $CONH_2$, CONHOH, $CONHR_{2e}$, $CONHOR_{2e}$, $C(NOH)NH$, $CONR_2R_{2f}$, $SO_2R_{2e}$, $SO_3H$, $SO_2NH_2$, $SO_2NR_{2e}R_{2f}$, wherein $R_{2e}$ and $R_{2f}$ are independently selected from $C_{1-6}$ alkyl, substituted $C_{1-6}$ alkyl, aryl, heteroaryl, $C_{3-8}$ cycloalkyl and heterocyclyl, or $R_{2e}$ and $R_{2f}$, together with the heteroatom to which they are joined, can form heterocyclyl;

$R_5$ is selected from H, $C_{1-2}$ alkyl, and halogen, $R_6$ is selected from aryl and heteroaryl, wherein, when $R_6$ is heteroaryl, $R_6$ may optionally be substituted with one or more anionic oxygen atoms, and when $R_6$ is aryl or heteroaryl, $R_6$ may optionally be substituted with one or more groups selected from halogen, substituted $C_{1-6}$ alkyl, $C_{3-8}$ cycloalkyl, $C_{1-6}$ alkyl, $C_{1-6}$ alkynyl, aryl, heteroaryl, heterocyclyl, aryloxy, heteroaryloxy, heterocyclyloxy, aryl $C_{1-6}$ alkoxy, heteroaryl $C_{1-6}$ alkoxy, heterocyclyl $C_{1-6}$ alkoxy, OH, $OR_{6c}$, $OCOR_{6c}$, SH, $SR_{6c}$, $SCOR_{6c}$, $NH_2$, $NO_2$, $NHR_{6c}$, $NHSO_2NH_2$, $NHC(NH)NH_2$, $NHSO_2R_{6c}$, $NR_{6c}COR_{6d}$, $NHCOR_{6c}$, $NR_{6c}R_{6d}$, $COR_{6c}$, $CSR_6$, CN, COOH, $COOR_{6c}$, $CONH_2$, $CONHR_{6c}$, $CONHOR_{6c}$, CONHOH, $C(NOH)NH_2$, $CONR_{6c}R_{6d}$, $SO_2R_{6c}$, $SO_3H$, $SO_2NH_2$, $SO_2NR_{6c}R_{6d}$, wherein $R_{6c}$ and $R_{6d}$ are independently selected from $C_{1-6}$ alkyl, substituted $C_{1-6}$ alkyl, aryl, heteroaryl, $C_{3-8}$ cycloalkyl and heterocyclyl, or $R_{6c}$ and $R_{6d}$, together with the heteroatom to which they are joined, can form heterocyclyl, wherein, when the substituent of $R_6$ is heteroaryl or heterocyclyl, each of these moieties may optionally be substituted with one or more anionic oxygen atoms, or when the substituent of $R_6$ is a moiety selected from the group consisting of (a) $C_{1-6}$ alkyl, (b) $C_{1-6}$ alkynyl, (c) aryl, (d) heteroaryl, (e) heterocyclyl, (f) $OR_{6c}$, wherein $R_{6c}$ is $C_{1-6}$ alkyl, (g) aryloxy, (h) heteroaryloxy, (i) heterocyclyloxy, (j) a substituted $C_{1-6}$ alkyl selected from the group consisting of aryl $C_{1-6}$ alkyl, heteroaryl $C_{1-6}$ alkyl, and heterocyclyl $C_{1-6}$ alkyl, (k) aryl $C_{1-6}$ alkoxy, (l) heteroaryl $C_{1-6}$ alkoxy, (m) heterocyclyl $C_{1-6}$ alkoxy, and (n) $C_{3-8}$ cycloalkyl, or is a group containing at least one moiety selected from the group consisting of (a), (b), (c), (d), (e), (f), (g), (h), (i), (j), (k), (l), (m), or (n), each moiety (a), (b), (c), (d), (e), (f), (g), (h), (i), (j), (k), (l), (m), and (n) may optionally be substituted with one or more groups selected from halogen, substituted $C_{1-6}$ alkyl, aryl, heteroaryl, $C_{3-8}$ cycloalkyl, heterocyclyl, $C_{1-6}$ alkyl, $C_{1-4}$ alkoxy, OH, $OR_{6e}$, $OCOR_{6e}$, SH, $SR_{6e}$, $SCOR_{6e}$, $NH_2$, $NO_2$, $NHR_{6e}$, $NHSO_2NH_2$, $NHC(NH)NH_2$, $NHSO_2R_{6e}$, $NR_{6e}COR_{6f}$, $NHCOR_{6e}$, $NR_{6e}R_{6f}$, $COR_{6e}$, $CSR_{6e}$, CN, COOH, $COOR_{6e}$, $CONH_2$, CONHOH, $CONHR_{6e}$, $CONHOR_{6e}$, $C(NOH)NH_2$, $CONR_{6e}R_{6f}$, $SO_2R_{6e}$, $SO_3H$, $SO_2NH_2$, $SO_2NR_{6e}R_{6f}$, wherein $R_{6e}$ and $R_{6f}$ are independently selected from $C_{1-6}$ alkyl, substituted $C_{1-6}$ alkyl, aryl, heteroaryl, $C_{3-8}$ cycloalkyl and heterocyclyl, or $R_{6e}$ and $R_{6f}$, together with the heteroatom to which they are joined, can form heterocyclyl; and $R_8$ is H, or a pharmaceutically acceptable salt or ester thereof;

provided that when $R_1$ is methyl, $R_2$ is not 4-chlorobutyl, 4-azidobutyl, or 4-isothiocyanatobutyl; and provided that the compound is not (4-phenyl-1H-imidazol-1-yl)(4-(quinolin-2-ylmethyl)piperazin-1-yl)methanone.

2. The compound according to claim 1, wherein $R_1$ is methyl or ethyl.

3. The compound according to claim 1, wherein $R_2$ is saturated heterocyclyl or $C_{3-10}$ cycloalkyl, wherein the $C_{3-10}$ cycloalkyl is $C_{5-8}$ cycloalkyl and wherein the saturated heterocyclyl and the $C_{5-8}$ cycloalkyl are monocyclic.

4. The compound according to claim 1, wherein $R_2$ is unsubstituted monocyclic $C_{5-8}$ cycloalkyl.

5. The compound according to claim 1, wherein $R_2$ is an unsubstituted cyclohexyl.

6. The compound according to claim 1, wherein $R_2$ is a monocyclic saturated heterocyclyl containing a single heteroatom.

7. The compound according to claim 6, wherein the heteroatom is a nitrogen or oxygen atom.

8. The compound according to claim 7, wherein the heterocyclyl is six membered.

9. The compound according to claim 6, wherein the heteroatom is an oxygen atom and the heterocyclyl is unsubstituted.

10. The compound according to claim 6, wherein the heteroatom is a nitrogen atom.

11. The compound according to claim 6, wherein the heteroatom is nitrogen, wherein the nitrogen is substituted with a group selected from (a) $C_{1-6}$ alkyl, (b) aryl, (c) heteroaryl, (d) heterocyclyl, (e) $C_{3-10}$ cycloalkyl, (f) substituted $C_{1-6}$ alkyl selected from the group consisting of aryl $C_{1-6}$ alkyl, heteroaryl $C_{1-6}$ alkyl, heterocyclyl $C_{1-6}$ alkyl, and $C_{3-10}$ cycloalkyl $C_{1-6}$ alkyl.

12. The compound according to claim 11, wherein the nitrogen is substituted with a group selected from $C_{1-4}$ alkyl, aryl $C_{1-4}$ alkyl, heteroaryl $C_{1-4}$ alkyl, heterocyclyl $C_{1-4}$ alkyl, and $C_{5-8}$ cycloalkyl $C_{1-4}$ alkyl.

13. The compound according to claim 12, wherein the nitrogen is substituted with a group selected from aryl $C_{1-4}$ alkyl, and heteroaryl $C_{1-4}$ alkyl, wherein the aryl and heteroaryl are monocyclic.

14. The compound according to claim 13, wherein the nitrogen is substituted with a group selected from phenyl $C_{1-2}$ alkyl, and pyridyl $C_{1-2}$ alkyl.

15. The compound according to claim 6, wherein the heteroatom is at the 4 position relative to the position of attachment of the heterocyclyl to the urea nitrogen of Formula (IIa).

16. The compound according to claim 6, wherein $R_6$ is a monocyclic aryl or heteroaryl.

17. The compound according to claim 16, wherein the monocyclic aryl or heteroaryl is six membered.

18. The compound according to claim 6, wherein $R_6$ is an unsubstituted phenyl.

19. The compound according to claim 6, wherein $R_6$ is a pyridyl.

20. The compound according to claim 6, wherein $R_6$ is heteroaryl and the heteroaryl is substituted with an anionic oxygen atom.

21. The compound according to claim 1, wherein $R_1$ and $R_2$, together with the N to which they are attached, form a heterocyclyl group.

22. The compound according to claim 21, wherein the heterocyclyl group is a 5 or 6 membered monocyclic ring.

23. The compound according to claim 21, wherein the said heterocyclyl group further comprises one or two additional heteroatoms.

24. The compound according to claim 21, wherein the heterocyclyl group is oxazolidinyl.

25. The compound according to claim 24, wherein the oxygen atom in the oxazolidinyl is at the 3 position relative to the urea nitrogen of Formula (IIa).

26. The compound according to claim 24, wherein the oxazolidinyl is substituted with one, two or three methyl or ethyl groups.

27. The compound according to claim 24, wherein the oxazolidinyl is substituted with two methyl or ethyl groups.

28. The compound according to claim 27, wherein the oxazolidinyl is substituted with two methyl groups on the same carbon atom.

29. The compound according to claim 28, wherein the oxazolidinyl is 4,4-dimethyloxazolidin-3-yl.

30. The compound according to claim 21, wherein $R_6$ is aryl.

31. The compound according to claim 1, wherein:

$R_2$ is a moiety selected from the group consisting of (a) aryl, (b) heteroaryl, (c) heterocyclyl, (d) $C_{3-10}$ cycloalkyl, and (e) a substituted $C_{1-6}$ alkyl selected from the group consisting of aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, wherein each moiety (a), (b), (c), (d), and (e) may optionally be substituted with one or more groups selected from $C_{1-6}$ alkyl, substituted $C_{1-6}$ alkyl, aryl, heteroaryl, $C_{3-8}$ cycloalkyl, heterocyclyl, halogen, OH, $OR_{1c}$, $OCOR_{1c}$, SH, $SR_{1c}$, $SCOR_{1c}$, $NH_2$, $NHR_{1c}$, $NHSO_2NH_2$, $NHSO_2R_{1c}$, $NR_{1c}COR_{1d}$, $NHC(NH)NH_2$, $NHCOR_{1c}$, $NR_{1c}R_{1d}$, $COR_{1c}$, $CSR_{1c}$, CN, COOH, $COOR_{1c}$, $CONH_2$, CONHOH, $CONHR_{1c}$, $CONHOR_{1c}$, $C(NOH)NH_2$, $SO_2R_{1c}$, $SO_3H$, $SO_2NH_2$, $CONR_{1c}R_{1d}$, $SO_2NR_{1c}R_{1d}$, wherein $R_{1c}$ and $R_{1d}$ are independently selected from $C_{1-6}$ alkyl, substituted $C_{1-6}$ alkyl, aryl, heteroaryl, $C_{3-8}$ cycloalkyl and heterocyclyl, or $R_{1c}$ and $R_{1d}$, together with the heteroatom to which they are joined, can form heterocyclyl, wherein, when the substituent of $R_2$ is a moiety selected from the group consisting of (a) $C_{1-10}$ alkyl, wherein the $C_{1-10}$ alkyl is $C_{1-6}$ alkyl, (b) substituted $C_{1-6}$ alkyl, (c) aryl, (d) heteroaryl, (e) $C_{3-8}$ cycloalkyl, and (f) heterocyclyl or is a group containing at least one moiety selected from the group consisting of (a), (b), (c), (d), (e), and (f), each moiety (a), (b), (c), (d), (e), and (f) may optionally be substituted with one or more groups selected from $C_{1-6}$ alkyl, substituted $C_{1-6}$ alkyl, aryl, heteroaryl, $C_{3-8}$ cycloalkyl, heterocyclyl, halogen, OH, $OR_{1e}$, $OCOR_{1e}$, SH, $SR_{1e}$, $SCOR_{1e}$, $NH_2$, $NHR_{1e}$, $NHSO_2NH_2$, $NHSO_2R_{1e}$, $NR_{1e}COR_{1f}$, $NHC(NH)NH_2$, $NHCOR_{1e}$, $NR_{1e}R_{1f}$, $COR_{1e}$, $CSR_{1e}$, CN, COOH, $COOR_{1e}$, $CONH_2$, CONHOH, $CONHR_{1e}$, $CONHOR_{1e}$, $C(NOH)NH_2$, $SO_2R_{1e}$, $SO_3H$, $SO_2NH_2$, $CONR_{1e}R_{1f}$, $SO_2NR_{1e}R_{1f}$, wherein $R_{1e}$ and $R_{1f}$ are independently selected from $C_{1-6}$ alkyl, substituted $C_{1-6}$ alkyl, aryl, heteroaryl, $C_{3-8}$ cycloalkyl and heterocyclyl, or $R_{1e}$ and $R_{1f}$ together with the heteroatom to which they are joined, can form heterocyclyl, and $R_6$ is selected from aryl and heteroaryl, each of which may optionally be substituted with one or more groups selected from $C_{1-6}$ alkyl, aryl, heteroaryl, heterocyclyl, substituted $C_{1-6}$ alkyl, $C_{3-8}$ cycloalkyl, halogen, OH, $OR_{6c}$, $OCOR_{6c}$, SH, $SR_{6c}$, $SCOR_{6c}$, $NH_2$, $NHR_{6c}$, $NHSO_2NH_2$, $NHSO_2R_{6c}$, $NR_{6c}COR_{6d}$, $NHC(NH)NH_2$, $NHCOR_{6c}$, $NR_{6c}R_{6d}$, $COR_{6c}$, $CSR_{6c}$, CN, COOH, $COOR_{6c}$, $CONH_2$, CONHOH, $CONHR_{6c}$, $CONHOR_{6c}$, $C(NOH)NH_2$, $SO_2R_{6c}$, $SO_3H$, $SO_2NH_2$, $CONR_{6c}R_{6d}$, $SO_2NR_{6c}R_{6d}$, wherein $R_{6c}$ and $R_{6d}$ are independently selected from $C_{1-6}$ alkyl, substituted $C_{1-6}$ alkyl, aryl, heteroaryl, $C_{3-8}$ cycloalkyl and heterocyclyl, or $R_{6c}$ and $R_{6d}$ together with the heteroatom to which they are joined, can form heterocyclyl, and wherein, when $R_6$ is heteroaryl, $R_6$ may optionally be substituted with one or more anionic oxygen atoms, wherein, when the substituent of $R_6$ is a moiety selected from the group consisting of (a) $C_{1-6}$ alkyl, (b) substituted $C_{1-6}$ alkyl, (c) aryl, (d) heteroaryl, (e) $C_{3-8}$ cycloalkyl, and (f) heterocyclyl or is a group containing at least one moiety selected from the group consisting of (a), (b), (c), (d) (e), and (f), each moiety (a), (b), (c), (d), (e), and (f) may optionally be substituted with one or more groups selected from $R_{6c}$, halogen, OH, $OR_{6e}$, $OCOR_{6e}$, SH, $SR_{6e}$, $SCOR_{6e}$, $NH_2$, $NHR_{6e}$, $NHSO_2NH_2$, $NHSO_2R_{6e}$, $NR_{6e}COR_{6f}$, $NHC(NH)NH_2$, $NHCOR_{6e}$, $NR_{6e}R_{6f}$, $COR_{6e}$, $CSR_{6e}$, CN, COOH, $COOR_{6e}$, $CONH_2$, CONHOH, $CONHR_{6e}$, $CONHOR_{6e}$, $C(NOH)NH_2$, $SO_2R_{6e}$, $SO_3H$, $SO_2NH_2$, $CONR_{6e}R_{6f}$, $SO_2NR_{6e}R_{6f}$, wherein $R_{6e}$ and $R_{6f}$ are independently selected from $C_{1-6}$ alkyl, substituted $C_{1-6}$ alkyl, aryl, heteroaryl, $C_{3-8}$ cycloalkyl and heterocyclyl, or $R_{6e}$ and $R_{6f}$ together with the heteroatom to which they are joined, can form heterocyclyl, and wherein, when the substituent of $R_6$ is heteroaryl or heterocyclyl, each of these moieties may optionally be substituted with one or more anionic oxygen atoms.

32. The compound according to claim 31, wherein $R_2$ is selected from fully saturated monocyclic heterocyclyl, and $C_{5-8}$ monocyclic cycloalkyl.

33. The compound according to claim 32, wherein $R_2$ is an unsubstituted cyclopentyl or unsubstituted cyclohexyl.

34. The compound according to claim 32, wherein $R_2$ is a fully saturated heterocyclyl which contains a single heteroatom.

35. The compound according to claim 34, wherein the heterocyclyl is six membered and the single heteroatom is at the 4-position relative to the position of attachment of the heterocyclyl to the urea nitrogen of Formula (IIa).

36. The compound according to claim 35, wherein the heteroatom is a nitrogen heteroatom which is substituted with a group selected from CN, $CONH_2$, $C(NOH)NH_2$, $SO_2$—$C_{1-4}$ alkyl, $SO_2$-aryl, CO-heteroaryl, CO—$C_{1-4}$ alkyl, COO—$C_{1-4}$ alkyl, $C_{1-4}$ alkyl, aryl $C_{1-3}$ alkyl, heteroaryl $C_{1-3}$ alkyl, heterocyclyl $C_{1-3}$ alkyl, aryl, heteroaryl, and heterocyclyl, wherein (a) the $C_{1-4}$ alkyl may optionally be substituted with OH, CN, or COOH, (b) the $SO_2$-aryl may optionally be substituted with a $C_{1-4}$ alkyl or $C_{1-4}$ haloalkyl, (c) the CO-heteroaryl may optionally be substituted with a heteroaryl or halogen, (d) the heteroaryl $C_{1-3}$ alkyl may optionally be substituted with COO—$C_{1-3}$ alkyl, and (e) the heteroaryl may optionally be substituted with one or more halogens.

37. The compound according to claim 36, wherein the nitrogen heteroatom is substituted with phenyl $C_{1-3}$ alkyl.

38. The compound according to claim 31, wherein $R_6$ is selected from monocyclic aryl and monocyclic heteroaryl.

39. The compound according to claim 38, wherein $R_6$ is aryl, substituted with one or more groups selected from halogen, $R_{6a}$, OH, $OR_{6a}$, $NH_2$, $NO_2$, $NHC(NH)NH_2$, $NHR_{6a}$, $NR_{6a}R_{6b}$, $C(NOH)NH_2$, $COR_{6a}$, COOH, $COOR_{6a}$, $CONH_2$, CONHOH, $SO_2R_{6a}$, $SO_2NR_{6a}R_{6b}$, wherein $R_{6a}$ and $R_{6b}$ are independently selected from $C_{1-6}$ alkyl, substituted $C_{1-6}$ alkyl, aryl, heteroaryl, $C_{3-8}$ cycloalkyl and heterocyclyl, wherein $R_{6a}$ and $R_{6b}$ are independently selected from $C_{1-6}$ alkyl, substituted $C_{1-6}$ alkyl, aryl, heteroaryl, $C_{3-8}$ cycloalkyl and heterocyclyl, wherein, when the substituent of $R_6$ is a moiety selected from the group consisting of (a) $C_{1-6}$ alkyl, (b) substituted $C_{1-6}$ alkyl, (c) aryl, heteroaryl, (d) $C_{3-8}$ cycloalkyl, and (e) heterocyclyl or is a group containing at least one moiety selected from the group consisting of (a), (b), (c), (d), and (e), each moiety (a), (b), (c), (d), and (e) may optionally be substituted with one or more groups selected from $OR_{6c}$, OH, and $CONH_2$, wherein $R_{6c}$ and $R_{6d}$ are independently selected from $C_{1-6}$ alkyl, substituted $C_{1-6}$ alkyl, aryl, heteroaryl, $C_{3-8}$ cycloalkyl and heterocyclyl, and wherein, when the substituent of $R_6$ is heteroaryl or heterocyclyl, each of the heteroaryl and heterocyclyl may optionally be substituted with one or more anionic oxygen atoms.

40. The compound according to claim 39, wherein $R_6$ is aryl substituted with one or more groups selected from halogen, OH, $C_{1-4}$ alkoxy, $CONH_2$, $C(NOH)NH_2$, CONHOH, $SO_2$—$C_{1-4}$ alkyl, heterocyclyl, and aryl, wherein the heterocyclyl may optionally be substituted with an anionic oxygen atom and wherein the aryl may optionally be substituted with $CONH_2$.

41. The compound according to claim 38, wherein $R_6$ is a monocyclic heteroaryl which is substituted with an anionic oxygen atom.

42. The compound according to claim 1, wherein $R_6$ is substituted with a group selected from $C_{1-6}$ alkoxy, $C_{1-6}$ alkoxy $C_{1-6}$ alkyl, and $C_{0-6}$ alkyl-CO—$C_{0-6}$ alkyl, wherein the $C_{1-6}$ alkoxy, $C_{1-6}$ alkoxy $C_{1-6}$ alkyl, or $C_{0-6}$ alkyl-CO—$C_{0-6}$ alkyl group is substituted with a group selected from aryl, heteroaryl, heterocyclyl, and $C_{3-10}$ cycloalkyl.

43. The compound according to claim 42, wherein $R_6$ is a group selected from aryl and heteroaryl, wherein the $R_6$ group is substituted with a group selected from $C_{1-6}$ alkoxy substituted with a heterocyclyl and $C_{1-6}$ alkoxy $C_{1-6}$ alkyl substituted with a heterocyclyl.

44. The compound according to claim 43, wherein $R_6$ is a monocyclic aryl which is substituted with a group selected from $C_{1-6}$ alkoxy substituted with a heterocyclyl and $C_{1-6}$ alkoxy $C_{1-6}$ alkylsubstituted with a heterocyclyl.

45. The compound according to claim 44, wherein the heterocyclyl is a six membered monocyclic heterocyclyl.

46. A pharmaceutical composition comprising a compound according to claim 1, together with one or more pharmaceutically acceptable excipients.

47. The pharmaceutical composition of claim 46, further comprising one or more additional active pharmaceutical ingredients.

48. The compound of claim 1, wherein $R_2$ is selected from (a) aryl, (b) heteroaryl, (c) partially or fully saturated heterocyclyl, (d) $C_{3-10}$ cycloalkyl, (e) a substituted $C_{1-6}$ alkyl selected from the group consisting of aryl $C_{1-6}$ alkyl, hetaryl $C_{1-6}$ alkyl, heterocyclyl $C_{1-6}$ alkyl, and $C_{3-10}$ cycloalkyl $C_{1-6}$ alkyl.

49. The compound of claim 1, wherein $R_5$ is H.

50. The compound of claim 1, wherein:
$R_1$ is methyl;
$R_2$ is selected from monocyclic $C_{5-8}$ cycloalkyl andmonocyclic six membered saturated heterocyclyl, wherein the heterocyclyl contains a single nitrogen or oxygen heteroatom at the 4-position relative to the position of attachment of the heterocyclyl to the urea nitrogen of Formula (Ha) and wherein, when the heteroatom is a nitrogen atom, the nitrogen atom is optionally substituted with benzyl;
$R_5$ is H; and
$R_6$ is selected from phenyl, wherein the phenyl may optionally be substituted with one or more groups selected from halogen, methoxy, OH, $CONH_2$, $NH_2$ and phenyl; and pyridyl, wherein the nitrogen atom of the pyridyl may be substituted with an anionic oxygen atom.

51. The compound of claim 1, wherein:
$R_1$ is methyl;
$R_2$ is selected from the group consisting of monocyclic $C_{5-8}$ cycloalkyl, tetrahydropyranyl, and piperidinyl, wherein the heteroatom in the tetrahydropyranyl and piperidinyl is at the 4-position relative to the position of attachment of the heterocyclyl to the urea nitrogen of Formula (IIa), and wherein the nitrogen atom of the piperidinyl is substituted with benzyl;
$R_5$ is H; and
$R_6$ is selected from the group consisting of (a) phenyl, wherein the phenyl is optionally substituted with one or more groups selected from halogen, methoxy, $CONH_2$, $NH_2$ and phenyl, and (b) pyridyl, wherein the nitrogen atom of the pyridyl is substituted with an anionic oxygen atom.

52. The compound of claim 1, wherein $R_1$ is methyl and $R_2$ is a monocyclic saturated heterocyclyl containing a single nitrogen heteroatom, wherein the single nitrogen heteroatom is substituted with $CONR_{1c}R_{1d}$.

53. The compound of claim 1, wherein $R_6$ is phenyl substituted with at least two groups selected from OH and $C_{1-6}$ alkyl.

54. The compound of claim 1, wherein $R_6$ is phenyl substituted with $NHSO_2NH_2$.

55. The compound of claim 1, wherein $R_1$ is methyl and $R_2$ is a monocyclic saturated heterocyclyl containing a single nitrogen heteroatom, wherein the single nitrogen heteroatom is substituted with a group selected from aryl and $SO_2R_{1c}$.

56. A compound having Formula IIa:

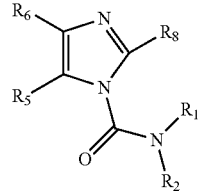

Formula IIa wherein:
$R_1$ is $C_1$-$C_4$ alkyl,
$R_2$ is selected from H, $C_{1-20}$ alkyl, aryl, heteroaryl, partially or fully saturated heterocyclyl, $C_{3-10}$ cycloalkyl, substituted $C_{1-6}$ alkyl, halogen, OH, $OR_{1a}$, $OCOR_{1a}$, SH, $SCOR_{1a}$, $NH_2$, $NHR_{1a}$, $NHSO_2NH_2$, $NHSO_2R_{1a}$, $NR_{1a}COR_{1b}$, $NHCOR_{1a}$, $NR_{1a}R_{1b}$, $COR_{1a}$, CN, COOH, $COOR_{1a}$, $CONH_2$, CONHOH, $CONHR_{1a}$, $CONHOR_{1a}$, $SO_2R_{1a}$, $SO_3H$, $SO_2NH_2$, $CONR_{1a}R_{1b}$, and $SO_2NR_{1a}R_{1b}$, wherein $R_{1a}$ and $R_{1b}$ are independently selected from $C_{1-6}$ alkyl, substituted $C_{1-6}$ alkyl, aryl, heteroaryl, $C_{3-8}$ cycloalkyl and heterocyclyl, or $R_{1a}$ and $R_{1b}$, together with the heteroatom to which they are joined, can form heterocyclyl,
wherein, when $R_2$ is a moiety selected from the group consisting of (a) $C_{1-20}$ alkyl, (b) $OR_{1a}$, wherein $R_{1a}$ is $C_{1-6}$ alkyl, (c) aryl, (d) heteroaryl, (e) heterocyclyl, (f) $C_{3-10}$ cycloalkyl, (g) a substituted $C_{1-6}$ alkyl selected from the group consisting of aryl $C_{1-6}$ alkyl, heteroaryl $C_{1-6}$ alkyl, heterocyclyl $C_{1-6}$ alkyl, and $C_{3-10}$ cycloalkyl $C_{1-6}$ alkyl, or is a group containing at least one moiety selected from the group consisting of (a), (b), (c), (d), (e), (f), and (g), each moiety (a), (b), (c), (d), (e), (f), and (g) may optionally be substituted with one or more groups selected from $C_{1-6}$ alkyl, $C_{3-8}$ cycloalkyl, halogen, aryl, heteroaryl, heterocyclyl, aryloxy, heteroaryloxy, heterocyclyloxy, substituted $C_{1-6}$ alkyl, aryl $C_{1-6}$ alkoxy, heteroaryl $C_{1-6}$ alkoxy, heterocyclyl $C_{1-6}$ alkoxy, $C_{1-6}$ alkylamino, $C_{1-6}$ dialkylamino, $C_{1-10}$ alkyl, OH, $OR_{1c}$, $OCOR_{1c}$, SH, $SR_{1c}$, $SCOR_{1c}$, $NH_2$, $NO_2$, $NHR_{1e}$, $NHSO_2NH_2$, $NHSO_2R_{1c}$, $NR_{1c}COR_{1d}$, $NHC(NH)NH_2$, $NHCOR_{1c}$, $NR_{1c}R_{1d}$, $COR_{1c}$, $CSR^{1c}$, CN, COOH, $COOR_{1c}$, $CONH_2$, CONHOH, $CONHR_{1c}$, $CONHOR_{1c}$, $C(NOH)NH_2$, $CONR_{1c}R_{1d}$, $SO_2R_{1c}$, $SO_3H$, $SO_2NH_2$, $SO_2NR_{1c}R_{1d}$, wherein $R_{1c}$ and $R_{1d}$ are independently selected from $C_{1-6}$ alkyl, substituted $C_{1-6}$ alkyl, aryl, heteroaryl, $C_{3-8}$ cycloalkyl and heterocyclyl, or $R_{1c}$ and $R_{1d}$, together with the heteroatom to which they are joined, can form heterocyclyl,
wherein, when the substituent of $R_2$ is a moiety selected from the group consisting of (a) $C_{1-10}$ alkyl, (b) aryl, (c) heteroaryl, (d) heterocyclyl, (e) $OR_{1c}$, wherein $R_{1c}$ is $C_{1-6}$ alkyl, (f) aryloxy, (g) heteroaryloxy, (h) heterocyclyloxy, (i) a substituted $C_{1-6}$ alkyl selected from the group consisting of aryl $C_{1-6}$ alkyl, heteroaryl $C_{1-6}$ alkyl, and heterocyclyl $C_{1-6}$ alkyl, (j) aryl $C_{1-6}$ alkoxy, (k) heteroaryl $C_{1-6}$ alkoxy, (l) heterocyclyl $C_{1-6}$ alkoxy, (m) $C_{1-6}$ alkylamino, (n) $C_{1-6}$ dialkylamino, and (o) $C_{3-8}$ cycloalkyl or is a group containing at least one moiety selected from the group consisting of (a), (b), (c), (d), (e), (f), (g), (h), (i), (j), (k), (l), (m), (n), and (o), each moiety (a), (b), (c), (d), (e), (f), (g), (h), (i), (j), (k), (l), (m), (n), and (o) may optionally be substituted with one or more groups selected from substituted $C_{1-6}$ alkyl, aryl, heteroaryl, C$_{3-8}$ cycloalkyl, heterocyclyl, halogen, C$_{1-10}$ alkyl, OH, OR$_{1e}$, OCOR$_{1e}$, SH, SR$_{1e}$, SCOR$_{1e}$, NH$_2$, NO$_2$, NHR$_{1e}$, NHSO$_2$NH$_2$, NHSO$_2$R$_{1e}$, NR$_{1e}$COR$_{1f}$, NHC(NH)NH$_2$, NHCOR$_{1e}$, NR$_{1e}$R$_{1f}$, COR$_{1e}$, CSR$_{1e}$, CN, COOH, COOR$_{1e}$, CONH$_2$, CONHOH, CONHR$_{1e}$, CONHOR$_{1e}$, C(NOH)NH$_2$, CONR$_{1e}$R$_{1f}$, SO$_2$R$_{1e}$, SO$_3$H, SO$_2$NH$_2$, SO$_2$NR$_{1e}$R$_{1f}$, wherein R$_{1e}$ and R$_{1f}$ are independently selected from C$_{1-6}$ alkyl, substituted C$_{1-6}$ alkyl, aryl, heteroaryl, C$_{3-8}$ cycloalkyl and heterocyclyl, or R$_{1e}$ and R$_{1f}$, together with the heteroatom to which they are joined, can form heterocyclyl, with the exception that R$_1$ and R$_2$ are not both methyl, or R$_1$ and R$_2$, together with the N to which they are attached, can form a heteroaryl or heterocyclyl group, each of which may optionally be substituted with one or more anionic oxygen atoms or one or more groups selected from aryl, heteroaryl, partially or fully saturated heterocyclyl, C$_{3-8}$ cycloalkyl, C$_{1-6}$ alkyl, substituted C$_{1-6}$ alkyl, C$_{1-6}$ alkoxy, aryloxy, heteroaryloxy, heterocyclyloxy, halogen, OH, OR$_{2a}$, OCOR$_{2a}$, SH, SR$_{2a}$, SCOR$_{2a}$, NH$_2$, NO$_2$, NHR$_{2a}$, NHSO$_2$NH$_2$, NHSO$_2$R$_{2a}$, NR$_{2a}$COR$_{2b}$, NHC(NH)NH$_2$, NHCOR$_{2a}$, NR$_{2a}$R$_{2b}$, COR$_{2a}$, CSR$_{2a}$, CN, COOH, COOR$_{2a}$, CONH$_2$, CONHOH, CONHR$_{2a}$, CONHOR$_{2a}$, C(NOH)NH$_2$, CONR$_{2a}$R$_{2b}$, SO$_2$R$_{2a}$, SO$_3$H, SO$_2$NH$_2$, SO$_2$NR$_{2a}$R$_{2b}$, wherein R$_{2a}$ and R$_{2b}$ are independently selected from C$_{1-6}$ alkyl, substituted C$_{1-6}$ alkyl, aryl, heteroaryl, C$_{3-8}$ cycloalkyl and heterocyclyl, or R$_{2a}$ and R$_{2b}$, together with the heteroatom to which they are joined, can form heterocyclyl, wherein, when the substituent of the heteroaryl or heterocyclyl formed by R$_1$ and R$_2$ together is a moiety selected from the group consisting of (a) aryl, (b) heteroaryl, (c) heterocyclyl, (d) C$_{3-8}$ cycloalkyl, (e) C$_{1-6}$ alkyl, (f) a substituted C$_{1-6}$ alkyl selected from the group consisting of aryl C$_{1-6}$ alkyl, heteroaryl C$_{1-6}$ alkyl, heterocyclyl C$_{1-6}$ alkyl, and C$_{3-8}$ cycloalkyl C$_{1-6}$ alkyl, (g) OR$_{1a}$, wherein R$_{1a}$ is C$_{1-6}$ alkyl, (h) aryloxy, (i) heteroaryloxy, and (j) heterocyclyloxy, or is a group containing at least one moiety selected from the group consisting of (a), (b), (c), (d), (e), (f), (g), (h), (i), and (j), each moiety (a), (b), (c), (d), (e), (f), (g), (h), (i), and (j) may optionally be substituted with one or more groups selected from halogen, hydroxyl, C$_{1-6}$ alkyl, aryl, heteroaryl, heterocyclyl, C$_{3-8}$ cycloalkyl, aryloxy, heteroaryloxy, heterocyclyloxy, C$_{3-8}$ cycloalkyloxy, aryl C$_{1-4}$ alkoxy, heteroaryl C$_{1-6}$ alkoxy, heterocyclyl C$_{1-4}$ alkoxy, C$_{3-8}$ cycloalkyl C$_{1-4}$ alkoxy, substituted C$_{1-6}$ alkyl, OR$_{2c}$, OCOR$_{2c}$, SH, SR$_{2c}$, SCOR$_{2c}$, NH$_2$, NO$_2$, NHR$_{2c}$, NHSO$_2$NH$_2$, NHSO$_2$R$_{2c}$, NR$_{2c}$COR$_{2d}$, NHC(NH)NH$_2$, NHCOR$_{2c}$, NR$_{2c}$R$_{2d}$, COR$_{2c}$, CSR$_{2c}$, CN, COOH, COOR$_{2c}$, CONH$_2$, CONHOH, CONHR$_{2c}$, CONHOR$_{2c}$, C(NOH)NH$_2$, CONR$_{2c}$R$_{2d}$, SO$_2$R$_{2c}$, SO$_3$H, SO$_2$NH$_2$, SO$_2$NR$_{2c}$R$_{2d}$, wherein R$_{2c}$ and R$_{2d}$ are independently selected from C$_{1-6}$ alkyl, substituted C$_{1-6}$ alkyl, aryl, heteroaryl, C$_{3-8}$ cycloalkyl and heterocyclyl, or R$_{2c}$ and R$_{2d}$, together with the heteroatom to which they are joined, can form heterocyclyl, wherein, when the substituent of the substituent of the heteroaryl or heterocyclyl formed by R$_1$ and R$_2$ together is a moiety selected from the group consisting of (a) C$_{1-6}$ alkyl, (b) aryl, (c) heteroaryl, (d) heterocyclyl, (e) C$_{3-8}$ cycloalkyl, OR$_{2e}$, wherein R$_{2e}$ is C$_{1-6}$ alkyl, (g) aryloxy, (h) heteroaryloxy, (i) heterocyclyloxy, (j) C$_{3-8}$ cycloalkyloxy, (k) aryl C$_{1-4}$ alkoxy, (l) heteroaryl C$_{1-4}$ alkoxy, (m) heterocyclyl C$_{1-4}$ alkoxy, and (n) C$_{3-8}$ cycloalkyl C$_{1-4}$ alkoxy, or is a group containing at least one moiety selected from the group consisting of (a), (b), (c), (d), (e), (g), (h), (i), (j), (k), (l), (m), and (n), each of (a), (b), (c), (d), (e), (g), (h), (i), (j), (k), (l), (m), and (n) may optionally be substituted with one or more groups selected from C$_{1-6}$ alkyl, substituted C$_{1-6}$ alkyl, aryl, heteroaryl, C$_{3-8}$ cycloalkyl, heterocyclyl, halogen, OH, OR$_{2e}$, OCOR$_{2e}$, SH, SR$_{2e}$, SCOR$_{2e}$, NH$_2$, NO$_2$, NHR$_{2e}$, NHSO$_2$NH$_2$, NHSO$_2$R$_{2e}$, NR$_{2e}$COR$_{2f}$, NHC(NH)NH$_2$, NR$_{2e}$R$_{2f}$, NHCOR$_{2e}$, COR$_{2e}$, CSR$_{2e}$, CN, COOH, COOR$_{2e}$, CONH$_2$, CONHOH, CONHR$_{2e}$, CONHOR$_{2e}$, C(NOH)NH$_2$, CONR$_{2e}$R$_{2f}$, SO$_2$R$_{2e}$, SO$_3$H, SO$_2$NH$_2$, SO$_2$NR$_{2e}$R$_{2f}$, wherein R$_{2e}$ and R$_{2f}$ are independently selected from C$_{1-6}$ alkyl, substituted C$_{1-6}$ alkyl, aryl, heteroaryl, C$_{3-8}$ cycloalkyl and heterocyclyl, or R$_{2e}$ and R$_{2f}$, together with the heteroatom to which they are joined, can form heterocyclyl;

R$_5$ is selected from H, C$_{1-2}$ alkyl, and halogen;

R$_6$ is pyridyl substituted with a group selected from NHR$_{6c}$, NR$_{6c}$R$_{6d}$, NHSO$_2$NH$_2$, NHCOR$_{6c}$ and NHSO$_2$R$_{6c}$; and R$_8$ is H, or a pharmaceutically acceptable salt or ester thereof.

57. The compound of claim 1, wherein R$_6$ is pyrazinyl or pyrimidyl.

58. The compound of claim 1, wherein R$_{1c}$ is C$_{1-6}$ alkyl.

59. The compound of claim 1, wherein R$_{1c}$ is C$_{3-8}$ cycloalkyl.

60. The compound of claim 1, wherein R$_1$ is methyl and R$_2$ is a monocyclic saturated six membered heterocyclyl containing a single nitrogen heteroatom, wherein the single nitrogen heteroatom is substituted with aryl C$_{1-4}$ alkyl.

61. A compound selected from the group consisting of:

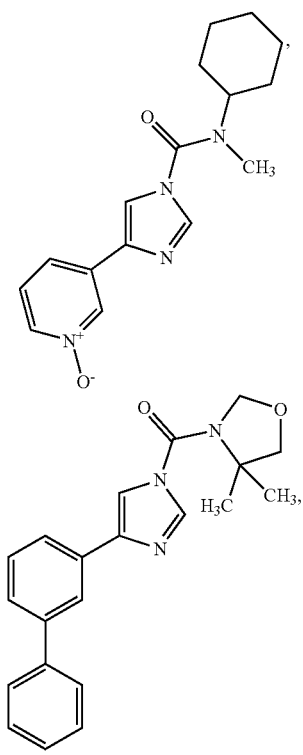

| 453 -continued | 454 -continued |
|---|---|
| 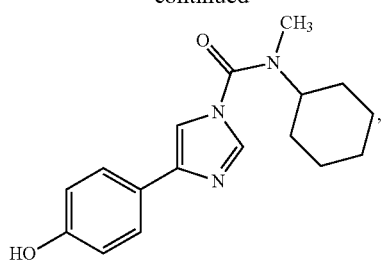 | 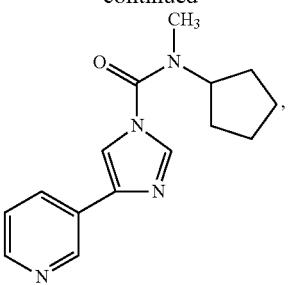 |
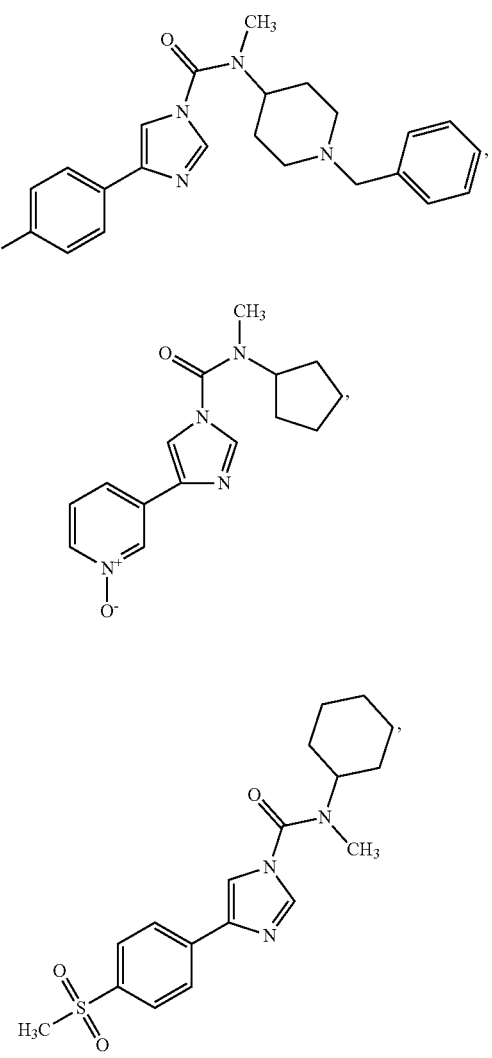

-continued
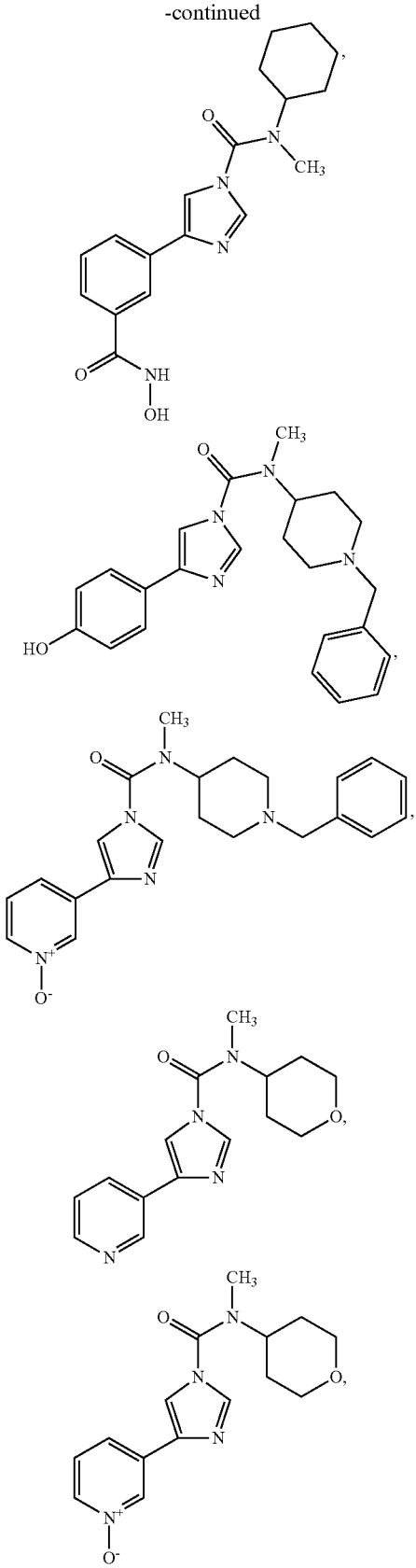
-continued
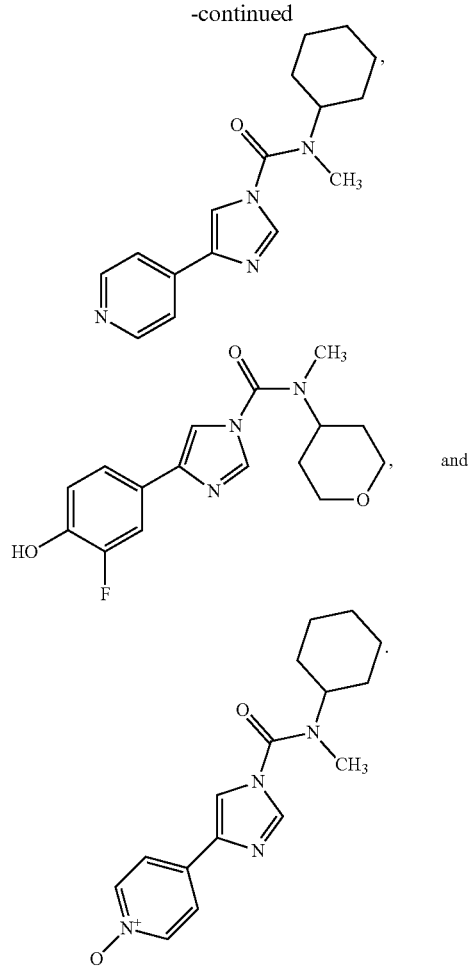
62. The compound
63. The compound of claim 1, wherein $R_1$ and $R_2$, together with the N to which they are attached, form a heterocyclyl group.
64. The compound of claim 1, wherein $R_1$ and $R_2$, together with the N to which they are attached, form a heteroaryl group.
* * * * *